US012138256B2

(12) United States Patent
Becker-Pelster et al.

(10) Patent No.: US 12,138,256 B2
(45) Date of Patent: Nov. 12, 2024

(54) TREATMENT OF CARDIOPULMONARY DISORDERS

(71) Applicants: Bayer Aktiengesellschaft, Leverkusen (DE); Bayer Pharma Aktiengesellschaft, Berlin (DE)

(72) Inventors: Eva Maria Becker-Pelster, Wuppertal (DE); Hanna Tinel, Wuppertal (DE); Michael Hahn, Langenfeld (DE); Dieter Lang, Velbert (DE); Gerrit Weimann, Bergisch-Gladbach (DE); Johannes Nagelschmitz, Wuppertal (DE); Lisa Dietz, Wuppertal (DE); Soundos Saleh, Wuppertal (DE); David Jung, Wittenberg (DE); Ildiko Terebesi, Berlin (DE); Tobias Mundry, Berlin (DE); Annett Richter, Berlin (DE); Britta Olenik, Bottrop (DE); Birgit Keil, Dusseldorf (DE); Bernd Rösler, Wuppertal (DE); Peter Fey, Wuppertal (DE); Heiko Schirmer, Solingen (DE); Guido Becker, Krefeld (DE); Clemens Bothe, Leverkusen (DE); Helene Faber, Dormagen (DE); Julian Egger, Remscheid (DE); Mark Parry, Essex (GB); David Ward, Cambridgeshire (GB); Cecile Vitre, Cambridgeshire (GB)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 18/506,944

(22) Filed: Nov. 10, 2023

(65) Prior Publication Data

US 2024/0148715 A1 May 9, 2024

Related U.S. Application Data

(63) Continuation of application No. PCT/EP2022/087954, filed on Dec. 28, 2022.

(30) Foreign Application Priority Data

Dec. 29, 2021 (EP) .................................... 21218165

(51) Int. Cl.

| | |
|---|---|
| ***A61K 31/47*** | (2006.01) |
| ***A61K 9/00*** | (2006.01) |
| ***A61P 9/12*** | (2006.01) |

(52) U.S. Cl.

CPC ............ *A61K 31/47* (2013.01); *A61K 9/0075* (2013.01); *A61P 9/12* (2018.01)

(58) Field of Classification Search

CPC .......... A61K 31/47; A61K 9/0075; A61P 9/12

See application file for complete search history.

(56) References Cited

U.S. PATENT DOCUMENTS

| | | | |
|---|---|---|---|
| 4,873,262 | A | 10/1989 | Junge et al. |
| 4,880,802 | A | 11/1989 | Schohe et al. |

(Continued)

FOREIGN PATENT DOCUMENTS

| | | | |
|---|---|---|---|
| CA | 2804470 | A1 | 1/2012 |
| CA | 2809911 | A1 | 3/2012 |

(Continued)

OTHER PUBLICATIONS

U.S. Appl. No. 18/506,737, filed Nov. 10, 2023.

(Continued)

*Primary Examiner* — Jeffrey S Lundgren
*Assistant Examiner* — Ibrahim D Bori
(74) *Attorney, Agent, or Firm* — COOLEY LLP; Heidi A. Erlacher; Christine E. Dunne

(57) ABSTRACT

The present invention relates to the use of (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid of formula (I), prefer-ably in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate (I) of formula (I-M-I) or (5S)-{[2-(4-carboxyphenyl)ethyl][2-(2-{[3-chloro-4'-(trifluoromethyl) biphenyl-4-yl]methoxy}phenyl)-ethyl]-amino}-5,6,7,8-tetrahydroquinoline-2-carboxylic acid inform of mono hydrate (II) of formula (I-M-II), in the inhalative treatment of cardiopulmonary and pulmonary disorders, such as pulmonary arterial hypertension (P AH), chronic tromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), characterized in that an inhalative dosage form comprising 240 to 4000 μg, preferably 480 to 2000 μg of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxy lie acid of formula (I), preferably in form of one of its salts or solvates or hydrates, preferably in form of monohydrate I of formula (I-M-I) or (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxy lie acid in form of mono hydrate (II) of formula (I-M-II), is administered to a patient in need thereof once or twice daily for a period of at least two consecutive days, preferably at least 2 to 7 consecutive days, preferably for a period of at least 14 consecutive days, in particular from after onset of treatment for the whole course of the disease, wherein the inhalative dosage form preferably comprises the combination of the active ingredient and a pharmaceutically suitable excipient or carrier, while preferably (Continued)

Figure 1:
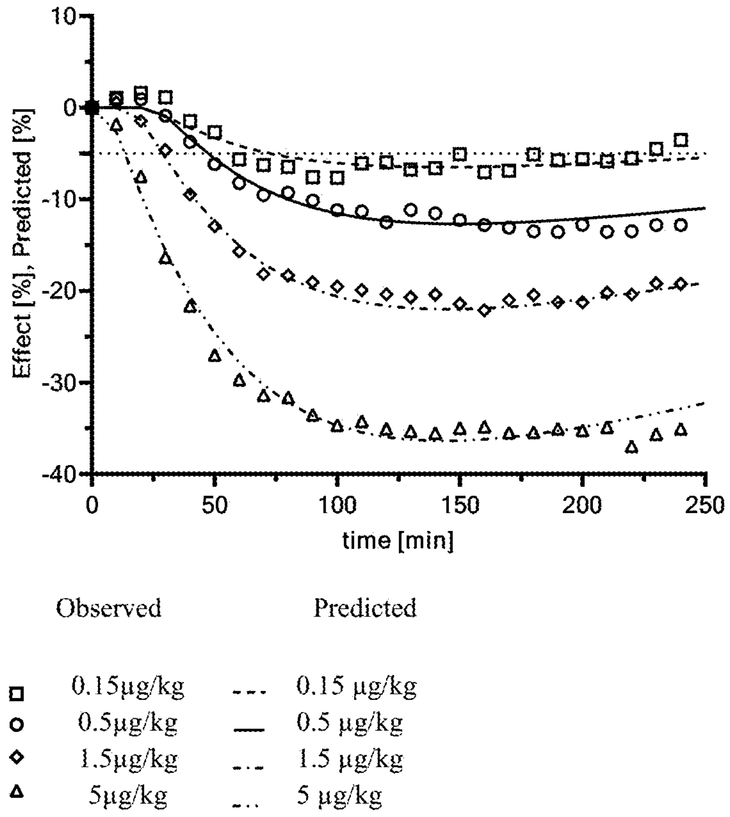

the active ingredient and a pharmaceutically suitable excipient are filled in a hard capsule.

30 Claims, 62 Drawing Sheets

(56) References Cited

U.S. PATENT DOCUMENTS

| | | | |
|---|---|---|---|
| 5,047,422 | A | 9/1991 | Junge et al. |
| 6,693,102 | B2 | 2/2004 | Stasch et al. |
| 6,743,798 | B1 | 6/2004 | Straub et al. |
| 6,833,364 | B1 | 12/2004 | Straub et al. |
| 6,939,989 | B2 | 9/2005 | Härter et al. |
| 6,939,990 | B2 | 9/2005 | Härter et al. |
| 7,087,644 | B1 | 8/2006 | Alonso-Alija et al. |
| 7,173,037 | B2 | 2/2007 | Alonso-Alija et al. |
| 7,705,043 | B2 | 4/2010 | Alonso-Alija et al. |
| 8,420,656 | B2 | 4/2013 | Follmann et al. |
| 8,653,099 | B2 | 2/2014 | Colburn et al. |
| 8,673,903 | B2 | 3/2014 | Hübsch et al. |
| 8,921,377 | B2 | 12/2014 | Follmann et al. |
| 8,981,104 | B2 | 3/2015 | Hahn et al. |
| 9,096,592 | B2 | 8/2015 | Follmann et al. |
| 9,688,636 | B2 | 6/2017 | Hahn et al. |
| 10,053,428 | B2 | 8/2018 | Hahn et al. |
| 10,729,647 | B2 | 8/2020 | Green |
| 2004/0082658 | A1 | 4/2004 | Harter et al. |
| 2004/0082798 | A1 | 4/2004 | Alonso-Alija et al. |
| 2004/0092593 | A1 | 5/2004 | Harter et al. |
| 2004/0110840 | A1 | 6/2004 | Harter et al. |
| 2004/0176446 | A1 | 9/2004 | Alonso-Alija et al. |
| 2006/0052397 | A1 | 3/2006 | Alonso-Alija et al. |
| 2009/0227640 | A1 | 9/2009 | Bartel et al. |
| 2011/0141409 | A1 | 6/2011 | Ashida |
| 2013/0237551 | A1 | 9/2013 | Follmann et al. |
| 2013/0267548 | A1 | 10/2013 | Follmann et al. |
| 2014/0031391 | A1 | 1/2014 | Hahn et al. |
| 2014/0350020 | A1 | 11/2014 | Follmann et al. |
| 2015/0080414 | A1 | 3/2015 | Follmann et al. |
| 2015/0148376 | A1 | 5/2015 | Hahn et al. |
| 2015/0174113 | A1 | 6/2015 | Hübsch et al. |
| 2017/0260139 | A1 | 9/2017 | Hahn et al. |
| 2023/0183181 | A1 | 6/2023 | Fey et al. |

FOREIGN PATENT DOCUMENTS

| | | | | |
|---|---|---|---|---|
| CA | 2816671 | A1 | 5/2012 | |
| EP | 0041488 | A1 | 12/1981 | |
| EP | 0064964 | B1 | 8/1984 | |
| EP | 0270947 | B1 | 5/1993 | |
| EP | 1617820 | B1 | 3/2018 | |
| FR | 2659853 | A1 | 9/1991 | |
| WO | WO-9015047 | A1 | 12/1990 | |
| WO | WO-9518617 | A1 | 7/1995 | |
| WO | WO-9962505 | A2 | 12/1999 | |
| WO | WO-0006568 | A1 | 2/2000 | |
| WO | WO-0006569 | A1 | 2/2000 | |
| WO | WO-0035882 | A1 | 6/2000 | |
| WO | WO-0119780 | A2 | 3/2001 | |
| WO | WO-0242301 | A1 | 5/2002 | |
| WO | WO-02070459 | A1 | 9/2002 | |
| WO | WO-02070460 | A1 | 9/2002 | |
| WO | WO-02070461 | A1 | 9/2002 | |
| WO | WO-02070462 | A1 | 9/2002 | |
| WO | WO-02070510 | A2 | 9/2002 | |
| WO | WO-03095451 | A1 | 11/2003 | |
| WO | WO-2005012291 | A1 | 2/2005 | |
| WO | WO-2006104826 | A2 | 10/2006 | |
| WO | WO-2009023669 | A1 | 2/2009 | |
| WO | WO-2009032249 | A1 | 3/2009 | |
| WO | WO-2011147809 | A1 | 12/2011 | |
| WO | WO-2011161099 | A1 | 12/2011 | |
| WO | WO-2012004258 | A1 | 1/2012 | |
| WO | WO-2012028647 | A1 | 3/2012 | |
| WO | WO-2012059549 | A1 | 5/2012 | |
| WO | WO-2012122340 | A1 | 9/2012 | |
| WO | WO-2013024895 | A1 | 2/2013 | |
| WO | WO-2013157528 | A1 | 10/2013 | |
| WO | WO-2014012934 | A1 * | 1/2014 | ............ A61K 31/47 |
| WO | WO-2014068099 | A1 | 5/2014 | |
| WO | WO-2019081456 | A1 | 5/2019 | |
| WO | WO-2021233783 | A1 | 11/2021 | |
| WO | WO-2023126436 | A1 | 7/2023 | |
| WO | WO-2023126437 | A1 | 7/2023 | |
| WO | WO-2023126438 | A1 | 7/2023 | |

OTHER PUBLICATIONS

Artursson et al., "Correlation between oral drug absorption in humans and apparent drug permeability coefficients in human intestinal epithelial (Caco-2) cells", Biochem. Biophys, 1991, 175 (3), 880-885.

Becker et al., "Effects of different pulmonary vasodilators on arterial saturation in a model of pulmonary hypertension," PLoS One 2013, 8: 1-8.

Becker et al., "V/Q mismatch" in secondary pulmonary hypertension—riociguat in comparison, Pulmonology 65, Suppl. 2, 2011, S122-S123.

Becker-Pelster et al., "Inhaled mosliciguat (BAY 1237592): targeting pulmonary vasculature via activating apo-sGC", Respiratory Research, vol. 23, No. 1, Oct. 1, 2022, 15 pages.

Begg et al., "Translation of Inhaled Drug Optimization Strategies into Clinical Pharmacokinetics and Pharmacodynamics Using GSK2292767A, a Novel Inhaled Phosphoinositide 3-Kinase d Inhibitor," J. Pharmacol. Exp. Ther. 2019; 369: 443-453.

Beyer et al., "Stimulation of soluble guanylate cyclase reduces experimental dermal fibrosis," Ann Rheum Dis, Jun. 2012; 71: 1019-1026.

Bice et al., "NO-independent stimulation or activation of soluble guanylyl cyclase during early reperfusion limits infarct size," Cardiovascular Research, Oxford Journal of Medicine, 2014, 101: 220-228.

Bitler, "The Preparation and Properties of Crystalline Firefly Luciferin," Arch Biochem Biophys., Dec. 1957; 72(2): 358-68.

Blanco, et al. "Hemodynamic and Gas Exchange Effects of Sildenafil in Patients with Chronic Obstructive Pulmonary Disease and Pulmonary Hypertension," Am. J. Respir. Crit. Care Med., Feb. 2010; 181(3): 270-278.

CAS-Registry No. 1000533-03-8, "2-(5-fluoro-2-Methoxyphenyl) ethanamine", Jan. 23, 2008, 2 pages.

CAS-Registry No. 192139-92-7, Aug. 5, 1997, 2 pages.

CAS-Registry No. 56985-32-1, "9,11-dideoxy-9a,11a-epoxymethano-prosta-5E,13E-dien-1-oic acid," Cayman Chemical: Product Information 5-trans U-44069; Item No. 16442; 2020, 1 page.

CAS-Registry No. 885050-65-7, May 21, 2006, 1 page.

ClinicalTrials.gov Identifier: NCT04609943; Oct. 30, 2020, 7 pages.

"DAS-1802HC Keithley 12-Bit Multifunctional I/O Board", Artisan Technology Group, Stock # 66977-9; 1999. 3 pages.

Dasgupta et al., "Soluble Guanylate Cyclase: A New Therapeutic Target for Pulmonary Arterial Hypertension and Chronic Thromboembolic Pulmonary Hypertension," Clinical Pharmacology and Therapeutics, vol. 97, No. 1, Nov. 28, 2014, pp. 88-102.

De Boer et al., "A critical view on lactose-based drug formulation and device studies for dry powder inhalation: Which are relevant and what interactions to expect?" Advanced Drug Delivery Reviews 64 (2012) 257-274.

De Boer et al., "Dry powder inhalation: past, present and future," Expert Opinion on Drug Delivery, 2017, vol. 14(4), pp. 499-512.

Durgin et al., "Loss of smooth muscle CYB5R3 amplifies angiotensin II-induced hypertension by increasing sGC heme oxidation" JCI Insight 2019; 4(19): e129183, 16 pages.

Elkins et al., "Inspiratory Flows and Volumes in Subjects with Cystic Fibrosis Using a New Dry Powder Inhaler Device," The Open Respiratory Medicine Journal, 2014, 8, pp. 1-7.

Elkins et al., "Inspiratory Flows and Volumes in Subjects with Non-CF Bronchiectasis Using a New Dry Powder Inhaler Device," The Open Respiratory Medicine Journal, 2014, 8, pp. 8-13.

(56) References Cited

OTHER PUBLICATIONS

Erlanson et al., "Fragment-Based Drug Discovery," J. Med. Chem.; Jun. 2004; 47(14): 3463-3482.
Evgenov et al., "Inhaled Agonists of Soluble Guanylate Cyclase Induce Selective Pulmonary Vasodilation," Am. J. Resplr. Crit. Care Med., 2007, 176: 1138-1145.
Evgenov et al., "NO-Independent Stimulators and Activators of Soluble Guanylate Cyclase: Discovery and Therapeutic Potential," Nature Reviews: Drug Discovery, Sep. 2006, 5(9): 755-768.
FDA World Health Organization, "FDA Approves Bayer's New Class of Drug Adempas® (riociguat) tablets to Treat Adults with PAH and Persistent, Recurrent or Inoperable CTEPH," PR Newswire; Oct. 8, 2013, 7 pages.
Gerlach et al., "Synthesis of Benzoic and Tetralone Carboxylic Acid Esters from Phenols by Palladium Catalyzed Alkoxy/Aryloxy Carbonylation," Tetrahedron Letters; 1992. 33(38): 5499-5502.
Ghofrani et al., "Acute effects of riociguat in borderline or manifest pulmonary hypertension associated with chronic obstructive pulmonary disease," Pulm Gire. Jun. 2015;5{2):296-304.
Ghofrani et al., "Interventional and pharmacological management of chronic thromboembolic pulmonary hypertension," Respiratory Medicine, Elsevier, Amsterdam, NL, vol. 177, Jan. 6, 2021, 12 pages.
Ghofrani et al., "New therapeutic options in the treatment of pulmonary arterial hypertension," Herz, 2005, 30(4): 296-302.
Ghosh et al., "An inherent dysfunction in soluble guanylyl cyclase is present in the airway of severe asthmatics and is associated with aberrant redox enzyme expression and compromised NO-cGMP signaling," in Redox Biology 39 (2021) 101832, pp. 1-13.
Ghosh, "Studies on oxygen heterocycles: Part-1: Acid catalysed and photochemical reactions of some aryldiazoketones," Tetrahedron, 1989, 45(5):1441-1446.
Glaab et al., "Repetitive measurements of pulmonary mechanics to inhaled cholinergic challenge in spontaneously breathing mice,". J Appl Physiol 2004; 97:1104-1111.
Grasmeijer et al. "Recent advances in the fundamental understanding of adhesive mixtures for inhalation," Curr Pharm Des. 2015; 21(40): 5900-14.
Greene, "The Role of Protective Groups In Organic Synthesis," Fifth Edition, Wiley, New York, 2014, 17 pages.
Gur, S. et al., "Exploring the Potential of NO-Independent Stimulators and Activators of Soluble Guanylate Cyclase for the Medical Treatment of Erectile Dysfunction", Current Pharmaceutical Design, 2010, vol. 16, No. 14, 1619-1633.
Healy et al., "Dry powders for oral inhalation free of lactose carrier particles," Advance Drug Delivery reviews 75, (2014), pp. 32-52.
Hoenicka, "Purified soluble guanylyl cyclase expressed in a baculovirus/Sf9 system: stimulation by YC-1, nitric oxide, and carbon monoxide," J Mol Med (Berl); Jan. 1999; 77(1): 14-23.
Hoeper et al., "Diagnosis, Assessment, and Treatment of Non-Pulmonary Arterial Hypertension Pulmonary Hypertension," Journal of the Am. College of Cardiology, 2009, 54(1): S85-S96.
Horig et al., "From bench to clinic and back: Perspective on the 1st IQPC Translational Research conference," Dec. 2004, Journal of Translational Medicine, 2(1): 44, 8 pages.
Hoymann et al., "Measurement of lung function in rodents in vivo," Methods in Pulmonary Research: Birkhäuser Basel; 1998: 1-28.
Hoymann et al., "New developments in lung function measurements in rodents," Exp 5 Toxicol Pathol 2006; 57 Suppl 2: 5-11.
Hoymann, "Lung function measurements in rodents in safety pharmacology studies," Front Pharmacol. Aug. 28, 2012 (3), 156: 1-11.
Humbert et al., "Cellular and Molecular Pathobiology of Pulmonary Arterial Hypertension," Journal of The Am. College of Cardiology, 2004, 43(12): S13-S24.
Humbert et al., "The 4th World Symposium on Pulmonary Hypertension," Journal of the Am. College of Cardiology, 2009, 54(1): S1-S2.
Ito et al., "Current Drug Targets and Future Therapy of Pulmonary Arterial Hypertension," Current Med. Chemistry, 2007, 14: 719-733.
Jindal N. et al., "Inhalation of nitric oxide in acute respiratory distress syndrome," J Lab Clin Med Jul. 2000; 136: 21-28.
Johnson E. et al., "Acute lung injury: epidemiology, pathogenesis, and treatment," J Aerosol Med Pulm Drug Deliv. Aug. 2010; 23(4): 243-252.
Kinnunen et al., "An Investigation into the Effect of Fine Lactose Particles on the Fluidization Behaviour and Aerosolization Performance of Carrier-Based Dry Powder Inhaler Formulations", AAPS Pharmscitech, vol. 15, No. 4, Apr. 23, 2014, 12 pages.
Kou et al., "Physico-chemical aspects of lactose for inhalation," Adv. Drug Del. Reviews 64 (2012), 220-232.
Liu et al., "(R )-and (S)-5,6, 7,8-Tetrahydro-1-hydroxy-N,N-dipropyl-9H-benzocyclohepten-8-ylaminen. Stereoselective Interactions with 5-HT1A Receptors in the Brain," J. Med. Chem., 1989, 32: 2311-2318.
Maggie et al., "A New Pathway to Airway Relaxation: Targeting the "Other Cyclase" in Asthma" American Journal of Respiratory Cell and Molecular Biology vol. 62, No. 1, Jan. 2020, 2 pages.
Martin, "Structure of Cinaciguat (BAY 58-2667) Bound to Nostoc H-NOX Domain Reveals Insights into Heme-mimetic Activation of the Soluble Guanylyl Cyclase," Journal of Biol. Chem., Jul. 16, 2010, 285(29): 22651-22657.
Montani et al., "Updated clinical classification of pulmonary hypertension," Pulmonary Circulation, Disease and their treatment, Third Edition, Hodder Arnold Pub., Peacock et al (Eds.), 2011, 197-206.
Moon et al., "Delivery Technologies for Orally Inhaled Products: an Update", AAPS PharmSciTech., Feb. 19, 2019; 20(3):117, pp. 1-17.
Munzel et al., "Targeting heme-oxidized soluble guanylate cyclase: solution for all cardiorenal problems in heart failure?" Hypertension 2007; 49: 974-976.
Nossaman et al., "Stimulators and Activators of Soluble Guanylate Cyclase: Review and Potential Therapeutic Indications," Critical Care Research and Practice, 2012, 290805: 1-12.
Pettit et al., "Synthesis of the 6-and 7-Hydroxy-5,8-dioxocarbostyrils," Journal of Organic Chemistry, Mar. 1968, 33(3): 1089-1092.
Pilcer et al., "Lactose characteristics and the generation of the aerosol," Adv Drug Del Reviews 64 (2012), 233-256.
Raabe et al., "Regional Deposition of Inhaled Monodisperse Coarse and Fine Aerosol Particles in Small Laboratory Animals," The Annals of Occupational Hygiene 1988; 32:53-63.
Rahaman et al., "Cytochrome b5 Reductase 3 Modulates Soluble Guanylate Cyclase Redox State and cGMP Signaling," Circ Res 2017; 121: 137-148.
Rosenzweig et al., "Emerging treatments for pulmonary arterial hypertension," Expert Opinion Emerging Drugs, 2006, 11(4): 609-619.
Sandner et al., "Discovery and development of sGC stimulators for the treatment of pulmonary hypertension and rare diseases," Nitric Oxide 2018; 77: 88-95.
Sandner et al., "Soluble guanylate cyclase stimulators and activators," Handbook Exp Pharmacol., 264, 2018, pp. 355-394.
Sandner P. et al., "Anti-fibrotic effects of soluble guanylate cyclase stimulators and activators: A review of the preclinical evidence," Respir Med. Jan. 2017: 122 Suppl: S1-S9.
Schafer, et al., "Failure is an option: learning from unsuccessful proof-of-concept trials," Drug Discov. Today. Nov. 2008; 13(21-22): 913-916.
Schmidt et al., "NO-and Haem-Independent Soluble Guanylate cyclase Activators," Handbook of Experimental Pharmacology, 2009; 191: 309-339.
Schuhmacher et al., "High-throughput determination of the free fraction of drugs strongly bound to plasma proteins," J Pharm Sci., Apr. 2004; 93(4): 816-30.
Shekunov et al., "Particle size analysis in pharmaceutics: Principles, Methods and Applications," Pharm. Res. 2007, 24 (2), S203-S227.
Simonneau et al., "Haemodynamic definitions and updated clinical classification of pulmonary hypertension", European Respiratory Journal, 2019; 53: 1801913, pp. 1-13.
Singh et al., "Plethysmography and impulse oscillometry assessment of tiotropium and ipratropium bromide; a randomized, double-blind, placebo controlled, cross-over study in healthy subjects," Br. Journal Clin Pharmacol, 2006, 61:4, 398-404.

(56) References Cited

OTHER PUBLICATIONS

Stachel et al., "Discovery of pyrrolidine-based b-secretase inhibitors: Lead advancement through conformational design for maintenance of ligand binding efficiency," Bioorganic Med. Chem. Letters, 2012, 22: 240-244.
Stasch et al., "NO-and Haem-Independent Activation of Soluble Guanylyl Cyclase: Molecular Basis and Cardiovascular Implications of a New Pharmacological Principle," British Journal of Pharmacology, 2002, Bd. 136 (5): 773-783.
Stasch et al., "Renal effects of soluble guanylate cyclase stimulators and activators: a review of the preclinical evidence," Current Opinions in Pharmacology (2015) 21: 95-104.
Stasch et al., "Targeting the Heme-Oxidized Nitric Oxide Receptor for Selective Vasodilation of Diseased Blood Vessels," J. Clin. Invest., Sep. 2006, 116(9): 2552-2561.
Stasch J et al., "Soluble guanylate cyclase as an emerging therapeutic target in cardiopulmonary disease," Circulation, May 24, 2011; 123(20): 2263-73.
Stolz et al., "A randomised, controlled trial of bosentan in severe COPD," European Resp. Journal, 2008 32: 619-628.
Takeuchi et al., "Rhodium Complex-Catalyzed Desilylative Cyclocarbonylation of 1-Aryl-2-(trimethylsilyl)acetylenes: A New Route to 2,3,-Dihydro-1H-inden-1-ones," J. Org. Chem. 1993; 58(20): 5386-5392.
Vanejevs et al., "Positive and Negative Modulation of Group I Metabotropic Glutamate Receptors," Journal Med. Chem., 2008, 51: 634-647.
Voswinckel et al., Favorable effects of inhaled Treprostinil in severe pulmonary hypertension, Journal of American College of Cardiology vol. 48, No. 8, Oct. 17, 2006: 1672-81.
White et al., "Soluble Guanylate Cyclase Agonists Induce Bronchodilation in Human Small Airways," Am J Respir Cell Mol Biol vol. 62, Issue 1, Jan. 2020, pp. 43-48.
Witte et al., "Experimental heart failure in rats: effects on cardiovascular circadian rhythms and on myocardial 13-adrenergic signaling," 2000, 47: 350-358.
Wood et al., "Smooth muscle cytochrome b5 reductase 3 deficiency accelerates pulmonary hypertension development in sickle cell mice," Blood Adv 2019; 3: 4104-4116.
Wunder et al., "A cell-based cGMP assay useful for ultra-high-throughput screening and identification of modulators of the nitric oxide/cGMP pathway," Anal Biochem. Apr. 2005; 339(1): 104-12.
Zhang et al., "Compilation of 222 drugs' plasma protein binding data and guidance for study designs," Drug Discovery Today 2012; 9-10(17): 475-485.

* cited by examiner

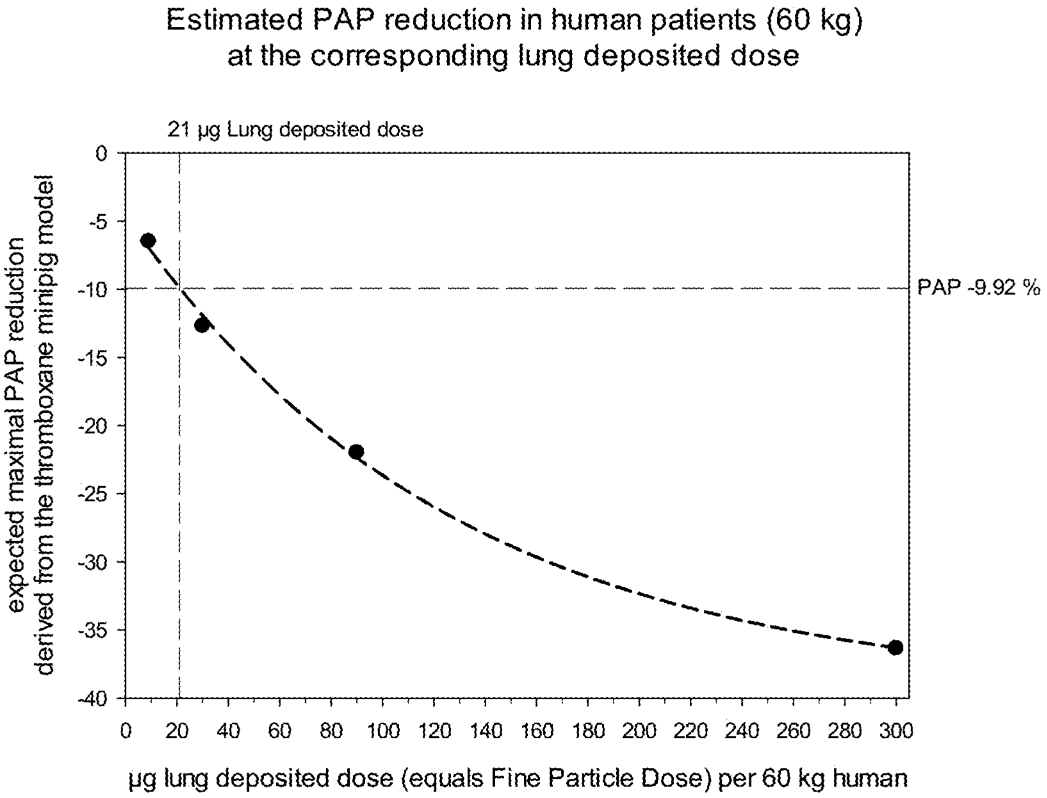
Fig. 2
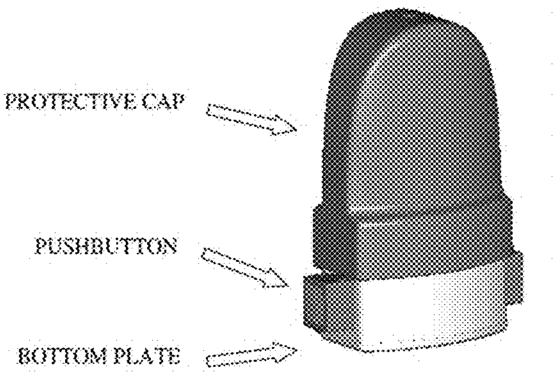
Fig. 3a: capsule based single-unit dose inhaler

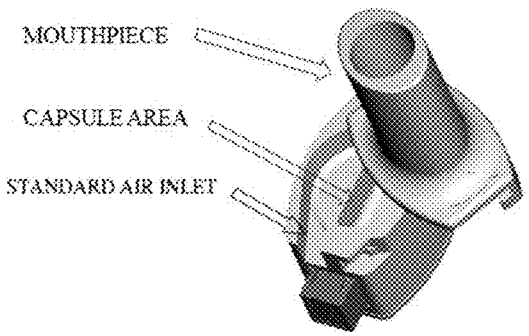
Fig. 3b: capsule based single-unit dose inhaler
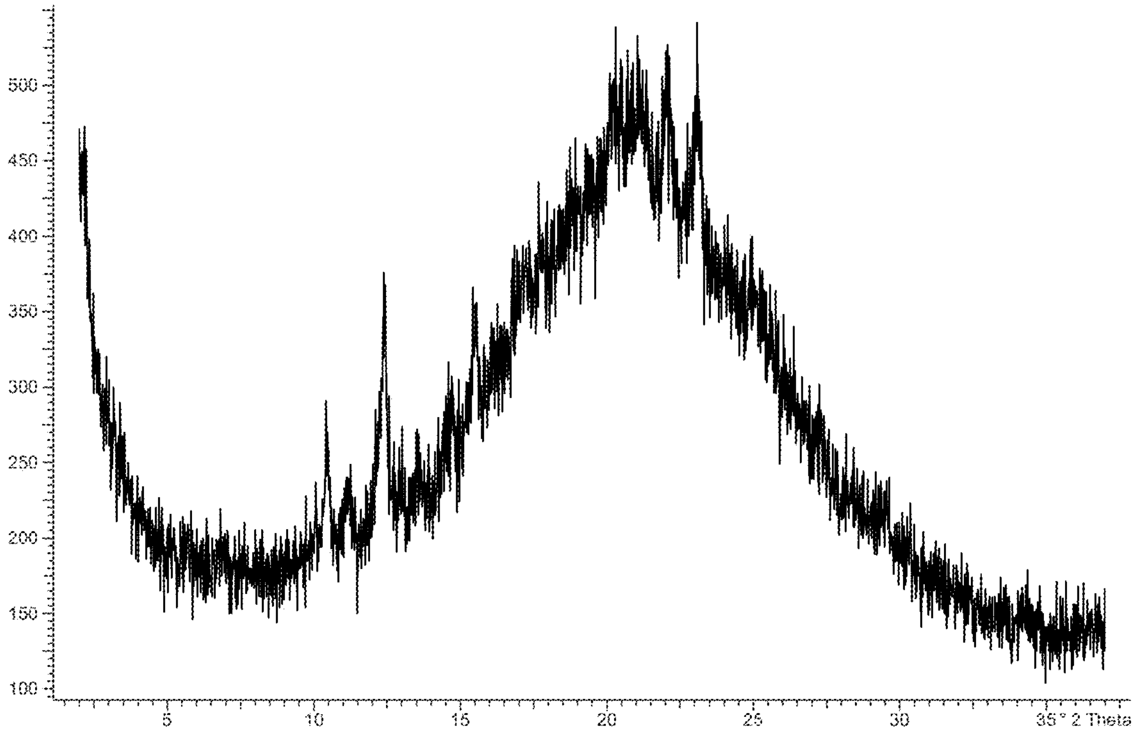
Fig. 4: X-Ray powder diffractogram of the amorphous residue build on salt screening experiments with L-arginine

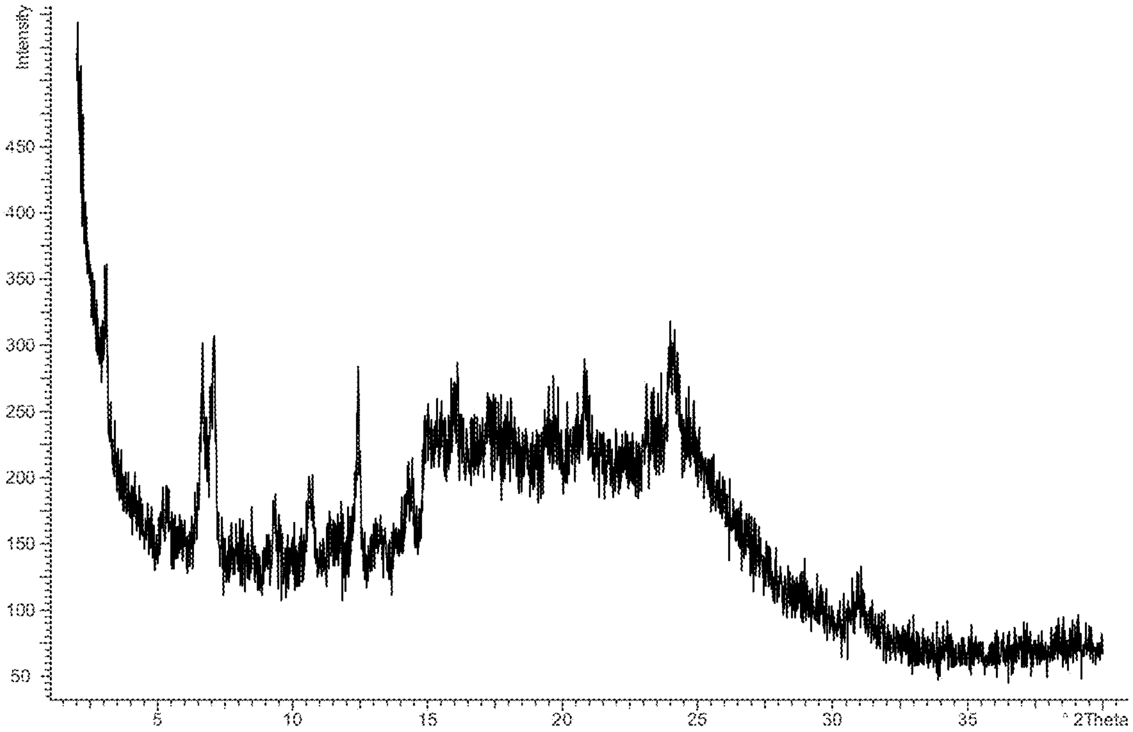
Fig. 5: X-Ray powder diffractogram of the Semihydrate, example 6a

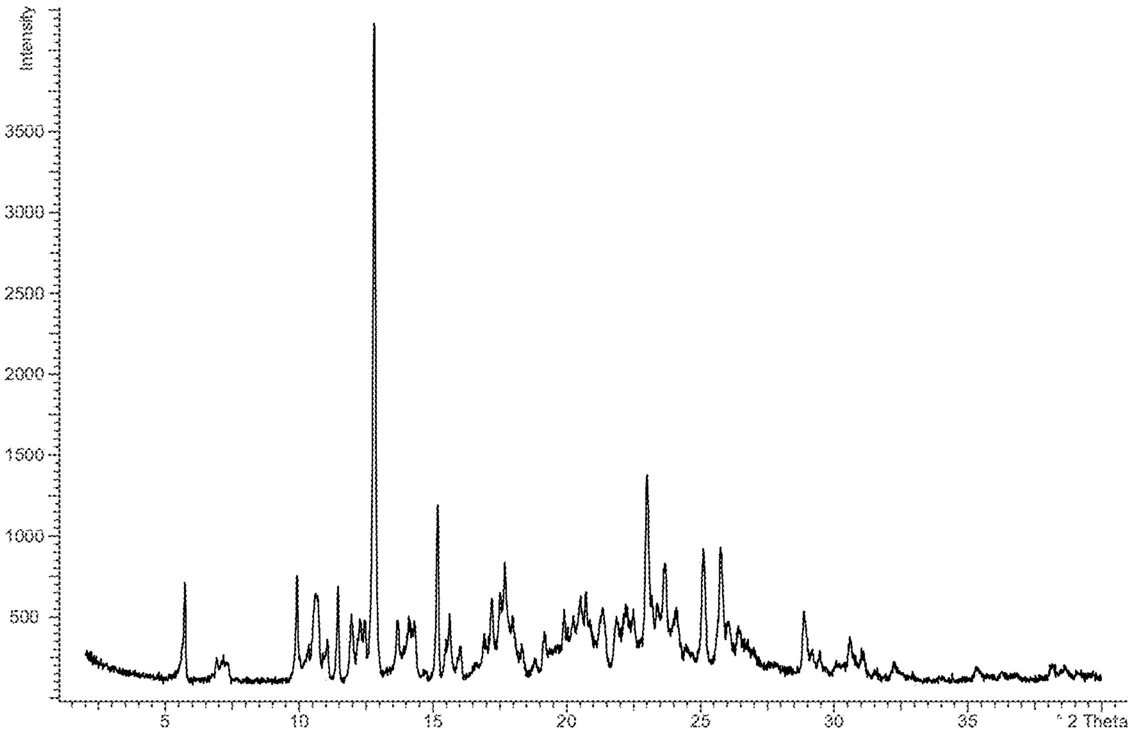
Fig. 6: X-Ray powder diffractogram of the Monohydrate I, example 6b
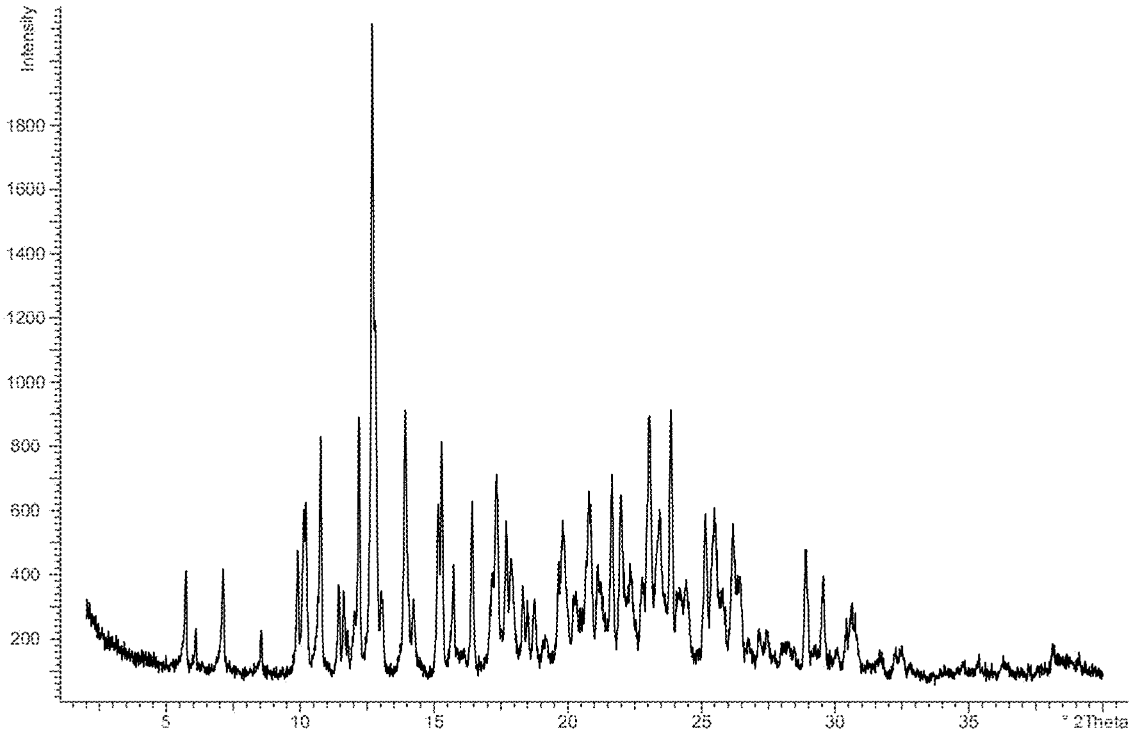
Fig. 7: X-Ray powder diffractogram of the Monohydrate II, example 6c

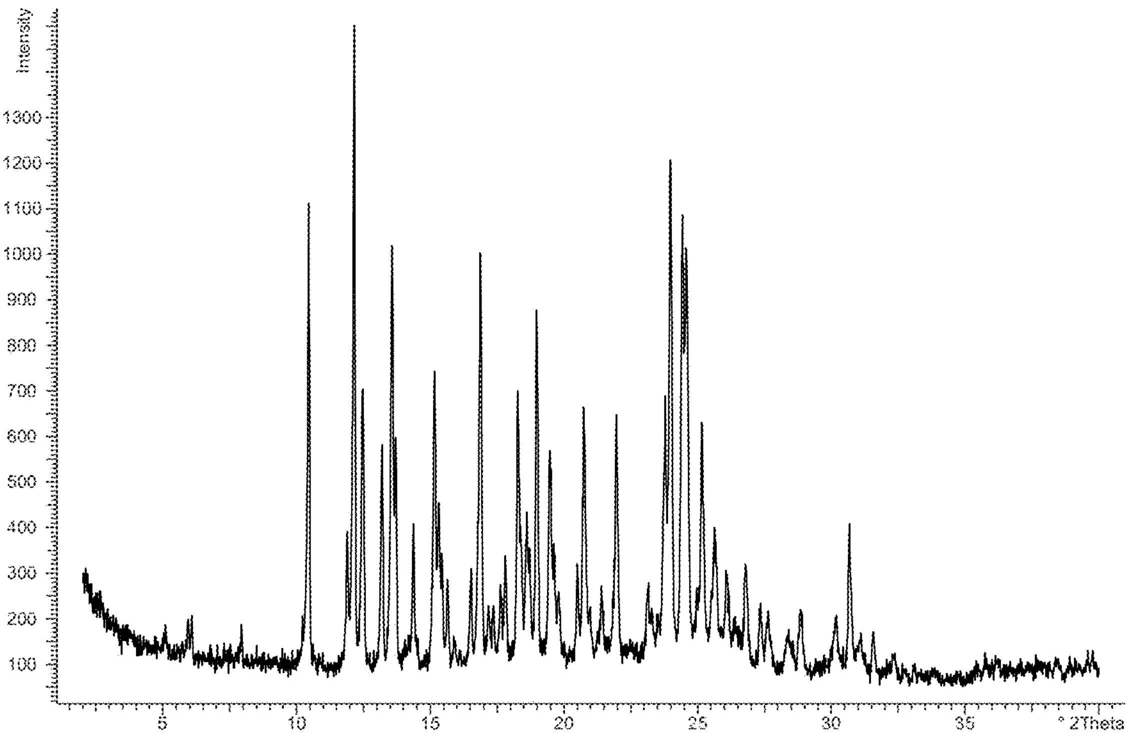
Fig. 8: X-Ray powder diffractogram of the 1,25-Hydrate, example 6d
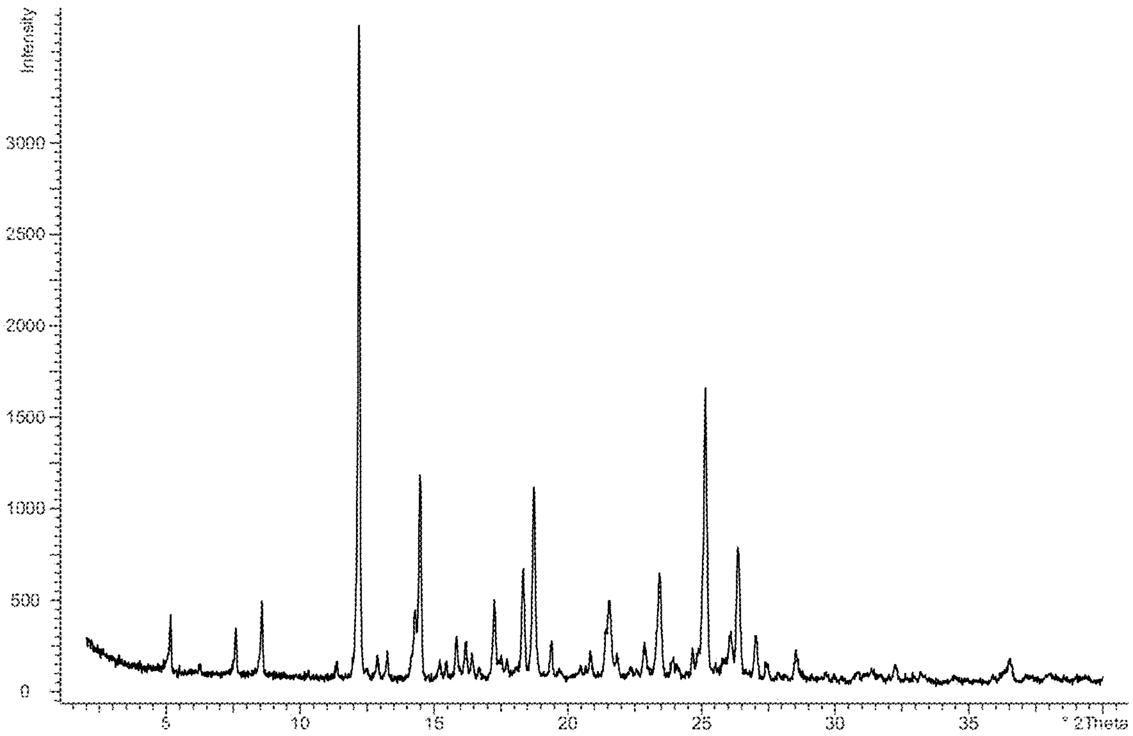
Fig. 9: X-Ray powder diffractogram of the Sesquihydrate, example 6e

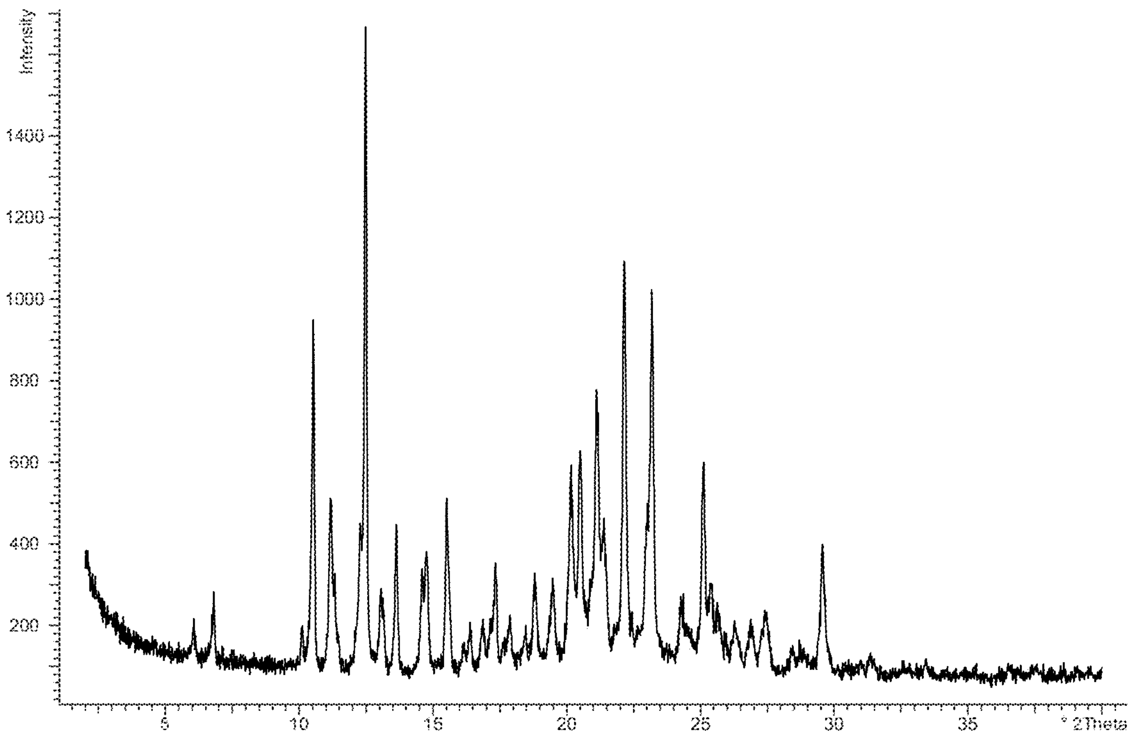
Fig. 10: X-Ray powder diffractogram of the Dihydrate, example 6f
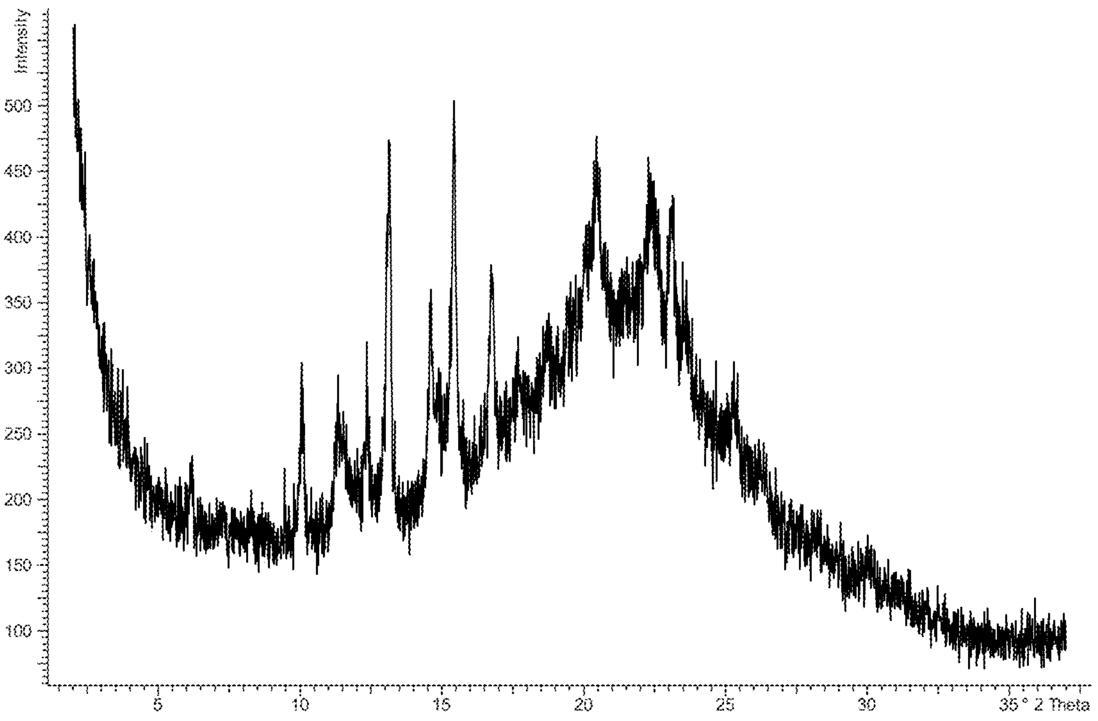
Fig. 10a: X-ray powder diffractogram of example 6f after drying

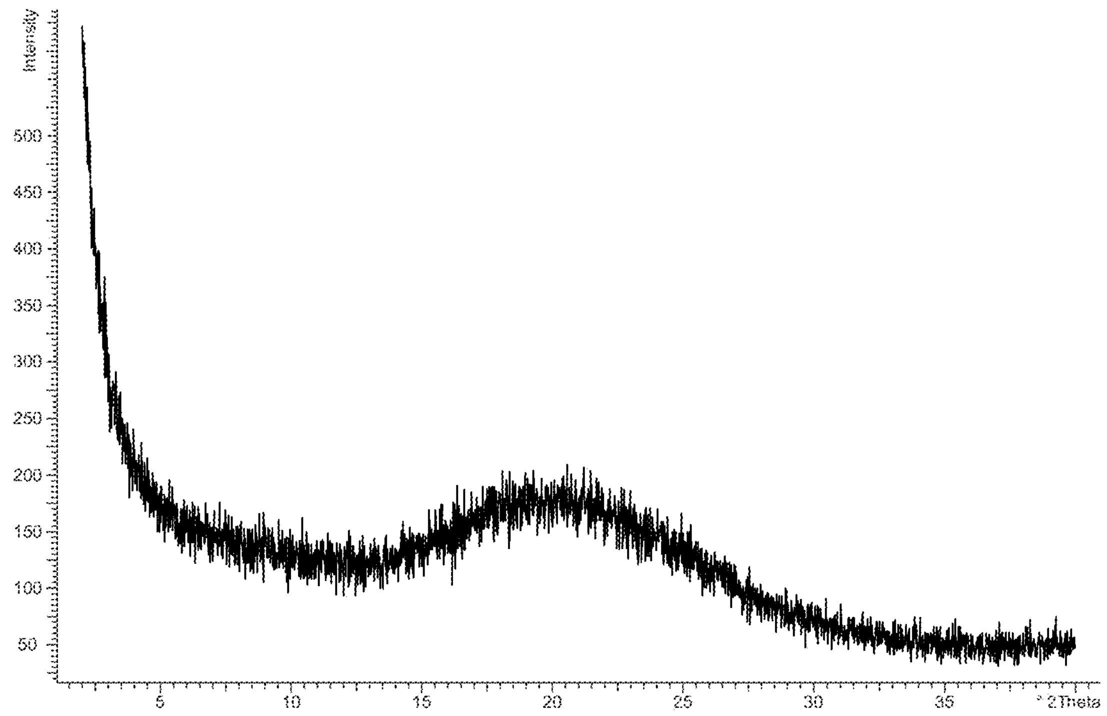
Fig. 11: X-Ray powder diffractogram of the amorphous form, example 6g
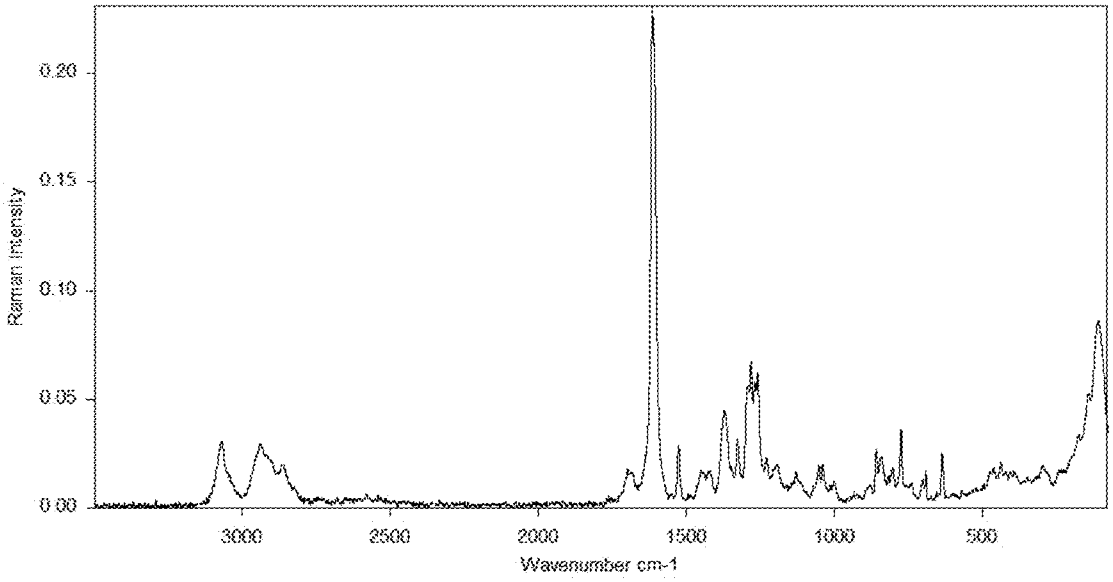
Fig. 12: Raman spectrum of the Semihydrate, example 6a

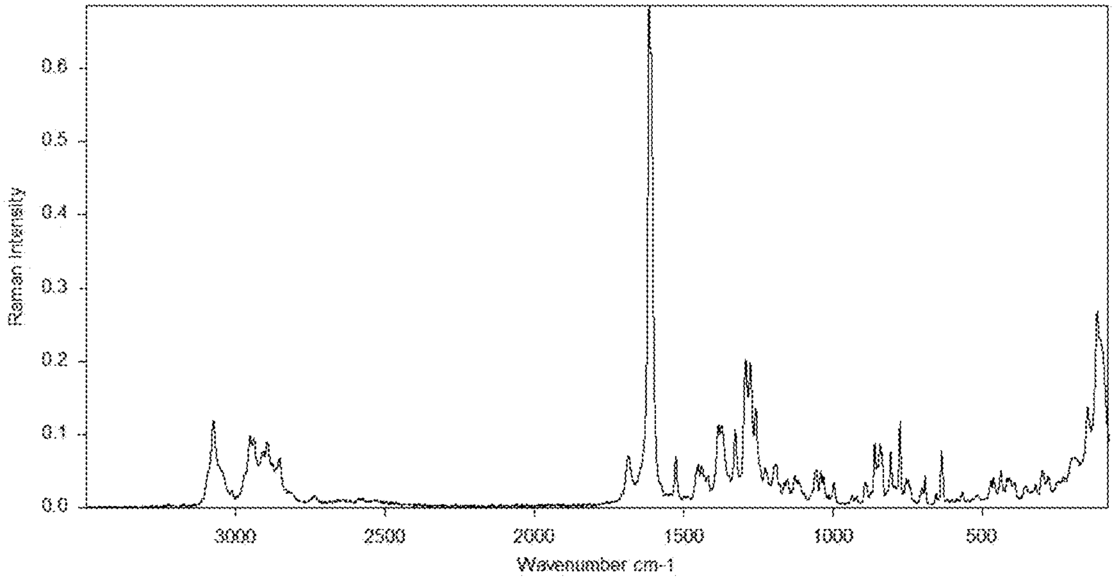
Fig. 13: Raman spectrum of the Monohydrate I, example 6b
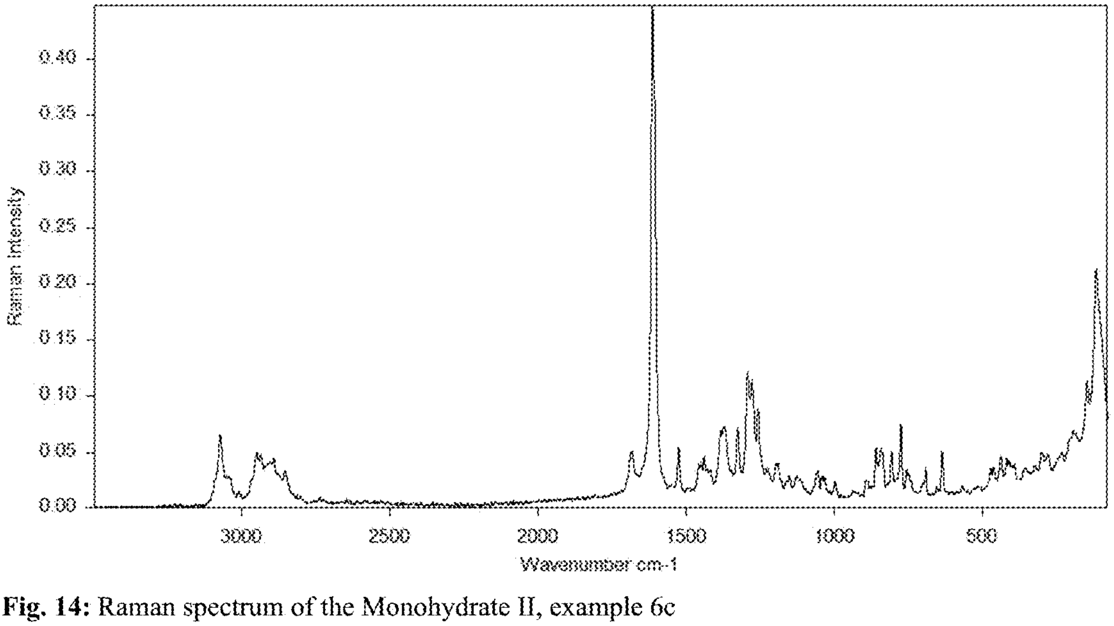
Fig. 14: Raman spectrum of the Monohydrate II, example 6c

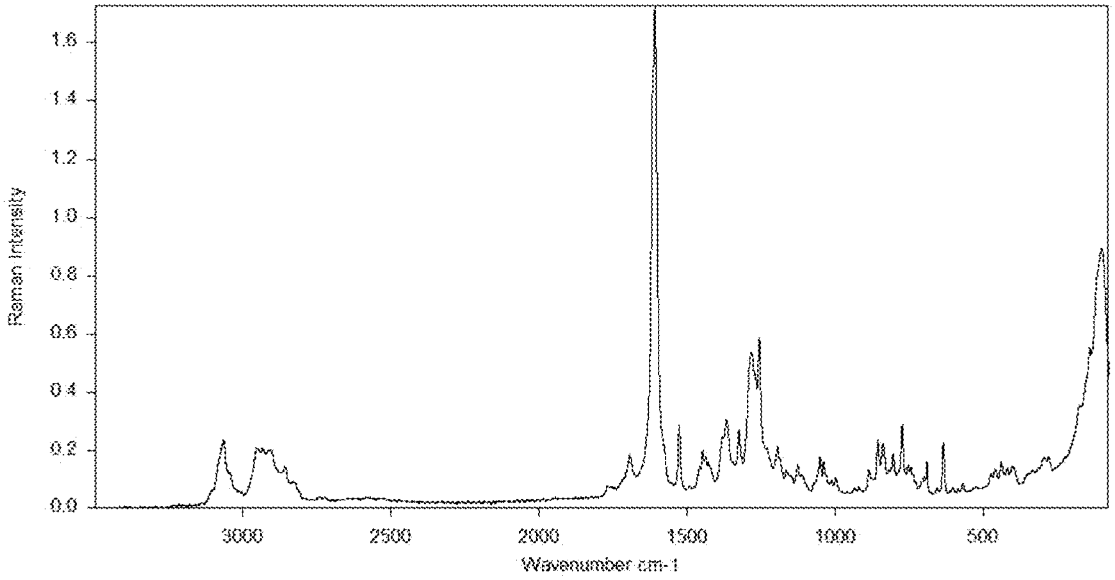
Fig. 15: Raman spectrum of the 1,25-Hydrate, example 6d
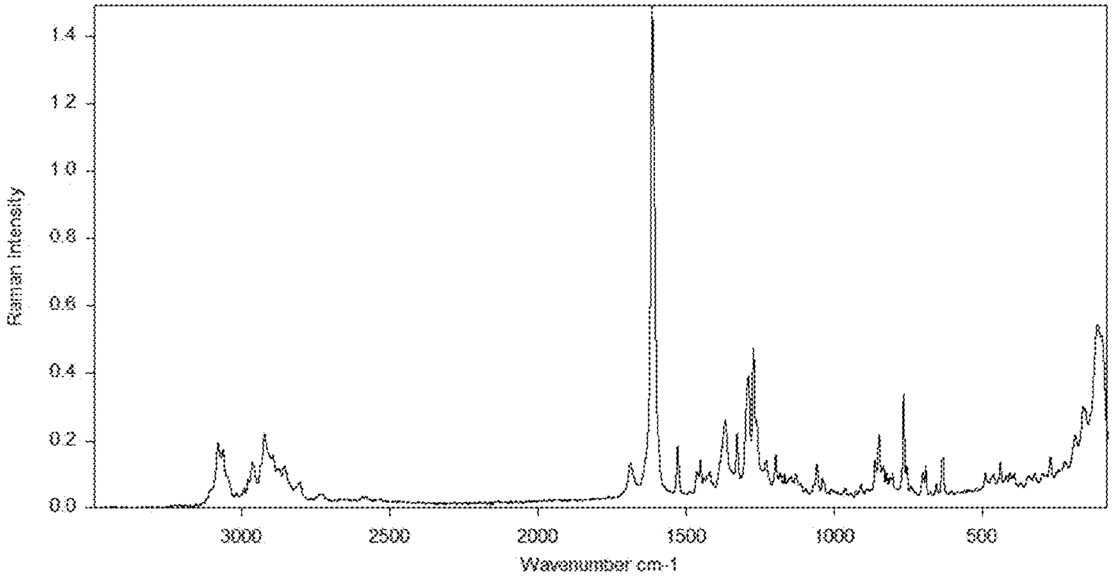
Fig. 16: Raman spectrum of the Sesquihydrate, example 6e

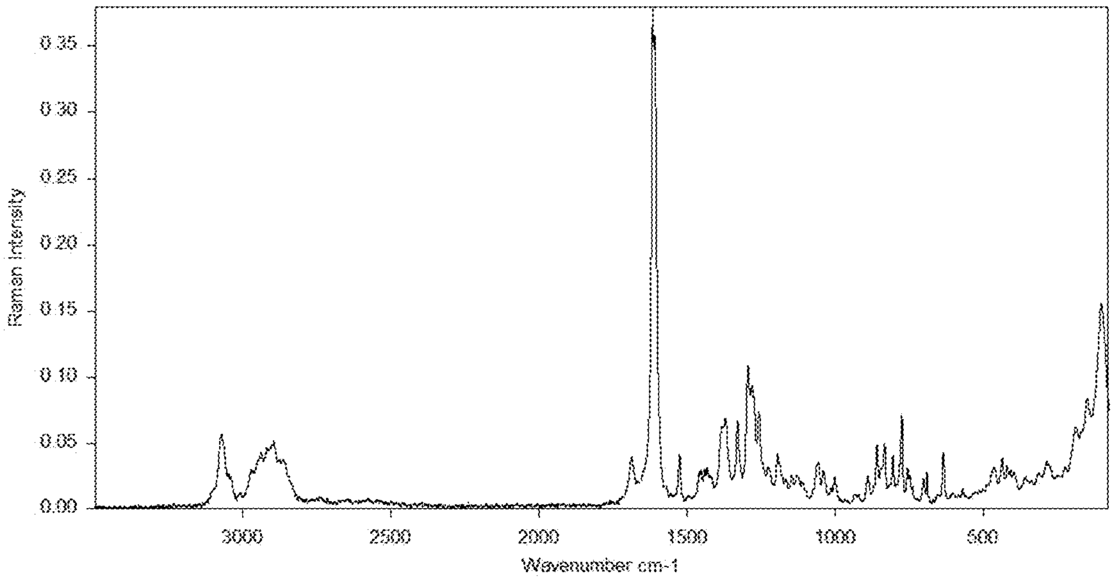
Fig. 17: Raman spectrum of the Dihydrate, example 6f
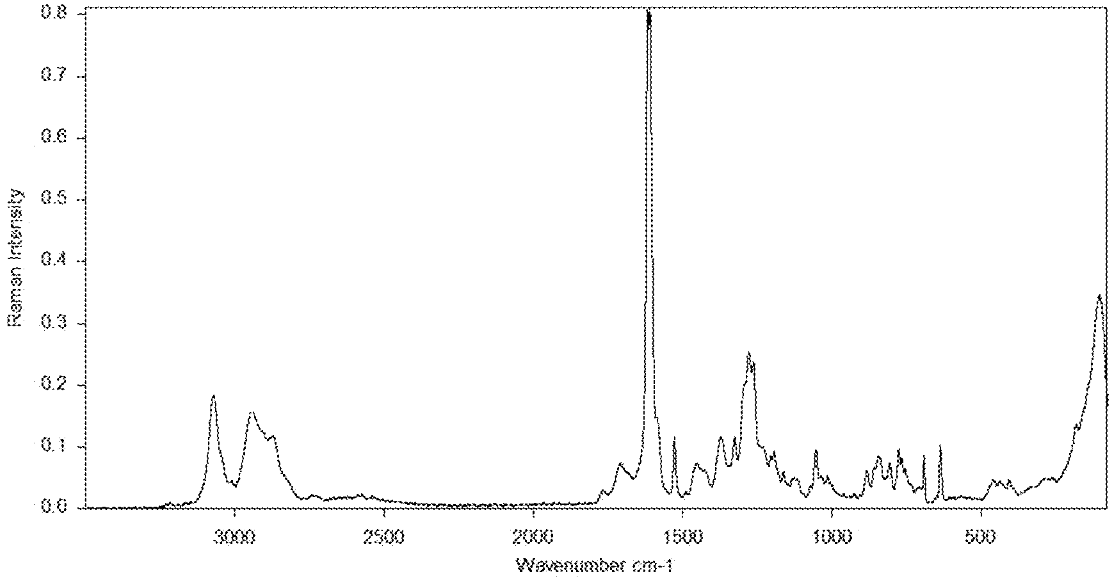
Fig. 18: Raman spectrum of the amorphous form, example 6g

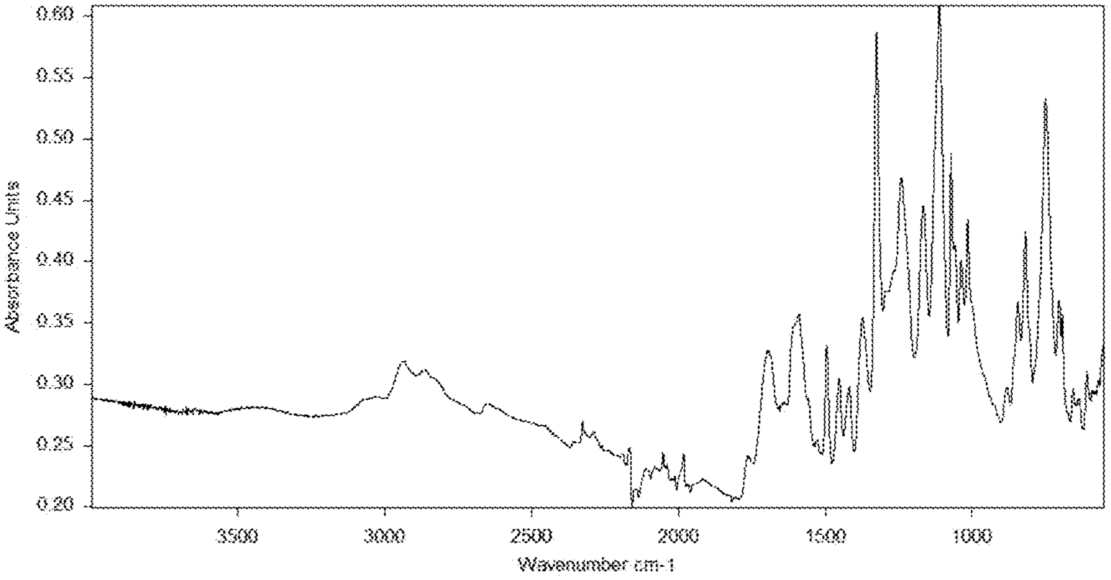
Fig. 19: IR spectrum of the Semihydrate, example 6a
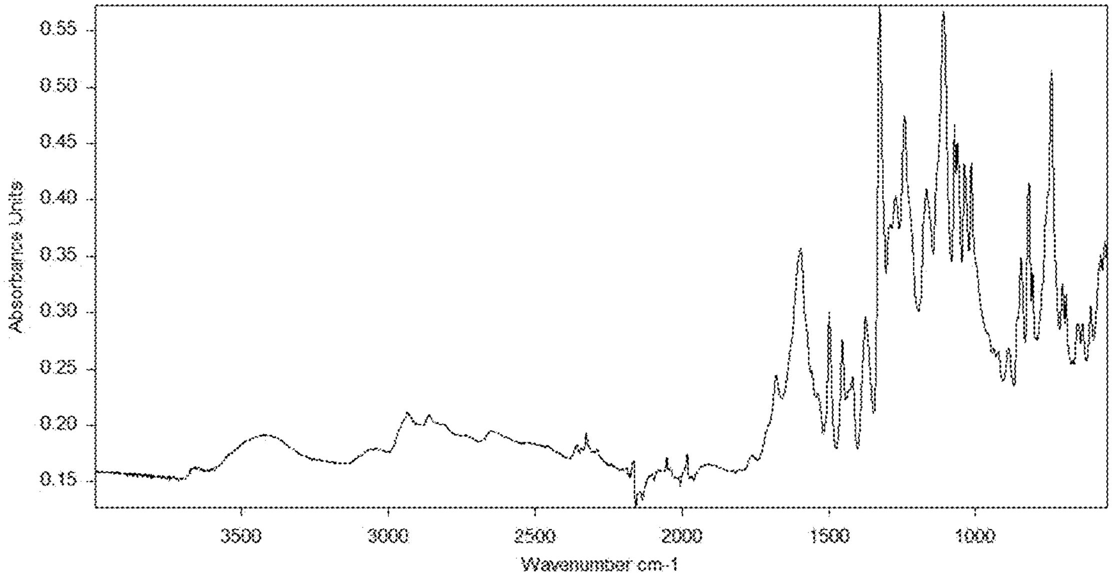
Fig. 20: IR spectrum of the Monohydrate I, example 6b

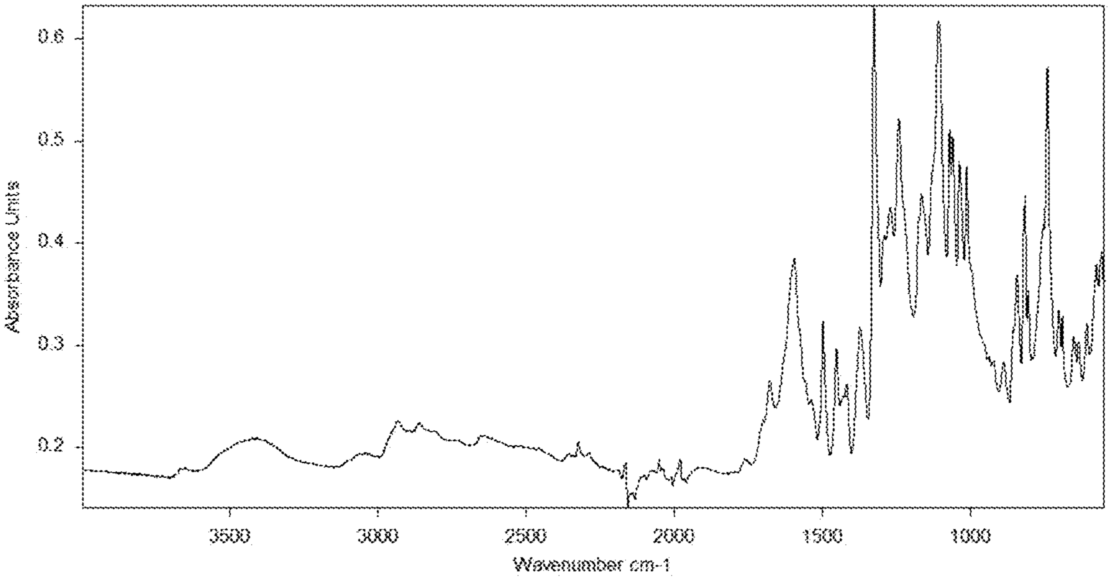
Fig. 21: IR spectrum of the Monohydrate II, example 6c
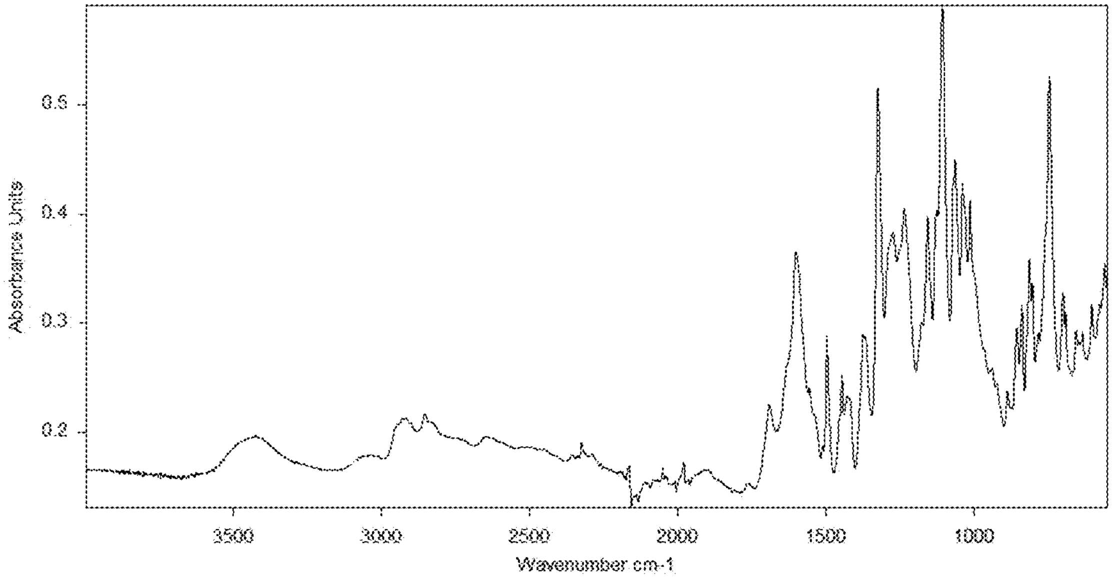
Fig. 22: IR spectrum of the 1,25-Hydrate, example 6d

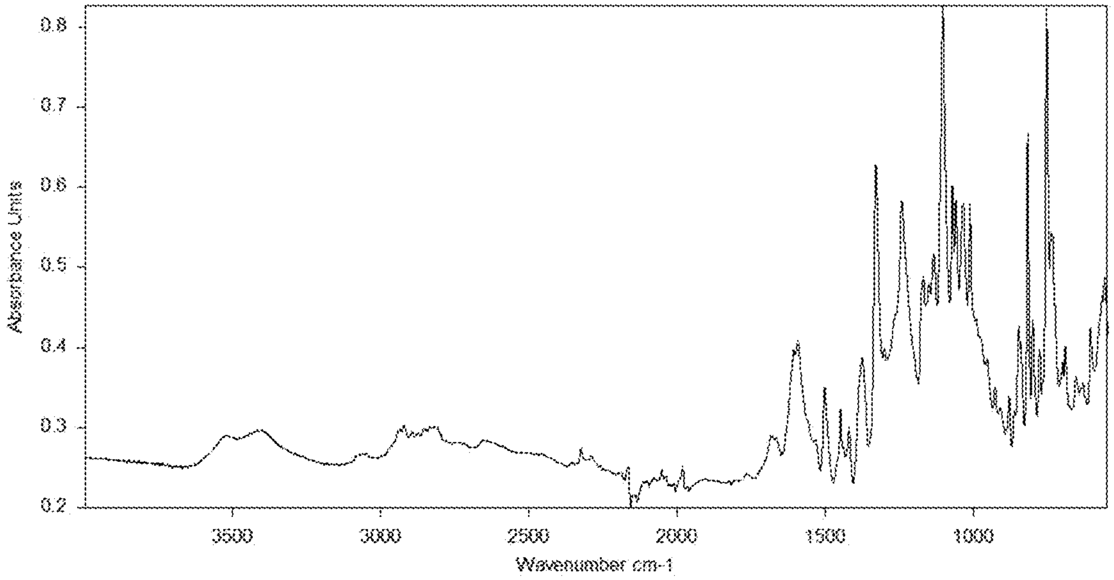
Fig. 23: IR spectrum of the Sesquihydrate, example 6e
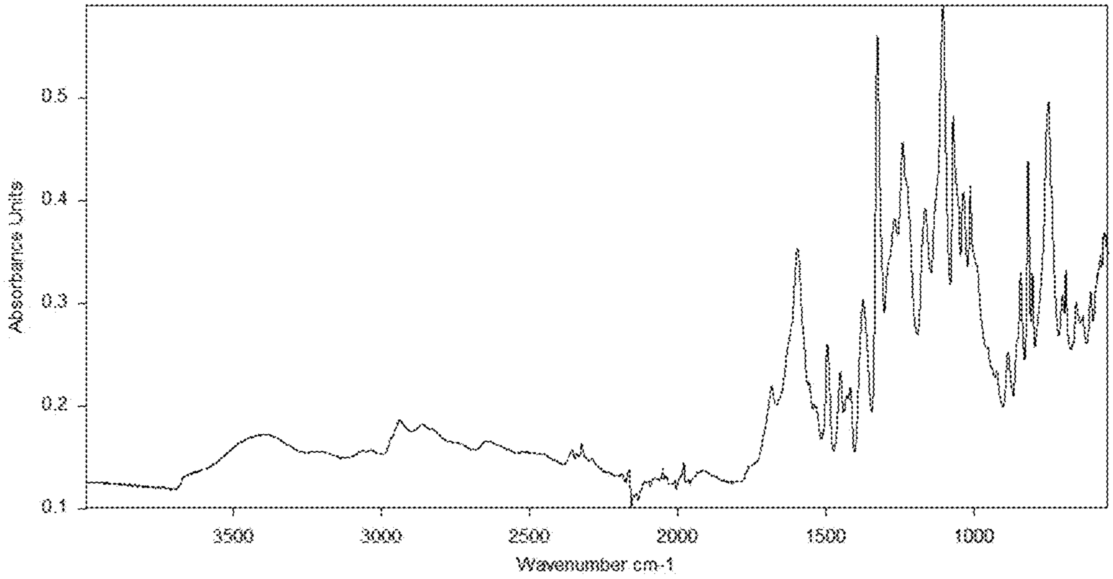
Fig. 24: IR spectrum of the Dihydrate, example 6f

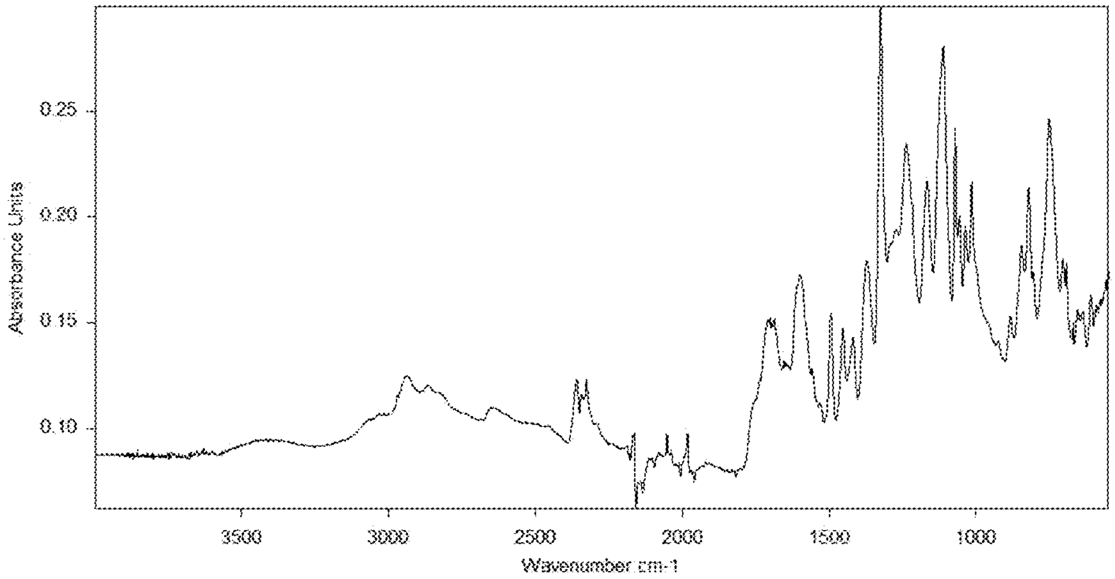
Fig. 25: IR spectrum of the amorphous form, example 6g
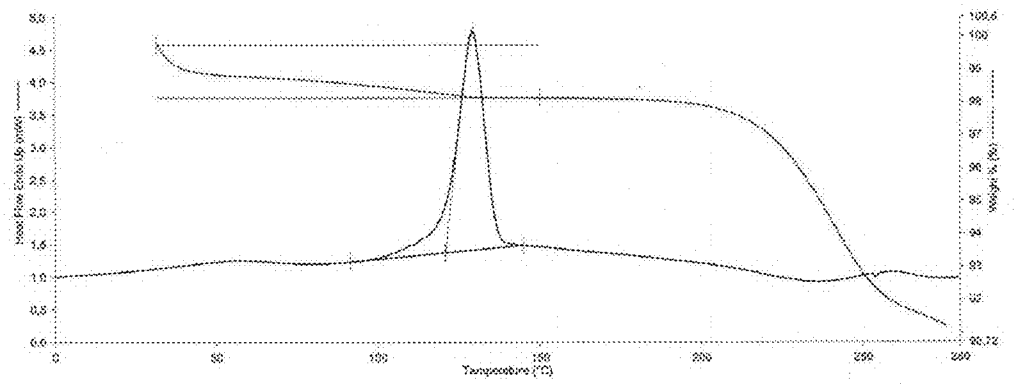
Fig. 26: DSC- and TGA-thermogram of the Semihydrate, example 6a

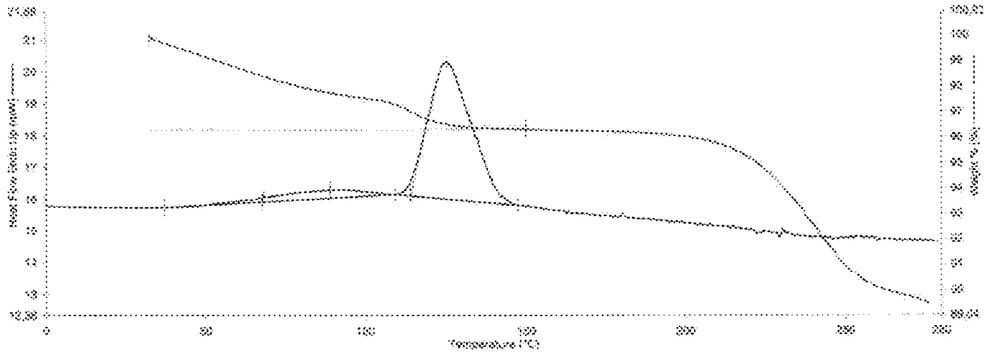
Fig. 27: DSC- and TGA-thermogram of the Monohydrate I, example 6b
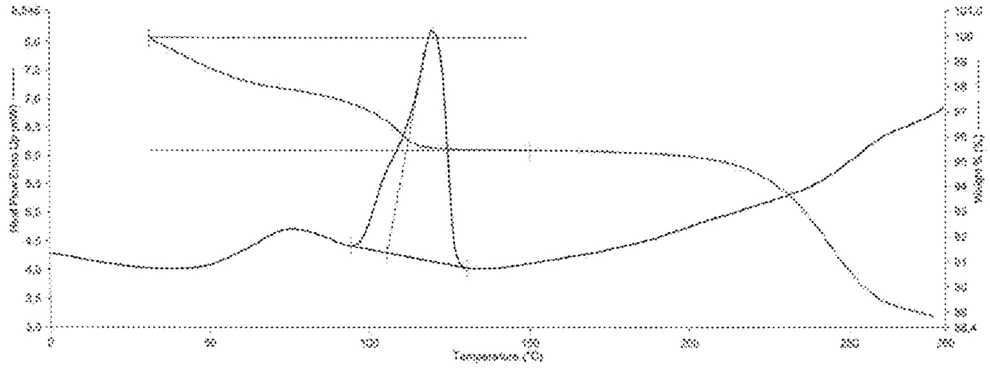
Fig. 28: DSC- and TGA-thermogram of the Monohydrate II, example 6c

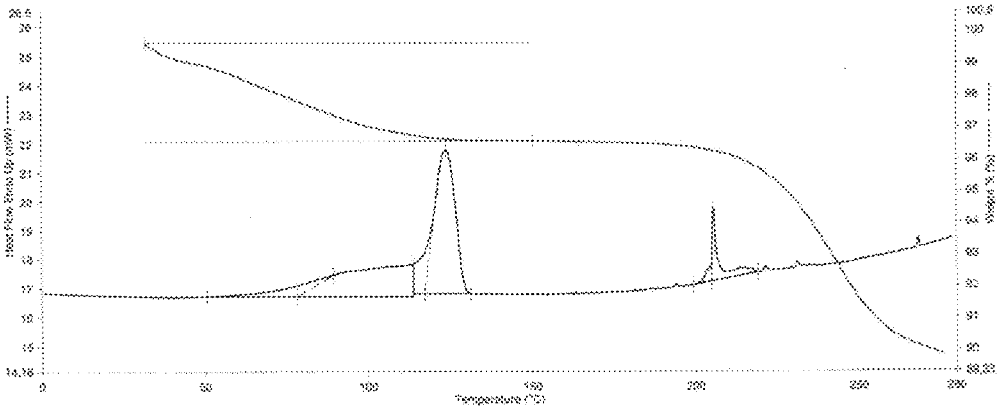
Fig. 29: DSC- and TGA-thermogram of the 1,25-Hydrate, example 6d
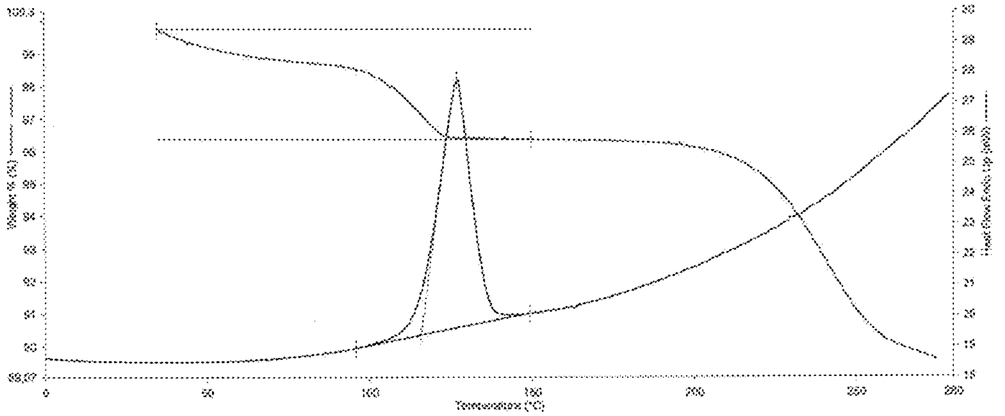
Fig. 30: DSC- and TGA-thermogram of the Sesquihydrate, example 6e

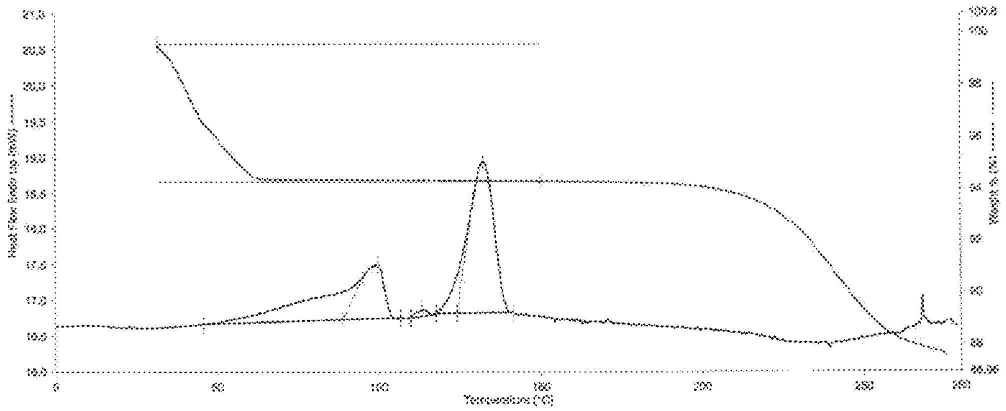
Fig. 31: DSC- and TGA-thermogram of the Dihydrate, example 6f
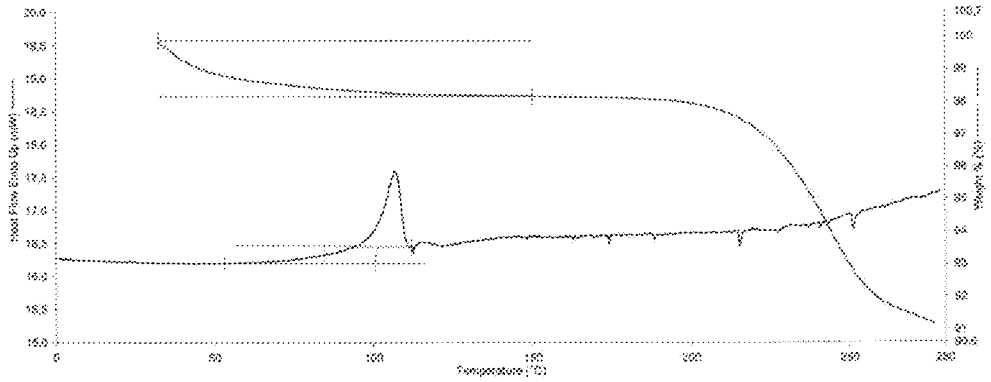
Fig. 32: DSC- and TGA-thermogram of the amorphous form, example 6g

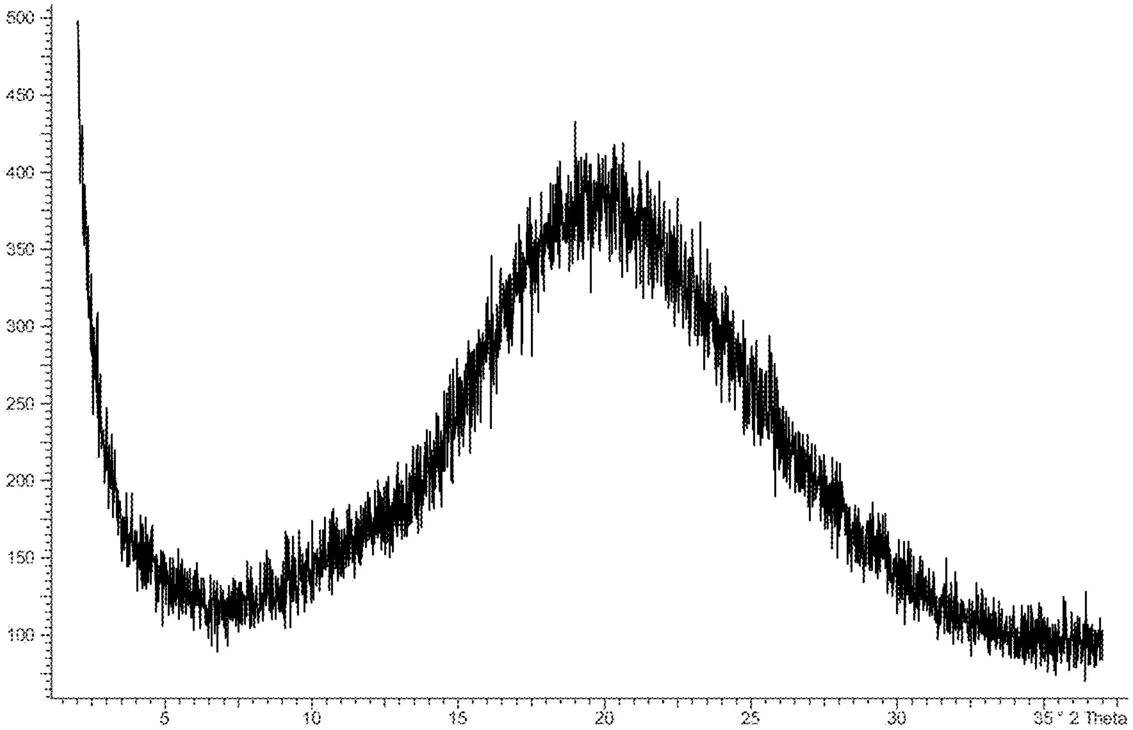
Fig. 33: X-Ray powder diffractogram of comparative example 11, amorphous form
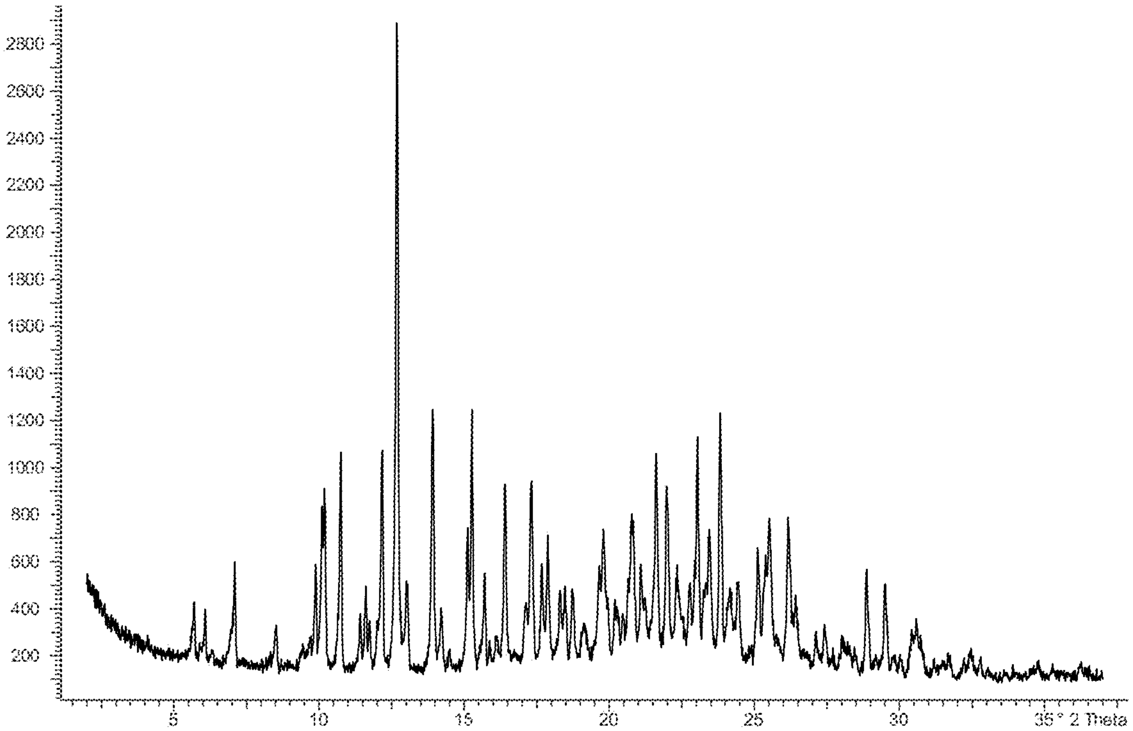
Fig. 34: X-Ray powder diffractogram of example 1, monohydrate II

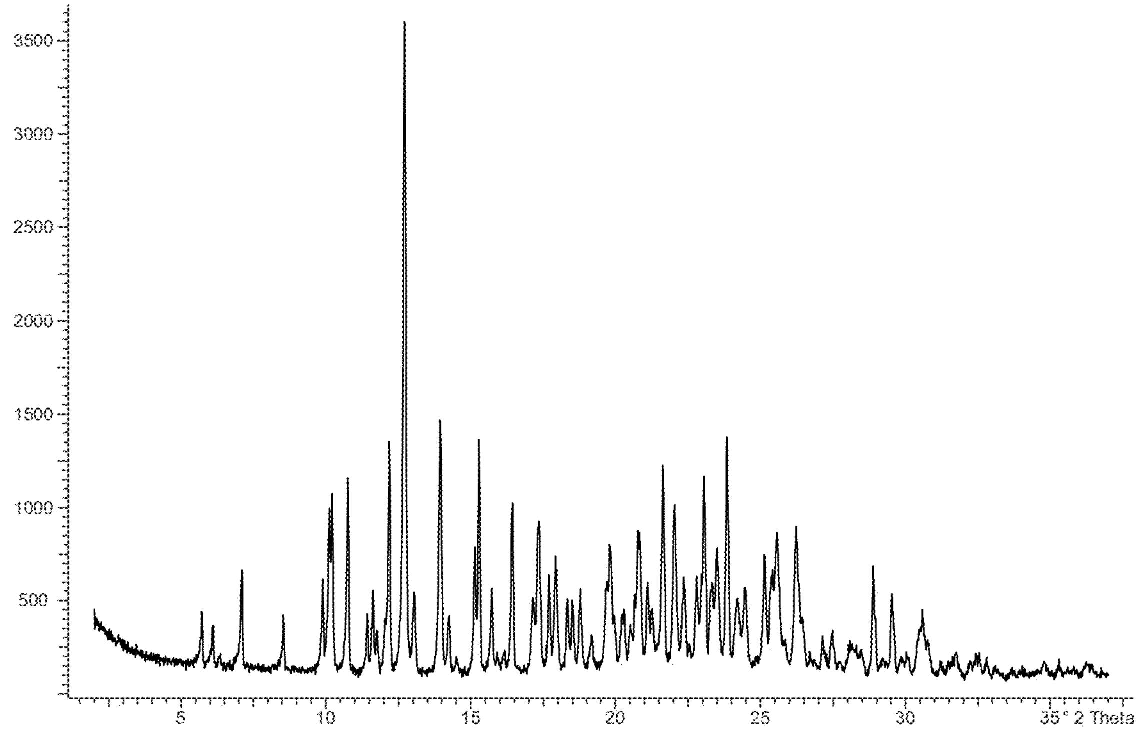
Fig. 35: X-Ray powder diffractogram of example 2 before micronization, monohydrate II
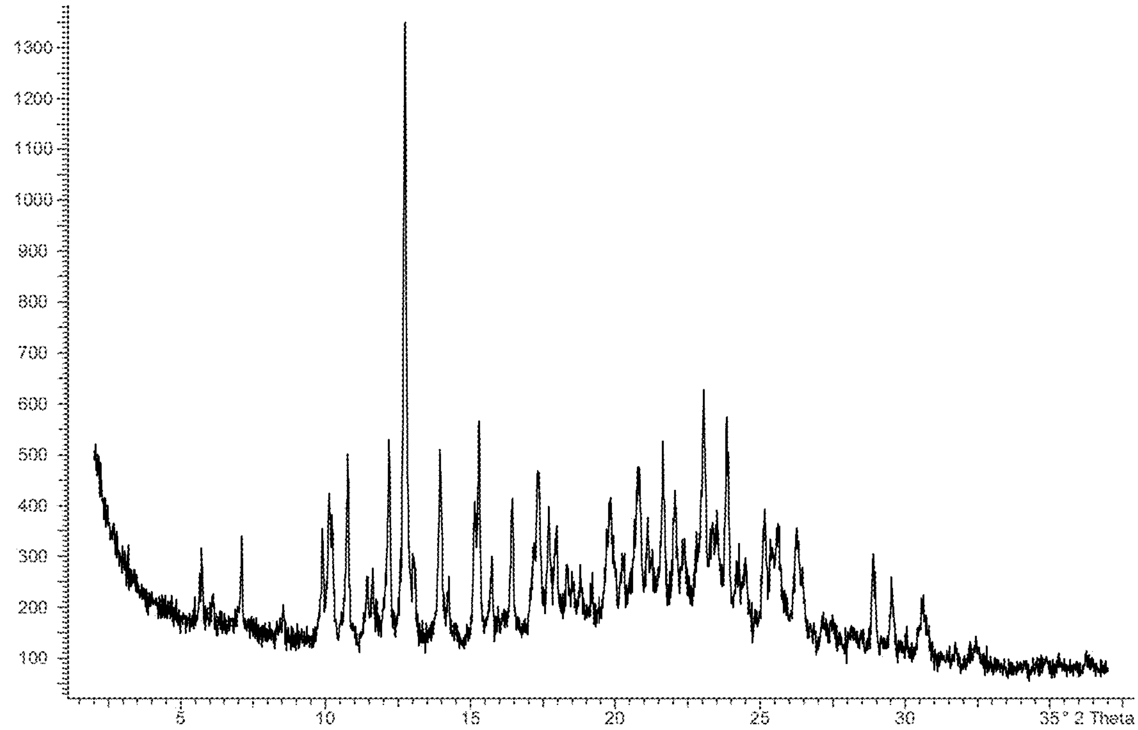
Fig. 36: X-Ray powder diffractogram of example 2 after micronization, monohydrate II, partial amorphization

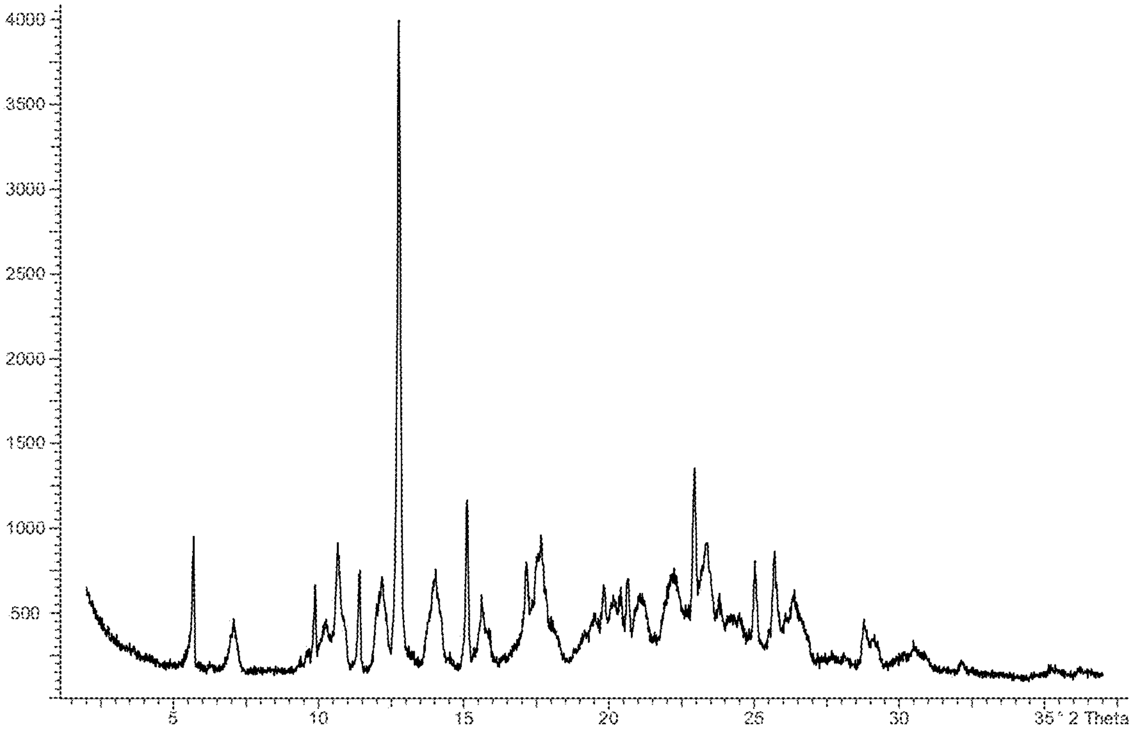
Fig. 37: X-Ray powder diffractogram of example 3, monohydrate I
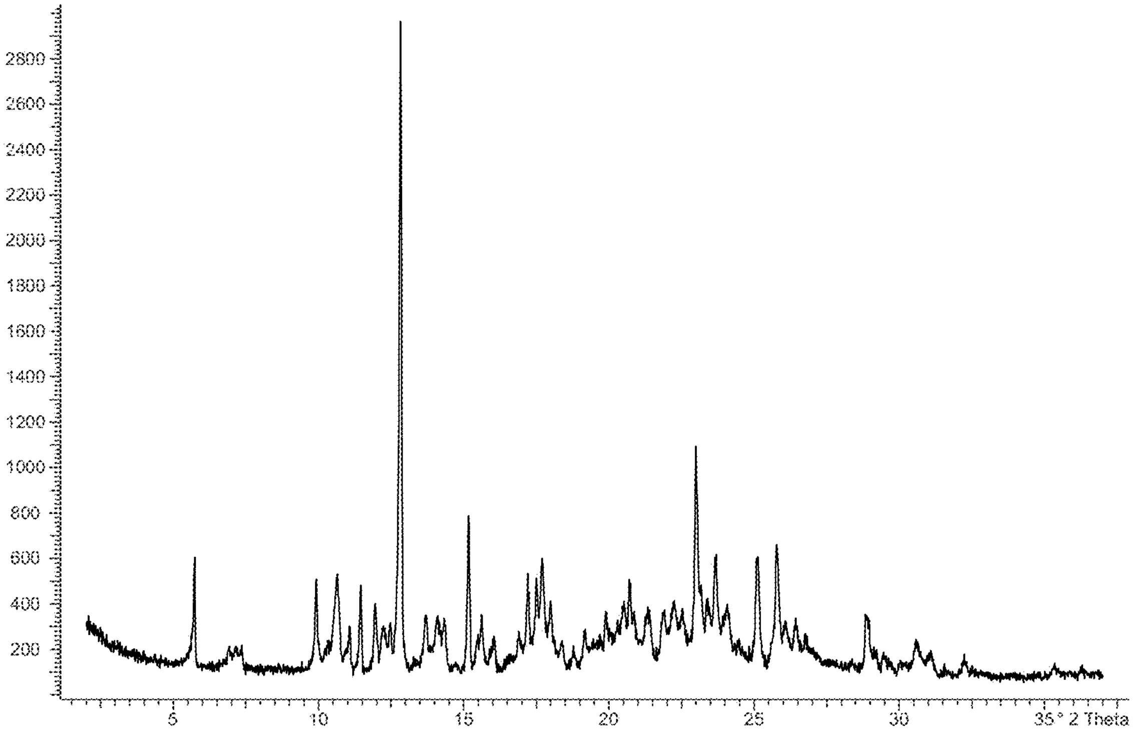
Fig. 38: X-Ray powder diffractogram of Example 4, monohydrate I

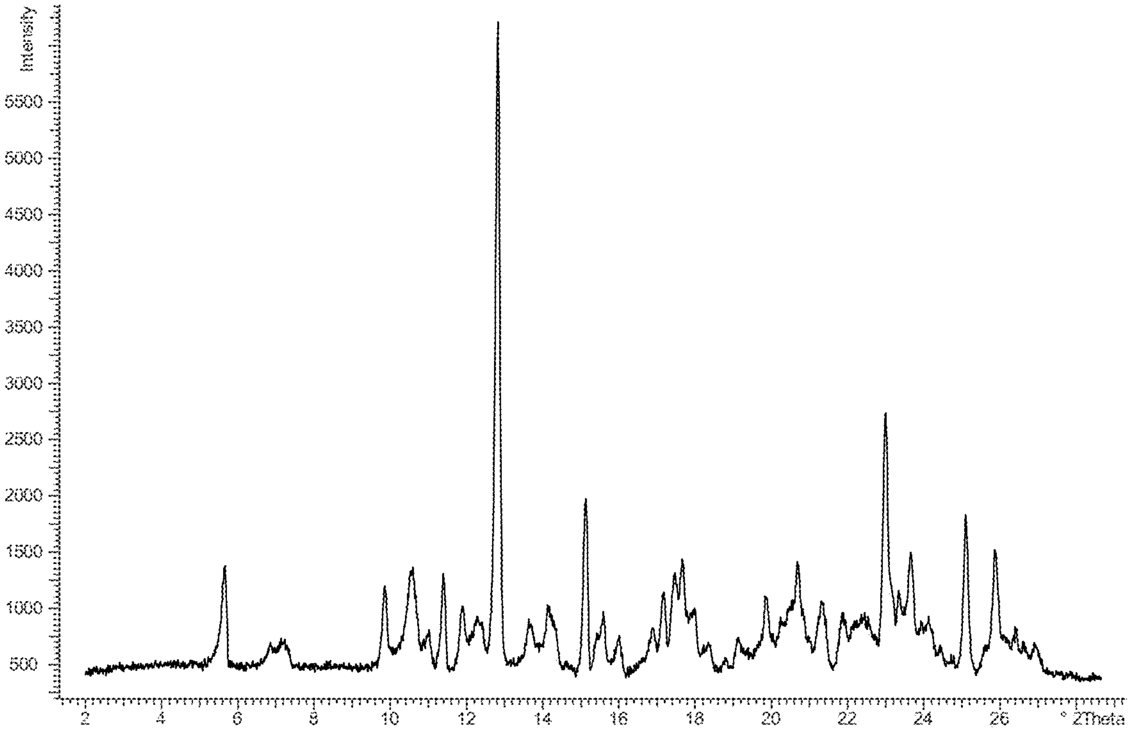
Fig. 39: X-Ray powder diffractogram of example 5, monohydrate I
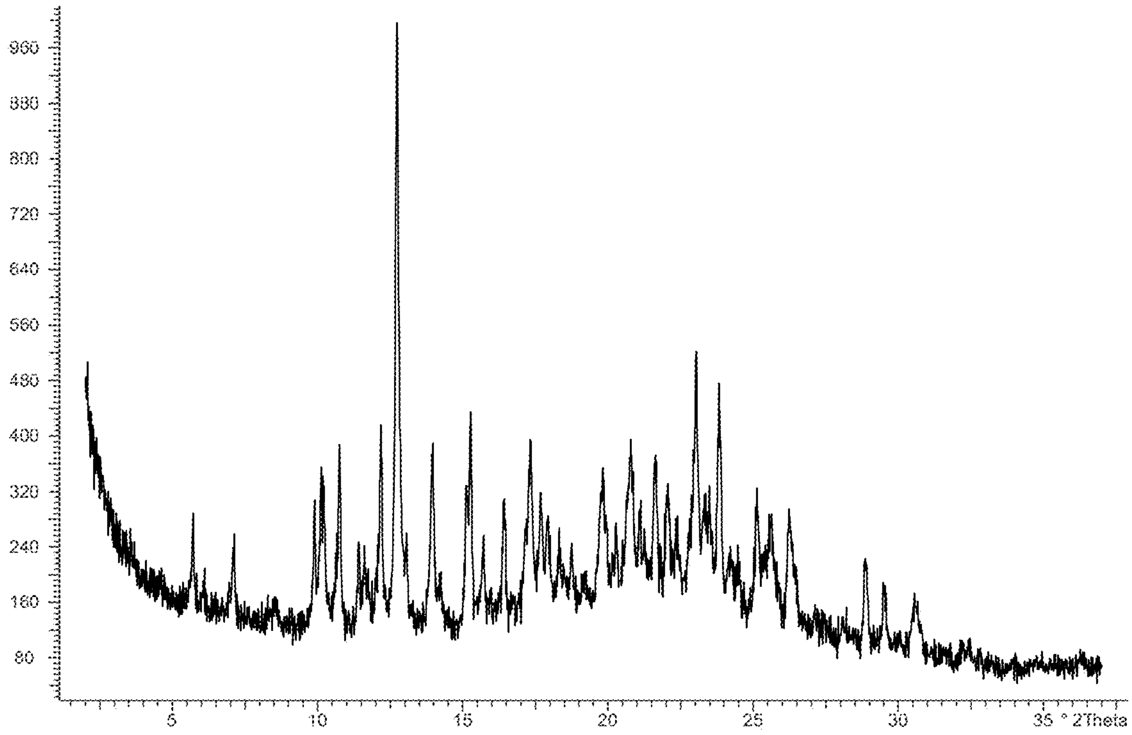
Fig. 40

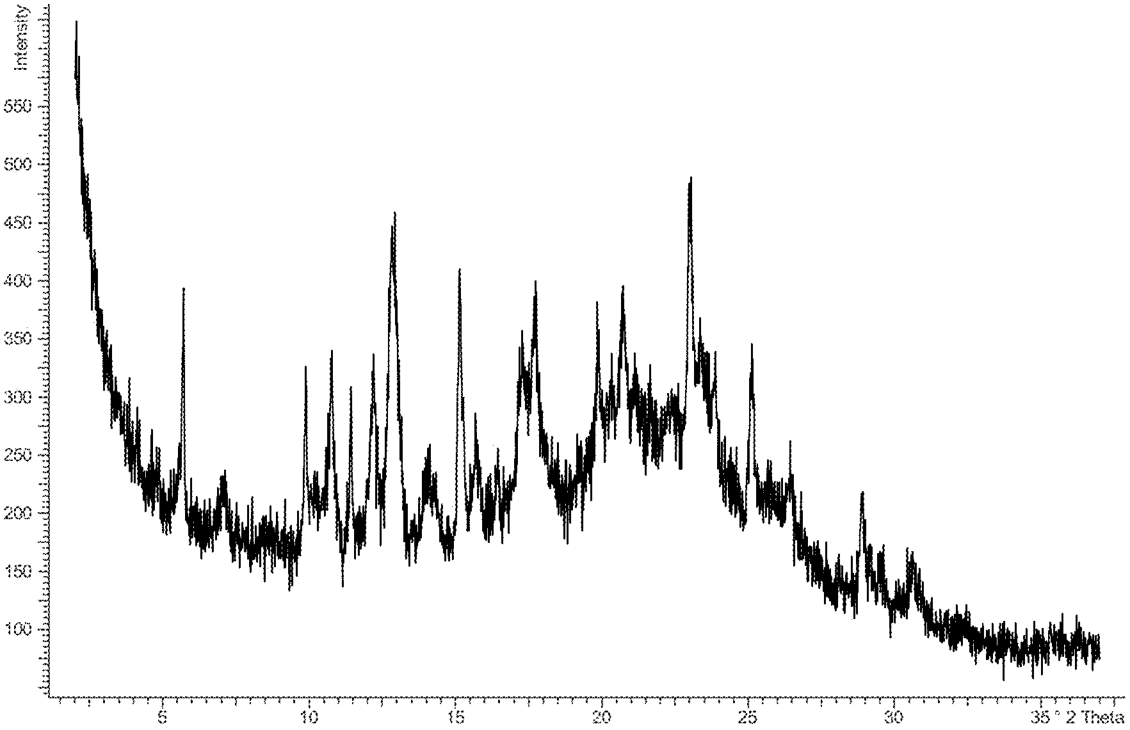
Fig. 43
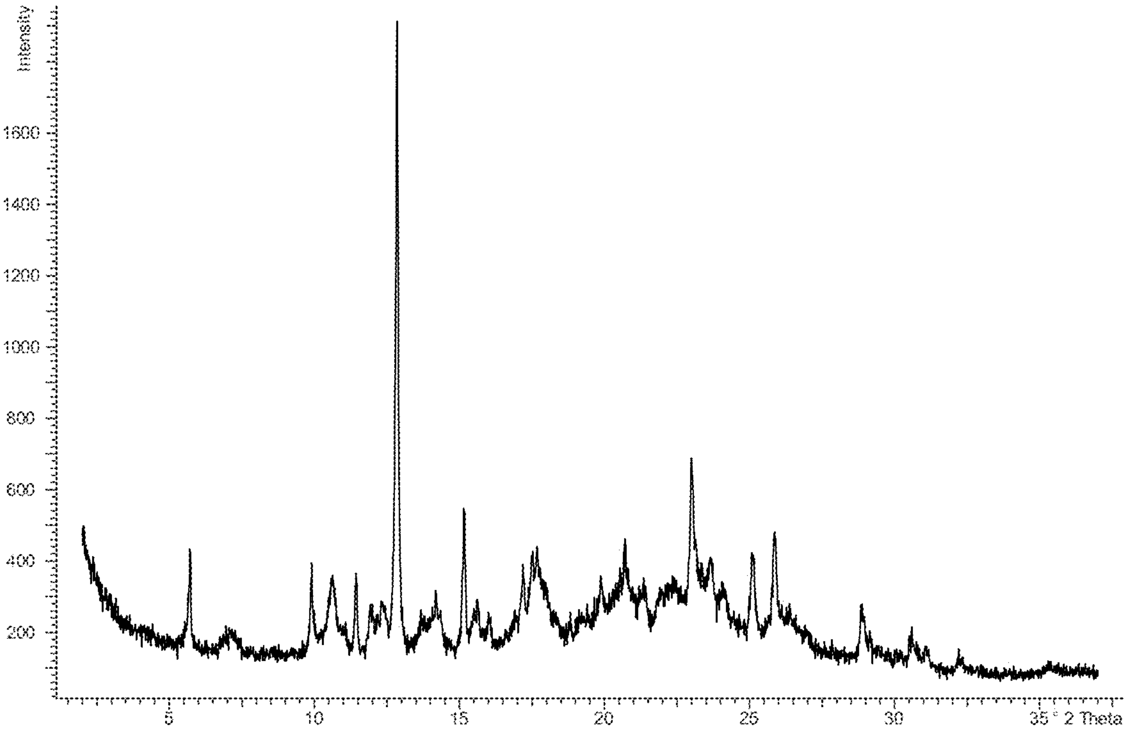
Fig. 44: X-ray powder diffractogram (example 8e): after micronization (monohydrate I)

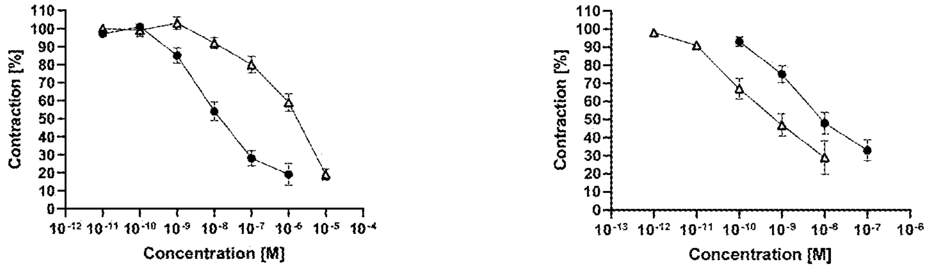
Comparative example 1 (Cinaciguat) 0.5h [$IC_{50}$ = 17nM]
Comparative example 11 0.5h [$IC_{50}$ = 911nM]
Comparative example 1 (Cinaciguat) 2.5h [$IC_{50}$ = 8.4nM]
Comparative example 11 2.5h [$IC_{50}$ = 0.8nM]
Fig. 45a + 45b
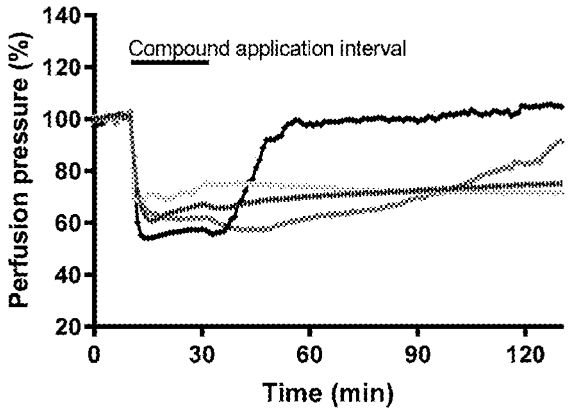
Comparative example 11
Comparative example 2 (Riociguat)
Comparative example 1 (Cinaciguat)
Comparative example 3
Fig. 46

- Vehicle (n=4)
- Comparative example 11 (30 μg/kg (n=2))
- Comparative example 2 (Riociguat 100 μg/kg (n=2))
- Comparative example 1 (Cinaciguat 3 μg/kg (n=2))
- Comparative example 1 (Cinaciguat 10 μg/kg (n=2))
- Comparative example 3 (30 μg/kg (n=2))

5-7min Inhalation of Vehicle (n=4) or Comparative example 11 (n=3) or Comparative example 5 (n=3) or Comparative example 4 (n=3)

PAP Vehicle

PAP Comparative example 5 100 μg/kg

PAP Comparative example 4 100 μg/kg

PAP Comparative example 11 100 μg/kg

BP Vehicle

BP Comparative example 5 100 μg/kg

BP Comparative example 4 100 μg/kg

BP Comparative example 11 100 μg/kg

Inhalations: @60min: Ventavis 10µg/kg; @120min: Vehicle ;@150min: Comparative example 11 30µg/kg BP wo ODQ — BP with ODQ PAP wo ODQ — PAP with ODQ Inhalations: @60min: Ventavis 10µg/kg; @120min: Vehicle ;@150min: Comparative example 11 30µg/kg BP wo L-NAME
PAP with L-NAME
PAP wo L-NAME
BP with L-NAME Bosentan 1mg/kg Sildenafil 300μg/kg/h Riociguat 3μg/kg/h Comparative example 11 30 μg/kg Comparative example 11 100 μg/kg Comparative example 11 30μg/kg on top of Bosentan 1mg/kg Comparative example 11 30μg/kg on top of Sildenafil 300 μg/kg/h Comparative example 11 30μg/kg on top of comaparative example 2 (Riociguat) 3μg/kg/h Comparative example 11 30μg/kg @0 min: Lactose 1.5mg/4kg; @90 min: Lactose formulation I (2%) 1.5mg/4kg @0 min: Lactose 1.5mg/4kg; @90 min: Lactose formulation II (6%) 1.5mg/4kg @30 min: Lactose 1.5mg/4kg; @90 min: micronized example 6e 1.5mg/4kg @90 min: Example 6e (mikro.) or lactose formulation I or II (2 or 6%) or Lactose 1.5mg/4kg PAP Lactose LH300/LH200 20:78m/m
PAP Lactose LH300/LH200 20:80m/m
PAP Lactose LH300/LH200 20:80m/m
PAP Lactose formulation I (2%)
PAP Lactose formulation II (6%)
PAP Micronized example 6e

@0 min: Lactose LH300/LH200 1.5mg/4kg @60min: Hydrates of comparative example 11 micronized 1.5mg/4kg

PAP mean example 2 Monohydrate (n=3)

BP mean example 2 Monohydrate (n=3)

PAP mean Semihydrate in analogy to example 6a (n=3)

BP mean Semihydrate in analogy to example 6a (n=3)

PAP mean Sesquihydrate in analogy to example 6e (n=3)

BP mean Sesquihydrate in analogy to example 6e (n=3)

↙ @60 min: Hydrates of comparative example 11 micronized 1.5mg/4kg

- PAP mean example 2 Monohydrate (n=3)
- BP mean example 2 Monohydrate (n=3)
- PAP mean Semihydrate in analogy to example 6a (n=3)
- BP mean Semihydrate in analogy to example 6a (n=3)
- PAP mean Sesquihydrate in analogy to example 6e (n=3)
- BP mean Sesquihydrate in analogy to example 6e (n=3)

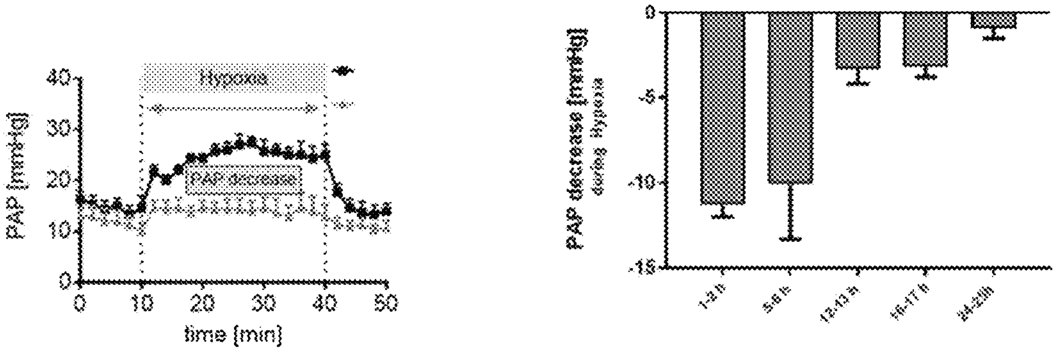
Placebo
Comparative example 11 100 μg/kg
Fig. 60 a and 60b

Comparative example 11

Comparative example 4

3: Inhalation Vehicle 4: i.v. Bolus Vehicle 5: Inhalation comparative example 11 100μg/kg or Placebo 7: i.v. Bolus comparative example 11 30μg/kg or Placebo 18: i.v. Bolus comparative example 11 100μg/kg or Placebo PAP Comparative example 11

BP Comparative example 11

PAP Vehicle

BP Vehicle

--- BP Placebo group

— BP comparative example 11 group

..... HR Placebo grpoup

.... HR comparative example 11 group

3: Inhalation Vehicle 4: i.v. Bolus Vehicle 5: Inhalation comparative example 11 100μg/kg or Placebo 7: i.v. Bolus comparative example 11 30μg/kg or Placebo 18: i.v. Bolus comparative example 11 100μg/kg or Placebo Inhalation Vehicle Cycle 3
Inhalation Cycle 5
90 min. after Inhalation Cycle 6

Vehicle Bolus Cycle 4
i.v. Bolus 30μg Cycle 7
i.v. Bolus 100μg Cycle 8

Vehicle (DMSO), n=13
Comparative example 11 1 µM, n=11
Comparative example 1 (cinaciguat) 1 nM, n=12
Comparative example 2 (Riociguat) 1 µM, n=9

BAY Start compound application wash Carbachol 10-7M start wash Carbachol 10-7M

1: Control; 2: Tiotropium; 3: Comparative example 11 (~1µg); 4: Comparative example 11 (~10µg); 5: Comparative example 11 (~100µg)

1: Positive Control; 2: Negative Control; 3: Dexamethason (100 µg) 4: Comparative example 11 (~10µg); 5: Comparative example 11 (~100µg)

1: Positive Control; 2: Negative Control; 3: Dexamethason (100 µg) 4: Comparative example 11 (~10µg);
5: Comparative example 11 (~100µg)

Fig. 69a-c

480µg Example 2 od (N=9)   1000µg Example 2 od (N=9)

2000µg Example 2 od (N=9)   Placebo (N=9)

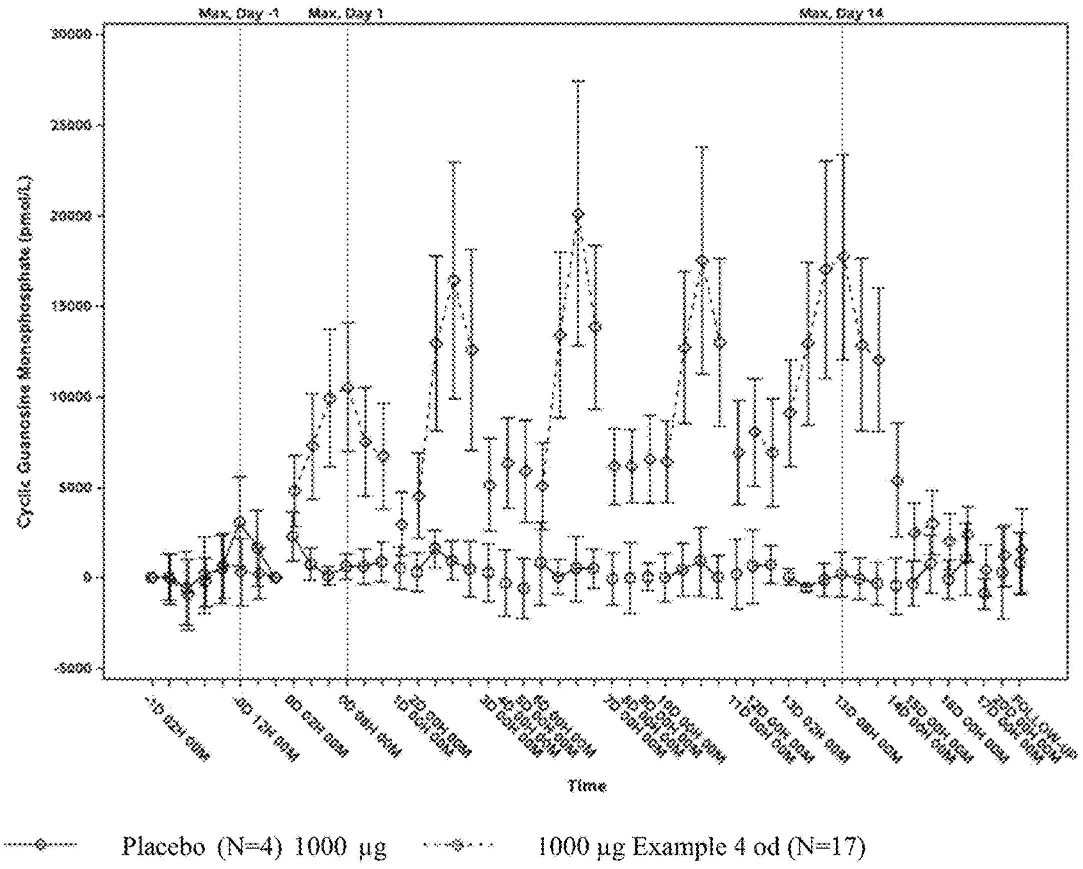
Fig. 76
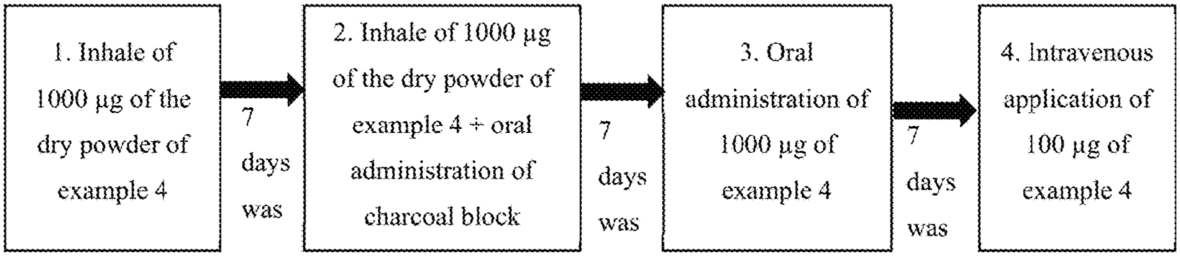
Fig. 77: scheme of the treatments conducted to investigate lung deposition 100 µg Example 4 intrevenous, n= 15, 1000 µg inhale of example 4, n= 16

1000 µg inhale of example 4 + charcoal, n=16, 1000 µg oral dose of example 4, n= 16

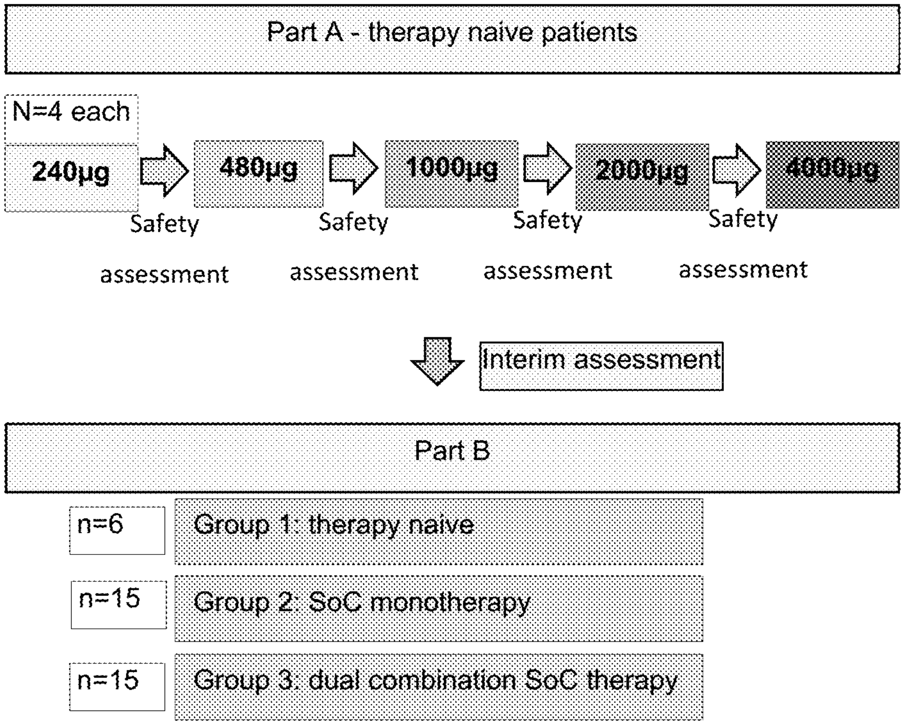
Fig. 80: study design of clinical study in patients with PAH or CTEPH
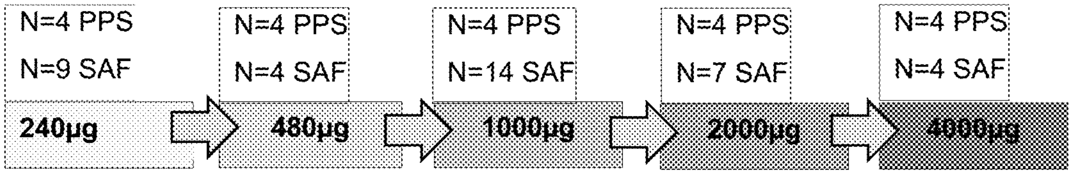
*SAF: safety analysis set: all patients matching in- and exclusion criteria (IC/EC)
*PPS: per protocol set: IC/EC met + PVR > 400 dyn + PAP decrease during inhaled nitric oxide (NO) challenge < 10 mmHG (exclusion of vasoresponsivness)
Fig. 81: summary of conducted Part A of clinical study in patients with PAH or CTEPH

TREATMENT OF CARDIOPULMONARY DISORDERS

CROSS-RELATED APPLICATIONS

This application is a continuation of International Application No. PCT/EP2022/087954, filed Dec. 28, 2022, which claims the benefit of Provisional European Patent Application No. 21218165.5, filed Dec. 29, 2021, each of which are hereby incorporated by reference in their entirety.

The present invention relates to the use of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula (I), preferably in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I) or (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate II of formula (I-M-II), in the inhalative treatment of cardiopulmonary and pulmonary disorders, such as pulmonary arterial hypertension (PAH), chronic tromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), characterized in that an inhalative dosage form comprising 240 to 4000 μg, preferably 480 to 2000 μg of (5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid of formula I, preferably in form of one of its salts or solvates or hydrates, preferably in form of monohydrate I of formula (I-M-I) or (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate II of formula (I-M-II), is administered to a patient in need thereof once or twice daily for a period of at least two consecutive days, preferably at least 2 to 7 consecutive days, preferably for a period of at least 14 consecutive days, in particular from after onset of treatment for the whole course of the disease, wherein the inhalative dosage form preferably comprises the combination of the active ingredient and a pharmaceutically suitable excipient or carrier, while preferably the active ingredient and a pharmaceutically suitable excipient are filled in a hard capsule.

Furthermore the present invention relates to medicaments for use in the inhalative treatment of cardiopulmonary disorders, such as pulmonary arterial hypertension (PAH), chronic tromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), comprising (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula (I), preferably in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I) or (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate II of formula (I-M-II) and optionally a pharmaceutically suitable excipient or carrier, preferably in form of a dry powder formulation, optionally filled in a cavity, e.g. a hard capsule, which are administered via inhalation to a patient in need thereof, once or twice daily, for a period of equal or more than two days, preferably at least 2 to 7 consecutive days, preferably for a period of at least 14 consecutive days, in particular from after onset of treatment for the whole course of the disease, comprising 240 to 4000 μg, preferably 480 to 2000 μg of active ingredient.

Furthermore the present invention relates to the use of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula (I), preferably in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) or (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate II of formula (I-M-II) for preparing an inhalative medicament for use in the treatment of cardiopulmonary disorders, such as pulmonary arterial hypertension (PAH), chronic tromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IP), in form of an inhalative dosage form, preferably as dry powder formulation, comprising the active ingredient and a pharmaceutically suitable excipient or carrier, preferable the active ingredient and a pharmaceutically suitable excipient, optionally filled in a hard capsule, wherein the medicament is administered to a patient in need thereof once or twice daily for a period of equal or more than two days, preferably at least 2 to 7 consecutive days, preferably for a period of at least 14 consecutive days, in particular from after onset of treatment for the whole course of the disease, and wherein the medicament comprises 240 to 4000 μg, preferably 480 to 4000 μg preferably 480 to 2000 μg of (5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid, preferably in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) or (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate II of formula (I-M-II).

(5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid corresponds to formula (I)

(I)

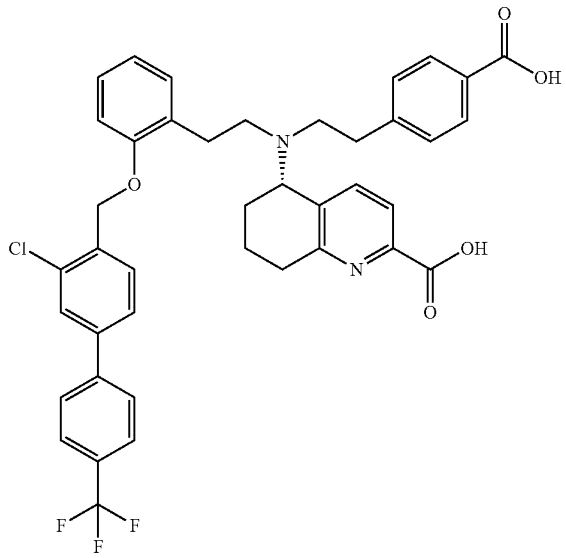

Novel crystalline forms of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, which are i.a. the pseudopolymorphic form monohydrate I (I-M-I) or the pseudopolymorphic form monohydrate II (I-M-II) correspond to formula (I-M-I), (I-M-II), (I-M-I) (I-M-II)

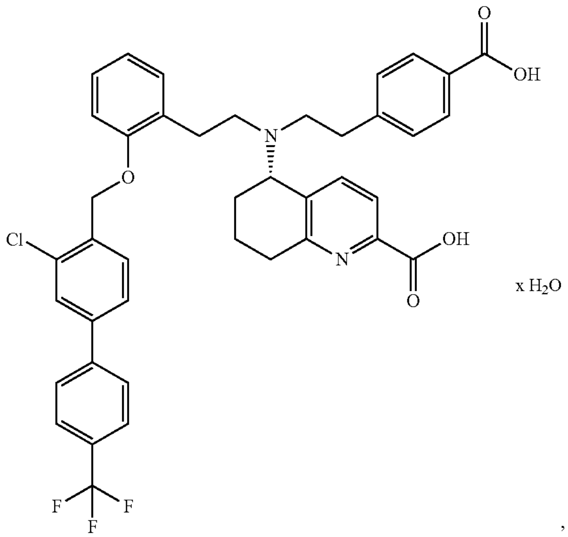

,

Compounds of formulae (I), (I-M-I) and (I-M-II) act as activators of soluble guanylate cyclase and can be used as a medicament for use in the prophylaxis and/or the treatment of pulmonary, cardiopulmonary and cardiovascular diseases, such as for example for the treatment of pulmonary arterial hypertension (PAH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-LIP), more specifically it relates to a method of treating a cardiopulmonary disorder, such as pulmonary arterial hypertension (PAH), chronic tromboembolic pulmonary hypertension (CTEPH) and pulmonary hypertension (PH) associated with chronic lung disease (PH group 3) such as PH-COPD and PH-LIP.

BACKGROUND OF THE INVENTION

Pulmonary hypertension (PH) is a progressive lung disorder which, untreated, leads to death within a few years after diagnosis. Pulmonary hypertension is defined by an elevation of the mean pulmonary aterial pressure (mPAP) (normal value<20 mmHg at rest). The pathophysiology of pulmonary hypertension is characterized by vasoconstriction and remodeling of the pulmonary vessels. In chronic PH there is neomuscularization primarily of unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH) is very common, and it is thought that the latter is currently the third most common group of cardiovascular disorders after coronary heart disease and systemic hypertension. Since 2008, pulmonary hypertension is classified in accordance with the Dana Point classification into various sub-groups according to the respective etiology [M. Humbert and V. V. McLaughlin, *J. Am. Coll. Cardiol.* 2009, 54 (1), S1-S2; D. Montana and G. Simonneau, in: A. J. Peacock et al. (Eds.), *Pulmonary Circulation. Diseases and their treatment,* 3rd edition, Hodder Arnold Publ., 2011, pp. 197-206; updated Nizza classification Gérald Simonneau, David Montani, David S. Celermajer, Christopher P. Denton, Michael A. Gatzoulis, Michael Krowka, Paul G. Williams, Rogerio Souza: *Haemodynamic definitions and updated clinical classification of pulmonary hypertension*, in: *European Respiratory Journal,* 2018; DOI: 10.1183/13993003.01913-2018].

Despite all the advances in the therapy of PH there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. These are therapeutic principles which are mainly administered systemically (beside inhaled Treprostinil and inhaled Iloprost or NO) and act primarily haemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH) and chronic thromboembolic pulmonary hypertension (CTEPH). In the case of secondary forms of PH related to lung diseases (PH group 3) such as PH-COPD or PH-IIP, these therapeutic principles (for example sildenafil, bosentan) have failed in clinical studies since, as a result of non-selective vasodilatation, they lead to a reduction (desaturation) of the arterial oxygen content in the patients. The probable reason for this is an unfavourable effect on the ventilations-perfusion adaptation in the lung in heterogenous lung disorders owing to the systemic administration of non-selective vasodilators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular, novel therapeutic approaches which can be combined with the therapy concepts already on the market may form the basis of a more efficient treatment and thus be of great advantage for the patients. In addition, selective pulmonary applicability of such a novel principle of action could offer the option of not only using it for PAH, but especially also provide a first therapy option for patients suffering from secondary forms of PH (PH group 3) because they avoid unselective systemic vasodilation by targeted application to ventilated areas of the lung via inhaled application.

Oxidative stress associated with many cardio-pulmonary diseases leads to impairment in the nitric oxide/soluble guanylate cyclase signaling pathway, shifting native soluble guanylate cyclase toward heme-free apo-soluble guanylate cyclase. Targeting specifically this NO-insensitive form of sGC offers the potential of outlining its unprecedented therapeutic opportunity for treating a variety of cardiopulmonary diseases. An sGC activator via its unique mode of action by restoring pivotal cGMP-signaling under oxidative stress conditions, combined with a novel, local and lung-selective application, could become a powerful new treatment option with both, enhanced efficacy and less adverse effects, for pulmonary hypertension patients.

In an animal model of pulmonary hypertension, it was demonstrated that inhalative administration of the sGC activator BAY 58-2667 (cinaciguat) in the form of microparticles leads to a dose-dependent selective reduction of the pulmonary arterial pressure. In this model, intravenous administration of 1H-1,2,4-oxadiazolo[4,3-a]quinoxalin-1-one (ODQ), which oxidizes the prosthetic haem group of the sGC, reduced the vasodilative effect of inhaled NO (iNO), whereas this was increased by BAY 58-2267. These results led to the hypothesis that inhalative administration of an sGC activator might represent a novel effective treatment method for patients suffering from pulmonary hypertension, in particular if the response of these patients to iNO and/or to PDE5 inhibitors is reduced as a consequence of a lack of NO or an oxidation of sGC [O. V. Evgenov et al., *Am. J. Respir. Crit. Care Med.* 2007, 176, 1138-1145]. However, in this model cinaciguat for its part did not have a sufficient duration of action, and in addition higher dosages led to unwanted systemic side effects.

Merck Sharp Dohme is developing a sGC stimulator inhaled application as dry powder (MK5475; NCT04609943) for PAH. However, as in PH and other lung diseases, the responsiveness to inhaled nitric oxide (iNO) and sGC stimulators could be impaired by the oxidation of sGC. An inhaled sGC activator targeted to the lungs may overcome this limitation.

In the field of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), patients with PH due to underlying lung disease (PH group 3) are first line treated by administration of drugs developed for the associated lung disease (e.g. COPD). Specific PH drugs (e.g. IP agonists, PDE5 inhibitors, endothelin antagonists and sGC stimulators) are only approved for PAH and CTEPH and are only experimentally used in the forms of PH group 3 due to observed desaturation effects of these systemically applied vasodilators.

Oral application is often a preferable route of administration for an active drug. With respect to cardiopulmonary indications a local application of the drug to the target organ lung is preferred to improve efficacy by increase of local drug concentration and avoid systemic side effects of a drug caused by systemic availability. In general less frequent dose regimen is desirable e.g. to improve patient's adherence (patient's compliance) to therapy, but 24 h coverage has to be ascertained for sustained efficacy of haemodynamically active drugs during the dosing interval. A lot of lung targeted, inhaled drugs require frequent application schemes (e.g. Iloprost/Ventavis) due to their e.g. short half-lives and/or lung retention time, which require multiple daily applications for a 24 hours coverage. In particular, once daily application is preferred due to favourable convenience for the patient and for compliance reasons. However, this goal is sometimes difficult to achieve depending on the specific behaviour and properties of the drug substance, especially its lung selectivity and lung retention time.

A further way of systemic administration, injection, is even more associated with many drawbacks (e.g. inconvenience of clinical visit required, discomfort, patient aversion to needle-based delivery methods, drug reactions at the administration side), all the more requiring alternative administration routes.

Pulmonary delivery by inhalation is one such alternative administration route which can offer several advantages over oral and injection administration. These advantages are especially the higher efficacy by increased local concentration and the potential for reduced systemic drug side effects but also include the convenience of patient self-administration, ease of delivery by inhalation, the elimination of needles, and the like.

For the pharmaceutical preparation for inhalation, where no adjuvants are necessary, especially in the case of solid preparations for suspension inhalation, preparations may consist of active ingredient alone. However, for practical reasons, e.g. to facilitate drug delivery of very low doses of active ingredients, the preparations are often medicaments which, besides the active ingredient, contain one or more pharmacologically inactive and physiologically acceptable excipients or carrier. A review of various suitable preparations and corresponding inhalation drug delivery technologies can be found for example in the book from Paolo Colombo, Daniela Traini and Francesca Buttini "Inhalation Drug Delivery—Techniques and Products" (published by Wiley-Blackwell 2013). In 2019, Moon et al published an updated review on delivery technologies for orally inhaled products (Moon et al, AAPS PharmSciTech 20:117 pp 1-17).

PRIOR ART

Various 5-amino-5,6,7,8-tetrahydroquinoline-2-carboxylic acids as well as their pharmaceutical use in cardiovascular and cardiopulmonary diseases, like e.g. PAH are disclosed in the patent application WO 14/012934-A1.

However some of these compounds, e.g. examples 2, 37 and 39 (see comparative examples 3, 4 and 5 in the experimental part) do only show a limited or moderate duration of action in PAH animal models. Furthermore some of these compounds, e.g. example 37 (see comparative example 3 in the experimental part) are not lung selective.

In addition, several examples disclosed in WO 14/012934-A1 do only show limited thermal stability (at 90° C., 7 days): e.g. example 2 (comparative example 5, experimental part), 24 (comparative example 6, experimental part), 25 (comparative example 7, experimental part), 28 (comparative example 8, experimental part), 29 (comparative example 9, experimental part) and for example 31 (comparative example 10, experimental part).

Additionally the document WO 14/012934-A1 does not disclose the suitability of the described compounds for use in a once or twice daily inhalative treatment regime nor any specific dosages.

Therefore there was a need to provide a novel, suitable once or twice daily inhalative dosage regimen for use in the treatment of cardiopulmonary diseases based on an active ingredient with advantageous properties like e.g. a sufficient duration of action, pulmoselective action (in contrast to a systemic action), e.g. a high lung selectivity, low to no VQ-mismatch, its lung retention time. Furthermore the drug substance should show improved ventilation, e.g. a bronchodilatory effect and/or an inhibitory effect on airway hyper-responsiveness and inflammation and thus be suitable in particular for use in the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

Furthermore there was the need to provide a stable active ingredient being suitable for use in the above mentioned inhalative dosage regime.

(5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I (comparative example 11) was found to be stable in a thermal stability test.

Additionally the acid of formula I (=comparative example 11) (example 23 according to WO2014/012934-A1) surprisingly showed further advantageous properties, like e.g. an excellent, long lasting efficacy in predictive PAH animal models as well as an intrapulmonary selectivity (C-2.1). Comparative example 11 effectively reduced the pulmonary arterial pressure (PAP) in the unilateral broncho-occlusion model. In contrast to systemic administration, no negative effect on desaturation area could be detected after inhalation providing a better risk-benefit ratio for this route of administration. As a result, comparative example 11 showed strong pulmonary and intrapulmonary selectivity after inhaled application. Moreover, our data indicate that comparative example 11 not only improved circulation but also showed bronchodilatory properties (C-3.1; C-3.2) which may be beneficial in the treatment of PH patients with chronic lung diseases or even have a potential in the treatment of asthmatics (C-3.3). Therefore, comparative example 11 might be a suitable inhaled drug which targets ventilated areas of the lung and evokes vasodilation only in ventilated areas thereby overcoming this limitation in current PAH treatment options who suffer from exaggerated V/Q mismatch.

In human airway smooth muscle cells (HASMC), relaxation can be driven by the NO-soluble guanylyl cyclase (sGC)-cGMP signaling pathway. In particular, a majority of severe asthma donor HASMC and lung samples primarily expressed the dysfunctional oxidized sGC. Therefore especially sGC activators might be a new target option for these patients (Arnab Ghosh, Cynthia J. Koziol-White, William F. Jester Jr., Serpil C. Erzurum, Kewal Asosingh, Reynold A. Panettieri Jr. see, Dennis J. Stuehr: An inherent dysfunction in soluble guanylyl cyclase is present in the airway of severe asthmatics and is associated with aberrant redox enzyme expression and compromised NO-cGMP signaling in Redox Biology 39 (2021) 101832; Maggie Lam, Jane E. Bourke, Ph.D., A New Pathway to Airway Relaxation: Targeting the "Other" Cyclase in Asthma American Journal of Respiratory Cell and Molecular Biology Volume 62 Number 1|January 2020) It is reported that sGC modulators induce bronchodilation in human small airways (Cynthia J. Koziol-White, Arnab Ghosh, Peter Sandner, Serpil E. Erzurum, Dennis J. Stuehr, and Reynold A. Panettieri, Jr.: Soluble Guanylate Cyclase Agonists Induce Bronchodilation in Human Small Airways, Am J Respir Cell Mol Biol Vol 62, Iss 1, pp 43-48, January 2020). Therefore we compared the bronchodilatory properties of comparative example 11 to the launched sGC stimulator Riociguat (comparative example 2) and the sGC activator Cinaciguat (comparative example 1) with the goal to test for the duration of action of bronchodilatory properties after local application (recovery factor as index for duration (C-3.1)). Compared to vehicle, all sGC modulators Cinaciguat (comparative example 1), Riociguat (comparative example 2) and comparative example 11 induced a relaxation. Relaxation via Cinaciguat (comparative example 1) and Riociguat (comparative example 2) reached a steady state within 1 h. Surprisingly, relaxation via comparative example 11 was further increasing. The relaxation induced by Riociguat (comparative example 2) was completely washed out within 1 h (recovery factor 0.34), relaxation induced by Cinaciguat (comparative example 1) was stable with a slight reduction trend (recovery factor 0.91) similar to vehicle (recovery factor 0.99). In contrast, surprisingly relaxation induced by comparative example 11 was further enhanced with a recovery factor of 1.41, suggesting a longer duration of action also with respect to bronchodilatory properties for comparative example 11.

Previous studies have shown that orally administered PAH drugs (e.g., bosentan, sildenafil, riociguat) dose-dependently decreased hypoxic PAP (i.e., a positive treatment effect) but increased the desaturation area (i.e., an unwanted desaturation effect) (Becker E M, Stasch J P, Bechem M, Keldenich J, Klipp A, Schaefer K, Ulbrich H F, Truebel H. Effects of different pulmonary vasodilators on arterial saturation in a model of pulmonary hypertension. PLoS One 2013; 8:1-8.). sGC activation focused on ventilated areas after inhaled application (intrapulmonary selectivity) may selectively and potently decrease vasoconstriction in the lungs without influence on V/Q mismatch. Inhaled comparative example 11 effectively reduced PAP in the unilateral broncho-occlusion model. In contrast to systemic administration, no negative effect on desaturation area could be detected after inhalation providing a better risk-benefit ratio for this route of administration. In particular, comparative example 11 showed strong pulmonary and intrapulmonary selectivity after inhaled application (C-2.3). Therefore, comparative example 11 might be a suitable inhaled drug which targets ventilated areas of the lung and evokes vasodilation only in ventilated areas thereby overcoming this limitation in current PAH treatment options which are burdened with exaggerated V/Q mismatch. Moreover, our data indicate that comparative example 11 not only improved circulation but also showed bronchodilatory properties with long duration of action (C-3.1; C-3.2; C-4.1) which may be beneficial in the treatment of PH patients with chronic lung diseases or even have a potential in the treatment of asthmatics (C-3.3).

To provide a novel, suitable inhalative dosage regimen for use in the treatment of cardiopulmonary diseases an inhalative dosage form comprising comparative example 11 (disclosed as example 23 in WO2014/012934-A1) as active ingredient is needed. As preferred option dry powder inhale dosage forms were chosen due to their suitability, convenience and patient compliance and adherence. Dry powder inhale dosage forms require that the active ingredient (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula (I) needs to be provided in a single, defined crystalline form.

However as disclosed in example 23 of WO 14/012934-A1, (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula (I) is only obtainable in amorphous form, which is unsuitable for use in inhalative dosage forms applied by dry powder inhalers.

Furthermore in the document WO 14/012934-A1 there is no disclosure of a specific carrier based inhalative medicament comprising a dry powder formulation of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid and a lactose carrier for use in the treatment of cardiopulmonary diseases.

Therefore there was a need to provide a novel, suitable inhalative dosage regimen for use in the treatment of cardiopulmonary diseases based on a stable, crystalline form of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I with a sufficient duration of action in humans (such as e.g. improved haemodynamic effect, decreased pulmonary vascular resistance (PVR), Intrapulmonary selectivity, bronchodilatory effect, cGMP and bronchodilatatory effects specific airway resistance) suitable for chronic treatment/use.

For inhaled therapy generally three drug product formulation options are available and can be selected based on required dose, patient population and associated properties, active ingredient stability. If solubility and stability of the active ingredient allows, one form of formulation is a solution which is nebulized. Disadvantages of nebulized drugs are often poor delivery efficiency (generation of low portion of inhaled droplets <5 μm), prolonged application time per treatment, lack of portable device options (and need for power supply) for on demand therapy.

A second option are pressurized metered dose inhalers (pMDIs) which provide enhanced portability, no need for power supply and the opportunity to deliver low doses (while higher doses are often not feasible). Disadvantages include use of organic solvents (propellants), requirement for special manufacturing technology and, very importantly, the need for coordination of breathing manouever with the actuation of the device. This often results in inadequate drug delivery (and therapy) and low patient compliance.

Dry powder inhalers (DPIs) have important advantages, such as small portable design, the possibility to deliver drug over a wide range of doses, independence from drug solubility and the absence of coordination of a breathing manouever with the device actuation (passive device). Therefore, for many applications and therapy options DPIs constitute a preferred technology to be chosen.

Dry powder inhalers (DPI) are commonly used to treat pulmonary diseases such as asthma and lung infections and are comprised of a powder formulation in a device which can be inhaled into the lower respiratory tract. The key features which make inhalation an attractive mode of drug delivery are: optimized drug delivery by means of direct targeting of drug to the site of action, reduction of systemic side effects, rapid onset of action, improved patient acceptance, adherence and compliance due to the non-invasiveness of this drug administration route. The delivery efficiency of dry-powder products for inhalation is dependent upon the drug formulation, the inhaler device, and the inhalation technique.

It is a general target when using pharmaceutical formulations for pulmonary delivery that the delivered drug amount with respect to the nominal content of a dose unit is as high as possible. Deposition of inactive ingredients in the lung in contrast should be minimized to the lowest amount possible and justified. There are different general formulation strategies towards inhalable formulations, all of which follow the strategy to optimize and increase active ingredient fine particle deposition of drug particles <5 μm while minimizing exposure to inactive ingredients.

The simplest approach to address this goal is to deliver the active ingredient in micronized form alone without any carrier, but this strategy is limited due to the nature of the drug and more importantly the typically very low amounts of target human doses. For DPI formulations, this approach however is of low practical importance.

Another strategy is to formulate micronized drug particles or dissolved drug into engineered particles where the drug is formulated with inactive ingredients and results in shaped particles which may be coated drug micro-particles or porous particles or matrix particles with more or less homogeneous or narrow particle size distribution at or below 5 μm to increase the drug amount delivered into the deep lung and airways. One disadvantage of those formulations is that carrier and drug are tied together and will be delivered together to the site of action. A comprehensive overview of non carrier based dry powder inhalation formulations was published by Healy et al (Advance Drug Delivery reviews 75 (2014) pp 32-52.

There are a number of published studies investigating the effects of variables in adhesive drug carrier mixtures however fundamental understanding is still limited. As there are many potential effects which occur concurrently and may have competing or synergistic or antagonistic potential it is still overall difficult to predict aerosol performance for a given mixture, not least because of specific surface and physical properties of the active ingredient compound particles themselves.

Many years of research and development have been spent in order to investigate the mechanisms involved in the formulation and dispersion of carrier-based mixtures for inhalation. [de Boer et al. in: A critical view on lactose-based drug formulation and device studies for dry powder inhalation: Which are relevant and what interactions to expect? Advanced Drug Delivery Reviews 64 (2012) 257-274].

However there are currently no clear guidances nor guidelines existing nor derivable of how to design a novel carrier-based mixture for inhalation for a novel drug substance as the different factors and ingredients influence each other and are additionally highly dependent on the drug substance properties. Consequently the skilled person in drug product development when confronted with the task to develop novel carrier-based mixtures for inhalation has to follow a de novo design and development approach for each new active ingredient.

The overall most common strategy is to formulate an active ingredient with inactive carrier compounds into a dry powder blend where the micronized drug particles adhere to an inactive carrier which in most cases is lactose or other sugar related compounds e.g. sugar alcohols as mannitol. Basic mechanism of drug delivery is here the temporary adhesion of micronized drug particles on inactive larger carrier material particles and the subsequent deagglomeration or release of the active micronized drug particles from carrier affected by the airflow energy created within a dry powder inhaler use for application of the formulation. The majority of the carrier material is not intended to be inhaled and due to its size will settle down in the upper airways, mainly mouth and throat. During the inhalation it is necessary to overcome the adhesive forces to release the drug particles from the carrier and thus it is pivotal to control the adhesion forces of drug on carrier in way that allows the optimum release of a high portion of the dose becoming available for drug delivery into the deep lung.

The majority of DPI products are carrier-based formulations consisting of finely milled drug particles mixed with coarse carrier particles which are usually lactose monohydrate. However, alternative carriers such as glucose, trehalose, sorbitol and (freeze-dried) mannitol are also used s lactose has some disadvantages when utilized as excipient for DPIs. For example, lactose is incompatible with drugs that have a primary amine group and therefore it is less suitable for the next generation of inhalable products comprising sensitive drugs.

Lactose can be obtained in either of two basic isomeric forms, namely α- and β-lactose, or in an amorphous form. α-Lactose exists both in monohydrate and in anhydrous forms, the former being the most thermodynamically stable form. α-Lactose monohydrate is prepared by crystallisation from supersaturated solutions below 93.5° C. Its crystalline shape can be a prism, a pyramidal or a tomahawk and is dependent on the precipitation and crystallisation methods. Anhydrous lactose (typically containing 70-80% anhydrous β-lactose and 20-30% anhydrous α-lactose) is most often produced by roller drying a lactose solution above 93.5° C. Next, both resulting products are milled to decrease particle size and sieved to select an appropriate particle size distribution. Spray-dried lactose is obtained by spray-drying a suspension of α-lactose monohydrate crystals in water in a lactose solution. Above a temperature of 93.5° C., β-lactose anhydrous is formed, while below this temperature, α-lactose monohydrate is obtained. [11] G. Pilcer, N. Wauthoz, K. Amighi, *Lactose characteristics and the generation of the aerosol, Adv Drug Del Reviews* 64(2012) 233-256]

There is a wide variety of lactose existing with different physico-chemical properties that could be used in DPI formulations. Lactose can be either processed by milling, sieving, spray-drying or granulating leading to different properties. Lactose excipients are commercially available therefore come in various grades which have different physico-chemical characteristics related to i.a. roughness, shape, particle size, particle size distribution, water content, compressibility or surface area. The aerosol performance of a powder is highly dependent on the lactose characteristics, such as particle size distribution and shape and surface properties. [11] G. Pilcer, N. Wauthoz, K. Amighi, *Lactose characteristics and the generation of the aerosol, Adv Drug Del Reviews* 64(2012) 233-256]

Additional processes for lactose particle engineering such as seeding, crystallisation, coating, shaping, condensation and precipitation are reported and result also in material with different physico-chemical properties related to e.g. particle size, size distribution, fine content, shape, surface roughness, flow properties, electrostatic charge, solid state alterations. [[12]X. Kou, L. Wah Chan, H. Steckel, P. W. S. Heng, *Physico-chemical aspects of lactose for inhalation, Adv. Drug Del. Reviews* 64 (2012) 220-232]

In carrier-based mixtures for inhalation a proper balance has to be adjusted between the stability of the blend during storage and handling, and dispersibility during inhalation. It has been shown that the variables that are relevant to these processes may influence each other in different ways and that by changing one variable, the effect of some others may be reversed. This may explain why opposite conclusions have been drawn in literature regarding the effect of a single variable. [De Boer, 2012]

It is agreed upon that a series of subsequent processes which comprises selection or production of the starting materials, the mixing process, dispersion and de-agglomeration in the inhaler device and finally the aerosol characterization is necessary to identify a suitable formulation which result in beneficial in vitro deposition results.

The required carrier properties depend on the type of drug to be processed, the drug concentration (% w/w) in the mixture as well as the determined drug dose and the amount of powder to be metered by (or into) the dose system, and the type of mixing process intended to be used. [De Boer, 2012]

Interfacial forces between drug and carrier have been discussed in conjunction with particle preparation techniques such as milling, condensation, spray drying, precipitation and crystallisation which yield different particle surface properties that may directly affect the drug-to-carrier interaction. [De Boer, 2012]

The major challenge is to find the optimal balance between the three types of forces that govern the particle deposition from dry powder inhaler (DPI) systems: the interparticulate forces in the mixture, the dispersion forces generated by the inhaler device during inhalation and the deposition forces for the aerosol particles in the respiratory airways. [De Boer, 2012]

The design of DPI controls powder deagglomeration in the device. All marketed passive DPI have three common design features: a mouthpiece, air inlets and a powder storage/dispensing system. Other features, such as grids and rotating capsules, may also be present to facilitate powder deagglomeration. [De Boer, 2012]

Additional factors might be the role of rotating capsule and the influence of air flow rate in the device. De Boer et al. depicted variables having an effect on the preparation and dispersion process of carrier-based formulations for inhalation and additionally interact on each other: Drug properties, carrier surface properties, carrier bulk properties, carrier surface payload, mixing process, mixture properties, inhalation process, storage and conditioning, to name a few. [de Boer et al. in: Dry powder inhalation: past, present and future. EXPERT OPINION ON DRUG DELIVERY, 2017 VOL. 14, NO. 4,499-512]

Therefore, in practice, a) the pharmaceutical formulation of mixtures for inhalation and (b) selection of a suitable carrier as well as (c) selection or design of an inhalation device is still an empirical process which needs a development and an adaption and engineering of certain parameters in order to obtain a customized formulation for the respective drug substance which has sufficient stability and aerosol performance.

The latter important properties are not predictable from the prior art references.

The manufacturing of DPI carrier-based powders generally includes various steps such as the production of drug and carrier particles in a suitable size range (by sieving, milling, spray-drying, etc.), mixing the various components in appropriate blending conditions with optimised parameters and, if necessary, the modification of the surface properties of the particles to enhance aerosol performance.

An optimal mixing is required to obtain drug uniformity, especially for low-drug-dose formulations containing micronised drug particles. In the case of cohesive powders, such as those encountered in dry powder formulations for inhalation, the presence of small drug particles in combination with coarse lactose particles promotes the formation of a stable ordered mixing, in which the drug particles adhere to the larger particles that act as carriers. However, in the case of ternary mixtures, where a certain proportion of fine excipient is added, some mixing issues are encountered, such as agglomeration (formation of fine and/or drug clusters due to cohesive properties of these small particles) and segregation (or demixing, characterised by the separation of the coarse particles from the fine particles induced by differences in particle size, shape and density or by agglomeration of the particles). In fact, the fine excipient, which improves the aerosol performance by promoting the adhesion of drug particles to sites with lower energy than the active sites of carrier, decreases adhesion and therefore affects drug uniformity. For an optimal dry-powder formulation, a balance is necessary between adhesion forces that are sufficient to guarantee drug uniformity and a blend that is stable for handling but weak enough to quickly release drug particles from the carrier during inhalation. Consequently, the segregation rate occurring during the mixing could be an interesting factor in predicting the aerosol-dispersion performance.

An optimal mixing depends on the optimisation of the container filling to guarantee sufficient expansion of powder bed, the mixer and powder characteristics, and the mixing conditions. The mixers are based on one or more of the following mechanisms: 1) convection, which is the movement of groups of adjacent particles from one place to another within the blend, 2) shear, which is the change in the configuration of ingredients through the formation of slip planes or shearing strains within a powder bed, and 3) diffusion, which is the redistribution of individual particles by their random movement relative to one another. Mixers can be classified into segregating mixers and non-segregating mixers. The choice of mixer depends on the tendency of the powder blend to segregate and to form agglomerates. For mixtures containing a powder blend that promotes particle separation, a non-segregating mixer must be used, whilst any type of mixer can be used for a mixture that does not suffer from demixing. In the case of agglomeration due to the cohesiveness of the smaller components, additional stress (shear) is required to break agglomerates during mixing. Therefore, high-shear mixers are frequently used to prepare premixes of cohesive drug substances. An optimal mixing time is required to obtain a homogeneous blend. Increasing the mixing time may improve the homogeneity of a non-segregating mixture but not necessarily that of a segregating mixture. The use of pre-blending steps, i.e., where drug is blended with a small amount of excipient, could reduce the total mixing time. In contrast, the achievement of a multicomponent mixture could increase the mixing time to reach homogeneity. [[x] G. Pilcer, N. Wauthoz, K. Amighi, *Lactose characteristics and the generation of the aerosol, Adv Drug Del Reviews* 64(2012) 233-256].

DETAILED DESCRIPTION OF THE INVENTION

Solid Forms of Acid of Formula (I)

The preparation of the compound of the formula (I) is disclosed in WO 2014/012934 (see example 23), starting from the precursor Ethyl-5-([2-(2-{[3-chlor-4'-(trifluormethyl)biphenyl-4-yl]methoxy}phenyl)ethyl]{2-[4-(methoxycarbonyl)-phenyl]ethyl-}amino)-5,6,7,8-tetrahydro-chinolin-2-carboxylat (example 92A in WO 2014/012934) and outlined in scheme 1 below.

Scheme 1: synthesis of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as disclosed in WO 2014/012934

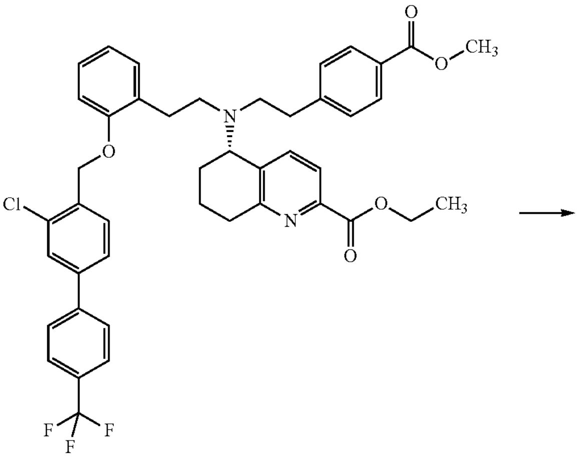

example 92A

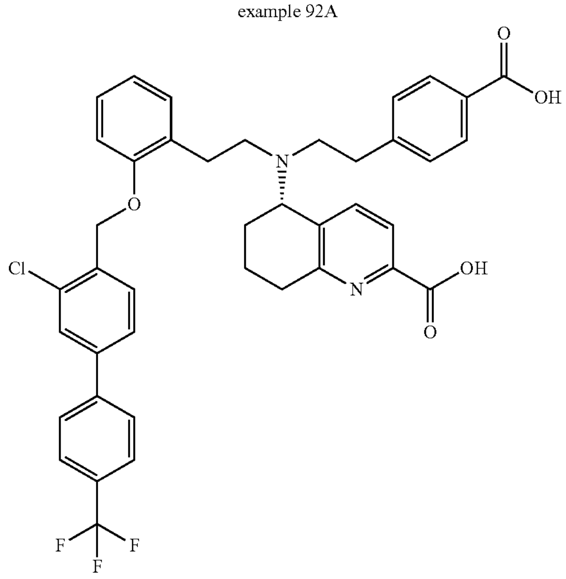

(I)

However, by this process the compound of the formula I is obtained in an amorphous form only (see comparative example 11).

An improved synthesis of another precursor of the compound of formula (I), namely ethyl-5-([2-(2-{[3-chloro-4'-

(trifluoromethyl)biphenyl-4-yl]methoxy}phenyl)ethyl]{2-[4-(methoxycarbonyl)phenyl]ethyl}amino)-5,6,7,8-tetrahydrochinoline carboxylate (compound XII)

(XII)

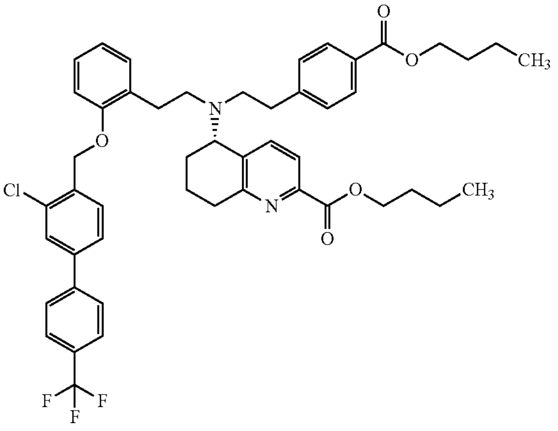

has been disclosed in WO2021/233783. However a synthetic approach to compound of formula (I) itself has not been disclosed in this reference.

A novel, unpublished process as shown in scheme 2, is characterized in, that purification steps of the intermediates are done via salt formation/extraction/clarification filtration and thereby chromatographic purification steps are avoided. Additionally the process according to the present invention offers high flexibility as the target compound of formula (I) can be made by three routes:

A) route 1 starts with the ester of formula (XII) (process steps [A] and [B]=route 1), B) route 2 starts with an intermediate of formula (X) (WO2021/233783) of a telescope process (process steps [C], [A] and [B]=route 2), C) route 3 starts with the solid NSA salt of formula (XII-NSA) (process steps [D], [A] and [B]=route 3).

Scheme 2: novel, unpublished process of making compound of formula (I), including process routes 1,2 and 3

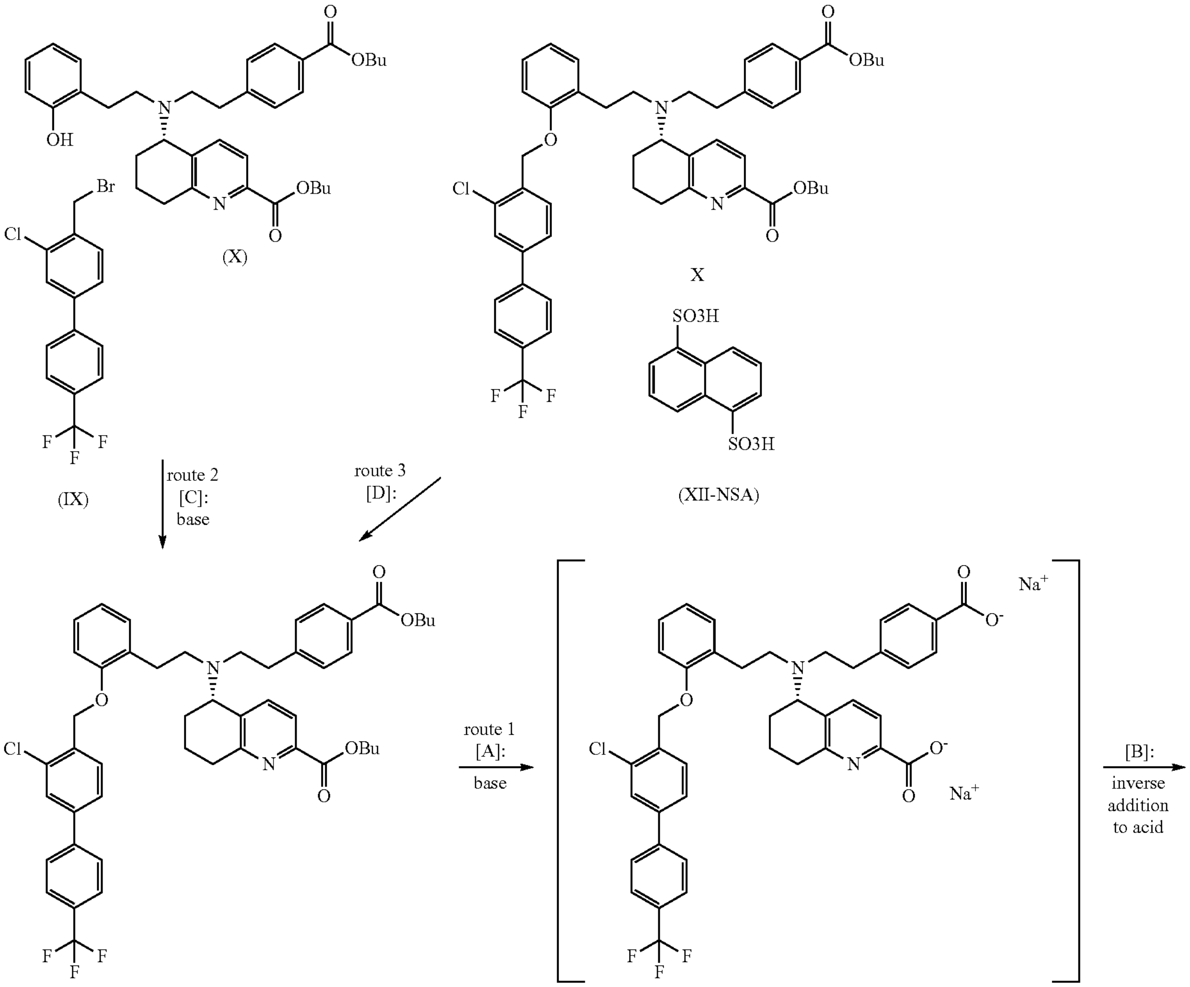

(X) (IX) X (XII-NSA) (XII) (I-DiNa)

-continued

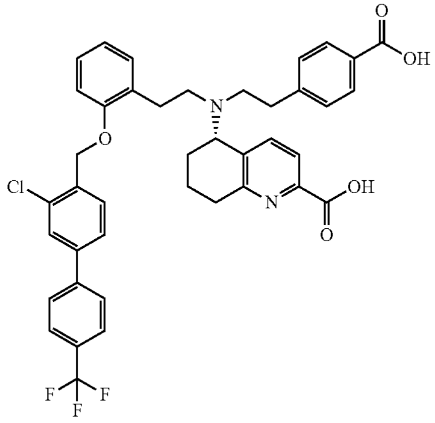

(I)

The core process (route 1) comprising the steps [A] and [B] is utilized in all three alternative routes. This process according to the present invention has several advantages over the prior art process disclosed in WO 2014/012934. Several byproducts which inevitably were included in the product of formula I if made according to the prior art procedure can be avoided or at least easier be separated. The present inventors identified the formation of the target acid of formula (I) from the disodium salt of formula (1-diNa) in step [B] as a major issue. It is crucial to run this step in an inverse manner controlling the pH of the reaction mixture (carefully monitored to stay within a window of between pH values of 3.8-4.2). Therefore process step [B] requires the inverse addition of the disodium salt intermediate of formula (I-DiNa) to an equimolar amount of acid equivalents. By this inverse addition the formation of the sparingly soluble mono sodium salt of compound of formula (I) is significantly reduced in comparison to the prior art process (see comparative example 11). However principally formed low amounts of the mono sodium salt as well as other sparingly soluble impurities can be separated by clarification filtration of the disodium salt solution. Additionally further byproducts like hydrochlorides are avoided by the inverse addition.

Alternatively, the compound of the formula (I) can be prepared without isolating intermediates starting from compounds (X) and (XI) by coupling, subsequent cleavage of the diester and acidic release (shown by way of example in process step [C], [A] and [B], see scheme 2 (route 2).

In an alternative route 3) the compound of the formula (I) can be prepared via its NSA salt, characterized in that in a first step [D] the dibutylester has to be released from the NSA salt of formula (XII-NSA) which is than further transformed into the free acid via two steps (basic saponification of the dibutylester (step [A]) and thereafter inverse addition to acid to release the free acid of formula (I) (step [B]).

For the development of a medicinal form, especially in form of a dry powder inhalation form comprising (5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid of the formula (I) in solid form, there is a high demand for the reproducible manufacturing and isolation of the compound of the formula (I) in one defined crystalline form.

Many efforts were needed to crystallize compound of formula I finally into a defined solid form.

Surprisingly compound of formula I was obtained in several pseudopolymorphic forms, no anhydrous crystalline form was found.

However out of the several identified pseudopolymorphic forms the most suitable and stable form had to be identified during several stages.

It was found that the dihydrate underwent amorphization during drying processes (see FIG. 10*a*). The crystalline lattice of the semihydrate exhibits disorder (see FIG. 5), which can support phase transitions and/or amorphization in mechanical processing, like e. g. formulation processes. The crystallization of the sesquihydrate was not feasible for scale up, because of very long stirring procedures.

Both monohydrates were found to overcome these unwanted properties of the different pseudopolymorphic forms.

By certain studies it was found that the (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula (I) exists in specific polymorphic forms, especially the monohydrate form I (I-M-I) and monohydrate form II (I-M-II):

(I-M-I) (I-M-II)

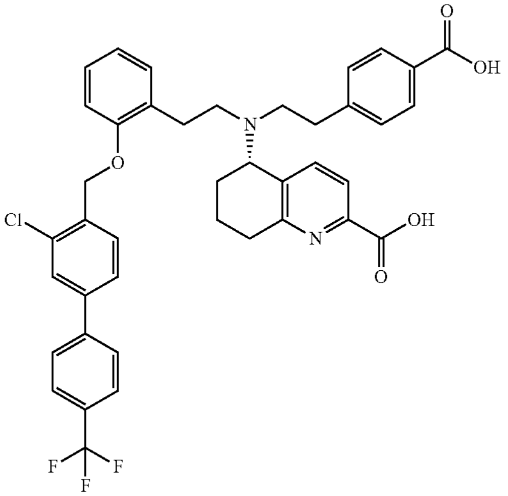

x1 $H_2O$

.

However finally it turned out that only one of these monohydrate forms is stable during micronization and therefore the most suitable form e.g. for use in the production of an inhalative medicament, especially as a dry powder based inhalative medicament. Surprisingly during micronization it was found that monohydrate II showed depending on the micronization conditions either partial amorphization (see example 8b, FIG. 42) or in addition to that a transformation to monohydrate I (see example 8a, FIG. 43). Furthermore it was observed that monohydrate II showed transformation to monohydrate I also during storage (see example 7b, FIGS. 40 and 41). Pseudopolymorphic form monohydrate I is therefore suitable and preferred over the other solid forms of the compound of formula I for use in the pharmaceutical field, in particular suitable for pharmaceutical compositions, especially for dry powder inhalative dosage forms.

The pseudopolymorphic forms, especially the hydrates, preferably the monohydrate in forms I and II can be made by crystallization of the acid of formula (I) (see scheme 3).

Depending on the used solvent either the monohydrate (I-M-I) is formed or the monohydrate (I-M-II). Surprisingly crystallization from a mixture of methanol, acetone and water or methanol and water selectively yields compound (I-M-I) whereas crystallization from acetone water yields selectively the monohydrate in form II (I-M-II).

Furthermore it was surprisingly found, that monohydrate (I-M-I) ensures that an undesired conversion into another form of the compound of formula (I) and an associated change in the properties as described above is prevented. Therefore the monohydrate I form is the most preferred crystalline form of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula (I).

The monohydrate I of (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid can be characterized by X-ray powder Scheme 3: selective crystallization of the acid of formula (I) to yield monohydrate forms thereof

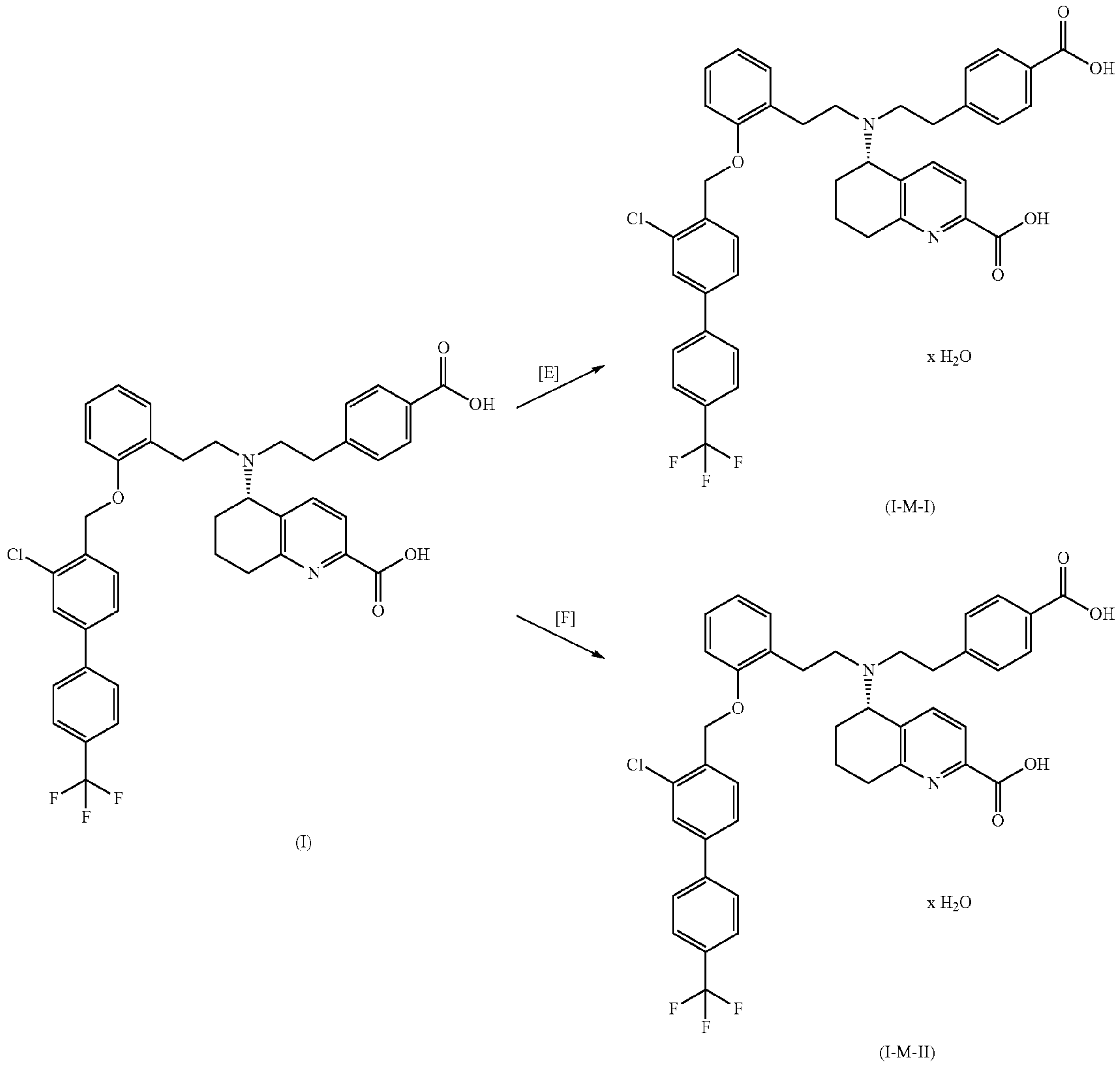

(I)

(I-M-I)

(I-M-II)

diffractometry on the basis of the respective diffraction diagrams, which are recorded at 25° C. and with Cu-K alpha 1 radiation (1.5406 Å). The monohydrate I according to the present invention displays at least 3, often at least 5, in particular at least 7, more particularly at least 10, and especially all of the reflections quoted in the following as values:

The pseudopolymorphic form of compound of formula (I), the monohydrate I of formula (I-M-I) can be characterized by a X-Ray powder diffractogram (at 25° C. and with Cu-K alpha 1 as radiation source) which displays at least the following reflections: 12.8 and 29.2 or at least 6.9, 7.2 and 7.3 or at least 6.9, 7.2, 7.3, 12.8 and 29.2 or at least 6.9, 7.2, 7.3, 12.8, 29.2, 23.0 and 15.2, or at least the following reflections: 6.9, 7.2, 7.3, 12.8, 29.2, 23.0, 15.2, 25.8 and 25.1 or at least the following reflections: 6.9, 7.2, 7.3 12.8, 29.2, 23.0, 15.2, 25.8, 25.1, 17.7 and 23.7, or at least the following reflections: 6.9, 7.2, 7.3, 12.8, 29.2, 23.0, 15.2, 25.8, 25.1, 17.7, 23.7, 9.9, 5.7 and 11.5, each quoted as 2θ value±0.2°.

In another embodiment the pseudopolymorphic form of compound of formula (I), the monohydrate I of formula (I-M-I) can be characterized by a X-Ray powder diffractogram (at 25° C. and with Cu-K alpha 1 as radiation source) which displays at least the following reflections: 12.8, 16.0 and 25.8 or at least 6.9, 7.2 and 7.3, or at least 6.9, 7.2, 7.3, 12.8, 16.0 and 25.8 or at least 6.9, 7.2, 7.3, 12.8, 16.0, 25.8, 15.2 and 25.1 or at least 6.9, 7.2, 7.3, 12.8, 16.0, 25.8, 15.2, 25.1 and 23.7 or at least 6.9, 7.2, 7.3, 12.8, 16.0, 25.8, 15.2, 25.1, 23.7, 9.9, 5.7 and 11.5, each quoted as 2θ value±0.2°.

In another embodiment the pseudopolymorphic form of compound of formula (I), the monohydrate I of formula (I-M-I) can be characterized by a X-Ray powder diffractogram (at 25° C. and with Cu-K alpha 1 as radiation source) which displays at least the following reflections: 12.8, 20.5 and 25.8 or at least 6.9, 7.2 and 7.3 or at least 6.9, 7.2, 7.3, 12.8, 20.5, 25.8, 15.2 and 25.1 or at least 6.9, 7.2, 7.3, 12.8, 20.5, 25.8, 15.2, 25.1 and 23.7 or at least 6.9, 7.2, 7.3, 12.8, 20.5, 25.8, 15.2, 25.1, 23.7, 9.9, 5.7 and 11.5, each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha 1 as radiation source) which displays the following reflections: 5.7, 6.9, 7.2, 7.3, 9.9, 10.4, 10.6, 11.1, 11.5, 12.0, 12.3, 12.4, 12.8, 13.7, 14.1, 14.3, 15.2, 15.6, 16.0, 16.9, 17.2, 17.5, 17.7, 18.0, 18.4, 18.8, 19.2, 19.9, 20.2, 20.5, 20.7, 21.3, 21.9, 22.2, 22.5, 23.0, 23.4, 23.7, 24.1, 25.1, 25.8, 26.0, 26.4, 28.9, 29.2, 29.4, 30.6, 31.1, 32.2, 35.3 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha 1 as radiation source) which does not display at least the following reflections 3.1 and 9.3 each quoted as 2θ value±0.2°. The pseudopolymorphic form of compound of formula (I), the monohydrate I of formula (I-M-I) can additionally be characterized by a X-Ray powder diffractogram (at 25° C. and with Cu-K alpha 1 as radiation source) which does not display at least the following reflections: 6.1 and 8.5 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha 1 as radiation source) which does not display at least the following reflections: 8.5 and/or 30 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha 1 as radiation source) which does not display at least the following reflections: 7.9 and/or 31.6 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha 1 as radiation source) which does not display at least the following reflections: 7.6 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha 1 as radiation source) which does not display at least the following reflections: 14.8 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha I as radiation source) which displays at least the following reflections: 12.8 and 29.2 or at least 6.9, 7.2 and 7.3 or at least 6.9, 7.2, 7.3, 12.8 and 29.2 or at least 6.9, 7.2, 7.3 12.8, 29.2, 23.0 and 15.2, or at least the following reflections: 6.9, 7.2, 7.3, 12.8, 29.2, 23.0, 15.2, 25.8 and 25.1 or at least the following reflections: 6.9, 7.2, 7.3 12.8, 29.2, 23.0, 15.2, 25.8, 25.1, 17.7 and 23.7, or at least the following reflections: 6.9, 7.2, 7.3, 12.8, 29.2, 23.0, 15.2, 25.8, 25.1, 17.7, 23.7, 9.9, 5.7 and 11.5 and at the same does not display at least the following reflections: 6.1 and 8.5 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha I as radiation source) which displays at least the following reflections: 12.8, 16.0 and 25.8 or at least 6.9, 7.2 and 7.3, or at least 6.9, 7.2, 7.3, 12.8, 16.0 and 25.8 or at least 6.9, 7.2, 7.3, 12.8, 16.0, 25.8, 15.2 and 25.1 or at least 6.9, 7.2, 7.3, 12.8, 16.0, 25.8, 15.2, 25.1 and 23.7 or at least 6.9, 7.2, 7.3, 12.8, 16.0, 25.8, 15.2, 25.1, 23.7, 9.9, 5.7 and 11.5 and at the same does not display at least the following reflections: 6.1 and 8.5 each quoted as 2θ value±0.2°.

The pseudopolymorphic form of compound of formula (I), the monohydrate I of formula (I-M-I) can additionally be characterized by a X-Ray powder diffractogram (at 25° C. and with Cu-K alpha 1 as radiation source) which displays at least the following reflections: 12.8, 20.5 and 25.8 or at least 6.9, 7.2 and 7.3 or at least 6.9, 7.2, 7.3, 12.8, 20.5, 25.8, 15.2 and 25.1 or at least 6.9, 7.2, 7.3, 12.8, 20.5, 25.8, 15.2, 25.1 and 23.7 or at least 6.9, 7.2, 7.3, 12.8, 20.5, 25.8, 15.2, 25.1, 23.7, 9.9, 5.7 and 11.5 and at the same does not display at least the following reflections: 6.1 and 8.5 each quoted as 2θ value±0.2°.

The compound of formula (I) in the polymorphic form Monohydrate I can also be characterized unambiguously by the X-Ray powder diffractogram (at 25° C. and with Cu-K alpha I as radiation source) as shown in FIG. 6.

The pseudopolymorphic form of the compound of formula (I), the monohydrate I of formula (I-M-I) can be characterized by a Raman spectroscopy which exhibits at least the following band maxima at: 3073, 2950, 2937, 1685, 1616, 1527, 1293, 1278, 1259 cm-1.

The pseudopolymorphic form monohydrate I of the compound of formula (I) can be characterized by a IR spectroscopy which exhibits at least the following band maxima at: 2933, 1595, 1375, 1327, 1272, 1242, 1167, 1110 cm-1.

Embodiment 7 (Monohydrate I of Formula (I-M-I))

The present invention provides the compound of the formula (I) in crystalline form monohydrate I of formula (I-M-I)

(I-M-I)

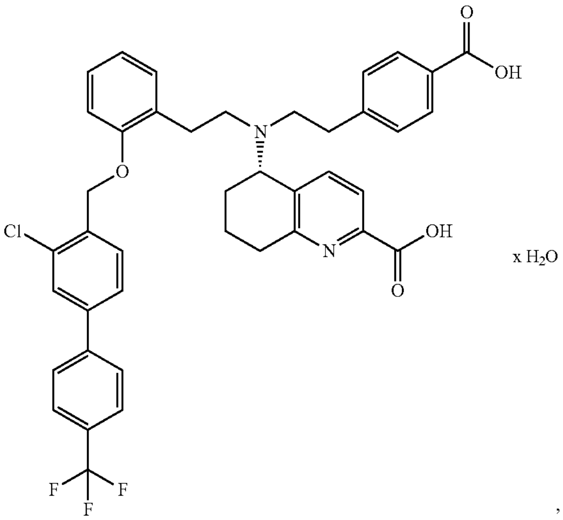

x $H_2O$

, characterized in that the x-ray diffractogram (at 25° C. and with Cu-K alpha 1 as radiation source) of the compound displaying at least the following reflections, quoted as 2θ value±0.2°: 12.8 and 29.2.

The present invention further provides the compound of the formula (I) in crystalline form of monohydrate I of formula (I-M-I) according to embodiment 7, characterized in that the x-ray diffractogram (at 25° C. and with Cu-K alpha 1 as radiation source) of the compound displaying at least the following reflections, quoted as 2θ value±0.2°: 6.9, 7.2 and 7.3.

The present invention further provides the compound of the formula (I) in crystalline form of monohydrate I of formula (I-M-I) according to embodiment 7, characterized in that the x-ray diffractogram (at 25° C. and with Cu-K alpha 1 as radiation source) of the compound displaying at least the following reflections, quoted as 2θ value±0.2°: 6.9, 7.2, 7.3, 12.8, 29.2, 23.0 and 15.2.

The present invention further provides the compound of the formula (I) in crystalline form of monohydrate I of formula (I-M-I) according to embodiment 7 and one or more further embodiments above, characterized in that the x-ray diffractogram (at 25° C. and with Cu-K alpha 1 as radiation source) of the compound displaying at least the following reflections, quoted as 26 value±0.2°: 6.9, 7.2, 7.3, 12.8, 29.2, 23.0, 15.2, 25.8, 25.1, 17.7 and 23.7.

The present invention further provides the compound of the formula (I) in crystalline form monohydrate I of formula (I-M-I) according to embodiment 7 and one or more further embodiments above, characterized in that the x-ray diffractogram (at 25° C. and with Cu-K alpha I as radiation source) of the compound displaying at least the following reflections, quoted as 2θ value±0.2°: 6.9, 7.2 and 7.3, 12.8, 29.2, 23.0, 15.2, 25.8, 25.1, 17.7, 23.7, 9.9, 5.7 and 11.5.

Alternatively the present invention provides the compound of the formula (I) in crystalline form monohydrate I of formula (I-M-I)

(I-M-I)

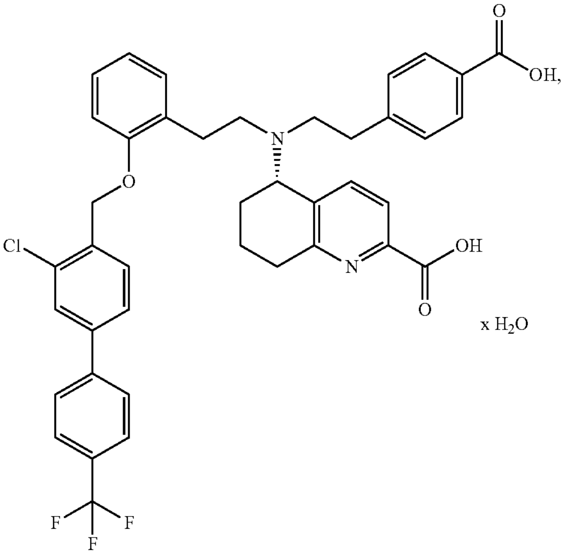

x $H_2O$ characterized in that the x-ray diffractogram (at 25° C. and with Cu-K alpha 1 as radiation source) of the compound displaying at least the following reflections, quoted as 2θ value±0.2°: 12.8, 16.0 and 25.8.

The present invention further provides the compound of the formula (I) in crystalline form of monohydrate I of formula (I-M-I) according to embodiment 7, characterized in that the x-ray diffractogram (at 25° C. and with Cu-K alpha 1 as radiation source) of the compound displaying at least the following reflections, quoted as 2θ value±0.2°: 12.8, 16.0, 25.8, 6.9, 7.2 and 7.3.

The present invention further provides the compound of the formula (I) in crystalline form of monohydrate I of formula (I-M-I) according to embodiment 7, characterized in that the x-ray diffractogram (at 25° C. and with Cu-K alpha 1 as radiation source) of the compound displaying at least the following reflections, quoted as 2θ value±0.2°: 6.9, 7.2 and 7.3, 12.8, 29.2, 23.0 and 15.2.

The present invention further provides the compound of the formula (I) in crystalline form of monohydrate I of formula (I-M-I) according to embodiment 7 and one or more further embodiments above, characterized in that the x-ray diffractogram (at 25° C. and with Cu-K alpha 1 as radiation source) of the compound displaying at least the following reflections, quoted as 2θ value±0.2°: 6.9, 7.2, 7.3, 12.8, 29.2, 23.0, 15.2, 25.8 and 25.1.

The present invention further provides the compound of the formula (I) in crystalline form monohydrate I of formula (I-M-I) according to embodiment 7 and one or more further embodiments above, characterized in that the x-ray diffractogram (at 25° C. and with Cu-K alpha I as radiation source) of the compound displaying at least the following reflections, quoted as 2θ value±0.2°: 6.9, 7.2 and 7.3, 12.8, 29.2, 23.0, 15.2, 25.8, 25.1, 17.7, 23.7, 9.9, 5.7 and 11.5.

The present invention further provides the compound of the formula (I) in crystalline form monohydrate I of formula (I-M-I)

(I-M-I)

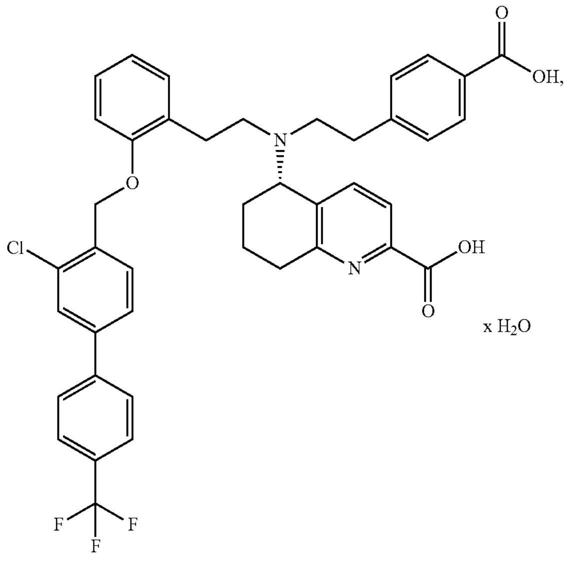

characterized in that the IR spectrum of the compound exhibits band maxima at 2933, 1595, 1375, 1327, 1272, 1242, 1167, 1110 cm-1 cm-1.

The present invention further provides the compound of the formula (I) in crystalline form monohydrate I of formula (I-M-I)

(I-M-I)

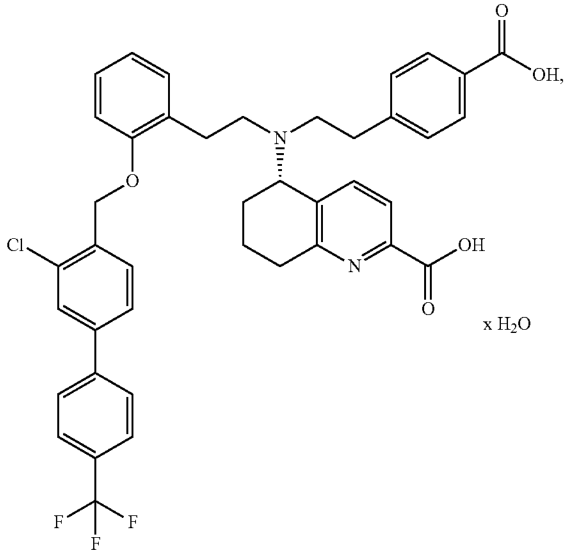

characterized in that the Raman spectrum of the compound exhibits band maxima at 3073, 2950, 2937, 1685, 1616, 1527, 1293, 1278, 1259 cm-1.

The other different forms of the compound of formula (I) can be distinguished by X-ray powder diffraction, differential scanning calorimetry (DSC), IR- and Raman-spectroscopy.

In addition to the monohydrate I, further pseudopolymorphic forms monohydrate II, semihydrate, 1,25-hydrate, sesquihydrate as well as dihydrate (see example 6, FIGS. 2-29) have been identified, which are further characterized in the following.

The pseudopolymorphic forms monohydrate II, semihydrate, 1,25-hydrate, sesquihydrate as well as dihydrate of (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid can be characterized by X-ray powder diffractometry on the basis of the respective diffraction diagrams, which are recorded at 25° C. and with Cu-Kalpha I radiation (1.5406 Å). The pseudopolymorphic forms monohydrate II, semihydrate, 1,25-hydrate, sesquihydrate as well as dihydrate display at least 3, often at least 5, in particular at least 7, more particularly at least 10, and especially all of the reflections quoted in the following as values:

The pseudopolymorphic form monohydrate II of the compound of formula (I) can be characterized unambiguously by a X-Ray powder diffractogram (at 25° C. and with Cu-K alpha 1 as radiation source) which displays at least the following reflections: 6.1 and 8.5, also at least 6.1, 8.5, 12.7, 23.9 and 13.9, preferably at least the following reflections: 6.1, 8.5, 12.7, 23.9, 13.9, 23.0 and 12.2, more preferably at least the following reflections: 6.1, 8.5, 12.7, 23.9, 13.9, 23.0, 12.2, 10.8 and 15.3, most preferably at least the following reflections: 6.1, 8.5, 12.7, 23.9, 13.9, 23.0, 12.2, 10.8, 15.3, 17.3, 21.7 and 22, also most preferably at least the following reflections: 6.1, 8.5, 12.7, 23.9, 13.9, 23.0, 12.2, 10.8, 15.3, 17.3, 21.7 and 22, each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha I as radiation source) which displays the following reflections: 5.7, 6.1, 7.1, 8.5, 9.9, 10.2, 10.8, 11.4, 11.6, 11.8, 12.0, 12.2, 12.7, 13.0, 13.9, 14.2, 15.2, 15.3, 15.7, 16.4, 17.3, 17.7, 17.9, 18.3, 18.5, 18.8, 19.2, 19.8, 20.2, 20.8, 21.1, 21.7, 22.0, 22.4, 22.8, 23.1, 23.4, 23.9, 24.2, 24.4, 25.1, 25.5, 25.7, 26.2, 26.4, 26.8, 27.2, 27.5, 28.9, 30.0, 30.1, 30.6, 32.2, 32.4, each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 3.1 and 9.3 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 6.9, 7.2 and 7.3 each quoted as 2θ value±0.2°.

The pseudopolymorphic form of compound of formula (I), the monohydrate II of formula (I-M-II) can additionally be characterized by a X-Ray powder diffractogram (at 25° C.

and with Cu-K alpha 1 as radiation source) which does not display at least the following reflections: 29.2 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 7.9 and/or 31.6 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 7.6 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 14.8 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which displays at least the following reflections: 6.1 and 8.5, also at least 6.1, 8.5, 12.8, 23.0, and 15.2, preferably at least the following reflections: 6.1, 8.5, 12.8, 23.0, 15.2, 25.8 and 25.1, more preferably at least the following reflections: 6.1, 8.5, 12.8, 23.0, 15.2, 25.8, 25.1, 17.7 and 23.7, most preferably at least the following reflections: 6.1, 8.5, 12.8, 23.0, 15.2, 25.8, 25.1, 17.7, 23.7, 9.9, 5.7 and 11.5, also most preferably at least the following reflections: 12.8, 23.0, 15.2, 25.8, 25.1, 17.7, 23.7, 9.9, 5.7, 6.1, 8.5 and 11.5 and at the same time does not display at least the following reflections: 6.9, 7.2 and 7.3 each quoted as 2θ value±0.2°.

The compound of formula (I) in the pseudopolymorphic form monohydrate II can also be characterized unambiguously by the X-Ray powder diffractogram (at 25° C. and with Cu-K alpha 1 as radiation source) as shown in FIG. 7.

The pseudopolymorphic form monohydrate II of the compound of formula (I-M-II) can be characterized by a Raman spectroscopy which exhibits at least the following band maxima at: 3073, 2950, 2936, 1685, 1615, 1526, 1294, 1279, 1259 cm-1.

The pseudopolymorphic form monohydrate I of the compound of formula (I) can be characterized by a IR spectroscopy which exhibits at least the following band maxima at: 2934, 1595, 1375, 1327, 1272, 1242, 1167, 1110 cm-1.

Embodiment 8 (Monohydrate II of Formula (I-M-II))

The present invention further provides the compound of the formula (I) in crystalline form monohydrate II of formula (I-M-II)

(I-M-II)

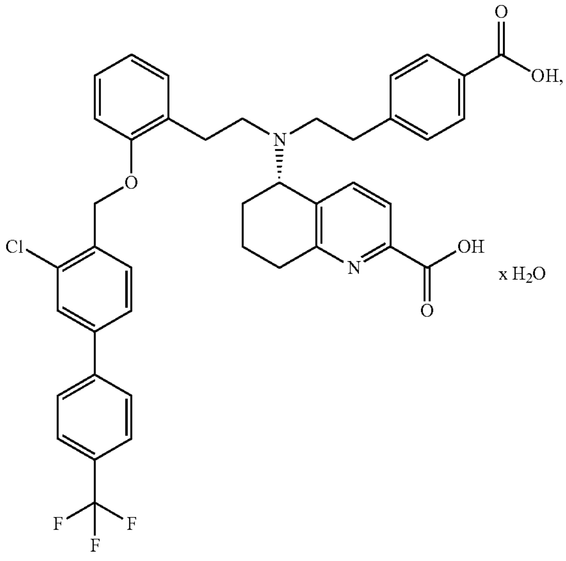

characterized in that that the x-ray diffractogram (at 25° C. and with Cu-K alpha 1 as radiation source) of the compound displaying at least the following reflections, quoted as 2θ value±0.2°: 6.1 and 8.1, preferably 6.1, 8.1, 12.7, 23.9 and 13.9, preferably at least the following reflections: 6.1, 8.1, 12.7, 23.9, 13.9, 23.1 and 12.2, more preferably at least the following reflections: 6.1, 8.1, 12.7, 23.9, 13.9, 23.1, 12.2, 10.8 and 15.3, most preferably at least the following reflections: 6.1, 8.1, 12.7, 23.9, 13.9, 23.1, 12.2, 10.8, 15.3, 17.3, 21.7 and 22.0.

The compound of formula (I) in the pseudopolymorphic form monohydrate II can also be characterized unambiguously by the X-Ray powder diffractogram (at 25° C. and with Cu-K alpha 1 as radiation source) as shown in FIG. 7.

The pseudopolymorphic form of compound of formula (I), the monohydrate II of formula (I-M-I) can additionally be characterized by a X-Ray powder diffractogram (at 25° C. and with Cu-K alpha 1 as radiation source) which does not display at least the following reflections: 3.1 and 9.3 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 6.9, 7.2 and 7.3 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 29.2 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 7.9 and/or 31.6 each quoted as 2θ value±0.2°.

The pseudopolymorphic form of compound of formula (I), the monohydrate II of formula (I-M-II) can additionally be characterized by a X-Ray powder diffractogram (at 25° C.

and with Cu-K alpha 1 as radiation source) which does not display at least the following reflections: 7.6 each quoted as 2θ value±0.2°.

The pseudopolymorphic form of compound of formula (I), the monohydrate II of formula (I-M-II) can additionally be characterized by a X-Ray powder diffractogram (at 25° C. and with Cu-K alpha 1 as radiation source) which does not display at least the following reflections: 14.8 each quoted as 2θ value±0.2°.

Embodiment 9 (Semihydrate of Compound of Formula (I))

The pseudopolymorphic form of compound of formula (I), the semihydrate can unambiguously be characterized by a X-Ray powder diffractogram (at 25° C. and with Cu-K alpha 1 as radiation source) which displays the following reflections: 3.1, 5.3, 6.7, 7.1, 9.3, 10.6, 12.4, 14.3, 16.1, 19.7, 20.8, 24.0, 31.1 each quoted as 2θ value±0.2°.

The pseudopolymorphic form of compound of formula (I), the semihydrate can unambiguously be characterized by a X-Ray powder diffractogram (at 25° C. and with Cu-K alpha 1 as radiation source) which displays at least the following reflections: 3.1, 5.3, 6.7, 7.1, 9.3 and 31.1 each quoted as 2θ value±0.2°.

The compound of formula (I) in the pseudopolymorphic form semihydrate can also be characterized unambiguously by the X-Ray powder diffractogram (at 25° C. and with Cu-K alpha 1 as radiation source) as shown in FIG. 5.

The pseudopolymorphic form of compound of formula (I), the semihydrate can additionally be characterized by a X-Ray powder diffractogram (at 25° C. and with Cu-K alpha 1 as radiation source) which does not display at least the following reflections: 6.9, 7.2 and 7.3 each quoted as 2θ value±0.2°.

The pseudopolymorphic form of compound of formula (I), the semihydrate can additionally be characterized by a X-Ray powder diffractogram (at 25° C. and with Cu-K alpha 1 as radiation source) which does not display at least the following reflections: 29.2 each quoted as 2θ value±0.2°.

The pseudopolymorphic form of compound of formula (I), the semihydrate can additionally be characterized by a X-Ray powder diffractogram (at 25° C. and with Cu-K alpha 1 as radiation source) which does not display at least the following reflections: 8.5 and/or 30.0 each quoted as 2θ value±0.2°.

The pseudopolymorphic form of compound of formula (I), the semihydrate can additionally be characterized by a X-Ray powder diffractogram (at 25° C. and with Cu-K alpha 1 as radiation source) which does not display at least the following reflections: 7.9 and/or 31.6 each quoted as 2θ value±0.2°.

The pseudopolymorphic form of compound of formula (I), the semihydrate can additionally be characterized by a X-Ray powder diffractogram (at 25° C. and with Cu-K alpha 1 as radiation source) which does not display at least the following reflections: 7.6 each quoted as 2θ value±0.2°.

The pseudopolymorphic form of compound of formula (I), the semihydrate can additionally be characterized by a X-Ray powder diffractogram (at 25° C. and with Cu-K alpha 1 as radiation source) which does not display at least the following reflections: 14.8 each quoted as 2θ value±0.2°.

Embodiment 10 (1.25 Hydrate of Compound of Formula (I))

The pseudopolymorphic form of compound of formula (I), the 1.25 hydrate can unambiguously be characterized by a X-Ray powder diffractogram (at 25° C. and with Cu-K alpha 1 as radiation source) which displays the following reflections: 5.9, 6.1, 7.9, 10.5, 11.9, 12.2, 12.5, 13.2, 13.6, 13.7, 14.4, 15.2, 15.3, 15.4, 15.7, 15.9, 16.5, 16.9, 17.2, 17.4, 17.6, 17.8, 18.3, 18.6, 18.7, 19.0, 19.5, 19.6, 19.8, 20.5, 20.7, 21.0, 21.4, 22.0, 23.2, 23.8, 24.0, 24.4, 24.6, 25.0, 25.2, 25.6, 26.1, 26.8, 27.4, 27.6, 28.4, 28.8, 30.2, 30.7, 31.1, 31.6, 32.3 each quoted as 2θ value±0.2°.

The pseudopolymorphic form of compound of formula (I), the 1.25 hydrate can unambiguously be characterized by a X-Ray powder diffractogram (at 25° C. and with Cu-K alpha 1 as radiation source) which displays at least the following reflections: 7.9, 10.5, 12.2, 12.5, 13.6, 15.2, 16.9, 19.0, 24.0, 24.4, 24.6, 31.6 each quoted as 2θ value±0.2°.

The compound of formula (I) in the pseudopolymorphic form 1.25 hydrate can also be characterized unambiguously by the X-Ray powder diffractogram (at 25° C. and with Cu-K alpha 1 as radiation source) as shown in FIG. 8.

The pseudopolymorphic form of compound of formula (I), the 1.25 hydrate can additionally be characterized by a X-Ray powder diffractogram (at 25° C. and with Cu-K alpha 1 as radiation source) which does not display at least the following reflections: 3.1 and 9.3 each quoted as 2θ value±0.2°.

The pseudopolymorphic form of compound of formula (I), the 1.25 hydrate can additionally be characterized by a X-Ray powder diffractogram (at 25° C. and with Cu-K alpha 1 as radiation source) which does not display at least the following reflections: 6.9, 7.2 and 7.3 each quoted as 2θ value±0.2°.

The pseudopolymorphic form of compound of formula (I), the 1.25 hydrate can additionally be characterized by a X-Ray powder diffractogram (at 25° C. and with Cu-K alpha 1 as radiation source) which does not display at least the following reflections: 29.2 each quoted as 2θ value±0.2°.

The pseudopolymorphic form of compound of formula (I), the 1.25 hydrate can additionally be characterized by a X-Ray powder diffractogram (at 25° C. and with Cu-K alpha 1 as radiation source) which does not display at least the following reflections: 8.5 and/or 30.0 each quoted as 2θ value±0.2°.

The pseudopolymorphic form of compound of formula (I), the 1.25 hydrate can additionally be characterized by a X-Ray powder diffractogram (at 25° C. and with Cu-K alpha 1 as radiation source) which does not display at least the following reflections: 7.9 and/or 31.6 each quoted as 2θ value±0.2°.

The pseudopolymorphic form of compound of formula (I), the 1.25 hydrate can additionally be characterized by a X-Ray powder diffractogram (at 25° C. and with Cu-K alpha 1 as radiation source) which does not display at least the following reflections: 7.6 each quoted as 2θ value±0.2°.

The pseudopolymorphic form of compound of formula (I), the 1.25 hydrate can additionally be characterized by a X-Ray powder diffractogram (at 25° C. and with Cu-K alpha 1 as radiation source) which does not display at least the following reflections: 14.8 each quoted as 2θ value±0.2°.

Embodiment 11 (Sesquihydrate of Compound of Formula (I))

The pseudopolymorphic form sesquihydrate of the compound of formula (I) can be characterized unambiguously by a X-Ray powder diffractogram (at 25° C. and with Cu-K alpha 1 as radiation source) which displays at least the following reflections: 12.2, 25.1 and 14.5, preferably at least 12.2, 25.1, 14.5, 18.7 and 26.4 preferably at least the following reflections: 12.2, 25.1, 14.5, 18.7, 26.4, 18.3 and 23.4 more preferably at least the following reflections: most preferably at least the following reflections: 12.2, 25.1, 14.5, 18.7, 26.4, 18.3, 23.4, 21.5, 8.6 and 5.1, and 7.6 each quoted as 2θ value±0.2°.

The pseudopolymorphic form of compound of formula (I), the sesquihydrate can also unambiguously be characterized by a X-Ray powder diffractogram (at 25° C. and with Cu-K alpha 1 as radiation source) which displays at least the following reflections: 5.1, 7.6, 8.6, 12.2, 14.5, 18.3, 18.7, 21.5, 23.4, 24.7, 25.1, 26.4, each quoted as 2θ value±0.2°.

The pseudopolymorphic form of compound of formula (I), the sesquihydrate can unambiguously be characterized by a X-Ray powder diffractogram (at 25° C. and with Cu-K alpha 1 as radiation source) which displays the following reflections: 5.1, 6.3, 7.6, 8.6, 11.4, 12.2, 12.5, 12.9, 13.3, 14.3, 14.5, 15.2, 15.5, 15.8, 16.2, 16.4, 16.7, 17.3, 17.5, 17.7, 18.3, 18.7, 19.4, 20.5, 20.7, 20.8, 21.4, 21.5, 21.8, 22.4, 22.9, 23.4, 24.0, 24.7, 25.1, 26.1, 26.4, 27.0, 27.4, 28.5, 32.2, 36.5 each quoted as 2θ value±0.2°.

The compound of formula (I) in the pseudopolymorphic form sesquihydrate can also be characterized unambiguously by the X-Ray powder diffractogram (at 25° C. and with Cu-K alpha 1 as radiation source) as shown in FIG. 9.

The pseudopolymorphic form of compound of formula (I), the sesquihydrate can additionally be characterized by a X-Ray powder diffractogram (at 25° C. and with Cu-K alpha 1 as radiation source) which does not display at least the following reflections: 3.1 and 9.3 each quoted as 2θ value±0.2°.

The pseudopolymorphic form of compound of formula (I), the sesquihydrate can additionally be characterized by a X-Ray powder diffractogram (at 25° C. and with Cu-K alpha 1 as radiation source) which does not display at least the following reflections: 6.9, 7.2 and 7.3 each quoted as 2θ value±0.2°.

The pseudopolymorphic form of compound of formula (I), the sesquihydrate can additionally be characterized by a X-Ray powder diffractogram (at 25° C. and with Cu-K alpha 1 as radiation source) which does not display at least the following reflections: 29.2 each quoted as 2θ value±0.2°.

The pseudopolymorphic form of compound of formula (I), the sesquihydrate can additionally be characterized by a X-Ray powder diffractogram (at 25° C. and with Cu-K alpha 1 as radiation source) which does not display at least the following reflections: 8.5 and/or 30.0 each quoted as 2θ value±0.2°.

The pseudopolymorphic form of compound of formula (I), the sesquihydrate can additionally be characterized by a X-Ray powder diffractogram (at 25° C. and with Cu-K alpha 1 as radiation source) which does not display at least the following reflections: 7.9 and/or 31.6 each quoted as 2θ value±0.2°.

The pseudopolymorphic form of compound of formula (I), the sesquihydrate can additionally be characterized by a X-Ray powder diffractogram (at 25° C. and with Cu-K alpha 1 as radiation source) which does not display at least the following reflections: 14.8 each quoted as 2θ value±0.2°.

Embodiment 12 (Dihydrate of Compound of Formula (I))

The pseudopolymorphic form of compound of formula (I), the dihydrate can be characterized unambiguously by a X-Ray powder diffractogram (at 25° C. and with Cu-K alpha 1 as radiation source) which displays at least the following reflections: 10.1, 10.5, 11.2, 12.5, 13.6, 14.8, 15.5, 20.2, 20.5, 21.1, 22.2, 23.2, 25.1, 29.6 each quoted as 2θ value±0.2°.

The pseudopolymorphic form of compound of formula (I), the dihydrate can be characterized unambiguously by a X-Ray powder diffractogram (at 25° C. and with Cu-K alpha 1 as radiation source) which displays the following reflections: 6.1, 6.8, 10.1, 10.5, 11.2, 11.3, 12.3, 12.5, 13.1, 13.6, 14.6, 14.8, 15.5, 16.2, 16.4, 16.8, 17.1, 17.3, 17.9, 18.5, 18.8, 19.5, 20.2, 20.5, 21.1, 21.4, 22.2, 23.2, 24.3, 25.1, 25.4, 25.6, 26.3, 26.9, 27.4, 28.5, 28.7, 29.6 each quoted as 2θ value±0.2°.

The compound of formula (I) in the pseudopolymorphic form dihydrate can also be characterized unambiguously by the X-Ray powder diffractogram (at 25° C. and with Cu-K alpha 1 as radiation source) as shown in FIG. 10.

The pseudopolymorphic form of compound of formula (I), the dihydrate can additionally be characterized by a X-Ray powder diffractogram (at 25° C. and with Cu-K alpha 1 as radiation source) which does not display at least the following reflections: 3.1 and 9.3 each quoted as 2θ value±0.2°.

The pseudopolymorphic form of compound of formula (I), the dihydrate can additionally be characterized by a X-Ray powder diffractogram (at 25° C. and with Cu-K alpha 1 as radiation source) which does not display at least the following reflections: 6.9, 7.2 and 7.3 each quoted as 2θ value±0.2°.

The pseudopolymorphic form of compound of formula (I), the dihydrate can additionally be characterized by a X-Ray powder diffractogram (at 25° C. and with Cu-K alpha 1 as radiation source) which does not display at least the following reflections: 29.2 each quoted as 2θ value±0.2°.

The pseudopolymorphic form of compound of formula (I), the dihydrate can additionally be characterized by a X-Ray powder diffractogram (at 25° C. and with Cu-K alpha 1 as radiation source) which does not display at least the following reflections: 8.5 and/or 30.0 each quoted as 2θ value±0.2°.

The pseudopolymorphic form of compound of formula (I), the dihydrate can additionally be characterized by a X-Ray powder diffractogram (at 25° C. and with Cu-K alpha 1 as radiation source) which does not display at least the following reflections: 7.9 and/or 31.6 each quoted as 2θ value±0.2°.

The pseudopolymorphic form of compound of formula (I), the dihydrate can additionally be characterized by a X-Ray powder diffractogram (at 25° C. and with Cu-K alpha 1 as radiation source) which does not display at least the following reflections: 7.6 each quoted as 2θ value±0.2°.

Method for Treatment

The crystalline forms of the compound of formula (I), preferably the monohydrate I (I-M-I) or the monohydrate II (I-M-II), more preferably the monohydrate I (I-M-I) according to the invention have useful pharmacological properties and can be employed for the prevention and treatment of disorders in humans and animals. The forms of the compound of formula (I) according to the invention can open up a further treatment alternative and may therefore be an enrichment of pharmacy.

In the context of the present invention, the term “treatment” or “treat” includes the inhibition, delay, arrest, amelioration, attenuation, limitation, reduction, suppression, reversal or cure of a disease, a condition, a disorder, an injury or a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

The term "therapeutic efficacy" within the context of the present invention is defined as a reduction of the mean pulmonary artery pressure with simultaneously clinically not relevantly changed systemic blood pressure of the patient by administering the pharmaceutical dry powder formulation comprising a therapeutically effective amount of compound of formula (I), especially of comparative example 11 or a salt, a solvate or a polymorphic form or a solvate or a crystal modification of a salt of the compound of formula (I) or a metabolite of compound of formula (I), especially its pseudopolymorphic forms, like e.g. (I-M-I) and (I-M-II).

The term "pulmonary vascular resistance (PVR)" within the context of the present invention is defined as the parameter 1) to characterize the severity of pulmonary hypertension as wall tension in the main pulmonary blood vessels, analysed by an invasive method of measuring the blood pressure in the pulmonary artery and 2) to evaluate the effect of a new drug by substantially lowering this parameter directly related to the blood pressure in the pulmonary artery (see D. Singh, R. Tal-Singer, I. Faiferman, S. Lasenby, A. Henderson, D. Wessels, A. Goosen, N. Dallow, R. Vessey & M. Goldman, Plethysmography and impulse oscillometry assessment of tiotropium and ipratropium bromide; a randomized, double-blind, placebo-controlled, cross-over study .in healthy subjects, Br. Journal Clin Pharmacol, 2006, 61, 398-404).

An improved 6 minutes walking test result within the context of the present invention is defined as an improvement in the distance patients are able to walk within a time window of 6 minutes, which corresponds to the increased physical ability of the patients with severe disease under treatment.

A shift in "NYHA class" within the context of the present invention is defined as the improvement to a lower class number of the NYHA classification from a higher class, corresponding to an improved heart function with better cardial capability.

The physiological function of the lung is evaluated in lung function tests like spirometry or bodyplethysmography under standardized conditions to get standardized and validated measurements for parameters like e.g. forced expiratory volume in 1 second (FEV1) that allow a direct assessment of drug effects like bronchodilation, an effect that is therapeutically used by different drugs for improvement of lung function in pulmonary diseases with bronchoconstriction like COPD or asthma.

The terms "improved haemodynamic effect" within the context of the present invention is defined as the drug's vasodilative effect to decrease pulmonary artery pressure, to improve the circulation of blood in ventilated areas of the lung as well as to improve lung function without systemic side effects and thereby causing a clinical relevant improvement of physical capability and general situation for the individual patient.

The term "Intrapulmonary selectivity" in the context of this invention means the property of the inhaled active ingredient to unfold its pharmacodynamic property of vasodilation only in the ventilated areas of the lung and not in the unventilated areas. This is to prevent a worsening of the mismatch between ventilation and perfusion (by increase of perfusion in the unventilated areas) which could happen if the active ingredient also reached the unventilated areas. Intrapulmonary selectivity is ensured in particular by the inhaled route of application which is carried out by active inhalation of the patient.

The term "bronchodilatory effect" within the context of the present invention is defined as improvement in parameters such as e.g. relaxation of carbachol preconstricted guinea pig trachea (C-3.1), lung resistance (RL) and dynamic compliance (Cdyn) (C-3.2 and C-3.3), specific airway resistance in humans (C-4.2), FEV1 in humans or other parameters indicating improvement in ventilation.

The term "chronic treatment/use" within the context of the present invention is defined as once or twice daily inhalative treatment of patients for a period of at least two consecutive days, preferably at least 2 to 7 consecutive days, preferably for a period of at least 14 consecutive days, in particular from after onset of treatment for the whole course of the disease, optionally also in combination with standard of care (SoC e.g. endothelin antagonists such as bosentan, PDE5 inhibitors e.g. sildenafil, IP agonists e.g. Ilomedin or treprostinil, calcium channel blockers, sotatercept and sGC stimulators e.g. riociguat).

The term "once daily" is well known by those skilled in the art and means administration of the drug once a day and includes the administration of one dosage form as well as administration of two or more dosage forms simultaneously or consecutively within a short time period.

The term "once or twice daily" is well known by those skilled in the art and means administration of the drug once a day or twice a day whereas the administration of the drug at each corresponding time point of the day includes the administration of one dosage form as well as administration of two or more dosage forms simultaneously or consecutively within a short time period.

The term "consecutive days" means a period of days occurring one after the other with no intervening days and does not mean sequential days or cyclical days.

The term "inhalative dosage form" means the combination of the drug substance, i.e. the active ingredient, preferably in one crystalline form, e.g. in form of the monohydrate I or the monohydrate H or the sesquihydrate, preferably in form of the monohydrate I or the monohydrate II, more preferably in form of the monohydrate I of formula (I-M-I), in combination with a pharmaceutically suitable carrier for inhalation. The combination of the drug substance and the pharmaceutically suitable carrier for inhalation are in the form of a dry powder. Preferably the dry powder is filled in a cavity, more preferably filled in a capsule. Preferably the pharmaceutically suitable carrier is lactose for inhalation.

The terms "reflection(s)" or "peak(s)" are synonyms and have the same meaning in connection with X-ray values and diffractograms. Crystalline forms are most commonly characterized by X-ray powder diffraction (XRPD). An XRPD pattern of reflections (peaks, typically expressed in degrees 2-theta) is commonly considered a fingerprint of a particular crystalline form.

The term "respiratory organs" (or respiratory system) refers for the purposes of the invention to the airways—including nose, oral cavity and pharynx, larynx, trachea, bronchi and the lung—as functional organ system.

The terms "Local administration" or "local control" in connection with cardiopulmonary disorders, means for the purposes of the invention—in contrast to oral administration of dosage forms intended for absorption via the gastrointestinal tract, and in contrast to intravenous administration, both leading to systemic drug distribution via bloodstream—administration of the active ingredient by inhalation in inhalable dosage form to primarily cover the lung as target organ, which requires a lower dose and causes a lower general drug exposure. The preparation in powder form or powder-containing suspensions to be used according to the invention are preparations which are inhaled.

The term "inhalation" or "administration by inhalation" refers in this connection to the introduction into the respiratory organs, especially into and/or via the airways, preferably into and/or via the nasal cavity or oral cavity, particularly preferable via oral cavity in order to achieve a deposition of the active ingredient to the bronchi and lung as the sites of action.

The term "intratracheal" or "intratracheal administration" refers for the purposes of the invention to introduce the compound into the trachea not by inhalation, in particular for pulmonary disease control in experimental animals such as rats or piglets and dogs as a model of administration (e.g. intratracheal application via PennCentury Device, applicable for dry powder as well as drug solutions and suspensions).

The compounds according to the invention, like (5S)-{[2-(4-carboxyphenyl)ethyl][2-(2-{[3-chloro-4-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) are potent activators of soluble guanylate cyclase. They lead to vasorelaxation, inhibition of platelet aggregation and a lowering of the blood pressure, as well as an increased coronary blood flow and microcirculation. Furthermore they have a bronchodilatory effect. These activities are mediated via direct haem-independent activation of soluble guanylate cyclase and an increase in intracellular cGMP levels.

In addition, the compounds according to the invention, especially (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) have further advantageous pharmacological properties, in particular with respect to their pulmoselective action (in contrast to a systemic action), their lung retention time and/or their duration of action following intrapulmonary administration (C-2.1, C-2.2) and a low to no VQ-mismatch (intrapulmonary selectivity) (C-2.3). Furthermore after inhaled application of the drug substance an improved ventilation, e.g. a bronchodilatory effect (C-3.1 and C-3.2) and an inhibitory effect on airway hyper-responsiveness and inflammation (C-3.3) could be shown preclinically.

Also a good therapeutical efficacy and target engagement of the compounds according to the invention, especially (5S)-{[2-(4-carboxyphenyl)ethyl][2-(2-{[3-chloro-4'-(trifluoromethyl)biphenyl-4-yl]methoxy}-phenyl)ethyl]amino}-5,6,7,8-tetrahydro-quino-line-2-carboxylic acid of formula I as well as its pseudopolymorphic forms, like e.g. (I-M-I) and (I-M-II) could be shown clinically: after inhaled application a reduced total specific airway resistance (C-4.1), an increase in plasma cGMP concentrations as surrogate for drug concentration in the lung (indicative of target engagement) (C-4.1, C-4.2) and a selective decrease in pulmonary artery pressure and pulmonary vascular resistance (C-4.4) was observed.

Furthermore suitable pharmacokinetic properties of the drug substance for inhaled applications could be shown. The analysis of plasma concentrations after oral, intravenous and inhalative administration of the drug substance showed the longest half-life of the active ingredient after inhaled application (C-4.3).

Finally the emitted dose has been determined to be 720 μg after inhalation of 1000 μg in humans. The outcome from this investigation confirms the deposited lung dose and that the half-life is adequate for an inhaled dry powder administration enabling a once daily treatment for a sufficient 24 h drug coverage of the drug substance (as shown for example 4) in the lung.

In conclusion all results show that (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II), especially the monohydrate I of formula (I-M-I) are suitable in particular for the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP) and are adequate for an inhaled dry powder administration enabling a once daily treatment for a sufficient 24 h drug coverage of the drug substance (as shown for example 4) in the lung.

The compounds according to the invention, (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) are particularly suitable for the treatment and/or prevention of cardiovascular, cardiopulmonary and pulmonary disorders, preferably for cardiopulmonary disorders.

Accordingly, the compounds according to the invention, especially (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid as well as its pseudopolymorphic forms, like e.g. (I-M-I) and (I-M-II) can be used in medicaments for the treatment and/or prevention of cardiovascular and cardiopulmonary disorders such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), as well as pulmonary disorders such as asthma, chronic obstructive pulmonary disease (COPD) or pulmonary fibrosis.

In the context of the present invention, the term "sGC modulators" encompasses two distinct compound classes capable of modulating sGC, the sGC stimulators and sGC activators (Sandner P, Becker-Pelster E M, Stasch J P. Discovery and development of sGC stimulators for the treatment of pulmonary hypertension and rare diseases. Nitric Oxide 2018; 77:88-95.; Hoenicka M, Becker E M, Apeler H, Sirichoke T, Schröder H, Gerzer R, Stasch J P. Purified soluble guanylyl cyclase expressed in a baculovirus/

Sf9 system: stimulation by YC-1, nitric oxide, and carbon monoxide. J Mol Med (Berl) 1999; 77:14-23; Evgenov O V, Kohane D S, Bloch K D, Stasch J P, Volpato G P, Bellas E, Evgenov N V, Buys E S, Gnoth M J, Graveline A R, Liu R, Hess D R, Langer R, Zapol W M. Inhaled agonists of soluble guanylate cyclase induce selective pulmonary vasodilation. Am J Respir Crit Care Med 2007; 176:1138-1145). Both classes of compounds directly bind to sGC as allosteric modulators. sGC stimulators have a dual mode of action, directly stimulating the native sGC independently of NO and also sensitizing sGC to low levels of NO by stabilizing NO-sGC binding. In contrast, sGC activators bind to the unoccupied heme-binding domain, thereby mimicking NO-bound heme, and activate the pathologically changed, NO-unresponsive apo-sGC. Recent evidence has shown that oxidative stress associated with many cardiopulmonary diseases shifts intracellular levels of native sGC toward the apo-sGC form (Evgenov O V, Pacher P, Schmidt P M, Hasko G, Schmidt H H, Stasch J P. NO-independent stimulators and activators of soluble guanylate cyclase: discovery and therapeutic potential. Nat Rev Drug Discov 2006; 5:755-768; Münzel T, Genth-Zotz S, Hink U. Targeting heme-oxidized soluble guanylate cyclase: solution for all cardio-renal problems in heart failure?Hypertension 2007; 49:974-976), providing the rationale for sGC activators (Wood K C, Durgin B G, Schmidt H M, Hahn S A, Baust J J, Bachman T, Vitturi D A, Ghosh S, Ofori-Acquah S F, Mora A L, Gladwin M T, Straub A C. Smooth muscle cytochrome b5 reductase 3 deficiency accelerates pulmonary hypertension development in sickle cell mice. Blood Adv 2019; 3:4104-4116.; Rahaman M M, Nguyen A T, Miller M P, Hahn S A, Sparacino-Watkins C, Jobbagy S, Carew N T, Cantu-Medellin N, Wood K C, Baty C J, Schopfer F J, Kelley E E, Gladwin M T, Martin E, Straub A C. Cytochrome b5 Reductase 3 Modulates Soluble Guanylate Cyclase Redox State and cGMP Signaling. Circ Res 2017; 121:137-148.; Durgin B G, Hahn S A, Schmidt H M, Miller M P, Hafeez N, Mathar I, Freitag D, Sandner P, Straub A C. Loss of smooth muscle CYB5R3 amplifies angiotensin II-induced hypertension by increasing sGC heme oxidation. JCI Insight 2019; 4:e129183.; Sandner P, Zimmer D P, Milne G T, Follmann M, Hobbs A, Stasch J P. Soluble guanylate cyclase stimulators and activators. Handb Exp Pharmacol 2019; doi:10.1007/164_2018_197) in various cardiovascular pathophysiological conditions such as PH.

In the context of the present invention, the term "pulmonary hypertension" encompasses both primary and secondary subforms thereof, as defined below by the Dana Point/Nizza classification according to their respective aetiology [see D. Montana and G. Simonneau, in: A. J. Peacock et al. (Eds.), *Pulmonary Circulation. Diseases and their treatment,* 3$^{rd}$ edition, Hodder Arnold Publ., 2011, pp. 197-206; M. M. Hoeper et al., *J. Am. Coll. Cardiol.* 2009, 54 (1), S85-S96] updated Nizza classification Gérald Simonneau, David Montani, David S. Celermajer, Christopher P. Denton, Michael A. Gatzoulis, Michael Krowka, Paul G. Williams, Rogerio Souza: *Haemodynamic definitions and updated clinical classification of pulmonary hypertension, in: European Respiratory Journal,* 2018; DOI: 10.1183/13993003.01913-2018]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and pulmonary arterial hypertension associated with collagenosis (APAH), congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia (e.g. sleep apnoe syndrome, alveolar hypoventilation, chronic high-altitude sickness, hereditary deformities). Group 4 includes PH patients having chronic thrombotic and/or embolic disorders, for example in the case of thromboembolic obstruction of proximal and/or distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

The compounds according to the invention, especially (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) are also suitable for treatment and/or prevention of pulmonary disorders such as asthma, chronic-obstructive pulmonary disease (COPD) and pulmonary fibrosis.

In the context of the present invention, the term "Asthma" encompasses a heterogenous chronic inflammatory disease of the airways of the lungs. It is characterized by variable and recurring symptoms, from reversible airflow obstruction, often caused by a hyperreagibility of the bronchi up to bronchospasms. Symptoms include episodes of wheezing, coughing, chest tightness, and shortness of breath. These may occur a few times a day or a few times per week. Depending on the person, asthma symptoms may become worse at night or with exercise. Asthma is thought to be caused by a combination of genetic and environmental factors. Environmental factors include exposure to air pollution and allergens. Other potential triggers include medications such as aspirin and beta blockers. Diagnosis is usually based on the pattern of symptoms, response to therapy over time, and spirometry lung function testing. Asthma is classified according to the frequency of symptoms, forced expiratory volume in one second (FEV1), and peak expiratory flow rate. It may also be classified as atopic or non-atopic, where atopy refers to a predisposition toward developing a type 1 hypersensitivity reaction. There is no known cure for asthma, but it is well treatable systematically. Symptoms can be prevented by avoiding triggers, such as allergens and respiratory irritants, and suppressed with the use of inhaled corticosteroids. Long-acting beta agonists (LABA), and other substances, e.g. antileukotriene agents may be used in addition to inhaled corticosteroids if asthma symptoms remain uncontrolled. Treatment of acute worsening symptoms is usually performed with an inhaled short-acting beta-2 agonist such as salbutamol and corticosteroids. In severe cases, systemic corticosteroids, magnesium sulfate, and hospitalization may be required. A subset of asthmatics develop a severe form of the disease whose etiology involves airway inflammation along with inherent drivers that remain ill-defined. To address this, we studied human airway smooth muscle cells (HASMC), whose relaxation drives airway bronchodilation and whose dysfunction contributes to airway obstruction and hypersensitivity in severe asthma. Because HASMC relaxation can be driven by the NO-soluble guanylyl cyclase (sGC)-cGMP signaling pathway, HASMC from severe asthma donors might possess inherent defects in their sGC or in redox enzymes that support sGC function. A majority of the severe asthma donor HASMC (12/17) and lung samples primarily expressed a dysfunctional sGC that was NO-unresponsive and had low heterodimer content and high Hsp90 association. This sGC phenotype correlated with lower expression levels of the supporting redox enzymes cytochrome b5 reductase, catalase, and thioredoxin-1, and higher expression of heme oxygenases 1 and 2 hinting towards a hypothesis that severe asthmatics are predisposed toward defective NO-sGC-cGMP signaling in their airway smooth muscle due to an inherent sGC dysfunction, which in turn is associated with inherent changes in the cell redox enzymes that impact sGC maturation and function. Therefore sGC activators might be a new target option for these patients with respect to optimized bronchodilation under these pathophysiologic conditions (see for example the following references: Arnab Ghosh, Cynthia J. Koziol-White, William F. Jester Jr., Serpil C. Erzurum, Kewal Asosingh, Reynold A. Panettieri Jr. see, Dennis J. Stuehr: An inherent dysfunction in soluble guanylyl cyclase is present in the airway of severe asthmatics and is associated with aberrant redox enzyme expression and compromised NO-cGMP signaling in Redox Biology 39 (2021) 101832; Maggie Lam, Jane E. Bourke, Ph.D., A New Pathway to Airway Relaxation: Targeting the "Other" Cyclase in Asthma American Journal of Respiratory Cell and Molecular Biology Volume 62 Number 1|January 2020; Cynthia J. Koziol-White, Amab Ghosh, Peter Sandner, Serpil E. Erzurum, Dennis J. Stuehr, and Reynold A. Panettieri, Jr.: Soluble Guanylate Cyclase Agonists Induce Bronchodilation in Human Small Airways, Am J Respir Cell Mol Biol Vol 62, Iss 1, pp 43-48, January 2020.).

By virtue of their activity profile, the compounds according to the invention, especially (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quinoline-2-carboxylic acid of formula I as well as its pseudopolymorphic forms, like e.g. (I-M-I) and (I-M-II) are particularly suitable for the treatment and/or prevention of cardiovascular and cardiopulmonary disorders such as primary and secondary forms of pulmonary hypertension.

The present invention furthermore provides the use of the compounds according to the invention, especially (5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I as well as its pseudopolymorphic forms, like e.g. (I-M-I) and (I-M-II) for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides the use of the compounds according to the invention especially (5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I as well as its pseudopolymorphic forms, like e.g. (I-M-I) and (I-M-II) for preparing a medicament for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides a medicament comprising at least one of the compounds according to the invention, especially (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quinoline-2-carboxylic acid of formula I as well as its pseudopolymorphic forms, like e.g. (I-M-I) and (I-M-II) for use in the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides the use of the compounds according to the invention, especially (5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I as well as its pseudopolymorphic forms, like e.g. (I-M-I) and (I-M-II) in a method for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The present invention furthermore provides a method for the treatment and/or prevention of disorders, in particular cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), comprising administering (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I, especially comparative example 11 as well as its pseudopolymorphic forms, like e.g. (I-M-I) and (I-M-II) once or twice daily for a period of equal or more than two days, preferably at least 2 to 7 consecutive days, preferably for a period of at least 14 consecutive days, in particular from after onset of treatment for the whole course of the disease in an inhalative dosage form, e.g. a dry powder inhaler in form of a dry powder formulation to a patient in need thereof, wherein said sGC activator has a sustained efficacy over a period of 24 hours, when inhalatively administered to a patient in need thereof.

The present invention further relates to the use of an inhalative dosage form of a sGC activator of formula I, especially comparative example 11, (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II) for the manufacture of a medicament for the treatment of a cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), administered once or twice daily for a period of equal or more than two days, preferably at least 2 to 7 consecutive days, preferably for a period of at least 14 consecutive days, in particular from after onset of treatment for the whole course of the disease, wherein said sGC activator has a sustained efficacy over a period of 24 hours when inhalatively administered to a patient in need thereof.

The present invention further relates to a packaged pharmaceutical composition comprising a container containing a dry powder inhaler (=DPI) and a pharmaceutical formulation comprising (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I as well as its pseudopolymorphic forms, like e.g. (I-M-I) and (I-M-II), said container furthermore containing instructions for using said dry powder, e.g. that after one deep inhalative breath the subjects have to hold breath for about 2 seconds, so that the dry powder drug condenses from the airstream onto the surface of the deeper lung areas where it is deposited close to its site of intended pharmacological action, to treat a cardiopulmonary disorder, preferably pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

In a preferred embodiment the present invention further relates to a packaged pharmaceutical composition comprising a container containing a dry powder inhaler (=DPI) and a pharmaceutical formulation comprising (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I as well as its pseudopolymorphic forms, like e.g. (I-M-I) and (I-M-II), said packaged pharmaceutical composition, comprising a container containing dry powder comprising (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid, said container furthermore containing instructions for administering said dry powder at a frequency of once or twice daily to treat a cardiopulmonary disorder, preferably pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP), furthermore a pulmonary disorder.

The present invention further relates to medicaments that contain at least one compound according to the invention, usually together with one or more inert, non-toxic, pharmaceutically suitable excipients, and use thereof for the aforementioned purposes.

The compounds according to the invention especially (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid of formula I as well as its pseudopolymorphic forms, like e.g. (I-M-I) and (I-M-II) can be used alone or in combination with other active compounds if necessary. The present invention further relates to medicaments containing at least one of the compounds according to the invention, especially (5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydro-quino-line-2-carboxylic acid of formula I as well as its pseudopolymorphic forms, like e.g. (I-M-I) and (I-M-II) and one or more further active compounds, in particular for the treatment and/or prophylaxis of the aforementioned diseases. As suitable combination active compounds, we may mention for example and preferably:

organic nitrates and NO-donors, for example sodium nitroprusside, nitroglycerin, isosorbide mononitrate, isosorbide dinitrate, molsidomine or SIN-1, and inhalational NO Ca-channel blockers used for PAH patients with preserved vasoresponsiveness compounds that inhibit the degradation of cyclic guanosine monophosphate (cGMP) and/or cyclic adenosine monophosphate (cAMP), for example inhibitors of phosphodiesterases (PDE) 1, 2, 3, 4 and/or 5, in particular PDE 3 inhibitors as ensifentrine, PDE 4 inhibitors such as roflumilast, tanimilast or revamilast and PDE 5 inhibitors such as sildenafil, vardenafil, tadalafil, udenafil, dasantafil, avanafil, mirodenafil or lodenafil;

NO-independent but haem-dependent stimulators of guanylate cyclase, in particular riociguat and the compounds described in WO 00/06568, WO 00/06569, WO 02/42301, WO 03/095451, WO 2011/147809, WO 2012/004258, WO 2012/028647, WO 2012/059549 and WO2014/068099;

prostacyclin analogs and IP receptor agonists, for example and preferably iloprost, beraprost, treprostinil, epoprostenol or NS-304;

endothelin receptor antagonists, for example and preferably bosentan, darusentan, ambrisentan or sitaxsentan;

human neutrophile elastase (HNE) inhibitors, for example and preferably sivelestat or DX-890 (Reltran);

compounds which inhibit the signal transduction cascade, in particular from the group of the tyrosine kinase inhibitors, for example and preferably dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib, masitinib or tandutinib;

compounds which act as ligand trap with high selectivity for multiple proteins within the TGF-beta superfamily, including activins, GDFs, and others with its believed ability to block the TGF-beta superfamily signaling pathway, and thereby could promote a rebalancing of bone morphogenetic protein receptor type II (BMPR-II) signaling and, potentially, restore vascular homeostasis as sotatercept Rho kinase inhibitors, for example and preferably fasudil, Y-27632, SLx-2119, BF-66851, BF-66852, BF-66853, KI-23095 or BA-1049;

anti-obstructive agents as used, for example, for the therapy of chronic-obstructive pulmonary disease (COPD) or bronchial asthma, for example and preferably inhalatively or systemically administered beta-receptor mimetics (e.g. salbutamol, salmeterol) or inhalatively administered anti-muscarinergic substances (e.g. ipratropium, tiotropium);

- antiinflammatory and/or immunosuppressive agents as used, for example for the therapy of chronic-obstructive pulmonary disease (COPD), of bronchial asthma or pulmonary fibrosis, for example and preferably systemically or inhalatively administered corticosteroides, flutiform, pirfenidone, acetylcysteine, azathioprine or BIBF-1120, nintedanib or treprostinil;
- active compounds used for the systemic and/or inhalative treatment of pulmonary disorders, for example for cystic fibrosis (alpha-1-antitrypsin, aztreonam, ivacaftor, lumacaftor, ataluren, amikacin, levofloxacin), chronic obstructive pulmonary diseases (COPD) (Tiotropium, LABA/LAMA, LAS40464, PT003, SUN-101), acute respiratory distress syndrome (ARDS) and acute lung injury (ALI) (interferon-beta-la, traumakines, PEG-Adrenomedullin, inhaled sGC modulators e.g. BAY1211163), obstructive sleep apnoe (VI-0521, TASK channel blocker and ADRA2C antagonists), bronchiectasis (mannitol, ciprofloxacin), Bronchiolitis obliterans (cyclosporine, aztreonam);
- antithrombotic agents, for example and preferably from the group of platelet aggregation inhibitors, anticoagulants or profibrinolytic substances.

Antithrombotic agents are preferably to be understood as compounds from the group of platelet aggregation inhibitors, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, melagatran, dabigatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

The agents for lowering pulmonary blood pressure are preferably to be understood as compounds from the group of calcium antagonists, PDE5 inhibitors, sGC stimulators and activators, prostacyclin analogs and IP receptor agonists, and endothelin receptor antagonists.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an endothelin receptor antagonist, for example and preferably bosentan, darusentan, ambrisentan or sitaxsentan.

Technical Objective

Considering the background and state of the art it was a technical objective of the present invention to provide a suitable inhalative dosage form/medicament for use in the treatment of cardiopulmonary disorders as well as a suitable inhalative dosage regime for treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

In order to develop a suitable inhalative medicament for use in the treatment of cardiopulmonary disorders as well as a suitable inhalative dosage regime for treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP) certain technical and medical needs and requirements regarding the drug substance as well as the drug product need to be fulfilled.

First of all the active ingredient (drug substance) needs to have suitable physicochemical, pharmacokinetic and pharmacodynamic properties. e. g. the drug substance needs to be suitable for an inhalative treatment and it needs to have sufficient efficacy to treat cardiopulmonary disorders. Furthermore the active ingredient should have clear efficacy in the envisaged PH forms, also on top of standard of care (SoC e.g. endothelin antagonists such as bosentan, PDE5 inhibitors e.g. sildenafil, IP agonists e.g. Ilomedin, calcium channel blockers e.g. and sGC stimulators e.g. riociguat). Additionally the active ingredient should have further advantageous properties, in particular with respect to its pulmoselective action (in contrast to a systemic action), e.g. a high lung selectivity, low to no VQ-mismatch, its lung retention time and/or its duration of action following intrapulmonary administration. The drug substance should be suitable for a chronic treatment regime/use. Furthermore the drug substance should show improved ventilation, e.g. a bronchodilatory effect and/or an inhibitory effect on airway hyper-responsiveness and inflammation and thus be suitable in particular for the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

The drug substance (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quinoline-2-carboxylic acid of formula (I) as well as its pseudopolymorphic forms of formulae (I-M-I) and (I-M-II) should have a sustained vasodilative and bronchodilative efficacy over a period of more than 12 hours, of up to 24 hours, characterized by e.g. an improvement of pulmonary haemodynamics, leading to a lower pulmonary vascular resistance (PVR), an improved walking distance in the 6 minutes walking test, a shift in NYHA (New York Health Association) patient classification or an improved lung function e.g. a higher FEV1 (forced expiratory volume a person can exhale during the first second of a forced breath) and a lower specific airway resistance (sRaw), a parameter indicating bronchodilative activity in the healthy lung, when inhalatively administered.

Furthermore the active ingredient (drug substance) needs to be provided in a defined stable, crystalline form to be suitable for dry powder pharmaceutical formulations and to be administered in a specific, optimized inhalative dosage regimen for treatment of cardiopulmonary disorders.

Additionally the final drug product (formulation) needs to have suitable properties, e.g. a sufficient chemical stability and a sufficient aerosol performance in order to have the drug substance delivered to the target organs, e.g. the lungs, in sufficient amounts with low to no adverse effects for the patient. An adequate physicochemical stability is required to keep the active ingredient in its chemical constitution and avoid unacceptable degradation or stereochemical conversion. Even more importantly, the physical, morphic form needs to be maintained as not to alter biopharmaceutical properties affecting pharmacokinetic behavior of the active ingredient. Stable and proper aerosol performance means a reproducible drug delivery in the sense of a mean delivered dose and the uniformity of delivered dose as well as a reproducible drug delivery of a desirably high portion of the available nominal drug dose in the final dosage form to the site of action. In practical terms and tested by appropriate analytical methods such as aerodynamic particle size distribution by cascade impaction a high portion of micronized fine active ingredient particles should be recovered as fine particle dose (alternatively fine particle mass) and fine particle fraction in % relative to the delivered dose and/or nominal dose.

The present inventors surprisingly found, that (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I can be manufactured in a larger scale in a reliable manner by an improved chemical process.

Additionally the present inventors found that (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I exists in stable crystalline forms like e.g. (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) or monohydrate II of formula (I-M-II), preferably monohydrate I of formula (I-M-I).

Furthermore the present inventors surprisingly found, that crystalline forms of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I can be made available by a novel, selective crystallization process, preferably the monohydrate form I (I-M-I) can be selectively obtained by crystallization form methanol and water or methanol, acetone and water.

Therefore the drug substance 5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I is made available for the first time in a suitable format for inhalative dosage forms, medicaments and inhalative dosage regimes, preferably DPIs.

Surprisingly preclinical experiments revealed for the sGC activator (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II) (see C-2.1), that it showed slower penetration of the saphenous artery compared to Cinaciguat in isolated vessels, a prolonged recovery factor in isolated bronchioles as well as an increased wash-out score in Langendorff heart experiments (see experimental part C-1.1 (isolated vessels) C-3.1 (bronchioles) and C-1.2 (Langendorff)) as well as an improved lung selectivity and extended duration of action (prolonged selective pulmonary arterial pressure (=PAP) reduction without systemic blood pressure (=BP) reducing effects after inhaled application) in PAH animal models (pig and dog) (see experimental part C-2.1 (pig) and C-2.2 (dog)).

Furthermore the prediction of duration of action and prediction of human dose has been investigated.

Considering 100 μg/kg as effective dose in the minipig model, 300-1370 μg lung deposited dose is postulated as effective dose, depending on the consideration of different interspecies protein binding (see C-2.1).

Finally the pharmacological effects of different pseudopolymorphic forms of the active ingredients have been investigated. All dry powder formulations comprising crystalline forms of comp. example 11, e.g. sesquihydrate example 6e selectively and dose-dependently reduced PAP after inhaled application in this model of acute PAH with a long duration of action of at least 4 h. A clear dose-response curve was observed for increasing applied doses (see C-2.1).

These findings support the suitability of 5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms monohydrate I (example 4) or monohydrate II (example 2) for a once or twice daily inhalative treatment regime comprising 240 to 4000 μg, preferably 480 to 2000 μg, of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid as well as its pseudopolymorphic forms, like e.g. (I-M-I) and (I-M-II) for the use in the treatment of cardiopulmonary diseases, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

(5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid of formula I (comparative example 11) as well as its polymorphic forms monohydrate I of formula (I-M-I) according to the present invention and comparative examples 3, 4 and 5 were tested to evaluate lung selectivity as well as duration of action in the minipig model (C-2.1). Whereas all 3 compounds show a suitable lung selectivity only comparative example 11 and comparative example 4 show a sufficient duration of action. Comparative example 11 shows a selective PAP effect with a maximal effect for the whole observation interval of 240 min whereas comparative example 3 shows its maximal effect on PAP 30 min after inhaled application which was again completely resolved after 120 min. Comparative example 11 and comparative example 4 were evaluated with respect to duration of action in the conscious hypoxia challenged dog model (C-2.2). In this model, in contrast to comparative example 4, comparative example 11 showed a consistent long duration of effect (PAP reduction) for up to 17 hrs. Therefore in contrast to comparative examples 3, 4 and 5 (disclosed as examples 2, 37 and 39 in WO 14/012934-A1), comparative example 11, corresponding to the present invention, is most suitable for a once to twice daily treatment regime.

To evaluate intrapulmonary selectivity, comparative example 11 was evaluated vs. systemic applied vasodilators in a model of unilateral broncho-occlusion. In this model, after inhaled application no negative effect on desaturation area in contrast to systemic applied comparative example 11 or standard of care could be detected. Thus, after inhaled application, comparative example 11 showed a better risk-benefit ratio compared to systemic applied vasodilators and might be an effective but also safe treatment for patients with PH, being at risk for a ventilation-perfusion-mismatch under treatment of systemic applied vasodilators (C-2.3). Furthermore after inhaled application of the drug substance an improved ventilation, e.g. a bronchodilatory effect (C-3.1 and C-3.2) and an inhibitory effect on airway hyper-responsiveness and inflammation (C-3.3) could be shown preclinically.

Furthermore we found for the sGC activator (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid in form of its crystalline form monohydrate I of formula (I-M-I) (example 4) in first clinical studies (see experimental part C-4.1) increased cGMP levels as second messenger molecule of sGC activation as surrogate for drug concentration in the lung (indicative of target engagement) as well as beneficial bronchodilatory properties in healthy volunteers over a time period of more than 12 hrs, up to 24 hrs after dry powder application (e.g. a decrease of total specific airway resistance (sRaw), a parameter indicating bronchodilative activity in the lung) supporting the long lung retention time clinically as well as the suitability of example 4 to be successfully used in the treatment of cardiopulmonary diseases. Up to a dose of 4000 μg no clinically meaningful effect on systemic blood pressure were observed in healthy volunteers.

Moreover, we found a selective decrease in pulmonary arterial pressure and pulmonary vascular resistance in patients with pulmonary hypertension without clinically relevant effects on systemic blood pressure at doses up to 4000 μg (including). The effect was sustained with no decrease in response until the end of the measurement period of 3 h (a measurement period of >3 h was technically not feasible). A lung retention time of example 4 beyond the 3 h (presumably over a time period of more than 12 hrs, up to 24 hrs after dry powder application) can be concluded from the long plasma half-life measured in the investigation described in C 4-3 (see experimental part C-4.3).

Additionally the analysis of plasma concentrations after oral, intravenous and inhalative administration of the drug substance (example 4) showed the longest half-life of the active ingredient after inhaled application (C-4.3). The emitted (lung) dose has been determined to be 720 μg after inhalation of 1000 μg in humans. The outcome from this investigation confirms the lung dose and that the half-life is adequate for an inhaled dry powder administration enabling a once daily treatment for a sufficient 24 h drug coverage of example 4 in the lung.

In conclusion all results show that (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II), especially the monohydrate I of formula (I-M-I) are suitable in particular for the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP) and are adequate for an inhaled dry powder administration enabling a once daily treatment for a sufficient 24 h drug coverage of example 4 in the lung.

Also these findings support the suitability of example 4 for a once or twice daily inhalative treatment regime comprising 240 to 4000 μg, preferably 480 to 2000 μg for a period of equal or more than two days, preferably at least 2 to 7 consecutive days, preferably for a period of at least 14 consecutive days, in particular from after onset of treatment for the whole course of the disease, of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid as well as its crystalline form monohydrate I of formula (I-M-I) for the use in the treatment of cardiopulmonary diseases, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

Surprisingly, it has now been found in healthy volunteers after medication on 7 days (after a first dose a dose free period of 48 hours follows, afterwards 6 doses every 24 hours) that a once daily inhalative administration of a sGC activator of formula I, especially example 4, (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid in form of monohydrate I of formula (I-M-I) has a prolonged sustained effect over a period of more than 12 hours, up to 24 hours, that may lead in patients to e.g. an improved hemodynamic effect, like e.g. a lower pulmonary vascular resistance (PVR), an improved 6 minutes walking test, a shift in NYHA patient classification or an improved lung function e.g. a higher FEV1 via bronchodilation when inhalatively administered once or twice daily.

Additionally we found that (5S)-{[2-(4-carboxyphenyl) ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid of formula I (comparative example 11) has beneficial physicochemical properties e.g. protein binding and CACO flux (see experimental part C-5.1 (Caco permeability) and C-5.2 (protein binding)) which make comparative example 11 a suitable compound for local treatment of cardiopulmonary diseases by dry powder inhalation to the lung. Moreover, our data indicate that comparative example 11, esp. monohydrate form I not only shows effective reduction of the PAP via selective vasodilation in the lungs but also showed longer lasting bronchodilatory properties compared to cinaciguat which may be beneficial in the once or twice daily inhalative treatment of PH patients with chronic lung diseases (PH group 3) or even have a potential in the treatment of patients with restricted lung function, e.g. asthmatics.

Therefore the drug substance, e.g. (5S)-{[2-(4-carboxyphenyl)ethyl][2-(2-{[3-chloro-4'(trifluoromethyl)biphenyl- 4-yl]methoxy}phenyl)ethyl]-amino}-5,6,7,8-tetrahydroquinoline-2-carboxylic acid of formula (I), as well as its pseudopolymorphic forms (I-M-I) and (I-M-II) according to the present invention have excellent primary pharmacological properties:

- (5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid is a potent and selective sGC activator and provides a new approach in the treatment of PH after inhalation.
- (5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid selectively decreased elevated PAP after inhaled application in different disease relevant animal models (thromboxane and hypoxia challenged rats, pigs, and dogs) with a long duration of action, suggesting a once to twice daily application.
- In an unilateral ventilated minipig model as a proxy of VQ-mismatch, (5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid after inhaled application lowered PAP without negative effects on oxygenation in contrast to systemic applied vasodilators.
- On top of PAH standard-of-care (SoC) (e.g. bosentan, sildenafil, Ilomedin, and riociguat), (5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid selectively decreased elevated PAP after inhaled application in the PAH-minipig model.
- The efficacy of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid was enhanced under experimental conditions of oxidative stress (1H-[1,2,4]Oxadiazolo[4,3-a]quinoxalin-1-one, a highly selective, irreversible, heme-site inhibitor of soluble guanylyl cyclase [ODQ], L-No-Nitroarginine methyl ester [L-NAME] treatment).
- With respect to ventilation, (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid showed a bronchodilatory effect (acetylcholine [ACh] rat model) and an inhibitory effect on airway hyper-responsiveness and inflammation (chronic ovalbumin asthma mice model).
- Plasma concentrations of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid especially in the form of its monohydrate I (example 4) were measured after three different types of administrations (oral, intravenous, inhalation) and revealed the longest elimination half-life after inhaled application.
- The emitted (lung) dose has been determined to be 720 μg after inhalation of 1000 μg in humans.
- First studies in humans with the sGC activator (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of its crystalline form monohydrate I of formula (I-M-I) (example 4) showed sGC activation and long lung retention time combined with bronchodilatory properties and selective decrease of pulmonary arterial pressure and pulmonary vascular resistance at a good local and systemic tolerability up to the highest tested dose of 4000 μg (including).

Therefore the drug substance, e.g. (5S)-{[2-(4-carboxyphenyl)ethyl][2-(2-{[3-chloro-4'(trifluoromethyl)biphenyl-4-yl]methoxy}phenyl)ethyl]-amino}-5,6,7,8-tetrahydroquinoline-2-carboxylic acid of formula (I), as well as its pseudopolymorphic forms (I-M-I) and (I-M-II) according to the present invention has excellent primary pharmacological and pharmacodynamic properties in patients including reduction of pulmonary artery pressure (mPAP) and pulmonary vascular resistance (PVR), bronchodilation as measured by e.g. FEV1, pulmonary selectivity with low to no systemic adverse effects (especially on systemic hemodynamics, such as clinically relevant changes in blood pressure or heart rate) and low to no increase of VQ-mismatch to avoid relevant desaturation, furthermore sufficient lung retention time and/or sufficient duration of action following intrapulmonary administration.

Surprisingly, it has been found, that local administration, esp. inhalative administration of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, esp. in form of monohydrate I has the potential of being successful in the control of cardiopulmonary disorders, such as pulmonary arterial hypertension (PAH), chronic thromboembolic pulmonary hypertension (CTEPH), and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP). The active ingredient concentration in the lungs can be kept for a long period at a level desirable from the medical viewpoint for optimal treatment. Besides the higher and long-lasting active ingredient level at the site of the disease, it is possible to achieve simultaneously a comparatively low systemic concentration of the active ingredient, so that side effects of the medication could be avoided, e.g. no clinically relevant systemic blood pressure decrease.

Surprisingly the drug substance can be provided in a single, crystalline and chemically stable form, the monohydrate I of formula (I-M-I). This form is also stable under micronization conditions.

Surprisingly the pharmaceutical dry powder formulations according to the present invention are characterized through an excellent aerosol performance (e.g. high fine particle dose, fine particle fraction and delivered dose with respect to the nominal dose) and a sufficient chemical stability. Furthermore the pharmaceutical dry powder formulations according to the present invention can be made in a technically reliable manner by a novel process (e.g. blend uniformity).

Surprisingly pharmaceutical dry powder formulations, comprising (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) in combination with a lactose carrier, comprising lactose monohydrate as a mixture of lactose coarse and lactose fine, are suitable for an inhalative treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

In view of the prior art these findings were not foreseeable as the excellent primary pharmacological and pharmacodynamic properties of (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid of formula I especially its longer duration of action in comparison to similar 5,6,7,8-tetrahydroquinoline-2-carboxylic acids like e.g. comparative examples 3, 4 and 5 were not publicly known.

Moreover these findings were not foreseeable as the pseudopolymorphic forms, especially the crystalline stable hydrates were not publicly known.

Surprisingly monohydrate form I (I-M-I) (example 4) was identified as the stable pseudopolymorphic form of (5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid of formula I after micronzation and stability studies.

Furthermore it was surprising that modification I (I-M-I) was available by a selective crystallization from methanol, acetone water.

Furthermore no inhalative solid carrier formulation comprising acid of formula (I) nor any of its crystalline forms like e.g. monohydrate form I (I-M-I) or monohydrate form II (i-M-II) was known.

Therefore the technical objective of the present invention was to provide a novel, suitable inhalative dosage regimen for treatment of cardiopulmonary disorders, comprising administering (5S)-{[2-(4-carboxyphenyl)ethyl][2-(2-{[3-chloro-4'-(trifluoromethyl)biphenyl-4-yl]methoxy}phenyl) ethyl]-amino}-5,6,7,8-tetrahydroquinoline-2-carboxylic acid of formula I, preferably in form of one of its salts or solvates or hydrates, preferably (5S)-{[2-(4-carboxyphenyl) ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid monohydrate I of formula (I-M-I) in form of a dry powder application to a patient in need thereof wherein the active ingredient has excellent primary pharmacological and pharmacodynamic properties in patients including reduction of pulmonary artery pressure (mPAP) and pulmonary vascular resistance (PVR), bronchodilation as measured by e.g. FEV1, pulmonary selectivity with low to no systemic adverse effects (especially on systemic hemodynamics, such as clinically relevant changes in blood pressure or heart rate) and low to no increase of VQ-mismatch to avoid relevant desaturation, furthermore sufficient lung retention time and/or sufficient duration of action following intrapulmonary administration.

The present inventors surprisingly found, that the novel, suitable inhalative dosage regime for treatment of cardiopulmonary disorders comprises administering (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid of formula (I), preferably in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl) ethyl]-amino}-5,6,7,8-tetrahydroquinoline-2-carboxylic acid monohydrate I of formula (I-M-I) or (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid monohydrate II of formula (I-M-II) once or twice daily for a period of equal or more than two days, preferably at least 2 to 7 consecutive days, preferably for a period of at least 14 consecutive days, in particular from after onset of treatment for the whole course of the disease in an inhalative dosage form, comprising 240 to 4000 μg, preferably 480 to 2000 μg, of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, to a patient in need thereof, preferably as dry powder application, preferably as a combination of a dry powder inhaler and (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid as a dry powder formulation, comprising the active ingredient and a pharmaceutically suitable excipient or carrier, while preferably the active ingredient and a pharmaceutically suitable excipient are filled in a hard capsule.

In order to provide the suitable inhalative dosage regimen for the treatment of cardiopulmonary disorders according to the present invention it is important to provide a specific dosage of the specific drug substance in a defined inhalable format, wherein the nominal dosage is sufficient to treat the envisaged cardiopulmonary diseases.

In order to determine the sufficient human dose it was necessary to select the most predictive animal model for PAH and to determine the minimum effective dose as well as to define the dosage range to be evaluated in first clinical studies (minimal effective dose, effective dose and maximal tolerable dose).

Therefore the active ingredient should be adminstered to a patient in need thereof once or twice daily, for a period of equal or more than two days, preferably at least 2 to 7 consecutive days, preferably for a period of at least 14 consecutive days, in particular from after onset of treatment for the whole course of the disease in an inhalative dosage form, comprising 240 to 4000 μg, preferably 480 to 2000 μg.

Consequently the novel inhalative dosage regimen for treatment of cardiopulmonary disorders according to the present invention is suitable for use in the treatment of cardiopulmonary disorders, such as pulmonary arterial hypertension (PAH), chronic thromboembolic pulmonary hypertension (CTEPH), and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

Human Dose Estimation

The formulation according to the invention can be characterized regarding delivered dose (DD), determined by filter collection tube method and fine particle dose (FPD) determined by cascade impaction. The analytical methods to determine delivered dose and fine particle dose are generally described in Pharmacopoeia as these are harmonized for inhalable dosage forms e.g. dry powder inhalation formulations and constitute conventions for quality control for e.g. Release of DPI products for clinical use.

It has been discovered that different formulations with different nominal doses lead to a different delivered dose and, more importantly, to a certain fine particle dose that characterize the effective dose as this is being delivered into the deep lung to the site of action. In theory the delivered dose and fine particle dose and fraction would have a linear relationship in correlation to the filled powder dose, but due to several interacting factors this cannot be predicted reliably, may practically differ and requires associated studies. It is desirable that a delivered dose is as close to the nominal dose as possible. In practice, the delivered dose will never match the nominal by 100% as residuals are always left to some degree on surfaces of inhalation capsules and on the aerosol path of the used dry powder inhaler. Of course, this property is highly depending on the physicochemical properties of the active ingredient and its release behaviour from the powder blend. Analogously the fine particle dose and fine particle fraction are desired to be as high as possible in relation to filled nominal active ingredient content to exploit the available drug amount as good as possible and to reduce loss of active ingredient or to decrease portions delivered to other compartments than the deep lung (e.g. by swallowing via oral impact of larger drug particles).

Due to the nature of inhalable formulations and in contrast to e.g. oral solid formulations not all of the nominal content will be delivered into the lung. Several fractions can be defined that are characterized by specific analytical methods in-vitro and support the estimation of dose fractions delivered to the patient during inhalation (delivered dose or emitted dose) and the fraction of fine particles below e.g. 5 μm or 4.5 μm as that is expected to reach the deep airways and alveoli (fine particle dose). For an overview refer to the table 1 below.

TABLE 1

Definition of terms with respect to dosages

| Terminology | Abbreviation | Definition | Synonyms or equivalent terms |
|---|---|---|---|
| Nominal Dose | ND | Total dose of API filled in the capsule (clinical studies) or nebulizer (pharmacological animal experiments). | Capsule dose, Capsule strength, Quantity of drug substance labeled on the capsule. |
| Emitted Dose | ED | Dose that actually leaves the device at the mouthpiece under defined laboratory test conditions. | Corresponds to the delivered dose |
| Delivered Dose | DD | Dose that is estimated or calculated to be inhaled by the animal (from the tip of the nose/mouth up to the alveoli) or quantity of drug substance that is available to the human, ex-device, on a per dose basis. | Corresponds to the emitted dose |
| Lung Deposited Dose | LDD/LD | Dose that is considered to reach the lung (tracheobronchial and pulmonary deposition) of the respective animal or human. | It is considered that the FPD (measured in-vitro) is corresponding to the lung deposited dose in humans. |
| Fine Particle Dose | FPD | Parameter calculated from the aerodynamic particle size distribution (ASPD) function determined by in-vitro cascade impaction analysis. The mass of active pharmaceutical ingredient (API) per actuation or dose delivery of the inhaler contained in particles finer than 4.5-5 μm aerodynamic diameter (e.g. according to European Pharmacopoeia). | For DPI, it is assumed that the FPD is basically equivalent to the human lung deposited dose |
| Fine Particle Fraction | FPF | The fraction of fine particle mass according to FPD related to the ED/DD or to the nominal dose (in %) | |

Evaluation of Pharmacokinetic/Pharmacodynamic (PK/PD) Relationship

The anesthetized thromboxane A2 challenged PAH-minipig model (see experimental part C-2.1) is considered to be the most relevant and sensitive model for the prediction of the human minimal effective and effective doses (MED, ED). To determine effective LDs, experiments in minipigs were repeated with the difference that absorbing filters were attached at the end of the tubes to determine the deposited lung dose. Nebulization of comparative example 11 resulted in a mean nebulization efficiency of 5% of nominally applied doses resulting in LDs of about 0.15 μg/kg (3 μg/kg ND), 0.5 μg/kg (10 μg/kg ND), 1.5 μg/kg (30 μg/kg ND) and 5 μg/kg (100 μg/kg ND). Assuming a minimal effective ND of 3 μg/kg (5% reduction in PAP) the minimal effective deposited LD is considered as 0.15 μg/kg (see FIG. 1).

The resulting lung deposited doses in the minipig of 0.15, 0.5, 1.5 and 5 μg/kg were multiplied by 60 kg to achieve the lung dose in humans. Thus, the FPD reflecting the PAP reduction for a 60 kg human are calculated to be 9, 30, 90 and 300 μg.

Thus, via a direct up-scaling from minipig, the predictive MED (5% PAP reduction) for a human based on a 60 kg body weight is calculated to be 9 μg LDD, not considering protein binding within the respiratory tract. As a surrogate for unbound concentrations, which are the likely active concentrations in the lung, we considered respective differences in fractions unbound in plasma of minipig and human. This consideration results in a minimum effective lung dose (LD) for a 60 kg participant of 41 μg LDD for the assumed 5% reduction on PAP. Consequently, the predictive minimal human effective dose is in the range from 9 μg LDD to 41 μg LDD based on a 60 kg body weight (see FIG. 2).

TABLE 2

| Effective lung dose with and without consideration of interspecies differences in protein binding | | |
|---|---|---|
| | Total lung deposited dose in a 60 kg human [µg] | |
| Relative lung deposited dose in minipig [µg/kg] | Interspecies difference in protein binding not considered[a] | Interspecies difference in protein binding considered[b] |
| 0.15 µg/kg (3 µg/kg nominal dose) | 9 | 41 |
| 0.50 µg/kg (10 µg/kg nominal dose) | 30 | 137 |
| 1.5 µg/kg (30 µg/kg nominal dose) | 90 | 410 |
| 5.0 µg/kg (100 µg/kg nominal dose) | 300 | 1370 |

[a]Calculation (relative lung deposited dose in minipig × 60 kg)

[b]Calculation (relative lung deposited dose in minipig × 60 kg × 4.55 (ratio of fraction unbound minipig (plasma fu 0.348%)/human (plasma fu 0.0764%))

This translation was also conducted for effective doses (effective PAP reduction>five up to 35 percent for longer time periods up to the complete observation period of 4 hrs) based on the relative lung deposited doses in minipigs as listed in Table 2.

Thus, effective lung deposited doses in humans based on the minipig data were expected in the range of 9 µg to 1370 µg.

Considering 100 µg/kg as highest effective dose in the minipig model without systemic side effects (BP reduction), with a corresponding maximal effective human LDD of 1370 µg, 9-1370 µg lung deposited dose is postulated as effective doses, depending on different interspecies protein binding (see table 2). For DPI products, it is assumed that the fine particle dose (FPD) is basically equivalent to the human lung deposited dose.

To address the need for a wide range of lung deposited doses and translate them into technical specifications for fine particle dose (FPD targets) of the dry powder inhalation capsules to be manufactured, some calculations and approximations were done. Generally, an inhalable product based on a powder blend carrier formulation is considered to have an excellent performance if a fine particle fraction of greater than 20% of the nominal dose is achieved. Further, a high FPF(%) related to the delivered dose is desired for a high performance inhalation product and was targeted at ≥30%. Taking technical and practical considerations into account (active concentration in powder blend and capsule fill mass of the blends) the FPD targets were subsequently used to establish defined nominal doses for the finished dry powder inhalation capsules. FPD and DD targets as well as corresponding nominal doses are outlined in the following two tables 3 and 4.

TABLE 3

| Nominal dose targets and targets for fine particle dose and % fraction (ds) | | | | |
|---|---|---|---|---|
| Capsule nominal dose [µg] | Mean FPF (FPD % of nominal) | Mean FPF (FPD % of DD) | Mean FPD <4.5 µm (target[a]) [µg] | Min FPD <4.5 µm (65% of target[b]) [µg] |
| 60 | ≥20% | ≥30% | 12 | 8 |
| 75 | ≥20% | ≥30% | 15 | 10 |
| 120 | ≥20% | ≥30% | 24 | 16 |
| 480 | ≥20% | ≥30% | 96 | 62 |
| 500 | ≥20% | ≥30% | 100 | 65 |
| 1000 | ≥20% | ≥30% | 200 | 130 |
| 2000 | ≥20% | ≥30% | 400 | 260 |
| 3000 | ≥20% | ≥30% | 600 | 390 |
| 6000 | ≥20% | ≥30% | 1200 | 780 |
| 9000 | ≥20% | ≥30% | 1800 | 1170 |

[a]target value calculated from FPF % of nominal target

[b]minimum targets were established due to expected variability in manufacturing and analytical determinations.

For the relation between delivered and nominal dose there is no general binding (e.g. compendial) requirement as this cannot be defined due to the very different nature of different active ingredients, having different properties and the manufactured pharmaceutical formulations thereof. Rather the uniformity of delivered dose is defined by pharmacopoeia to assure dose-to-dose consistency. The target delivered dose is an empirical parameter resulting from multiple determinations of a defined dosage form with a defined dry powder inhalation device under standardized conditions. The expected mean delivered dose should fall within 85-115% of the target DD. The minimum delivered dose requirement accounts for the 85% lower limit of the mean delivered dose range. A target delivered dose percentage (from 50% to 65% of nominal) was defined for all nominal doses which is not linear and needs to take into consideration the relatively higher content of active ingredient adhesion on e.g. capsule and device surfaces specifically with lower nominal filled doses.

TABLE 4

Nominal doses, DD targets and related min delivered dose

| Capsule nominal dose [μg] | Mean DD (% of nominal) | Mean DD (target[4]) [μg] | Min DD (85% of target) [μg] |
|---|---|---|---|
| 60 | ≥50% | 30 | 26 |
| 75 | ≥50% | 38 | 32 |
| 120 | ≥60% | 72 | 61 |
| 480 | ≥60% | 288 | 245 |
| 500 | ≥60% | 300 | 255 |
| 1000 | ≥65% | 650 | 553 |
| 2000 | ≥65% | 1300 | 1105 |
| 3000 | ≥65% | 1950 | 1658 |
| 6000 | ≥65% | 3900 | 3315 |
| 9000 | ≥65% | 5850 | 4973 |

Therefore the pharmaceutical dry powder formulations according to the present invention are suitable medicaments for treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

Considering the background and state of the art it was a technical objective of the present invention to provide suitable carrier based dry powder formulations, comprising (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I, preferably (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid monohydrate I of formula (I-M-I) in combination with a lactose carrier in order to obtain a suitable inhalative medicament for use in the treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

In order to develop a suitable inhalative medicament for use in the treatment of cardiopulmonary disorders, such as pulmonary arterial hypertension (PAH) chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP) certain technical and medical needs and requirements regarding the drug substance as well as the drug product need to be fulfilled.

First of all the active ingredient (drug substance) needs to have suitable physicochemical, pharmacokinetic and pharmacodynamic properties. e. g. the drug substance needs to be suitable for an inhalative treatment and it needs to have sufficient efficacy to treat cardiopulmonary disorders. Furthermore the active ingredient should have clear efficiency in the envisaged PH forms, also on top of standard of care (SoC e.g. endothelin antagonists such as bosentan, PDE5 inhibitors e.g. sildenafil, IP agonists e.g. Ilomedin, calcium channel blockers e.g. and sGC stimulators e.g. riociguat). The active ingredient should also have further advantageous properties, in particular with respect to high lung selectivity with pulmoselective action (in contrast to a systemic action), low to no VQ-mismatch, its lung retention time, and/or its duration of action following intrapulmonary administration. Therefore the drug substance should be suitable for chronic treatment regime/use. Furthermore the drug substance should cause improved ventilation, e.g. a bronchodilatory effect and an inhibitory effect on airway hyper-responsiveness and inflammation and thus be suitable in particular for the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-LIP).

The drug substance (5S)-{[2-(4-carboxyphenyl)ethyl][2-(2-{[3-chloro-4'-(trifluoromethyl)biphenyl-4-yl] methoxy}phenyl)ethyl]amino}-5,6,7,8-tetrahydro-quinoline-2-carboxylic acid of formula (I) as well as its polymorphic forms of formulae (I-M-I) and (I-M-II) should have a sustained vasodilative and bronchodilative efficacy over a period of more than 12 hours, of up to 24 hours, characterized by e.g. an improved haemodynamic effect, leading to a lower pulmonary vascular resistance (PVR), an improved walking distance in the 6 minutes walking test, a shift in NYHA (New York Health Association) patient classification or an improved lung function, e.g. a higher FEV1 (forced expiratory volume a person can exhale during the first second of a forced breath) or a lower specific airway resistance (sRaw), a parameter indicating bronchodilative activity in the healthy lung, when inhalatively administered.

Furthermore the active ingredient (drug substance) needs to be provided in a defined stable, crystalline form suitable for dry powder pharmaceutical formulations and corresponding inhalative dosage regime for treatment of cardiopulmonary disorders.

Additionally the final drug product (formulation) needs to have suitable properties, e.g. a sufficient chemical stability and a sufficient aerosol performance in order to deliver the drug substance to the target organs, e.g. the lungs, in sufficient amounts with low to no adverse effects for the patient. An adequate physicochemical stability is required to keep the active ingredient in its chemical constitution and avoid unacceptable degradation or stereochemical conversion. Even more importantly, the physical, morphic form needs to be maintained as not to alter biopharmaceutical properties affecting pharmacokinetic behavior of the active ingredient. Stable and proper aerosol performance means a reproducible drug delivery in the sense of a mean delivered dose and the uniformity of delivered dose as well as a reproducible drug delivery of the a desirably high portion of the available nominal drug dose in the final dosage form to the site of action. In practical terms and tested by appropriate analytical methods such as aerodynamic particle size distribution by cascade impaction a high portion of micronized fine active ingredient particles should be recovered as fine particle dose (alternatively fine particle mass) and fine particle fraction in % relative to the delivered dose and/or nominal dose.

The present inventors surprisingly found, that (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I can be manufactured in a larger scale in a reliable manner by an improved chemical process.

Additionally the present inventors found that (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I exists in stable crystalline forms like e.g. (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) or monohydrate II of formula (I-M-II), preferably monohydrate I of formula (I-M-I).

Furthermore the present inventors surprisingly found, that crystalline forms of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I can be made available by a novel, selective crystallization process, preferably the monohydrate form I (I-M-I) can be selectively obtained by crystallization form methanol, acetone, water.

Therefore the drug substance 5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I is made available for the first time in a suitable format for inhalative dosage forms, medicaments and inhalative dosage regimes, preferably DPIs.

Surprisingly preclinical experiments revealed for the sGC activator (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I (=comparative example 11) that it showed slower penetration of the saphenous artery compared to Cinaciguat in isolated vessels, a prolonged recovery factor in isolated bronchioles as well as an increased wash-out score in Langendorff heart experiments (see experimental part C-1.1 (isolated vessels) C-3.1 (bronchioles) and C-1.2 (Langendorff) as well as an improved lung selectivity and extended duration of action (prolonged selective pulmonary arterial pressure (=PAP) reduction without systemic blood pressure (=BP) lowering effects after inhaled application) in PAH animal models (pig and dog) (see experimental part C-2.1 (pig) and C-2.2 (dog). These findings support the suitability of comparative example 11 for a once or twice daily inhalative treatment regime comprising 240 to 4000 µg, preferably 480 to 2000 µg, of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid for the use in the treatment of cardiopulmonary diseases, such as pulmonary arterial hypertension (PAH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

(5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid of formula I (=comparative example 11) according to the present invention and comparative examples 3, 4 and 5 were tested to evaluate lung selectivity as well as duration of action in the minipig model (C-2.1). Whereas all 3 compounds show a suitable lung selectivity only comparative example 11 and comparative example 4 show a sufficient duration of action. Comparative example 11 shows a selective PAP effect with a maximal effect for the whole observation interval of 240 min whereas comparative example 3 shows its maximal effect on PAP 30 min after inhaled application which was again completely resolved after 120 min. Comparative example 11 and comparative example 4 were evaluated with respect to duration of action in the conscious hypoxia challenged dog model (C-2.2). In this model, in contrast to comparative example 4, comparative example 11 showed a consistent long duration of effect (PAP reduction) for up to 17 hrs. Therefore in contrast to comparative examples 3, 4 and 5 (disclosed as examples 2, 37 and 39 in WO 14/012934-A1), comparative example 11, corresponding to the present invention, is most suitable for a once to twice daily treatment regime.

Furthermore we found for the sGC activator (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I (=comparative example 11) in form of its monohydrate I of formula (I-M-I) (example 4) in first clinical studies (see experimental part C-4) increased cGMP levels as second messenger molecule of sGC activation as well as beneficial bronchodilatory properties in healthy volunteers over a time period of more than 12 hrs, up to 24 hrs after dry powder application, e.g. a decrease of total specific airway resistance (sRaw), a parameter indicating bronchodilative activity in the lung, supporting the long lung retention time clinically as well as the suitability of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I (=comparative example 11) in form of its monohydrate I of formula (I-M-I) to be successfully used in the treatment of cardiopulmonary diseases. Up to 4000 µg no clinically meaningful effect on systemic blood pressure was observed in healthy volunteers.

Moreover, we found a selective decrease in pulmonary arterial pressure and pulmonary vascular resistance in patients with pulmonary hypertension without clinically relevant effects on systemic blood pressure at doses up to 4000 µg (including) (see experimental part C-4.4). The effect was sustained with no decrease in response until the end of the measurement period of 3 h (a measurement period of >3 h was technically not feasible). A lung retention time of example 4 beyond the 3 h of measurement (presumably over a time period of more than 12 hrs, up to 24 hrs after dry powder application) can be concluded from the long plasma half-life measured after inhaled application (see experimental part C-4.3)

Additionally the analysis of plasma concentrations after oral, intravenous and inhalative administration of the drug substance showed the longest half-life of the active ingredient after inhaled application (C-4.3). The emitted (lung) dose has been determined to be 720 µg after inhalation of 1000 μg in humans. The outcome from this investigation confirms the lung dose and that the half-life is adequate for an inhaled dry powder administration enabling a once daily treatment for a sufficient 24 h drug coverage of example 4 in the lung.

In conclusion all results show that (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I as well as its pseudopolymorphic forms, like e.g. (I-M-I) and (I-M-II), especially the monohydrate I of formula (I-M-I) are suitable in particular for the treatment of pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP) and are adequate for an inhaled dry powder administration enabling a once daily treatment for a sufficient 24 h drug coverage of example 4 in the lung.

Also these findings support the suitability of (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid of formula I (=comparative example 11) in form of its monohydrate I of formula (I-M-I) for a once or twice daily inhalative treatment regime comprising 240 to 4000 μg, preferably 480 to 2000 μg for a period of equal or more than two days, preferably at least 2 to 7 consecutive days, preferably for a period of at least 14 consecutive days, in particular from after onset of treatment for the whole course of the disease, of (5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid of formula I (=comparative example 11) in form of its monohydrate I of formula (I-M-I) for the use in the treatment of cardiopulmonary diseases, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

Additionally we found that (5S)-{[2-(4-carboxyphenyl) ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid of formula I (=comparative example 11) has beneficial physicochemical properties e.g. protein binding and CACO flux (see experimental part C-5.1 (Caco permeability) and C-5.2 (protein binding) which make comparative example 11 a suitable compound for local treatment of cardiopulmonary diseases by dry powder inhalation to the lung. Moreover, our data indicate that Comparative example 11 esp. in monohydrate form I of formula (I-M-I) not only shows effective reduction of the PAP via selective vasodilation in the lungs but also showed longer lasting bronchodilatory properties compared to cinaciguat which may be beneficial in the once or twice daily inhalative treatment of PH patients with chronic lung diseases (PH group 3) or even have a potential in the treatment of patients with restricted lung function, e.g. asthmatics.

Therefore the drug substance, e.g. (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula (I), as well as its pseudopolymorphic forms (I-M-I) and (I-M-II) according to the present invention have excellent primary pharmacological properties:

(5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid is a potent and selective sGC activator and provides a new approach in the treatment of PH after inhalation.

(5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid selectively decreased elevated PAP after inhaled application in different disease relevant animal models (thromboxane and hypoxia challenged rats, pigs, and dogs) with a long duration of action, suggesting a once or twice daily, preferably a once daily application.

In an unilateral ventilated minipig model as a proxy of VQ-mismatch, (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid after inhaled application, lowered PAP without negative effects on oxygenation in contrast to systemic applied vasodilators.

On top of standard-of-care (SoC) in PAH (bosentan, sildenafil, Ilomedin, and riociguat), (5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid selectively decreased elevated PAP after inhaled application in the PAH-minipig model.

The efficacy of (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid was enhanced under experimental conditions of oxidative stress (1H-[1,2,4] Oxadiazolo[4,3-a]quinoxalin-1-one, a highly selective, irreversible, heme-site inhibitor of soluble guanylyl cyclase [ODQ], L-Nω-Nitroarginine methyl ester [L-NAME] treatment).

With respect to ventilation, (5S)-{[2-(4-carboxyphenyl) ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid showed a bronchodilatory effect (acetylcholine [ACh] rat model) and an inhibitory effect on airway hyper-responsiveness and inflammation (chronic ovalbumin asthma mice model).

The analysis of plasma concentrations after oral, intravenous and inhalative administration of the drug substance showed the longest half-life of the active ingredient after inhaled application.

The emitted (lung) dose has been determined to be 720 μg after inhalation of 1000 μg in humans.

First studies in humans with the sGC activator (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of its crystalline form monohydrate I of formula (I-M-I) (example 4) showed sGC activation and long lung retention time combined with bronchodilatory properties and selective decrease of pulmonary arterial pressure and pulmonary vascular resistance at a good local and systemic tolerability up to the highest tested dose of 4000 μg (including).

Therefore the drug substance (5S)-{[2-(4-carboxyphenyl) ethyl][2-(2-{[3-chloro-4'(trifluoromethyl)biphenyl-4-yl] methoxy}phenyl)ethyl]-amino}-5,6,7,8-tetrahydroquinoline-2-carboxylic acid of formula (I), as well as its pseudopolymorphic forms (I-M-I) and (I-M-II) according to the present invention has excellent primary pharmacological and pharmacodynamic properties in patients including reduction of pulmonary artery pressure (mPAP) and pulmonary vascular resistance (PVR), bronchodilation as measured by e.g. FEV1, pulmonary selectivity with low to no systemic adverse effects (especially on systemic hemodynamics, such as clinically relevant changes in blood pressure or heart rate) and low to no increase of VQ-mismatch to avoid relevant desaturation, furthermore sufficient lung retention time and/or sufficient duration of action following intrapulmonary administration.

Surprisingly, it has been found, that local administration, esp. inhalative administration of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I, esp. in form of its monohydrate I of formula (I-M-I) has the potential of being successful in the control of cardiopulmonary disorders, such as pulmonary arterial hypertension (PAH), chronic thromboembolic pulmonary hypertension (CTEPH), and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP). The active ingredient concentration in the lungs can be kept for a long period at a level desirable from the medical viewpoint for optimal treatment. Besides the higher and long-lasting active ingredient level at the site of the disease, it is possible to achieve simultaneously a comparatively low systemic concentration of the active ingredient, so that side effects of the medication could be avoided, e.g. no clinically relevant systemic blood pressure decrease.

Surprisingly the drug substance can be provided in a single, crystalline and chemically stable form, the monohydrate I of formula (I-M-I). This form is also stable under micronization conditions.

Surprisingly the pharmaceutical dry powder formulations according to the present invention are characterized through an excellent aerosol performance (e.g. high fine particle dose, fine particle fraction and delivered dose with respect to the nominal dose) and a sufficient chemical stability. Furthermore the pharmaceutical dry powder formulations according to the present invention can be made in a technically reliable manner by a novel process (e.g. blend uniformity).

Surprisingly pharmaceutical dry powder formulations, comprising (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) in combination with a lactose carrier, comprising lactose monohydrate as a mixture of lactose coarse and lactose fine, are suitable for an inhalative treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

In view of the prior art these findings were not foreseeable as the excellent primary pharmacological and pharmacodynamic properties of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I especially its longer duration of action in comparison to similar 5,6,7,8-tetrahydroquinoline-2-carboxylic acids like e.g. comparative examples 3, 4 and 5 were not publicly known.

Moreover these findings were not foreseeable as the pseudopolymorphic forms, especially the crystalline stable hydrates were not publicly known.

Surprisingly monohydrate form I (I-M-I) (example 4) was identified as the stable pseudopolymorphic form of (5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid of formula I after micronzation and stability studies.

Furthermore it was surprising that modification I (I-M-I) was available by a selective crystallization from methanol, acetone water.

Furthermore no inhalative solid carrier formulation comprising acid of formula (I) nor any of its crystalline forms like e.g. monohydrate form I (I-M-I) or monohydrate form II (I-M-II) was known.

Therefore the technical objective of the present invention was to provide novel, stable pharmaceutical dry powder formulations comprising (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) with an excellent aerosol performance (e.g. high results of fine particle dose, fine particle fraction and delivered dose with respect to nominal dose) and a sufficient chemical stability with these attributes being achieved by blending of micronized (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) with a lactose carrier consisting of a coarse and fine particle portion.

The present inventors surprisingly found, that novel, stable pharmaceutical dry powder formulations comprising (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) can be manufactured by combining the active ingredient with a carrier, wherein the carrier is a lactose carrier, which comprises lactose monohydrate as a mixture of lactose coarse and lactose fine.

In order to obtain the pharmaceutical dry powder formulations according to the present invention it is of importance to adjust a specific ratio between a) the drug substance and the lactose carrier and b) to use an engineered and customized lactose carrier, which comprises lactose monohydrate as a mixture of lactose coarse and lactose fine, and c) to use drug substance and lactose coarse and lactose fine, with specific particle sizes, especially with the following specifications:

A) active ingredient (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid Monohydrate I of formula (I-M-I) having a particle size X90≤6 μm and/or X50 of between 1.0 and 3.0 μm B) coarse lactose having a particle size of X90 at least or ≥115 μm or at least or ≥120 μm or being at least or ≥200 μm; and/or coarse lactose having a particle size of X50 at least or ≥50 μm or being at least or ≥75 μm or being at least or ≥125 μm X50≥50 μm C) fine lactose having a particle size of X90<30 μm or ≤10 μm; and/or fine lactose having a particle size of X50≤5 μm or <10 μm and wherein the coarse lactose content of the formulation/dry powder blend is between 94.25% and 75%, also between 98.25% and 75%.

The specific combination of the drug substance with the specific ratio of lactose carrier components, namely coarse lactose and fine lactose, all components having specific particle sizes and furthermore a defined coarse lactose content of the formulation/dry powder blend causes the technical effect, that the underlying pharmaceutical dry powder formulations show an excellent aerosol performance (e.g. high fine particle dose, fine particle fraction and delivered dose with respect to nominal dose) and are sufficiently chemically stable over certain periods of time.

A superior aerosol performance results from the effect that the drug particles are temporarily bound to the carrier particles, but need to be subsequently released from those during inhalation in the inhaled aerosol stream and thereby can reach deep lung areas. Strong binding of micronized drug particles on lactose carrier particles can occur specifically with compounds like I-M-I for which it has been observed to have strong adhesive properties to multiple types of surfaces (e.g. surfaces of analytical glassware and pharmaceutical production equipment, surfaces of hard capsules and dry powder inhalation device). Lactose fine particles can occupy active sites on lactose carrier particles, thereby reducing the ratio of strongly bound drug particles in the adhesive mixture and increasing the released portion under condition of inhalation (fine particle dose/fine particle fraction). The excellent aerosol performance of the carrier based dry powder formulations according to the present invention is the result from an optimum temporary binding of micronized active ingredient particles designed for deep lung delivery that can be overcome by the energy of the airstream in the dry powder inhalation device to detach and deagglomerate the drug particles from the carrier.

This result, the optimum temporary binding of micronized active ingredient particles has been achieved by optimizing and customizing the following technical parameters:

the specific ratio of lactose carrier components, namely coarse lactose and fine lactose, selection of specific particle sizes for all components and furthermore a defined coarse lactose content of the formulation/dry powder blend These parameters are crucial in order to obtain the carrier based dry powder formulations according to the present invention with an excellent aerosol performance.

Therefore the pharmaceutical dry powder formulations according to the present invention comprising (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid of formula I in form of one of its salts or solvates or hydrates, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) are suitable medicaments for treatment of cardiopulmonary disorders, such as pulmonary arterial hypertension (PAH), chronic thromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

DETAILED DESCRIPTION OF THE INVENTION

Formulations for Inhalation Active Ingredient

Solid preparations according to the present invention for dry powder inhalation contain an amount of active ingredient (i.e. (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid of formula I, preferably (5S)-{[2-(4-carboxyphenyl)ethyl][2-(2-{[3-chloro-4'-(trifluoromethyl)biphenyl-4-yl] methoxy}phenyl)-ethyl]-amino}-5,6,7,8-tetrahydroquinoline-2-carboxylic acid in form of monohydrate I of formula (I-M-I)) or (5S)-{[2-(4-carboxyphenyl)ethyl][2-(2-{[3-chloro-4'-(trifluoromethyl)biphenyl-4-yl]methoxy}phenyl)-ethyl]-amino}-5,6,7,8-tetrahydroquinoline-2-carboxylic acid in form of monohydrate II of formula (I-M-II)), particularly preferable (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid in form of monohydrate I of formula (I-M-I)) in a matrix of a suitable inhalation grade carrier for the active compound which is not more than about 20%. Usually the amount of active ingredient is between 0.5% and 20%, preferably between 0.75% and 10%. The amount of active ingredient therein is usually at least 0.75%, or at least 3%, or at least 5% or at least 10% by weight based on the preparation ready for use. Very preferable are powder blends which have 3%, 10% or 20% content of active ingredient.

Solid preparations according to the present invention for dry powder inhalation contain the active ingredient (i.e. (5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid of formula I, preferably (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid in form of monohydrate I of formula (I-M-I)) or (5S)-{[2-(4-carboxyphenyl)ethyl][2-(2-{[3-chloro-4'-(trifluoromethyl)biphenyl-4-yl]methoxy}phenyl) ethyl]-amino}-5,6,7,8-tetrahydroquinoline-2-carboxylic acid in form of monohydrate II of formula (I-M-II)), particularly preferable (5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid in form of monohydrate I of formula (I-M-I)) in a certain particle size, suitable for inhalative application.

The particle size distribution for the active ingredient ((5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, preferably (5S)-{[2-(4-carboxyphenyl)ethyl][2-(2-{[3-chloro- 4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I) or (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid in form of monohydrate II of formula (I-M-II)), particularly preferable (5S)-{[2-(4-carboxyphenyl)ethyl][2-(2-{[3-chloro-4'-(trifluoromethyl) biphenyl-4-yl]methoxy}phenyl)ethyl]-amino}-5,6,7,8-tetrahydroquinoline-2-carboxylic acid in form of monohydrate I of formula (I-M-I)) according to the invention is defined as in below table.

TABLE 5

| Particle size distribution of active ingredient, e.g. compound of formula (I-M-I) or (I-M-II) | |
|---|---|
| Particle size upper X90 | max.6 μm |
| Particle size mean X50 | 1-3 μm |
| Particle size lower X10 | max. 1 μm |

For inhalative drug products it is important to guarantee a homogeneous drug substance with defined particle size <5 μm to secure delivery to the deep lung compartments. This technical requirement can be achieved by micronization of the drug substance particles (see experimental part B, ex.8).

Appropriate specifications for a particle size distribution of the active ingredient to achieve this requirement were set as specified in table 5.

Therefore in order to secure a suitable delivery of the active at the target site, esp. the deep airways and aeveoli the present inventors found that is essential to provide the active ingredient (5S)-{[2-(4-carboxyphenyl)ethyl][2-(2-{[3-chloro-4'-(trifluoromethyl)biphenyl-4-yl]methoxy}phenyl) ethyl]-amino}-5,6,7,8-tetrahydroquinoline-2-carboxylic acid of formula I, preferably (5S)-{[2-(4-carboxyphenyl) ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid in form of monohydrate I of formula (I-M-I)) or in form of monohydrate II of formula (I-M-II)), preferably in form of monohydrate I of formula (I-M-I)) in a particle size of X90=max. 6 μm and/or X50 1-3 μm and/or X10 max. 1 μm.

Lactose Carrier

Solid preparations according to the invention for dry powder inhalation generally contain an amount of a suitable carrier for the active compound which is not more than about 99.25%. Usually the amount of inhalation grade carrier is between 99.25% and 80%, preferably between 99.25% and 90%. The amount of carrier therein is usually at least 99.25%, or at least 97%, or at least 95% or at least 90% by weight based dry powder blend.

Different materials of inhalation grade carriers are principally available.

The present inventors found that the excellent aerosol performance of the formulations for inhalation according to the present invention is achieved by choosing lactose as carrier material.

Lactose for inhalation is available in different particle size ranges and different characteristics.

One would expect that a coarse lactose carrier alone with a particle size distribution centered at higher particle sizes compared to the active ingredient may lead to poor aerosol performance due to relatively strong binding of the fine drug particles to active sites of the coarse carrier particles (Paolo Colombo, Daniela Traini and Francesca Buttini "Inhalation Drug Delivery—Techniques and Products" (published by Wiley-Blackwell 2013). Advanced aerosol performance is characterized by increased fine particle dose and fraction as well as delivered dose with related to the nominal dose. This is expected by an equilibrium between drug to carrier adhesion and subsequent segregation once the powder is aerosolized, often also described as powder or drug dispersion. One may also expect that the aerosol performance behavior will improve with the addition of fine carrier particles or by use of lactose materials that contain intrinsic portions of lactose fines, although the extent cannot be predicted (de Boer et al 2012, Grasmejier et al 2015). As an expression of the improvement of drug dispersion and release from the carrier, measurements by cascade impactors are the established method of choice and fine particle dose (alternatively fine particle mass) as well as the fine particle fraction (percentage fraction of drug mass with a defined particle size upper limit, e.g. 5 μm or 4.5 μm in relation to the delivered dose or nominal dose of the single dosage unit). These methods are also established as mandatory quality control methods for inhalation products in current pharmacopoeia (e.g. Pharmacopoeia Europaea (Pharm Eur.) or United States Pharmacopoeia (USP).

However, the potential effect of addition of fine lactose and its magnitude cannot be predicted as there may be other major effects within the dry powder adhesive mixture that superimpose the lactose fines effect. Very importantly the properties of the micronized drug itself can have an impact on the adhesive and cohesive properties (e.g. cohesive: adhesive balance (CAB) or surface energy) of a binary or ternary mixture of particles of a specific drug molecule which makes a prediction even more difficult.

The present inventors found that the excellent aerosol performance of the formulations for inhalation according to the present invention is achieved by choosing fine lactose and coarse lactose as carrier material with specific particle sizes.

The coarse lactose material according to the present invention is a sieved or milled, crystalline, a-lactose monohydrate with low fine particle content (e.g. commercially available as Lactohale® 100 or Lactohale® 206).

Coarse lactose according to the invention having a similar particle size distribution may also be selected from other brands e.g. Meggle Inhalac® 120 or DFE Respitose® SV010.

To select a primary coarse carrier, a lactose quality was selected that would have a particle size X90 larger by at least the factor of 10 compared to the X90 of the active ingredient and a low intrinsic fines content to allow for consistent quality of the major part of the carrier.

Fine lactose was selected to improve the aerosol performance. The present inventors assumed that a particle size similar to the active ingredient could be suitable to control the temporary binding of the active ingredient particles to the coarse carrier particles although other fine lactose particle size specifications were potentially also suitable. A selection of a fine lactose product with a particle size of X90<10 μm or X90<30 μm or X50≤5 μm or 1.0-3.0 μm was therefore regarded adequate to compose the lactose carrier.

The fine lactose material according to the present invention is a milled or micronized, crystalline, a-lactose monohydrate with a low particle size ("Lactose fines") of X90≤10 μm (e.g. commercially available as Lactohale® 300) or X90<30 μm or X50≤5 μm or 1.0-3.0 μm (e.g. commercially available as Lactohale® 230). Fine milled or micronized lactose with similar properties and particle size may also be selected e.g. Meggle Inhalac® 500. Particle size distribution of materials and powder mixtures are usually measured by laser diffraction spectroscopy, microscopic techniques or conventional sieve analysis and classification [B. Y. Shekunov, P. Chattopadhyay, H. H. Y. Tong and A. H. L. Chow, Particle size analysis in pharmaceutics, *Pharm. Res.* 2007, 24 (2), S203-S227] (see also D.4).

The particle size distributions for commercial available Lactose for inhalation qualities according to the invention (e.g. Lactohale® 100, Lactohale® 300) are summarized in below table 6.

TABLE 6

Particle size distribution (specifications) for lactose for inhalation according to the invention

| | Coarse lactose | Fine Lactose |
|---|---|---|
| Trade name | Lactohale ® 100 | Lactohale ® 300 |
| Particle size upper X90 | 200-250 μm | ≤10 μm |
| Particle size mean X50 | 125-145 μm | ≤5 μm |
| Particle size lower X10 | 45-65 μm | not defined |
| Trade name | Lactohale ® 200 | |
| Particle size upper X90 | 120-160 μm | |
| Particle size mean X50 | 50-100 μm | |
| Particle size lower X10 | 5-15 μm | |
| Trade name | Lactohale ® 206 | Lactohale ® 230 |
| Particle size upper X90 | 115-170 μm | <30 μm |
| Particle size mean X50 | 75-95 μm | <10 μm |
| Particle size lower X10 | 20-50 μm | 1.0-3.0 μm |

Solid preparations according to the invention for dry powder inhalation contain a mixture of coarse lactose (e.g. Lactohale® 100) and fine lactose (e.g. Lactohale® 300).

The present inventors found out that the coarse lactose particle size can be varied over a certain range without jeopardizing the aerosol performance or the blend uniformity of the carrier based formulations according to the present invention.

According to the present invention the coarse lactose has a particle size of X90=200-250 μm or 120-160 μm or 115-170 μm, or 115-250 μm. Furthermore according to the present invention the coarse lactose has a particle size of X90≤250 μm or ≤170 μm or ≤160 μm. Furthermore according to the present invention the coarse lactose has a particle size of X90 being at least or ≥115 μm or being at least or ≥120 μm or being at least or ≥200 μm.

According to the present invention the coarse lactose has a particle size of X50=125-145 μm or 50-100 μm or 75-95 μm or 50-145 μm. Furthermore according to the present invention the coarse lactose has a particle size of X50≥145 μm or ≤100 μm or ≤95 μm. Furthermore according to the present invention the coarse lactose has a particle size of X50 being at least or ≥50 μm or being at least or ≥75 μm or being at least or ≥125 μm and/or X10=45-65 μm or 5-15 μm or 20-50 μm.

According to the present invention the fine lactose has a particle size of X90=≤10 μm or ≤30 μm, X50≤5 μm or 1.0-3.0 μm. By utilizing the Lactohale 200® with an inherent content of fine particles there is no need to add any further fine lactose particles to the lactose carrier. Therefore the present carrier based formulation may be formulated with Lactohale 200® or similar Lactose product with intrinsic lactose fines content.

According to the present invention, Lactohale 100® and Lactohale 300® are preferred.

Furthermore the present inventors found that the excellent aerosol performance of the formulations for inhalation according to the present invention is achieved by adjusting a specific content of fine lactose and a specific content of coarse lactose within the dry powder blend.

The present inventors identified the fine lactose content of the lactose carrier as an important critical parameter. In order to obtain the formulations for inhalation according to the present invention characterized by an excellent aerosol performance the content of fine lactose should be selected within a certain range. For example a higher content of fine lactose in the powder blend/lactose carrier, e.g. a content of 20% or more was found to have a negative impact on the blend uniformity (see e.g. comparative example 20). It was shown that the powder blends and formulations according to the present invention can have a varying content of fine lactose within a range of between 1% and 10%, also between 5% and 10% whereas the fine lactose content may also be an intrinsic part of the lactose for inhalation, i.e. calculated as an X10 of 5-15 μm as in the case of Lactohale 2000® (see emb. 34) without jeopardizing the aerosol performance.

According to the present invention the content of fine lactose in the powder blend is between 1% and 10%, preferably between 5% and 10%, preferably between 2.5% and 7.5%, preferably between 5% and 7.5%, more preferably 5%.

The present inventors identified the coarse lactose content of the powder blend also as an important parameter. In order to obtain the formulations for inhalation according to the present invention characterized by an excellent aerosol performance the content of coarse lactose should be selected within a certain range.

According to the present invention the content of coarse lactose in the powder blend is between 98.25% and 75%, preferably between 94.25% and 75%, preferably between 92.00% and 75%, more preferably from 90.00% to 75% and especially preferably from 90% to 85%.

As the dry powder blend according to the present invention is a ternary mixture all three components need to be provided in form of defined maximum particle sizes and in certain specific ratios.

The present inventors found that the excellent aerosol performance of the formulations for inhalation according to the present invention is achieved by choosing a specific ratio of fine lactose and coarse lactose and active ingredient.

According to the present invention the ratio of the coarse lactose to fine lactose in the powder blend is between 445:5 and 65:5, preferably 94.25:5 and 65:5, preferably 94.25:5 and 75:5, 91.75:7.5 and 89.25:10, preferably between 92:5 and 75:5, particular preferred are ratios of 92:5, 85:5 as well as 75:5.

According to the present invention the ratio of the active ingredient of formula (I) or (I-M-I) to Coarse Lactose in the powder blend is between 1:126 and 1:3.8, preferably between 1:31 and 1:3.8.

According to the present invention the ratio of the active ingredient of formula (I) or (I-M-I) to Fine Lactose in the powder blend is from 1:13 and 1:0.1, preferably between 1:13 and 1:0.25, preferably between 1:1.67 and 1:0.25.

Further Excipients

The preparations according to the invention can generally contain further pharmacologically acceptable excipients, including, inter alia, carriers (e.g. inhalation grade lactose, lactose monohydrate, mannitol), dispersants, wetting agents, lubricants (e.g. magnesium stearate), surface active compounds (e.g. sodium lauryl sulfate, Disteaorylphosphatidycholine), ionic compounds (e.g. calcium chloride, sodium chloride, potassium chloride), synthetic and natural polymers (for example carrageenan, hydroxypropylmethylcellulose, gelatine) or pH modifiers (e.g. sodium hydroxide, sodium chloride, citric acid salts Trisodium citrate) colorants (e.g. inorganic pigments such as, for example, iron or titanium oxides).

Cavity

According to the present invention the dry powder blend comprising the active ingredient in form of its monohydrate forms I-M-T or I-M-II and lactose can be administered via dry powder inhalers such as single-unit dose inhalers in which each dose is loaded into the device before use, multi-unit dose inhalers in which several single doses are individually sealed (pre-metered) and can be discharged in a dosing chamber prior to each actuation or reservoir multi-unit dose inhalers in which a bulk supply of drug is pre-loaded into the device and discharged (metered by device) in a dosing chamber prior to each actuation. Preferably the dry powder blend according to the present invention is administered via a single-unit dose inhaler which is equipped/loaded with cavities, such as capsules or blisters comprising the dry powder blend. Preferably the cavities are individual capsules, preferably hard capsules of gelatin or of hydroxypropylmethylcellulose, most preferably hydroxypropylmethylcellulose capsules.

The dry powder blends comprising the active ingredient, e.g. the monohydrate I of formula (I-M-I) or the monohydrate II of formula (I-M-II), according to examples 2 or 4, micronized are filled into hard capsules (hydroxypropylmethylcellulose=Hypromellose=HPMC, e.g. in size 3) or alternative capsules from hard gelatine or other suitable materials. Pharmaceutical hard capsules sizes are standardized and characterized by defined measures, where e.g. a size 3 capsule has a length of 157 mm a and a diameter of 57 mm, whereas a size 2 capsule has a length of 176 mm and a diameter of 62 mm and a size 1 capsule has a length of 194 mm and a diameter of 68 mm.

Depending on the fill weight and active ingredient concentration different nominal dose can be achieved. Exemplary compositions for capsules with different nominal doses of active ingredient, e.g. the monohydrate I of formula (I-M-I) or the monohydrate II of formula (I-M-II), according to examples 2 or 4, are given in exemplary embodiments 1-3 and are displayed in below table 7.

TABLE 7

Examples of formulations according to the present invention with defined nominal dose (filled powder in hard capsules).

| | Exemplary Embodiment 1 | Exemplary Embodiment 2 | Exemplary Embodiment 3 |
|---|---|---|---|
| Nominal dose | 120 µg | 480 µg | 1000 µg |
| concentration of active ingredient (example 4) in powder blend | 0.75% | 3% | 10% |
| Fill weight | 16 mg | 16 mg | 10 mg |

On intrapulmonary administration, the amount of active ingredient (nominal dose), (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I (see example 4) is about 10 µg to 50000 µg per inhalation, preferably about 100 µg to 10000 µg per inhalation, further preferably about 100 to 6000 µg per inhalation, further preferably about 120 to 4000 µg per inhalation, further preferably about 200 to 4000 µg per inhalation, very particularly preferably about 240 µg to 4000 µg, very particularly preferably about 240 µg to 2000 µg, very particularly preferably about 240 µg to 1000 µg, very particularly preferably about 240 µg to 480 µg, very particularly preferably about 480 µg to 4000 µg, very particularly preferably about 480 µg to 2000 µg, very particularly preferably about 480 µg to 1000 µg, very particularly preferably about 1000 µg to 4000 µg, very particularly preferably about 1000 mg to 2000 µg, very particularly preferably about 1000 µg, very particularly preferably about 2000 µg, very particularly preferably about 4000 µg.

The cavity, preferably a HMPC based hard capsule, size 3 according to the present invention contains a filled mass of 8-40 mg of the formulation for inhalation, preferably a filled mass of 10-30 mg of the formulation for inhalation, more preferably a filled mass of 10-20 mg of the formulation for inhalation, more preferably a filled mass of 16-20 mg of the formulation for inhalation.

According to the present invention, mostly preferred are the following compositions:

TABLE 8 final capsule formulations comprising dry powder blends, percentage based

| Nominal dose | Capsule, e.g. HMPC | Powder Fill mass | API content (%) in powder blend | Coarse Lactose content (%) | Fine Lactose content (%) | Ratio API:Coarse Lactose | Ratio API:Fine Lactose |
|---|---|---|---|---|---|---|---|
| 480 µg | Size 3 | 16 mg | 3% | 92% | 5% | 1:31 | 1:1.67 |
| 1000 µg | Size 3 | 10 mg | 10% | 89% | 1% | 1:8.9 | 1:0.1 |
| 1000 µg | Size 3 | 10 mg | 10% | 87.5% | 2.5% | 1.8.75 | 1:0.25 |
| 1000 µg | Size 3 | 10 mg | 10% | 85% | 5% | 1:8.5 | 1:0.5 |
| 2000 µg | Size 3 | 20 mg | 10% | 85% | 5% | 1:8.5 | 1:0.5 |
| 3000 µg | Size 3 | 30 mg | 10% | 85% | 5% | 1:8.5 | 1:0.5 |
| 4000 µg | Size 3 | 40 mg | 10% | 85% | 5% | 1:8.5 | 1:0.5 |
| 2000 µg | Size 3 | 10 mg | 20% | 75% | 5% | 1:3.8 | 1:0.25 |
| 3000 µg | Size 3 | 15 mg | 20% | 75% | 5% | 1:3.8 | 1:0.25 |
| 4000 µg | Size 3 | 20 mg | 20% | 75% | 5% | 1:3.8 | 1:0.25 |

According to the present invention a powder blend with a content of 3% active ingredient of formula (I) or (I-M-I) in the powder blend comprises 480 µg active ingredient of formula (I) or (I-M-I), 92% coarse lactose and 5% fine lactose and might be filled as a corresponding mass of 16 mg powder blend in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 10% active ingredient of formula (I) or (I-M-I) in the powder blend comprises 1000 µg, 2000 µg, 3000 µg or 4000 µg active ingredient of formula (I) or (I-M-I), 85% coarse lactose and 5% fine lactose and might be filled (as a corresponding mass of 10 mg, 20 mg, 30 mg or 40 mg powder blend) in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 20% active ingredient of formula (I) or (I-M-I) in the powder blend comprises 2000 µg, 3000 µg or 4000 µg active ingredient of formula (I) or (I-M-I), 75% coarse lactose and 5% fine lactose and might be filled (as a corresponding mass of 10 mg, 15 mg or 20 mg powder blend) in a hard capsule, preferably a HMPC capsule of size 3 and which might then be administered via a "single unit dose" Inhaler, e.g. preferable Plastiape (Berry) RS01 low resistance device.

TABLE 9 final capsule formulations comprising dry powder blends, mass based characterization:

| Nominal dose | Capsule | Powder Fill mass | API content (mg/g) in powder blend | Coarse Lactose content (mg) | Fine Lactose content (mg) | Ratio API:Coarse Lactose | Ratio API:Fine Lactose |
|---|---|---|---|---|---|---|---|
| 480 µg | Size 3 | 16 mg | 30 mg/g | 14.72 mg | 0.8 mg | 1:31 | 1:1.67 |
| 1000 µg | Size 3 | 10 mg | 100 mg/g | 8.9 mg | 0.1 mg | 1:8.9 | 1:0.1 |
| 1000 µg | Size 3 | 10 mg | 100 mg/g | 8.75 mg | 0.25 mg | 1.8.75 | 1:0.25 |
| 1000 µg | Size 3 | 10 mg | 100 mg/g | 8.5 mg | 0.5 mg | 1:8.5 | 1:0.5 |
| 2000 µg | Size 3 | 20 mg | 100 mg/g | 17.0 mg | 1.0 mg | 1:8.5 | 1:0.5 |
| 3000 µg | Size 3 | 30 mg | 100 mg/g | 25.5 mg | 1.5 mg | 1:8.5 | 1:0.5 |
| 4000 µg | Size 3 | 40 mg | 100 mg/g | 34.0 mg | 2.0 mg | 1:8.5 | 1:0.5 |
| 2000 µg | Size 3 | 10 mg | 200 mg/g | 7.5 mg | 0.5 mg | 1:3.8 | 1:0.25 |
| 3000 µg | Size 3 | 15 mg | 200 mg/g | 11.25 mg | 0.75 mg | 1:3.8 | 1:0.25 |
| 4000 µg | Size 3 | 20 mg | 200 mg/g | 15.0 mg | 1.0 mg | 1:3.8 | 1:0.25 |

According to the present invention a powder blend with a content of 30 mg/g active ingredient of formula (I) or (I-M-I) in the powder blend comprises 480 µg active ingredient of formula (I) or (I-M-I), 14.72 mg coarse lactose and 0.8 mg fine lactose and might be filled as a mass of 16 mg powder blend in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 100 mg/g active ingredient of formula (I) or (I-M-I) in the powder blend comprises 1000 µg, 2000 µg, 3000 µg or 4000 µg active ingredient of formula (I) or (I-M-I), 8.9 mg, 8.75 mg, 8.5 mg, 17.0 mg, 25.5 mg or 34.0 mg coarse lactose and 0.1 mg, 0.25 mg, 0.5 mg, 1.0 mg, 1.5 mg or 2.0 mg fine lactose and might be filled (as a corresponding mass of 10 mg, 20 mg, 30 mg or 40 mg powder blend) in a hard capsule, preferably a HMPC capsule of size 3 and which might then be administered via a "single unit dose" Inhaler, e.g. preferable Plastiape (Berry) RS01 low resistance device.

According to the present invention a powder blend with a content of 200 mg/g active ingredient of formula (I) or (I-M-I) in the powder blend comprises 2000 µg, 3000 µg or 4000 µg active ingredient of formula (I) or (I-M-I), 7.5 mg, 11.25 mg or 15.0 mg coarse lactose and 0.5 mg, 0.75 mg or 1.0 mg fine lactose and might be filled (as a corresponding mass of 10 mg, 15 mg or 20 mg powder blend) in a hard capsule, preferably a HMPC capsule of size 3 and which might then be administered via a "single unit dose" Inhaler, e.g. preferable Plastiape (Berry) RS01 low resistance device.

Manufacturing Process

The preparations according to the invention can generally be produced—as is usual in the production of inhalable free-flowing medicaments in powder form, by micronizing the active ingredient and optionally blending the micronized active ingredient with inactive carrier compounds.

The compounds according to the invention can be converted into the stated administration forms. This can take place in a manner known per se by mixing with inert, non-toxic, pharmaceutically suitable excipients.

Figure 84:
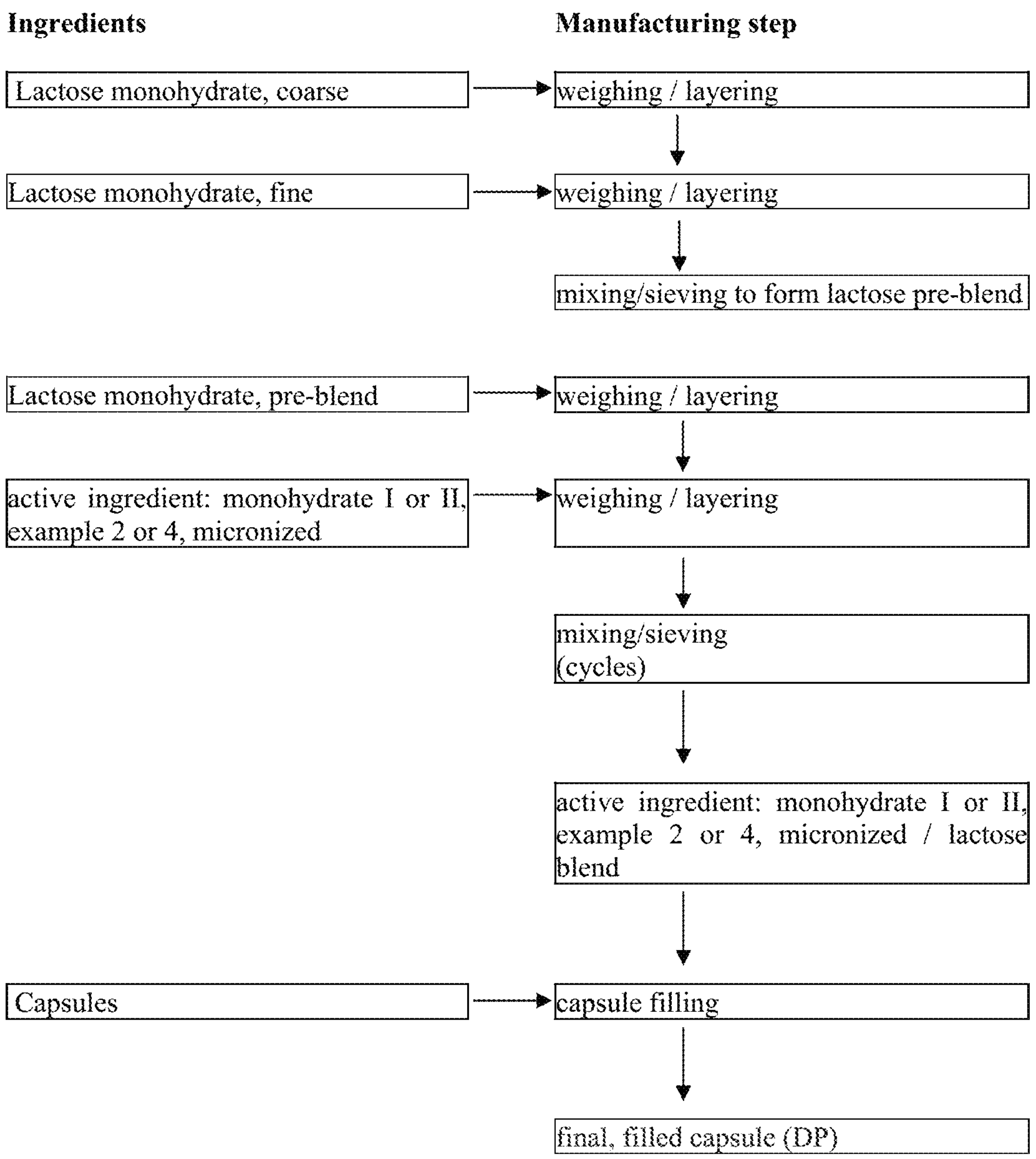

The dry powder formulation and finished products (dry powder blend filled hard capsules) are manufactured according to the flow chart depicted in FIG. 84.

The steps illustrated in the FIG. 84 flowchart are described as follows:

Step 1:

The fine lactose portion was weighed and layered in between two layers of coarse lactose prior to start of mixing.

Step 2:

Mixing of the lactose pre-blend was performed in a tumble mixer 2 times (2 cycles) at 72 rpm, 67 rpm or 34 rpm or 32 rpm or 30 rpm, preferably 32 rpm for 20 min. The lactose pre-blend was sieved through a 500 µg sieve between the cycles.

Step 3:

active ingredient: monohydrate I or II, example 2 or 4, micronized was sieved through a 500 µm sieve and added to the pre-blended lactose. Prior to start of mixing cycles, the lactose pre-blend and active ingredient were layered alternating with 6 layers of lactose pre-blend and 5 layers of active ingredient (monohydrate I or II, example 2 or 4) in between.

Step 4:

The components were mixed in cycles, e.g. 3-5 cycles, preferably 3 cycles in a tumble mixer, e.g. glass or stainless steel, preferably stainless steel. Each cycle was conducted at 72 rpm, 67 rpm, 34 rpm or 32 rpm preferably 32 rpm for 20-30 minutes, preferably 30 minutes (90 min overall mixing time), preferably 32 rpm for 30 minutes with a rest time of 10 minutes between the mixing cycles. If necessary (e.g. visual agglomerates) the blend maybe sieved between blending cycles, respectively.

Step 5:

The blend was left to rest at room temperature (15-25° C.) and 35-65% relative humidity in a stainless steel container for a certain period of time, preferably 24-72 hours, more preferably 48 h.

Step 6:

Using a capsule filling machine (e.g. MG2 Flexalab) the blend was filled into capsules at the desired fill weight.

Inhaler Device

In the context of the present invention the sGC activator, e.g. example 2 or 4 is applied as dry powder or dry powder formulation by means of a dry powder Inhaler device.

The preferred dry powder Inhaler device within the context of the present invention is defined as a capsule based single-unit dose inhaler which is a pre-metered inhalation device (see FIGS. 3*a* and 3*b*). In the context of the present invention doses were applied using the Plastiape (Berry) RSO1 low resistance device. This device (in a higher resistance type) is disclosed and described in publications (ELKINS et al. Inspiratory Flows and Volumes in Subjects with Cystic Fibrosis Using a New Dry Powder Inhaler Device, The Open Respiratory Medicine Journal, 2014, 8, 1-7 and ELKINS et al. Inspiratory Flows and Volumes in Subjects with Non-CF Bronchiectasis Using a New Dry Powder Inhaler Device, The Open Respiratory Medicine Journal, 2014, 8, 8-13) relating to treatment of other patient populations, e.g. cystic fibrosis (CF) or non-CF bronchiectasis.

The inhaler is operated by inserting a single capsule filled with the dry powder formulation into the device. Two buttons (pushbuttons) are pressed to puncture the capsule and the user places his/her mouth around the mouthpiece and inhales deeply and forcefully. The energy from the inhalation pulls the drug preparation out of the capsule, disperses the powder as an aerosol, the active ingredient particles are released from the lactose carrier particles and carried it into the respiratory tract. The used capsule is removed and discarded. The device may be reused depending upon the patient's therapy requirements and corresponding labeling of the clinical devices. The number of capsules administered determines the dose of medication.

Other pre-metered dry powder inhalation devices such as blister strip based multi-unit dose devices may also be used for the preferred method of application and may lead to comparable results if the aerosol path has similar design or properties (e.g. device resistance and pressure drop at defined flow rates).

In the context of the invention there are also disclosed devices which contain preparations containing example 4 or can have a receptacle to incorporate these preparations in a capsule or blister and which are suitable for the administration by inhalation thereof in solid form, i.e. aerosolizers which are able to administer preparations containing active ingredient: e.g. monohydrate I or II, example 2 or 4, by inhalation in solid form (powder inhalers).

In the case of multiple dose application the target plasma concentration (approximate steady state) can be reached after 3 to 5 half lives (Donald J. Birkett, in "Pharmacokinetics Made Easy", McGraw-Hill Education: 2000; p 20). At steady state the concentrations of drugs which rise and fall during each interdose interval are repeated identically in each interdose interval (Goodman and Gillmans "The Pharmacological Basis of Therapeutics" 7th Edition, Macmillan Publishing Company, New York, 1985, p 28).

On intrapulmonary administration the active compound, (5S)-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydro-quino-line-2-carboxylic acid is administered once or twice daily, preferably twice daily, particularly preferably once daily.

It may nevertheless be necessary where appropriate to deviate from the stated amounts, in particular as a function of body weight, administration route, individual response to the active compound, type of preparation and time or interval over which administration takes place. Thus, in some cases it may be sufficient to use less than the aforementioned minimum amount, whereas in other cases the upper limit mentioned must be exceeded. Where relatively large amounts are administered, it may be advisable to distribute these in a plurality of single doses over the day.

Other pre-metered dry powder inhalation devices such as blister strip based multi-unit dose devices may also be used for the preferred method of application and may lead to comparable results if the aerosol path has similar design or properties (e.g. device resistance and pressure drop at defined flow rates).

Specific Embodiments of the Invention (Dosage Regime)

1. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy})¬phenyl)-ethyl]-amino}-5,6,7,8-tetrahydroquinoline-2-carboxylic acid of formula I in form of one of its salts or solvates or hydrates, is administered to a patient in need thereof once or twice daily for a period of at least two consecutive days.
2. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°, is administered to a patient in need thereof once or twice daily for a period of at least two consecutive days.

3. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 2, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), wherein the X-ray powder diffractogram (measured at 25° C. and with Cu-K alpha 1 as radiation source) of the compound comprises at least peaks at 12.8 and 29.2, preferably at 6.9, 7.2, 7.3, 12.8 and 29.2 quoted as 2θ value±0.2°, is administered to a patient in need thereof once or twice daily for a period of at least two consecutive days.

4. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 3, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), wherein the X-ray powder diffractogram (measured at 25° C. and with Cu-K alpha 1 as radiation source) of the compound comprises at least peaks at 12.8, 16.0 and 25.8, preferably at 6.9, 7.2, 7.3, 12.8, 16.0 and 25.8 quoted as 2θ value±0.2°, is administered to a patient in need thereof once or twice daily for a period of at least two consecutive days.

5. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 4, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), which shows in the x-ray diffractogram (at 25° C. and with Cu-K alpha 1 as radiation source) at least the following reflections: 12.8, 20.5 and 25.8, preferably 6.9, 7.2, 7.3, 12.8, 20.5 and 25.8 quoted as 2θ value±0.2°, is administered to a patient in need thereof once or twice daily for a period of at least two consecutive days.

6. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 5, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), which shows in the x-ray diffractogram (at 25° C. and with Cu-K alpha 1 as radiation source) at least the following reflections: 12.8, 5.7, 6.9, 7.2, 7.3 and 9.9 quoted as 2° value±0.2°, is administered to a patient in need thereof once or twice daily for a period of at least two consecutive days.

7. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 6, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), which shows in the x-ray diffractogram (at 25° C. and with Cu-K alpha 1 as radiation source) at least the following reflections: 12.8, 5.7 and 16.0, preferably at 12.8, 5.7, 6.9, 7.2, 7.3 and 16.0 quoted as 2θ value±0.2°, is administered to a patient in need thereof once or twice daily for a period of at least two consecutive days.

8. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 7, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), which shows in the x-ray diffractogram (at 25° C. and with Cu-K alpha 1 as radiation source) at least the following reflections: 12.8, 5.7 and 20.5, preferably at 12.8, 5.7, 6.9, 7.2, 7.3 and 20.5, quoted as 2θ value±0.2°, is administered to a patient in need thereof once or twice daily for a period of at least two consecutive days.

9. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 8, characterized in that an inhalative dosage form comprising 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), which shows in the x-ray diffractogram (at 25° C. and with Cu-K alpha 1 as radiation source) at least the following reflections: 12.8, 5.7 and 29.2, preferably at 12.8, 5.7, 6.9, 7.2, 7.3 and 29.2 quoted as 2θ value±0.2°, is administered to a patient in need thereof once or twice daily for a period of at least two consecutive days.

10. (5S)-{[2-(4-carboxyphenyl)ethyl][2-(2-{[3-chloro-4'-(trifluoromethyl)biphenyl-4-yl]methoxy}¬phenyl)

¬ethyl]-amino}-5,6,7,8-tetrahydroquinoline-2-carboxylic acid for use in the inhalative treatment of a cardiopulmonary disorder according to any one of claims 1 to 9, characterized in that the x-ray powder diffractogram further comprises peaks at 23.0, 15.2, 25.8 and 25.1.

11. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 10, characterized in that the compound in form of monohydrate I has an X-ray powder diffraction pattern as shown in FIG. 6 (measured at 25° C. and with Cu-K alpha 1 as radiation source).

12. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 11, characterized in that the compound in form of monohydrate II has an X-ray powder diffraction pattern as shown in FIG. 7 (measured at 25° C. and with Cu-K alpha 1 as radiation source).

13. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 12, characterized in that the compound in form of sesquihydrate has an X-ray powder diffraction pattern as shown in FIG. 9 (measured at 25° C. and with Cu-K alpha 1 as radiation source).

14. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 13, characterized in that the compound in its crystalline modification monohydrate I of formula (I-M-I) is stable during micronization.

15. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 14, characterized in that the X-ray powder diffractogram (measured at 25° C. and with Cu-K alpha 1 as radiation source) of the compound comprises a peak at least at 12.8 and lacks peaks at 27.2 and 27.5, at diffraction angle 2θ value±0.2°.

16. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 15, characterized in that the X-ray powder diffractogram (measured at 25° C. and with Cu-K alpha 1 as radiation source) of the compound comprises a peak at least at 12.8 and 5.7 and lacks peaks at 8.5 and 6.1, at diffraction angle 2θ value±0.2°.

17. 5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 16, characterized in that the active ingredient is administered for a period of at least two to seven consecutive days.

18. 5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 17, characterized in that the active ingredient is administered for a period of at least 14 consecutive days, in particular from after onset of treatment for the whole course of the disease.

19. 5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 18, characterized in that the inhalative dosage form comprises the active ingredient in the form of a dry powder.

20. 5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 19, characterized in that the inhalative dosage form comprises the active ingredient in the form of a dry powder within a capsule.

21. 5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 20, characterized in that the inhalative dosage form is administered via a dry powder inhaler.

22. 5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 21, characterized in that the inhalative dosage form comprises the active ingredient in combination with a pharmaceutically suitable carrier.

23. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 22, characterized in that the inhalative dosage form comprises lactose monohydrate as carrier, wherein preferably the carrier comprises a mixture of coarse and fine lactose.

24. (5S)-{[2-(4-carboxyphenyl)ethyl][2-(2-{[3-chloro-4'-(trifluoromethyl)biphenyl-4-yl]methoxy}¬phenyl) ¬ethyl]-amino}-5,6,7,8-tetrahydroquinoline-2-carboxylic acid for use in the inhalative treatment of a cardiopulmonary disorder according to any one of claims 1 to 23, characterized in that the coarse lactose has a particle size of X50≥50 μm or ≥75 μm or ≥125 μm and that the fine lactose has a particle size of X50<10 μm or ≤5 μm.

25. (5S)-{[2-(4-carboxyphenyl)ethyl][2-(2-{[3-chloro-4'-(trifluoromethyl)biphenyl-4-yl]methoxy}¬phenyl) ¬ethyl]-amino}-tetrathydroquinoline-2-carboxylic acid for use in the inhalative treatment of a cardiopulmonary disorder according to any one of claims 1 to 24, characterized in that the coarse lactose has a particle size of X50≤145 μm or ≤100 μm or ≤95 μm and that the fine lactose has a particle size of X50<10 μm or ≤5 μm.

26. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 25, characterized in that the coarse lactose has a particle size of X90≥115 μm or being at least or 2120 μm or being at least or ≥200 μm and that the fine lactose has a particle size of X90<30 μm or ≤10 μm.

27. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 26, characterized in that the coarse lactose has a particle size of X90≤250 μm or ≤170 μm or ≤160 μm and that the fine lactose has a particle size of X90<30 μm or ≤10 μm.

28. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 27, characterized in that monohydrate I of formula (I-M-I) has a particle size of X90≤6 μm.

29. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 28, characterized in that monohydrate I of formula (I-M-I) has a particle size of X50 of between 1-3 μm.

30. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 29, characterized in that the inhalative dosage form comprises 480 to 4000 μg of (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

31. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 30, characterized in that the inhalative dosage form comprises 480 to 2000 μg (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

32. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 31, characterized in that the inhalative dosage form comprises 480 to 1000 μg (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

33. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 32, characterized in that the inhalative dosage form comprises 240 μg, 480 μg, 1000 μg, 2000 μg or 4000 μg (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

34. (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid for use in the inhalative treatment of a cardiopulmonary disorder according to any one of claims 1 to 33, characterized in that the cardiopulmonary disorder is selected from the group consisting of pulmonary arterial hypertension (PAH), chronic tromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

35. A method of treating a cardiopulmonary disorder, comprising administering an inhalative dosage form, comprising 240 to 4000 μg of (5S)-{[2-(4-carboxyphenyl)ethyl][2-(2-{[3-chloro-4-(trifluoromethyl)biphenyl-4-yl]methoxy}¬phenyl)-ethyl]-amino}-5,6,7,8-tetrahydroquinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°, once or twice daily for at least two consecutive days.

36. A method of treating a cardiopulmonary disorder according to claim 35, characterized in that the compound in form of monohydrate I has an X-ray powder diffraction pattern as shown in FIG. 6 (measured at 25° C. and with Cu-K alpha 1 as radiation source).

37. A method of treating a cardiopulmonary disorder according to any one of claims 35 to 36, characterized in that the X-ray powder diffractogram (measured at 25° C. and with Cu-K alpha 1 as radiation source) of the compound comprises a peak at least at 12.8 and lacks peaks at 27.2 and 27.5, at diffraction angle 2θ value±0.2°.

38. A method of treating a cardiopulmonary disorder according to any one of claims 35 to 37, characterized in that the X-ray powder diffractogram (measured at 25° C. and with Cu-K alpha 1 as radiation source) of the compound comprises a peak at least at 12.8 and 5.7 and lacks peaks at 8.5 and 6.1, at diffraction angle 2θ value±0.2°.

39. A method of treating a cardiopulmonary disorder according to any one of claims 35 to 38, characterized in that the compound in form of monohydrate II has an X-ray powder diffraction pattern as shown in FIG. 7 (measured at 25° C. and with Cu-K alpha 1 as radiation source).

40. A method of treating a cardiopulmonary disorder according to any one of claims 35 to 39, characterized in that the compound in form of sesquihydrate has an X-ray powder diffraction pattern as shown in FIG. 9 (measured at 25° C. and with Cu-K alpha 1 as radiation source).

41. A method of treating a cardiopulmonary disorder according to any one of claims 35 to 40, characterized in that the active ingredient is administered for a period of at least two to seven consecutive days.

42. A method of treating a cardiopulmonary disorder according to any one of claims 35 to 41, characterized in that the active ingredient is administered for a period of at least 14 consecutive days, in particular from after onset of treatment for the whole course of the disease.

43. A method of treating a cardiopulmonary disorder according to any one of claims 35 to 42, characterized in that the inhalative dosage form comprises the active ingredient in the form of a dry powder.

44. A method of treating a cardiopulmonary disorder according to any one of claims 35 to 43, characterized in that the inhalative dosage form comprises the active ingredient in the form of a dry powder within a capsule.

45. A method of treating a cardiopulmonary disorder according to any one of claims 35 to 44, characterized in that the inhalative dosage form comprises the active ingredient in combination with a pharmaceutically suitable carrier.

46. A method of treating a cardiopulmonary disorder according to any one of claims 35 to 45, characterized in that the inhalative dosage form comprises lactose monohydrate as carrier, wherein preferably the carrier comprises a mixture of coarse and fine lactose.

47. A method of treating a cardiopulmonary disorder according to claim 46, characterized in that the coarse lactose has a particle size of X50≥50 μm or ≥75 μm or ≥125 μm and that the fine lactose has a particle size of X50<10 μm or ≤5 μm.

48. A method of treating a cardiopulmonary disorder according to claim 46 or 47, characterized in that the coarse lactose has a particle size of X50≤145 μm or ≤100 μm or ≤95 μm and that the fine lactose has a particle size of X50<10 μm or ≤5 μm.

49. A method of treating a cardiopulmonary disorder according to any one of claims 46 to 48, characterized in that the characterized in that the coarse lactose has a particle size of X90 2115 μm or being at least or ≥120 μm or being at least or ≥200 μm and that the fine lactose has a particle size of X90<30 μm or ≤10 μm.

50. A method of treating a cardiopulmonary disorder according to any one of claims 46 to 49, characterized in that the coarse lactose has a particle size of X90≤250 μm or ≤170 μm or ≤160 μm and that the fine lactose has a particle size of X90<30 μm or ≤10 μm.

51. A method of treating a cardiopulmonary disorder according to any one of claims 35 to 50, characterized in that the monohydrate I of formula (I-M-I) has a particle size of X90≤6 μm.

52. A method of treating a cardiopulmonary disorder according to any one of claims 35 to 51, characterized in that the monohydrate I of formula (I-M-I) has a particle size of X50 of between 1-3 μm.

53. A method of treating a cardiopulmonary disorder according to any one of claims 35 to 52, characterized in that the inhalative dosage form comprises 480 to 4000 μg (5S)-{[2-(4-carboxyphenyl)ethyl][2-(2-{[3-chloro-4'-(trifluoromethyl)biphenyl-4-yl] methoxy}¬phenyl)¬ethyl]-amino}-5,6,7,8-tetrahydro-quinoline-2-carboxylic acid in form of its crystalline form monohydrate I.

54. A method of treating a cardiopulmonary disorder according to any one of claims 35 to 53, characterized in that the inhalative dosage form comprises 480 to 2000 μg (5S)-{[2-(4-carboxyphenyl)ethyl][2-(2-{[3-chloro-4'-(trifluoromethyl)biphenyl-4-yl] methoxy}¬phenyl)¬ethyl]-amino}-5,6,7,8-tetrahydro-quinoline-2-carboxylic acid in form of its crystalline form monohydrate I.

55. A method of treating a cardiopulmonary disorder according to any one of claims 35 to 54, characterized in that the inhalative dosage form comprises 480 to 1000 μg (5S)-{[2-(4-carboxyphenyl)ethyl][2-(2-{[3-chloro-4'-(trifluoromethyl)biphenyl-4-yl] methoxy}¬phenyl)¬ethyl]-amino}-5,6,7,8-tetrahydro-quinoline-2-carboxylic acid in form of its crystalline form monohydrate I.

56. A method of treating a cardiopulmonary disorder according to any one of claims 35 to 55, characterized in that the inhalative dosage form comprises 240 μg, 480 μg, 1000 μg, 2000 μg or 4000 μg (5S)-{[2-(4-carboxyphenyl)ethyl][2-(2-{[3-chloro-4'-(trifluorom-ethyl)biphenyl-4-yl]methoxy)}¬phenyl)¬ethyl]-amino}-5,6,7,8-tetrahydroquinoline-2-carboxylic acid in form of its crystalline form monohydrate I.

57. A method of treating a cardiopulmonary disorder according to any one of claims 35 to 56, characterized in that the cardiopulmonary disorder is selected from the group consisting of pulmonary arterial hypertension (PAH), chronic tromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

58. A medicament for use in the inhalative treatment of a cardiopulmonary disorder, characterized in that it comprises an inhalative dosage form, which comprises 240 to 4000 μg of (5S)-{[2-(4-carboxyphenyl)ethyl][2-(2-{[3-chloro-4'-(trifluoromethyl)biphenyl-4-yl] methoxy}¬phenyl)¬ethyl]-amino}-5,6,7,8-tetrahydro-quinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°, wherein the medicament is administered once or twice daily for at least two consecutive days to a patient in need thereof.

59. A medicament for use in the inhalative treatment of a cardiopulmonary disorder according to claim 58, characterized in that the compound in form of monohydrate I has an X-ray powder diffraction pattern as shown in FIG. 6 (measured at 25° C. and with Cu-K alpha 1 as radiation source).

60. A medicament for use in the inhalative treatment of a cardiopulmonary disorder according to any one of claim 58 to 59, characterized in that the X-ray powder diffractogram (measured at 25° C. and with Cu-K alpha 1 as radiation source) of the compound comprises a peak at least at 12.8 and lacks peaks at 27.2 and 27.5, at diffraction angle 2θ value±0.2°.

61. A medicament for use in the inhalative treatment of a cardiopulmonary disorder according to any one of claim 58 to 60, characterized in that the X-ray powder diffractogram (measured at 25° C. and with Cu-K alpha 1 as radiation source) of the compound comprises a peak at least at 12.8 and 5.7 and lacks peaks at 8.5 and 6.1, at diffraction angle 2θ value±0.2°.

62. A medicament for use in the inhalative treatment of a cardiopulmonary disorder according to any one of claim 58 to 61, characterized in that the compound in form of monohydrate II has an X-ray powder diffraction pattern as shown in FIG. 7 (measured at 25° C. and with Cu-K alpha 1 as radiation source).

63. A medicament for use in the inhalative treatment of a cardiopulmonary disorder according to any one of claim 58 to 62, characterized in that the compound in form of sesquihydrate has an X-ray powder diffraction pattern as shown in FIG. 9 (measured at 25° C. and with Cu-K alpha 1 as radiation source).

64. A medicament for use in the inhalative treatment of a cardiopulmonary disorder according to any one of claim 58 to 63, characterized in that the active ingredient is administered for a period of at least two to seven consecutive days.

65. A medicament for use in the inhalative treatment of a cardiopulmonary disorder according to any one of claim 58 to 64, characterized in that the active ingredient is administered for a period of at least 14 consecutive days, in particular from after onset of treatment for the whole course of the disease.

66. A medicament for use in the inhalative treatment of a cardiopulmonary disorder according to any one of claim 58 to 65, characterized in that the inhalative dosage form comprises the active ingredient in the form of a dry powder.

67. A medicament for use in the inhalative treatment of a cardiopulmonary disorder according to any one of claim 58 to 66, characterized in that the inhalative dosage form comprises the active ingredient in the form of a dry powder within a capsule.

68. A medicament for use in the inhalative treatment of a cardiopulmonary disorder according to any one of claim 58 to 67, characterized in that the inhalative dosage form comprises the active ingredient in combination with a pharmaceutically suitable carrier.

69. A medicament for use in the inhalative treatment of a cardiopulmonary disorder according to any one of claim 58 to 68, characterized in that the inhalative dosage form comprises lactose monohydrate as carrier, wherein preferably the carrier comprises a mixture of coarse and fine lactose.

70. A medicament for use in the inhalative treatment of a cardiopulmonary disorder according to any one of claim 58 to 69, characterized in that the coarse lactose has a particle size of X50≥50 μm or ≥75 μm or ≥125 μm and that the fine lactose has a particle size of X50<10 μm or ≤5 μm.

71. A medicament for use in the inhalative treatment of a cardiopulmonary disorder according to any one of claim 58 to 70, characterized in that the coarse lactose has a particle size of X50≤145 μm or ≤100 μm or ≤95 μm and that the fine lactose has a particle size of X50<10 μm or ≤5 μm.

72. A medicament for use in the inhalative treatment of a cardiopulmonary disorder according to any one of claim 58 to 71, characterized in that the coarse lactose has a particle size of X90≥115 μm or being at least or ≥120 μm or being at least or ≥200 μm and that the fine lactose has a particle size of X90<30 μm or ≤10 μm.

73. A medicament for use in the inhalative treatment of a cardiopulmonary disorder according to any one of claim 58 to 72, characterized in that the coarse lactose has a particle size of X90≤250 μm or ≤170 μm or ≤160 μm and that the fine lactose has a particle size of X90<30 μm or ≤10 μm.

74. A medicament for use in the inhalative treatment of a cardiopulmonary disorder according to any one of claim 58 to 73, characterized in that the monohydrate I of formula (I-M-I) has a particle size of X90≤6 μm.

75. A medicament for use in the inhalative treatment of a cardiopulmonary disorder according to any one of claim 58 to 74, characterized in that the monohydrate I of formula (I-M-I) has a particle size of X50 of between 1-3 μm.

76. A medicament for use in the inhalative treatment of a cardiopulmonary disorder according to any one of claim 58 to 75, characterized in that the inhalative dosage form comprises 480 to 4000 μg (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

77. A medicament for use in the inhalative treatment of a cardiopulmonary disorder according to any one of claim 58 to 76, characterized in that the inhalative dosage form comprises 480 to 2000 μg (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

78. A medicament for use in the inhalative treatment of a cardiopulmonary disorder according to any one of claim 58 to 77, characterized in that the inhalative dosage form comprises 480 to 1000 μg (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

79. A medicament for use in the inhalative treatment of a cardiopulmonary disorder according to any one of claim 58 to 78, characterized in that the inhalative dosage form comprises 240 μg, 480 μg, 1000 μg, 2000 μg or 4000 μg (5S)-{[2-(4-carboxyphenyl)ethyl][2-(2-{[3-chloro-4'-(trifluoromethyl)biphenyl-4-yl]

methoxy}¬phenyl)¬ethyl]-amino}-5,6,7,8-tetrahydro-quinoline-2-carboxylic acid in form of its crystalline form monohydrate I.

80. A medicament for use in the inhalative treatment of a cardiopulmonary disorder according to any one of claim 58 to 79, characterized in that the cardiopulmonary disorder is selected from the group consisting of pulmonary arterial hypertension (PAH), chronic tromboembolic pulmonary hypertension (CTEPH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

81. A packaged pharmaceutical composition for use in the inhalative treatment of a cardiopulmonary disorder, characterized in that it contains a dry powder inhaler and a dry powder formulation comprising 240 to 4000 μg of (5S)-{[2-(4-Carboxyphenyl)ethyl][2-(2-{[3-chloro-4'-(trifluoromethyl)biphenyl-4-yl] methoxy}¬phenyl)¬ethyl]amino}-5,6,7,8-tetrahydro-quinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°, wherein the package contains instructions for administering said dry powder formulation at a frequency of once or twice daily for a period of at least two consecutive days.

82. A packaged pharmaceutical composition for use in the inhalative treatment of a cardiopulmonary disorder according to claim 81, characterized in that the cardiopulmonary disorder is selected from the list consisting of pulmonary arterial hypertension (PAH) and pulmonary hypertension (PH) associated with chronic lung disease (PH group 3) such as pulmonary hypertension in chronic obstructive pulmonary disease (PH-COPD) and pulmonary hypertension with idiopathic interstitial pneumonia (PH-IIP).

83. A packaged pharmaceutical composition for use in the inhalative treatment of a cardiopulmonary disorder according to any one of claims 81 to 82, characterized in that said package furthermore contains instructions for using said dry powder formulation to treat a cardiopulmonary disorder by inhalation, wherein the inhalation procedure is described as follows: to put the capsule into the dry powder inhaler, than after one deep inhalative breath the patient should hold breath for about 2 seconds, so that the dry powder drug condenses from the airstream onto the surface of the deeper lung areas where it is deposited close to its site of intended pharmacological action.

84. A packaged pharmaceutical composition for use in the inhalative treatment of a cardiopulmonary disorder according to any one of claims 81 to 83, characterized in that the dry powder inhaler is a capsule based single-unit dose inhaler (see FIG. 3*a*).

85. A packaged pharmaceutical composition for use in the inhalative treatment of a cardiopulmonary disorder according to any one of claims 81 to 84, characterized in that it contains a dry powder formulation comprising 240 to 4000 μg of (5S)-{[2-(4-Carboxyphenyl)ethyl] [2-(2-{[3-chloro-4'-(trifluoromethyl)biphenyl-4-yl] methoxy}¬phenyl)¬ethyl]amino}-5,6,7,8-tetrahydro-quinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°, but not the dry powder inhaler.

86. A packaged pharmaceutical composition for use in the inhalative treatment of a cardiopulmonary disorder according to any one of claims 81 to 85, characterized in that the dry powder formulation comprises (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid, preferably in form of monohydrate form I of formula (I-M-I) or in form of monohydrate form II of formula (I-M-II) in combination with lactose monohydrate as carrier, wherein the carrier comprises a mixture of coarse and fine lactose.

87. A packaged pharmaceutical composition for use in the inhalative treatment of a cardiopulmonary disorder according to any one of claims 81 to 86, characterized in that the compound in form of monohydrate I has an X-ray powder diffraction pattern as shown in FIG. 6 (measured at 25° C. and with Cu-K alpha 1 as radiation source).

88. A packaged pharmaceutical composition for use in the inhalative treatment of a cardiopulmonary disorder according to any one of claims 81 to 87, characterized in that the X-ray powder diffractogram (measured at 25° C. and with Cu-K alpha 1 as radiation source) of the compound comprises a peak at least at 12.8 and lacks peaks at 27.2 and 27.5, at diffraction angle 2θ value±0.2°.

89. A packaged pharmaceutical composition for use in the inhalative treatment of a cardiopulmonary disorder according to any one of claims 81 to 88, characterized in that the X-ray powder diffractogram (measured at 25° C. and with Cu-K alpha 1 as radiation source) of the compound comprises a peak at least at 12.8 and 5.7 and lacks peaks at 8.5 and 6.1, at diffraction angle 2θ value±0.2°.

90. A packaged pharmaceutical composition for use in the inhalative treatment of a cardiopulmonary disorder according to any one of claims 81 to 89, characterized in that the compound in form of monohydrate H has an X-ray powder diffraction pattern as shown in FIG. 7 (measured at 25° C. and with Cu-K alpha 1 as radiation source).

91. A packaged pharmaceutical composition for use in the inhalative treatment of a cardiopulmonary disorder according to any one of claims 81 to 90, characterized in that the compound in form of sesquihydrate has an X-ray powder diffraction pattern as shown in FIG. 9 (measured at 25° C. and with Cu-K alpha 1 as radiation source).

92. A packaged pharmaceutical composition for use in the inhalative treatment of a cardiopulmonary disorder according to any one of claims 81 to 91, characterized in that the active ingredient is administered for a period of at least two to seven consecutive days.

93. A packaged pharmaceutical composition for use in the inhalative treatment of a cardiopulmonary disorder according to any one of claims 81 to 92, characterized in that the active ingredient is administered for a period of at least 14 consecutive days, in particular from after onset of treatment for the whole course of the disease.

94. A packaged pharmaceutical composition for use in the inhalative treatment of a cardiopulmonary disorder according to any one of claims 81 to 93, characterized in that the inhalative dosage form comprises the active ingredient in the form of a dry powder.

95. A packaged pharmaceutical composition for use in the inhalative treatment of a cardiopulmonary disorder according to any one of claims 81 to 94, characterized in that the inhalative dosage form comprises the active ingredient in the form of a dry powder within a capsule.

96. A packaged pharmaceutical composition for use in the inhalative treatment of a cardiopulmonary disorder according to any one of claims 81 to 95, characterized in that the coarse lactose has a particle size of X50≥50 μm or ≥75 μm or ≥125 μm and that the fine lactose has a particle size of X50<10 μm or ≤5 μm.

97. A packaged pharmaceutical composition for use in the inhalative treatment of a cardiopulmonary disorder according to any one of claims 81 to 96, characterized in that the coarse lactose has a particle size of X50≤145 μm or ≤100 μm or ≤95 μm and that the fine lactose has a particle size of X50<10 μm or ≤5 μm.

98. A packaged pharmaceutical composition for use in the inhalative treatment of a cardiopulmonary disorder according to any one of claims 81 to 97, characterized in that the coarse lactose has a particle size of X90≥115 μm or being at least or ≥120 μm or being at least or ≥200 μm and that the fine lactose has a particle size of X90<30 μm or ≤10 μm.

99. A packaged pharmaceutical composition for use in the inhalative treatment of a cardiopulmonary disorder according to any one of claims 81 to 98, characterized in that the coarse lactose has a particle size of X90≤250 μm or ≤170 μm or ≤160 μm and that the fine lactose has a particle size of X90<30 μm or ≤10 μm.

100. A packaged pharmaceutical composition for use in the inhalative treatment of a cardiopulmonary disorder according to any one of claims 81 to 99, characterized in that the monohydrate I of formula (I-M-I) has a particle size of X90≤6 μm.

101. A packaged pharmaceutical composition for use in the inhalative treatment of a cardiopulmonary disorder according to any one of claims 81 to 100, characterized in that the monohydrate I of formula (I-M-I) has a particle size of X50 of between 1-3 μm.

102. A packaged pharmaceutical composition for use in the inhalative treatment of a cardiopulmonary disorder according to any one of claims 81 to 101, characterized in that the inhalative dosage form comprises 480 to 4000 μg (5S)-{[2-(4-carboxyphenyl)ethyl][2-(2-{[3-chloro-4'-(trifluoromethyl)biphenyl-4-yl] methoxy}¬phenyl)¬ethyl]-amino}-5,6,7,8-tetrahydro-quinoline-2-carboxylic acid in form of its crystalline form monohydrate I.

103. A packaged pharmaceutical composition for use in the inhalative treatment of a cardiopulmonary disorder according to any one of claims 81 to 102, characterized in that the inhalative dosage form comprises 480 to 2000 μg (5S)-{[2-(4-carboxyphenyl)ethyl][2-(2-{[3-chloro-4'-(trifluoromethyl)biphenyl-4-yl] methoxy}¬phenyl)¬ethyl]-amino}-5,6,7,8-tetrahydro-quinoline-2-carboxylic acid in form of its crystalline form monohydrate I.

104. A packaged pharmaceutical composition for use in the inhalative treatment of a cardiopulmonary disorder according to any one of claims 81 to 103, characterized in that the inhalative dosage form comprises 480 to 1000 μg (5S)-{[2-(4-carboxyphenyl)ethyl][2-(2-{[3-chloro-4'-(trifluoromethyl)biphenyl-4-yl] methoxy}¬phenyl)¬ethyl]-amino}-5,6,7,8-tetrahydro-quinoline-2-carboxylic acid in form of its crystalline form monohydrate I.

105. A packaged pharmaceutical composition for use in the inhalative treatment of a cardiopulmonary disorder according to any one of claims 81 to 103, characterized in that the inhalative dosage form comprises 240 μg, 480 μg, 1000 μg, 2000 μg or 4000 μg (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid in form of its crystalline form monohydrate I.

Further Specific Embodiments of the Invention (Formulation)

1. A formulation for inhalation, characterized in that the formulation contains a dry powder blend consisting of a) (5S)-{[2-(4-carboxyphenyl)ethyl][2-(2-{[3-chloro-4'-(trifluoromethyl)biphenyl-4-yl]methoxy}phenyl) ethyl]-amino}-5,6,7,8-tetrahydroquinoline-2-carboxylic acid in form of one of its salts or solvates or hydrates b) a lactose carrier in a concentration by weight from 99.25% (w/w) to 80% (w/w), further characterized in that c) the active ingredient (5S)-{[2-(4-carboxyphenyl)ethyl] [2-(2-{[3-chloro-4'-(trifluoromethyl)biphenyl-4-yl] methoxy}phenyl)ethyl]-amino}-5,6,7,8-tetrahydroquinoline-2-carboxylic acid in form of one of its salts or solvates or hydrates has a particle size of X90≤6 μm and/or X50 of between 1 and 3 μm d) the lactose carrier is lactose monohydrate for inhalation further characterized in that e) the lactose has a particle size of X90≥120 μm; and/or X50≥50 μm and/or X10 5-15 μm.

2. A formulation for inhalation according to claim 1, characterized in that the formulation contains (5S)-{[2-(4-carboxyphenyl)ethyl][2-(2-{[3-chloro-4'-(trifluoromethyl) biphenyl-4-yl]methoxy}¬phenyl)-ethyl]-amino}-5,6,7,8-tetrahydroquinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°.

3. A formulation for inhalation according to any of claims 1 to 2, characterized in that the formulation contains a dry powder blend consisting of a) (5S)-{[2-(4-carboxyphenyl)ethyl][2-(2-{[3-chloro-4'-(trifluoromethyl)biphenyl-4-yl]methoxy}phenyl) ethyl]-amino}-5,6,7,8-tetrahydroquinoline-2-carboxylic acid in form of monohydrate I of formula (I-M-I) or monohydrate II of formula (I-M-II), preferably monohydrate I of formula (I-M-I) as active ingredient, wherein the x-ray diffractogram (at 25° C. and with Cu-K alpha 1 as radiation source) of the monohydrate form I of formula (I-M-I) displays at least the following reflections, 12.8 and 29.2, preferably at 6.9, 7.2, 7.3, 12.8 and 29.2 quoted as 2θ value±0.2°, in a concentration by weight from 0.75% (w/w) to 20% (w/w) in combination with b) a lactose carrier in a concentration by weight from 99.25% (w/w) to 80% (w/w),
further characterized in that c) the active ingredient (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I) or monohydrate II of formula (I-M-II) has a particle size of X90≤6 μm and/or X50 of between 1 and 3 μm d) the lactose carrier is lactose monohydrate for inhalation consisting of coarse lactose and fine lactose
further characterized in that e) the coarse lactose, has a particle size of X50≥50 μm or ≥75 μm or ≥125 μm f) the fine lactose has a particle size of X50<10 μm or ≤5 μm g) wherein the coarse lactose content of the dry powder blend is between 98.25% and 75%, preferably between 94.25% and 75%.

4. A formulation for inhalation according to any of claims 1 to 3, characterized in that e) the coarse lactose, has a particle size of X50≤145 μm or ≤100 μm or ≤95 μm f) the fine lactose has a particle size of X50<10 μm or ≤5 μm.

5. A formulation for inhalation according to any of claims 1 to 4, characterized in that e) the coarse lactose, has a particle size of X90≥115 μm or being at least or ≥120 μm or being at least or ≥200 μm f) the fine lactose has a particle size of X90<30 μm or ≤10 μm.

6. A formulation for inhalation according to any of claims 1 to 5, characterized in that e) the coarse lactose, has a particle size of ≤250 μm or ≤170 μm or ≤160 μm and f) the fine lactose has a particle size of X90<30 μm or ≤10 μm.

7. A formulation for inhalation according to any of claims 1 to 6, characterized in that the process for the manufacture of the formulation j) does involve sieving or no sieving between mixing cycles, preferably no sieving and at least a rest time of 10 min between mixing cycles.

8. A formulation for inhalation according to any of claims 1 to 6, characterized in that during the process for the manufacture of the formulation k) no glass vessel but stainless steel vessels are used.

9. A formulation for inhalation according to any one of claims 1 to 8,
characterized in that the content of fine lactose in the dry powder blend is between 1% and up to 15%, 1% and 10%, or 5% and 10%.

10. A formulation for inhalation according to any one of claims 1 to 9,
characterized in that the ratio of active ingredient to coarse lactose is between 1:126 and 1:3.8

11. A formulation for inhalation according to any one of claims 1 to 10,
characterized in that the ratio of active ingredient to coarse lactose is between 1:31 and 1:3.8.

12. A formulation for inhalation according to any one of claims 1 to 11,
characterized in that the ratio of active ingredient to coarse lactose is 1:31.

13. A formulation for inhalation according to any one of claims 1 to 12,
characterized in that the ratio of active ingredient to coarse lactose is 1:8.5.

14. A formulation for inhalation according to any one of claims 1 to 13,
characterized in that the ratio of active ingredient to coarse lactose is 1:3.8.

15. A formulation for inhalation according to any one of claims 1 to 14, characterized in that the ratio of active ingredient to fine lactose is between 1:13 to 1:0.1

16. A formulation for inhalation according to any one of claims 1 to 15, characterized in that the ratio of active ingredient to fine lactose is between 1:1.67 and 1:0.25

17. A formulation for inhalation according to any one of claims 1 to 16, characterized in that the ratio of active ingredient to fine lactose is 1:1.67.

18. A formulation for inhalation according to any one of claims 1 to 17, characterized in that the ratio of active ingredient to fine lactose is 1:0.5.

19. A formulation for inhalation according to any one of claims 1 to 18, characterized in that the ratio of active ingredient to fine lactose is 1:0.25 or is 1:0.1.

20. A formulation for inhalation according to any one of claims 1 to 19, characterized in that the ratio of coarse lactose to fine lactose is between 445:5 and 65:5 or between 94.25:5 and 65:5.

21. A formulation for inhalation according to any one of claims 1 to 20, characterized in that the ratio of coarse lactose to fine lactose is 92:5.

22. A formulation for inhalation according to any one of claims 1 to 21, characterized in that the ratio of coarse lactose to fine lactose is 85:5.

23. A formulation for inhalation according to any one of claims 1 to 22, characterized in that the ratio of coarse lactose to fine lactose is 75:5.

24. A formulation for inhalation according to any one of claims 1 to 23, characterized in that the active ingredient is (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I).

25. A formulation for inhalation according to any one of claims 1 to 24, characterized in that the active ingredient (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) has a particle size of X50=1-3 μm.

26. A formulation for inhalation according to any one of claims 1 to 25, characterized in that the active ingredient is (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate II of formula (I-M-II).

27. A formulation for inhalation according to any one of claims 1 to 26, characterized in that the active ingredient (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate II of formula (I-M-II) has a particle size of X50=1-3 μm.

28. A formulation for inhalation according to any one of claims 1 to 27, characterized in that the active ingredient (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid Monohydrate I of formula (I-M-I) has a particle size of X10=max 1 μm.

29. A formulation for inhalation according to any one of claims 1 to 28, characterized in that fine lactose has a particle size of X50≤10 μm or of X50=≤5 μm.

30. A formulation for inhalation according to any one of claims 1 to 29, characterized in that the fine lactose is Lactohale® 300 or Lactohale®230.

31. A formulation for inhalation according to any one of claims 1 to 30, characterized in that the coarse lactose is in form of sieved or milled, crystalline lactose.

32. A formulation for inhalation according to any one of claims 1 to 31, characterized in that the coarse lactose has a particle size of X90=200-250 μm or 120-160 μm or 115-170 μm.

33. A formulation for inhalation according to any one of claims 1 to 32, characterized in that the coarse lactose has a particle size of X50=125-145 μm or 50-100 μm or 75-95 μm.

34. A formulation for inhalation according to any one of claims 1 to 33, characterized in that the coarse lactose has a particle size of X10=45-65 μm or 5-15 μm or 20-50 μm.

35. A formulation for inhalation according to any one of claims 1 to 34, characterized in that the fine lactose has a particle size of X90≤10 μm or <30 μm.

36. A formulation for inhalation according to any one of claims 1 to 35, characterized in that the fine lactose has a particle size of X50≤5 μm or <10 μm.

37. A formulation for inhalation according to any one of claims 1 to 36, characterized in that the coarse lactose has a particle size of X10=1-3 μm.

38. A formulation for inhalation according to any one of claims 1 to 37, characterized in that the coarse lactose is Lactohale® 100, Lactohale®200 or Lactohale® 206.

39. A formulation for inhalation according to any one of claims 1 to 38, characterized in that it contains a nominal dose of 60 μg-6000 μg of 5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I).

40. A formulation for inhalation according to any one of claims 1 to 39, characterized in that it contains a nominal dose of 240-4000 μg of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I).

41. A formulation for inhalation according to any one of claims 1 to 40, characterized in that it contains a nominal dose of 480-4000 μg of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I).

42. A formulation for inhalation according to any one of claims 1 to 41, characterized in that it contains a nominal dose of 480-2000 μg of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I).

43. A formulation for inhalation according to any one of claims 1 to 42, characterized in that it contains a nominal dose of 480-1000 μg of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I).

44. A formulation for inhalation according to any one of claims 1 to 43, characterized in that it contains a nominal dose of 240 μg, 480 μg, 1000 μg, 2000 μg or 4000 μg of (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid in form of monohydrate I of formula (I-M-I).

45. A formulation for inhalation according to any one of claims 1 to 44, characterized in that the coarse lactose content in the dry powder blend is 98.25% to 75% or preferably between 94.25% and 75% or more preferably from 90.00% to 75% or more preferably from 90% to 85% and the fine lactose content in the dry powder blend is from 1.0.% up to 15% or preferably 1% up to 10%, preferably between 5% and 10%, or more preferably 2.5%-7.5%, preferably between 5% and 7.5% or more preferably 3-7% or more preferably 4%-6%

46. A formulation for inhalation according to any one of claims 1 to 45, characterized in that it has a blend assay of 90-110% preferably 95-105% (m/m) and a blend uniformity of RSD (=relative standard deviation) (n=10) of NMT (=not more than) 10% preferably 7.5% more preferably 5%.

47. A formulation for inhalation according to any one of claims 1 to 46, characterized in that it has a FPF (% of nominal dose of active, <4.5 μm) of ≥20% and a FPF (% of DD of active<4.5 μm) of ≥30% of active ingredient measured by Cascade Impaction and Dose Unit Sampling Apparatus (DUSA).

48. A formulation for inhalation filled into hard capsules according to any one of claims 1 to 47, characterized in that it has a minimum fine particle dose of 8-780 μg depending on the active ingredient concentration and capsule fill mass.

49. A formulation for inhalation filled in hard capsules according to any one of claims 1 to 48, characterized in that it has a minimum delivered dose of 26-3315 μg depending on the active ingredient concentration and capsule fill mass.

50. A cavity comprising the formulation for inhalation according to any one of claims 1 to 49, which can be administered via a dry powder inhaler to a patient in need thereof.

51. A cavity according to claim 50 being a capsule or a blister strip.

52. A cavity according to claim 50 being a capsule.

53. A cavity according to any one of claims 50 to 52, characterized in that it contains a filled mass of 8-40 mg of the dry powder blend.

54. A cavity according to any one of claims 50 to 52, characterized in that it contains a filled mass of 10-30 mg of the formulation for inhalation.

55. A cavity according to any one of claims 50 to 52, characterized in that it contains a filled mass of 10-20 mg of the formulation for inhalation.

56. A cavity according to any one of claims 50 to 52, characterized in that it contains a filled mass of 16-20 mg of the formulation for inhalation.

57. A manufacturing process for manufacturing the formulation for inhalation according to any one of claims 1 to 49, characterized in that a) in a first step 1)

fine Lactose is weighed and layered in between two layers of coarse lactose prior to start of mixing both lactose components, b) in a second step 2)

the blending of the 2 components is carried out in a tumble mixer 2 times (2 cycles) at 72 rpm, 67 rpm or 34 rpm or 32 rpm or 30 rpm for 20 min and the pre-blend sieved through a 500 μm sieve between the cycles, c) in a third step 3) (5S)-{[2-(4-carboxyphenyl)ethyl][2-(2-{[3-chloro-4'-(trifluoromethyl)biphenyl-4-yl] methoxy}phenyl)ethyl]-amino}-5,6,7,8-tetrahydroquinoline-2-carboxylic acid of formula (I), preferably (5S)-{[2-(4-carboxyphenyl)ethyl][2-(2-{[3-chloro-4'-(trifluoromethyl)biphenyl-4-yl]methoxy}phenyl) ethyl]-amino}-5,6,7,8-tetrahydroquinoline-2-carboxylic acid Monohydrate I of formula (I-M-I) is pre-sieved through a 500 μm sieve and added to the Lactose pre-blend as produced in step A and B and layered alternating with 10 layers of lactose pre-blend and 9 layers of active ingredient, 6 layers of lactose pre-blend and 5 layers of active ingredient (ex. 4) in between or 4 layers of lactose pre-blend and 3 layers of active ingredient (ex. 4) in between or 2 layers of lactose pre-blend and 1 layer of active ingredient (ex. 4) in between, preferably 6/5 layers prior to start of mixing d) in a fourth step 4)

the pre-layered blend obtained in step 3) is mixed in a vessel (glass or stainless steel) in 3-5 cycles preferably 3 cycles at 72 rpm, 67 rpm, 34 rpm or 32 rpm preferably 32 rpm for 20-30 minutes preferably 30 minutes (90 min overall mixing time), with a rest time of 10 minutes between the mixing cycles, characterized in, that the product obtained in step 4) is mixed in a stainless steel container, wherein the blend is sieved between each mixing cycle or preferably without sieving the blend between mixing cycles, e) in a fifth step E the product obtained in step 4) is left to rest at room temperature (15-25° C.) and 35-65% relative humidity in a stainless steel container for a certain period of time, preferably 24-72 hours, more preferably 48 h before blend uniformity sampling and final capsule filling is performed, f) in a sixth step 6) the dry powder blend obtained in step E is finally filled into a capsule.

58. Use of a formulation for inhalation according to any one or more of claims 1 to 49 for the production of a medicament for the use in the treatment of cardiopulmonary disorders, characterized in that the medicament comprising an inhalative dosage form, which comprises 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid in form of monohydrate I of formula (I-M-I), wherein the x-ray diffractogram (at 25° C. and with Cu-K alpha 1 as radiation source) of the monohydrate form I of formula (I-M-I) displays at least the following reflections 6.9, 7.2, 7.3, 12.8 and 29.2 quoted as 2θ value±0.2°, is administered to a patient in need thereof once or twice daily for a period of at least two consecutive days.

59. Use of a formulation for inhalation according to any one or more of claims 1 to 49 in the treatment of cardiopulmonary disorders, characterized in that an inhalative dosage form, which comprises 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), wherein the X-ray powder diffractogram (measured at 25° C. and with Cu-K alpha 1 as radiation source) of the compound comprises at least peaks at 12.8 and 29.2, preferably at 6.9, 7.2, 7.3, 12.8 and 29.2 quoted as 2θ value±0.2°, is administered to a patient in need thereof once or twice daily for a period of at least two consecutive days.

60. Use of a formulation for inhalation according to any one or more of claims 1 to 49 in the method of treatment of cardiopulmonary disorders, characterized in that an inhalative dosage form, which comprises 240 to 4000 μg of (5S)-{[2-(4-carboxyphenyl)ethyl][2-(2-{[3-chloro-4'-(trifluoromethyl)biphenyl-4-yl]methoxy}¬phenyl)-ethyl]-amino}-5,6,7,8-tetrahydroquinoline-2-carboxylic acid of formula I in form of its crystalline modification monohydrate I of formula (I-M-I), wherein the X-ray powder diffractogram (measured at 25° C. and with Cu-K alpha 1 as radiation source) of the compound comprises at least peaks at 12.8 and 29.2, preferably at 6.9, 7.2, 7.3, 12.8 and 29.2 quoted as 2θ value±0.2°, is administered to a patient in need thereof once or twice daily for a period of at least two consecutive days.

61. A medicament for use in the inhalative treatment of a cardiopulmonary disorder, characterized in that it comprises an inhalative dosage form, which comprises 240 to 4000 μg of (5S)-{[2-(4-carboxyphenyl)ethyl][2-(2-{[3-chloro-4'-(trifluoromethyl)biphenyl-4-yl]methoxy}¬phenyl)¬ethyl]-amino}-5,6,7,8-tetrahydroquinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°, in an inhalative dosage form, and wherein the inhalative dosage form comprises the active ingredient in the form of a dry powder.

62. A packaged pharmaceutical composition for use in the inhalative treatment of a cardiopulmonary disorder, characterized in that it contains a dry powder inhaler and a dry powder formulation comprising 240 to 4000 μg of (5S)-{[2-(4-Carboxyphenyl)ethyl][2-(2-{[3-chloro-4'-(trifluoromethyl)biphenyl-4-yl]methoxy}¬phenyl)¬ethyl]amino}-5,6,7,8-tetrahydroquinoline-2-carboxylic acid of formula I in form of one of its crystalline modifications selected from the list consisting of monohydrate I of formula (I-M-I) or monohydrate II of formula (I-M-II) or sesquihydrate, wherein the X-ray powder diffractogram (measured at 25° C. and with Cu-K alpha 1 as radiation source) of the compound of formula (I-M-I) comprises at least peaks at 12.8 and 29.2, preferably at 6.9, 7.2, 7.3, 12.8 and 29.2 quoted as 2θ value±0.2°, or wherein the X-ray powder diffractogram (measured at 25° C. and with Cu-K alpha 1 as radiation source) of the compound of formula (I-M-II) comprises at least peaks at 12.7, 5.7, 6.1, and 7.1 or at 12.7, 5.7, and 8.5, or wherein the X-ray powder diffractogram (measured at 25° C. and with Cu-K alpha 1 as radiation source) of the compound in form of its sesquihydrate comprises at least peaks at 12.2 and 7.6, alternatively at 12.2, 8.6 and 14.5 quoted as 2θ value±0.2°, wherein the package contains instructions for administering said dry powder formulation at a frequency of once or twice daily for a period of at least two consecutive days.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

EXPERIMENTAL PART

Abbreviations and Acronyms:

abs. Absolute
acac Acetylacetonato
BINAP (2,2'-bis(diphenylphosphino)-1,1'-binaphthyl)
cat. Catalytic
CI chemical ionization (in MS)
coe Cyclooctene
d day(s)
TLC thin layer chromatography
DCM Dichloromethane
DMA Dimethylacetamide
DMF Dimethylformamide
DMSO dimethyl sulfoxide
ee enantiomeric excess
EI electron impact ionization (in MS)
ent enantiomer/enantiomerically pure
eq equivalent(s)
ESI electrospray ionization (in MS)
EtOAc ethyl acetate
GC-MS gas chromatography-coupled mass spectrometry
% by weight percent by weight
h hour(s)
HPLC high-pressure, high-performance liquid chromatography
ID internal diameter
iPrOAc isopropyl acetate
iPrOH isopropanol
conc. concentrated
LC-MS liquid chromatography-coupled mass spectrometry
LDA lithium diisopropylamide
LiHMDS lithium bis(trimethylsilyl)amide
min minute(s)
MS mass spectrometry
MTBE 2-methoxy-2-methylpropane
NMR nuclear magnetic resonance spectrometry
NMP N-methyl-2-pyrrolidone
Ph Phenyl
pTsOH p-toluenesulfonic acid
$R_f$ retention index (in TLC)
RP-HPLC reversed phase high performance liquid chromatography
RRT relative retention time
$R_t$ retention time
RT room temperature
TESCI Chlorotriethylsilane
THF Tetrahydrofuran
v/v volume to volume ratio (of a solution)
$T_{internal}$ internal temperature
$T_{sheath}$ sheath temperature
CI Chemical Ionisation (at MS)
D day(s)
DC Thin layer Chromatography
DMSO Dimethylsulfoxide
o. th. of theoretical (yield)
ee Excess of enatiomer
EI Electron Impact-Ionisation (at MS)
Ent Enantiomer/enantiomerically pure
wt.-% Weight percent
h hour(s)
HPLC High pressure liquid chromatography
iPrOAc Isopropyl acetate
iPrOH Isopropanol
conc. concentrated
l liter
LC-MS Liquid chromatography-coupled mass spectrometry
min minute(s)
MS Mass sectrometry
pTsOH p-Toluolsulfonsäure
Rf Retention index (bei DC)
RP-HPLC reversed phase high performance liquid chromatography
RRT relative retention time
Rt Retention time
RT Room temperature
THF Tetrahydrofurane
v/v Volume-to-Volume-ratio (in a solution)
Tinternal Internal Temperature
Tsheath Sheath temperature Analytical Methods

DSC/TG

DSC thermograms were recorded using Differential Scanning Calorimeters (model DSC7, Pyris-1 or Diamond) from Perkin-Elmer. The measurements were performed with a heating rate of 20 $Kmin^{-1}$ using non-gastight aluminium pans. Flow gas was nitrogen. There was no sample preparation.

TGA thermograms were recorded using thermobalances (model TGA7 and Pyris 1) from Perkin-Elmer. The measurements were performed with a heating rate of 10 $Kmin^{-1}$ using open platinum pans. Flow gas was nitrogen. There was no sample preparation.

XRPD

X-Ray diffraction patterns were recorded at room temperature using XRD—diffractometers X'Pert PRO (PANalytical) and STOE STADI-P (radiation Cu K alpha 1, wavelength 1.5406 Å). There was no sample preparation. All X-Ray reflections are quoted as °2θ (theta) values (peak maxima) with a resolution of ±0.2°.

Raman

Raman spectra were recorded at room temperature using FT-Raman-spectrophotometers (model RFS 100 and MultiRam) from Bruker. Resolution was 2 $cm^{-1}$. Measurements were performed in glass vials or aluminium discs. There was no sample preparation.

IR

IR-ATR-spectra were recorded at room temperature using a FT-IR-spectrophotometer Tensor 37 with universal diamond ATR device from Bruker. Resolution was 4 $cm^{-1}$. There was no sample preparation.

LC-MS Methods

Method A

Instrument: Waters ACQUITY SQD UPLC System; column: Waters Acquity UPLC HSS T3 1.8 μm 50×1 mm; eluent A: 1 1 Wasser+0.25 ml 99% ige formic acid, eluent B: 1 1 acetonitrile+0.25 ml 99% ige formic acid; gradient: 0.0 min 90% A→1.2 min 5% A→2.0 min 5% A oven: 50° C.; flow: 0.40 ml/min; UV-detection: 210 nm.

HPLC Methods

Method B

High performance liquid chromatograph with thermostatized column oven, UV detector and data evaluation system, measuring wavelength 206 nm, bandwidth: 6 nm, oven temperature 30° C., column: chiralpak AD-H, length: 250 mm, inner diameter: 4.6 mm, grain size: 5 μm, mobile Phase: A: N-heptane, B: ethanol+0.1% diethylamine, gradient program: start 1 ml/min 70% eluent a, 30% eluent B; 12 min 1 ml/min 40% eluent A, 60% eluent B. Sample solvent: ethanol+0.1% diethylamine, Test solution: approx. 1.0 mg/ml of the substance, dissolved with sample solvents, injection volume: 5 μl RT: Enantiomer 1:5.8 min (RRT 1.00), Enantiomer 2: 7.2 min RRT1.25

Method C

High performance liquid chromatograph with thermostatized column oven, UV detector and data evaluation system, measuring wavelength 204 nm, bandwidth: 6 nm, oven temperature 45° C., column: chiralpak AD-H, length: 250 mm, inner diameter: 4.6 mm, grain size: 5 m, mobile Phase: A: N-heptane, B: ethanol+0.2% trifluoroacetic acid+0.1% diethylamine, gradient program: 1.5 ml/min 60% eluent a, 40% eluent b; Sample solvent: ethanol, test solution: approx. 1.0 mg/ml of the substance, dissolved with sample solvents, injection volume: 10 μl RT: Enantiomer 1 2.9 min RRT 1.00 Enantiomer 2 3.7 min RRT 1.28

Method L

Device type MS: Waters Synapt G2S; Device type UPLC: Waters Acquity I-CLASS; Column: Waters, HSST3, 2.1×50 mm, C18 1.8 μm; Eluent A: 1 1 water+0.01% formic acid; Eluent B: 1 1 acetonitrile+0.01% formic acid; Gradient: 0.0 min 2% B→2.0 min 2% B→13.0 min 90% B→15.0 min 90% B; Oven: 50° C.; Flow rate: 1.20 ml/min; UV detection: 210 nm Method M High-performance liquid chromatograph with thermostated column oven, UV detector and data evaluation system, measuring wavelength 226 nm, bandwidth: 40 nm.

Column: Zorbax Bonus-RP, length: 150 mm, inner diameter: 3.0 mm, grain size: 3.5 μm, mobile phase: A: Water+0.1% TFA, B: ACN+0.1% TFA/methanol=2+1, gradient program: 0.0 min 50% B→12.0 min 70% B→17.0 min 90% B→25.0 min 90% B; Flow rate: 0.60 ml/min; Sample solvent: isopropanol+0.1% diethylamine, test solution: dissolve approx. 35 mg of the substance in 25 ml ACN and fill up to 50 ml with water+0.1% TFA. (0.7 mg/mL); Injection volume: 3 μL new method M High-performance liquid chromatograph with thermostated column oven, UV detector and data evaluation system, measuring wavelength 226 nm, bandwidth: 40 nm. Column: XBridge Phenyl length: 50 mm, inner diameter: 4.6 mm, grain size: 2.5 μm; column oven temperature: 22° C.

mobile phase: A: buffer pH7 (0.66 g/L $(NH_4)_2HPO_4$ and 0.58 g/L $NH_4H_2PO_4$); B: ACN gradient program: 0.00 min=95% A, 5% B; t 8.3→11=20% A, 80% B Flow rate: 1.2 mL/min.; UV-Lampe: 210 nm Method N High-performance liquid chromatograph with thermostated column oven, UV detector and data evaluation system, measuring wavelength 210 nm. Column: XBridge BEH Phenyl length: 50 mm, inner diameter: 4.6 mm, grain size: 2.5 μm, mobile phase: A: 0.66 g $(NH_4)_2HPO_4$ and 0.58 g $(NH_4)H_2PO_4$ in 1 1 milipore water; B: ACN, gradient program: 0.00 min 95% B→8.3 min 80% B→11.0 min 80%; Flow rate: 1.2 ml/min; Sample solvent: ACN+Water, Injection volume: 3 μL.

A—CHEMICAL EXAMPLES

Starting Materials and Intermediates

Example 1A (5S)-5-([2-(2-{[3-chloro-4'-(trifluoromethyl)[biphenyl]-4-yl]methoxy}phenyl)ethyl]{2-[4-(methoxycarbonyl)phenyl]ethyl}amino)-5,6,7,8-tetrahydroquinoline-2-carboxylate (Enantiomer 2)

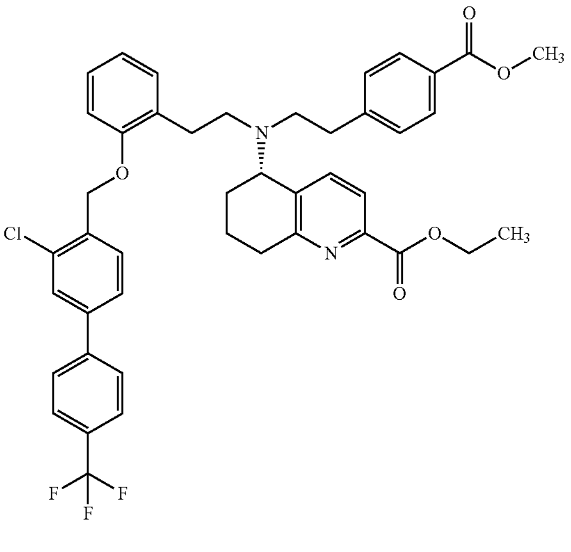 [SMILES: CCOC(=O)c1ccc2c(n1)CCC[C@@H]2N(CCc1ccc(C(=O)OC)cc1)CCc1ccccc1OCc1ccc(-c2ccc(C(F)(F)F)cc2)cc1Cl]

The compound was synthesized according to procedures as disclosed in example 92A, WO 2014/012934.

Example 2A

Butyl-(5S)-5-({2-[4-(butoxycarbonyl)phenyl]ethyl}[2-(2-hydroxyphenyl)ethyl]amino)-5,6,7,8-tetrahydrochinoline-2-carboxylate

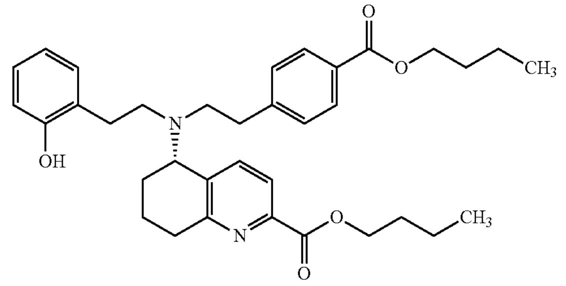 [SMILES: CCCCOC(=O)c1ccc(CCN(CCc2ccccc2O)[C@H]2CCCc3nc(C(=O)OCCCC)ccc32)cc1]

The compound was synthesized according to procedures as disclosed in example 10, WO2021/233783.

Example 3A

Butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydrochinoline-2-carboxylate

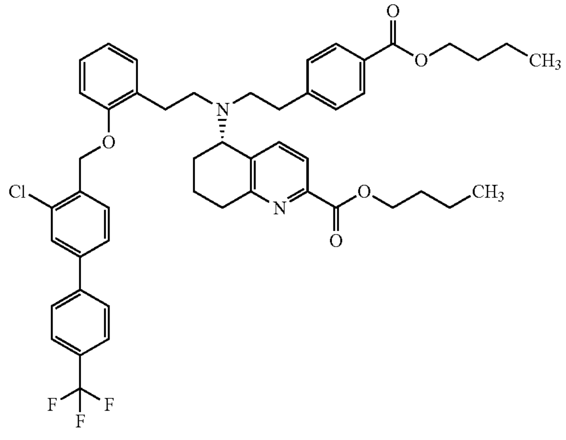 [SMILES: CCCCOC(=O)c1ccc(CCN(CCc2ccccc2OCc2ccc(-c3ccc(C(F)(F)F)cc3)cc2Cl)[C@H]2CCCc3nc(C(=O)OCCCC)ccc32)cc1]

The compound was synthesized according to procedures as disclosed in example 11, WO2021/233783.

A further starting material 4-(Bromomethyl)-3-chloro-4'-(trifluoromethyl)[biphenyl] (compound of the formula XI) is commercial available.

Example 4A

Naphthalene-1,5-disulfonic acid-butyl-(5S)-5-({2-[4-(butoxycarbonyl)phenyl]ethyl)[2-(2-([3-chloro-4'-(trifluoromethyl)[biphenyl]-4-yl]methoxy}phenyl)ethyl]amino)-5,6,7,8-tetrahydroquinoline-2-carboxylate (1:1) adduct

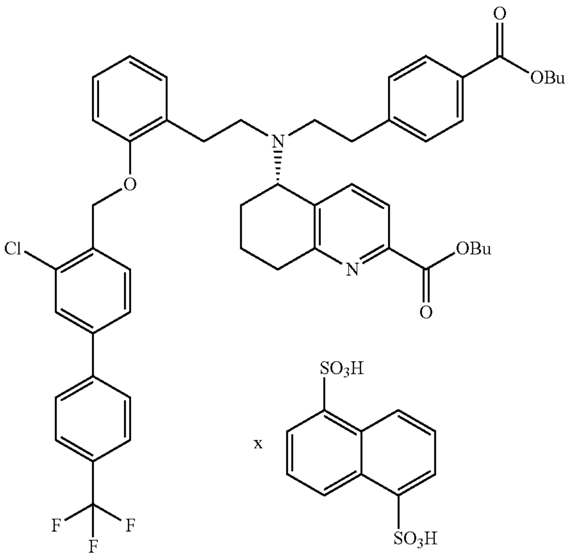

In a 3 L flask, 889.1 g (1.06 mol) of butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydroquinoline-2-carboxylate (oil) dissolved in 1850 ml of tetrahydrofuran. 304.6 g (1.06 mol) of naphthalene-1,5-disulfonic acid were added at room temperature, the mixture was stirred until it was completely dissolved. Subsequently the solution was concentrated on a rotary evaporator at 40° C. The residue (solid) was dried to 1126.3 g in a vacuum drying cabinet at 40° C. in a stream of nitrogen.

Yield (raw-product): 1126.3 g; 94.4% of the theoretical yield

Enantiomeric purity (HPLC method B): 95.3% ee

Purity (area): 81.8% (Method N), $R_t$ 16.11 (BP-Diester))

Examples 4B-4E

Trials to form stable salts of Butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydrochinoline-2-carboxylate with different acids 4B: Addition of (+)-di-p-toluoyl-D-tartaric acid 4 g (0.005 mol) of butyl-(5S)-5-({2-[4-(butoxycarbonyl)phenyl]ethyl)[2-(2-{[3-chloro-4'-(trifluoromethyl)[biphenyl]-4-yl]methoxy}phenyl)ethyl]amino}-5,6,7,8-tetrahydroquinoline-2-carboxylate (oil) were gradually dissolved in a total amount of 75 ml of methanol at a temperature of 50° C. A warm solution of 1.8 g (0.005 mol) (+)-di-p-toluoyl-D-tartaric acid in 2.5 ml methanol was added. Finally the mixture was stirred over the weekend.

To smaller parts of the reaction mixture different solvents were added to initiate crystallization. The following solvents were tried without any effect: MTBE, MIBK, methylenchloride, toluene. After addition of a mixture of cyclohexane, n-hexane and methylcyclohexane two layers formed.

A few drops of the reaction mixture were dried on a watchglass and the resulting dried mass was scraped off and stirred finally in a mixture of cyclohexane, n-hexane and methylcyclohexane. The resulting solids melted.

With methylcyclohexane a solid separated. HPLC analysis of the solids revealed tartaric acid.

After addition of water to another part of the reaction mixture a solid separated. The solids were difficult to be separated.

The reaction mixture was stripped off the solvents. 3.1 g of yellowish foam crystals were obtained.

To the foam crystals 31 ml of methylcyclohexane were added and stirred for 4 hours. 2.8 g of light-yellowish solids were obtained.

No defined salt could be detected.

4C: Addition of Trifluoro Acetic Acid (=TFA)

0.21 g (0.2 mmol) of butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydroquinoline-2-carboxylate (oil) were dissolved in 2 ml of acetonitrile. 0.1 ml of TFA was added. An orange solution was formed. The solvents were evaporated in vacuo to yield an orange oil.

No salt formation observable.

4D: Addition of Methane Sulfonic Acid 0.26 g (0.3 mmol) of butyl-(5S)-5-({2-[4-(butoxycarbonyl)phenyl]ethyl)[2-(2-{[3-chloro-4'-(trifluoromethyl)[biphenyl]-4-yl]methoxy}phenyl)ethyl]amino}-5,6,7,8-tetrahydroquinoline-2-carboxylate (oil) were dissolved in 1.5 ml of dichloromethane. 20.1 µl of methane sulfonic acid was added. An orange solution was formed. After stirring for 1 hour at room temperature no crystallization.

The solvents were evaporated in vacuo at 40° C. to yield yellow foam crystals.

Several solvents were screened to initiate either crystallization or purification.

Dichloromethane, MIBK, MTBE, ethylacetate, acetone, acetonitrile, dioxane, n-butanol, methanol, ethanol, tetrahydrofurane, toluene resulted in a solution at room temperature.

Diisopropylether, water, diethylether, cyclohexane resulted in a sticky mass.

Further stirring in n hexane at room temperature resulted again in a sticky mass.

No salt isolatable.

4E: Addition of Camphor Sulfonic Acid 0.29 g (0.34 mmol) of butyl-(5S)-5-({2-[4-(butoxycarbonyl)phenyl]ethyl)[2-(2-{[3-chloro-4'-(trifluoromethyl)[biphenyl]-4-yl]methoxy}phenyl)ethyl]amino}-5,6,7,8-tetrahydroquinoline-2-carboxylate (oil) were dissolved in 1.5 ml of dichloromethane. 80.05 µg of camphor sulfonic acid was added. An orange solution was formed.

The solvents were evaporated in vacuo at 40° C. to yield yellow foam crystals.

Several solvents were screened to initiate either crystallization or purification.

Dichloromethane, MIBK, ethylacetate, acetone, acetonitrile, dioxane, n-butanol, methanol, ethanol, tetrahydrofurane, toluene resulted in a solution at room temperature.

MTBE addition resulted in oily drops formation.

Water, diisopropylether, diethylether, cyclohexane and n heptane all afforded only sticky masses.

No salt isolatable.

Example 5A and Example 6A

Ethyl 5-{(tert-butoxycarbonyl)[2-(2-{[3-chloro-4'-(trifluoromethyl)biphenyl-4-yl]methoxy}phenyl)-ethyl]amino}-5,6,7,8-tetrahydroquinoline-2-carboxylate (Enantiomers 1 and 2)

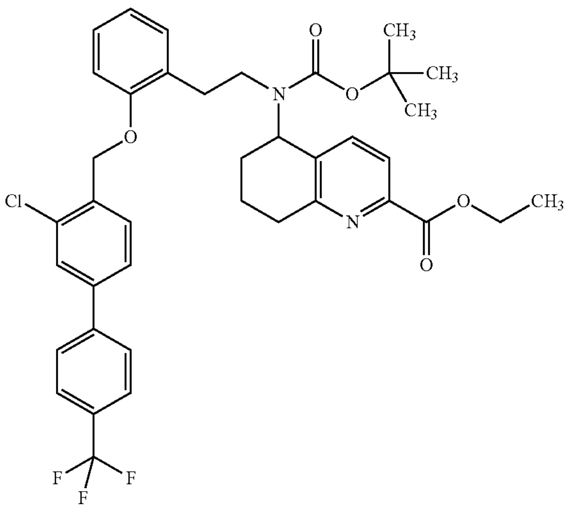 [SMILES: CCOC(=O)c1ccc2c(n1)CCCC2N(CCc1ccccc1OCc1ccc(-c2ccc(C(F)(F)F)cc2)cc1Cl)C(=O)OC(C)(C)C]

15 g (21.42 mmol) of the racemic ethyl 5-{(tert-butoxycarbonyl)[2-(2-{[3-chloro-4'-(trifluoromethyl)-biphenyl-4-yl]methoxy}phenyl)ethyl]amino}-5,6,7,8-tetrahydroquinoline-2-carboxylate (Example 22A) were separated by supercritical fluid chromatography (SFC) on a chiral phase into the enantiomers [column: Chiralpak OD-H, 20 µm, 400 mm×50 mm; mobile phase: carbon dioxide/isopropanol 70:30 (v/v); flow rate: 400 ml/min; pressure: 80 bar; UV detection: 220 nm; temperature: 37° C.]:

Example 5A (Enantiomer 1)

Yield: 5830 mg $R_t$=2.83 min; chemical purity>99.9%; >99% ee

[column: Chiralpak OD-H, 5 µm, 250 mm×4.6 mm; mobile phase: carbon dioxide/isopropanol 70:30 (v/v); flow rate: 3 ml/min; UV detection: 210 nm].

Example 6A (Enantiomer 2)

Yield: 6330 mg

Rt=5.30 min; chemical purity>99%; >98% ee

[column: Chiralpak OD-H, 5 μm, 250 mm×4.6 mm; mobile phase: carbon dioxide/isopropanol 70:30 (v/v); flow rate: 3 ml/min; UV detection: 210 nm].

Example 7A

Ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate dihydrochloride (Enantiomer 1)

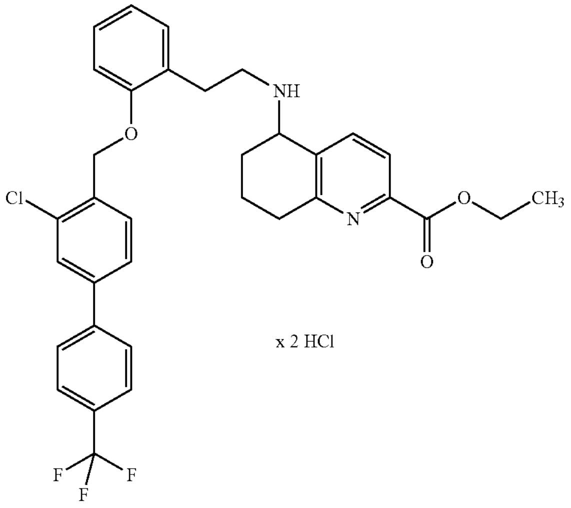 [SMILES: CCOC(=O)c1ccc2c(n1)CCCC2NCCc1ccccc1OCc1ccc(-c2ccc(C(F)(F)F)cc2)cc1Cl]

x 2 HCl 3208 ml of a 4 N solution of hydrogen chloride in dioxane, diluted with a further 2240 ml of dioxane, were added to 455 g (641.56 mmol) of ethyl 5-{(tert-butoxycarbonyl)[2-(2-{[3-chloro-4'-(trifluoromethyl)biphenyl-4-yl]methoxy}phenyl)ethyl]amino}-5,6,7,8-tetrahydroquinoline-2-carboxylate (Enantiomer 1, Example 1A), and the mixture was stirred at room temperature overnight. The reaction solution was then concentrated to dryness and the residue was dried under high vacuum overnight. This gave 448.7 g (641.59 mmol, about 100% of theory) of the target product.

LC-MS (Method A): $R_t$=1.06 min; m/z=609/611 (M+H)+.

Example 8A

Ethyl 5-{[2-(2-{[3-chloro-4'-(trifluoromethyl)biphenyl-4-yl]methoxy}phenyl)ethyl]amino}-5,6,7,8-tetrahydroquinoline-2-carboxylate (Enantiomer 1)

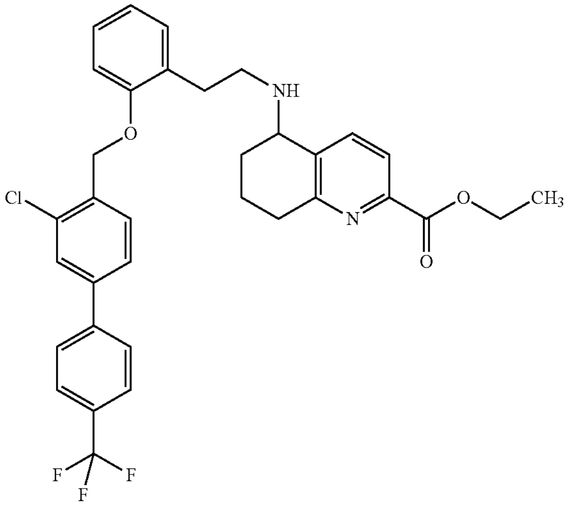 [SMILES: CCOC(=O)c1ccc2c(n1)CCCC2NCCc1ccccc1OCc1ccc(-c2ccc(C(F)(F)F)cc2)cc1Cl]

448.7 g (641.59 mmol) of ethyl 5-{[2-(2-{[3-chloro-4'-(trifluoromethyl)biphenyl-4-yl]methoxy}phenyl)-ethyl]amino}-5,6,7,8-tetrahydroquinoline-2-carboxylate dihydrochloride (Enantiomer 1, Example 3A) were taken up in 6869 ml of THF, 268 ml of triethylamine were added and the mixture was stirred at room temperature for 1 h. The precipitated triethylammonium chloride crystals were then filtered off and washed with THF. The filtrate obtained was evaporated to dryness. The residue was dissolved in ethyl acetate, washed twice with 10% strength aqueous sodium chloride solution, dried over magnesium sulphate, filtered and once more evaporated to dryness. This gave 391 g (620.59 mmol, 97% of theory) of the target compound.

LC-MS (Method A): $R_t$=1.08 min; m/z=609/611 (M+H)+.

$^1$H-NMR (400 MHz, DMSO-$d_6$, δ/ppm): 1.27 (t, 3H), 1.57-1.72 (m, 2H), 1.76-1.87 (m, 1H), 1.87-1.95 (m, 1H), 1.95-2.07 (m, 1H), 2.65-2.88 (m, 6H), 3.75 (br. s, 1H), 4.28 (q, 2H), 5.19 (s, 2H), 6.92 (t, 1H), 7.08 (d, 1H), 7.16-7.26 (m, 2H), 7.65-7.77 (m, 3H), 7.84 (d, 3H), 7.89 (s, 1H), 7.95 (d, 2H).

Example 9A

Ethyl 5-([2-(2-{[3-chloro-4'-(trifluoromethyl)biphenyl-4-yl]methoxy}phenyl)ethyl]{2-[4-(methoxycarbonyl)phenyl]ethyl}amino)-5,6,7,8-tetrahydroquinoline-2-carboxylate (Enantiomer 1)

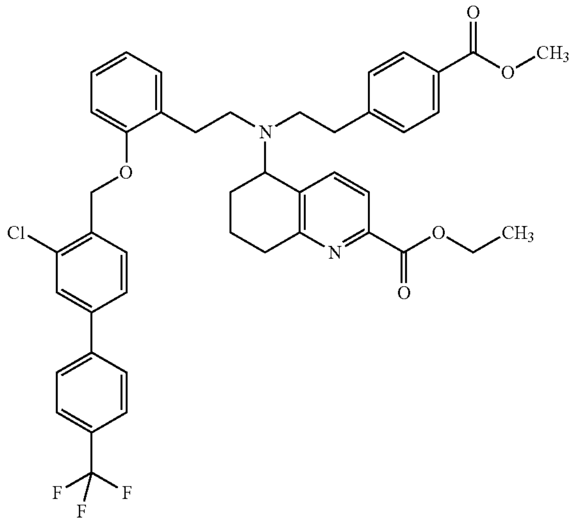 [SMILES: CCOC(=O)c1ccc2c(n1)CCCC2N(CCc1ccc(C(=O)OC)cc1)CCc1ccccc1OCc1ccc(-c2ccc(C(F)(F)F)cc2)cc1Cl]

A suspension of 378 g (620.59 mmol) of ethyl 5-{[2-(2-{[3-chloro-4'-(trifluoromethyl)biphenyl-4-yl]-methoxy}phenyl)ethyl]amino}-5,6,7,8-tetrahydroquinoline-2-carboxylate (Enantiomer 1, Example 4A), 360 g (1241.19 mmol) of methyl 4-(2-iodoethyl)benzoate and 98.66 g (930.89 mmol) of anhydrous sodium carbonate in 8191 ml of dry acetonitrile was stirred at a bath temperature of 110° C. overnight. A further 360 g (1241.19 mmol) g of methyl 4-(2-iodoethyl)benzoate and 128.65 g (930.89 mmol) of powdered potassium carbonate were then added, and the mixture was heated under reflux for another 72 h. After cooling of the reaction mixture, the inorganic salts were filtered off and the filtrate obtained was evaporated to dryness. The resulting residue was taken up in ethyl acetate, washed twice with 10% strength aqueous sodium chloride solution, dried over magnesium sulphate, filtered and then once more evaporated to dryness. The residue obtained was purified chromatographically on silica gel (9 kg) in 2 portions (mobile phase:petroleum ether/ethyl acetate 8:2→7:3). This gave 397 g (551.32 mmol, 89% of theory) of the target compound.

LC-MS (Method A): Rc=1.67 min; m/z=771/773 $(M+H)^+$.

$^1$H-NMR (400 MHz, DMSO-$d_6$, δ/ppm): 1.27 (t, 3H), 1.37-1.52 (m, 1H), 1.52-1.67 (m, 1H), 1.85-1.96 (m, 1H), 1.96-2.05 (m, 1H), 2.56-2.80 (m, 10H), 3.81 (s, 3H), 3.97-4.09 (m, 1H), 4.26 (q, 2H), 5.07 (m, 2H), 6.87 (t, 1H), 7.01-7.16 (m, 4H), 7.23 (t, 1H), 7.35-7.48 (m, 2H), 7.53 (d, 1H), 7.61 (d, 1H), 7.74 (d, 2H), 7.77-7.89 (m, 5H).

COMPARATIVE EXAMPLES

Comparative Example 1 (Cinaciguat)

4-[((4Carboxybutyl)-{2-[(4-phenethylbenzyl)oxy]phenethyl}amino)methyl]benzoic acid

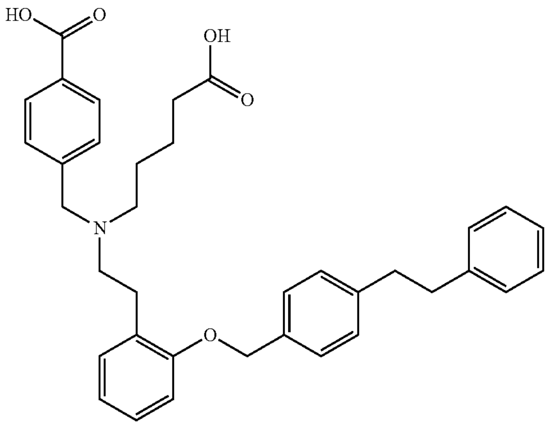 [SMILES: O=C(O)CCCCN(CCc1ccccc1OCc1ccc(CCc2ccccc2)cc1)Cc1ccc(C(=O)O)cc1]

The compound was synthesized analogously to example 8A, WO 01/019780-A1.

Comparative Example 2 Riociguat

Methyl-4,6-diamino-2-[1-(2-fluorobenzyl)-1H-pyrazolo[3,4-b]pyridine-3-yl]-5-pyrimi-dinyl(methyl) carbamate

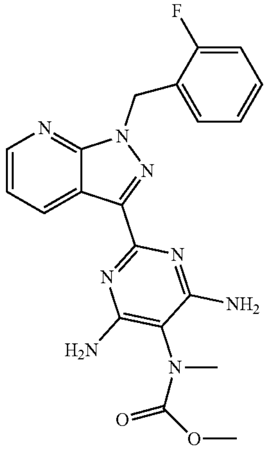 [SMILES: COC(=O)N(C)c1c(N)nc(-c2nn(Cc3ccccc3F)c3ncccc23)nc1N]

The compound was synthesized analogously to example 8, WO 03/095451-A1.

Comparative Example 3

(5)-{(4-carboxybutyl)[2-(2-{[4-(5-chloro-1,3-benzoxazol-2-yl)benzyl]oxy}-5-fluorophenyl)ethyl]amino}-5,6,7,8-tetrahydroquinoline-2-carboxylic acid (enantiomer 2)

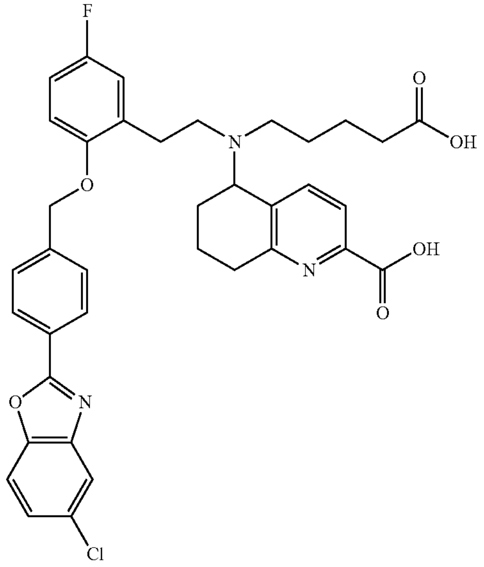 [SMILES: O=C(O)CCCCN(CCc1cc(F)ccc1OCc1ccc(-c2nc3cc(Cl)ccc3o2)cc1)C1CCCc2nc(C(=O)O)ccc21]

The compound was synthesized analogously to example 37, WO 2014/012934-A1.

LC-MS (Method A): $R_t$=1.10 min; m/z=672/674 $(M+H)^+$.

Comparative Example 4

5-{[2-(4-Carboxyphenyl)ethyl][2-(2-{[4-(5-chloro-1,3-benzoxazol-2-yl)benzyl]oxy}-5-fluorophenyl)ethyl]amino}-5,6,7,8-tetrahydroquinoline-2-carboxylic acid (Enantiomer 2)

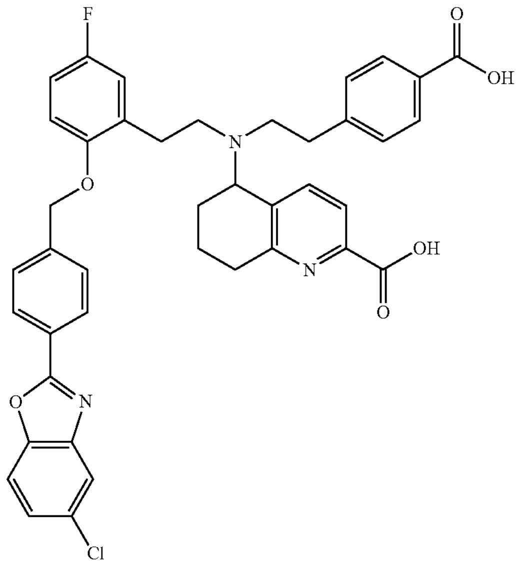 [SMILES: O=C(O)c1ccc(CCN(CCc2cc(F)ccc2OCc2ccc(-c3nc4cc(Cl)ccc4o3)cc2)C2CCCc3nc(C(=O)O)ccc32)cc1]

The compound was synthesized analogously to example 39, WO 2014/012934-A1.

LC-MS (Method A): $R_t$=1.28 min; m/z=720/722 $(M+H)^+$.

$^1$H-NMR (400 MHz, DMSO-$d_6$): δ [ppm]=1.40-1.72 (m, 2H), 1.88-2.11 (m, 2H), 2.59-2.84 (m, 10H), 4.02-4.13 (m, 1H), 5.00-5.14 (m, 2H), 6.96 (d, 1H), 7.02 (d, 2H), 7.13 (d, 2H), 7.41-7.57 (m, 5H), 7.75 (d, 2H), 7.83 (d, 1H), 7.93 (d, 1H), 8.11 (d, 2H), 12.05-13.41 (br. s, about 2H).

$[\alpha]_D^{20}$=+58.77°, c=0.405, DMSO.

Comparative Example 5

(+)-5-{(4-Carboxybutyl)[2-(2-{[4-(5-methyl-1,3-benzoxazol-2-yl)benzyl]oxy}phenyl)ethyl]amino}-5,6,7,8-tetrahydroquinoline-2-carboxylic acid (Enantiomer 2)

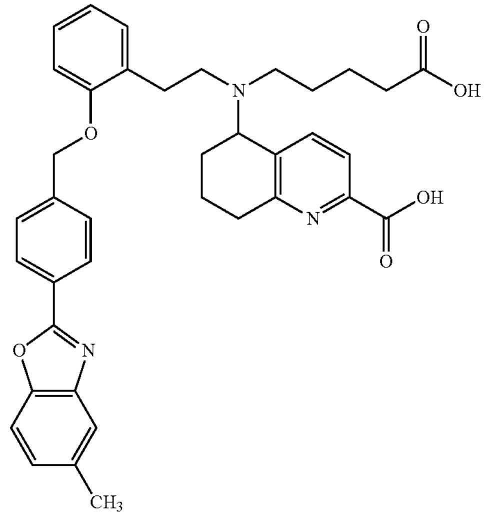 [SMILES: Cc1ccc2oc(-c3ccc(COc4ccccc4CCN(CCCCC(=O)O)C4CCCc5nc(C(=O)O)ccc54)cc3)nc2c1]

The compound was synthesized analogously to example 2, WO 2014/012934-A1.

LC-MS (Method A): $R_t$=1.03 min; m/z=634 $(M+H)^+$.

$^1$H-NMR (400 MHz, DMSO-$d_6$): δ [ppm]=1.32-1.70 (m, 7H), 1.89-2.03 (m, 2H), 2.07-2.16 (m, 2H), 2.39-2.64 (m, 3H, partially obscured by DMSO signal), 2.46 (s, 3H), 2.65-2.87 (m, 4H), 3.95-4.03 (m, 1H), 5.08 (q, 2H), 6.87 (t, 1H), 6.99 (d, 1H), 7.13 (d, 1H), 7.18 (t, 1H), 7.25 (d, 1H), 7.52 (d, 2H), 7.61 (s, 1H), 7.67 (d, 2H), 7.85 (d, 1H), 8.16 (d, 2H), 11.30-12.97 (br. s, 2H).

$[\alpha]_D^{20}$=+62.89°, c=0.380, methanol.

Comparative Example 6

5-([2-(4-carboxyphenyl)ethyl]{2-[2-({4-[5-(trifluoromethyl)-1,3-benzoxazol-2-yl]benzyl}oxy)phenyl]-ethyl}amino)-5,6,7,8-tetrahydroquinoline-2-carboxylic acid (Enantiomer 2)

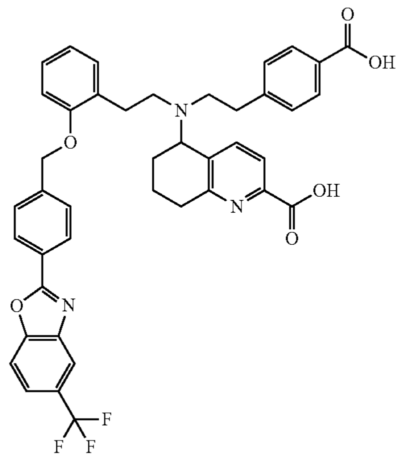 [SMILES: O=C(O)c1ccc(CCN(CCc2ccccc2OCc2ccc(-c3nc4cc(C(F)(F)F)ccc4o3)cc2)C2CCCc3nc(C(=O)O)ccc32)cc1]

The compound was synthesized analogously to example 24, WO 2014/012934-A1.

LC-MS (Method A): $R_t$=1.32 min; m/z=736 $(M+H)^+$.

$^1$H-NMR (400 MHz, DMSO-$d_6$): δ [ppm]=1.41-1.55 (m, 1H), 1.55-1.71 (m, 1H), 1.88-2.10 (m, 2H), 2.58-2.89 (m, 10H), 4.01-4.14 (m, 1H), 5.03-5.16 (m, 2H), 6.86 (t, 1H), 6.99-7.10 (m, 2H), 7.14 (d, 2H), 7.21 (t, 1H), 7.46 (d, 1H), 7.49-7.60 (m, 3H), 7.72-7.86 (m, 3H), 8.03 (d, 1H), 8.14 (d, 2H), 8.24 (s, 1H), 12.01-13.42 (br. s, about 2H).

Comparative Example 7

5-[(4-carboxybutyl)(2-[2-({4-[5-(trifluoromethyl)-1,3-benzoxazol-2-yl]benzyl}oxy)phenyl]ethyl)amino]-5,6,7,8-tetrahydroquinoline-2-carboxylic acid (Enantiomer 2)

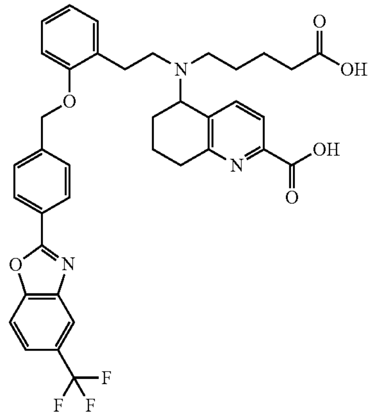 [SMILES: O=C(O)CCCCN(CCc1ccccc1OCc1ccc(-c2nc3cc(C(F)(F)F)ccc3o2)cc1)C1CCCc2nc(C(=O)O)ccc21]

The compound was synthesized analogously to example 25, WO 2014/012934-A1.

LC-MS (Method A): $R_t$=1.07 min; m/z=688 $(M+H)^+$.

$^1$H-NMR (400 MHz, DMSO-$d_6$): δ [ppm]=1.30-1.71 (m, 6H), 1.90-2.04 (m, 2H), 2.07-2.18 (m, 2H), 2.39-2.65 (m, 4H, partially obscured by DMSO signal), 2.65-2.91 (m, 4H), 3.87-4.07 (m, 1H), 5.10 (q, 2H), 6.87 (t, 1H), 7.00 (d, 1H), 7.10-7.23 (m, 2H), 7.56 (d, 2H), 7.66 (d, 1H), 7.85 (d, 2H), 8.04 (d, 1H), 8.16-8.30 (m, 3H), 11.10-13.31 (br. s, about 2H).

Comparative Example 8

5-[(4-carboxybutyl){2-[2-({4-[5-(trifluoromethoxy)-1,3-benzoxazol-2-yl]benzyl}oxy)phenyl]ethyl}-amino]-5,6,7,8-tetrahydroquinoline-2-carboxylic acid (Enantiomer 2)

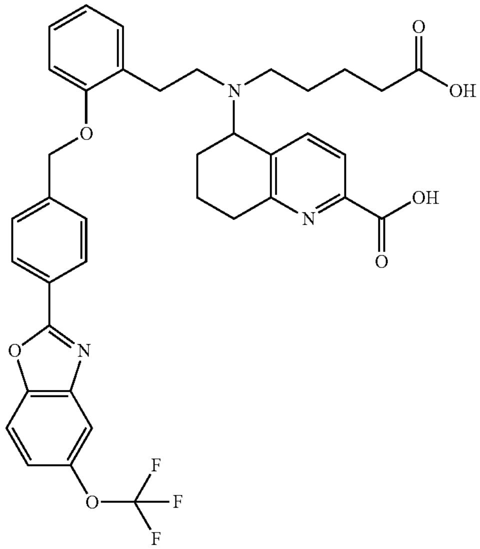 [SMILES: O=C(O)CCCCN(CCc1ccccc1OCc1ccc(-c2nc3cc(OC(F)(F)F)ccc3o2)cc1)C1CCCc2nc(C(=O)O)ccc21]

The compound was synthesized analogously to example 28, WO 2014/012934-A1.

LC-MS (Method A): $R_t$=1.09 min; m/z=704 $(M+H)^+$.

$^1$H-NMR (400 MHz, DMSO-$d_6$): δ [ppm]=1.32-1.71 (m, 6H), 1.88-2.05 (m, 2H), 2.07-2.17 (m, 2H), 2.39-2.64 (m, 4H, partially obscured by DMSO signal), 2.64-2.88 (m, 4H), 3.93-4.05 (m, 1H), 5.10 (q, 2H), 6.87 (t, 1H), 6.99 (d, 1H), 7.09-7.23 (m, 2H), 7.46 (dd, 1H), 7.54 (d, 2H), 7.66 (d, 1H), 7.85 (d, 1H), 7.89-7.98 (m, 2H), 8.18 (d, 2H), 11.10-13.04 (br. s, about 2H).

Comparative Example 9

5-([2-(4-carboxyphenyl)ethyl]{2-[2-({4-[5-(trifluoromethoxy)-1,3-benzoxazol-2-yl]benzyl}oxy)-phenyl]ethyl}amino)-5,6,7,8-tetrahydroquinoline-2-carboxylic acid (Enantiomer 2)

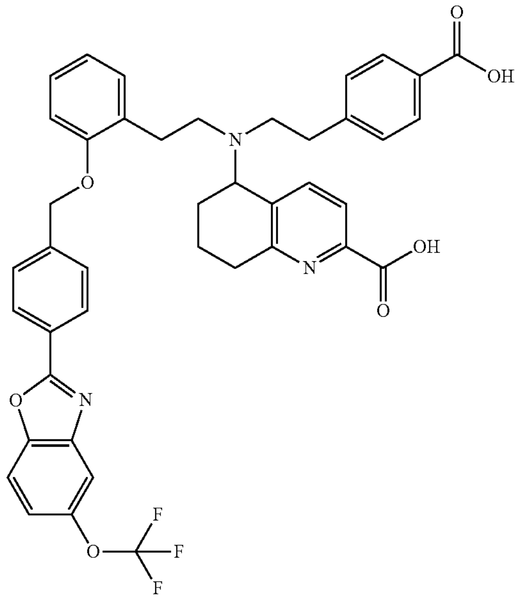 [SMILES: O=C(O)c1ccc(CCN(CCc2ccccc2OCc2ccc(-c3nc4cc(OC(F)(F)F)ccc4o3)cc2)C2CCCc3nc(C(=O)O)ccc32)cc1]

The compound was synthesized analogously to example 29, WO 2014/012934-A1.

LC-MS (Method A): $R_t$=1.34 min; m/z=752 $(M+H)^+$.

$^1$H-NMR (400 MHz, DMSO-$d_6$): δ [ppm]=1.42-1.55 (m, 1H), 1.55-1.71 (m, 1H), 1.88-2.11 (m, 2H), 2.59-2.87 (m, 10H), 3.99-4.13 (m, 1H), 5.09 (q, 2H), 6.88 (t, 1H), 6.98-7.09 (m, 2H), 7.15 (d, 2H), 7.20 (t, 1H), 7.41-7.58 (m, 5H), 7.77 (d, 2H), 7.87-7.96 (m, 2H), 8.12 (d, 2H), 11.89-13.63 (br. s, about 2H).

Comparative Example 10

5-{(4-carboxybutyl)[2-(2-{[4-(5-cyano-1,3-benzoxazol-2-yl)benzyl]oxy}phenyl)ethyl]amino}-5,6,7,8-tetrahydroquinoline-2-carboxylic acid (Enantiomer 2)

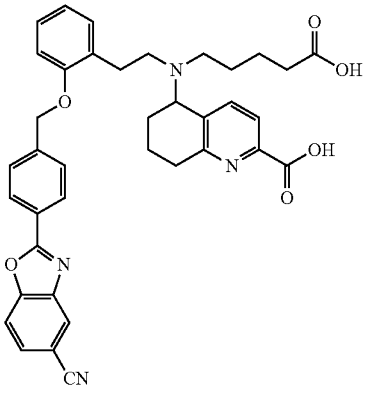 [SMILES: N#Cc1ccc2oc(-c3ccc(COc4ccccc4CCN(CCCCC(=O)O)C4CCCc5nc(C(=O)O)ccc54)cc3)nc2c1]

The compound was synthesized analogously to example 31, WO 2014/012934-A1.

LC-MS (Method A): $R_t$=0.93 min; m/z=645 $(M+H)^+$.

$^1$H-NMR (400 MHz, DMSO-$d_6$): δ [ppm]=1.31-1.77 (m, 6H), 1.90-2.05 (m, 2H), 2.05-2.18 (m, 2H), 2.39-2.64 (m, 4H, partially obscured by DMSO signal), 2.65-2.88 (m, 4H), 3.92-4.05 (m, 1H), 5.10 (q, 2H), 6.87 (t, 1H), 6.99 (d, 1H), 7.10-7.22 (m, 2H), 7.55 (d, 2H), 7.67 (d, 1H), 7.85 (d, 1H), 7.93 (d, 1H), 8.04 (d, 1H), 8.19 (d, 2H), 8.44 (s, 1H), 11.38-12.79 (br. s, about 2H).

Comparative Example 11

(5S)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid

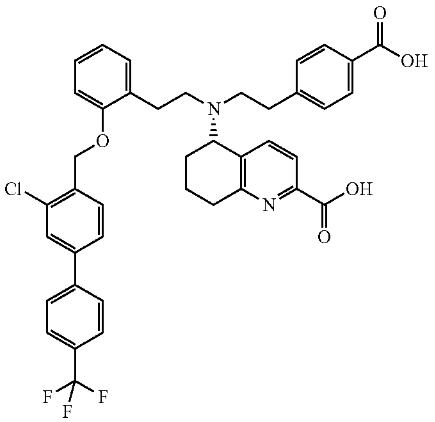

2450 mg (3.18 mmol) of ethyl (5S)-5-([2-(2-{[3-chloro-4'-(trifluoromethyl)[biphenyl]-4-yl]methoxy}phenyl)ethyl]{2-[4-(methoxycarbonyl)phenyl]ethyl}amino)-5,6,7,8-tetrahydroquinoline-2-carboxylate (example 1A, Enantiomer 2) were dissolved in 25 ml of dioxane, 9.5 ml of 1 N aqueous sodium hydroxide solution were added and the mixture was then stirred at room temperature overnight. After the reaction had gone to completion, the dioxane was removed on a rotary evaporator and the mixture that remained was diluted with about 50 ml of water. The mixture was then acidified to pH 4-5 using acetic acid. The precipitated solid was filtered off with suction and washed repeatedly with water (about 50 ml of water in total). The solid was then taken up in 50 ml of water and stirred at room temperature overnight. After another filtration with suction, the solid was again washed with water and then dried under high vacuum overnight at 40° C. In this manner, 2300 mg (2.9 mmol, 93% purity, contains unknown amounts of mono sodium salt, having same retention time)) of the title compound were obtained.

LC-MS (Method A): $R_t$=1.37 min; m/z=729/731 $(M+H)^+$.

$^1$H-NMR (400 MHz, DMSO-$d_6$): δ [ppm]=1.38-1.71 (m, 2H), 1.84-2.08 (m, 2H), 2.59-2.84 (m, 10H), 3.97-4.11 (m, 1H), 4.99-5.16 (m, 2H), 6.87 (t, 1H), 7.05 (br. d, 2H), 7.12 (br. d, 2H), 7.23 (br. t, 1H), 7.38-7.48 (i, 2H), 7.54 (d, 1H), 7.62 (d, 1H), 7.71-7.91 (m, 7H), 11.90-13.60 (br. s, about 2H).

XRPD: amorphous phase, see FIG. 33

Determination of the absolute configuration of comparative example 11 via VCD spectroscopy:

Vibrational circular dichroism (VCD) is an established methodology to determine absolute configuration of chiral molecules (see United States Pharmacopeial Convention (USP) and The National Formulary (USP-NF), second suppl. USP-NF 34, chapters 782 and 1782, Jun. 1, 2016 and Abs. config. by VCD, white paper BioTools, 2017).

The steps involved in determination are as follows:

1. The experimental VCD spectrum was measured using DMSO. The sample, example 1 was measured at a concentration of 5.5 mg/0.15 ml.

2. The VCD of one of the enantiomers is calculated using ab initio calculations using Gaussian09™ (commercially available software package). The VCD spectrum of the other enantiomer is then obtained by reversing the signs of all the bands or calculating the VCD of the mirror-image structure.

3. The last step is a comparison of the experimental spectrum to the two calculated spectra to determine the enantiomer that gives the best correlation between the signs and the signal intensities. The confidence level of overlap between two such spectra can be calculated using CompareVOA™ software.

VCD spectrometer: ChirallR-2X w/DualPEM

Concentration: 5.5 mg/0.15 ml of example 1 in DMSO

Resolution: 4 cm-1

PEM setting: 1400 cm-1

Number of scans/measurement time: 20 hours

Sample cell: $BaF_2$

Path length: 100 m

Calculation Details:

Gaussian version: Gaussian 09

Total low-energy conformer used for Boltzman sum: 92

Methodology and basis set for DFT calculation: B3LYP/6-31G(d)

Absolute configuration calculated: S

Absolute configuration of comparative example 11 was assigned as (S)-enantiomer based on the agreement of VCD spectra. The confidence level of assignment was 94%.

Determination of Thermal Stability of Comparative Example 11

0.3 mg of the test compound, e.g. comparative example 11 were solved in 0.1 ml dimethylsulfoxide and 0.4 ml acetonitrile. Then 1.0 ml water was added. For complete dissolution the HPLC vial was shaken and sonicated. This solution was immediately analyzed by HPLC (reference at t0). 0.3 mg of the test compound was weighed into another HPLC vial. The vial was capped and stored for 7 days in a heating block at 90° C.

After this time the vial was decapped and 0.1 ml dimethylsulfoxide and 0.4 ml acetonitrile were added to the stressed compound. Then 1.0 ml water was added. For complete dissolution the HPLC vial was shaken and sonicated. The sample was analyzed by HPLC (sample after 1 week). The peak areas in percentage are used for quantification.

TABLE 11

| HPLC-method | | | | | | |
|---|---|---|---|---|---|---|
| eluent: | A = 5ml HClO4/L water<br>B = ACN | | gradient: | Time<br>(min.) | % B | flow<br>(mL/min.) |
| column: | Nucleodur 100 C18ec<br>3 μm 50*2 mm | | | 0.00 | 2.0 | 0.750 |
| Temp.: | 30 | ° C. | | 1.00 | 2.0 | 0.750 |
| UV WL.: | 210 | nm | | 9.00 | 98.0 | 0.750 |
| HPLC flow: | 0.750 | mL/min. | | 13.00 | 98.0 | 0.750 |
| | | | | 13.50 | 2.0 | 0.750 |
| | | | | 15.00 | 2.0 | 0.750 |

Comparative example 11 was found to be stable during the test period.

In addition, several examples disclosed in WO 14/012934-A1 do only show limited thermal stability (at 90° C., 7 days): e.g. example 2 (comparative example 5, experimental part), 24 (comparative example 6, experimental part), 25 (comparative example 7, experimental part), 28 (comparative example 8, experimental part), 29 (comparative example 9, experimental part) and for example 31 (comparative example 10, experimental part).

Comparative Example 12

(5R)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid (Enantiomer 1)

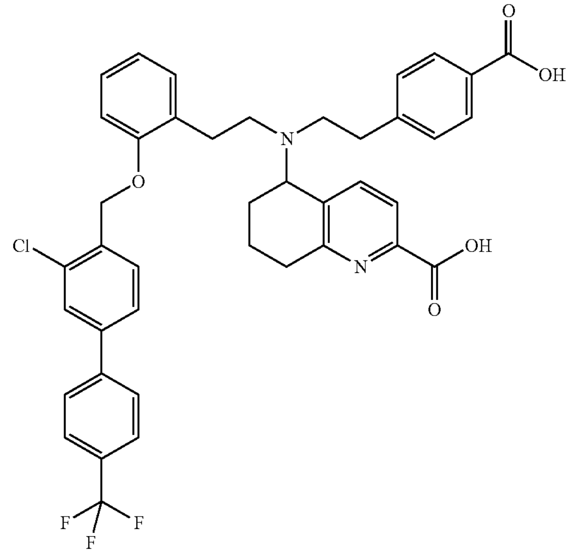 [SMILES: O=C(O)c1ccc(CCN(CCc2ccccc2OCc2ccc(-c3ccc(C(F)(F)F)cc3)cc2Cl)C2CCCc3nc(C(=O)O)ccc32)cc1]

291 g (377.29 mmol) of ethyl 5-([2-(2-{[3-chloro-4'-(trifluoromethyl)biphenyl-4-yl]methoxy}phenyl)-ethyl]{2-[4-(methoxycarbonyl)phenyl]ethyl}amino)-5,6,7,8-tetrahydroquinoline-2-carboxylate (Enantiomer 1, Example 5A) were dissolved in 3000 ml of dioxane, 1132 ml of 1 N aqueous sodium hydroxide solution were added and the mixture was then stirred at room temperature overnight. After the reaction had gone to completion, the dioxane was removed on a rotary evaporator and the mixture that remained was diluted with about 6000 ml of water. The mixture was then acidified to pH 4-5 using acetic acid. The precipitated solid was filtered off with suction and washed repeatedly with water (about 3000 ml of water in total). The solid was then dried under high vacuum 3 d at room temperature using the drying agent phosphorus pentoxide. The drying agent was then removed and the solid was dried at 40° C. for a further 48 h. In this manner, 249 g (342.15 mmol, 91% of theory) of the title compound were obtained.

LC-MS (Method A): $R_t$=1.33 min; m/z=729/731 $(M+H)^+$.

H-NMR (400 MHz, DMSO-$d_6$): 5 [ppm]=1.37-1.66 (m, 2H), 1.84-2.05 (m, 2H), 2.56-2.81 (m, 10H), 3.98-4.08 (m, 1H), 5.01-5.14 (m, 2H), 6.87 (t, 1H), 7.05 (d, 2H), 7.12 (d, 2H), 7.23 (t, 1H), 7.39-7.47 (m, 2H), 7.54 (d, 1H), 7.62 (d, 1H), 7.71-7.90 (m, 7H), 11.60-13.85 (br. s, about 2H).

As for comparative example 11 the absolute configuration was determined to be (5S) the corresponding absolute configuration of comparative example 12 should be the opposite, i.e. (5R).

Comparative Example 13

Mono sodium (5R)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylate (Enantiomer 1)

A vessel was charged with 60 g amorphous (5R)-5-([2-(2-{[3-chloro-4'-(trifluoromethyl)[biphenyl]-4-yl]methoxy}phenyl)ethyl]{2-[4-(methoxycarbonyl)phenyl]ethyl amino}-5,6,7,8-tetrahydroquinoline-2-carboxylate (comparative example 12) and 800 g acetone. The vessel was heated to reflux temperature. The solid which formed under reflux temperature, was filtered after cooling to room temperature.

Yield: 8 g of dry product, 13% o. th.

Enantiomeric purity (HPLC method C): 100% ee (ICP): sodium content: 3.1% sodium

Comparative Example 14

(5R)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid monohydrate II (Enantiomer 1)

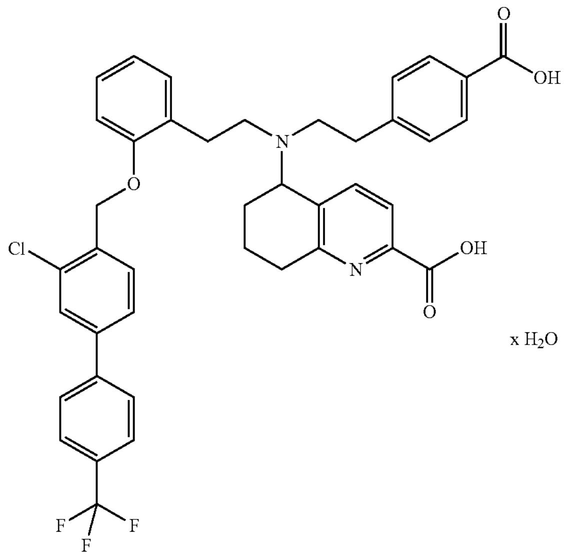 [SMILES: O=C(O)c1ccc(CCN(CCc2ccccc2OCc2ccc(-c3ccc(C(F)(F)F)cc3)cc2Cl)C2CCCc3nc(C(=O)O)ccc32)cc1]

174.2 g comparative example 12 were stirred under reflux with 2003.3 g acetone. The mixture was cooled to 20° C. and insoluble solid (19.5 g after drying) was filtered off. 273 g acetone were added to the filtrate, it was heated to 57° C. and 1101.4 g water and 0.4 g seed crystals of monohydrate II, R enantiomer (prepared from small scale pre experiments analogously to the present procedure) were added. Further 1101.4 g water were added and it was stirred overnight at room temperature. The product was filtered off and dried at 55° C. in vacuum (30 mbar) to 143.8 g.

Further 20.3 g have been obtained from 21.0 g comparative example 12 prepared according to the same procedure.

The solids were combined to 164.1 g and 161.0 g of these solids were stirred under reflux with 1993.0 g acetone. At this temperature 930.0 g water and 0.8 g seed crystals of monohydrate II, R enantiomer (prepared from small scale pre experiments analogously to the present procedure) were added and it was cooled to 50° C. Further 200.0 g water and 400.0 g acetone were added to improve stirrability. It was stirred for 1 h at 50° C., 1263.0 g water were added, it was stirred for 30 min, cooled within 2 h to 20° C. and stirred overnight at room temperature. The product was filtered off and dried at 55° C. in vacuum (30 mbar) to 154.4 g.

A part of the solid (95.0 g) was dissolved at 40° C. in 916.7 g of acetone, cooled to room temperature and the solution was filtered for clarification. 170.1 g of water were added, after 30 min seed crystals of monohydrate II, R enantiomer (prepared from small scale pre experiments analogously to the present procedure) were added and it was stirred overnight. The thin suspension was heated to 50° C., the resulting solution was cooled to room temperature, inoculated with seed crystals of monohydrate II, R enantiomer (prepared from small scale pre experiments analogously to the present procedure) and stirred overnight. The solid was filtered off, washed with a mixture of 76.0 g acetone and 19.0 g water (8:2) and sucked dry to 68.4 g.

The filtrate was concentrated at 40° C./250 to 15 mbar and the precipitated solid was filtered off. 28.2 g solid were dissolved in 157.2 g acetone water mixture (9:1 w/w) at 55° C., cooled to 15° C. After addition of 10 g water it was inoculated with seed crystals of monohydrate II, R enantiomer (prepared from small scale pre experiments analogously to the present procedure) and stirred overnight at 15° C. The suspension was heated to 50° C., stirred for 30 min and cooled to 20° C. within 4 h. It was again heated to 50° C. within 1 h, cooled to 15° C. within 4.5 h and stirred overnight at 15° C. The solid was filtered off, washed with 28 g of an acetone water (8:2 w/w) mixture and sucked dry to 20.6 g.

The solids were combined to 87.0 g of the target compound.

Enantiomeric purity (HPLC method C): 99.8% ee

Purity (Method M, area): 99.7%, $R_f$ 9.33 min

XRPD: Monohydrate II

EXAMPLES

Example 1

(5S)-{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid monohydrate II (seed crystals)

(I-M-II)

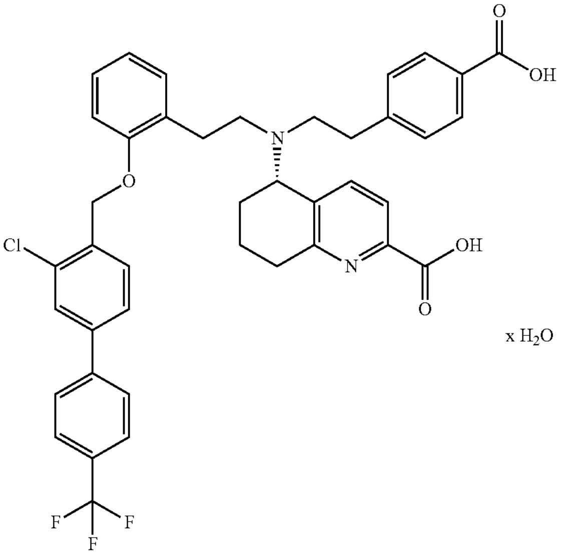 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

2.0 g of (5S)-{[2-(4-Carboxyphenyl)ethyl][2-(2-{[3-chloro-4'-(trifluoromethyl)biphenyl-4-yl]methoxy}-phenyl) ethyl]amino}-5,6,7,8-tetrahydroquinoline-2-carboxylic acid of formula (I) (manufactured in analogy to comparative example 11) were dissolved in 16.2 g acetone and 1.8 g water (8:1 mixture), there were more 1.8 g of water added. The clear solution was stirred overnight and crystallization began after 1.5 h. The solid was filtered off with suction, washed with 2 g of acetone/water (8:2) and dried overnight at 60° C. in vacuo with nitrogen air:

Yield: 1.5 g of white solid, 75% of theory

XRPD: monohydrate II, X-Ray powder diffractogram is shown in FIG. 34

| Reflections (Peak maxima) [°2 Theta] |
|---|
| 5.7 |
| 6.1 |
| 7.1 |
| 8.5 |
| 9.4 |
| 9.9 |
| 10.2 |
| 10.8 |
| 11.4 |
| 11.6 |
| 11.7 |
| 12.2 |
| 12.7 |
| 13.0 |
| 13.9 |
| 14.2 |
| 14.5 |
| 15.1 |
| 15.3 |
| 15.7 |
| 15.9 |
| 16.1 |
| 16.4 |
| 17.1 |
| 17.3 |
| 17.7 |
| 17.9 |
| 18.3 |
| 18.5 |
| 18.7 |
| 19.1 |
| 19.7 |
| 19.8 |
| 20.2 |
| 20.4 |
| 20.8 |
| 21.1 |
| 21.2 |
| 21.6 |
| 22.0 |
| 22.3 |
| 22.8 |
| 23.0 |
| 23.4 |
| 23.8 |
| 24.2 |
| 24.4 |
| 24.4 |
| 25.1 |
| 25.5 |
| 26.2 |
| 26.4 |
| 27.1 |
| 27.4 |
| 27.7 |
| 28.0 |
| 28.5 |
| 28.9 |
| 29.2 |
| 29.5 |
| 29.7 |
| 30.0 |
| 30.4 |
| 30.6 |
| 31.2 |
| 31.6 |
| 32.2 |
| 32.4 |
| 32.8 |

Example 2

(5S)-{[2-(4-Carboxyphenyl)ethyl][2-(2-{[3-chloro-4'-(trifluoromethyl) biphenyl-4-yl]methoxy}phenyl)-ethyl]amino}-5,6,7,8-tetrahydroquinoline-2-carboxylic acid as Monohydrate II (route 3, crystallization from acetone, methanol and water)

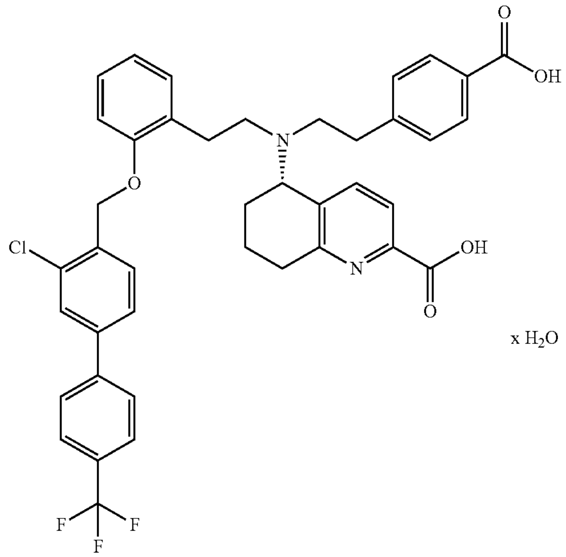 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

x $H_2O$ 1067 g of tetrahydrofuran were placed in a 6 L glass stirring apparatus and 333 g (0.396 mol) of naphthalene-1, 5-disulfonic acid-butyl (5S)-5-({2-[4-(butoxycarbonyl)phenyl]ethyl)[2-(2-{[3-chloro-4'-(trifluoromethyl)[biphenyl]-4-yl]methoxy}phenyl)ethyl]amino}-5,6,7,8-tetrahydroquinoline-2-carboxylate (1:1) adduct (example 4A) added in portions with stirring. 1335 ml of water and then aqueous ammonia (27%) were added at 20° C. to 25° C. until a pH of 7.8 to 8.2 was reached (approx. 46 g). 1440 g of diisopropyl ether were added, the aqueous phase was separated off, the organic phase was washed again with 1335 ml of water/1 ml of 27% ammonia water and then with 1335 ml of water. The organic phase was filtered through a Seitz filter plate covered with 200 g of sodium sulfate (anhydrous), it was rinsed with 200 g of diisopropyl ether and the filtrate was concentrated in vacuo at 40° C. to give 267 g of evaporation residue.

The residue after evaporation was dissolved in 848 g of dioxane, 1583 g of 1N sodium hydroxide solution were added and the mixture was stirred at 60° C. for 5.5 h. 1480 g of ethyl acetate were then added at 20° C., the aqueous product phase (disodium salt solution) was separated off, washed with 1480 g of ethyl acetate and residual ethyl acetate was distilled off at a maximum of 40° C. in vacuo. The residue was diluted with 2500 g of water and a portion of the disodium salt solution (1178 g) was added dropwise to a mixture of 1095 g of tetrahydrofuran and 137 g of 10% hydrochloric acid until a pH of 4.0 was reached.

The consumption of disodium salt solution is set in relation to the amount of hydrochloric acid submitted and the amount of hydrochloric acid for the conversion of the further partial amounts is calculated. The second aliquot of the disodium salt solution (1789 g) was added dropwise to the calculated amounts of tetrahydrofuran (1789 g) and 10% strength hydrochloric acid (208 g) until a pH of 4.0 was reached.

The third aliquot of the disodium salt solution (1510 g) was added dropwise to the calculated amounts of tetrahydrofuran (1505 g) and 10% strength hydrochloric acid (175 g) until a pH of 4.0 was reached.

The combined organic phases were concentrated in vacuo at a maximum of 40° C. until solvent-free water condensed on the reflux condenser. The precipitated solid was filtered off with suction and washed with 750 g of water.

Using the same procedure, a 2nd and 3rd part each 333 g of naphthalene-1,5-disulphonic acid butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydroquinoline-2-carboxylate (1:1) adduct (example 4A) were converted according to the procedure described above.

The combined moist products were dried at 60° C. in a stream of nitrogen under vacuum to give 587 g (ca. 91% o.th.) of target compound of formula I.

Crystallization:

The solid (587 g) was heated to 50° C. with a mixture of 3674 g of acetone and 470 g of water. The solution obtained was filtered through a Seitz filter plate and heated to 40° C. The filtrate was mixed with 1.5 g of seed crystals of (5S)-5-{[2-(4-carboxyphenyl)ethyl][2-(2-{[3-chloro-4'-(trifluoromethyl)[biphenyl]-4-yl]methoxy}phenyl)ethyl] amino}-5,6,7,8-tetrahydroquinoline-2-carboxylic acid monohydrate II (example 1), cooled to 20° C. in 2 h, stirred for 0.5 h and within 2 h heated again to 50° C. The mixture was stirred for 0.5 h, cooled to 20° C. in 3 h, stirred for 0.5 h and heated again to 50° C. over the course of 2 h. It was cooled to 20° C. in 3 h, stirred for 0.5 h and the solid was filtered off with suction. The moist product was washed with a mixture of 800 g of acetone and 90 g of water and dried to a constant weight of 361 g at 25° C. in a stream of nitrogen under vacuum.

The in-process control of the quality and modification of the product received did not meet the requirements. Therefore, it was re-crystallized again.

The solid (361 g) was heated to 50° C. with a mixture of 1949 g of acetone and 217 g of water. The solution obtained was filtered through a Seitz filter plate and heated to 50° C. It was mixed with 1.5 g of seed crystals of (5S)-5-{[2-(4-carboxyphenyl)ethyl][2-(2-{[3-chloro-4'-(trifluoromethyl) [biphenyl]-4-yl]methoxy}phenyl)ethyl]amino}-5,6,7,8-tetrahydroquinoline-2-carboxylic acid monohydrate II (example 1), cooled to 20° C. in 3 h, stirred for 0.5 h and within 3 h heated again to 50° C. The mixture was stirred for 0.5 h, cooled to 20° C. in 3 h, stirred for 0.5 h and again heated to 50° C. over 3 h and stirred for 0.5 h. It was cooled to 20° C. in 3 h, stirred for 0.5 h and the solid was filtered off with suction. The moist product was dried at 25° C. in a stream of nitrogen under vacuum to constant weight of 271 g.

The in-process control confirmed sufficient quality, but not the desired modification of the product obtained. Therefore, it was recrystallized again.

The solid (271 g) was heated to 50° C. with a mixture of 1668 g of acetone and 75 g of water. The solution obtained was filtered through a Seitz filter plate and heated to 50° C. It was cooled to 45° C., 1.5 g of seed crystals of (5S)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid monohydrate II (example 1), cooled to 20° C. in 3 h, stirred for 0.5 h and heated to 40° C. within 1 h. The suspension was stirred for 0.5 h, cooled to 20° C. in 3 h and stirred, and the solid was filtered off with suction. The moist product was dried to constant weight at 25° C. in a stream of nitrogen under vacuum.

The in-process control confirmed the quality and modification of the product in accordance with the requirements.

Yield: 117 g monohydrate II; 18% of the theoretically yield.

Enantiomeric purity (HPLC method C): 99.6% ee

Purity (area): 99.8% (Method M, $R_t$ 9.33 min)

XRPD: monohydrate II, X-Ray powder diffractogram is shown in FIG. 35 after micronization:

Enantiomeric purity (HPLC method C): 100.0% ee

Purity (area): 99.7% (Method M, $R_t$ 9.35 min)

XRPD: monohydrate II with partial amorphization, X-Ray powder diffractogram is shown in FIG. 36

Monohydrate II before micronization: see FIG. 35

| Reflections (Peak maxima) [°2 Theta] |
|---|
| 5.7 |
| 6.1 |
| 6.3 |
| 7.1 |
| 8.5 |
| 9.9 |
| 10.1 |
| 10.2 |
| 10.8 |
| 11.4 |
| 11.6 |
| 11.8 |
| 12.2 |
| 12.7 |
| 13.0 |
| 13.9 |
| 14.3 |
| 14.5 |
| 15.1 |
| 15.3 |
| 15.7 |
| 15.9 |
| 16.2 |
| 16.4 |
| 17.1 |
| 17.3 |
| 17.7 |
| 17.9 |
| 18.3 |
| 18.5 |
| 18.8 |
| 19.2 |
| 19.8 |
| 20.3 |
| 20.5 |
| 20.8 |
| 21.1 |
| 21.3 |
| 21.6 |
| 22.0 |
| 22.4 |
| 22.8 |
| 23.1 |
| 23.3 |
| 23.5 |
| 23.8 |
| 24.2 |
| 24.5 |
| 25.1 |
| 25.4 |
| 25.6 |
| 26.2 |
| 26.4 |
| 26.7 |

-continued

| Reflections (Peak maxima) [°2 Theta] |
|---|
| 27.1 |
| 27.4 |
| 27.7 |
| 28.1 |
| 28.3 |
| 28.5 |
| 28.9 |
| 29.2 |
| 29.5 |
| 29.8 |
| 30.0 |
| 30.6 |
| 30.7 |
| 31.2 |
| 31.7 |
| 32.2 |
| 32.4 |
| 32.8 |
| 34.8 |
| 35.3 |
| 36.3 |

Monohydrate II after micronization (partial amorphization), FIG. 36

| Reflections (Peak maxima) [°2 Theta] |
|---|
| 5.7 |
| 6.1 |
| 7.1 |
| 8.5 |
| 9.9 |
| 10.1 |
| 10.8 |
| 11.5 |
| 11.6 |
| 12.2 |
| 12.7 |
| 13.0 |
| 13.9 |
| 14.2 |
| 15.2 |
| 15.3 |
| 15.7 |
| 16.4 |
| 17.2 |
| 17.3 |
| 17.7 |
| 18.0 |
| 18.3 |
| 18.5 |
| 18.8 |
| 19.1 |
| 19.8 |
| 20.2 |
| 20.8 |
| 21.1 |
| 21.3 |
| 21.6 |
| 22.1 |
| 22.4 |
| 23.1 |
| 23.4 |
| 23.5 |
| 23.9 |
| 24.3 |
| 24.5 |
| 25.2 |
| 25.4 |
| 25.6 |
| 26.3 |

-continued

| Reflections (Peak maxima) [°2 Theta] |
|---|
| 27.1 |
| 27.5 |
| 28.9 |
| 29.5 |
| 30.6 |
| 32.4 |

Example 3

(5S)-{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid monohydrate I (seed crystals)

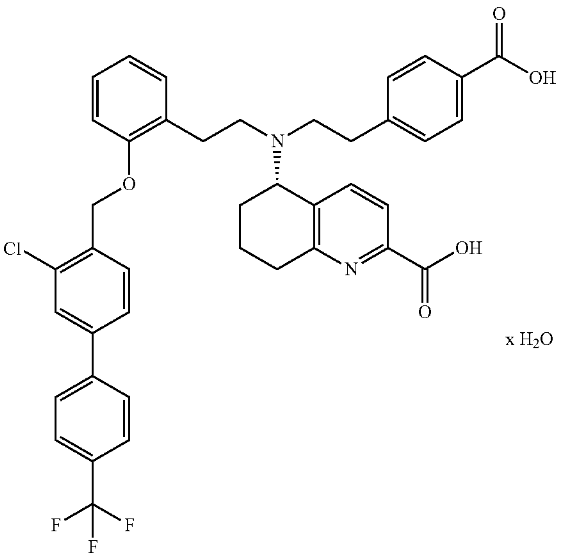 [SMILES: O=C(O)c1ccc(CCN(CCc2ccccc2OCc2ccc(-c3ccc(C(F)(F)F)cc3)cc2Cl)[C@H]2CCCc3nc(C(=O)O)ccc32)cc1]

2.0 g (5S)-{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid of formula (I) (manufactured in analogy to comparative example 11) were dissolved in 8.1 g of methanol and 1.8 g of water, 8.1 g of acetone and a further 1.8 g of water were added. It was stirred overnight. The solid was filtered off with suction, washed with 2 g of acetone/water (8:2) and dried overnight at 60° C. in vacuo with nitrogen air.

Yield: 1.8 g of white solid, 90% of theory.

Enantiomeric purity (HPLC method C): 92.0% ee

Purity (area): 97.3% (Method M, $R_t$ 8.94 min)

XRPD: monohydrate I, see FIG. 37

| Reflections (Peak maxima) [°2 Theta] |
|---|
| 5.7 |
| 7.1 |
| 9.9 |
| 10.2 |
| 10.7 |
| 11.4 |
| 12.2 |
| 12.8 |
| 14.0 |
| 15.1 |
| 15.6 |
| 15.9 |
| 17.2 |
| 17.7 |
| 19.2 |
| 19.5 |
| 19.8 |
| 20.2 |
| 20.3 |
| 20.7 |
| 21.0 |
| 22.2 |
| 22.9 |
| 23.4 |
| 23.8 |
| 24.2 |
| 24.5 |
| 25.0 |
| 25.7 |
| 26.0 |
| 26.4 |
| 28.8 |
| 29.1 |
| 30.5 |
| 32.1 |

Example 4

(5S)-{[2-(4-Carboxyphenyl)ethyl][2-(2-{[3-chloro-4'-(trifluoromethyl) biphenyl-4-yl]methoxy}phenyl)-ethyl]amino}-5,6,7,8-tetrahydroquinoline-2-carboxylic acid as monohydrate I

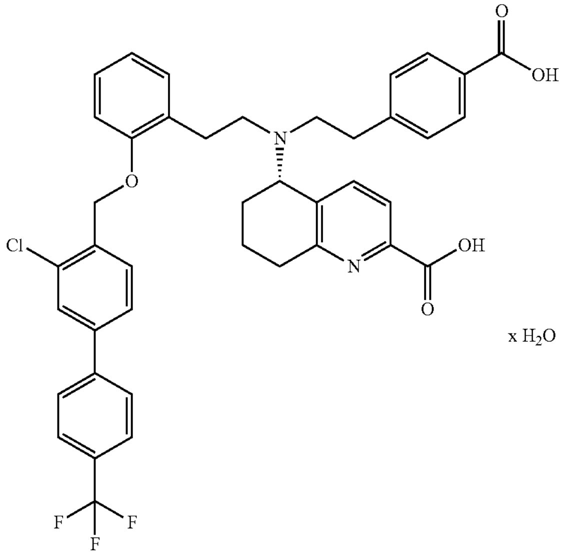

Release of Dibutylester from NSA Salt:

800 g of tetrahydrofuran were placed in a 6 L glass stirring apparatus and 250 g (0.30 mol) of naphthalene-1,5-disulfonic acid-butyl-(5S)-5-({2-[4-(butoxycarbonyl)phenyl]ethyl}[2-(2-{[3-chloro-4'-(trifluoromethyl)[biphenyl]-4-yl]methoxy}phenyl)ethyl]amino)-5,6,7,8-tetrahydroquinoline-2-carboxylate (1:1) (example 4A) was added in portions with stirring. 1 L of water and then 27% ammonia water were added at 20° C. to 25° C. until a pH of 7.8 to 8.2 was reached (approx. 27 g). 1080 g of diisopropyl ether were added, the aqueous phase was separated off, the organic phase was extracted again with 1 L of water/0.8 ml of 27% ammonia water and then washed with 1 L of water. The organic phase was filtered through a Seitz filter plate covered with 150 g of sodium sulfate (anhydrous), it was rinsed with 150 g of diisopropyl ether and the filtrate was concentrated at 40° C. in vacuo to 192 g of evaporation residue.

Saponification of Dibutylester:

The evaporation residue was dissolved in 610 g of tetrahydrofuran, 1139 g of 1N sodium hydroxide solution were added and the mixture was stirred at 60° C. for 24 h. 875 g of ethyl acetate were then added at 20° C., the aqueous product phase (disodium salt solution) was separated off and residual ethyl acetate was distilled off at a maximum of 40° C. in vacuo.

Formation of Free Acid of Formula I:

The residue was diluted with 1875 g of water, filtered through a Seitz filter plate and a portion of the disodium salt solution (835 g) was added dropwise to a mixture of 821 g of tetrahydrofuran and 103 g of 10% hydrochloric acid until a pH value of 4.0 was reached. 174 g of sodium chloride and 420 g of tetrahydrofuran were added and the organic product phase was separated off.

The consumption of disodium salt solution is set in relation to the amount of hydrochloric acid submitted and the amount of hydrochloric acid for the conversion of the further partial amounts is calculated. The second aliquot of the disodium salt solution (2000 g) was added dropwise to the calculated amounts of tetrahydrofuran (2116 g) and 10% strength hydrochloric acid (246 g) until a pH of 4.0 was reached. 174 g of sodium chloride and 420 g of tetrahydrofuran were added and the organic product phase was separated off. The combined aqueous phases were added with 261 g of sodium chloride and 1043 g of tetrahydrofuran and the organic product phase was separated off. The combined organic phases were concentrated in vacuo to a residual volume of 800 ml at a maximum of 40° C.

Crystallization:

184 g of tetrahydrofuran were added and a mixture of 646 g of methanol and 291 g of water was added at 20° C. with stirring added dropwise. It was mixed with 0.8 g of (5S)-5-{[2-(4-carboxyphenyl)ethyl][2-(2-{[3-chloro-4'-(trifluoromethyl)[biphenyl]-4-yl]methoxy}phenyl)ethyl]amino}-5,6,7,8-tetrahydroquinoline-2-carboxylic acid monohydrate I (example 3) and stirred for 12 h. The solid was separated and washed with a mixture of 112 g of methanol and 112 g of water. The solid was then dried to 127 g in vacuo at 20° C. A second portion of 128 g was prepared using the same procedure.

The combined solids were heated to 50° C. with a mixture of 1020 g acetone and 1020 g methanol and cooled to 20° C. The solution obtained was filtered through a Seitz filter plate, heated to 50° C. and 460 g of water were added dropwise over a period of 30 minutes. It was inoculated with 1.5 g of seed crystals of monohydrate I (example 3), stirred for 30 min, cooled to 20° C. in at least 30 min and the solid was filtered off with suction. The moist product was stirred with 2550 g of water for 12 hours, then filtered off with suction and washed twice with 510 g of water. The moist product was dried to constant weight at 20° C. in a stream of nitrogen under vacuum.

Yield: 230 g monohydrate I, (I-M-I); 71% o. Th.

Purity (area): 96.0% (Method M, $R_t$ 8.94 min)

Enantiomeric purity (HPLC method C): 99.3% ee

XRPD: monohydrate form I; see FIG. 38

| Reflections (Peak maxima) [°2 Theta] |
|---|
| 5.7 |
| 6.9 |
| 7.2 |
| 7.4 |
| 9.9 |
| 10.7 |
| 11.1 |
| 11.5 |
| 12.0 |
| 12.2 |
| 12.4 |
| 12.8 |
| 13.7 |
| 14.1 |
| 14.3 |
| 15.2 |
| 15.6 |
| 16.0 |
| 16.9 |
| 17.2 |
| 17.5 |
| 17.7 |
| 18.0 |
| 18.4 |
| 18.8 |
| 19.1 |
| 19.9 |
| 20.3 |
| 20.5 |
| 20.7 |
| 20.9 |
| 21.3 |
| 21.9 |
| 22.2 |
| 22.5 |
| 23.0 |
| 23.2 |
| 23.4 |
| 23.7 |
| 24.1 |
| 24.4 |
| 25.1 |
| 25.8 |
| 26.1 |
| 26.5 |
| 26.8 |
| 28.8 |
| 29.4 |
| 30.0 |
| 30.6 |
| 31.0 |
| 32.2 |
| 35.4 |

Example 5

(5S)-{[2-(4-Carboxyphenyl)ethyl][2-(2-{[3-chloro-4'-(trifluoromethyl) biphenyl-4-yl]methoxy}phenyl)-ethyl]amino}-5,6,7,8-tetrahydroquinoline-2-carboxylic acid as monohydrate I In an inertized 2 L reactor, butyl (5S)-5-({2-[4-(butoxycarbonyl)phenyl]ethyl)[2-(2-hydroxyphenyl)ethyl]amino}-5.6 7,8-tetrahydroquinoline-2-carboxylate (example 2A, WO2021/233783) was dissolved at $T_{sheatht}$=22° C. (50.8 g, 1.0 eq.) in acetonitrile (380 mL). The solution was distilled at $T_{sheatht}$=50° C. and 120 mbar. Then again acetonitrile (380 ml) was added and the mixture was distilled again under the same conditions. Acetonitrile (660 mL) was added to the solution and stirred for 5 min. Then 4-(bromomethyl)-3-chloro-4'-(trifluoromethyl)[biphenyl](biarylbenzylbromide) (53.5 g, 1.2 eq.) was added and the mixture was again stirred for 5 min until it was dissolved. Then cesium carbonate (83.1 g, 2.0 eq.) was added and the mixture was stirred for 4 hours. Cesium carbonate (20.8 g, 0.5 eq.) was added again to the suspension and the mixture was stirred for 1 h. The product suspension was clarified by filtration and the filter cake was washed once over a kettle with acetonitrile (110 mL). The filter cake was disposed of.

The organic reaction solution was concentrated in the inerted 2 L reactor at 90 mbar and $T_{sheath}$=45° C. until the distillate has dried up. When $T_{sheath}$=23° C., THF (425 mL) was added. The solution was concentrated at 150 mbar and $T_{sheath}$=45° C. until the distillate has dried up. THF (425 mL) and 4% NaOH (680 mL) were added to the solution. The emulsion was heated to $T_{internal}$=60° C. and stirred for a further 20 hours.

The solution was cooled to $T_{internal}$=23° C. and deionized water (800 ml) and ethyl acetate (435 ml) were added and the mixture was stirred for 15 min. The phases were separated. The organic phase was discarded and the aqueous phase was extracted with ethyl acetate (435 mL). The organic phase was discarded and the aqueous phase was distilled at 140-160 mbar and $T_{sheath}$=45-40° C. to $T_{internal}$=36° C. The product solution was clarified by filtration and the filter cake was washed once with deionized water (80 mL). The residue was disposed of.

The product solution was titrated. For this purpose, 25% HCl, deionized water and THF were placed in the inerted 4-liter reactor. The organic product solution was added at $T_{internal}$=20° C.±5° C. up to pH 3.8-4.2. THF (360 mL) and sodium chloride (471 g) were then added and the mixture was stirred for 30 min. The phases were separated and the aqueous phase was extracted with THF (450 mL). The aqueous phase was disposed of and the organic phase was crystallized. For this purpose, it was concentrated to the sump mass at 200 mbar and ΔT=30° C. THF was then added and the mixture was again distilled to 4 times the theoretical yield under the same conditions. At $T_{internal}$=22° C., a mixture of deionized water (49 mL) and methanol (144 ml) was metered in, inoculated and stirred for 15 min. A mixture of deionized water (113 ml) and Methanol (335 mL) was further metered in and the mixture was stirred overnight. The suspension was filtered and the product was washed once over a kettle with a mixture of deionized water and methanol (1:1). It was then dried at 40-50° C. and 40-30 mbar.

Yield: 23.4 g, 67% of theory

Purity (area): 99.3% (new method M, $R_t$ 6.28)

XRPD: monohydrate I, see FIG. 39

Example 6

Study to investigate crystalline/polymorphic forms of (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of formula I Example 6a (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid semihydrate 2.9 g (5S)-{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I (material prepared in analogy to example 3/4) were suspended in 20 ml of acetone. The suspension was stirred at ambient conditions for three days. The residue was filtered and the resulting solid was dryed at ambient conditions.

water content: 1.5% water

Raman: see table 13, see FIG. 12

IR: see table 14, see FIG. 19

XRPD: see table 12, see FIG. 5

Example 6b (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid monohydrate I The target compound was prepared in analogy to example 3 (monohydrate I).

water content: 3.9% before and 2.4% water after drying

Raman: see table 13, see FIG. 13

IR: see table 14, see FIG. 20

XRPD: see table 12, see FIG. 6

Example 6c (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid monohydrate II The target compound was prepared in analogy to example 1 (monohydrate II).

water content: 3.9% before and 2.4% water after drying

Raman: see table 13, see FIG. 14

IR: see table 14, see FIG. 21

XRPD: see table 12, see FIG. 7

Example 6d (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid 1.25 hydrate 3 g (5S)-{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I, (material prepared in analogy to example 3/4) were suspended in 20 mL of an isopropanole/water mixture (1:1). The suspension was stirred at 60° C. for eight days. The residue was filtered and the resulting solid was dryed at ambient conditions.

water content: 2.9% water

Raman: see table 13, see FIG. 15

IR: see table 14, see FIG. 22

XRPD: see table 12, see FIG. 8

Example 6e (5S)-{[2-(4-Carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid sesquihydrate 3 g (5S)-{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I, (material prepared in analogy to example 3/4) were suspended in 15 mL of an isopropanole/water mixture (1:1). The suspension was stirred at 80° C. for four weeks. Additional 10 mL of the solvent mixture were added to improve the stirring properties of the suspension. The residue was filtered and the resulting solid was dryed at ambient conditions.
water content: 3.7% water
Raman: see table 13, see FIG. 16
IR: see table 14, see FIG. 23
XRPD: see table 12, see FIG. 9

Example 6f (5S)-{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid dihydrate 3 g (5S)-{[2-(4-Carboxyphenyl)ethyl][2-(2-{[3-chloro-4'-(trifluoromethyl)biphenyl-4-yl]methoxy}-phenyl)ethyl]amino}-5,6,7,8-tetrahydroquinoline-2-carboxylic acid monohydrate I, (material prepared in analogy to example 3/4) were suspended in 20 mL of methanol. The suspension was stirred at ambient conditions for eight days. The residue was filtered and the resulting solid was dryed at ambient conditions.
water content: 4.8% water
Raman: see table 13, see FIG. 17
IR: see table 14, see FIG. 24
XRPD: see table 12, see FIG. 10
After drying the dihydrate form went amorphous.
XRPD: amorphous form, see FIG. 10a

Example 62

(5S)-{[2-(4-Carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid The amorphous form was prepared in analogy to comparative example 11.
Raman: see table 13, see FIG. 18
IR: see table 14, see FIG. 25
XRPD: see table 12, see FIG. 11

Physical characterization of polymorphic forms of (5S)-{[2-(4-Carboxyphenyl)ethyl][2-(2-{[3-chloro-4'-(trifluoromethyl) biphenyl-4-yl]methoxy}phenyl) ethyl]amino}5,6,7,8-tetrahydroquinoline-2-carboxylic acid of formula (I)

TABLE 12

XRPD (X-ray powder diffraction) data of pseudopolymorphic forms of compound of formula (I)
XRPD were recorded according to the general procedure described under the headline methods.
Reflections (Peak maxima) [2 Theta]

| Semihydrate | Monohydrate I | Monohydrate II | 1,25-Hydrate | Sesquihydrate | Dihydrate |
|---|---|---|---|---|---|
| 3.1 | 5.7 | 5.7 | 5.9 | 5.1 | 6.1 |
| 5.3 | 6.9 | 6.1 | 6.1 | 6.3 | 6.8 |
| 6.7 | 7.2 | 7.1 | 7.9 | 7.6 | 10.1 |
| 7.1 | 7.3 | 8.5 | 10.5 | 8.6 | 10.5 |

TABLE 12-continued

XRPD (X-ray powder diffraction) data of pseudopolymorphic forms of compound of formula (I)
XRPD were recorded according to the general procedure described under the headline methods.
Reflections (Peak maxima) [2 Theta]

| Semihydrate | Monohydrate I | Monohydrate II | 1,25-Hydrate | Sesquihydrate | Dihydrate |
|---|---|---|---|---|---|
| 9.3 | 9.9 | 9.9 | 11.9 | 11.4 | 11.2 |
| 10.6 | 10.4 | 10.2 | 12.2 | 12.2 | 11.3 |
| 12.4 | 10.6 | 10.8 | 12.5 | 12.5 | 12.3 |
| 14.3 | 11.1 | 11.4 | 13.2 | 12.9 | 12.5 |
| 16.1 | 11.5 | 11.6 | 13.6 | 13.3 | 13.1 |
| 19.7 | 12.0 | 11.8 | 13.7 | 14.3 | 13.6 |
| 20.8 | 12.3 | 12.0 | 14.4 | 14.5 | 14.6 |
| 24.0 | 12.4 | 12.2 | 15.2 | 15.2 | 14.8 |
| 31.1 | 12.8 | 12.7 | 15.3 | 15.5 | 15.5 |
|  | 13.7 | 13.0 | 15.4 | 15.8 | 16.2 |
|  | 14.1 | 13.9 | 15.7 | 16.2 | 16.4 |
|  | 14.3 | 14.2 | 15.9 | 16.4 | 16.8 |
|  | 15.2 | 15.2 | 16.5 | 16.7 | 17.1 |
|  | 15.6 | 15.3 | 16.9 | 17.3 | 17.3 |
|  | 16.0 | 15.7 | 17.2 | 17.5 | 17.9 |
|  | 16.9 | 16.4 | 17.4 | 17.7 | 18.5 |
|  | 17.2 | 17.3 | 17.6 | 18.3 | 18.8 |
|  | 17.5 | 17.7 | 17.8 | 18.7 | 19.5 |
|  | 17.7 | 17.9 | 18.3 | 19.4 | 20.2 |
|  | 18.0 | 18.3 | 18.6 | 20.5 | 20.5 |
|  | 18.4 | 18.5 | 18.7 | 20.7 | 21.1 |
|  | 18.8 | 18.8 | 19.0 | 20.8 | 21.4 |
|  | 19.2 | 19.2 | 19.5 | 21.4 | 22.2 |
|  | 19.9 | 19.8 | 19.6 | 21.51 | 23.2 |
|  | 20.2 | 20.2 | 19.8 | 21.8 | 24.3 |
|  | 20.5 | 20.8 | 20.5 | 22.4 | 25.1 |
|  | 20.7 | 21.1 | 20.7 | 22.9 | 25.4 |
|  | 21.3 | 21.7 | 21.0 | 23.4 | 25.6 |
|  | 21.9 | 22.0 | 21.4 | 24.0 | 26.3 |
|  | 22.2 | 22.4 | 22.0 | 24.7 | 26.9 |
|  | 22.5 | 22.8 | 23.2 | 25.1 | 27.4 |
|  | 23.0 | 23.1 | 23.8 | 26.1 | 28.5 |
|  | 23.4 | 23.4 | 24.0 | 26.4 | 28.7 |
|  | 23.7 | 23.9 | 24.4 | 27.0 | 29.6 |
|  | 24.1 | 24.2 | 24.6 | 27.4 |  |
|  | 25.1 | 24.4 | 25.0 | 28.5 |  |
|  | 25.8 | 25.1 | 25.2 | 32.2 |  |
|  | 26.0 | 25.5 | 25.6 | 36.5 |  |
|  | 26.4 | 25.7 | 26.1 |  |  |
|  | 28.9 | 26.2 | 26.8 |  |  |
|  | 29.2 | 26.4 | 27.4 |  |  |
|  | 29.4 | 26.8 | 27.6 |  |  |
|  | 30.6 | 27.2 | 28.4 |  |  |
|  | 31.1 | 27.5 | 28.8 |  |  |
|  | 32.2 | 28.9 | 30.2 |  |  |
|  | 35.3 | 30.0 | 30.7 |  |  |
|  |  | 30.1 | 31.1 |  |  |
|  |  | 30.6 | 31.6 |  |  |
|  |  | 32.2 | 32.3 |  |  |
|  |  | 32.4 |  |  |  |

TABLE 13

Raman data of pseudopolymorphic forms of compound of formula (I)
Raman spectra were recorded according to the general procedure described under the headline Methods.
Bands [Peak maxima in $cm^{-1}$]

| Semihydrate | Monohydrate I | Monohydrate II | 1,25-Hydrate | Sesquihydrate | Dihydrate | Amorphous |
|---|---|---|---|---|---|---|
| 3069 | 3073 | 3073 | 3064 | 3081 | 3073 | 3069 |
| 2941 | 2950 | 3042 | 2954 | 3064 | 2971 | 3008 |
| 2917 | 2937 | 3003 | 2933 | 3019 | 2940 | 2938 |
| 2862 | 2906 | 2950 | 2907 | 2993 | 2897 | 2869 |
| 2825 | 2892 | 2936 | 2858 | 2979 | 2877 | 2732 |
| 1700 | 2852 | 2892 | 2828 | 2965 | 2864 | 1769 |

TABLE 13-continued

Raman data of pseudopolymorphic forms of compound of formula (I)
Raman spectra were recorded according to the general procedure described under the headline Methods.
Bands [Peak maxima in $cm^{-1}$]

| Semi-hydrate | Mono-hydrate I | Mono-hydrate II | 1,25-Hydrate | Sesqui-hydrate | Di-hydrate | Amor-phous |
|---|---|---|---|---|---|---|
| 1689 | 1685 | 2854 | 1765 | 2924 | 1689 | 1708 |
| 1617 | 1616 | 1685 | 1694 | 2897 | 1617 | 1617 |
| 1528 | 1527 | 1615 | 1610 | 2873 | 1611 | 1610 |
| 1496 | 1451 | 1526 | 1528 | 2858 | 1573 | 1587 |
| 1487 | 1440 | 1458 | 1492 | 2805 | 1527 | 1527 |
| 1452 | 1420 | 1451 | 1459 | 2736 | 1497 | 1489 |
| 1423 | 1384 | 1441 | 1449 | 1690 | 1460 | 1450 |
| 1372 | 1374 | 1420 | 1439 | 1616 | 1454 | 1372 |
| 1349 | 1328 | 1384 | 1430 | 1530 | 1443 | 1326 |
| 1329 | 1293 | 1372 | 1381 | 1463 | 1433 | 1279 |
| 1294 | 1278 | 1328 | 1369 | 1453 | 1422 | 1263 |
| 1283 | 1259 | 1294 | 1327 | 1440 | 1384 | 1231 |
| 1269 | 1228 | 1279 | 1283 | 1421 | 1372 | 1205 |
| 1260 | 1191 | 1259 | 1258 | 1370 | 1332 | 1194 |
| 1229 | 1162 | 1228 | 1233 | 1330 | 1296 | 1162 |
| 1207 | 1153 | 1196 | 1197 | 1291 | 1282 | 1126 |
| 1196 | 1128 | 1162 | 1166 | 1274 | 1259 | 1072 |
| 1163 | 1116 | 1153 | 1128 | 1263 | 1228 | 1054 |
| 1131 | 1056 | 1128 | 1116 | 1231 | 1196 | 1037 |
| 1074 | 1042 | 1057 | 1053 | 1199 | 1169 | 1015 |
| 1054 | 1033 | 1043 | 1041 | 1183 | 1149 | 960 |
| 1042 | 1015 | 1016 | 1015 | 1169 | 1128 | 926 |
| 1014 | 99 | 998 | 999 | 1148 | 1115 | 883 |
| 1002 | 937 | 894 | 938 | 1131 | 1059 | 859 |
| 936 | 922 | 861 | 922 | 1115 | 1042 | 843 |
| 885 | 893 | 843 | 887 | 1096 | 1015 | 804 |
| 860 | 861 | 837 | 858 | 1071 | 1003 | 777 |
| 844 | 844 | 808 | 840 | 1060 | 937 | 766 |
| 819 | 808 | 777 | 817 | 1040 | 924 | 755 |
| 804 | 793 | 757 | 806 | 964 | 891 | 738 |
| 776 | 776 | 750 | 775 | 944 | 873 | 692 |
| 745 | 756 | 701 | 755 | 928 | 861 | 638 |
| 702 | 750 | 693 | 746 | 911 | 835 | 457 |
| 693 | 703 | 655 | 739 | 863 | 806 | 440 |
| 657 | 692 | 638 | 701 | 850 | 777 | 408 |
| 638 | 655 | 569 | 658 | 835 | 757 | 183 |
| 572 | 638 | 473 | 637 | 826 | 750 | 107 |
| 476 | 568 | 463 | 605 | 814 | 741 | |
| 464 | 473 | 439 | 587 | 805 | 703 | |
| 439 | 464 | 419 | 571 | 767 | 692 | |
| 423 | 439 | 410 | 477 | 757 | 658 | |
| 407 | 419 | 394 | 462 | 743 | 652 | |
| 395 | 410 | 357 | 441 | 701 | 637 | |
| 349 | 393 | 323 | 421 | 693 | 601 | |
| 300 | 359 | 302 | 403 | 678 | 571 | |
| 242 | 323 | 281 | 333 | 656 | 465 | |
| 176 | 301 | 233 | 316 | 634 | 438 | |
| 145 | 281 | 208 | 297 | 491 | 422 | |
| 110 | 230 | 195 | 282 | 464 | 410 | |
| | 197 | 148 | 226 | 440 | 399 | |
| | 149 | 117 | 177 | 422 | 360 | |
| | 117 | | 142 | 409 | 314 | |
| | | | 102 | 394 | 287 | |
| | | | | 372 | 226 | |
| | | | | 349 | 190 | |
| | | | | 341 | 152 | |
| | | | | 326 | 103 | |
| | | | | 301 | | |
| | | | | 271 | | |
| | | | | 251 | | |
| | | | | 243 | | |
| | | | | 224 | | |
| | | | | 187 | | |
| | | | | 156 | | |
| | | | | 113 | | |

TABLE 14

IR data of pseudopolymorphic forms of compound of formula (I)
IR spectra were recorded according to the general procedure described under the headline Methods.
Bands [Peak maxima in $cm^{-1}$]

| Semi-hydrate | Mono-hydrate I | Mono-hydrate II | 1,25-Hydrate | Sesqui-hydrate | Di-hydrate | Amor-phous |
|---|---|---|---|---|---|---|
| 3032 | 3660 | 3659 | 3426 | 3516 | 3395 | 3405 |
| 2937 | 3416 | 3416 | 3044 | 3404 | 3197 | 3036 |
| 2864 | 3038 | 3039 | 2921 | 3073 | 3037 | 2941 |
| 2648 | 2933 | 2934 | 2854 | 2939 | 2938 | 2864 |
| 1761 | 2863 | 2892 | 2832 | 2922 | 2865 | 2644 |
| 1695 | 2809 | 2862 | 2650 | 2895 | 2646 | 1701 |
| 1640 | 2644 | 2809 | 1767 | 2876 | 1684 | 1685 |
| 1590 | 1761 | 2733 | 1692 | 2854 | 1597 | 1599 |
| 1558 | 1678 | 2647 | 1602 | 2815 | 1558 | 1559 |
| 1528 | 1595 | 1762 | 1511 | 2733 | 1539 | 1494 |
| 1495 | 1539 | 1679 | 1497 | 2650 | 1497 | 1453 |
| 1452 | 1498 | 1595 | 1448 | 1683 | 1453 | 1419 |
| 1418 | 1454 | 1539 | 1429 | 1668 | 1431 | 1371 |
| 1373 | 1419 | 1498 | 1376 | 1607 | 1419 | 1325 |
| 1325 | 1375 | 1454 | 1325 | 1594 | 1376 | 1272 |
| 1293 | 1327 | 1431 | 1275 | 1559 | 1327 | 1238 |
| 1241 | 1292 | 1419 | 1237 | 1533 | 1270 | 1166 |
| 1166 | 1272 | 1375 | 1178 | 1503 | 1241 | 1112 |
| 1112 | 1242 | 1327 | 1158 | 1450 | 1167 | 1072 |
| 1072 | 1167 | 1292 | 1128 | 1377 | 1106 | 1057 |
| 1059 | 1110 | 1272 | 1109 | 1330 | 1072 | 1036 |
| 1038 | 1072 | 1242 | 1066 | 1302 | 1037 | 1014 |
| 1014 | 1062 | 1167 | 1040 | 1242 | 1013 | 925 |
| 924 | 1039 | 1110 | 1014 | 1171 | 954 | 882 |
| 883 | 1014 | 1072 | 939 | 1152 | 924 | 845 |
| 844 | 956 | 1062 | 924 | 1136 | 886 | 821 |
| 818 | 938 | 1039 | 887 | 1105 | 844 | 805 |
| 750 | 923 | 1014 | 858 | 1073 | 819 | 751 |
| 703 | 887 | 938 | 840 | 1060 | 804 | 704 |
| 692 | 858 | 923 | 815 | 1036 | 750 | 692 |
| 656 | 845 | 888 | 805 | 1013 | 703 | 669 |
| 635 | 818 | 858 | 783 | 992 | 691 | 654 |
| 591 | 806 | 845 | 748 | 954 | 656 | 637 |
| 582 | 742 | 818 | 701 | 928 | 634 | 609 |
| 569 | 703 | 806 | 692 | 910 | 608 | 589 |
| | 692 | 756 | 657 | 881 | 575 | 577 |
| | 654 | 742 | 646 | 862 | 564 | 558 |
| | 637 | 703 | 641 | 849 | 558 | |
| | 608 | 692 | 635 | 819 | | |
| | 575 | 654 | 604 | 802 | | |
| | 559 | 637 | 577 | 778 | | |
| | | 609 | 560 | 755 | | |
| | | 576 | | 740 | | |
| | | 558 | | 700 | | |
| | | | | 692 | | |
| | | | | 655 | | |
| | | | | 640 | | |
| | | | | 632 | | |
| | | | | 606 | | |
| | | | | 566 | | |
| | | | | 559 | | |

B—PROPERTIES OF PSEUDOPOLYMORPHIC FORMS

Example 7

Properties of pseudopolymorphic forms of [(5S)-{[2-(4-carboxyphenyl)ethyl][2-(2-{[3-chloro-4'-(trifluoromethyl)biphenyl-4-yl]methoxy}¬phenyl)¬ethyl]amino}-5,6,7,8-tetrahydroquinoline-2-carboxylic acid of the formula (I), e.g monohydrate II of formula (I-M-II)

Storage Stability

Compound stability and uniformity is a key requirement for a pharmaceutical and a prerequisite for an approval by health authorities. It increases the safety and quality of preparations and formulations comprising of the compound of the formula (I) and thus reduces the risk to the patient.

(5S)-{[2-(4-carboxyphenyl)ethyl][2-(2-{[3-chloro-4'-(trifluoromethyl)biphenyl-4-yl]methoxy}phenyl)-ethyl]amino}-5,6,7,8-tetrahydroquinoline-2-carboxylic acid of the formula (I) in form of the monohydrate II was used for storage stability studies under various conditions for one, three and six months:

TABLE 15 storage stability study results, monohydrate II as starting material

| example | Container | Temperature | Relative humidity | Result |
|---|---|---|---|---|
| 7a | Brown glass snap on closure | 25° C. | 60% | monohydrate II |
| 7b | Polyethylene | 25° C. | 60% | monohydrate I |
| 7c | Polyethylene | 40° C. | 75% | monohydrate I |
| 7d | Brown glass closed with paper filter disc | 40° C. | 75% | monohydrate I |

Figure 41:
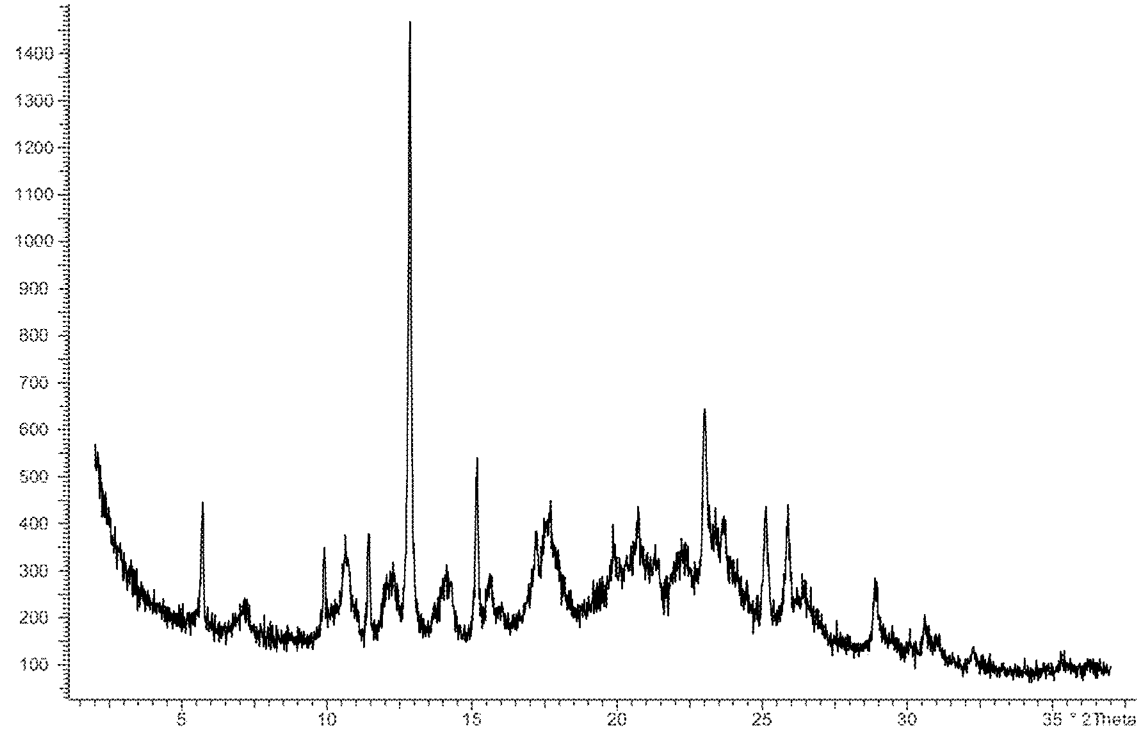

Under most of these storage conditions the monohydrate II (starting material, see FIG. 40) underwent conversion to monohydrate I (see e.g. FIG. 41: example 7b, XRPD).

In comparison the monohydrate I of formula (I-M-I) was stable under these conditions.

In particular the monohydrate I of the compound of the formula (I) ensures that an undesired conversion into another form of the compound of formula (I) and an associated change in the properties as described above is prevented.

Example 8

Properties of pseudopolymorphic forms of [(5S)-{[2-(4-carboxyphenyl)ethyl][2-(2-{[3-chloro-4'-(trifluoromethyl)biphenyl-4-yl]methoxy}¬phenyl)¬ethyl]amino}-5,6,7,8-tetrahydroquinoline-2-carboxylic acid of the formula (I), e.g monohydrate II of formula (I-M-II)

Micronization

For inhalative drug products it is important to guarantee a homogeneous drug substance with defined particle size <5 μm to secure delivery to the deep lung compartments. This technical requirement can be afforded by micronization of the drug substance particles.

Appropriate specifications for a particle size distribution of the active ingredient to achieve this requirement were set as specified in table 16a.

TABLE 16a

Particle size distribution of active ingredient, e.g. compound of formula (I-M-I) or (I-M-II)

| | |
|---|---|
| Particle size upper X90 | max. 6 μm |
| Particle size mean X50 | 1-3 μm |
| Particle size lower X10 | max. 1 μm |

In order to investigate the feasibility of monohydrate II of formula (I-M-II) for drug product manufacturing several micronization conditions were tested. Generally no amorphization even partial nor form conversion should happen during the necessary micronization step. Even a partial amorphization during micronization could lead to the risk of recrystallization of active ingredient and/or later of active ingredient in final drug product during storage.

The corresponding batches (examples 8a-8d) were micronized using a 50 mm spiral jet mill and pressurized nitrogen with the following parameters (see table 16b).

TABLE 16b different micronization conditions, mononohydrate II as starting material

| example | mill type | Temperature | Injector pressure | Grinding pressure | Throughput | PSD | observation |
|---|---|---|---|---|---|---|---|
| 8a | VA jet mill | 25° C. | 4.5 bar | 4.0 bar | 4.5 g/min | X10: 0.4 μm, X50: 1.7 μm, X90: 4.2 μm (dry measurement 4 bar) | transformation to monohydrate I |
| 8b | PTFE coated jet mill | 25° C. | 4.5 bar | 4.0 bar | 4.5 g/min | X10: 0.7 μm, X50: 1.9 μm, X90: 5.0 μm (dry measurement 4 bar) | partial amorphization of monohydrate II |
| 8c | VA jet mill | −65° C. | 4.5 bar | 4.0 bar | 5.5 g/min | X10: 0.4 μm, X50: 1.8 μm, X90: 4.8 μm (dry measurement 4 bar) | partial amorphization of monohydrate II |
| 8d | VA jet mill (Low stress conditions) | −65° C. | 4.5 bar | 3.0 bar | 10.6 g/min | X10: 0.5 μm, X50: 2.3 μm, X90: 9.6 μm (dry measurement 4 bar) | partial amorphization of monohydrate II |

Firstly it was found during an orienting experiment under standard conditions (VA jet mill (50 mm) at a temperature of 25° C.) that form II could be principally micronized to obtain the desired particle size distribution (see tables 16a and 16b, ex. 8a).

Figure 42:
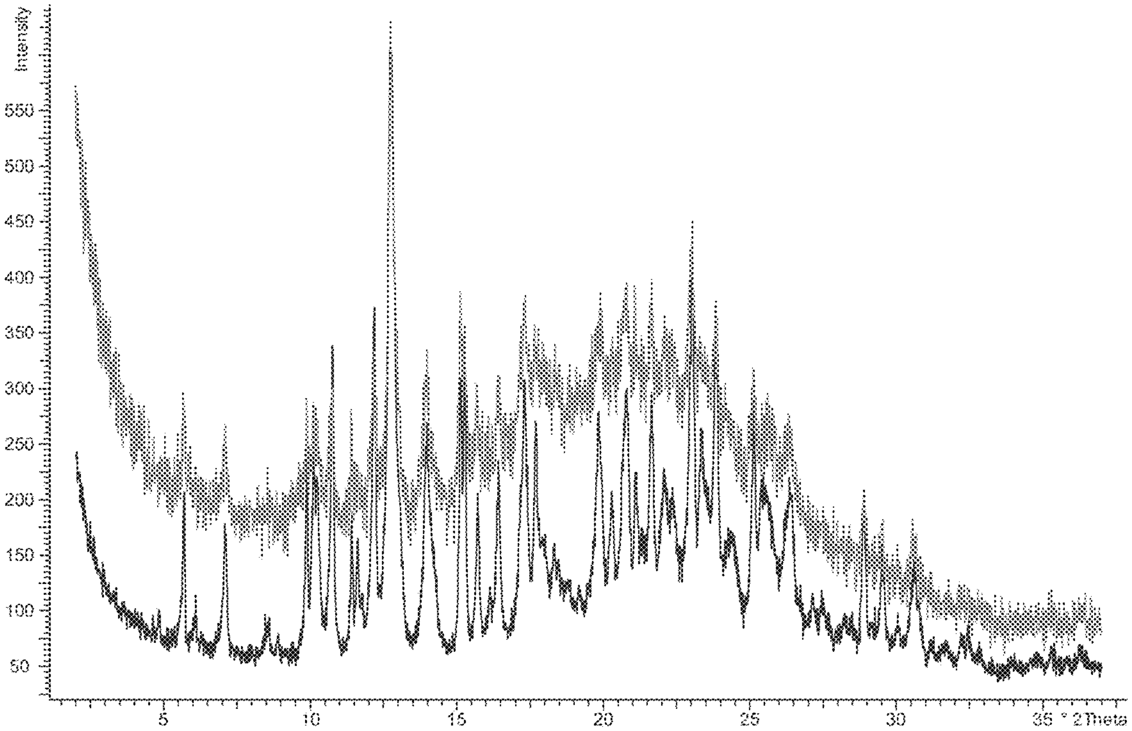

During micronization of monohydrate 11 of formula (I-M-II) partial amorphization occurred under several conditions, even under "low stress" (see table 16b above and FIG. 42, XRPD).

XRPD: monohydrate II with partial amorphization, example 8b

Additionally it was found that besides partial amorphization also a transformation from monohydrate II to monohydrate I occurred under micronization with a VA jet mill (diameter 50 mm), 25° C. (see table 16b, example 8a and FIG. 43, XRPD).

As all studied conditions showed either a form transformation to form I or a partial amorphization of form 11 the monohydrate I was further investigated in order to check feasibility of monohydrate I for a reliable drug manufacturing.

The corresponding batches were micronized using a 100 mm spiral jet mill and pressurized nitrogen with the following parameters (see table 16c).

TABLE 16c large batch micronization conditions, monohydrate I as starting material

| example | mill type | temper-ature | Injector pressure | Grinding pressure [bar] | Throughput | PSD | observation |
|---|---|---|---|---|---|---|---|
| 8e | PTFE coated jet mill | 25° C. | 5 bar | 4.5 bar | 22.8 g/min | X10: 0.7 μm, X50: 2.1 μm, X90: 6.1 μm (dry measurement 4 bar) | monohydrate I |
| 8f | PTFE coated jet mill | −65° C. | 5 bar | 4.0 bar | 23 to 28 g/min | X10: 0.6 μm, X50: 2.4 μm, X90: 6.3 μm (dry measurement 3 bar, N=3) | monohydrate I |
| 8g | VA (stainless steel) jet mill | 25° C. | 6 bar | 4.5 bar | 8.5 g/min | X10: 0,5 μm, X50: 1.8 μm, X90: 3.9 μm (dry measurement 3 bar) | monohydrate I |

All measurements cited in the above tables were obtained by laser diffraction with dry dispersion using compressed air. Measuring in aqueous suspension with surfactants may lead to smaller particle sizes (×90 up to 1 μm smaller).

In comparison the monohydrate I of formula (I-M-I) was stable under micronization conditions (see table 16c, example 8e).

XRPD: monohydrate form I; see FIG. 44

C—BIOLOGICAL EXAMPLES

The following abbreviations are use:

| Abbreviation | Explanation |
|---|---|
| ° C. | degrees Celsius |
| /D | divided by dose |
| μg | Microgram |
| ACh | Acetylcholine |
| AE | adverse event |

-continued

| Abbreviation | Explanation |
|---|---|
| AHR | airway hyperresponsiveness |
| API | active pharmaceutical ingredient |
| AUC | area under the concentration-vs-time curve from zero to infinity after single (first) dose |
| $AUC_\tau$ | AUC for the actual dose interval. If applicable, the day of $AUC_\tau$ is specified as $AUC_\tau$(day n) |
| $AUC_{(0-t)}$ | area under the concentration time curve from time 0 to t hours |
| $AUC_{(0-t).md}$ | area under the concentration time curve from time 0 to t hours after multiple dose |
| $AUC_{(0-t), u}$ | unbound $AUC_{(0-t)}$ |
| $AUC(0-t)_{\tau, md}$ | $AUC_{(0-t)\tau}$ after multiple administration |
| $AUC_{\tau, md}$ | $AUC_\tau$ after multiple administration |
| $AUC_{(0-tlast)}$ | AUC from time 0 to the last data point >LLOQ |
| $AUC_{(0-tlast)norm}$ | AUC from time zero to the last data point above the lower limit of quantification divided by dose per kg body weight |
| $AUC_{norm}$ | AUC divided by dose (mg) per kg body weight |
| BAL | bronchoalveolar lavage |
| BALB/c | mouse fibroblast cells |
| BDC | bile duct cannulated |
| BP | blood pressure |
| bpm | beats per minute |
| BPsys | systolic blood pressure |
| BSEP | bile salt export pump |
| Caco-2 cell | human colon adenocarcinoma cell |
| CB | charcoal block |
| cGMP | cyclic guanosine monophosphate |
| CHO | Chinese hamster ovary |
| CKD | chronic kidney disease |
| CL | Clearance |
| CL/F | total body clearance of drug calculated after extravascular administration (e.g., apparent oral clearance) |
| $C_{max}$ | maximum drug concentration in measured matrix after single-dose administration |
| $C_{max, md}$ | $C_{max}$ after multiple dosing |
| $C_{max, norm}$ | $C_{max}$ divided by dose (mg) per kg body weight |
| $C_{max.u}$ | unbound $C_{max}$ |
| CNS | central nervous system |
| CI | confidence interval |
| Conc. | Concentration |
| CTEPH | chronic thromboembolic pulmonary hypertension |
| $C_{trough}$ | concentration at the end of the dosage interval |
| CV | coefficient of variation |
| CYP | cytochrome P450 |
| D | Dose |
| d | Day |
| DD | delivered dose |
| DDI | drug-drug interaction |
| DEA/NO | diethylamine/nitric oxide |
| DMSO | dimethyl sulfoxide |
| DPI | dry powder for inhalation |
| DSUR | development safety update report |
| $EC_{50}$ | half-maximum effective concentration |
| ECG | Electrocardiogram |
| ESTP | European Society of Toxicologic Pathology |
| EtOH | Ethanol |
| F | Bioavailability |
| f | Female |
| FiM | first-in-man |
| FPD | fine particle dose |
| $f_u$ | fraction of free (unbound) drug |
| GCP | Good Clinical Practices |
| GGT | gamma-glutamyl transferase |
| GLP | Good Laboratory Practice |
| h | Hours |
| Hb | Hemoglobin |
| HEK-293 | human embryonic kidney-293 cells |
| hERG | human ether-à-go-go related gene |
| HF | heme-free |
| HPMC | hydroxypropylmethylcellulose |
| HR | heart rate |
| i.e. | id est = that is |
| i.t. | intratracheal(ly) |
| i.v./iv./iv/IV | intravenous(ly) |
| IB | Investigator's Brochure |
| $IC_{50}$ | half-maximal inhibitory concentration |
| ICH | International Conference on Harmonisation of technical requirements for the registration of pharmaceuticals for human use |

-continued

| Abbreviation | Explanation |
|---|---|
| ID | Identifier |
| IF | inhalable fraction |
| IH | Inhaled |
| IIP | idiopathic interstitial pneumonia |
| incl. | Including |
| inf. | Infusion |
| inhal | Inhalation |
| IP | prostacyclin receptor |
| kg | Kilogram |
| $K^+$ | potassium ion |
| $K_i$ | inhibitory constant |
| LC-MS/MS | high-pressure liquid chromatography and tandem mass spectrometry |
| LD | lung dose |
| LDD | lung deposited dose |
| LDH | lactate dehydrogenase |
| LF | lung fraction |
| LLOQ | lower limit of quantitation |
| L-MDR1 | multidrug resistant gene |
| L-NAME | L-Nω-nitroarginine methyl ester |
| LOEL | lowest-observed-effect-level |
| LS | least squares |
| LSC | liquid scintillation counting |
| m | Male |
| $m^3$ | cubic meter |
| MAD | maximum administered dose |
| MAP | mean arterial pressure |
| mBP | mean blood pressure |
| MBq | Megabecquerel |
| MCh | mean corpuscular hemoglobin |
| MCV | mean corpuscular volume |
| MDCKII | Madin Darby canine kidney type II |
| MEC | molar extinction coefficient |
| MED | minimal effective dose |
| MedDRA | Medical Dictionary for Regulatory Activities |
| mg | Milligram |
| min | Minutes |
| MMAD | mass median aerodynamic diameter |
| MNT | micronucleus test |
| MoE | multiples of exposure |
| mPAP | mean pulmonary artery pressure |
| MPPD | multiple-path particle dosimetry model |
| MRT | mean residence time |
| $MRT_{IV}$ | mean residence time after intravenous administration |
| MS/MS | tandem mass spectrometry |
| MTD | maximum tolerated dose |
| myocard | Myocardium |
| N/n | Number |
| n.a. | not applicable |
| n.c. | not calculated |
| n.d. | not determined |
| NaCl | sodium chloride |
| NADPH | nicotinamide adenine dinucleotide phosphate |
| ND | nominal dose |
| NET | norepinephrine transporter |
| NO | nitric oxide |
| NOAEL | no-observed-adverse-effect level |
| NOEL | no-observed effect level |
| NRU | neutral red uptake |
| OATP | organic anion transporting polypeptide |
| od/o.d. | once daily |
| ODQ | 1H-[1,2,4]axadiazolo[4,3-a]quinoxalin-1-one |
| OECD | The Organisation for Economic Co-operation and Development |
| OP | Opiate |
| Ova | Ovalbumin |
| P | pulmonary region |
| PAH | pulmonary arterial hypertension |
| PAP | pulmonary artery pressure |
| $P_{app}$ | apparent permeability |
| PD | Pharmacodynamic |
| PDE-5 | phosphodiesterase 5 |
| PE | Phenylepinephrine |
| PEG | polyethylene glycol |
| PEG 400 | polyethylene glycol 400 |
| PenH | pause enhanced |
| P-gp | P-glycoprotein |
| PH | pulmonary hypertension |
| pH | pondus Hydrogenii, numeric scale to measure acidity of a aqueous solution |

-continued

| Abbreviation | Explanation |
|---|---|
| PH-COPD | PH in chronic obstructive pulmonary disease |
| PH-IIP | PH related to IIP |
| physiol./Physiol. | Physiologic |
| PK | Pharmacokinetic |
| PMN | polymorphonuclear cells |
| PO/po | per os (oral) |
| PP | perfusion pressure |
| PQ | PQ interval in ECG |
| PRA | plasma renin activity |
| PT | preferred term |
| PVOD | pulmonary veno-occlusive disease |
| PVR | pulmonary vascular resistance |
| QRS | QRS interval in ECG |
| QT | QT interval in ECG |
| QTc | QT interval corrected for HR |
| QWBA | quantitative whole-body autoradiography |
| $R_A$AUC | accumulation ratio (AUC(0-$t_{last}$)$_{ss}$/AUC(0-$t_{last}$)$_{Day\ 1}$) |
| $R_A$AUC(0-$t_{last}$) | difference in the ratio of accumulation after repeated dosing and accumulation ratio calculated from AUC from zero time to the last data point above LLOQ |
| $R_AC_{max}$ | accumulation ratio calculated from $C_{max}$ after multiple dosing and $C_{max}$ after single dosing |
| Ref. | Reference |
| $R_L$ | lung resistance |
| $R_{LIN}$ | linearity factor of pharmacokinetics after repeated administration of identical doses calculated from $AUC_\tau$ after multiple dosing and AUC after single dosing |
| RLU | relative light unit |
| RMV | respiratory minute volume |
| RT | room temperature |
| RV | right ventricle |
| RVPsys | systemic right ventricular blood pressure |
| SAE | serious adverse event |
| SAF | safety analysis set |
| $SaO_2$ | arterial oxygen saturation of hemoglobin |
| SD/sd | standard deviation |
| SEM | standard error of the mean |
| sGC | soluble guanylate cyclase |
| SHR | spontaneously hypertensive rats |
| SNAP | S-nitroso-N-acetyl-DL-penicillamine |
| SOC | system organ class |
| SoC | standard-of-care |
| SOP | standard operating procedure |
| sPAP | systolic pulmonary artery pressure |
| SUSAR | suspected unexpected serious adverse reaction |
| $t_{(int)}$/$t_{int}$ | last time point during a sampling interval |
| $t_{1/2}$/$T_{1/2}$ | half-life |
| $t_{1/2,\ md}$ | time to reach maximum observed drug concentration in plasma after the first dose followed by multiple dose administration |
| TB | tracheobronchial region |
| TEAE | treatment-emergent adverse event |
| TK | Toxicokinetic |
| $t_{last}$ | time to the last data point above LLOQ |
| $t_{max}$ | time to reach maximum concentration |
| $t_{max.md}$ | time to reach maximum concentration after multiple dose |
| UGT | uridine-5'diphospho glucuronosyltransferase |
| URT | upper respiratory tract |
| v | per volume |
| v/v | volume/volume |
| Vol. | Volume |
| VQ | ventilation perfusion |
| VQ-M | ventilation perfusion mismatch |
| vs. | Versus |
| $V_{SS}$ | volume of distribution at steady state after intravascular administration |
| $V_z$ | volume of distribution during terminal phase after intravascular administration |
| $V_Z$/F | apparent volume of distribution during terminal phase after extravascular administration |
| w | per weight |
| w/w | weight/weight |
| w/wo | with/without |
| w/v | weight/volume |
| WHO | World Health Organization |
| wo | Without |
| WU | Wistar Unilever (HsdCpb: WU) |

Biological Investigations

The example testing experiments described herein serve to illustrate the present invention and the invention is not limited to the examples given.

The following assays can be used to illustrate the commercial utility of the compounds according to the present invention.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

The pharmacological effect of the compounds according to the invention can be shown in the following assays:

C-1 Haemodynamic Vasorelaxant Effects In Vitro and In Vivo

C-1.1 Vasorelaxant Effect In Vitro

Rabbits were anaesthetized and sacrificed by intravenous injection of thiopental sodium (about 50 mg/kg) and exsanguinated. The saphenous artery was removed and divided into rings 3 mm wide. The rings were mounted singly on in each case a pair of triangular hooks open at the end and made of 0.3 mm-thick special wire (Remanium®). Each ring was placed under an initial tension in 5 ml organ baths with Krebs-Henseleit solution which was at 37° C., was gassed with carbogen and had the following composition: NaCl 119 mM; KCl 4.8 mM; $CaCl_2$)x2 $H_2O$ 1 mM; $MgSO_4$x7 $H_2O$ 1.4 mM; $KH_2PO_4$1.2 mM; $NaHCO_3$25 mM; glucose 10 mM; bovine serum albumin 0.001%. The force of contraction was detected with Statham UC2 cells, amplified and digitized via A/D converters (DAS-1802 HC, Keithley Instruments, Munich) and recorded in parallel on chart recorders. Contractions were induced by addition of phenylephrine.

After several (generally 4) control cycles, the substance to be investigated was added in each further run in increasing dosage, and the level of the contraction achieved under the influence of the test substance was compared with the level of the contraction reached in the last preceding run. The concentration necessary to reduce the contraction reached in the preceding control by 50% was calculated from this ($IC_{50}$). The standard application volume was 5 μl. The proportion of DMSO in the bath solution corresponded to 0.1%.

TABLE C1.1.1

Effects on % contraction of comparative example 11 in comparison to comparative example 1 (Cinaciguat) in ascending concentrations on PE-induced contraction of rabbit saphenous artery (incubation time 0.5 h vs. 2.5 h). Data are presented as mean +/− SEM (number)

| | $10^{-12}$ M/L | $10^{-11}$ M/L | $10^{-10}$ M/L | $10^{-9}$ M/L | $10^{-8}$ M/L | $10^{-7}$ M/L | $10^{-6}$ M/L | $10^{-5}$ M/L |
|---|---|---|---|---|---|---|---|---|
| comparative example 1 (Cinaciguat) 0.5 h | n.d. | 97 ± 1.2 (3) | 101 ± 1.7 (15) | 85 ± 4.2 (20) | 54 ± 5.2 (20) | 28 ± 4.2 (20) | 19 ± 6.1 (8) | n.d. |
| comparative example 1 (Cinaciguat) 2.5 h | n.d. | n.d. | 93 ± 2.6 (7) | 75 ± 4.6 (7) | 48 ± 6.0 (4) | 33 ± 5.8 (8) | n.d. | n.d. |
| comparative example 11 0.5 h | n.d. | 100 ± 1.5 (4) | 99 ± 3.4 (4) | 103 ± 3.5 (4) | 92 ± 3.0 (22) | 80 ± 4.6 (22) | 59 ± 4.9 (22) | 19 ± 3.0 (18) |
| comparative example 11 2.5 h | 98 ± 0 (1) | 91 ± 2.0 (2) | 67 ± 5.7 (12) | 47 ± 6.2 (13) | 29 ± 9.3 (10) | n.d. | n.d. | n.d. |

Compared to comparative example 1 (Cinaciguat), comparative example 11 inhibited concentration dependently phenylephrine induced contractions of rabbit saphenous artery rings with an $IC_{50}$ values of 911 nM (Cinaciguat $IC_{50}$ value of 17 nM) 30 min after incubation (see FIGS. 45*a* and 45*b*). After a longer preincubation period of 2.5 h, comparative example 11 was even more potent ($IC_{50}$ value of 0.8 nM) compared to Cinaciguat ($IC_{50}$ value of 3 nM). These results indicate a slower penetration of the saphenous artery by comparative example 11 compared to Cinaciguat. This would be indicative for minimization of unwanted systemic side effects, like e.g. systemic blood pressure decrease compared to the intended local vasodilatory effect in the lung which needs to be as potent as possible.

C-1.2. Isolated Perfused Heart According to Langendorff

Male Wistar rats (strain HsdCpb:WU) with a body weight of 200-250 g were anaesthetized with Narcoren® (100 mg/kg). The thorax was opened and the heart was then exposed, excised and connected to a Langendorff apparatus by placing a cannula into the aorta. The heart was perfused retrogradely at 9 ml/min at constant flow with a Krebs-Henseleit buffer solution (gassed with 95% $O_2$ and 5% $CO_2$, pH 7.4, 35° C.; composition in mmol/l: NaCl 118; KCl 3; $NaHCO_3$ 22; $KH_2PO_4$ 1.2; $MgSO_4$ 1.2; $CaCl_2$ 1.8; Glucose 10; Na pyruvate 2). A pressure transducer registered the perfusion pressure in the perfusion system. The left ventricular pressure (LVP) was measured using a second pressure transducer connected to a water-filled balloon which was inserted into the left ventricle via the left atrium. The end diastolic pressure was initially set to 8 mm Hg by adjusting the volume of the balloon. The hearts were spontaneously beating. The signals from the pressure transducer were amplified, registered by a personal computer (Powerlab Chart software, ADInstruments).

After an equilibration time of 40 min the test compounds were added to the perfusion solution for 20 min, which resulted in a drop of PP as a sign of coronary dilatation. Then the hearts were perfused for a further 120 min without the test substance (wash-out phase). The reversibility of the effect (wash-out score) was calculated as a percentage of the PP recovery after 60 min of washout related to the maximum drop of PP induced by the test compound. The wash-out score obtained in this manner was taken as a measure for the residence time of the test substance at the site of action.

In Langendorff-perfused rat heart comparative example 11 (300 nmol/l; n=6), comparative example 1 (Cinaciguat; 100 nmol/1; n=6), comparative example 2 (Riociguat; 100 nmol/l; n=6) and comparative example 3 (100 nmol/l; n=6) induced a pronounced reduction of perfusion pressure (PP) (FIG. 46). In hearts treated with comparative example 2 (Riociguat) the PP during the wash-out phase increased rapidly and reached the levels observed before the application of the compound. The wash-out score for Riociguat (comparative example 2) was 98%. In contrast the wash-out phase of comparative example 1 (Cinaciguat) was delayed resulting in a wash out score of 30%. The effects of comparative example 11 and comparative example 3 were even much less reversible. The wash-out score for comparative example 11 and comparative example 3 were 2.9% and 25.4%, respectively.

These results indicate that comparative example 11 and comparative example 3 showed prolonged vasodilatory activity and thereby tissue retention in Langendorff hearts compared to Riociguat. Comparative example 3 is comparable to Cinaciguat with a slightly lower wash out score, but comparative example 11 showed an even more prolonged tissue retention under wash out conditions.

TABLE C1.2.1

Effects of different compounds (300 nmol/l comparative example 11, 100 nmol/l Riociguat (comparative example 2), 100 nmol/l Cinaciguat (comparative example 1) and 100 nmol/l comparative example 3 on coronary flow of isolated Langendorff-perfused rat heart and their wash-out. Data are presented as mean +/− SEM (standard error of the mean).

| | Perfusion pressure (%) (timepoint at 20 min) | | | Perfusion pressure (%) (timepoint at 90 min) | | | Wash-out score (%) after |
|---|---|---|---|---|---|---|---|
| Compound | Mean | SEM | n | Mean | SEM | n | 60 min |
| Comparative example 11 | 69.0 | 3.62 | 6 | 71.9 | 2.09 | 6 | 2.9 |
| Cinaciguat (comparative example 1) | 62.1 | 3.90 | 7 | 69.3 | 5.20 | 7 | 29.5 |
| Riociguat (comparative example 2) | 55.4 | 2.47 | 6 | 99.9 | 1.76 | 6 | 98.0 |
| Comparative example 3 | 63.3 | 3.18 | 6 | 72.5 | 3.62 | 6 | 25.4 |

C-2 Inhalative Administration of sGC Activators in PAH Animal Models

Experiments were carried out in anesthetized Göttingen minipigs, anesthetized rats and conscious, telemetrically instrumented dogs. Acute pulmonary hypertension was induced for example by infusion of a thromboxane $A_2$ analogon, by acute hypoxia treatment or hypoxia treatment over a number of weeks and/or by administration of monocrotaline. Test substances were applied via nebulization using the Nebutec® or Aeroneb® Pro nebulizer system, and/or by means of powder and/or solution applicators for experimental intratracheal administration (Liquid MicroSprayer®, Dry Powder Insufflator™, MicroSprayer®, Penn-Century Inc., Wyndmoor, PA, USA) or after solid nebulization inserted into the inspiration arm of the ventilation. Compounds were employed as solids or solutions depending on the molecular structure and the technical possibility depending on the experiment. The haemodynamic signals were recorded and evaluated by means of pressure transducers/amplifiers (Combitransducer B. Braun, Melsungen, Germany or CardioMEMS Inc., Atlanta, GA, USA) and Ponemah® or CardioMems® as data aquisition software. After long-term experiments (for example monocrotaline rat), it is also possible to carry out a histological evaluation.

C-2.1 Haemodynamics in the Anesthetized Thromboxane Challenged Minipig

Lung Selectivity and Duration of Action

Healthy Gottingen Minipigs® Ellegaard (Ellegaard, Denmark) of both sexes and having a weight of 2-6 kg were used. The animals were sedated by i.m. administration of about 25 mg/kg ketamine and about 10 mg/kg azaperone. Anaesthesia was initiated by i.v. administration of about 2 mg/kg ketamine and about 0.3 mg/kg midazolam. Maintenance of anaesthesia was by i.v. administration of about 7.5-30 mg/kg/h ketamine and about 1-4 mg/kg/h midazolam (rate of infusion 1-4 ml/kg/h) and about 150 μg/kg/h pancuronium bromide (for example Pancuronium-Actavis). After intubation, the animals were ventilated by the ventilator at a constant respiratory volume (10-12 ml/kg, 35 breaths/min; Avea®, Viasys Healthcare, USA, or Engstrom Carestation, GE Healthcare, Freiburg, Germany) such that an end-tidal $CO_2$ concentration of about 5% was achieved. Ventilation was performed with room air, enriched with about 40% oxygen (normoxia). For the measurement of the haemodynamic parameters such as pulmonary arterial pressure (PAP), blood pressure (BP) and heart rate (HR), catheters were inserted into the carotid artery to measure the blood pressure, and a Swan-Ganz® catheter was introduced in a flow-directed manner via the jugular vein into the pulmonary artery. The haemodynamic signals were recorded and evaluated by means of pressure transducers (Combitransducer, B. Braun, Melsungen, Germany)/amplifiers and Ponemah® as data aquisition software.

After the instruments have been placed into the animals, continuous infusion of a thromboxane $A_2$ analog was initiated to increase the pulmonary arterial pressure. About 0.3-0.75 μg/kg/min of 9,11-didesoxy-9α,11α-epoxymethanoprostaglandine $F_{2\alpha}$ (U-44069; Sigma, cat. no. D0400, or Cayman Chemical Company, cat. no. 16440), dissolved in physiological saline, were infused to achieve an increase of the mean pulmonary arterial pressure to values of over 25 mmHg. 30 minutes after the start of the infusion, a plateau was reached, and the experiment was started.

The test substances were administered as i.v. infusion or by inhalation. For the preparation of the solution for inhalation, the following procedure was adopted: For an animal having a weight of 4 kg, to prepare the stock solution (300 μg/kg), 1.2 mg of the test compound were weighed out and dissolved in a total volume of 3 ml (1% DMSO, 99% 0.2% strength citric acid solution, 1 N aqueous sodium hydroxide solution to adjust the pH to 8). The solution was then diluted to the concentration employed using 0.2% strength citric acid which had been adjusted to pH 8 beforehand with aqueous sodium hydroxide solution. In each test, 3 ml of the solution of test compound per 4 kg animal were nebulized in the inhalation arm of the respiratory circuit using the Aeroneb® Pro nebulizer system. The mean nebulization time was about 7 min from the start of the nebulization.

TABLE C2.1.1

Effects of vehicle solution, comparative example 11 (30 μg/kg), comparative example 1 (Cinaciguat; 3 and 10 μg/kg), comparative example 2 (Riociguat; 100 μg/kg) and comparative example 3 (30 μg/kg) after inhaled application under thromboxane analog U46619 induced PAH in minipigs on % changes in BP vs baseline (5 min interval prior to start of nebulization).

| Time [min] vs. start inhalation | Vehicle | | | | Cinaciguat (comparative example 1) 3μg/kg | | Cinaciguat 10 μg/kg | | comparative example 11 30 μg/kg | | Riociguat (comparative example 2) 100 μg/kg | | comparative example 3 30 μg/kg | |
|---|---|---|---|---|---|---|---|---|---|---|---|---|---|---|
| −5 | 99 | 100 | 99 | 99 | 100 | 100 | 100 | 99 | 96 | 101 | 100 | 100 | 99 | 96 |
| 0 | 102 | 10 | 100 | 100 | 100 | 99 | 100 | 101 | 99 | 99 | 100 | 102 | 100 | 99 |
| 10 | 105 | 98 | 99 | 100 | 91 | 89 | 89 | 86 | 100 | 99 | 91 | 86 | 98 | 93 |
| 20 | 107 | 92 | 100 | 103 | 76 | 82 | 83 | 82 | 98 | 96 | 91 | 85 | 94 | 87 |
| 30 | 109 | 94 | 100 | 103 | 74 | 86 | 82 | 82 | 95 | 94 | 94 | 94 | 95 | 84 |
| 40 | 110 | 100 | 100 | 104 | 73 | 89 | 84 | 84 | 91 | 91 | | | 97 | 81 |
| 50 | 110 | 105 | 99 | 107 | 82 | 94 | 87 | 85 | 90 | 89 | | | 98 | 86 |
| 60 | 112 | 108 | 100 | 108 | 88 | 94 | 91 | 87 | 88 | 86 | | | 101 | 88 |
| 70 | 112 | 109 | 99 | 109 | 100 | 99 | 94 | 88 | 85 | 86 | | | 103 | 88 |
| 80 | 113 | 109 | 99 | 109 | 103 | 100 | 95 | 90 | 86 | 85 | | | 104 | 92 |
| 90 | 113 | 110 | 100 | 109 | 105 | 102 | 99 | 92 | 85 | 85 | | | 106 | 95 |
| 100 | 113 | 111 | 99 | 109 | | | | | 84 | 85 | | | 107 | 96 |
| 110 | 112 | 112 | 99 | 110 | | | | | 84 | 84 | | | 109 | 100 |
| 120 | 112 | 110 | 99 | 111 | | | | | 84 | 85 | | | 111 | 107 |
| 130 | 111 | 111 | 99 | 113 | | | | | 85 | 85 | | | 111 | 104 |
| 140 | 111 | 112 | 100 | 112 | | | | | 85 | 85 | | | 112 | 103 |
| 150 | 111 | 112 | 101 | 112 | | | | | 84 | 84 | | | 112 | 107 |
| 160 | 110 | 113 | 102 | 114 | | | | | 84 | 85 | | | 112 | 110 |
| 170 | 110 | 114 | 101 | 114 | | | | | 85 | 86 | | | 113 | 108 |
| 180 | 109 | 114 | 101 | 115 | | | | | 86 | 86 | | | 113 | 108 |
| 190 | 110 | 112 | 102 | 115 | | | | | 84 | 86 | | | 113 | 113 |
| 200 | 109 | 112 | 102 | 116 | | | | | 83 | 87 | | | 112 | 110 |
| 210 | 108 | 113 | 103 | 117 | | | | | 84 | 88 | | | 112 | 109 |
| 220 | 110 | 112 | 104 | 116 | | | | | 87 | 87 | | | 113 | 113 |
| 230 | 110 | 110 | 104 | 115 | | | | | 86 | 89 | | | 111 | 112 |
| 240 | 108 | 110 | 104 | 114 | | | | | 85 | 88 | | | 110 | 112 |

TABLE C2.1.2

Effects of vehicle solution, comparative example 11 (30 μg/kg), comparative example 1 (Cinaciguat; 3 and 10 μg/kg), comparative example 2 (Riociguat; 100 μg/kg) and comparative example 3 (30 μg/kg) after inhaled application under thromboxane analog U46619 induced PAH in minipigs on % changes in PAP vs baseline (5 min interval prior to start of nebulization).

| Time [min] vs. start inhalation | Vehicle | | | | Cinaciguat (comparative example 1) 3 μg/kg | | Cinaciguat (comparative example 1) 10 μg/kg | | comparative example 11 30 μg/kg | | Riociguat (comparative example 2) 100 μg/kg | | comparative example 3 30 μg/kg | |
|---|---|---|---|---|---|---|---|---|---|---|---|---|---|---|
| −5 | 100 | 100 | 100 | 99 | 100 | 100 | 100 | 100 | 99 | 99 | 99 | 101 | 99 | 99 |
| 0 | 98 | 99 | 102 | 100 | 99 | 99 | 100 | 101 | 99 | 100 | 99 | 99 | 100 | 99 |
| 10 | 101 | 100 | 100 | 100 | 101 | 100 | 100 | 100 | 99 | 102 | 95 | 92 | 103 | 99 |
| 20 | 102 | 101 | 102 | 102 | 99 | 98 | 96 | 100 | 97 | 101 | 94 | 90 | 103 | 97 |
| 30 | 106 | 98 | 104 | 100 | 98 | 98 | 94 | 100 | 97 | 101 | 94 | 90 | 104 | 98 |
| 40 | 104 | 97 | 102 | 99 | 97 | 98 | 95 | 98 | 97 | 100 | | | 105 | 95 |
| 50 | 104 | 95 | 103 | 99 | 97 | 98 | 94 | 96 | 96 | 102 | | | 106 | 95 |
| 60 | 106 | 93 | 102 | 99 | 97 | 99 | 95 | 94 | 96 | 101 | | | 108 | 94 |
| 70 | 108 | 93 | 102 | 99 | 97 | 100 | 93 | 94 | 95 | 103 | | | 108 | 93 |
| 80 | 106 | 92 | 102 | 100 | 95 | 98 | 94 | 92 | 94 | 101 | | | 110 | 96 |
| 90 | 109 | 94 | 100 | 99 | 95 | 99 | 93 | 89 | 94 | 102 | | | 110 | 94 |
| 100 | 109 | 92 | 99 | 99 | | | | | 92 | 103 | | | 111 | 93 |
| 110 | 110 | 92 | 96 | 98 | | | | | 94 | 102 | | | 111 | 93 |
| 120 | 110 | 92 | 97 | 98 | | | | | 92 | 101 | | | 112 | 95 |
| 130 | 110 | 91 | 96 | 99 | | | | | 95 | 102 | | | 112 | 92 |
| 140 | 111 | 92 | 97 | 100 | | | | | 95 | 101 | | | 113 | 93 |
| 150 | 111 | 90 | 96 | 99 | | | | | 92 | 100 | | | 113 | 93 |
| 160 | 113 | 89 | 93 | 100 | | | | | 91 | 100 | | | 112 | 92 |
| 170 | 114 | 91 | 96 | 98 | | | | | 91 | 101 | | | 110 | 92 |
| 180 | 113 | 86 | 95 | 98 | | | | | 91 | 101 | | | 112 | 93 |
| 190 | 115 | 88 | 94 | 96 | | | | | 91 | 101 | | | 111 | 93 |
| 200 | 114 | 89 | 93 | 94 | | | | | 90 | 101 | | | 110 | 93 |
| 210 | 113 | 86 | 93 | 93 | | | | | 91 | 101 | | | 109 | 93 |
| 220 | 114 | 87 | 93 | 89 | | | | | 92 | 99 | | | 109 | 96 |
| 230 | 113 | 88 | 92 | 85 | | | | | 91 | 102 | | | 109 | 94 |
| 240 | 113 | 85 | 92 | 79 | | | | | 92 | 99 | | | 109 | 94 |

In the PAH minipig model the effect of different compounds after inhaled application (nebulization) on PAP and BP was evaluated. Cinaciguat (comparative example 1) and Riociguat (comparative example 2) induced a sharp decrease in PAP with an early onset, a maximum effect between 10 and 30 min and a short duration of action of maximal 120 min. In contrast comparative example 11 showed a slower onset, a maximum of the effect on PAP around 60 min with a much longer duration of action for the complete observation interval of 240 min or even longer (see FIGS. 47 and 48). In addition, with respect to systemic BP, comparative example 11 did not show any decrease on systemic BP beside strong and long efficacy on PAP compared to Cinaciguat and Riociguat. Comparative example 3 showed good lung selectivity with respect to the hemodynamic effect but with much shorter duration of action with respect to the PAP decrease for only 120 min.

Figure 49:
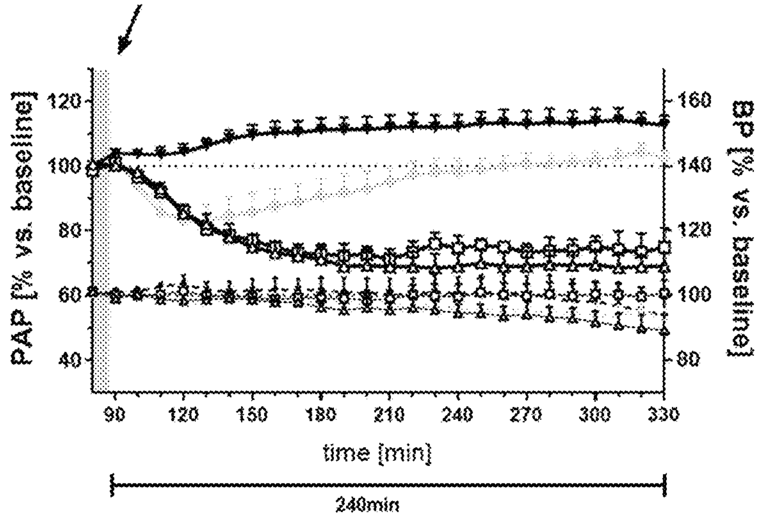

In further experiments comparative example 11 was compared to comparative example 4 and comparative example 5 (see FIG. 49). Again comparative example 5 showed only a moderate duration of action whereas comparative example 11 as well as comparative example 4 (all at a nominal dose of 100 μg/kg) showed a long duration of action of at least 4 hrs with good lung selectivity for all 3 compounds. Therefore comparative example 5 was deselected due to too short duration of action. Slight differences in BP especially at the end of the experiment between the three compounds might be influenced by long duration of anaesthesia.

TABLE C2.1.3

Effects of vehicle solution, comparative example 11, comparative example 4 and comparative example 5 (all compounds at 100 μg/kg nominal dose) after inhaled application under thromboxane analog U46619 induced PAH in minipigs on % changes in PAP and BP vs baseline (5 min interval prior to start of nebulization). Data are % changes for each individual animal.

| | Vehicle | | | | | | | |
|---|---|---|---|---|---|---|---|---|
| Time [min] | BP % change vs. baseline | | | | PAP % change vs. baseline | | | |
| 80 | 100.0 | 100.0 | 100.0 | 100.0 | 100.0 | 100.0 | 100.0 | 100.0 |
| 90 | 101.3 | 97.8 | 103.4 | 101.0 | 103.5 | 107.8 | 101.7 | 103.0 |
| 100 | 104.0 | 98.5 | 101.7 | 101.0 | 106.9 | 104.4 | 100.8 | 102.8 |
| 110 | 105.3 | 100.0 | 103.4 | 102.1 | 108.8 | 97.8 | 101.4 | 106.0 |
| 120 | 109.3 | 98.5 | 106.0 | 101.0 | 111.1 | 99.0 | 101.8 | 105.4 |
| 130 | 106.7 | 95.5 | 104.3 | 100.0 | 111.7 | 106.8 | 101.1 | 106.2 |
| 140 | 106.7 | 92.5 | 105.1 | 100.0 | 112.2 | 111.7 | 100.8 | 109.4 |
| 150 | 109.3 | 92.5 | 104.3 | 100.0 | 114.1 | 113.1 | 101.1 | 110.8 |
| 160 | 110.7 | 92.5 | 103.4 | 100.0 | 114.3 | 115.3 | 100.4 | 111.7 |
| 170 | 109.3 | 93.3 | 103.4 | 101.0 | 114.5 | 115.5 | 100.3 | 111.6 |
| 180 | 112.0 | 92.5 | 101.7 | 100.0 | 115.4 | 117.2 | 101.1 | 111.5 |
| 190 | 112.0 | 91.0 | 100.9 | 100.0 | 114.7 | 118.0 | 100.9 | 111.9 |
| 200 | 113.3 | 92.5 | 98.3 | 99.0 | 113.8 | 118.7 | 100.2 | 112.8 |
| 210 | 113.3 | 89.6 | 99.1 | 99.0 | 113.8 | 119.2 | 101.0 | 113.9 |
| 220 | 113.3 | 89.6 | 98.3 | 100.0 | 113.2 | 118.7 | 101.0 | 116.1 |
| 230 | 114.7 | 89.6 | 99.1 | 101.0 | 113.0 | 118.9 | 101.2 | 115.0 |
| 240 | 114.7 | 89.6 | 97.4 | 100.0 | 112.7 | 119.2 | 102.1 | 115.1 |
| 250 | 116.0 | 91.0 | 94.9 | 101.0 | 112.4 | 119.9 | 104.1 | 116.8 |
| 260 | 117.3 | 89.6 | 97.4 | 99.0 | 112.3 | 121.4 | 102.7 | 117.4 |
| 270 | 116.0 | 89.6 | 96.6 | 99.0 | 110.5 | 120.6 | 102.7 | 118.1 |
| 280 | 118.7 | 86.6 | 95.7 | 96.9 | 111.5 | 121.4 | 103.2 | 118.4 |
| 290 | 117.3 | 85.1 | 94.9 | 94.8 | 110.9 | 119.4 | 103.9 | 119.1 |
| 300 | 116.0 | 88.1 | 94.9 | 93.8 | 109.9 | 119.9 | 104.9 | 120.4 |
| 310 | 117.3 | 85.1 | 94.9 | 89.7 | 111.8 | 121.1 | 105.2 | 119.0 |
| 320 | 116.0 | 85.8 | 94.0 | 85.6 | 111.8 | 118.4 | 105.2 | 118.3 |
| 330 | 116.0 | 85.8 | 94.0 | 79.4 | 110.3 | 118.0 | 105.8 | 117.0 |

| | Comparative Example 5 | | | | | |
|---|---|---|---|---|---|---|
| Time [min] | BP % change vs. baseline | | | PAP % change vs. baseline | | |
| 80 | 100.0 | 100.0 | 100.0 | 100.0 | 100.0 | 100.0 |
| 90 | 100.0 | 100.0 | 100.0 | 101.5 | 99.2 | 102.0 |
| 100 | 99.1 | 97.7 | 101.8 | 98.0 | 90.0 | 93.8 |
| 110 | 99.1 | 97.7 | 100.0 | 91.7 | 86.4 | 79.0 |
| 120 | 99.1 | 96.6 | 97.3 | 90.0 | 86.1 | 73.7 |
| 130 | 98.1 | 97.7 | 97.3 | 87.6 | 88.6 | 72.9 |
| 140 | 98.1 | 98.9 | 97.3 | 87.1 | 93.0 | 73.7 |
| 150 | 95.3 | 100.0 | 97.3 | 87.6 | 95.0 | 75.1 |
| 160 | 96.2 | 101.1 | 98.2 | 88.7 | 96.4 | 77.8 |
| 170 | 95.3 | 101.1 | 96.4 | 89.8 | 97.8 | 79.2 |
| 180 | 95.3 | 101.1 | 97.3 | 90.0 | 100.6 | 81.5 |
| 190 | 94.3 | 102.3 | 96.4 | 90.9 | 101.9 | 81.9 |
| 200 | 92.5 | 103.4 | 95.5 | 91.4 | 102.8 | 85.2 |
| 210 | 91.5 | 102.3 | 96.4 | 92.7 | 104.2 | 88.1 |
| 220 | 91.5 | 103.4 | 96.4 | 94.5 | 105.8 | 91.3 |
| 230 | 91.5 | 103.4 | 94.6 | 95.1 | 106.1 | 93.1 |
| 240 | 90.6 | 102.3 | 94.6 | 95.5 | 105.8 | 92.9 |
| 250 | 90.6 | 102.3 | 94.6 | 96.5 | 105.8 | 94.3 |
| 260 | 89.6 | 101.1 | 93.8 | 98.1 | 106.4 | 95.5 |
| 270 | 90.6 | 103.4 | 93.8 | 98.6 | 107.5 | 95.9 |

TABLE C2.1.3-continued

Effects of vehicle solution, comparative example 11, comparative example 4 and comparative example 5 (all compounds at 100 μg/kg nominal dose) after inhaled application under thromboxane analog U46619 induced PAH in minipigs on % changes in PAP and BP vs baseline (5 min interval prior to start of nebulization). Data are % changes for each individual animal.

| | | | | | | |
|---|---|---|---|---|---|---|
| 280 | 89.6 | 100.0 | 93.8 | 98.6 | 106.4 | 97.2 |
| 290 | 88.7 | 102.3 | 92.9 | 99.6 | 105.8 | 98.4 |
| 300 | 89.6 | 100.0 | 92.0 | 100.1 | 107.0 | 98.6 |
| 310 | 89.6 | 100.0 | 91.1 | 101.7 | 107.5 | 99.6 |
| 320 | 89.6 | 105.7 | 91.1 | 102.8 | 109.5 | 100.1 |
| 330 | 89.6 | 98.9 | 89.3 | 102.9 | 106.1 | 99.3 |

| | Comparative example 11 | | | | | | Comparative Example 4 | | | | | |
|---|---|---|---|---|---|---|---|---|---|---|---|---|
| Time [min] | BP % change vs. baseline | | | PAP % change vs. baseline | | | BP % change vs. baseline | | | PAP % change vs. baseline | | |
| 80 | 103.2 | 100.0 | 100.1 | 103.3 | 100.0 | 98.5 | 101.1 | 101.2 | 101.0 | 102.0 | 96.2 | 97.5 |
| 90 | 98.8 | 98.2 | 100.1 | 98.8 | 102.2 | 99.6 | 98.7 | 100.3 | 101.0 | 100.2 | 102.2 | 100.2 |
| 100 | 101.0 | 100.0 | 100.1 | 99.4 | 97.3 | 97.5 | 101.1 | 100.3 | 98.3 | 100.0 | 93.1 | 96.4 |
| 110 | 98.8 | 99.1 | 98.2 | 94.0 | 90.4 | 94.4 | 99.9 | 102.2 | 98.3 | 97.2 | 88.9 | 89.8 |
| 120 | 98.8 | 98.2 | 98.2 | 87.4 | 80.2 | 88.8 | 101.1 | 101.2 | 101.9 | 86.5 | 86.2 | 86.0 |
| 130 | 98.8 | 98.2 | 99.2 | 84.3 | 75.6 | 86.1 | 99.9 | 99.4 | 100.1 | 77.5 | 78.6 | 84.6 |
| 140 | 98.8 | 96.5 | 102.0 | 82.2 | 69.4 | 82.1 | 99.9 | 99.4 | 100.1 | 76.3 | 77.7 | 81.3 |
| 150 | 97.7 | 95.6 | 103.0 | 80.0 | 67.4 | 77.3 | 99.9 | 98.5 | 100.1 | 77.3 | 75.0 | 78.7 |
| 160 | 98.8 | 93.9 | 101.1 | 78.2 | 66.2 | 74.6 | 99.9 | 96.7 | 99.2 | 75.5 | 71.4 | 77.3 |
| 170 | 98.8 | 95.6 | 99.2 | 78.1 | 65.9 | 72.4 | 101.1 | 97.6 | 99.2 | 72.1 | 71.9 | 75.1 |
| 180 | 97.7 | 92.1 | 99.2 | 78.5 | 62.7 | 72.2 | 102.3 | 95.8 | 99.2 | 74.0 | 68.0 | 75.9 |
| 190 | 98.8 | 91.2 | 96.3 | 77.0 | 61.7 | 68.1 | 102.3 | 95.8 | 99.2 | 74.5 | 65.0 | 77.1 |
| 200 | 99.9 | 90.4 | 98.2 | 77.0 | 62.5 | 68.2 | 102.3 | 94.0 | 99.2 | 70.1 | 70.6 | 77.2 |
| 210 | 98.8 | 90.4 | 97.3 | 76.5 | 62.0 | 67.9 | 103.5 | 94.0 | 99.2 | 70.8 | 65.6 | 76.8 |
| 220 | 101.0 | 90.4 | 97.3 | 77.2 | 61.2 | 68.1 | 105.9 | 95.8 | 98.3 | 77.8 | 66.7 | 75.3 |
| 230 | 99.9 | 90.4 | 96.3 | 76.3 | 61.2 | 67.7 | 107.1 | 94.9 | 97.4 | 82.5 | 71.3 | 73.9 |
| 240 | 98.8 | 89.5 | 95.4 | 76.5 | 62.5 | 67.8 | 107.1 | 94.0 | 97.4 | 81.0 | 67.4 | 75.0 |
| 250 | 98.8 | 89.5 | 95.4 | 77.6 | 63.0 | 69.1 | 109.4 | 94.9 | 98.3 | 79.0 | 72.2 | 75.0 |
| 260 | 97.7 | 87.7 | 95.4 | 77.4 | 62.0 | 67.4 | 107.1 | 94.9 | 98.3 | 75.0 | 72.7 | 76.7 |
| 270 | 96.6 | 86.8 | 99.2 | 77.5 | 61.5 | 67.9 | 107.1 | 94.9 | 97.4 | 70.3 | 71.1 | 78.4 |
| 280 | 96.6 | 86.8 | 96.3 | 77.5 | 63.0 | 68.1 | 107.1 | 94.9 | 99.2 | 65.8 | 75.6 | 79.7 |
| 290 | 97.7 | 86.8 | 94.4 | 77.3 | 62.5 | 67.8 | 107.1 | 94.0 | 98.3 | 68.3 | 73.4 | 79.9 |
| 300 | 96.6 | 85.1 | 93.4 | 78.1 | 63.0 | 67.3 | 107.1 | 94.9 | 99.2 | 69.1 | 76.2 | 79.6 |
| 310 | 95.5 | 83.3 | 93.4 | 76.7 | 60.5 | 68.1 | 107.1 | 94.9 | 98.3 | 62.8 | 79.9 | 79.5 |
| 320 | 95.5 | 81.6 | 92.5 | 75.6 | 63.2 | 67.7 | 104.7 | 94.9 | 99.2 | 61.8 | 76.5 | 81.3 |
| 330 | 95.5 | 79.8 | 92.5 | 76.5 | 63.0 | 67.6 | 107.1 | 94.0 | 101.0 | 63.1 | 77.9 | 83.3 |

Prediction of Duration of the Effect in Humans

With respect to a prediction of the duration of action for human studies comparative example 11 was compared in the PAH minipig model after inhaled application to Ventavis® (=Iloprost, 10 μg/kg nominal dose), which we used as a clinical reference. Ventavis® had a maximal duration of action of about 40 min. All doses of comparative example 11 showed dose dependent efficacy during the whole 240 min observation interval (see FIG. 50). Therefore the duration of action is more than 6 times longer compared to Ventavis in this preclinical animal model. In clinical studies Ventavis showed a duration of action on haemodynamics (PVR) of about 60 min (Ref: Favorable Effects of Inhaled Treprostinil in Severe Pulmonary Hypertension Results From Randomized Controlled Pilot Studies Robert Voswinckel, MD,* Beate Enke, MD,* Frank Reichenberger, MD,* Markus Kohstall, MD,*Andree Kreckel, MD,* Stefanie Krick, MD,* Henning Gall, MD,* Tobias Gessler, MD, PHD, *Thomas Schmehl, PHD,* Hossein A. Ghofrani, MD,* Ralph Theo Schermuly, PHD,*Friedrich Grimminger, MD, PHD,* Lewis J. Rubin, MD,† Werner Seeger, MD,* Horst Olschewski, MD*‡ Journal of the American College of Cardiology Vol. 48, No. 8, 2006) which is in good correlation of our observed duration of action of about 40 min.

Under the assumption that the duration of action for comparative example 11 is comparable between the PAH minipig model and humans, as similarly shown and described for Ventavis, the duration of action of comparative example 11 in humans is supposed to be at least 6 hours or even longer.

TABLE C.2.1.4

Effects of vehicle solution, comparative example 11 (10, 30 and 100 μg/kg nominal dose) and Ventavis (10 μg/kg nominal dose) after inhaled application in the PAH minipigs model. % changes in PAP vs baseline (10 min interval prior to start of nebulization). Data are mean ± SD. PAP % changes vs prevalue

| | Vehicle n = 4 | | Ventavis ® n = 3 | | Comparative example 11 10 μg/kg n = 3 | | Comparative example 11 30 μg/kg n = 3 | | Comparative example 11 100 μg/kg n = 3 | |
|---|---|---|---|---|---|---|---|---|---|---|
| Time | mean | SD | mean | SD | mean | SD | Mean | SD | mean | SD |
| 0 | 0 | 0 | 0 | 0 | 0 | 0 | 0 | 0 | 0 | 0 |
| 10 | −0.2 | 2.7 | −30.3 | 9.0 | 0.6 | 0.5 | 0.3 | 0.6 | −2.1 | 2.7 |
| 20 | −0.4 | 6.3 | −20.7 | 21.6 | 0.2 | 0.3 | −2.0 | 1.0 | −7.2 | 3.8 |
| 30 | 0.5 | 6.5 | −6.9 | 13.5 | −0.7 | 0.4 | −4.6 | 0.8 | −14.6 | 6.0 |
| 40 | 2.4 | 4.1 | 1.7 | 2.9 | −1.5 | 2.2 | −7.8 | 0.9 | −18.1 | 6.9 |
| 50 | 4.3 | 4.0 | 4.9 | 0.9 | −2.3 | 2.7 | −9.8 | 0.6 | −22.2 | 8.6 |
| 60 | 5.6 | 4.6 | | | −3.5 | 3.3 | −11.8 | 1.0 | −25.1 | 7.9 |
| 70 | 6.2 | 5.2 | | | −4.2 | 3.2 | −14.1 | 0.7 | −27.0 | 7.4 |
| 80 | 6.2 | 5.2 | | | −3.7 | 4.2 | −14.2 | 0.7 | −27.9 | 7.3 |
| 90 | 7.0 | 5.3 | | | −4.3 | 4.6 | −14.4 | 0.2 | −28.9 | 9.1 |
| 100 | 7.0 | 5.3 | | | −5.3 | 4.9 | −14.8 | 0.3 | −31.1 | 8.8 |
| 110 | 7.0 | 5.7 | | | −6.2 | 4.9 | −15.3 | 0.3 | −30.8 | 8.4 |
| 120 | 7.6 | 5.5 | | | −6.7 | 5.4 | −15.3 | 1.0 | −31.3 | 8.4 |
| 130 | 7.9 | 5.9 | | | −6.2 | 4.9 | −15.5 | 1.9 | −31.2 | 9.1 |
| 140 | 7.7 | 5.5 | | | −7 | 5.0 | −15.3 | 2.2 | −31.6 | 8.7 |
| 150 | 7.9 | 5.1 | | | −7.6 | 5.3 | −16.3 | 1.7 | −31.1 | 8.2 |
| 160 | 8.9 | 4.8 | | | −7.6 | 6.1 | −16.3 | 2.3 | −30.1 | 8.5 |
| 170 | 9 | 5.8 | | | −8.2 | 5.9 | −14.9 | 2.1 | −31.1 | 8.9 |
| 180 | 8.6 | 6.0 | | | −8.0 | 4.4 | −14.7 | 2.1 | −31.1 | 9.2 |
| 190 | 9.2 | 6.0 | | | −7.8 | 4.7 | −15.1 | 2.1 | −30.5 | 8.5 |
| 200 | 8.9 | 5.7 | | | −7.3 | 3.6 | −15.3 | 2.6 | −30.9 | 8.6 |
| 210 | 9.4 | 6.0 | | | −7.5 | 4.5 | −13.8 | 2.3 | −30.6 | 8.9 |
| 220 | 9.9 | 5.3 | | | −7.2 | 3.7 | −13.6 | 2.2 | −31.6 | 9.2 |
| 230 | 9.1 | 4.7 | | | −7.2 | 3.4 | −12.8 | 2.4 | −31.2 | 7.4 |
| 240 | 8.4 | 4.1 | | | −7.6 | 2.7 | −13.4 | 1.9 | −31.0 | 8.0 |

Prediction of Human Dose

In order to generate a human dose estimate, experiments in the PAH minipig model for comparative example 11 were repeated with the difference that absorbing filters were attached at the end of the tubes to determine the deposited lung dose. Nebulization of comparative example 11 resulted in a nebulization efficiency of 3-6% of nominally applied doses. The arithmetic mean of the aerosol fraction deposited on the filters is 5% based on all results of the filter experiments, resulting in relative lung deposited doses of about 0.15 μg/kg (3 μg/kg nominal dose), 0.5 μg/kg (10 μg/kg nominal dose), 1.5 μg/kg (30 μg/kg nominal dose) and 5 μg/kg (100 μg/kg nominal dose). Assuming a minimal effective nominal dose of 3 μg/kg for a 5% reduction in PAP and a mean nebulization efficiency of 5%, the minimal effective deposited lung dose is considered as 0.15 μg/kg based on the PAH minipig model. Therefore, for a human patient of 60 kg body weight a minimal effective lung deposited dose of 9-41 μg, depending on whether or not an effect of different protein binding (see table 2.1.5) is postulated. Considering 100 μg/kg as effective dose in the minipig model, 300-1370 μg lung deposited dose is postulated as effective dose, again depending on the consideration of different interspecies protein binding.

TABLE C2.1.5.

Effective lung dose with and without consideration of interspecies differences in protein binding

| | Total lung deposited dose in a 60 kg human [μg] | |
|---|---|---|
| Relative lung deposited dose in minipig [μg/kg] | Interspecies difference in protein binding not considered[a] | Interspecies difference in protein binding considered[b] |
| 0.15 μg/kg (3 μg/kg nominal dose) | 9 | 41 |
| 0.50 μg/kg (10 μg/kg nominal dose) | 30 | 137 |
| 1.5 μg/kg (30 μg/kg nominal dose) | 90 | 410 |
| 5.0 μg/kg (100 μg/kg nominal dose) | 300 | 1370 |

[a]Calculation (relative lung deposited dose in minipig × 60 kg)
[b]Calculation (relative lung deposited dose in minipig × 60 kg × 4.55 (ratio of fraction unbound minipig (plasma fu 0.348%)/human (plasma fu 0.0764%))

Effects Under Conditions of Oxidative Stress

To simulate conditions of oxidative stress or low NO concentrations as assumed to be present in different cardiovascular disorders, comparative example 11 was evaluated with and without pretreatment by ODQ (inhibitor of sGC) or L-NAME (NOS inhibitor). Under PAH conditions, comparative example 11 (30 μg/kg ND) showed a selective decrease on PAP without any effects on BP (see FIGS. 51 and 52). Pretreatment of ODQ or L-NAME resulted in an enhanced decrease of PAP without effects on systemic BP by comparative example 11. In contrast, the effects of Ventavis® under conditions of oxidative stress or low NO concentrations were not enhanced. In addition, also under these pathophysiological conditions the duration of action of comparative example 11 was much longer compared to Ventavis®.

TABLE C2.1.6

Effects of Ventavis ® (10 μg/kg nominal dose), vehicle solution and comparative example 11 (30 μg/kg nominal dose) and after inhaled application in the PAH minipigs model. Data are shown as absolute numbers for each animal.

| | Animals without pretreatment | | | | | | Animals with L-NAME pretreatment | | | | | |
|---|---|---|---|---|---|---|---|---|---|---|---|---|
| Time | PAP | | | BP | | | PAP | | | BP | | |
| 50 | 37.2 | 36.0 | 37.3 | 105.0 | 106.0 | 110.0 | 36.5 | 37.8 | 40.3 | 103.0 | 130.0 | 115.0 |
| 60 | 37.5 | 36.8 | 38.6 | 103.0 | 106.0 | 110.0 | 40.7 | 38.7 | 40.2 | 104.0 | 127.0 | 115.0 |
| 70 | 26.1 | 28.2 | 29.6 | 107.0 | 109.0 | 116.0 | 31.7 | 27.4 | 28.7 | 105.0 | 133.0 | 125.0 |
| 80 | 34.7 | 36.7 | 37.4 | 102.0 | 110.0 | 113.0 | 41.2 | 33.5 | 29.7 | 106.0 | 131.0 | 123.0 |
| 90 | 38.9 | 38.9 | 41.2 | 99.0 | 109.0 | 111.0 | 42.2 | 37.9 | 32.1 | 102.0 | 124.0 | 121.0 |
| 100 | 37.9 | 39.2 | 41.9 | 98.0 | 106.0 | 108.0 | 41.5 | 39.6 | 38.9 | 101.0 | 124.0 | 117.0 |
| 110 | 38.4 | 39.5 | 42.2 | 95.0 | 105.0 | 106.0 | 41.5 | 41.0 | 41.0 | 101.0 | 125.0 | 114.0 |
| 120 | 39.4 | 39.9 | 42.1 | 95.0 | 106.0 | 107.0 | 41.5 | 40.7 | 43.4 | 101.0 | 126.0 | 114.0 |
| 130 | 39.3 | 39.3 | 42.1 | 94.0 | 105.0 | 107.0 | 41.0 | 40.3 | 40.7 | 100.0 | 128.0 | 116.0 |
| 140 | 39.0 | 39.9 | 42.4 | 92.0 | 106.0 | 106.0 | 41.2 | 41.3 | 41.7 | 102.0 | 129.0 | 116.0 |
| 150 | 40.2 | 39.3 | 43.3 | 92.0 | 107.0 | 107.0 | 42.1 | 41.2 | 41.1 | 102.0 | 128.0 | 114.0 |
| 160 | 40.6 | 39.2 | 43.3 | 92.0 | 109.0 | 108.0 | 41.0 | 41.0 | 39.8 | 102.0 | 130.0 | 119.0 |
| 170 | 39.7 | 38.0 | 42.6 | 90.0 | 108.0 | 108.0 | 39.5 | 36.2 | 34.6 | 103.0 | 135.0 | 123.0 |
| 180 | 38.5 | 37.1 | 41.5 | 90.0 | 108.0 | 108.0 | 38.9 | 29.1 | 30.8 | 104.0 | 139.0 | 127.0 |
| 190 | 37.0 | 35.9 | 40.3 | 90.0 | 107.0 | 108.0 | 38.0 | 25.9 | 28.4 | 104.0 | 137.0 | 127.0 |
| 200 | 36.5 | 35.2 | 39.0 | 89.0 | 109.0 | 109.0 | 36.8 | 24.6 | 28.1 | 104.0 | 135.0 | 129.0 |
| 210 | 35.6 | 34.2 | 38.5 | 89.0 | 108.0 | 109.0 | 36.5 | 23.9 | 26.6 | 105.0 | 133.0 | 127.0 |
| 220 | 34.7 | 33.9 | 36.8 | 88.0 | 110.0 | 108.0 | 36.6 | 23.8 | 25.5 | 107.0 | 131.0 | 127.0 |
| 230 | 34.8 | 33.4 | 37.1 | 87.0 | 108.0 | 108.0 | 35.5 | 23.6 | 25.6 | 108.0 | 127.0 | 129.0 |
| 240 | 34.5 | 33.6 | 37.0 | 87.0 | 109.0 | 108.0 | 35.0 | 24.0 | 25.0 | 106.0 | 128.0 | 128.0 |
| 250 | 34.3 | 33.5 | 36.7 | 86.0 | 110.0 | 109.0 | 34.5 | 23.5 | 24.8 | 106.0 | 126.0 | 130.0 |
| 260 | 34.1 | 33.3 | 36.5 | 87.0 | 109.0 | 110.0 | 34.6 | 24.2 | 24.7 | 107.0 | 126.0 | 130.0 |
| 270 | 34.0 | 33.6 | 36.2 | 86.0 | 108.0 | 110.0 | 34.1 | 24.0 | 24.3 | 104.0 | 126.0 | 129.0 |
| 280 | 34.5 | 33.5 | 35.6 | 88.0 | 109.0 | 109.0 | 33.4 | 23.7 | 24.4 | 103.0 | 125.0 | 129.0 |
| 290 | 34.7 | 33.6 | 35.5 | 88.0 | 108.0 | 110.0 | 34.4 | 23.4 | 24.2 | 104.0 | 126.0 | 128.0 |
| 300 | 34.1 | 33.2 | 35.4 | 86.0 | 107.0 | 111.0 | 34.2 | 24.1 | 24.0 | 105.0 | 125.0 | 127.0 |
| 310 | 34.0 | 33.6 | 35.1 | 85.0 | 107.0 | 109.0 | 33.3 | 23.6 | 24.3 | 103.0 | 125.0 | 128.0 |
| 320 | 34.5 | 34.0 | 35.8 | 85.0 | 108.0 | 109.0 | 33.8 | 23.1 | 24.0 | 104.0 | 125.0 | 126.0 |
| 330 | 34.8 | 34.0 | 35.9 | 85.0 | 108.0 | 109.0 | 34.1 | 22.8 | 23.9 | 105.0 | 126.0 | 125.0 |
| 340 | 34.3 | 34.1 | 35.8 | 85.0 | 108.0 | 109.0 | 33.7 | 23.4 | 24.1 | 104.0 | 126.0 | 125.0 |
| 350 | 33.8 | 34.4 | 35.7 | 84.0 | 108.0 | 109.0 | 33.7 | 23.7 | 23.8 | 103.0 | 126.0 | 123.0 |
| 360 | 34.3 | 34.9 | 36.6 | 85.0 | 108.0 | 112.0 | 34.0 | 25.3 | 23.9 | 103.0 | 124.0 | 122.0 |
| 370 | 35.2 | 34.5 | 36.3 | 86.0 | 106.0 | 113.0 | 34.0 | 22.3 | 24.0 | 105.0 | 122.0 | 122.0 |
| 380 | 35.1 | 35.2 | 36.6 | 85.0 | 109.0 | 113.0 | 34.8 | 24.0 | 24.0 | 101.0 | 124.0 | 122.0 |
| 390 | 34.7 | 34.8 | 36.7 | 86.0 | 106.0 | 112.0 | 35.0 | 25.9 | 25.2 | 106.0 | 125.0 | 124.0 |

| | Animals with ODQ pretreatment | | | | | |
|---|---|---|---|---|---|---|
| Time | PAP | | | BP | | |
| 50 | 37.5 | 38.2 | 39.8 | 98.0 | 107.0 | 85.0 |
| 60 | 37.6 | 39.8 | 37.7 | 95.0 | 107.0 | 89.0 |
| 70 | 33.6 | 26.4 | 25.9 | 97.0 | 103.0 | 92.0 |
| 80 | 37.4 | 32.8 | 32.1 | 98.0 | 105.0 | 92.0 |
| 90 | 38.5 | 37.5 | 38.2 | 100.0 | 104.0 | 92.0 |
| 100 | 38.8 | 40.6 | 39.2 | 101.0 | 104.0 | 93.0 |
| 110 | 39.3 | 39.5 | 40.0 | 103.0 | 103.0 | 94.0 |
| 120 | 38.2 | 40.6 | 39.6 | 104.0 | 102.0 | 95.0 |
| 130 | 38.1 | 38.3 | 38.9 | 103.0 | 101.0 | 95.0 |
| 140 | 38.5 | 40.4 | 40.2 | 104.0 | 100.0 | 94.0 |
| 150 | 38.8 | 39.6 | 40.2 | 107.0 | 100.0 | 94.0 |
| 160 | 39.6 | 40.1 | 40.9 | 109.0 | 100.0 | 94.0 |
| 170 | 37.2 | 35.4 | 38.0 | 108.0 | 99.0 | 95.0 |
| 180 | 35.2 | 34.5 | 36.6 | 108.0 | 99.0 | 96.0 |
| 190 | 33.8 | 31.5 | 32.3 | 107.0 | 100.0 | 96.0 |
| 200 | 32.1 | 30.6 | 30.2 | 107.0 | 101.0 | 95.0 |
| 210 | 31.0 | 28.4 | 31.6 | 106.0 | 99.0 | 97.0 |
| 220 | 31.4 | 27.5 | 31.1 | 106.0 | 98.0 | 97.0 |
| 230 | 29.9 | 26.3 | 31.7 | 106.0 | 97.0 | 98.0 |
| 240 | 30.6 | 25.0 | 30.7 | 106.0 | 96.0 | 98.0 |
| 250 | 29.4 | 25.6 | 31.4 | 107.0 | 96.0 | 100.0 |
| 260 | 30.1 | 24.0 | 29.3 | 109.0 | 95.0 | 97.0 |
| 270 | 29.4 | 23.7 | 31.4 | 107.0 | 95.0 | 98.0 |
| 280 | 29.6 | 22.8 | 30.8 | 109.0 | 92.0 | 99.0 |
| 290 | 29.5 | 23.2 | 33.0 | 109.0 | 91.0 | 96.0 |
| 300 | 29.3 | 22.3 | 30.6 | 105.0 | 89.0 | 101.0 |

TABLE C2.1.6-continued

Effects of Ventavis ® (10 μg/kg nominal dose), vehicle solution and comparative example 11 (30 μg/kg nominal dose) and after inhaled application in the PAH minipigs model. Data are shown as absolute numbers for each animal.

| | | | | | | |
|---|---|---|---|---|---|---|
| 310 | 29.6 | 22.9 | 32.4 | 105.0 | 89.0 | 102.0 |
| 320 | 29.5 | 21.4 | 31.7 | 104.0 | 86.0 | 101.0 |
| 330 | 29.3 | 23.4 | 32.0 | 105.0 | 85.0 | 101.0 |
| 340 | 30.7 | 21.8 | 32.4 | 108.0 | 83.0 | 100.0 |
| 350 | 30.8 | 22.8 | 32.3 | 108.0 | 83.0 | 100.0 |
| 360 | 31.4 | 21.0 | 32.7 | 108.0 | 80.0 | 100.0 |
| 370 | 31.7 | 22.6 | 30.6 | 109.0 | 82.0 | 98.0 |
| 380 | 31.6 | 21.3 | 31.9 | 109.0 | 80.0 | 97.0 |
| 390 | 32.1 | 22.2 | 31.4 | 109.0 | 79.0 | 97.0 |

Effects Compared to Standard of Care (SoC) in PAH

Figure 53A:
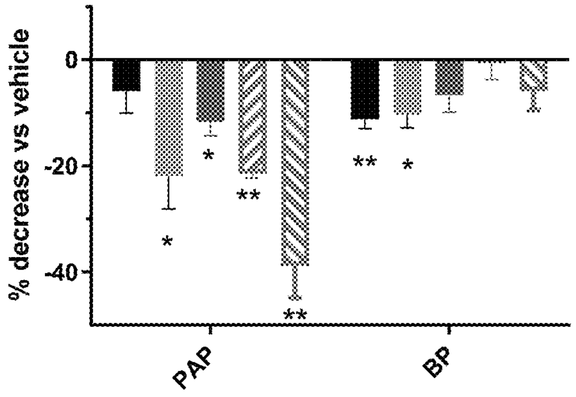

Efficacy of inhaled comparative example 11 was compared with systemically applied bosentan, sildenafil and riociguat (see FIG. 53*a*) in the PAH minipig model. Bosentan led to a decrease in BP with only minor effects on PAP, whereas infusion of sildenafil and riociguat led to decreases in both PAP and BP. Inhaled comparative example 11 led to similar (30 μg/kg) or even larger (100 μg/kg) effects on PAP with no or minor effects on BP.

Therefore inhaled application of comparative example 11 offers clear benefits as systemic effects are avoided, compared to standard of care. Comparative example 11 (30 μg/kg) maintained its efficacy regarding PAP when combined with either bosentan, sildenafil or riociguat compared with comparative example 11 treatment alone without additional effects on BP (see FIG. 53*b*).

TABLE C2.1.7.A

Effects on % decrease in PAP and BP of comparative example 11 (30 and 100 μg/kg nominal dose) after inhaled application compared to systemically applied bosentan (1 mg/kg), sildenafil (300 μg/kg/h) and riociguat (3 μg/kg/h) under thromboxane analog U46619 induced PAH in minipigs. Data are % changes for respective animals

| | PAP decrease % | | | | BP decrease % | | | |
|---|---|---|---|---|---|---|---|---|
| Bosentan 1 mg/kg | −3.7 | 3.9 | −7.7 | −16.0 | −6.7 | −15.0 | −10.3 | −12.7 |
| Sildenafil 300 μg/kg/h | −15.3 | −34.3 | −16.1 | | −10.6 | −6.1 | −14.5 | |
| Riociguat 3 μg/kg/h | −9.1 | −9.1 | −16.8 | | −0.3 | −8.8 | −10.9 | |
| Comparative example 11 30 μg/kg | −19.9 | −22.8 | −21.7 | | −6.8 | 1.6 | 3.5 | |
| Comparative example 11 100 μg/kg | −33.1 | −45.1 | −38.2 | | −4.5 | −9.9 | −3.1 | |

TABLE C2.1.7.B

Effects on % decrease in PAP and BP of comparative example 11 (30 μg/kg nominal dose) after inhaled application alone or on top of systemically applied bosentan (1 mg/kg), sildenafil (300 μg/kg/h) and riociguat (3 μg/kg/h) under thromboxane analog U46619 induced PAH in minipigs. Data are % changes for respective animals.

| | PAP decrease % | | | BP decrease % | | |
|---|---|---|---|---|---|---|
| Comparative example 11 30 μg/kg on top of Bosentan 1 mg/kg | −29.7 | −27.1 | | −12.8 | 3.6 | |
| Comparative example 11 30 μg/kg on top of Sildenafil 300 μg/kg/h | −33.6 | −36.9 | −42.8 | −6.9 | −6.4 | 1.2 |
| Comparative example 11 30 μg/kg on top of Riociguat 3 μg/kg/h | −29.7 | −24.2 | −26.3 | 3.1 | −1.1 | 11.5 |
| Comparative example 11 30 μg/kg | −19.9 | −22.8 | −21.7 | −6.8 | 1.6 | 3.5 |

Effects of Dry Powder Formulations

After characterization of the effects of comparative example 11 after nebulization of compound solutions, in a further step the effects of crystalline forms of comparative example 11, e.g. sesquihydrate, e.g. example 6e on PAP and BP after inhaled application of different dry powder lactose formulations (table C2.1.8) were studied in anesthetized PAH minipigs.

TABLE C2.1.8

Dry powder formulations of crystalline forms of comparative example 11, e.g. sesquihydrate, e.g. example 6e applied in minipig experiments

Figure 55:
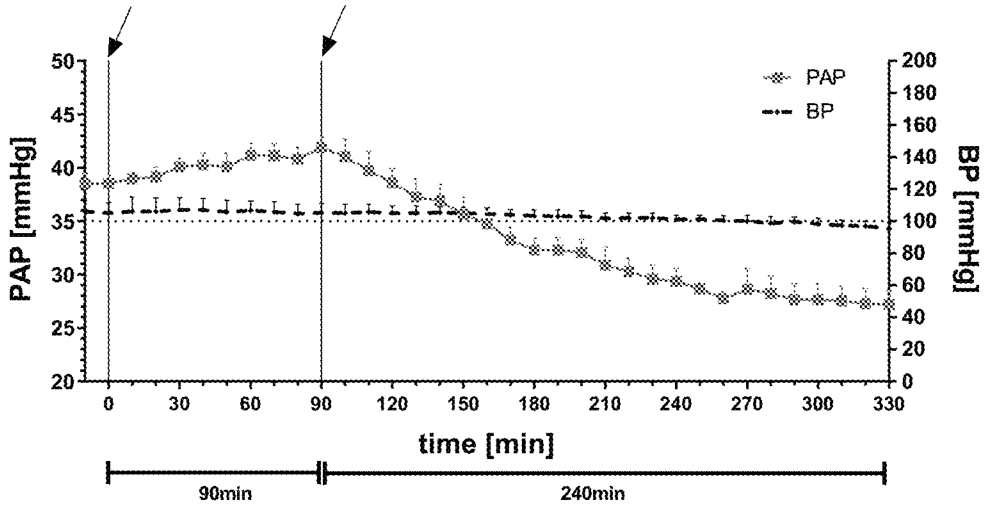
Figure 56:
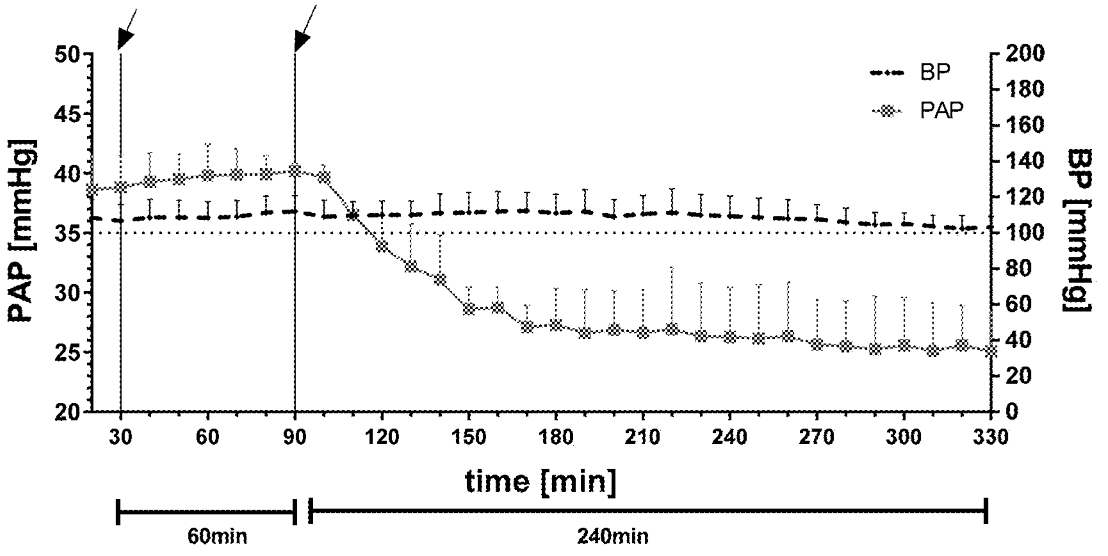
Figure 57:
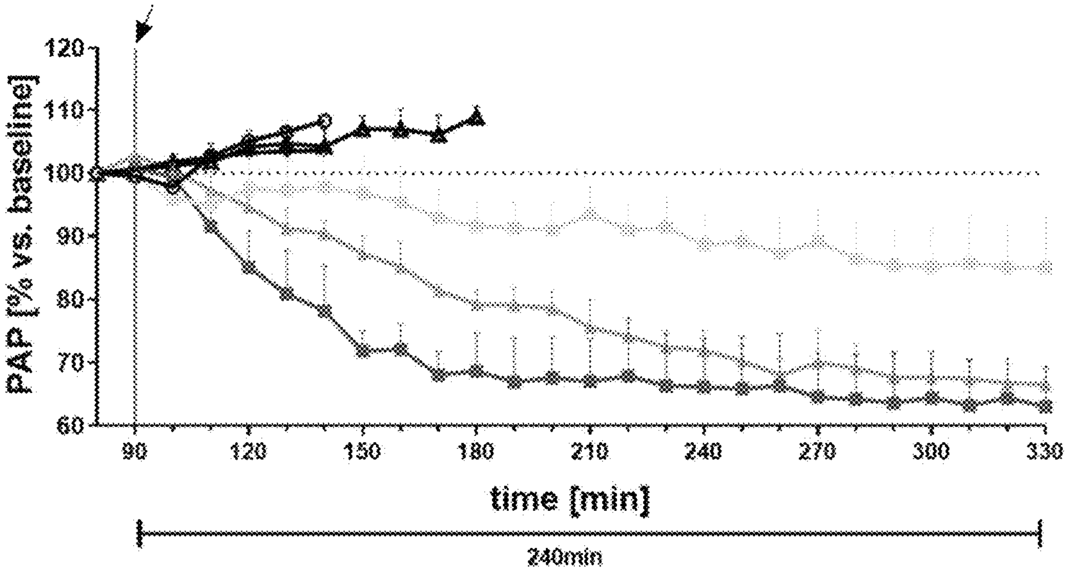

| Formulation | Drug load % (w/w) | Dry powder/drug dose applied per animal | crystalline forms of comparative example 11 dose applied |
|---|---|---|---|
| Lactose formulation I of cryst. form of comp. ex. 11 in lactose | 2 | 1.5 mg/30 μg | 7.5 μg/kg |
| Lactose formulation II of cryst. form of comp. ex. 11 in lactose | 6 | 1.5 mg/90 μg | 22.5 μg/kg |
| sesquihydrate ex. 6e, micronized | 100 | 1.5 mg/1500 μg | 375 μg/kg |

w/w: weight/weight 1.5 mg/4 kg animal weight lactose vehicle (LH300/LH200 20/78 or LH300/LH200 20/80), lactose formulation I (LH300/LH200 20/78 comprising 2 w-% cryst. form of comp. ex. 11), lactose formulation II (LH300/LH200 20/80 comprising 6 w-% cryst. form of comp. ex. 11 or micronized crystalline form of comp.ex. 11, e.g. sesquihydrate, e.g. example 6e were applied intratracheally (i.t.) via the PennCentury® dry powder insufflator attached to the air pump. In all animals, lactose application led to an increase in PAP without any effects on BP (see FIGS. 54-57). After i.t. application of lactose formulation 1(2% w/w), lactose formulation II (6% w/w) or as micronized crystalline form of comp.ex. 11, e.g. sesquihydrate example 6e a decrease of PAP without any effects on BP was observed (see FIGS. 54-56). As shown in FIG. 57 the onset of the effect was slow reaching the maximum effect with lactose formulation I (2% w/w) after approximately 190 min, with lactose formulation II (6% w/w) after approximately 170 min and with micronized sesquihydrate example 6e after approximately 80 min after i.t. application. The selective effect on PAP lasted for all doses for the complete 4 h observation interval. The maximal effect, achievable in this animal model under these experimental conditions, was reached in this model with lactose formulation II as well as the micronized sesquihydrate example 6e. As the lactose formulation I was already effective, the MED of comparative example 11 as well as its pseudopolymorphic forms, e.g. sesquihydrate and monohydrate I or monohydrate II (similar efficacy of the different pseudopolymorphic forms of compound of formula I has been shown in below tests) is <7.5 μg/kg which is well in line with the experiments for the derivation of human dose prediction with liquid solution (MED 3 μg/kg). Lower doses were not applicable due to technical limitations.

TABLE C2.1.9

Effects after intratracheal application of different lactose vehicles, lactose formulation I (7.5 μg/kg), lactose formulation II (22.5 μg/kg) and micronized sesquihydrate, e.g. example 6e (375 μg/kg). Data are shown as absolute values for PAP and BP [mmHg] (n = 3)

| | Lactose 1.5 mg/4 kg (@0 min) + lactose formulation I 2% 1.5 mg/4 kg (@90 min) | | | | | | Lactose 1.5 mg/4 kg (@0 min) + lactose formulation II 6% 1.5 mg/4 kg (@90 min) | | | | | |
|---|---|---|---|---|---|---|---|---|---|---|---|---|
| time | PAP | | | BP | | | PAP | | | BP | | |
| 0 | 38.8 | 37.1 | 37.2 | 101 | 106 | 119 | 38.6 | 36.8 | 40.0 | 110 | 115 | 93 |
| 10 | 37.3 | 37.7 | 37.6 | 95 | 110 | 118 | 39.4 | 37.1 | 39.2 | 111 | 112 | 92 |
| 20 | 35.3 | 36.8 | 38.4 | 96 | 106 | 119 | 39.9 | 37.9 | 39.1 | 113 | 117 | 88 |
| 30 | 40.4 | 37.2 | 38.7 | 101 | 105 | 119 | 40.3 | 37.4 | 39.8 | 114 | 115 | 89 |
| 40 | 41.8 | 37.8 | 39.4 | 103 | 105 | 119 | 40.9 | 38.5 | 40.9 | 113 | 116 | 92 |
| 50 | 41.9 | 39.4 | 39.2 | 105 | 102 | 118 | 41.7 | 38.1 | 41.0 | 113 | 115 | 93 |
| 60 | 41.9 | 40.9 | 39.7 | 107 | 100 | 118 | 42.4 | 38.0 | 39.8 | 112 | 114 | 91 |
| 70 | 40.9 | 41.2 | 39.6 | 108 | 101 | 116 | 42.8 | 39.2 | 41.6 | 112 | 113 | 95 |
| 80 | 37.6 | 42.4 | 37.4 | 108 | 94 | 111 | 43.3 | 39.5 | 40.6 | 111 | 113 | 93 |
| 90 | 35.5 | 42.3 | 38.4 | 111 | 97 | 111 | 43.0 | 39.2 | 40.2 | 111 | 110 | 93 |
| 100 | 38.1 | 43.8 | 37.5 | 113 | 100 | 110 | 43.2 | 40.0 | 42.5 | 110 | 112 | 94 |
| 110 | 38.8 | 43.8 | 36.5 | 114 | 93 | 107 | 44.2 | 38.5 | 40.4 | 110 | 111 | 94 |
| 120 | 40.9 | 43.8 | 35.3 | 115 | 96 | 107 | 42.7 | 36.5 | 40.1 | 110 | 111 | 96 |
| 130 | 40.9 | 43.6 | 34.2 | 115 | 89 | 106 | 40.8 | 36.4 | 38.6 | 110 | 109 | 96 |
| 140 | 41.3 | 42.3 | 33.5 | 116 | 86 | 105 | 40.6 | 35.6 | 35.6 | 109 | 110 | 96 |
| 150 | 41.3 | 39.5 | 33.2 | 117 | 89 | 104 | 39.9 | 35.0 | 35.9 | 110 | 108 | 98 |
| 160 | 40.4 | 39.0 | 32.9 | 116 | 87 | 103 | 38.8 | 34.1 | 34.1 | 110 | 107 | 98 |
| 170 | 40.9 | 38.1 | 32.9 | 116 | 86 | 102 | 37.1 | 34.8 | 32.5 | 110 | 106 | 97 |

TABLE C2.1.9-continued

Effects after intratracheal application of different lactose vehicles, lactose formulation I (7.5 µg/kg), lactose formulation II (22.5 µg/kg) and micronized sesquihydrate, e.g. example 6e (375 µg/kg). Data are shown as absolute values for PAP and BP [mmHg] (n = 3)

| | | | | | | | | | | | | |
|---|---|---|---|---|---|---|---|---|---|---|---|---|
| 180 | 40.9 | 38.1 | 32.6 | 114 | 88 | 101 | 35.5 | 31.6 | 32.6 | 109 | 105 | 98 |
| 190 | 41.5 | 39.7 | 33.6 | 116 | 90 | 102 | 34.4 | 31.7 | 30.8 | 108 | 106 | 96 |
| 200 | 39.3 | 39.7 | 32.5 | 112 | 89 | 103 | 34.5 | 31.7 | 30.5 | 108 | 106 | 95 |
| 210 | 40.2 | 39.7 | 32.3 | 112 | 90 | 102 | 34.5 | 31.5 | 30.3 | 107 | 106 | 96 |
| 220 | 38.6 | 38.7 | 31.5 | 110 | 89 | 104 | 34.2 | 29.9 | 28.6 | 106 | 104 | 95 |
| 230 | 39.3 | 38.7 | 31.5 | 111 | 88 | 105 | 32.7 | 29.5 | 28.6 | 106 | 104 | 96 |
| 240 | 38.2 | 38.5 | 30.5 | 109 | 89 | 104 | 32.2 | 28.6 | 28.0 | 106 | 104 | 96 |
| 250 | 40.3 | 38.1 | 31.2 | 110 | 90 | 103 | 31.6 | 29.1 | 27.4 | 105 | 102 | 96 |
| 260 | 39.6 | 36.4 | 30.0 | 107 | 90 | 100 | 29.6 | 28.7 | 27.7 | 105 | 102 | 97 |
| 270 | 38.7 | 36.9 | 29.3 | 108 | 94 | 98 | 28.8 | 27.9 | 26.6 | 104 | 103 | 94 |
| 280 | 39.6 | 36.2 | 28.9 | 106 | 91 | 98 | 32.5 | 27.2 | 26.2 | 105 | 102 | 93 |
| 290 | 40.1 | 37.0 | 28.3 | 107 | 91 | 95 | 31.5 | 26.6 | 26.6 | 105 | 100 | 91 |
| 300 | 38.2 | 37.9 | 28.0 | 104 | 90 | 92 | 30.6 | 26.6 | 25.7 | 104 | 101 | 94 |
| 310 | 40.0 | 37.1 | 27.4 | 105 | 91 | 92 | 30.6 | 26.3 | 26.0 | 105 | 97 | 93 |
| | | | | | | | 30.3 | 26.2 | 26.1 | 104 | 95 | 93 |
| | | | | | | | 30.2 | 26.0 | 25.7 | 103 | 95 | 93 |
| | | | | | | | 29.7 | 25.3 | 26.5 | 102 | 90 | 94 |

| | Lactose 1.5 mg/4 kg (@30 min) + cryst. form of sesquihydrate ex. 6e micronized 1.5 mg/4 kg (@90 min) | | | | | |
|---|---|---|---|---|---|---|
| time | PAP | | | BP | | |
| 0 | | | | | | |
| 10 | | | | | | |
| 20 | 42.0 | 36.4 | 37.5 | 99 | 107 | 119 |
| 30 | 41.9 | 37.1 | 37.5 | 99 | 104 | 117 |
| 40 | 42.0 | 37.3 | 38.6 | 99 | 108 | 119 |
| 50 | 41.4 | 37.4 | 39.8 | 99 | 109 | 118 |
| 60 | 41.4 | 36.8 | 41.2 | 100 | 107 | 118 |
| 70 | 41.0 | 37.4 | 41.3 | 100 | 109 | 118 |
| 80 | 40.9 | 38.1 | 40.8 | 101 | 114 | 119 |
| 90 | 40.4 | 39.5 | 40.7 | 102 | 116 | 118 |
| 100 | 40.7 | 38.7 | 39.6 | 99 | 111 | 117 |
| 110 | 36.5 | 37.6 | 35.4 | 101 | 112 | 116 |
| 120 | 34.3 | 36.4 | 30.8 | 101 | 114 | 115 |
| 130 | 32.3 | 35.7 | 28.6 | 101 | 114 | 115 |
| 140 | 30.8 | 35.0 | 27.5 | 99 | 120 | 114 |
| 150 | 30.3 | 29.0 | 26.6 | 99 | 121 | 114 |
| 160 | 29.0 | 30.3 | 26.9 | 100 | 122 | 114 |
| 170 | 28.0 | 28.3 | 25.1 | 101 | 121 | 115 |
| 180 | 25.8 | 30.8 | 25.3 | 99 | 119 | 115 |
| 190 | 25.1 | 30.8 | 23.9 | 99 | 123 | 114 |
| 200 | 25.5 | 30.6 | 24.6 | 98 | 116 | 113 |
| 210 | 25.0 | 30.8 | 24.2 | 99 | 117 | 116 |
| 220 | 24.3 | 32.9 | 23.6 | 97 | 123 | 114 |
| 230 | 24.0 | 31.5 | 23.6 | 97 | 119 | 114 |
| 240 | 24.3 | 31.0 | 23.5 | 97 | 119 | 112 |
| 250 | 24.2 | 31.3 | 22.9 | 97 | 118 | 111 |
| 260 | 24.0 | 31.5 | 23.5 | 96 | 116 | 112 |
| 270 | 24.5 | 29.8 | 22.6 | 99 | 115 | 109 |
| 280 | 23.9 | 29.8 | 22.8 | 97 | 111 | 110 |
| 290 | 23.5 | 30.3 | 22.0 | 97 | 110 | 107 |
| 300 | 24.6 | 30.0 | 22.2 | 98 | 109 | 108 |
| 310 | 23.9 | 29.6 | 21.9 | 97 | 109 | 105 |
| | 25.3 | 29.1 | 22.5 | 94 | 108 | 105 |
| | 25.1 | 28.5 | 21.6 | 97 | 108 | 105 |

TABLE C2.1.10

Effects after intratracheal application of different lactose vehicles, lactose formulation I (7.5 µg/kg), lactose formulation II (22.5 µg/kg) and micronized sesquihydrate example 6e (375 µg/kg). Data are shown as % changes vs. baseline on PAP as absolute values for each animal.

| timexx | Lactose formulation I 2% | | | Lactose LH300/LH200 20:78 m/m | | | Lactose formulation II 6% | | | Lactose LH300/LH200 20:80 m/m | | |
|---|---|---|---|---|---|---|---|---|---|---|---|---|
| 80 | 100.0 | 100.0 | 100.0 | 100.0 | 100.0 | 100.0 | 100.0 | 100.0 | 100.0 | 100.0 | 100.0 | 100.0 |
| 90 | 97.6 | 100.8 | 99.8 | 96.0 | 101.5 | 101.0 | 100.7 | 101.9 | 105.7 | 102.0 | 100.7 | 97.9 |
| 100 | 89.7 | 103.8 | 94.3 | 90.9 | 99.3 | 103.2 | 102.8 | 98.0 | 100.6 | 103.3 | 102.9 | 97.6 |
| 110 | 84.7 | 103.6 | 96.8 | 103.9 | 100.2 | 104.0 | 99.3 | 93.0 | 99.7 | 104.3 | 101.5 | 99.4 |
| 120 | 90.9 | 107.1 | 94.6 | 107.7 | 101.9 | 105.7 | 95.1 | 92.7 | 96.0 | 105.8 | 104.6 | 102.0 |
| 130 | 92.6 | 107.1 | 92.0 | 107.9 | 106.3 | 105.4 | 94.6 | 90.6 | 88.5 | 108.0 | 103.6 | 102.3 |
| 140 | 97.5 | 107.1 | 88.8 | 108.0 | 110.1 | 106.7 | 92.8 | 89.1 | 89.4 | 109.8 | 103.3 | 99.5 |

TABLE C2.1.10-continued

Effects after intratracheal application of different lactose vehicles, lactose formulation I (7.5 μg/kg), lactose formulation II (22.5 μg/kg) and micronized sesquihydrate example 6e (375 μg/kg). Data are shown as % changes vs. baseline on PAP as absolute values for each animal.

| | | | | | | | | | |
|---|---|---|---|---|---|---|---|---|---|
| 150 | 97.5 | 106.7 | 86.0 | 90.2 | 86.9 | 84.7 | 110.8 | 106.4 | 103.8 |
| 160 | 98.6 | 103.5 | 84.3 | 86.3 | 88.6 | 80.7 | 112.1 | 107.4 | 101.3 |
| 170 | 98.4 | 96.6 | 83.7 | 82.6 | 80.5 | 81.1 | 111.2 | 106.6 | 100.4 |
| 180 | 96.4 | 95.5 | 82.9 | 80.1 | 80.8 | 76.7 | 111.9 | 108.6 | 106.1 |
| 190 | 97.6 | 93.3 | 82.9 | 80.4 | 80.9 | 76.0 | | | |
| 200 | 97.6 | 93.3 | 82.1 | 80.2 | 80.1 | 75.4 | | | |
| 210 | 98.8 | 97.1 | 84.6 | 79.6 | 76.1 | 71.0 | | | |
| 220 | 93.7 | 97.3 | 81.9 | 76.1 | 75.2 | 71.2 | | | |
| 230 | 95.8 | 97.3 | 81.3 | 74.9 | 72.9 | 69.6 | | | |
| 240 | 92.1 | 94.6 | 79.4 | 73.5 | 74.1 | 68.2 | | | |
| 250 | 93.7 | 94.6 | 79.3 | 68.9 | 73.1 | 68.9 | | | |
| 260 | 91.0 | 94.1 | 76.8 | 66.9 | 71.1 | 66.1 | | | |
| 270 | 96.1 | 93.1 | 78.5 | 75.6 | 69.4 | 65.1 | | | |
| 280 | 94.5 | 89.2 | 75.5 | 73.4 | 67.8 | 66.1 | | | |
| 290 | 92.3 | 90.2 | 73.7 | 71.2 | 67.9 | 64.0 | | | |
| 300 | 94.3 | 88.6 | 72.8 | 71.2 | 67.1 | 64.7 | | | |
| 310 | 95.7 | 90.5 | 71.3 | 70.6 | 66.7 | 65.0 | | | |
| 320 | 91.0 | 92.8 | 71.3 | 70.2 | 66.3 | 63.9 | | | |
| 330 | 95.4 | 90.8 | 69.1 | 69.2 | 64.5 | 66.0 | | | |

| time | sesquihydrate example 6e micronized | | | Lactose LH300/LH200 20:80 m/m | | |
|---|---|---|---|---|---|---|
| 80 | 100.0 | 100.0 | 100.0 | 100.0 | 100.0 | 100.0 |
| 90 | 98.9 | 103.6 | 99.8 | 99.7 | 101.8 | 100.1 |
| 100 | 99.5 | 101.4 | 97.3 | 100.0 | 102.3 | 103.2 |
| 110 | 89.3 | 98.7 | 86.8 | 98.6 | 102.5 | 106.3 |
| 120 | 84.0 | 95.6 | 75.7 | 98.6 | 101.0 | 110.1 |
| 130 | 78.9 | 93.7 | 70.2 | 97.7 | 102.6 | 110.1 |
| 140 | 75.2 | 91.8 | 67.5 | 97.4 | 104.6 | 108.8 |
| 150 | 74.0 | 76.0 | 65.4 | | | |
| 160 | 71.0 | 79.5 | 65.9 | | | |
| 170 | 68.5 | 74.3 | 61.5 | | | |
| 180 | 63.2 | 80.8 | 62.0 | | | |
| 190 | 61.5 | 80.8 | 58.6 | | | |
| 200 | 62.3 | 80.3 | 60.2 | | | |
| 210 | 61.0 | 80.7 | 59.4 | | | |
| 220 | 59.5 | 86.3 | 57.8 | | | |
| 230 | 58.6 | 82.6 | 57.8 | | | |
| 240 | 59.3 | 81.5 | 57.6 | | | |
| 250 | 59.3 | 82.2 | 56.1 | | | |
| 260 | 58.8 | 82.7 | 57.6 | | | |
| 270 | 59.9 | 78.3 | 55.4 | | | |
| 280 | 58.4 | 78.3 | 55.9 | | | |
| 290 | 57.4 | 79.6 | 53.9 | | | |
| 300 | 60.1 | 78.7 | 54.5 | | | |
| 310 | 58.4 | 77.6 | 53.7 | | | |
| 320 | 61.8 | 76.3 | 55.1 | | | |
| 330 | 61.3 | 74.8 | 53.0 | | | |

In summary all dry powder formulations comprising crystalline forms of comp. example 11, e.g. sesquihydrate example 6e selectively and dose-dependently reduced PAP after inhaled application in this model of acute PAH with a long duration of action of at least 4 h (see FIG. 57). A clear dose-response curve was observed for increasing applied doses. Compared to nebulized liquid formulations (maximum effect about 90 min after start inhalation) the maximum effect was delayed to later time points (lactose formulation I (2% w/w) ~190 min, lactose formulation II (6% w/w) ~170 min) with the dry powder formulations.

Evaluation of Efficacy of Different Hydrates of Dry Powder

In addition, to evaluate efficacy of different hydrates of comparative example 11, comparative example 11 at the dose of 1.5 mg/4 kg (=375 μg/kg) was intratracheally applied as micronized monohydrate II (example 2), micronized semihydrate (in analogy to example 6a), as well as micronized sesquihydrate (in analogy to example 6e) via the PennCentury® dry powder insufflator in PAH minipigs. As reference pure Lactose vehicle was applied in the beginning of each experiment. All 3 hydrates showed comparable efficacy with regard to PAP reduction as well as to systemic BP reduction (see FIGS. 58 and 59). Systemic blood pressure was slightly affected with all 3 hydrates within the last hour of the observation interval. This slight systemic BP decrease might be caused via systemic overspill of the drug, applied at a relatively high dose of nominally 375 μg/kg i.t. It also might reflect some decrease in BP in anaesthetized animals over the course of duration of anaesthesia.

TABLE C2.1.11

Effects of comparative example 11 after intratracheal application of different hydrates: micronized monohydrate II (example 2), micronized semihydrate (example 6a) and micronized sesquihydrate (example 6e), on BP and PAP. Data are shown as absolute values [mmHg] as mean ± SEM (n = 3)

| | Monohydrate II (example 2) | | | | | | Semihydrate (example 6a) | | | | | |
|---|---|---|---|---|---|---|---|---|---|---|---|---|
| time | BP (mean) | | | PAP(mean) | | | BP (mean) | | | PAP(mean) | | |
| −10 | 116 | 126 | 139 | 37.9 | 37.8 | 39.4 | 99 | 85 | 86 | 38.7 | 40.6 | 38.7 |
| 0 | 109 | 127 | 136 | 35.8 | 38.7 | 39.7 | 101 | 85 | 85 | 39.6 | 40.8 | 38.5 |
| 10 | 110 | 126 | 135 | 35.8 | 38.7 | 37.1 | 103 | 83 | 79 | 40.2 | 41.1 | 41.1 |
| 20 | 117 | 128 | 139 | 38.9 | 38.2 | 40.2 | 101 | 83 | 84 | 40.4 | 41.3 | 41.3 |
| 30 | 121 | 128 | 139 | 39.8 | 38.6 | 40.0 | 100 | 81 | 88 | 40.2 | 41.3 | 41.3 |
| 40 | 123 | 127 | 137 | 40.4 | 39.0 | 40.7 | 98 | 81 | 90 | 40.4 | 41.8 | 41.0 |
| 50 | 120 | 127 | 135 | 39.7 | 39.2 | 40.2 | 99 | 78 | 89 | 40.7 | 41.7 | 40.9 |
| 60 | 121 | 127 | 136 | 39.9 | 39.2 | 40.8 | 100 | 79 | 86 | 41.2 | 42.0 | 40.9 |
| 70 | 124 | 126 | 137 | 39.1 | 36.0 | 37.2 | 102 | 78 | 87 | 38.8 | 40.6 | 40.1 |
| 80 | 123 | 124 | 135 | 39.1 | 36.1 | 35.9 | 102 | 79 | 90 | 34.1 | 39.9 | 37.7 |
| 90 | 122 | 125 | 134 | 37.9 | 35.2 | 34.5 | 101 | 81 | 92 | 30.1 | 37.7 | 36.6 |
| 100 | 122 | 124 | 132 | 36.8 | 33.2 | 32.7 | 100 | 80 | 95 | 28.3 | 35.9 | 35.0 |
| 110 | 122 | 125 | 133 | 35.5 | 31.9 | 31.2 | 99 | 79 | 99 | 27.2 | 34.8 | 34.0 |
| 120 | 121 | 125 | 132 | 34.8 | 30.2 | 29.8 | 99 | 79 | 96 | 26.4 | 34.1 | 32.9 |
| 130 | 120 | 124 | 131 | 34.2 | 29.7 | 29.3 | 98 | 81 | 97 | 25.7 | 33.7 | 31.7 |
| 140 | 119 | 125 | 131 | 34.3 | 29.3 | 28.6 | 99 | 82 | 98 | 25.3 | 33.2 | 31.3 |
| 150 | 117 | 124 | 130 | 33.7 | 28.4 | 28.4 | 97 | 82 | 97 | 25.0 | 32.9 | 30.7 |
| 160 | 117 | 121 | 130 | 33.7 | 27.8 | 27.8 | 96 | 81 | 97 | 24.5 | 32.5 | 30.2 |
| 170 | 116 | 120 | 129 | 33.5 | 27.5 | 28.0 | 95 | 79 | 95 | 24.0 | 32.4 | 29.9 |
| 180 | 114 | 117 | 132 | 33.5 | 27.1 | 28.1 | 94 | 79 | 94 | 23.7 | 31.9 | 29.7 |
| 190 | 112 | 116 | 133 | 33.6 | 26.7 | 28.3 | 94 | 85 | 93 | 24.4 | 32.4 | 29.2 |
| 200 | 109 | 115 | 131 | 33.5 | 26.8 | 28.0 | 92 | 85 | 92 | 24.8 | 32.4 | 29.4 |
| 210 | 110 | 117 | 130 | 33.4 | 26.3 | 27.6 | 90 | 81 | 91 | 24.8 | 31.9 | 29.2 |
| 220 | 110 | 116 | 128 | 33.7 | 26.3 | 27.1 | 89 | 79 | 89 | 24.7 | 31.7 | 29.1 |
| 230 | 111 | 115 | 129 | 33.8 | 26.0 | 27.6 | 87 | 78 | 89 | 24.0 | 31.3 | 28.6 |
| 240 | 111 | 113 | 121 | 33.3 | 26.6 | 26.8 | 87 | 77 | 87 | 24.1 | 31.3 | 28.1 |
| 250 | 109 | 110 | 123 | 33.2 | 26.0 | 26.3 | 85 | 76 | 85 | 24.2 | 30.7 | 28.1 |
| 260 | 109 | 108 | 119 | 33.4 | 26.3 | 26.7 | 85 | 76 | 84 | 24.1 | 30.6 | 28.1 |
| 270 | 108 | 106 | 119 | 33.6 | 25.9 | 26.3 | 85 | 76 | 87 | 24.4 | 30.6 | 27.8 |
| 280 | 108 | 104 | 116 | 33.4 | 26.3 | 26.2 | 85 | 75 | 84 | 24.3 | 30.7 | 28.0 |
| 290 | 106 | 102 | 114 | 33.2 | 25.9 | 25.8 | 84 | 75 | 83 | 24.1 | 30.7 | 27.6 |
| 300 | 105 | 101 | 114 | 33.1 | 25.9 | 25.7 | 83 | 77 | 82 | 23.7 | 30.5 | 27.7 |

| | Sesquihydrate (example 6e) | | | | | |
|---|---|---|---|---|---|---|
| time | BP (mean) | | | PAP(mean) | | |
| −10 | 99 | 107 | 119 | 42.0 | 36.4 | 37.5 |
| 0 | 99 | 104 | 117 | 41.9 | 37.1 | 37.5 |
| 10 | 99 | 108 | 119 | 42.0 | 37.3 | 38.6 |
| 20 | 99 | 109 | 118 | 41.4 | 37.4 | 39.8 |
| 30 | 100 | 107 | 118 | 41.4 | 36.8 | 41.2 |
| 40 | 100 | 109 | 118 | 41.0 | 37.4 | 41.3 |
| 50 | 101 | 114 | 119 | 40.9 | 38.1 | 40.8 |
| 60 | 102 | 116 | 118 | 40.4 | 39.5 | 40.7 |
| 70 | 99 | 111 | 117 | 40.7 | 38.7 | 39.6 |
| 80 | 101 | 112 | 116 | 36.5 | 37.6 | 35.4 |
| 90 | 101 | 114 | 115 | 34.3 | 36.4 | 30.8 |
| 100 | 101 | 114 | 115 | 32.3 | 35.7 | 28.6 |
| 110 | 99 | 120 | 114 | 30.8 | 35.0 | 27.5 |
| 120 | 99 | 121 | 114 | 30.3 | 29.0 | 26.6 |
| 130 | 100 | 122 | 114 | 29.0 | 30.3 | 26.9 |
| 140 | 101 | 121 | 115 | 28.0 | 28.3 | 25.1 |
| 150 | 99 | 119 | 115 | 25.8 | 30.8 | 25.3 |
| 160 | 99 | 123 | 114 | 25.1 | 30.8 | 23.9 |
| 170 | 98 | 116 | 113 | 25.5 | 30.6 | 24.6 |
| 180 | 99 | 117 | 116 | 25.0 | 30.8 | 24.2 |
| 190 | 97 | 123 | 114 | 24.3 | 32.9 | 23.6 |
| 200 | 97 | 119 | 114 | 24.0 | 31.5 | 23.6 |
| 210 | 97 | 119 | 112 | 24.3 | 31.0 | 23.5 |
| 220 | 97 | 118 | 111 | 24.2 | 31.3 | 22.9 |
| 230 | 96 | 116 | 112 | 24.0 | 31.5 | 23.5 |
| 240 | 99 | 115 | 109 | 24.5 | 29.8 | 22.6 |
| 250 | 97 | 111 | 110 | 23.9 | 29.8 | 22.8 |
| 260 | 97 | 110 | 107 | 23.5 | 30.3 | 22.0 |
| 270 | 98 | 109 | 108 | 24.6 | 30.0 | 22.2 |
| 280 | 97 | 109 | 105 | 23.9 | 29.6 | 21.9 |
| 290 | 94 | 108 | 105 | 25.3 | 29.1 | 22.5 |
| 300 | 97 | 108 | 105 | 25.1 | 28.5 | 21.6 |

TABLE C2.1.12

Effects of comparative example 11 after intratracheal application of different hydrates: micronized monohydrate II (example 2), micronized semihydrate (example 6a) and micronized sesquihydrate (example 6e), on BP and PAP. Data are shown as % changes vs. prevalues as absolute values for each animal.

| | Monohydrate II (example 2) | | | | | | Semihydrate (example 6a) | | | | | |
|---|---|---|---|---|---|---|---|---|---|---|---|---|
| time | PAP | | | BP | | | PAP | | | BP | | |
| 50 | 99.1 | 99.2 | 98.5 | 99.1 | 100.1 | 100.0 | 99.3 | 98.7 | 98.9 | 99.6 | 98.4 | 100.6 |
| 60 | 99.7 | 99.3 | 99.8 | 99.9 | 100.1 | 100.7 | 100.7 | 99.4 | 99.2 | 100.6 | 99.7 | 97.2 |
| 70 | 97.7 | 91.1 | 91.0 | 102.4 | 99.3 | 101.4 | 94.7 | 96.1 | 97.0 | 102.6 | 98.4 | 98.4 |
| 80 | 97.7 | 91.3 | 88.0 | 101.6 | 97.7 | 100.0 | 83.4 | 94.5 | 91.2 | 102.6 | 99.7 | 101.8 |
| 90 | 94.7 | 89.1 | 84.5 | 100.7 | 98.5 | 99.2 | 73.4 | 89.2 | 88.7 | 101.6 | 102.2 | 104.0 |
| 100 | 91.8 | 84.0 | 80.0 | 100.7 | 97.7 | 97.7 | 69.0 | 85.0 | 84.7 | 100.6 | 101.0 | 107.4 |
| 110 | 88.8 | 80.9 | 76.3 | 100.7 | 98.5 | 98.5 | 66.5 | 82.4 | 82.1 | 99.6 | 99.7 | 111.9 |
| 120 | 87.0 | 76.6 | 73.0 | 99.9 | 98.5 | 97.7 | 64.4 | 80.8 | 79.7 | 99.6 | 99.7 | 108.6 |
| 130 | 85.5 | 75.2 | 71.7 | 99.1 | 97.7 | 97.0 | 62.8 | 79.9 | 76.7 | 98.6 | 102.2 | 109.7 |
| 140 | 85.6 | 74.3 | 70.0 | 98.3 | 98.5 | 97.0 | 61.8 | 78.7 | 75.7 | 99.6 | 103.5 | 110.8 |
| 150 | 84.1 | 71.9 | 69.4 | 96.6 | 97.7 | 96.3 | 60.9 | 78.0 | 74.3 | 97.6 | 103.5 | 109.7 |
| 160 | 84.1 | 70.4 | 68.1 | 96.6 | 95.3 | 96.3 | 59.9 | 77.1 | 73.1 | 96.6 | 102.2 | 109.7 |
| 170 | 83.8 | 69.8 | 68.5 | 95.8 | 94.5 | 95.5 | 58.6 | 76.7 | 72.3 | 95.6 | 99.7 | 107.4 |
| 180 | 83.8 | 68.7 | 68.9 | 94.1 | 92.2 | 97.7 | 58.0 | 75.4 | 71.8 | 94.6 | 99.7 | 106.3 |
| 190 | 83.9 | 67.7 | 69.3 | 92.5 | 91.4 | 98.5 | 59.5 | 78.4 | 70.7 | 94.6 | 108.5 | 105.2 |
| 200 | 83.7 | 67.9 | 68.5 | 90.0 | 90.6 | 97.0 | 60.5 | 76.8 | 71.1 | 92.6 | 107.3 | 104.0 |
| 210 | 83.4 | 66.5 | 67.7 | 90.8 | 92.2 | 96.3 | 60.6 | 75.5 | 70.8 | 90.6 | 102.2 | 102.9 |
| 220 | 84.0 | 66.7 | 66.2 | 90.8 | 91.4 | 94.8 | 60.3 | 75.1 | 70.3 | 89.6 | 99.7 | 100.6 |
| 230 | 84.5 | 65.8 | 67.6 | 91.6 | 90.6 | 95.5 | 58.7 | 74.1 | 69.1 | 87.6 | 98.4 | 100.6 |
| 240 | 83.2 | 67.3 | 65.6 | 91.6 | 89.0 | 89.6 | 58.9 | 74.2 | 68.0 | 87.6 | 97.2 | 98.4 |
| 250 | 83.0 | 65.7 | 64.3 | 90.0 | 86.7 | 91.1 | 59.0 | 72.7 | 67.9 | 85.5 | 95.9 | 96.1 |
| 260 | 83.3 | 66.7 | 65.4 | 90.0 | 85.1 | 88.1 | 58.8 | 72.5 | 68.0 | 85.5 | 95.9 | 95.0 |
| 270 | 83.8 | 65.6 | 64.3 | 89.2 | 83.5 | 88.1 | 59.6 | 72.4 | 67.3 | 85.5 | 95.9 | 98.4 |
| 280 | 83.3 | 66.5 | 64.1 | 89.2 | 81.9 | 85.9 | 59.3 | 72.6 | 67.8 | 85.5 | 94.6 | 95.0 |
| 290 | 82.8 | 65.5 | 63.1 | 87.5 | 80.4 | 84.4 | 58.8 | 72.6 | 66.7 | 84.5 | 94.6 | 93.9 |
| 300 | 82.7 | 65.7 | 62.9 | 86.7 | 79.6 | 84.4 | 57.9 | 72.2 | 67.1 | 83.5 | 97.2 | 92.7 |

| | Sesquihydrate (example 6e) | | | | | |
|---|---|---|---|---|---|---|
| time | PAP | | | BP | | |
| 50 | 98.3 | 96.2 | 101.2 | 101.4 | 98.5 | 100.3 |
| 60 | 97.2 | 99.6 | 101.1 | 102.5 | 100.3 | 99.4 |
| 70 | 97.8 | 97.5 | 98.5 | 99.4 | 96.0 | 98.6 |
| 80 | 87.8 | 94.9 | 87.9 | 101.4 | 96.8 | 97.7 |
| 90 | 82.5 | 92.0 | 76.6 | 101.4 | 98.5 | 96.9 |
| 100 | 77.6 | 90.1 | 71.1 | 101.4 | 98.5 | 96.9 |
| 110 | 74.0 | 88.3 | 68.4 | 99.4 | 103.7 | 96.1 |
| 120 | 72.8 | 73.1 | 66.2 | 99.4 | 104.6 | 96.1 |
| 130 | 69.8 | 76.4 | 66.8 | 100.4 | 105.5 | 96.1 |
| 140 | 67.3 | 71.4 | 62.2 | 101.4 | 104.6 | 96.9 |
| 150 | 62.1 | 77.7 | 62.8 | 99.4 | 102.9 | 96.9 |
| 160 | 60.4 | 77.7 | 59.3 | 99.4 | 106.3 | 96.1 |
| 170 | 61.3 | 77.3 | 61.0 | 98.4 | 100.3 | 95.2 |
| 180 | 60.0 | 77.6 | 60.1 | 99.4 | 101.1 | 97.7 |
| 190 | 58.5 | 83.0 | 58.5 | 97.4 | 106.3 | 96.1 |
| 200 | 57.6 | 79.4 | 58.5 | 97.4 | 102.9 | 96.1 |
| 210 | 58.3 | 78.3 | 58.3 | 97.4 | 102.9 | 94.4 |
| 220 | 58.3 | 79.0 | 56.8 | 97.4 | 102.0 | 93.5 |
| 230 | 57.8 | 79.6 | 58.3 | 96.4 | 100.3 | 94.4 |
| 240 | 58.9 | 75.3 | 56.1 | 99.4 | 99.4 | 91.8 |
| 250 | 57.4 | 75.3 | 56.6 | 97.4 | 96.0 | 92.7 |
| 260 | 56.4 | 76.5 | 54.6 | 97.4 | 95.1 | 90.2 |
| 270 | 59.1 | 75.7 | 55.2 | 98.4 | 94.2 | 91.0 |
| 280 | 57.4 | 74.6 | 54.4 | 97.4 | 94.2 | 88.5 |
| 290 | 60.8 | 73.3 | 55.8 | 94.4 | 93.4 | 85.9 |
| 300 | 60.3 | 72.0 | 53.7 | 101.4 | 90.8 | 84.3 |

C-2.2 Haemodynamics in the Conscious Hypoxia Challenged Dogs

We evaluated the lung-selectivity and duration of effects of comparative example 11 under conscious conditions, in another species, and under a more physiological stimulus for PAP increase. Dogs were exposed to hypoxia for 30 minutes to induce a hypoxia-mediated PAP increase and comparative example 11 (100 μg/kg nominal dose) was applied by inhalation 1, 5, 12, 16 and 24 hours before hypoxia. Compared with vehicle-treated animals, attenuation of the hypoxia-induced PAP increase was observed for 1-17 hours with comparative example 11 and dissipated after 24 hours (see FIGS. 60*a*, 60*b*, 61*a-e*, and 62). No effects on HR were observed (data not shown).

TABLE C2.2.1

| Effects of comparative example 11 (100 ug/kg nominal dose) after inhaled application 1, 5, 12, 16 and 24 hours before hypoxia on hypoxia induced PAP increase in conscious dogs. Data are shown as absolute values vs. vehicle treated animals (n = 3) | | | |
|---|---|---|---|
| Time post inhalation | Comparative example 11 mPAP decrease during Hypoxia [mmHg] | | |
| 1-2 h | −12.44 | −11.44 | −10.13 |
| 5-6 h | −16.13 | −5.44 | −8.75 |
| 12-13 h | −3.44 | −4.81 | −1.69 |
| 16-17 h | −2.25 | −4.25 | −3.00 |
| 24-25 h | −0.13 | −1.94 | −0.50 |

The duration of action of comparative example 11 in this model is 16-17 hours. The nominal dose of 100 µg/kg was effective similar as in the minipig experiments, unfortunately determination of deposited lung dose was technically not possible.

The hypoxic dog model was also used to compare different drug candidates wrt duration of action under conscious conditions. Comparative example 11 as well as comparative example 4, which showed both similar lung selectivity as well as long duration of action in the PAH minipig model, were compared head to head in the hypoxic dog model after inhaled application of 100 µg/kg nominal dose. Both compounds showed comparable efficacy up to 6 hrs after inhalation. The experiments conducted 12 and 16 hrs after inhalation pointed towards an advantage of comparative example 11 wrt duration of action with more effective PAP decrease for comparative example 11 compared to comparative example 4. The decrease measured for example 4 24 hrs after inhalation was regarded as inconsistent finding, because it does not fit to the time course of the experiment also in comparison to comparative example 11 (see FIGS. 61*a*-61*e* and FIG. 62).

TABLE C2.2.2

Effects of comparative example 11 and comparative example 4 (100 µg/kg nominal dose) after inhaled application 1, 5, 12, 16 and 24 hours before hypoxia on hypoxia induced PAP increase in conscious dogs. Data are shown as absolute values for each animal

| time [min] | Vehicle | | | Comparative example 11 | | | Comparative Example 4 | | |
|---|---|---|---|---|---|---|---|---|---|
| 1 h | | | | | | | | | |
| 0 | 10 | 16 | 12 | 9 | 13 | 9 | 11 | 15 | 12 |
| 2 | 10 | 14 | 11 | 11 | 13 | 7 | 9 | 13 | 11 |
| 4 | 11 | 13 | 11 | 10 | 13 | 8 | 9 | 15 | 10 |
| 6 | 11 | 13 | 10 | 12 | 13 | 8 | 9 | 14 | 11 |
| 8 | 12 | 14 | 18 | 10 | 12 | 9 | 10 | 14 | 11 |
| 10 | 12 | 14 | 14 | 10 | 12 | 10 | 9 | 14 | 11 |
| 12 | 19 | 20 | 18 | 10 | 14 | 9 | 12 | 15 | 9 |
| 14 | 24 | 24 | 17 | 10 | 15 | 10 | 12 | 17 | 8 |
| 16 | 24 | 27 | 22 | 10 | 15 | 11 | 12 | 17 | 7 |
| 18 | 25 | 26 | 21 | 10 | 15 | 12 | 11 | 16 | 8 |
| 20 | 28 | 33 | 22 | 10 | 17 | 11 | 12 | 16 | 9 |
| 22 | 26 | 34 | 20 | 11 | 15 | 11 | 13 | 16 | 9 |
| 24 | 25 | 31 | 20 | 12 | 17 | 10 | 12 | 19 | 9 |
| 26 | 27 | 33 | 21 | 12 | 18 | 10 | 12 | 18 | 9 |
| 28 | 27 | 33 | 20 | 13 | 19 | 8 | 13 | 18 | 8 |
| 30 | 27 | 31 | 22 | 12 | 18 | 10 | 13 | 18 | 10 |
| 32 | 28 | 29 | 22 | 14 | 19 | 10 | 13 | 21 | 9 |
| 34 | 25 | 30 | 22 | 13 | 19 | 10 | 13 | 20 | 8 |
| 36 | 24 | 30 | 23 | 12 | 19 | 11 | 14 | 22 | 9 |
| 38 | 24 | 29 | 22 | 15 | 19 | 12 | 13 | 21 | 11 |
| 40 | 21 | 30 | 22 | 13 | 20 | 11 | 15 | 23 | 12 |
| 42 | 15 | 22 | 15 | 11 | 14 | 10 | 13 | 17 | 13 |
| 44 | 12 | 17 | 10 | 11 | 15 | 10 | 11 | 18 | 12 |
| 46 | 13 | 16 | 13 | 10 | 15 | 10 | 12 | 19 | 11 |
| 48 | 12 | 19 | 9 | 10 | 16 | 10 | 11 | 18 | 11 |
| 50 | 12 | 16 | 9 | 11 | 17 | 10 | 12 | 15 | 12 |
| 5 h | | | | | | | | | |
| 0 | 18 | 13 | 18 | 10 | 14 | 15 | 12 | 16 | 15 |
| 2 | 18 | 12 | 16 | 9 | 15 | 15 | 11 | 15 | 12 |
| 4 | 17 | 11 | 15 | 7 | 15 | 14 | 10 | 14 | 13 |
| 6 | 17 | 12 | 16 | 8 | 15 | 13 | 10 | 14 | 13 |
| 8 | 16 | 10 | 14 | 8 | 13 | 13 | 10 | 13 | 16 |
| 10 | 19 | 11 | 14 | 7 | 13 | 10 | 10 | 14 | 12 |
| 12 | 23 | 23 | 19 | 12 | 17 | 15 | 13 | 14 | 10 |
| 14 | 20 | 18 | 22 | 11 | 17 | 15 | 10 | 14 | 15 |
| 16 | 23 | 20 | 23 | 11 | 17 | 16 | 12 | 14 | 14 |
| 18 | 26 | 24 | 23 | 12 | 16 | 13 | 13 | 16 | 15 |
| 20 | 26 | 24 | 23 | 12 | 17 | 15 | 9 | 15 | 14 |
| 22 | 28 | 26 | 23 | 12 | 17 | 14 | 12 | 14 | 15 |
| 24 | 29 | 25 | 24 | 11 | 18 | 14 | 13 | 17 | 14 |
| 26 | 31 | 26 | 24 | 11 | 18 | 14 | 12 | 16 | 16 |
| 28 | 29 | 28 | 25 | 12 | 18 | 12 | 12 | 16 | 15 |
| 30 | 30 | 25 | 22 | 11 | 18 | 15 | 13 | 16 | 16 |
| 32 | 28 | 26 | 23 | 11 | 19 | 11 | 11 | 19 | 16 |
| 34 | 28 | 24 | 23 | 9 | 16 | 14 | 14 | 16 | 14 |
| 36 | 30 | 21 | 24 | 9 | 19 | 16 | 11 | 17 | 15 |
| 38 | 29 | 21 | 23 | 9 | 19 | 14 | 12 | 20 | 16 |

TABLE C2.2.2-continued

Effects of comparative example 11 and comparative example 4 (100 μg/kg nominal dose) after inhaled application 1, 5, 12, 16 and 24 hours before hypoxia on hypoxia induced PAP increase in conscious dogs. Data are shown as absolute values for each animal

| time [min] | Vehicle | | | Comparative example 11 | | | Comparative Example 4 | | |
|---|---|---|---|---|---|---|---|---|---|
| 40 | 28 | 21 | 26 | 9 | 17 | 13 | 13 | 18 | 16 |
| 42 | 21 | 16 | 16 | 9 | 14 | 11 | 9 | 16 | 12 |
| 44 | 18 | 12 | 14 | 9 | 13 | 11 | 8 | 16 | 11 |
| 46 | 18 | 12 | 11 | 9 | 13 | 12 | 8 | 14 | 11 |
| 48 | 17 | 11 | 12 | 9 | 12 | 10 | 9 | 15 | 12 |
| 50 | 17 | 13 | 12 | 8 | 13 | 11 | 8 | 18 | 10 |
| 12 h | | | | | | | | | |
| 0 | 8 | 17 | 6 | 6 | 15 | 9 | 6 | 15 | 9 |
| 2 | 9 | 14 | 7 | 5 | 16 | 10 | 4 | 14 | 7 |
| 4 | 7 | 13 | 7 | 7 | 15 | 7 | 4 | 15 | |
| 6 | 8 | 11 | 6 | 6 | 15 | | 5 | 13 | 7 |
| 8 | 8 | 13 | 6 | 5 | 15 | 7 | 5 | 16 | 8 |
| 10 | 11 | 13 | 7 | 4 | 15 | 7 | 5 | 14 | 6 |
| 12 | 17 | 16 | 11 | 20 | 17 | 10 | 18 | 16 | 11 |
| 14 | 18 | 19 | 11 | 19 | 17 | 10 | 22 | 16 | 11 |
| 16 | 19 | 19 | 12 | 19 | 17 | 10 | 23 | 20 | 14 |
| 18 | 20 | 24 | 16 | 22 | 21 | 14 | 22 | 18 | 14 |
| 20 | 24 | 25 | 15 | 21 | 20 | 15 | 25 | 19 | 15 |
| 22 | 23 | 26 | 15 | 24 | 23 | 19 | 26 | 19 | 16 |
| 24 | 23 | 25 | 18 | 20 | 22 | 13 | 26 | 20 | 16 |
| 26 | 24 | 28 | 17 | 19 | 22 | 13 | 23 | 22 | 16 |
| 28 | 26 | 32 | 17 | 18 | 21 | 15 | 25 | 22 | 17 |
| 30 | 23 | 28 | 20 | 21 | 23 | 16 | 25 | 23 | 17 |
| 32 | 27 | 30 | 17 | 21 | 22 | 15 | 24 | 23 | 17 |
| 34 | 24 | 29 | 19 | 19 | 20 | 18 | 20 | 23 | 16 |
| 36 | 30 | 27 | 19 | 18 | 21 | 17 | 24 | 25 | 18 |
| 38 | 24 | 32 | 18 | 18 | 23 | 14 | 20 | 24 | 19 |
| 40 | 22 | 29 | 17 | 17 | 21 | 16 | 19 | 24 | 17 |
| 42 | 8 | 21 | 8 | 9 | 15 | 10 | 12 | 16 | 10 |
| 44 | 8 | 18 | 7 | 7 | 15 | 9 | 8 | 15 | 7 |
| 46 | 8 | 16 | 6 | 6 | 15 | 11 | 6 | 15 | 7 |
| 48 | 5 | 17 | 7 | 7 | 15 | 11 | 6 | 15 | 7 |
| 50 | 9 | 17 | 8 | 6 | 15 | 10 | 6 | 13 | 7 |
| 16 h | | | | | | | | | |
| 0 | 8 | 17 | 8 | 8 | 13 | 9 | 5 | 16 | 10 |
| 2 | 7 | 16 | 7 | 7 | 13 | 7 | 5 | 16 | 7 |
| 4 | 6 | 14 | 8 | 7 | 14 | 6 | 6 | 16 | 8 |
| 6 | 7 | 15 | 7 | 7 | 13 | 7 | 6 | 15 | 6 |
| 8 | 6 | 15 | 8 | 8 | 13 | 5 | 7 | 15 | 7 |
| 10 | 10 | 16 | 7 | 8 | 13 | 5 | 7 | 15 | 7 |
| 12 | 18 | 20 | 14 | 20 | 16 | 8 | 19 | 24 | 11 |
| 14 | 20 | 20 | 11 | 19 | 21 | 13 | 19 | 22 | 14 |
| 16 | 20 | 24 | 15 | 18 | 21 | 13 | 25 | 23 | 16 |
| 18 | 21 | 30 | 17 | 15 | 20 | 12 | 23 | 25 | 16 |
| 20 | 23 | 26 | 19 | 23 | 18 | 15 | 24 | 22 | 16 |
| 22 | 22 | 22 | 13 | 23 | 23 | 12 | 23 | 26 | 13 |
| 24 | 23 | 30 | 18 | 21 | 27 | 14 | 23 | 26 | 14 |
| 26 | 27 | 28 | 15 | 23 | 24 | 12 | 21 | 32 | 15 |
| 28 | 22 | 31 | 21 | 21 | 25 | 15 | 22 | 29 | 17 |
| 30 | 24 | 32 | 20 | 21 | 23 | 14 | 26 | 31 | 18 |
| 32 | 24 | 31 | 19 | 18 | 26 | 16 | 24 | 29 | 16 |
| 34 | 21 | 34 | 20 | 18 | 28 | 15 | 23 | 32 | 21 |
| 36 | 22 | 32 | 22 | 17 | 25 | 18 | 20 | 29 | 19 |
| 38 | 20 | 28 | 20 | 18 | 27 | 17 | 25 | 29 | 12 |
| 40 | 19 | 29 | 13 | 17 | 28 | 17 | 25 | 30 | 22 |
| 42 | 13 | 21 | 9 | 9 | 19 | 13 | 12 | 21 | 8 |
| 44 | 7 | 19 | 9 | 7 | 18 | 9 | 9 | 17 | 7 |
| 46 | 7 | 20 | 8 | 7 | 18 | 6 | 9 | 16 | 8 |
| 48 | 7 | 19 | 8 | 6 | 16 | 9 | 6 | 16 | 8 |
| 50 | 7 | 18 | 9 | 7 | 15 | 8 | 6 | 15 | 6 |
| 24 h | | | | | | | | | |
| 0 | 10 | 16 | 12 | 10 | 15 | 15 | 10 | 16 | 15 |
| 2 | 10 | 14 | 11 | 9 | 14 | 12 | 12 | 16 | 17 |
| 4 | 11 | 13 | 11 | 8 | 14 | 10 | 10 | 15 | 16 |
| 6 | 11 | 13 | 10 | 8 | 16 | 11 | 10 | 13 | 14 |
| 8 | 12 | 14 | 18 | 8 | 14 | 9 | 9 | 14 | 12 |
| 10 | 12 | 14 | 14 | 9 | 11 | 10 | 10 | 15 | 14 |
| 12 | 19 | 20 | 18 | 20 | 20 | 15 | 18 | 22 | 14 |
| 14 | 24 | 24 | 17 | 23 | 22 | 19 | 18 | 19 | 15 |
| 16 | 24 | 27 | 22 | 27 | 24 | 22 | 20 | 23 | 17 |
| 18 | 25 | 26 | 21 | 27 | 26 | 20 | 23 | 25 | 17 |

TABLE C2.2.2-continued

Effects of comparative example 11 and comparative example 4 (100 μg/kg nominal dose) after inhaled application 1, 5, 12, 16 and 24 hours before hypoxia on hypoxia induced PAP increase in conscious dogs. Data are shown as absolute values for each animal

| time [min] | Vehicle | | | Comparative example 11 | | | Comparative Example 4 | | |
|---|---|---|---|---|---|---|---|---|---|
| 20 | 28 | 33 | 22 | 29 | 29 | 23 | 23 | 24 | 21 |
| 22 | 26 | 34 | 20 | 27 | 30 | 22 | 22 | 26 | 17 |
| 24 | 25 | 31 | 20 | 26 | 28 | 22 | 24 | 25 | 18 |
| 26 | 27 | 33 | 21 | 24 | 29 | 17 | 23 | 25 | 19 |
| 28 | 27 | 33 | 20 | 26 | 29 | 20 | 22 | 27 | 18 |
| 30 | 27 | 31 | 22 | 24 | 30 | 21 | 23 | 33 | 19 |
| 32 | 28 | 29 | 22 | 25 | 28 | 20 | 26 | 28 | 20 |
| 34 | 25 | 30 | 22 | 25 | 34 | 22 | 23 | 27 | 19 |
| 36 | 24 | 30 | 23 | 25 | 28 | 22 | 24 | 31 | 22 |
| 38 | 24 | 29 | 22 | 24 | 28 | 24 | 22 | 26 | 21 |
| 40 | 21 | 30 | 22 | 23 | 27 | 21 | 24 | 28 | 21 |
| 42 | 15 | 22 | 15 | 15 | 21 | 12 | 19 | 24 | 15 |
| 44 | 12 | 17 | 10 | 11 | 22 | 14 | 13 | 22 | 12 |
| 46 | 13 | 16 | 13 | 11 | 21 | 12 | 13 | 21 | 10 |
| 48 | 12 | 19 | 9 | 9 | 20 | 9 | 13 | 17 | 10 |
| 50 | 12 | 16 | 9 | 9 | 17 | 9 | 10 | 18 | 14 |

TABLE C2.2.3

Effects of comparative example 11 and comparative example 4 (100 μg/kg nominal dose) after inhaled application 1, 5, 12, 16 and 24 hours before hypoxia on hypoxia induced PAP increase in conscious dogs. Data are shown as mean PAP decrease during hypoxia in absolute values for each animal as well as mean ± SEM.

| Time post inhalation | Comparative example 11 mPAP decrease during Hypoxia [mmHg] n = 3 | | | Comparative example 11 mean +/− SEM | Comparative Example 4 mPAP decrease during Hypoxia [mmHg] n = 3 | | | Comparative Example 4 mean +/− SEM |
|---|---|---|---|---|---|---|---|---|
| 1-2 h | −12.44 | −11.44 | −10.13 | −11.33 ± 0.67 | −11.69 | −10.19 | −11.38 | −11.08 ± 0.46 |
| 5-6 h | −16.13 | −5.44 | −8.75 | −10.10 ± 3.16 | −14.81 | −6.69 | −8.00 | −9.83 ± 2.52 |
| 12-13 h | −3.44 | −4.81 | −1.69 | −3.31 ± 0.90 | −0.50 | −4.63 | −0.56 | −1.90 ± 1.36 |
| 16-17 h | −2.25 | −4.25 | −3.00 | −3.17 ± 0.58 | 0.81 | −0.56 | −1.06 | −0.27 ± 0.56 |
| 24-25 h | −0.13 | −1.94 | −0.50 | −0.85 ± 0.55 | −2.56 | −3.13 | −2.25 | −2.65 ± 0.26 |

Figure 63:
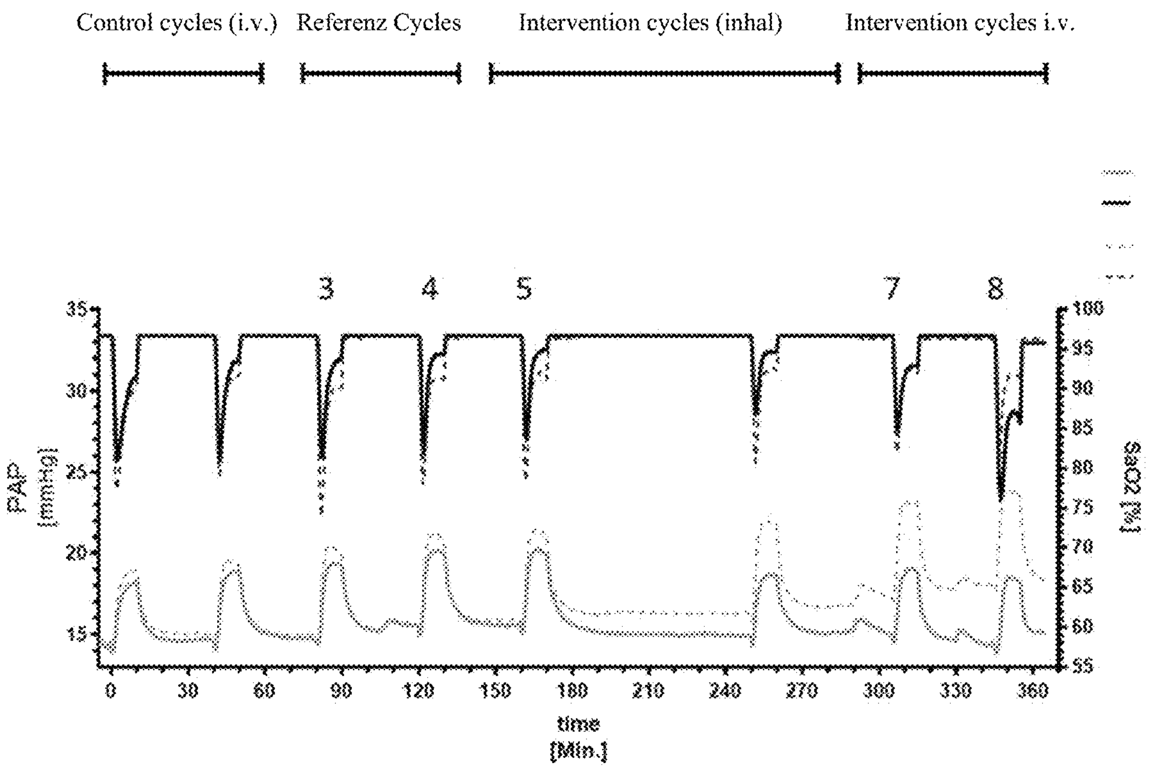
Figure 64:
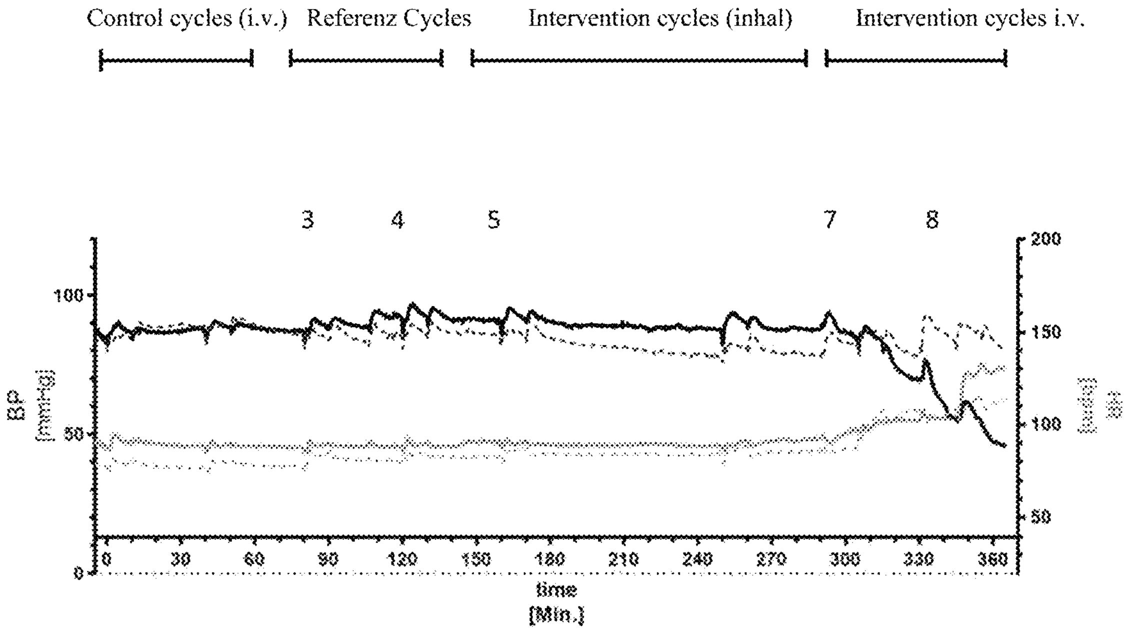

C-2.3 Effects on Arterial Oxygenation as a Proxy of VQ-Mismatch—Intrapulmonary Selectivity In vehicle-treated anesthetized minipigs (control animals) repetitive 10-min cycles of unilateral lung ventilation resulted in reproducible increases in PAP, accompanied by decreases in arterial oxygen saturation of hemoglobin ($SaO_2$) (see FIG. 63). HR and systemic BP were stable during the entire course of the experiment (see FIG. 64); only i.v. application of comparative example 11 (30 μg/kg and 100 μg/kg) induced the expected drop in BP. During the course of the experiment, vehicle-treated control animals demonstrated a trend towards a small incremental increase in PAP level throughout the later unilateral ventilation cycles. In animals treated with inhaled application of comparative example 11 (100 μg/kg nominal dose) a trend towards smaller desaturation areas was observed compared to vehicle treated control animals (Intervention cycles [inhal] FIG. 63) as well as a decrease in PAP under normoxic conditions but also under broncho-occlusion cycles. These effects were more pronounced 90 min after inhalation of comparative example 11 (second intervention cycles (inhal)). 90 min after inhalation comparative example 11 showed maximal effects. After i.v. application. comparative example 11 led to an increase in desaturation area as well as a further reduction in PAP compared to vehicle treated animals (Intervention cycles [i.v.].

Figure 65:
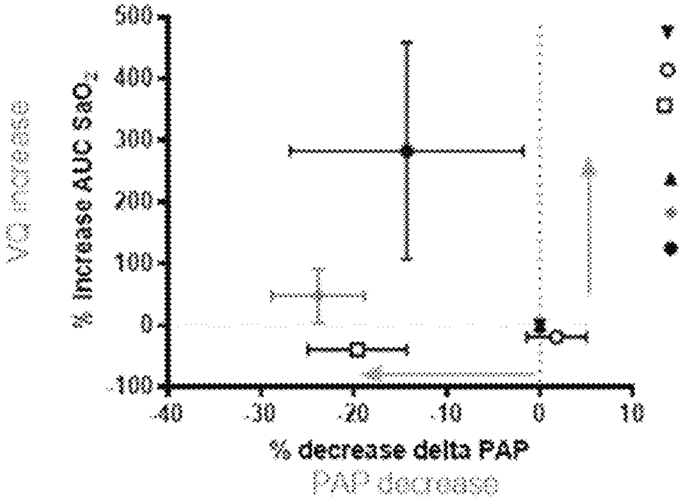

To determine the risk-benefit ratio of the inhaled vs. the i.v. application of comparative example 11, changes in maximal hypoxic PAP on the one hand (reduction as desired effect) and unwanted worsening of desaturation on the other hand were compared. Thus, the mean % changes in maximal hypoxic PAP and associated % changes in area under the oxygen saturation curve [$AUCSaO_2$] were compared (see FIG. 65) within the respective group. As reference cycles in each group, we used cycle 3 for the inhaled applications as well as cycle 4 for the i.v. applications. During unilateral ventilation cycles, hypoxia-induced increases in mean pulmonary artery pressure (mPAP) were effectively reduced by comparative example 11 after inhaled (cycle 6) as well as after i.v. application (cycles 7 and 8). There was no reduction observed in cycle 5, due to the simultaneous application. Regarding the desaturation effects, comparative example 11 did not increase desaturation area after inhaled application, but even showed a trend towards a reduction of the desaturation area. In contrast, after systemic application, comparative example 11 induced a dose dependent increase in desaturation area as described for other systemic applied vasodilators (e.g. bosentan. sildenafil. riociguat) (Ref Becker E M, Stasch J-P, Bechem M, Keldenich J, Klipp A, et al. (2013) Effects of Different Pulmonary Vasodilators on Arterial Saturation in a Model of Pulmonary Hypertension. PLoS ONE 8(8): e73502. doi:10.1371/journal.pone.0073502).

TABLE C2.3.1

Comparative example 11 capacity to decrease maximal hypoxic PAP (positive treatment effect) and AUCSaO2 (unwanted desaturation effect) based on effects of representative cycles (n = 4 animals); data are mean ± SEM (n = 4)

| Vehicle inhalation | | Inhalation I Cycle 5 | | Inhalation II Cycle 6 | | Vehicle Bolus | | iv Bolus 30 µg | | iv Bolus 100 µg | |
|---|---|---|---|---|---|---|---|---|---|---|---|
| % decrease delta PAP | % increase $AUC_{SaO2}$ | % decrease delta PAP | % increase $AUC_{SaO2}$ | % decrease delta PAP | % increase $AUC_{SaO2}$ | % decrease delta PAP | % increase $AUC_{SaO2}$ | % decrease delta PAP | % increase $AUC_{SaO2}$ | % decrease delta PAP | % increase $AUC_{SaO2}$ |
| 0 | 0 | 1.8 ± 3.2 | −18.6 ± 6.7 | −19.6 ± 5.3 | −39.4 ± 10.3 | 0 | 0 | −23.8 ± 5.0 | 48.1 ± 43.7 | −14.3 ± 12.5 | 282.8 ± 176.4 |

In summary, comparative example 11 effectively reduced PAP increase in a model of unilateral broncho-occlusion. In this model, after inhaled application no negative effect on desaturation area in contrast to systemic applied comparative example 11 could be detected. Thus, after inhaled application, comparative example 11 showed a better risk-benefit ratio compared to systemic applied vasodilators and might be an effective but also safe treatment for patients with PH, being at risk for a ventilation-perfusion-mismatch under treatment of systemic applied vasodilators.

C-3. Bronchodilatory Effect In Vitro and In Vivo

C-3.1 Bronchorelaxation In Vitro

Male Dunkin Hartley guinea pig were euthanized using carbon dioxide. The primary bronchus was removed and placed in ice-cold Krebs-Henseleit buffer of following composition (in mmol/l): NaCl 112, KCl 5.9, $CaCl_2$ 2.0 $MgCl_2$ 1.2, $NaH_2PO_4$ 1.2, $NaHCO_3$ 25, glucose 11.5. The bronchus was cut into rings which consisted of 2 bronchial rings and transferred to 20 ml organ baths containing Krebs-Henseleit solution equilibrated with 95% $O_2$, 5% $CO_2$ at 37° C. For recording of isometric tension, the bronchial rings were mounted between two hooks. One hook was connected to a force transducer the other was moveable and allowed a precise adjustment of resting tension at 1.5 g. During the equilibration period of 60 min the tissue was washed every 20 min with buffer. Each experiment was started by exposing the preparation to acetylcholine (10 µmol/1). The trachea rings were than pre-contracted using 0.1 µmol/l carbachol. After 30 min, a cumulative dose response curve of the test compound was constructed. Every concentration was incubated till the response was stable. The stabilized contraction induced by carbachol was defined as 100% tension. The relaxation was expressed as percentage tension. For washout experiments the test compound was applied to the baths at one concentration for 1 h and thereafter washed out using a Krebs-Henseleit buffer containing 0.1 µmol/1 carbachol.

The recovery factor was calculated as a ratio of bronchodilation 1 h after compound application and bronchodilation 1 h after removal (wash out) of test compound. Compared to vehicle control Cinaciguat (comparative example 1), Riociguat (comparative example 2) and Comparative example 11 induced a relaxation of pre-contracted guinea pig trachea rings (see FIG. 66). Relaxation via Cinaciguat (comparative example 1) and Riociguat (comparative example 2) reached a steady state within the 1 h incubation time. Relaxation via Comparative example 11 was further increasing. The relaxation induced by Riociguat (comparative example 2) was completely reversible (recovery factor 0.34). Relaxation induced by Cinaciguat (comparative example 1) remained stable with a slight reduction trend (recovery factor 0.91) similar to vehicle (recovery factor 0.99). In contrast, relaxation induced by comparative example 11 was further progressing during the wash out period (recovery factor 1.41).

These findings suggests a longer duration of action with respect to bronchodilatory properties for comparative example 11 compared to Riociguat and Cinaciguat.

TABLE C3.1.1

Effects of different compounds: comparative example 1 (Cinaciguat) 1 nmol/l, Comparative example 11 1 µmol/l, comparative example 2 (Riociguat) 1 µmol/l) on bronchodilation. Data are presented as mean +/− SEM.

| | Relaxation (%) (timepoint at 70 min) | | | Relaxation (%) (timepoint at 130 min) | | | Recovery factor after |
|---|---|---|---|---|---|---|---|
| Compound | Mean | SEM | n | Mean | SEM | N | 60 min |
| Vehicle | 88.3 | 4.72 | 13 | 88.4 | 4.04 | 13 | 0.99 |
| Comparative example 11 | 72.2 | 4.60 | 11 | 51.3 | 6.29 | 11 | 1.41 |
| comparative example 2, Riociguat | 29.1 | 11.26 | 9 | 85.1 | 5.52 | 9 | 0.34 |
| comparative example 1, Cinaciguat | 60.4 | 4.68 | 12 | 66.2 | 4.10 | 12 | 0.91 |

C-3.2 Bronchorelaxation In Vivo

The bronchoconstriction model (see Hoymann H G. Lung function measurements in rodents in safety pharmacology studies. Front Pharmacol 2012; 3:156) used Male Brown Norway rats (Charles River, Sulzfeld, Germany; 10-12 weeks old) randomized to three treatment groups (comparative example 11, 1 µg/kg, 10 µg/kg, and 100 µg/kg; n=12-13), one positive control group (tiotropium 1 µg/kg; n=12), and one vehicle control group (n=17). Animals were treated with the inhaled test compounds 60 minutes before provocation. Comparative example 11, vehicle, or tiotropium were aerosolized using a micro feeding system and a dispersion nozzle operated with pressurized air. The aerosol concentration was determined by filter sampling with gravimetrical analysis and monitored continuously by a photometer. The lung-deposited doses were assessed from the inhalation dose (Raabe O G, Al-Bayati M A, Teague S V, Rasolt A. Regional Deposition of Inhaled Monodisperse Coarse and Fine Aerosol Particles in Small Laboratory Animals. The Annals of Occupational Hygiene 1988; 32:53-63.). The generation of acetylcholine aerosols for the provocation tests was performed as previously described (Bronchy Type III and a Fraunhofer ITEM dispersion nozzle) (Hoymann H, Heinrich U. Measurement of lung function in rodents in vivo. In: Uhlig S, Taylor A, editors. Methods in Pulmonary Research: Birkhauser Basel; 1998. p. 1-28; Glaab T, Mitzner W, Braun A, Ernst H, Korolewitz R, Hohlfeld J M, Krug N, Hoymann H G. Repetitive measurements of pulmonary mechanics to inhaled cholinergic challenge in spontaneously breathing mice. J Appl Physiol 2004; 97:1104-1111; Hoymann H G. New developments in lung function measurements in rodents. Exp Toxicol Pathol 2006; 57 Suppl 2:5-11.). After treatment and an additional pause to meet the 60 minute-time period from the end of treatment to the beginning of acetylcholine provocation, animals were anesthetized (intraperitoneal 80 mg/kg ketamine and 4 mg/kg xylazine) for orotracheal intubation and placed in a body plethysmograph. Oxygen was adjusted to approximately 40%. After reaching a steady state in respiration, lung function of the spontaneously breathing animal was recorded as baseline values for ≥2 minutes; amongst other parameters, lung resistance (=RL) and dynamic compliance (=Cdyn) were used to assess bronchoconstriction. Data recording and processing were performed using HEM software, version 4.2 (Notocord Systems, Croissy, France). After recording baseline values 60±15 minutes after inhalational treatment, the animals were provoked with acetylcholine (5% aqueous solution aerosol). The assessment of lung function was continued during and for ≥3 minutes after the exposure.

Bronchodilatory efficacy of the test compounds was compared with the vehicle control group and the positive control tiotropium group; parametric tests, ANOVA and parametric Dunnett test were used to assess any significant differences between the groups. To assess efficacy, the inhibition of acetylcholine-induced bronchoconstrictive responses was calculated.

Figures 67A, 67B:
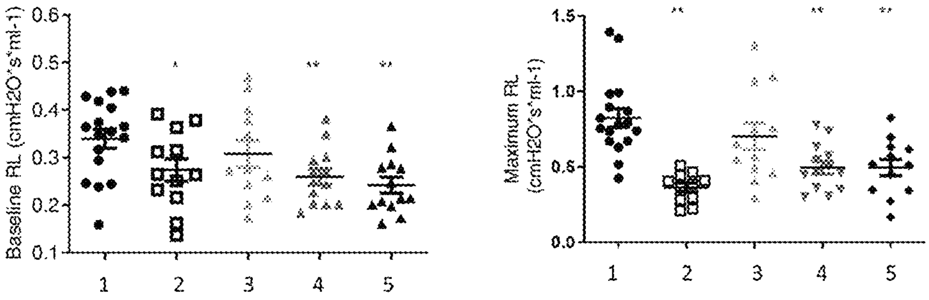

Lung function was measured in anesthetized rats at baseline and after bronchoconstriction (acetylcholine-provocation). To quantify the bronchoconstrictive response to acetylcholine, increases in RL and decreases in Cdyn were evaluated. The long acting cholinergic M3 receptor blocker, tiotropium was used as positive control and inhibited acetylcholine-induced bronchospasm, with RL decreased (see FIGS. 67*a* and 67*b*). Similarly, comparative example 11 induced a dose-dependent significant (1, 10 and 100 µg/kg) bronchodilating effect under baseline as well as acetylcholine-induced bronchospasm.

C-3.3 Chronic Asthma Model

The study was conducted to investigate whether inhalative treatment with comparative example 11 has a protective effect on the experimentally allergen-induced late airway hyperresponsiveness and inflammation in sensitized mice. Female BALB/c mice were sensitized and boosted with Ovalbumin (Ova) and aluminium hydroxide adjuvant (day 0. 14 and 21) with the exception of the negative control group receiving NaCl. On day 28 and 29. the animals were challenged with Ova aerosol. On day 30, a hyperresponsiveness test followed by bronchoalveolar lavage (BAL) was performed in all animals of all groups. The treatment groups D (10 µg) and E (100 µg) were treated with comparative example 11 inhalationally 2 h before each Ova challenge. Group A and B, the positive and negative control groups, were treated correspondingly with the vehicle. The Ova-sensitized positive control group A should show the full allergic reaction and, in contrast, the sham-sensitized negative control group B should show no allergic response. As a reference group, the animals of group C were treated inhalative with the corticosteroid dexamethasone but—due to its different mechanism of action—18 h and 1 h before each Ova challenge (on day 27, 28 and 29). On day 30, 24 h after Ova challenge in the late allergic phase, lung function—especially $R_L$—was measured in the orotracheally intubated mice and a test on airway hyperresponsiveness was performed (inhalational methacholine provocation in doubling dose steps). A marked airway hyperresponsiveness and eosinophilia in the late allergic phase were found in the positive control in comparison to the negative control group which demonstrates the validity of the animal model. The animals treated with dexamethasone showed an 89% and 70% inhibition of the airway hyperresponsiveness (maximum effective dose [$ED_{100}$], 150% of the maximum effective dose [$ED_{150}$]; effective inhalational MCh dose (µg) to produce a 100% or 150% increase in resistance) and a 100% inhibition of the eosinophilic influx. These inhibitory effects show the successful therapeutic intervention. In comparison, comparative example 11 showed no or only marginal effects at the low dose but a certain inhibitory effect at the high dose of 100 µg/kg with 38% and 32% inhibition of the airway hyperresponsiveness (see FIG. 68). Additionally, the pre-treatment with comparative example 11 in the low and high dose groups yielded higher lymphocyte counts than the positive control group but a 19% and 31% inhibition of the eosinophilic influx (see FIGS. 69*a-c*). Overall, in a prophylactic therapy concept using a mouse model of allergic asthma, comparative example 11 showed inhibitory effects on airway hyperresponsiveness and inflammation at a lung-deposited dose of 100 µg/kg.

C-4.1 Inhalative Administration of sGC Activators in Healthy Male Subjects for 7 Days—cGMP and Bronchodilatation Healthy White male subjects, aged 18 to 45 years and with a body mass index (BMI) above/equal 18.5 and below/equal 29.9 kg/m2 were treated in a clinical pharmacological phase I study on seven days with inhaled once daily doses of 480 µg or 1000 µg or 2000 µg (2 capsules of 1000 µg) (nominal dose) of dry powder formulations of example 2 or Placebo. The subjects inhaled the drug powder from capsules (see under D-1, e.g. tables 22 and 23) inserted into a handheld inhalation device by one deep inhalative breath. The dry powder formulation of the drug is dispersed into the air-stream and fine particles are transported into the deep parts of the lung where it is intended to cause a vasodilation of the blood vessels in PH patients for a substantial reduction of increased blood pressure in the central pulmonary blood vessels in PAH patients or other subtypes of PH. This effect cannot be shown in subjects with healthy lungs. In addition inhaled drug causes a dilation of the bronchial airways and thus also improves disease states of lung diseases in PH patients with pathological bronchoconstriction. This effect was measured via bodyplethysmography as reduction of Specific Airway Resistance in healthy subjects. After the deep inhalative breath the subjects hold breath for 2 seconds, so that the dry powder drug condenses from the airstream onto the surface of the deeper lung areas where it is deposited close to its site of intended pharmacological action. The drug dissolutes over the day and equilibrates the lung via lining fluid. As surrogate for drug concentration in the lung, plasma concentrations over time were analysed and showed a maximum blood concentration 2.0 to 2.5 h after inhalation. that thereafter supports drug equilibration of the lung via bloodstream. After first inhalation a measurable plasma concentration was generated that persisted for 48 h as seen for all doses administered, to generate a steady state drug concentration over 24 h after 14 days of once daily inhalation and thus supporting an 24/7 activity of the drug after od inhalation.

Drug activity in healthy men was controlled in the healthy subjects by analysing blood samples for cGMP, the immediate product of sGC pharmacological activation prior after the first and after the last drug inhalation of the 7 days treatment in comparison to measurements on the pretreatment day for all doses.

The analysis of changes from baseline of this parameter showed dose-dependent increases of cGMP, starting at approximately 2 h after first inhalation with a peak at 6 h (480 and 1000 μg dose) and 8 h (2000 μg dose) after administration of example 2 (see FIGS. 70-74). This prolonged activity in comparison to systemic drug concentration is caused by the mode of administration as inhaled dry powder, that deposits drug in the deeper part of the lung leading to an active drug concentration over 24 h after a once daily inhalation. The peak mean±SD cGMP values observed at the first profile day were 8.84±1.35, 11.69±1.86, and 16.52±4.24 nmol/L after administration of 480, 1000, and 2000 μg example 2.

After repeated dosing for 7 days, a further increase of mean peak values for cGMP were observed with 11.96±2.80, 16.70±2.96, and 32.67±9.48 nmol/L after administration of the resp. doses. At 10 days after the first treatment, mean cGMP concentrations had returned close to the concentration observed at the pre-dosing day. The cGMP data show that a once-daily inhalation of the drug example 2 causes the intended dose dependent effect at the sGC target (see FIG. 74).

TABLE C4.1.1

| cyclic guanosine monophosphate changes from baseline (nmol/L) (SAF) | | | | |
|---|---|---|---|---|
| | Placebo | 480 μg, ex. 2 | 1000 μg, ex. 2 | 2000 μg, ex. 2 |
| −0 D 22 H 00 M | 0.47 ± 0.90 | 1.17 ± 1.00 | 0.08 ± 1.41 | 0.66 ± 0.79 |
| −0 D 20 H 00 M | −0.11 ± 1.13 | 0.52 ± 0.95 | −0.24 ± 1.75 | 0.48 ± 0.71 |
| −0 D 18 H 00 M | 0.71 ± 1.41 | 0.21 ± 1.74 | −0.87 ± 1.44 | 0.17 ± 0.78 |
| −0 D 16 H 00 M | −0.26 ± 1.89 | 0.41 ± 0.96 | −0.43 ± 1.49 | 0.29 ± 1.17 |
| −0 D 12 H 00 M | −0.11 ± 1.34 | 0.22 ± 1.17 | −0.77 ± 1.72 | 0.28 ± 0.97 |
| −0 D 09 H 00 M | −0.67 ± 1.25 | 0.20 ± 1.59 | −0.84 ± 2.04 | −0.18 ± 0.90 |
| 0 D 00 H 00 M | −0.77 ± 1.27 | 0.11 ± 1.10 | −0.11 ± 1.62 | 0.68 ± 1.14 |
| 0 D 02 H 00 M | 0.42 ± 0.52 | 1.73 ± 0.82 | 3.26 ± 2.04 | 4.78 ± 1.35 |
| 0 D 04 H 00 M | −0.68 ± 2.23 | 3.04 ± 1.39 | 5.64 ± 2.54 | 9.18 ± 2.50 |
| 0 D 06 H 00 M | −0.40 ± 2.23 | 3.33 ± 1.39 | 6.78 ± 2.79 | 11.04 ± 3.21 |
| 0 D 08 H 00 M | 0.33 ± 2.56 | 2.94 ± 1.38 | 5.94 ± 2.65 | 11.69 ± 2.78 |
| 0 D 12 H 00 M | −0.24 ± 2.07 | 2.10 ± 1.18 | 4.86 ± 2.91 | 8.56 ± 2.19 |
| 0 D 15 H 00 M | −0.58 ± 2.14 | 1.53 ± 1.50 | 3.70 ± 2.59 | 7.54 ± 2.32 |
| 1 D 00 H 00 M | −0.18 ± 2.06 | 0.84 ± 0.89 | 1.26 ± 1.98 | 3.48 ± 0.90 |
| 2 D 00 H 00 M | −0.30 ± 2.26 | 0.74 ± 1.59 | 0.33 ± 1.99 | 1.57 ± 0.86 |
| 3 D 00 H 00 M | −0.14 ± 2.10 | 1.00 ± 1.92 | 2.31 ± 2.68 | 5.17 ± 1.51 |
| 4 D 00 H 00 M | 0.31 ± 1.99 | 1.46 ± 1.24 | 2.86 ± 2.63 | 9.33 ± 2.55 |
| 5 D 00 H 00 M | 0.27 ± 2.34 | 1.50 ± 0.98 | 3.59 ± 2.51 | 11.10 ± 3.49 |
| 6 D 00 H 00 M | 0.71 ± 2.21 | 1.92 ± 1.21 | 4.32 ± 2.82 | 11.71 ± 2.66 |
| 7 D 00 H 00 M | 0.21 ± 0.83 | 1.68 ± 0.85 | 4.74 ± 2.98 | 11.36 ± 3.37 |
| 7 D 02 H 00 M | 0.07 ± 0.81 | 4.22 ± 2.29 | 6.93 ± 2.99 | 17.33 ± 4.18 |
| 7 D 04 H 00 M | 0.20 ± 0.71 | 5.39 ± 2.34 | 10.84 ± 2.91 | 22.23 ± 4.75 |
| 7 D 06 H 00 M | 0.72 ± 1.06 | 6.44 ± 2.26 | 11.79 ± 3.70 | 27.39 ± 6.93 |
| 7 D 08 H 00 M | 1.26 ± 1.68 | 5.19 ± 1.64 | 11.00 ± 4.58 | 27.83 ± 7.77 |
| 7 D 12 H 00 M | 0.59 ± 1.00 | 3.71 ± 1.79 | 9.19 ± 5.26 | 23.33 ± 5.53 |
| 7 D 15 H 00 M | 0.02 ± 0.73 | 3.04 ± 2.09 | 8.00 ± 4.41 | 19.08 ± 4.95 |
| 8 D 00 H 00 M | 0.81 ± 0.54 | 1.69 ± 2.65 | 4.47 ± 3.81 | 11.17 ± 3.69 |
| 8 D 12 H 00 M | 0.66 ± 1.11 | 0.69 ± 1.53 | 2.30 ± 3.05 | 8.02 ± 2.45 |
| 9 D 00 H 00 M | 0.08 ± 0.73 | 0.13 ± 1.97 | 1.38 ± 2.59 | 5.64 ± 1.36 |
| 9 D 12 H 00 M | 0.70 ± 1.64 | 1.10 ± 1.01 | 1.02 ± 2.24 | 4.57 ± 2.15 |
| 10 D 00 H 00 M | 0.89 ± 1.47 | −0.00 ± 0.64 | 1.42 ± 2.87 | 3.26 ± 1.07 |

TABLE C4.1.2

Means (N = 9 each for Placebo, 480, 1000 and 2000 µg, example 2) for cGMP over time: prior to drug inhalation (baseline) (−1 d 02 h-0 d 00 h) after first inhalation day (0 d 00 h-2 d 00 h), trough measurements after inhalations on days 3 d 00 h-7 d 00 h and after last of 7 days of inhalation (7 d 00 h-10 d 00 h).

| | Placebo | 480 µg, ex. 2 | 1000 µg, ex. 2 | 2000 µg, ex. 2 |
|---|---|---|---|---|
| −1 D 02 H 00 M | 5.83 ± 2.01 | 5.40 ± 1.41 | 5.02 ± 1.59 | 4.16 ± 1.70 |
| −0 D 22 H 00 M | 6.30 ± 2.42 | 6.57 ± 1.22 | 5.10 ± 1.46 | 4.81 ± 2.22 |
| −0 D 20 H 00 M | 5.72 ± 2.00 | 5.92 ± 0.83 | 4.78 ± 1.37 | 4.63 ± 1.86 |
| −0 D 18 H 00 M | 6.54 ± 2.68 | 5.61 ± 0.71 | 4.16 ± 0.92 | 4.32 ± 1.33 |
| −0 D 16 H 00 M | 5.58 ± 2.13 | 5.81 ± 1.09 | 4.59 ± 1.06 | 4.44 ± 2.15 |
| −0 D 12 H 00 M | 5.72 ± 2.17 | 5.62 ± 1.26 | 4.26 ± 0.99 | 4.43 ± 2.24 |
| −0 D 09 H 00 M | 5.17 ± 1.90 | 5.60 ± 1.08 | 4.18 ± 0.82 | 3.98 ± 1.91 |
| 0 D 00 H 00 M | 5.07 ± 1.90 | 5.51 ± 1.00 | 4.91 ± 1.27 | 4.83 ± 2.52 |
| 0 D 02 H 00 M | 5.49 ± 2.03 | 7.24 ± 1.25 | 8.17 ± 1.07 | 9.61 ± 3.65 |
| 0 D 04 H 00 M | 4.39 ± 1.20 | 8.56 ± 1.45 | 10.56 ± 1.47 | 14.01 ± 4.51 |
| 0 D 06 H 00 M | 4.67 ± 1.25 | 8.84 ± 1.35 | 11.69 ± 1.86 | 15.88 ± 5.09 |
| 0 D 08 H 00 M | 5.40 ± 1.70 | 8.46 ± 1.59 | 10.86 ± 1.66 | 16.52 ± 4.24 |
| 0 D 12 H 00 M | 4.82 ± 1.35 | 7.61 ± 1.01 | 9.77 ± 2.11 | 13.39 ± 4.01 |
| 0 D 15 H 00 M | 4.49 ± 0.90 | 7.04 ± 1.50 | 8.61 ± 1.63 | 12.38 ± 4.17 |
| 1 D 00 H 00 M | 4.89 ± 1.16 | 6.36 ± 1.10 | 6.17 ± 1.05 | 8.31 ± 2.88 |
| 2 D 00 H 00 M | 4.77 ± 0.74 | 6.26 ± 2.17 | 5.24 ± 1.28 | 6.40 ± 2.09 |
| 3 D 00 H 00 M | 4.92 ± 0.87 | 6.51 ± 2.62 | 7.22 ± 2.04 | 10.00 ± 3.51 |
| 4 D 00 H 00 M | 5.38 ± 1.06 | 6.97 ± 1.96 | 7.77 ± 1.87 | 14.17 ± 4.36 |
| 5 D 00 H 00 M | 5.33 ± 1.07 | 7.01 ± 1.72 | 8.50 ± 2.13 | 15.93 ± 5.52 |
| 6 D 00 H 00 M | 5.78 ± 1.42 | 7.43 ± 1.69 | 9.23 ± 2.12 | 16.54 ± 4.60 |
| 7 D 00 H 00 M | 5.28 ± 1.86 | 7.19 ± 1.47 | 9.66 ± 2.30 | 16.19 ± 5.02 |
| 7 D 02 H 00 M | 5.13 ± 1.97 | 9.73 ± 3.00 | 11.84 ± 2.18 | 22.17 ± 6.07 |
| 7 D 04 H 00 M | 5.27 ± 2.05 | 10.90 ± 3.12 | 15.76 ± 2.29 | 27.07 ± 7.01 |
| 7 D 06 H 00 M | 5.79 ± 2.16 | 11.96 ± 2.80 | 16.70 ± 2.96 | 32.22 ± 8.83 |
| 7 D 08 H 00 M | 6.32 ± 3.30 | 10.70 ± 2.27 | 15.91 ± 3.86 | 32.67 ± 9.48 |
| 7 D 12 H 00 M | 5.66 ± 2.17 | 9.22 ± 2.37 | 14.10 ± 4.55 | 28.17 ± 7.50 |
| 7 D 15 H 00 M | 5.09 ± 1.97 | 8.56 ± 2.80 | 12.91 ± 3.72 | 23.91 ± 6.59 |
| 8 D 00 H 00 M | 5.88 ± 2.07 | 7.20 ± 3.23 | 9.38 ± 3.11 | 16.00 ± 5.77 |
| 8 D 12 H 00 M | 5.72 ± 2.10 | 6.20 ± 2.00 | 7.21 ± 2.24 | 12.86 ± 3.96 |
| 9 D 00 H 00 M | 5.14 ± 1.60 | 5.64 ± 2.53 | 6.29 ± 1.86 | 10.48 ± 3.49 |
| 9 D 12 H 00 M | 5.77 ± 3.38 | 6.61 ± 1.80 | 5.93 ± 1.39 | 9.40 ± 3.10 |
| 10 D 00 H 00 M | 5.96 ± 2.26 | 5.51 ± 1.39 | 6.33 ± 2.30 | 8.09 ± 2.81 |

Figure 75:
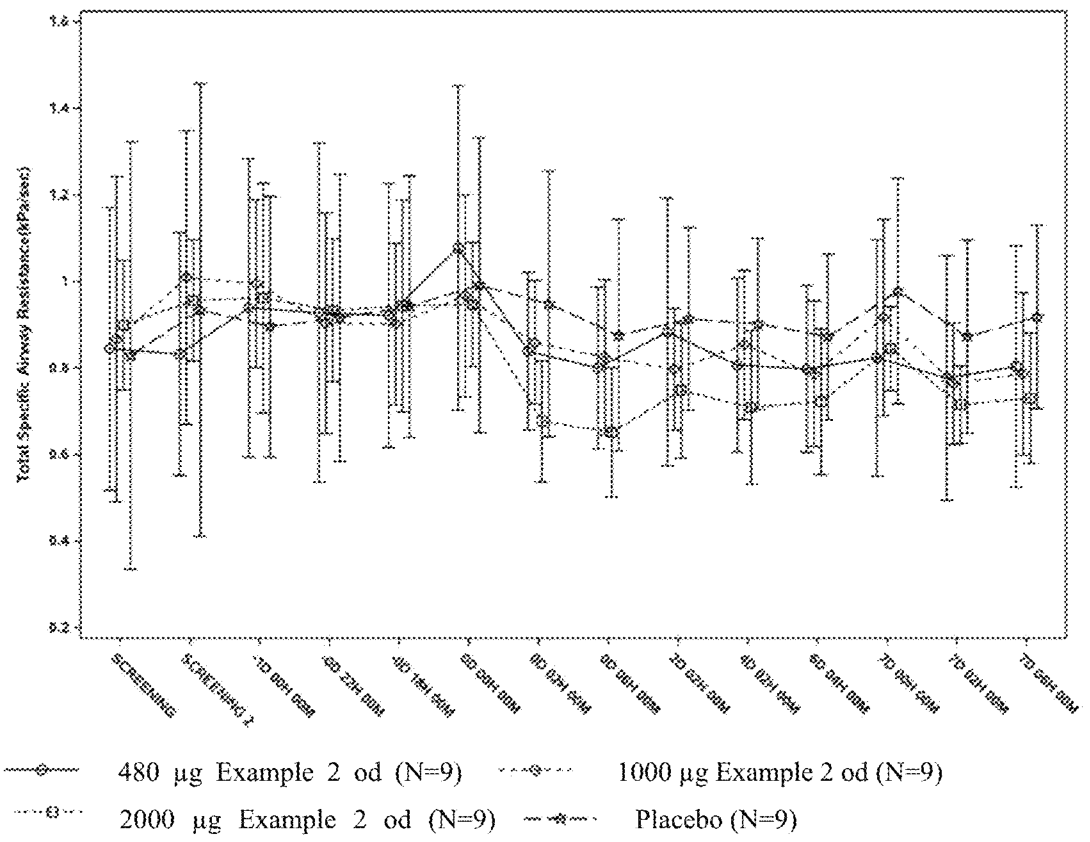

Measurement of lung function parameters via bodyplethysmography showed a decrease of total specific airway resistance sRaw, a parameter for bronchodilative activity in the healthy lung, of −0.142 to −0.296 kPa/sec, measured at 6 h after first dosing example 2 compared to baseline and was observed in all dose groups (see FIG. 75).

TABLE C4.1.3

Means (N = 9 each for Placebo, 480, 1000 and 2000 µg, example 2) for total specific airway resistance (kPa/sec) over time: screening ½, pretreatment day (−1 d 00 h-0 d 00 h) first inhalation day (0 d 00 h-0 d 06 h), measurements after inhalations 2 d 02 h-6 d 04 h) and after last of 7 days inhalation (7 d 00 h-7 d 06 h).

| | Placebo | 480 µg, ex. 2 | 1000 µg, ex. 2 | 2000 µg, ex. 2 |
|---|---|---|---|---|
| SCREENING | 0.829 ± 0.494 | 0.844 ± 0.327 | 0.867 ± 0.376 | 0.899 ± 0.150 |
| SCREENING 2 | 0.934 ± 0.522 | 0.832 ± 0.280 | 1.009 ± 0.340 | 0.957 ± 0.140 |
| −1 D 00 H 00 M | 0.896 ± 0.301 | 0.939 ± 0.344 | 0.996 ± 0.194 | 0.962 ± 0.266 |
| −0 D 22 H 00 M | 0.916 ± 0.332 | 0.928 ± 0.392 | 0.903 ± 0.255 | 0.933 ± 0.165 |
| −0 D 18 H 00 M | 0.942 ± 0.302 | 0.921 ± 0.305 | 0.901 ± 0.187 | 0.943 ± 0.245 |
| 0 D 00 H 00 M | 0.991 ± 0.341 | 1.078 ± 0.375 | 0.967 ± 0.233 | 0.947 ± 0.143 |
| 0 D 02 H 00 M | 0.948 ± 0.307 | 0.839 ± 0.182 | 0.859 ± 0.143 | 0.677 ± 0.139 |
| 0 D 06 H 00 M | 0.876 ± 0.268 | 0.800 ± 0.187 | 0.824 ± 0.180 | 0.651 ± 0.149 |
| 2 D 02 H 00 M | 0.913 ± 0.211 | 0.883 ± 0.310 | 0.797 ± 0.141 | 0.748 ± 0.155 |
| 4 D 02 H 00 M | 0.902 ± 0.197 | 0.807 ± 0.200 | 0.853 ± 0.172 | 0.709 ± 0.178 |
| 6 D 04 H 00 M | 0.872 ± 0.192 | 0.798 ± 0.193 | 0.787 ± 0.168 | 0.722 ± 0.168 |
| 7 D 00 H 00 M | 0.978 ± 0.261 | 0.823 ± 0.274 | 0.917 ± 0.227 | 0.844 ± 0.097 |
| 7 D 02 H 00 M | 0.872 ± 0.223 | 0.777 ± 0.282 | 0.764 ± 0.140 | 0.716 ± 0.089 |
| 7 D 06 H 00 M | 0.918 ± 0.212 | 0.803 ± 0.280 | 0.787 ± 0.188 | 0.730 ± 0.151 |

C-4.2 Inhalative Administration of sGC Activators in Healthy Male Subjects for 14 Days to Evaluate Steady State Pharmacokinetics Healthy white male subjects, aged 18 to 45 years and with a body mass index (BMI) above/equal 18.5 and below/equal 29.9 kg/m2 were treated in a clinical pharmacological phase I study for 14 days with inhaled once daily doses of 1000 μg (nominal dose) or Placebo of dry powder of example 4. The subjects inhaled the drug powder from capsules (see under D-1, e.g. tables 17 and 20) inserted into a handheld inhalation device by one deep inhalative breath into the deep parts of the lung. The intended substantial reduction of increased blood pressure in the central pulmonary blood vessels cannot be evaluated in subjects without pathophysiological impairment of lung function. As surrogate for drug concentration in the lung, plasma concentrations over time have been analysed. This analysis after the doses administered for 14 days to generate a steady state drug concentration over 24 h once daily inhalations showed that maximum drug concentration was reached after 7 to 11 days of inhalation. Drug activity/target engagement in healthy men was controlled in the healthy subjects by analysing blood samples for cGMP. Results are shown in as mean in table C4.2.1 and change to baseline in FIG. 76 and table C4.2.2. Maximum values were reached after 7 days treatment and no further increases were seen during ongoing treatment, showing that steady state of cGMP concentration was reached at latest after 11 days of treatment as biomarker for a constant target engagement.

TABLE C4.2.1

Means +/− standard deviation for Placebo (N = 4) and 1000 μg, (N = 17) example 4) for cGMP concntration over time (nmol/L) on pretreatment day (−1 d 00 h--0 d 09 h) first inhalation day (−0 d 02 h-1 d 00 h;), prior and after inhalations on days 2 d 00 h-2 d 12 h, 6 d 00 h-6 d 12 h, 10 d 00 h-10 d 12 h (profiles), at trough prior inhalation on days 3 d-5 d, 7 d-9 d, 11 d-12 d and prior to and after last of 14 days inhalation (12 d 22 h-20 d 00 h).

| Mean | Placebo (n = 4) | 1000 μg, (n = 17) ex. 4 |
|---|---|---|
| −1 D 02 H 00 M | 4775.0 +/− 1530.5 | 5264.7 +/− 2006.8 |
| −0 D 22 H 00 M | 4800.0 +/− 469.0 | 5164.7 +/− 1680.0 |
| −0 D 20 H 00 M | 4175.0 +/− 1345.1 | 4311.8 +/− 1956.4 |
| −0 D 18 H 00 M | 4925.0 +/− 797.4 | 5011.8 +/− 1875.5 |
| −0 D 16 H 00 M | 5250.0 +/− 914.7 | 5941.2 +/− 2641.7 |
| −0 D 12 H 00 M | 7900.0 +/− 3763.9 | 5570.6 +/− 2087.4 |
| −0 D 09 H 00 M | 6400.0 +/− 1180.4 | 5488.2 +/− 1654.9 |
| −0 D 02 H 00 M | 3900.0 +/− 668.3 | 4329.4 +/− 1509.5 |
| 0 D 02 H 00 M | 6200.0 +/− 1930.5 | 9170.6 +/− 2348.3 |
| 0 D 04 H 00 M | 4625.0 +/− 1173.0 | 11623.5 +/− 2636.9 |
| 0 D 06 H 00 M | 4000.0 +/− 559.8 | 14276.5 +/− 3557.1 |
| 0 D 08 H 00 M | 4500.0 +/− 469.0 | 14888.2 +/− 3618.2 |
| 0 D 12 H 00 M | 4500.0 +/− 1409.5 | 11812.5 +/− 2708.5 |
| 0 D 15 H 00 M | 4750.0 +/− 1443.4 | 11064.7 +/− 2963.1 |
| 1 D 00 H 00 M | 4425.0 +/− 590.9 | 7305.9 +/− 1593.5 |
| 2 D 00 H 00 M | 4200.0 +/− 697.6 | 8876.5 +/− 2507.6 |
| 2 D 03 H 00 M | 5366.7 +/− 1150.4 | 17282.4 +/− 4749.9 |
| 2 D 08 H 00 M | 4700.0 +/− 1493.3 | 20770.6 +/− 6604.0 |
| 2 D 12 H 00 M | 4233.3 +/− 1436.4 | 16941.2 +/− 5408.8 |
| 3 D 00 H 00 M | 4033.3 +/− 1050.4 | 9488.2 +/− 2238.5 |
| 4 D 00 H 00 M | 3466.7 +/− 1429.5 | 10694.1 +/− 2193.0 |
| 5 D 00 H 00 M | 3166.7 +/− 1059.9 | 10252.9 +/− 2390.4 |
| 6 D 00 H 00 M | 4566.7 +/− 2285.5 | 9423.5 +/− 2613.1 |
| 6 D 03 H 00 M | 3800.0 +/− 608.3 | 17735.3 +/− 4290.1 |
| 6 D 08 H 00 M | 4266.7 +/− 1222.0 | 24452.9 +/− 7374.6 |
| 6 D 12 H 00 M | 4266.7 +/− 750.6 | 18194.1 +/− 4785.2 |
| 7 D 00 H 00 M | 3700.0 +/− 1058.3 | 10511.8 +/− 2026.4 |
| 8 D 00 H 00 M | 3733.3 +/− 1331.7 | 10529.4 +/− 1910.7 |
| 9 D 00 H 00 M | 3800.0 +/− 173.2 | 10911.8 +/− 2620.6 |
| 10 D 00 H 00 M | 3766.7 +/− 1011.6 | 10776.5 +/− 2286.0 |
| 10 D 03 H 00 M | 4200.0 +/− 1212.4 | 17058.8 +/− 4319.2 |
| 10 D 08 H 00 M | 4666.7 +/− 1703.9 | 21858.8 +/− 6188.5 |
| 10 D 12 H 00 M | 3800.0 +/− 655.7 | 17329.4 +/− 4529.3 |
| 11 D 00 H 00 M | 3966.7 +/− 1357.7 | 11270.6 +/− 2814.9 |

TABLE C4.2.1-continued

Means +/− standard deviation for Placebo (N = 4) and 1000 μg, (N = 17) example 4) for cGMP concntration over time (nmol/L) on pretreatment day (−1 d 00 h--0 d 09 h) first inhalation day (−0 d 02 h-1 d 00 h;), prior and after inhalations on days 2 d 00 h-2 d 12 h, 6 d 00 h-6 d 12 h, 10 d 00 h-10 d 12 h (profiles), at trough prior inhalation on days 3 d-5 d, 7 d-9 d, 11 d-12 d and prior to and after last of 14 days inhalation (12 d 22 h-20 d 00 h).

| Mean | Placebo (n = 4) | 1000 μg, (n = 17) ex. 4 |
|---|---|---|
| 12 D 00 H 00 M | 4400.0 +/− 1389.2 | 12388.2 +/− 3016.4 |
| 12 D 22 H 00 M | 4466.7 +/− 1021.4 | 11276.5 +/− 3261.8 |
| 13 D 02 H 00 M | 3800.0 +/− 700.0 | 13447.1 +/− 2802.9 |
| 13 D 04 H 00 M | 3200.0 +/− 624.5 | 17276.5 +/− 4328.9 |
| 13 D 06 H 00 M | 3633.3 +/− 461.9 | 21370.6 +/− 5581.2 |
| 13 D 08 H 00 M | 3933.3 +/− 901.8 | 22047.1 +/− 5535.0 |
| 13 D 12 H 00 M | 3700.0 +/− 964.4 | 17217.6 +/− 4806.0 |
| 13 D 15 H 00 M | 3433.3 +/− 896.3 | 16382.4 +/− 4045.9 |
| 14 D 00 H 00 M | 3300.0 +/− 1053.6 | 9735.3 +/− 2740.0 |
| 15 D 00 H 00 M | 3433.3 +/− 960.9 | 6852.9 +/− 1222.3 |
| 15 D 12 H 00 M | 4533.3 +/− 1680.3 | 7370.6 +/− 1654.8 |
| 16 D 00 H 00 M | 3666.7 +/− 665.8 | 6329.4 +/− 1357.3 |
| 16 D 12 H 00 M | 4800.0 +/− 1500.0 | 6735.3 +/− 1394.6 |
| 17 D 00 H 00 M | 2866.7 +/− 577.4 | 4729.4 +/− 995.5 |
| 20 D 00 H 00 M | 4033.3 +/− 1893.0 | 5518.8 +/− 1505.2 |
| FOLLOW-UP | 4566.7 +/− 1078.6 | 5847.1 +/− 2013.4 |

TABLE C4.2.2 cGMP changes from baseline (nmol/L) on pretreatment day (−1 d 00 h--0 d 09 h) first inhalation day (−0 d 02 h-1 d 00 h;), after inhalations on days 2 d 00 h-2 d 12 h, 6 d 00 h-6 d 12 h, 10 d 00 h-10 d 12 h (profile days), at trough prior inhalation on days 3 d-5 d, 7 d-9 d, 11 d-12 d) and after last of 14 days inhalation (12 d 22 h-20 d 00 h)

| Delta baseline | Placebo (n = 4) | 1000 μg, (n = 17) ex. 4 |
|---|---|---|
| −1 D 02 H 00 M | baseline | baseline |
| −0 D 22 H 00 M | 25.0 +/− 1408.0 | −100.0 +/− 1403.1 |
| −0 D 20 H 00 M | −600.0 +/− 2219.6 | −952.9 +/− 1984.7 |
| −0 D 18 H 00 M | 150.0 +/− 2120.5 | −252.9 +/− 1345.9 |
| −0 D 16 H 00 M | 475.0 +/− 2091.8 | 676.5 +/− 1844.1 |
| −0 D 12 H 00 M | 3125.0 +/− 2742.7 | 305.9 +/− 1880.3 |
| −0 D 09 H 00 M | 1625.0 +/− 2118.8 | 223.5 +/− 1396.2 |
| −0 D 02 H 00 M | baseline | baseline |
| 0 D 02 H 00 M | 2300.0 +/− 1529.7 | 4841.2 +/− 2006.9 |
| 0 D 04 H 00 M | 725.0 +/− 981.1 | 7294.1 +/− 2972.3 |
| 0 D 06 H 00 M | 100.0 +/− 516.4 | 9947.1 +/− 3796.2 |
| 0 D 08 H 00 M | 600.0 +/− 778.9 | 10558.8 +/− 3607.1 |
| 0 D 12 H 00 M | 600.0 +/− 1067.7 | 7531.3 +/− 3057.2 |
| 0 D 15 H 00 M | 850.0 +/− 1097.0 | 6735.3 +/− 2917.4 |
| 1 D 00 H 00 M | 525.0 +/− 1158.7 | 2976.5 +/− 1785.2 |
| 2 D 00 H 00 M | 300.0 +/− 1067.7 | 4547.1 +/− 2374.4 |
| 2 D 03 H 00 M | 1600.0 +/− 1058.3 | 12952.9 +/− 4814.8 |
| 2 D 08 H 00 M | 933.3 +/− 1059.9 | 16441.2 +/− 6525.1 |
| 2 D 12 H 00 M | 466.7 +/− 1527.5 | 12611.8 +/− 5555.1 |
| 3 D 00 H 00 M | 266.7 +/− 1594.8 | 5158.8 +/− 2554.4 |
| 4 D 00 H 00 M | −300.0 +/− 1833.0 | 6364.7 +/− 2482.9 |
| 5 D 00 H 00 M | −600.0 +/− 1646.2 | 5923.5 +/− 2801.2 |
| 6 D 00 H 00 M | 800.0 +/− 2330.2 | 5094.1 +/− 2382.9 |
| 6 D 03 H 00 M | 33.3 +/− 945.2 | 13405.9 +/− 4568.6 |
| 6 D 08 H 00 M | 500.0 +/− 1819.3 | 20123.5 +/− 7302.6 |
| 6 D 12 H 00 M | 500.0 +/− 1081.7 | 13864.7 +/− 4528.5 |
| 7 D 00 H 00 M | −66.7 +/− 1429.5 | 6182.4 +/− 2095.9 |
| 8 D 00 H 00 M | −33.3 +/− 1934.8 | 6200.0 +/− 2018.7 |
| 9 D 00 H 00 M | 33.3 +/− 776.7 | 6582.4 +/− 2425.7 |
| 10 D 00 H 00 M | 0.0 +/− 1311.5 | 6447.1 +/− 2255.0 |
| 10 D 03 H 00 M | 433.3 +/− 1450.3 | 12729.4 +/− 4182.7 |
| 10 D 08 H 00 M | 900.0 +/− 1907.9 | 17529.4 +/− 6277.2 |
| 10 D 12 H 00 M | 33.3 +/− 1184.6 | 13000.0 +/− 4616.5 |
| 11 D 00 H 00 M | 200.0 +/− 1915.7 | 6941.2 +/− 2865.1 |
| 12 D 00 H 00 M | 633.3 +/− 2064.8 | 8058.8 +/− 2949.8 |
| 12 D 22 H 00 M | 700.0 +/− 1200.0 | 6947.1 +/− 3016.4 |
| 13 D 02 H 00 M | 33.3 +/− 503.3 | 9117.6 +/− 2994.0 |
| 13 D 04 H 00 M | −566.7 +/− 251.7 | 12947.1 +/− 4570.3 |
| 13 D 06 H 00 M | −133.3 +/− 896.3 | 17041.2 +/− 5998.9 |
| 13 D 08 H 00 M | 166.7 +/− 1422.4 | 17717.6 +/− 5772.9 |

TABLE C4.2.2-continued cGMP changes from baseline (nmol/L) on pretreatment day (−1 d 00 h--0 d 09 h) first inhalation day (−0 d 02 h-1 d 00 h;), after inhalations on days 2 d 00 h-2 d 12 h, 6 d 00 h-6 d 12 h, 10 d 00 h-10 d 12 h (profile days), at trough prior inhalation on days 3 d-5 d, 7 d-9 d, 11 d-12 d) and after last of 14 days inhalation (12 d 22 h-20 d 00 h)

| Delta baseline | Placebo (n = 4) | 1000 µg, (n = 17) ex. 4 |
|---|---|---|
| 13 D 12 H 00 M | −66.7 +/− 1331.7 | 12888.2 +/− 4847.5 |
| 13 D 15 H 00 M | −333.3 +/− 1159.0 | 12052.9 +/− 3938.8 |
| 14 D 00 H 00 M | −466.7 +/− 1550.3 | 5405.9 +/− 3158.2 |
| 15 D 00 H 00 M | −333.3 +/− 1436.4 | 2523.5 +/− 1666.0 |
| 15 D 12 H 00 M | 766.7 +/− 1628.9 | 3041.2 +/− 1792.7 |
| 16 D 00 H 00 M | −100.0 +/− 1058.3 | 2000.0 +/− 1581.1 |
| 16 D 12 H 00 M | 1033.3 +/− 2003.3 | 2405.9 +/− 1555.4 |
| 17 D 00 H 00 M | −900.0 +/− 964.4 | 400.0 +/− 1434.8 |
| 20 D 00 H 00 M | 266.7 +/− 2542.3 | 1218.8 +/− 1715.1 |
| FOLLOW-UP | 800.0 +/− 1743.6 | 1517.6 +/− 2343.9 |

C-4.3 Inhalative, Oral and Intravenous Administration of Single Doses of sGC an Activator in Healthy Male Subjects—Lung Deposition Healthy white male subjects, aged 18 to 45 years with a body mass index (BMI) above/equal 18.5 and below/equal 29.9 kg/$m^2$ were treated in a clinical phase I study with a single inhaled dose of 1000 µg (nominal dose), a single inhaled dose of 1000 µg (nominal dose)+charcoal block, a single oral dose of 1000 µg and a single infusion over 2 h of 100 µg of example 4. As the bioavailability of an intravenous application is generally 100% per definition and therefore higher than in case of an oral or intravenous administration, the intravenous dose was carefully selected to be lower than the oral and inhaled dose to avoid higher plasma concentration resulting from a high IV dose and potential side effect, e.g. reduction in blood pressure or syncope. Therefore, 100 µg was selected for the IV dose in this investigation. Seven days washout period between treatments was applied. The subjects swallowed a solution for oral administration (20 ml comprising 1000 µg, see under D-2, table 50). The subjects received a solution as a single infusion over 2 hours (see under D-2 table 50). The subjects inhaled the drug powder from capsules (see under D-1, e.g. tables 17 and 20) inserted into a handheld inhalation device by one deep inhalative breath. After inhalation of the dry powder formulation of this drug, some parts of the nominal dose remain in the capsule and the device, the dose which reaches the body at the mouthpiece is called the emitted dose. The emitted dose can be calculated/determined as followed: nominal dose−(remains in the capsule+remains in the device). After inhalation of the dry powder, one part of the emitted dose enters the gastrointestinal tract (GIT) and is called the oral part of the emitted dose, the other part of the emitted dose which reaches the lung through the respiratory airways is called the lung dose and represents the lung deposited dose. As the lung is the target organ of the effect, the lung deposited dose must be quantified. Lung deposition can be indirectly estimated, by determining the part of the nominal dose which reaches the GIT and the remains in the capsule and the device. To investigate and determine lung deposition, the following investigations were done (see also FIG. 77):

1—Inhaled application of a single dose of 1000 µg of the dry powder.

2—Inhaled application of a single dose of 1000 µg of the dry powder in combination with oral administration of charcoal block. The charcoal block capped the oral absorption of GIT part of the dose, as example 4 completely adsorbed to charcoal block. This implies that the concentrations of example 4 measured reach the systemic circulation via the lung.

3—Administration of a single oral dose of 1000 µg example 4 to determine the oral absorption.

4—Administration of a 2 h infusion of example 4 to investigate the elimination.

Plasma concentrations of example 4 were measured after all different types of administrations, in addition the remains in the device and the capsule were measured after inhaled application. The analysis of plasma concentrations showed a rapid elimination of example 4 after intravenous administration with an elimination half-life of 0.26 h. The elimination half-life after oral administration was 4.43 h. The elimination half-life after inhaled application with/without charcoal was 16.1 h and 15.1 h, respectively, see FIG. 78. The longer terminal half-life after inhalation can be explained by the formation of a pulmonary depot of example 4 in the lungs from which the substance is continuously transferred to the circulatory system.

The absolute bioavailability of the dry powder formulation administered with charcoal was 16.3% and 18.8% for example 4 administered without charcoal. This means 16.3% of the nominal dose of dry powder of example 4 reached the lung considered as the lung dose, and the total part of the dry powder reaching the body is 18.8% of the nominal dose. The relative bioavailability of example 4 after inhaled application with charcoal block to inhaled administration without charcoal block is 86.9%. This indicates that the oral part of the dose is approximately 13% of the nominal dose. See tables C4.3.1 and C4.3.2. The emitted dose is calculated to be 720 µg, as the remains in the capsule were 160 µg and the remains in the device were 120 µg, see FIG. 79.

The outcome from this investigation confirms the lung dose and that the half-life is adequate for an inhaled dry powder administration enabling a once daily treatment for a sufficient 24 h drug coverage of example 4 in the lung.

TABLE C4.3.1

Geometric mean of plasma concentrations (in µg/L) over time of example 4 and (geometric standard deviation SD in %) after administration of 1000 µg inhale, 1000 µg inhale + charcoal and 100 µg oral

| time after dose | 1000 µg ex. 4, inhale + Charcoal Block N = 16 | | 1000 µg ex. 4, inhale N = 16 | | 1000 µg ex. 4, oral N = 16 | |
|---|---|---|---|---|---|---|
| (h) | geo. mean | geo.SD | geo. mean | geo.SD | geo.mean | geo.SD |
| 0 | >0.0500 | n.a. | >0.0500 | n.a. | >0.0500 | n.a. |
| 0.25 | 0.0583 | (1.78) | 0.0628 | (1.79) | 0.777 | (1.44) |
| 0.5 | 0.261 | (1.56) | 0.316 | (1.32) | 3.64 | (1.30) |
| 0.75 | 0.491 | (1.46) | 0.622 | (1.32) | 5.28 | (1.32) |
| 1 | 0.662 | (1.43) | 0.869 | (1.29) | 5.68 | (1.35) |
| 1.5 | 0.900 | (1.39) | 1.16 | (1.30) | 4.69 | (1.31) |
| 2 | 0.969 | (1.38) | 1.20 | (1.31) | 3.32 | (1.33) |
| 2.5 | 1.02 | (1.31) | 1.18 | (1.32) | 2.26 | (1.31) |
| 3 | 0.933 | (1.33) | 1.07 | (1.32) | 1.60 | (1.36) |
| 4 | 0.812 | (1.29) | 0.927 | (1.31) | 1.01 | (1.46) |
| 6 | 0.508 | (1.31) | 0.583 | (1.30) | 0.424 | (1.33) |
| 8 | 0.373 | (1.37) | 0.415 | (1.36) | 0.233 | (1.31) |
| 12 | 0.220 | (1.43) | 0.250 | (1.37) | 0.126 | (1.38) |
| 15 | 0.157 | (1.46) | 0.181 | (1.43) | 0.0714 | (1.60) |
| 24 | 0.0931 | (1.81) | 0.106 | (1.69) | n.a. | n.a. |
| 28 | 0.0761 | (1.69) | 0.0793 | (1.77) | n.a. | n.a. |
| 32 | 0.0696 | (1.63) | 0.0698 | (1.79) | n.a. | n.a. |
| 36 | 0.054 | (1.79) | 0.058 | (1.86) | n.a. | n.a. |

TABLE C4.3.2

Geometric mean of plasma concentrations (in μg/L) over time of example 4 and (geometric standard deviation SD in %) after administration of 100 μg intravenously

| time after dose | 100 μg ex. 4, IV mg N = 15 | |
|---|---|---|
| (h) | geo.Mean | geo.SD |
| 0 | >0.0500 | n.a. |
| 0.25 | 1.76 | (1.20) |
| 0.5 | 2.52 | (1.11) |
| 0.75 | 2.68 | (1.14) |
| 1 | 2.99 | (1.12) |
| 1.5 | 3.15 | (1.17) |
| 2 | 3.07 | (1.19) |
| 2.083 | 2.57 | (1.16) |
| 2.25 | 1.42 | (1.20) |
| 2.5 | 0.559 | (1.19) |
| 2.75 | 0.264 | (1.23) |
| 3 | 0.132 | (1.24) |

C-4.4 Inhaled Administration of Single Doses to Patients with PAH or CTEPH to Investigate the Reduction of Pulmonary Vascular Resistance (PVR)

Patients with PAH or CTEPH were treated in a clinical phase 1b study with escalating orally inhaled single* doses of 240 μg (2 capsules of 120 μg), 480 μg, 1000 μg, 2000 (2 capsules of 1000 μg) or 4000 μg (4 capsules of 1000 μg) of a dry powder of example 4 (see under D-1, e.g. tables 17 and 20), inserted into a handheld inhalation device, inhaled by deep inhalative breath into the deep parts of the lung. (*single dose means the administration of one dosage form/capsule as well as administration of two or more dosage forms/capsules simultaneously or consecutively within a short time period). The included patients had no background treatment with standard of care (SoC) medication for PAH or CTEPH (such as endothelin antagonists, prostanoids, phosphodiesterase type 5 inhibitor or soluble guanylate cyclase stimulators). Patients in this study underwent invasive right heart catheterization as medically indicated routine diagnostic. Primary objective of the study was to investigate the peak percent reduction from baseline in PVR. Patients had to have a baseline pulmonary artery pressure (mPAP) of ≥25 mmHg and a PVR of ≥400 dyn·sec·$cm^{-5}$ (5 Wood Units) and were not to show vaso-responsiveness to initial iNO inhalation testing to be included in the per protocol analysis. Plasma concentrations (pharmacokinetics) of the administered drug at several time points after administration were measured and safety and tolerability was assessed.

The study is divided into two parts, Part A and Part B. In Part A escalating aforementioned single doses were administered to patients without background treatment with standard of care (SoC) medication for PAH or CTEPH (such as endothelin antagonists, prostanoids, phosphodiesterase type 5 inhibitor or soluble guanylate cyclase stimulators). In Part B, after finalization of Part A, a selected dose from PartA will be tested in further patients without background SoC treatment (group 1) and additionally in patients on monotherapy with SoC (group 2) and on dual combination therapy with SoC (group 3).

The PVR is a derived parameter from parameters directly measured during the right heart catheterization procedure. The direct parameters included in the calculation are: mean pulmonary arterial pressure [mmHg](mPAP), pulmonary capillary wedge pressure [mmHg] (PCWP), and cardiac output [l/min] (CO). The PVR is calculated according to the formula: PVR [dyn*see*$cm^{-5}$]=80*(mPAP-PCWP)/CO.

Figure 82:
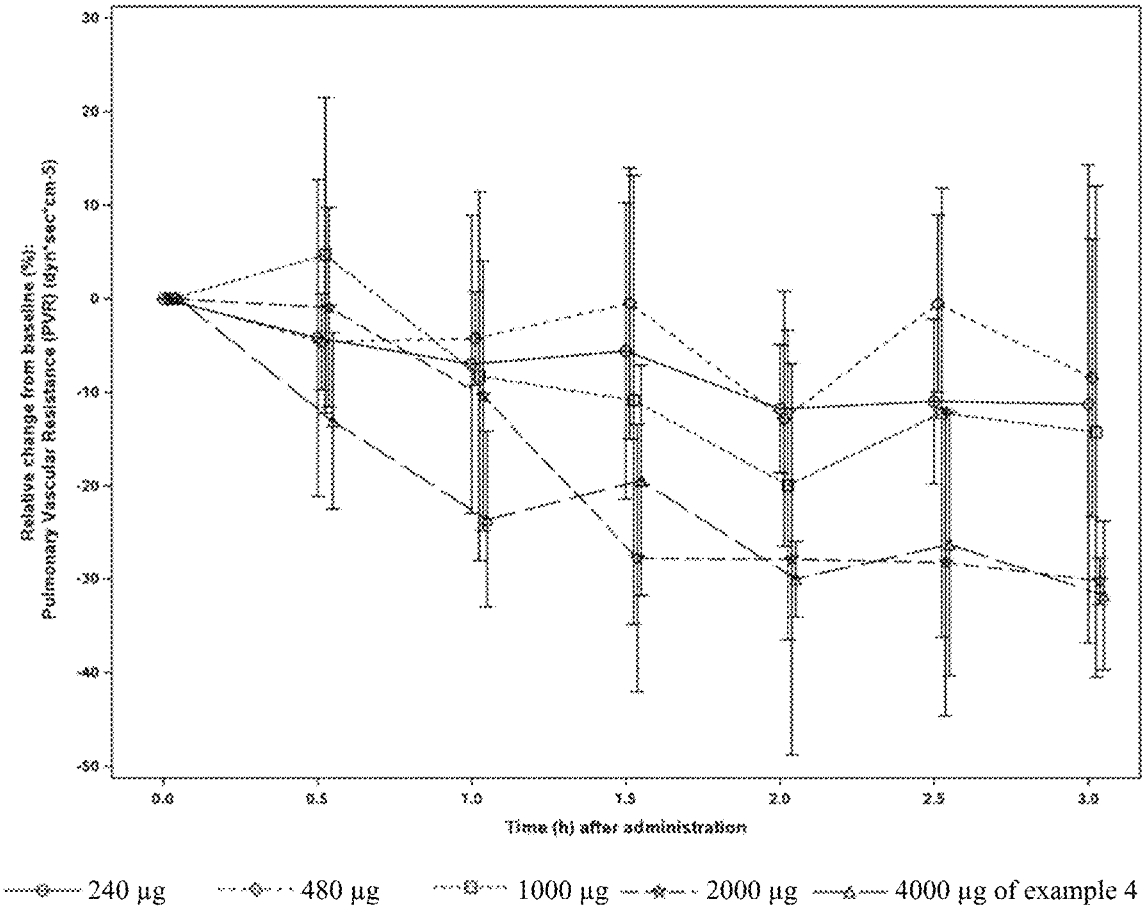

The study design is shown in FIG. 80 and the summary of the finalized Part A is shown in FIG. 81. Overall 38 patients received a dose of dry powder of example 4. A total of 4 patients in each dose group were included into the per protocol set as planned (total 20 patients). A dose-dependent mean change of PVR from baseline could be clearly observed peaking in an enduring mean change of approximately −30% in the 2000 μg and 4000 μg groups (for details of PVR see FIG. 82 and table C4.4.1). The decreases in PVR were predominantly driven by decreases in pulmonary arterial pressure (for details of mean PAP see FIG. 83 and table C4.4.2). A mean peak change level of −20%—as the predefined relevant threshold level—was clearly exceeded peaking in the 2000 μg and 4000 μg groups (mean peak changes were: −21.0%, −16.1%, −25.9%, −38.1%, −36.3% for 240, 480, 1000, 2000, and 4000 μg, respectively). The magnitude of mean change in PVR of −30% from baseline was at the same level as for the inhaled competitor Treprostinil (Tyvaso®) after single administration in a historical comparison [Voswinckel et al, *Journal of American College of Cardiology* Vol. 48, No. 8, 2006 Oct. 17, 2006:1672-81]. However, the effect after example 4 application was advantageously sustained with no decrease in response until the end of the measurement period of 3 h (a measurement period of >3 h was technically not feasible for the patients with right heart catheter in the study). A lung retention time beyond the 3 h of measurement (presumably over a time period of more than 12 hrs, up to 24 hrs after dry powder application) can be concluded from the long plasma half-life of example 4 as measured in an another study (see C-4-3). Increase of systemic cGMP (cyclic Guanosine Monophosphate) confirmed strong target engagement of sGC activation. Overall good tolerability was seen including the highest dose of 4000 μg. Observed changes of systemic blood pressure, heart rate and oxygen saturation did not represent a safety concern at any dose. Overall, the observed changes of the pulmonary haemodynamic parameters (PVR and mPAP) without relevant changes in systemic hemodynamics are in well accordance with the desired effect of selective pulmonary vasodilation.

TABLE C4.4.1

Means and SDs for pulmonary vascular resistance (PVR) over time at baseline (0 D 00 H 00 M) and after inhalation (0 D 00 H 30 M until 0 D 03 H 00 M) of example 4 in patients with PAH or CTEPH (N = 4 each for 240, 480, 1000, 2000 and 4000 μg group, per protocol set). Relative changes from baseline are shown in FiIG. 82.

| | 240 μg, N = 4 | 480 μg, N = 4 | 1000 μg, N = 4 | 2000 μg, N = 4 | 4000 μg, N = 4 |
|---|---|---|---|---|---|
| 0 D 00 H 00 M | 788.338 ± 416.914 | 1055.863 ± 317.077 | 608.898 ± 135.153 | 468.608 ± 20.537 | 713.998 ± 117.204 |
| 0 D 00 H 30 M | 749.012 ± 398.928 | 1003.264 ± 300.639 | 645.387 ± 211.946 | 464.586 ± 58.200 | 616.894 ± 97.774 |
| 0 D 01 H 00 M | 734.427 ± 396.799 | 1007.504 ± 290.883 | 558.324 ± 169.860 | 421.730 ± 81.602 | 542.417 ± 97.103 |
| 0 D 01 H 30 M | 726.362 ± 364.099 | 1031.647 ± 252.210 | 542.130 ± 187.227 | 340.782 ± 82.566 | 573.812 ± 123.865 |
| 0 D 02 H 00 M | 710.844 ± 410.668 | 908.704 ± 252.569 | 487.951 ± 144.546 | 339.924 ± 105.884 | 501.07 ± 97.979 |

TABLE C4.4.1-continued

Means and SDs for pulmonary vascular resistance (PVR) over time at baseline (0 D 00 H 00 M) and after inhalation (0 D 00 H 30 M until 0 D 03 H 00 M) of example 4 in patients with PAH or CTEPH (N = 4 each for 240, 480, 1000, 2000 and 4000 μg group, per protocol set). Relative changes from baseline are shown in FiIG. 82.

| | 240 μg, N = 4 | 480 μg, N = 4 | 1000 μg, N = 4 | 2000 μg, N = 4 | 4000 μg, N = 4 |
|---|---|---|---|---|---|
| 0 D 02 H 30 M | 716.209 ± 419.311 | 1038.344 ± 263.837 | 537.812 ± 204.640 | 338.404 ± 87.381 | 526.648 ± 144.679 |
| 0 D 03 H 00 M | 657.829 ± 291.191 | 909.265 ± 259.510 | 535.636 ± 235.786 | 327.284 ± 25.882 | 493.103 ± 130.480 |

TABLE C4.4.2

Figure 83:
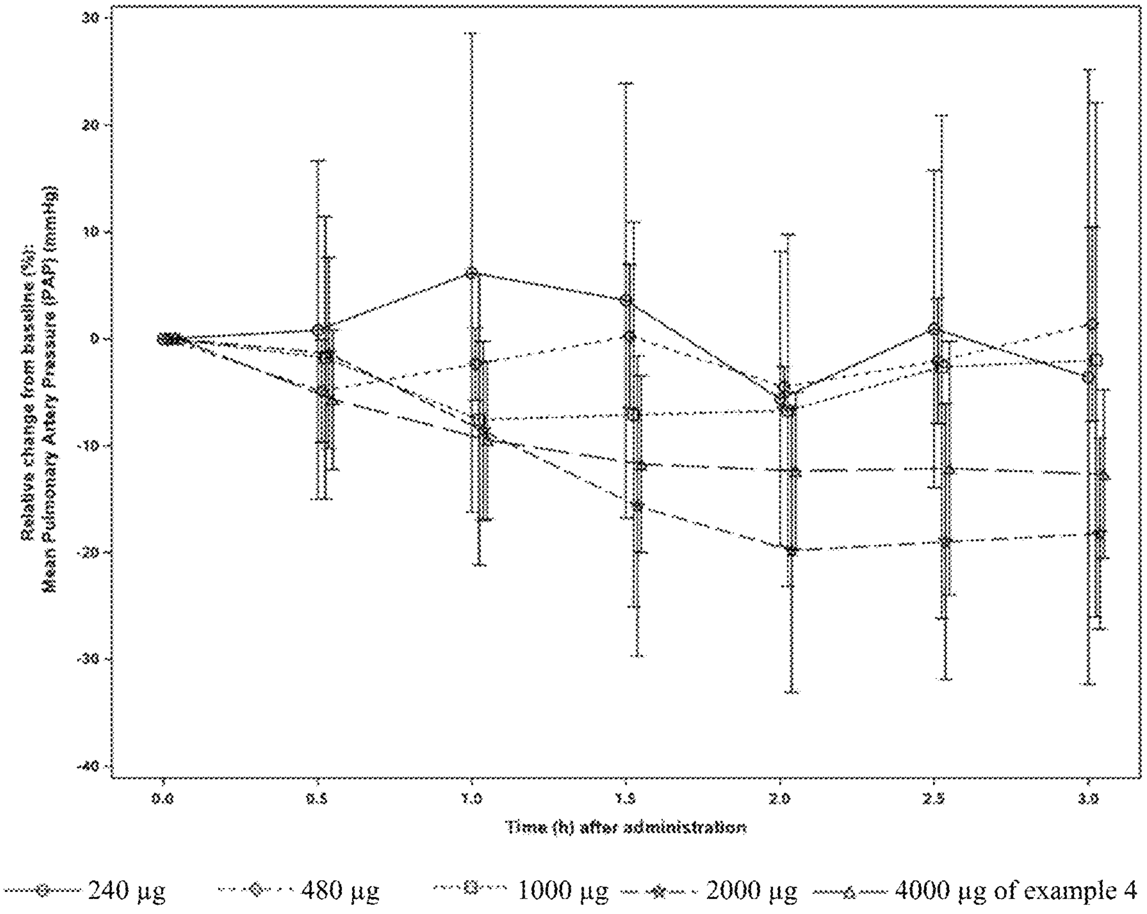

Means and SDs for mean pulmonary arterial pressure (mPAP) over time at baseline (0 D 00 H 00 M) and after inhalation (0 D 00 H 30 M until 0 D 03 H 00 M) of example 4 in patients with PAH or CTEPH (N = 4 each for 240, 480, 1000, 2000 and 4000 μg group, per protocol set). Relative changes from baseline are shown in FIG. 83.

| | 240 μg, N = 4 | 480 μg, N = 4 | 1000 μg, N = 4 | 2000 μg, N = 4 | 4000 μg, N = 4 |
|---|---|---|---|---|---|
| 0 D 00 H 00 M | 42.8 ± 11.1 | 55.0 ± 8.6 | 34.3 ± 4.9 | 33.5 ± 3.4 | 46.0 ± 8.1 |
| 0 D 00 H 30 M | 42.5 ± 11.0 | 52.3 ± 8.4 | 33.8 ± 7.5 | 33.3 ± 6.3 | 43.0 ± 4.6 |
| 0 D 01 H 00 M | 44.3 ± 10.4 | 53.8 ± 9.1 | 31.8 ± 7.4 | 30.8 ± 5.6 | 41.3 ± 4.6 |
| 0 D 01 H 30 M | 43.0 ± 8.0 | 55.0 ± 8.0 | 32.0 ± 8.9 | 28.5 ± 7.3 | 40.3 ± 5.1 |
| 0 D 02 H 00 M | 39.5 ± 7.9 | 52.5 ± 7.9 | 32.3 ± 9.0 | 27.0 ± 6.1 | 40.0 ± 5.3 |
| 0 D 02 H 30 M | 42.0 ± 6.5 | 54.0 ± 9.7 | 33.5 ± 10.7 | 27.3 ± 6.0 | 39.8 ± 3.0 |
| 0 D 03 H 00 M | 39.0 ± 4.2 | 56.0 ± 11.1 | 34 .0 ± 11.6 | 27.5 ± 5.2 | 39.8 ± 4.1 |

C-5. Further Characterization

C-5.1 Caco-2 Permeability Test

The in vitro permeation of a test compound across a Caco-2 cell monolayer is a well-established assay system to predict the permeability from the gastro-intestinal tract (1). The permeability of the compounds of the present invention in such Caco-2 cells was determined as described below:

Human caco-2 cells were seeded on 24-well insert plates and were allowed to grow for 14-16 days. For permeability studies, the test compounds were dissolved in DMSO and diluted to the final test concentration of 2 μM with transport buffer [Hanks' Buffered Salt Solution, Gibco/Invitrogen, further supplemented with glucose and HEPES]. For determination of the apical to basolateral permeability (PappA-B), the test compound solution was added to the apical side of the cell monolayer and transport buffer to the basolateral side of the monolayer; for determination of the basolateral to apical permeability (PappB-A), the test compound solution was added to the basolateral side of the cell monolayer and transport buffer to the apical side of the monolayer. Samples were taken from the donor compartment at the beginning of the experiment to confirm mass balance. After an incubation of 2 h at 37° C., samples were taken from both compartments. Samples were analyzed by LC-MS/MS, and the apparent permeability coefficients were calculated. Lucifer Yellow permeability was assayed for each cell monolayer to ensure cell monolayer integrity, and the permeability of Atenolol (low permeability marker) and Sulfasalazine (marker for active excretion) was determined for each batch as quality control.

TABLE C5.1.1

| Permeability test | | | |
|---|---|---|---|
| Caco-2 (2 μM) | Papp A-B (nm/s) (mean +/− SD) | Papp B-A (nm/s) (mean +/− SD) | Efflux ratio |
| comparative example 11 (2.0 μM) | 15.1 ± 1.7 | 9.7 ± 0.6 | 0.64 ± 0.1 |
| Comparative example 2 (Riociguat) (2.4 μM) | 35 ± 8.4 | 367 ± 75 | 11 ± 3.3 |
| Comparative example 1 (Cinaciguat) (2.0 μM) | 31 ± 3.9 | 631 ± 71 | 20 ± 3.5 |

All three examples showed moderate permeability in Caco-2 cells.

In comparison to comparative example 2 (Riociguat) and comparative example 1 (Cinaciguat), comparative example 11 shows the lowest permeability with 15.1+/−1.7 nm/s. Additionally comparative example 11 does not show an efflux ratio. Efflux ratios are indicating transporter involvement in e.g. the gut and or the liver. Transporter proteins as e.g. permeability glycoprotein (=PgP) or Breast Cancer Resistance Protein (=BCRP) could influence the systemic exposure of a drug.

Comparative example 11 shows here a clear benefit, because it shows the lowest permeability and no transporter involvement seems to be present thus showing its suitability for a local inhalative treatment with a potentially very low systemic exposure.

C-5.2 Proteinbinding

Proteinbinding of Comparative Example 11 and Comparative Example 1 was Analyzed Via Transil Assay, Described Below.

The distribution of a test substance between Transil® (phosphatidylcholine lipid bilayers immobilized on silica beads) and plasma is a characteristic feature of any pharmaceutical compound and is dependent on its extent of binding to plasma proteins. By comparing the distribution between Transil® and buffer with the distribution between Transil® and plasma of any species of interest, the unbound fraction in the plasma of the respective animal species can be calculated in vitro. The respective plasma and buffer concentrations were determined via a radioactivity analysis. A detailed description of the method and its validation was published by Schuhmacher et al. (2).

Proteinbinding of Comparative Example 2 was Analyzed Via Ultrafiltration Assay, Described Below.

For this assay, filter membranes of 30 kDa pore size were used to separate plasma and protein free ultrafiltrate. The driving force for filtration was applied by centrifugation. Prior to protein binding studies, the adsorption (recovery) of the test compound to the ultra-filtration device and the ability of the test compound to pass the filter membrane was checked by filtration of the test compound dissolved in buffer at four concentrations. Sufficient stability of the test compound and an almost complete recovery (≥90% of the actual amount of compound used for the experiment) was a prerequisite for the use of the ultrafiltration method. The amount of organic solvent added to the plasma may not exceed 2% of the total incubation volume. Blood samples were collected in heparinized tubes either pooled (all species except human and monkey) or individually (human and monkey) and were used within 24 h for incubation experiments in blood. Plasma was prepared by centrifugation of the heparinized blood samples. Plasma was stored at −15° C. until use. Plasma stability, Compound recovery, unspecific binding to the membrane and the test device as well as partitioning between blood cells and plasma were controlled. The substance-associated radioactivity was determined by liquid scintillation counting. With this analytical method, it is not possible to distinguish between unchanged substance and radioactive metabolites. For details of the radioanalytical methods and the work up of the samples see Goeller et al. (3). A description of the ultrafiltration method in general was published by Zhang et al. In 2012 (4).

TABLE C5.2.1 protein binding of compounds

| Fraction unbound (%) | Rat Wistar | Dog Beagle | Human (male) | Monkey Cynomolgus | Minipig (female) |
|---|---|---|---|---|---|
| Comparative Example 11 | 0.224 | 0.108 | 0.0764 | 0.0485 | 0.348 |
| Comparative example 2 (Riociguat) | 15.7 | 17.1 | 4.97 | n.d. | n.d. |
| Comparative example 1 (Cinaciguat) | 0.351 | 1.12 | 0.392 | 0.0799 | n.d. |

n.d. not determined

Comparative example 11 and comparative example 1 (cinaciguat) showed very high protein binding, with free fractions below 1% in all species investigated. But, example 1 showed the lowest free fractions in all tested species, where comparative results are given. In rat plasma the fraction unbound of comparative example 11 is 1.6 times lower, in human and monkey plasma free fractions is 2 times lower and in dog plasma fraction unbound is 10 times lower than comparative example 1. Comparative example 2 (Riociguat) showed much higher free fractions between 15.7 and 4.97%.

High protein binding is seen as an indicator for high lung selectivity as described by Begg et al. (5). Comparative example 11 shows therefore beneficial properties over the comparative examples 1 and 2.

REFERENCES

1. Artursson P and Karlsson J. Correlation between oral drug absorption in humans and apparent drug permeability coefficients in human intestinal epithelial (Caco-2) cells, High-throughput determination of the free fraction of drugs strongly bound to plasma proteins. Biochem. Biophys, 1991. 175 (3), 880-885.
2. Schuhmacher J, Kohlsdorfer C, Buhner K, Brandenburger T, Kruk R. High-throughput determination of the free fraction of drugs strongly bound to plasma proteins. J Pharm Sci. 2004; 93(4):816-30.
3. Goeller G, Daehler H P, Winkelmann H: Determination of Radioactivity in Liquid and Solid Biological Samples from Pharmacokinetic Experiments. 1996, Bayer Pharma Report No. 25507.
4. Zhang F, Xue J, Shao J, Jia. Compilation of 222 drugs' plasma protein binding data and guidance for study designs. Drug Discovery Today 2012; 9-10(17):475-485.
5. Begg M, Edwards C D, Hamblin N, Pefani E, Wilson R, Gilbert J, Vitulli G, Mallett D, Morrell J, Hingle M I, Uddin S, Ehtesham F, Marotti M, Harrell A, Newman C F, Fernando D, Clark J, Cahn A, Hessel E M. Translation of Inhaled Drug Optimization Strategies intoClinical Pharmacokinetics and Pharmacodynamics Using GSK2292767A, a Novel Inhaled Phosphoinositide 3-Kinase d Inhibitor. J. Pharmacol. Exp. Ther. 2019; 369:443-453.

D—PHARMACEUTICAL COMPOSITIONS

D-1 Dry Powder preparations for inhalation

The compounds according to the invention e.g. the monohydrate I of formula (I-M-I) (example 4) or the monohydrate II of formula (I-M-II) (example 2), were formulated and manufactured into pharmaceutical dry powder preparations in the following ways:

Manufacturing Process

The dry powder formulation and finished products (dry powder blend filled hard capsules) were manufactured according to the below description.

Step 1: The fine lactose portion was weighed and layered in between two layers or coarse lactose prior to start of mixing.

Step 2: Mixing of the lactose pre-blend was performed for 2×20 minutes with 32 rpm. The lactose pre-blend was sieved through a 500 μg sieve between the cycles.

Step 3: active ingredient, e.g. the monohydrate I of formula (I-M-I), example 4 or the monohydrate II of formula (I-M-II), example 2, micronized was sieved through a 500 μm sieve and added to the pre-blended lactose. Prior to start of mixing cycles, the lactose pre-blend and active ingredient were layered alternating with 10 layers of lactose pre-blend and 9 layers of active ingredient, 6 layers of lactose pre-blend and 5 layers of active ingredient, e.g. the monohydrate I of formula (I-M-I), example 4 or the monohydrate II of formula (I-M-II), example 2 in between or 2 layers of lactose pre-blend and 1 layer of active ingredient (ex. 4) in between, preferably 6/5 layers prior to start of mixing.

Step 4: The components were mixed in cycles in a tumble mixer. Each cycle was conducted at 32 rpm for 30 minutes with a rest time of 10 minutes between the mixing cycles. If necessary (e.g. visual agglomerates) the blend maybe sieved between blending cycles, respectively.

Step 5: The blend was left to rest at room temperature (15-25° C.) and 35-65% relative humidity in a stainless steel container for at least 48 hours Step 6: Using a capsule filling machine (e.g. MG2 Flexalab) the blend was filled into capsules at the desired fill weight.

Dry Powder Blends for Inhalation:

TABLE 17 composition (lactose content/ratio) of exemplary embodiments 1-3 (comprising ex. 4)

| | Exemplary Embodiment 1 (0.75% active, 300 g) | | Exemplary Embodiment 2 (3% active, 300 g) | | Exemplary Embodiment 3 (10% active, 300 g) | |
|---|---|---|---|---|---|---|
| API concentration and batch size | Amount (g) | Amount (%) | Amount (g) | Amount (%) | Amount (g) | Amount (%) |
| active ingredient: monohydrate I, example 4* | 2.25 | 0.75% | 9.00 | 3% | 30.00 | 10% |
| Coarse Lactose (Lactohale 100) | 282.75 | 94.25% | 276.00 | 92% | 255.00 | 85% |
| Fine Lactose (Lactohale 300) | 15.00 | 5% | 15.00 | 5% | 15.00 | 5% |
| Total | 300.00 | | 300.00 | | 300.00 | |
| Blend Uniformity | | 99% | | 102% | | 102% |
| Assay (RSD %) | | (2.1%) | | (2.2%) | | (4.4%) |
| LH 300 fines content in Lactose Mixture ** | | 5.0% | | 5.2% | | 5.6% |
| Ratio Active ingredient: LH 100 | | 1:126 | | 1:31 | | 1:8.5 |
| Ratio Active ingredient: LH 300* | | 1:6.7 | | 1:1.67 | | 1:0.5 |

** the ratio of fine lactose (LH 300) to coarse Lactose (LH 100) is varying slightly as for practical reasons the actual amount of fine lactose in the powder blend is kept constant and the varying amounts of API (compound 1) is adjusted by the LH 100 coarse lactose content being reduced. The percent content of fine lactose (LH 300) is constant in all formulations, the ratio of active ingredient to fine lactose portion and coarse lactose portion varies in the indicated ranges.

For inhalative drug products it is important to guarantee a homogeneous drug substance with defined particle size <5 μm to secure delivery to the deep lung compartments. This technical requirement can be achieved by micronization of the drug substance particles.

Appropriate specifications for a particle size distribution of the active ingredient to achieve this requirement were set as specified in table 16.

The particle size distribution for the active ingredient (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4) according to the invention is defined as in below table 18.

TABLE 18

| Particle size distribution of example 4 | |
|---|---|
| Particle size upper X90 | max. 6 μm |
| Particle size mean X50 | 1-3 μm |
| Particle size lower X10 | max. 1 μm |

Lactose for inhalation is used according to the invention in different particle size ranges and different characteristics.

The coarse lactose material according to the present invention is a sieved, crystalline, α-lactose monohydrate with low fine particle content (e.g. commercially available as Lactohale® 100).

A different medium coarse lactose is the milled Lactohale® 200 which already contains considerable amount of lactose fines which can be basically tailored for customers to a desired particle size and fines content.

A further different coarse lactose is Lactohale® 206, a milled α-lactose with tightly controlled particle size, without any fine particles.

The fine lactose material according to the present invention is a micronized, crystalline, α-lactose monohydrate with a low particle size ("Lactose fines") of X90≤10 μm (e.g. commercially available as Lactohale® 300). Fine micronized lactose according to the invention with similar properties and particle size may also be selected e.g. Meggle Inhalac® 500.

A different fine lactose material is Lactohale 230®, a α-lactose monohydrate with a low particle size, X90<30 μm, milled, with irregular shaped particles;

The particle size distribution for Lactose for inhalation according to the invention (e.g. Lactohale® 100, Lactohale® 300 and others) is defined as in below table 19.

TABLE 19

| Particle size distribution of lactose carrier components | | |
|---|---|---|
| | Coarse lactose Lactohale ® 100 | Fine lactose Lactohale ® 300 |
| Particle size upper X90 | 200-250 μm | ≤10 μm |
| Particle size mean X50 | 125-145 μm | ≤5 μm |
| Particle size lower X10 | 45-65 μm | not defined |
| | Lactohale ® 200* | |
| Particle size upper X90 | 120-160 μm | |
| Particle size mean X50 | 50-100 μm | |
| Particle size lower X10 | 5-15 μm | |

TABLE 19-continued

| Particle size distribution of lactose carrier components | | |
|---|---|---|
| | Lactohale ® 206** | Lactohale ® 230*** |
| Particle size upper X90 | 115-170 μm | <30 μm |
| Particle size mean X50 | 75-95 μm | <10 μm |
| Particle size lower X10 | 20-50 μm | 1.0-3.0 μm |

*as used for comparative example 20 and exemplary embodiments 34-35
**as used for exemplary embodiments 39-44
***as used for exemplary embodiments 36-38 and 42-44

The quality of the blends were assessed by measuring the blend assay and uniformity as described under D.3.

As quality requirement the blends according to the present invention should fullfill the following criteria:

a blend assay of 90-110%, preferably 95-105% (in % content of active ingredient)

and a blend uniformity of RSD (=relative standard deviation for n=10 samples) of NMT (=not more than) 10% preferably 7.5% more preferably 5%.

Dry Powder Blends in Capsules (Finished Formulation for Inhalation):

The dry powder blends comprising the active ingredient (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid, preferably (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I (example 4) micronized as well as the lactose carrier components: fine lactose and coarse lactose were filled into hard capsules (hydroxypropylmethylcellulose=Hypromellose=HPMC, e.g. in size 3) or alternative capsules made from hard gelatine or other suitable materials.

Depending on the fill weight and active ingredient concentration different nominal dose can be achieved. Exemplary compositions for capsules with different nominal doses of example 4 (monohydrate 1) are displayed in below table. The final products (dry powder compositions in hard gel capsules) were assessed for their corresponding aerosol performance (see table 20).

TABLE 20

| aerosol performance of exemplary embodiments 1-3 | | | |
|---|---|---|---|
| | Exemplary Embodiment 1 | Exemplary Embodiment 2 | Exemplary Embodiment 3 |
| Nominal dose | 120 μg | 480 μg | 1000 μg |
| concentration of active ingredient, example 4 in powder blend | 0.75% | 3% | 10% |
| Fill weight | 16 mg | 16 mg | 10 mg |
| Delivered Dose (DD) | 71 μg | 316 μg | 705 μg |
| DD (% of nominal) | 59% | 66% | 71% |
| Fine Particle Dose <4.5 μm (FPD) | 32 μg | 128 μg | 258 μg |
| FPF (% of nominal) | 27% | 27% | 26% |
| FPF (% of DD) | 45% | 41% | 37% |

The aerosol performance includes parameters like the delivered dose (DD), the fine particle dose (=FPD) and the fine particle fraction (=FPF). The DD was measured according to method D.1, the fine particle dose (=FPD) and the fine particle fraction (=FPF) were measured according to method D.2 (Aerodynamic particle size distribution).

As quality requirement the dry powder blends in capsules according to the present invention should fullfill the following criteria:

a FPF (% of nominal dose of active, <4.5 μm) of ≥20% and a FPF (% of DD of active<4.5 μm) of ≥30% of active ingredient As shown in tables above the exemplary embodiments 1-3 demonstrate excellent aerosol performance and appropriate uniformity of the blend and good chemical stability (see stability data).

Comparative Examples and Further Exemplary Embodiments of the Invention

Dry powder blends were also manufactured with (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate II of formula (I-M-I1) in physical form of Monohydrate II (example 2) and using a partially different manufacturing process (see below).

The particle size distribution for the active ingredient (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate II of formula (I-M-II), example 2) according to the invention is defined as in below table 21.

TABLE 21

| Particle size distribution of example 2 | |
|---|---|
| Particle size upper X90 | max. 6 μm |
| Particle size mean X50 | 1-3 μm |
| Particle size lower X10 | max. 1 μm |

The manufacturing process of the exemplary embodiments 4-6 differed in Steps 2, 3 and 4

TABLE 22 composition (lactose contents) of exemplary embodiments 4-6 comprising example 2

| | Exemplary Embodiment 4 (0.75% active, 300 g) | | Exemplary Embodiment 5 (3% active, 300 g) | | Exemplary Embodiment 6 (10% active, 300 g) | |
|---|---|---|---|---|---|---|
| API concentration and batch size | Amount (g) | Amount (%) | Amount (g) | Amount (%) | Amount (g) | Amount (%) |
| Active ingredient: (example 2)* | 3.75 | 0.75% | 9.00 | 3% | 20.00 | 10% |
| Coarse Lactose (Lactohale 100) | 471.25 | 94.25% | 276.00 | 92% | 170.00 | 85% |
| Fine Lactose (Lactohale 300) | 25.00 | 5% | 15.00 | 5% | 10.00 | 5% |
| Total | 500.00 | | 300.00 | | 200.00 | |
| Blend Uniformity Assay (RSD %) | | 96% (1.5%) | | 98% (0.8%) | | 103% (4.4%) |
| LH 300 fines content Lactose Mixture ** | | 5.0% | | 5.2% | | 5.6% |
| Ratio Active ingredient: LH 100** | | 1:126 | | 1:31 | | 1:8.5 |
| Ratio Active ingredient: LH 300** | | 1:6.7 | | 1:1.67 | | 1:0.5 |

*used as Monohydrate II

**the ratio of fine lactose (LH 300) to coarse Lactose (LH 100) is explained in the section for the exemplary embodiments 1-3 according to the invention.

Step 2: Mixing of the lactose pre-blend was performed for 2×20 minutes with 67 rpm (72 rpm for low strength blend of exemplary embodiment 4). The lactose pre-blend was sieved through a 500 µg sieve between the cycles.

Step 3: active ingredient: monohydrate II, example 2 micronized was added to the pre-blended lactose without sieving. Prior to start of mixing cycles, the lactose pre-blend and active ingredient were layered alternating with 4 layers of lactose pre-blend and 3 layers of active ingredient (example 2, monohydrate II compound 1) in between.

Step 4: The layered mix was sieved through a 500 µm sieve before start of the first mixing cycle. The components were mixed in 3 cycles in a tumble mixer. Each cycle was conducted at 67 rpm (72 rpm for low strength blend of exemplary embodiment 4) for 30 minutes and sieved through a 500 µm sieve between the mixing cycles.

The following results from filled capsules of the exemplary embodiments 4-6 were obtained.

TABLE 23

Aerosol performance of exemplary embodiments 4-6

| | Exemplary Embodiment 4.1 + 4.2 (low/high powder fill) | | Exemplary Embodiment 5 | Exemplary Embodiment 6 |
|---|---|---|---|---|
| Nominal dose | 60 µg | 120 µg | 480 µg | 1000 µg |
| concentration of active ingredient, example 2 in powder blend | 0.75% | 0.75% | 3% | 10% |
| Fill weight | 8 mg | 16 mg | 16 mg | 10 mg |
| Delivered Dose (DD) | 30 µg | 82 µg | 316 µg | 671 µg |
| DD (% of nominal) | 50% | 68% | 66% | 67% |
| Fine Particle Dose <4.5 µm (FPD) | 12 µg | 31 µg | 126 µg | 242 µg |
| FPF (% of nominal) | 20% | 26% | 26% | 24% |
| FPF (% of DD) | 40% | 38% | 40% | 36% |

Results from exemplary embodiments 4-6 show that similar favorable aerosol performance can be achieved using (5S)-{[2-(4-carboxyphenyl)ethyl][2-(2-{[3-chloro-4'-(trifluoromethyl)biphenyl-4-yl]methoxy}-phenyl)ethyl]-amino}-5,6,7,8-tetrahydroquinoline-2-carboxylic acid monohydrate II of formula (I-M-II) form, example 2 to formulate dry powder blends according to the invention.

Further dry powder blends were manufactured using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 as active ingredient and using a partially different manufacturing process.

The resulting comparative examples 7-9 are summarized in the below table 24.

TABLE 24 composition (lactose contents) of comparative examples 7-9 comprising example 4

| | Comparative Example 7 (0.75% active, 20 g) | | Comparative Example 8 (3% active, 20 g) | | Comparative Example 9 (10% active, 300 g) | |
|---|---|---|---|---|---|---|
| API concentration and batch size | Amount (g) | Amount (%) | Amount (g) | Amount (%) | Amount (g) | Amount (%) |
| Active ingredient: example 4* | 0.15 | 0.75% | 0.6 | 3% | 30.00 | 10% |
| Coarse Lactose (Lactohale 100) | 18.85 | 94.25% | 18.4 | 92% | 255.00 | 85% |
| Fine Lactose (Lactohale 300) | 1.0 | 5% | 1.0 | 5% | 15.00 | 5% |
| Total | 20.0 | | 20.0 | | 300.00 | |
| Blend Uniformity Assay (RSD %) | | 97% (2.4%) | | 102% (5.7%) | | 96% (1.5%) |
| LH 300 fines content Lactose Mixture** | | 5.0% | | 5.2% | | 5.6% |
| Ratio Active ingredient: LH 100** | | 1:126 | | 1:30 | | 1:8.5 |
| Ratio Active ingredient: LH 300** | | 1:6.7 | | 1:1.67 | | 1:0.5 |

*used as Monohydrate I

**the ratio of fine lactose (LH 300) to coarse Lactose (LH 100) is explained in the section for the exemplary embodiments according to the invention.

The manufacturing process of the comparative examples 7-9 differed in Step 4.

Step 4: The components were mixed in 3 cycles in a tumble mixer. Each cycle was conducted at 32 rpm for 30 minutes. The blend was sieved through a 500 μm sieve between the cycles. No rest-time between mixing cycles was implemented.

The results for aerosol performance for filled capsules of the comparative examples 7-9 are summarized in table 25.

TABLE 25 aerosol performance of exemplary embodiments 7-9

| | Comparative Example 7 | Comparative Example 8 | Comparative Example 9 |
|---|---|---|---|
| Nominal dose | 120 μg | 480 μg | 1000 μg |
| concentration of active ingredient, example 4 in powder blend | 0.75% | 3% | 10% |
| Fill weight | 16 mg | 16 mg | 10 mg |
| Delivered Dose (DD) | 64 μg* | 264 μg* | 585 μg |
| DD (% of nominal) | 53% | 55% | 58% |
| Fine Particle Dose <4.5 μm (FPD) | 16 μg | 62 μg | 163 μg |
| FPF (% of nominal) | 13% | 13% | 16% |
| FPF (% of DD) | 25% | 23% | 28% |

*determined by sum of recovery in NGI

The results for the aerosol performance using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 were not meeting the quality requirements.

The small batch size (20 g) of these exploratory batches together with a low drug substance concentration in the blend (0.75% and 3%) could potentially lead to active ingredient fine particles on the surfaces of the manufacturing equipment. In addition, with decreasing active concentration in the powder blend, surface adhesion in the powder filled capsule has an unfavorable effect on the fine particle dose and fraction due to higher relative loss of active ingredient. As observed with comparative example 9 manufactured with a larger batch size (300 g) as well as a higher drug concentration (10%) the aerosol performance is improved but still below the targets. This was similarly observed for comparative examples 23 (1-4) which were prepared with the same API batch. A possible explanation could be the specific characteristics of the used batch, e.g. adhesive or cohesive properties leading to agglomeration or adsorption losses. This could be caused as the batch had a comparably high residual acetone content (approx. 10 fold) which was not observed for other API batches.

Furthermore the process used for manufacturing of comparative embodiments 7-9 involved a deviation from the procedure used for all other embodiments (with the exception of comparative embodiments 23.1-4): sieving between mixing cycles and no rest time between mixing cycles.

The aerosol performance of product manufactured with this API batch could subsequently be improved by process changes to exclude sieving steps between mixing cycles (exemplary embodiment 11).

Further dry powder blends were manufactured with (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 but using a partially different manufacturing process.

Compositions of exemplary embodiments 10 and 11 are summarized in the below table 26.

TABLE 26 composition (lactose contents) of exemplary embodiments 10-11 comprising example 4

| | Exemplary embodiment 10 (10% active, 20 g) | | Exemplary embodiment 11 (10% active, 20 g) | |
|---|---|---|---|---|
| API concentration and batch size | Amount (g) | Amount (%) | Amount (g) | Amount (%) |
| Active ingredient example 4* | 2.0 | 10% | 2.0 | 10% |
| Coarse Lactose (Lactohale 100) | 17.0 | 85% | 17.0 | 85% |
| Fine Lactose (Lactohale 300) | 1.0 | 5% | 1.0 | 5% |
| Total | 20.0 | | 20.0 | |
| Blend Uniformity Assay (RSD %) | | 102% (2.8%) | | 100% (4.0%) |
| LH 300 fines content in Lactoes mixture** | | 5.5% | | 5.5% |
| Ratio Active ingredient: LH 100** | | 1:8.5 | | 1:8.5 |
| Ratio Active ingredient: LH 300** | | 1:0.5 | | 1:0.5 |

*used as Monohydrate I

**the ratio of fine lactose (LH 300) to coarse Lactose (LH 100) is explained in the section for the exemplary embodiments according to the invention.

The manufacturing process of the exemplary embodiments 10-11 differed from exemplary embodiments 1-3 in Step 3 and 4.

Step 3: monohydrate I of formula (I-M-I), example 4 micronized was sieved through a 500 μm sieve and added to the pre-blended lactose. Prior to start of mixing cycles, the lactose pre-blend and active ingredient were layered alternating with 6 layers of lactose pre-blend and 5 layers of active ingredient (example 4) in between. A 5% overage of monohydrate I of formula (I-M-I), example 4 micronized was used (exemplary embodiment 10)

Step 4: The components were mixed in cycles in a tumble mixer. Each cycle was conducted at 32 rpm for 30 minutes. The blend was sieved through a 500 μm sieve between the cycles (exemplary embodiment 10).

No sieving inbetween the mixing cycles was performed for exemplary embodiment 11. No rest-time between mixing cycles was given (exemplary embodiment 10 and 11).

The results for aerosol performance for filled capsules of the exemplary embodiments 10-11 are summarized in table 27.

TABLE 27 aerosol performance for filled capsules of the exemplary embodiments 10-11

| | Exemplary Embodiment 10 | Exemplary Embodiment 11 |
|---|---|---|
| Nominal dose | 1000 μg | 1000 μg |
| Powder blend concentration | 10% | 10% |
| Fill weight | 10 mg | 10 mg |
| Delivered Dose (DD) | 636 μg* | 567* μg |
| DD (% of nominal) | 64% | 57% |
| Fine Particle Dose <4.5 μm (FPD) | 190 μg | 290 μg |
| FPF (% of nominal) | 19% | 29% |
| FPF (% of DD) | 30% | 51% |

*determined by sum of recovery in NGI

The results for the aerosol performance omitting the sieving steps were significantly better as compared with the previous standard process with sieving steps between mixing cycles (as shown in comparative examples 7-8). FPD in % of nominal and % of DD are strongly increased compared to the process involving blend sieving between mixing cycles. As well the omission of the sieving steps did not compromise the blend homogeneity. This is surprising as sieving would have been expected to lead to better blend homogeneity. Not only was the BU of the sieved Blend (exemplary embodiment 10) after mixing of 30 mins (RSD=8.7% before and 8.5% after sieving, respectively) at a higher level, but also was the BU (% RSD) on an equal level between sieved and non-sieved blends at the final blending stage (90 min plus 48 h rest).

Further dry powder blends were manufactured with (5R)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate II (comparative example 14), micronized active ingredient using a partially different manufacturing process.

The study was performed to investigate the influence of Lactose fines content on blend homogeneity and aerosol performance.

The corresponding compositions of comparative example 12 (no fine lactose content) and exemplary embodiments 13-15 are summarized in the below table 28.

TABLE 28 compositions of comparative example 12 and exemplary embodiments 13-15, comprising comparative example 14

| API concentration and batch size | Comparative Example 12 (0.75% active, 50 g) Amount (g) | Amount (%) | Exemplary Embodiment 13 (0.75% active, 50 g) Amount (g) | Amount (%) | Exemplary Embodiment 14 (0.75% active, 50 g) Amount (g) | Amount (%) | Exemplary Embodiment 15 (0.75% active, 50 g) Amount (g) | Amount (%) |
|---|---|---|---|---|---|---|---|---|
| Active ingredient comparative example 14* | 0.375 | 0.75% | 0.375 | 0.75% | 0.375 | 0.75% | 0.375 | 0.75% |
| Coarse Lactose (Lactohale 100) | 49.625 | 99.25% | 47.125 | 94.25% | 45.875 | 91.75% | 44.625 | 89.25% |
| Fine Lactose (Lactohale 300) | | 0% | 2.5 | 5% | 3.75 | 7.5% | 5.0 | 10.0% |
| Total | 50.0 | | 50.0 | | 50.0 | | 50.0 | |
| Blend Uniformity Assay (RSD %) 30 min | | 96% (1.0%) | | 93% (5.8%) | | 89% (1.6%) | | 92% (8.2%) |
| 60 min | | 92% (0.6%) | | 91% (4.6%) | | 93% (5.0%) | | 92% (4.1%) |
| 90 min | | 92% (1.4%) | | 89% (5.6%) | | 96% (9.2%) | | 92% (1.7%) |
| 120 min | | 95% (11.6%) | | 92% (1.6%) | | 93% (10.3%) | | 96% (10.0%) |
| LH 300 fines content in Lactose mixture | | 0.0% | | 5.0% | | 7.6% | | 10.1% |
| Ratio Active ingredient: LH 100 | | 1:132 | | 1:126 | | 1:122 | | 1:119 |
| Ratio Active ingredient: LH 300 | | | | 1:6.6 | | 1:10 | | 1:13 |

*used as Monohydrate II

The manufacturing process of the comparative example 12 and exemplary embodiments 13-15 differed from exemplary embodiments 1-3 in all Steps 1-6.

Step 1: The fine and coarse lactose portions were weighed into a vessel, sieved and transferred to the mixing container of the mixer.

Step 2: No mixing of the lactose pre-blend was performed

Step 3: R enantiomer of monohydrate II (comparative example 14) micronized was added to the pre-weighed and sieved lactose. Prior to start of mixing, the lactose pre-blend and active ingredient were layered alternating with 4 layers of lactose pre-blend and 3 layers of active ingredient (R enantiomer of monohydrate II; comparative example 14) in between.

Step 4: The components were mixed in cycles in a tumble mixer. Each cycle (4 cycles overall) was conducted at 72 rpm for 30 minutes. The blend was sieved through a 500 μm sieve between the cycles. No rest-time between mixing cycles was given.

Step 5: No rest period of the final blend defined

Step 6: The blend was manually filled into capsules at the desired fill weight.

Aerosol performance of filled capsules for the comparative example 12 and exemplary embodiments 13-15 are shown in table 29 below.

TABLE 29

Aerosol performance of filled capsules for the comparative example 12 and exemplary embodiments 13-15

| | Comparative Example 12 | Exemplary Embodiment 13 | Exemplary Embodiment 14 | Exemplary Embodiment 15 |
|---|---|---|---|---|
| Nominal dose | 75 μg | 75 μg | 75 μg | 75 μg |
| Powder blend concentration | 0.75% | 0.75% | 0.75% | 0.75% |
| Fill weight | 10 mg | 10 mg | 10 mg | 10 mg |

TABLE 29-continued

Aerosol performance of filled capsules for the comparative example 12 and exemplary embodiments 13-15

| | Comparative Example 12 | Exemplary Embodiment 13 | Exemplary Embodiment 14 | Exemplary Embodiment 15 |
|---|---|---|---|---|
| Delivered Dose (DD) | 41 μg* | 38 μg* | 38 μg* | 39 μg* |
| DD (% of nominal) | 55% | 51% | 5% | 52% |
| Fine Particle Dose <4.5 μm (FPD) | 8 μg | 19 μg | 19 μg | 20 μg |
| FPF (% of nominal) | 11% | 25% | 25% | 27% |
| FPF (% of DD) | 20% | 50% | 50% | 51% |

*determined by sum of recovery in NGI

The above results show, that in case the composition is containing no fine lactose (see Comparative Example 12) the fine particle fraction with respect to nominal and delivered dose is decreased and is inferior to the Exemplary Embodiments 13-15. FPD and FPF are significantly higher for all variants manufactured independent from the lactose fines content (5%, 7.5% or 10%). It was surprising that the results for different amounts of lactose fines are almost the same. Therefore it was shown that the powder blends and formulations according to the present invention can have a varying content of fine lactose without jeopardizing the aerosol performance. Blend homogeneity results mostly show that there is no clear increase of BU with increasing mixing time. Rather, above 90 min another decrease in homogeneity is observed except for the formulation containing 5% lactose fines.

Further dry powder blends were manufactured with (5R)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate II (comparative example 14) as active ingredient using a partially different manufacturing process.

The study was performed to investigate the influence of the mixing time on homogeneity and aerosol performance of the final capsules at larger scale of the blends.

Compositions of comparative example 16 and exemplary embodiments 17-19 are summarized in the below table 30.

TABLE 30

Compositions of comparative example 16 and exemplary embodiments 17-19 and respective blend uniformities for different mixing times comprising comparative example 14

| API concentration | | Comparative Example 16 (0.75% active, 200 g) | | Exemplary Embodiment 17 (10% active, 50 g) | | Exemplary Embodiment 18 (0.75% active, 200 g) | | Exemplary Embodiment 19 (10% active, 200 g) | |
|---|---|---|---|---|---|---|---|---|---|
| and batch size | | Amount (g) | Amount (%) | Amount (g) | Amount (%) | Amount (g) | Amount (%) | Amount (g) | Amount (%) |
| Active ingredient (comparative example 14)* | | 1.5 | 0.75% | 5.0 | 10% | 1.5 | 0.75% | 20.0 | 10% |
| Coarse Lactose (Lactohale 100) | | 188.5 | 94.25% | 42.5 | 85% | 188.5 | 94.25% | 170.0 | 85% |
| Fine Lactose (Lactohale 300) | | 10.0 | 5% | 2.5 | 5% | 10.0 | 5% | 10.0 | 5% |
| Total | | 200.0 | | 50.0 | | 200.0 | | 200.0 | |
| Blend Uniformity | 30 min | | 84% (2.8%) | | 103% (6.7%) | | 93% (3.2%) | | 105% (7.2%) |
| | 60 min | | 81% (3.2%) | | 100% (9.8%) | | 95% (3.2%) | | 102% (9.4%) |
| | 90 min | | 91% (3.7%) | | 96% (5.4%) | | 93% (1.8%) | | 98% (0.6%) |
| | 120 min | | — (—) | | 94% (4.4%) | | 96% (9.3%) | | 97% (1.5%) |

TABLE 30-continued

Compositions of comparative example 16 and exemplary embodiments 17-19 and respective blend uniformities for different mixing times comprising comparative example 14

| API concentration and batch size | Comparative Example 16 (0.75% active, 200 g) | | Exemplary Embodiment 17 (10% active, 50 g) | | Exemplary Embodiment 18 (0.75% active, 200 g) | | Exemplary Embodiment 19 (10% active, 200 g) | |
|---|---|---|---|---|---|---|---|---|
| | Amount (g) | Amount (%) | Amount (g) | Amount (%) | Amount (g) | Amount (%) | Amount (g) | Amount (%) |
| LH 300 fines content in Lactose mixture | | 5.3% | | 5.9% | | 5.3% | | 5.9% |
| Ratio Active ingredient: LH 100 | | 1:126 | | 1:8.5 | | 1:126 | | 1:8.5 |
| Ratio Active ingredient: LH 300 | | 1:6.7 | | 1:0.5 | | 1:6.7 | | 1:0.5 |

*used as Monohydrate II

The manufacturing process of the comparative examples 16 and exemplary embodiments 17-19 differed from exemplary embodiments 1-3 in all steps 1-6.

Step 1: The fine and coarse lactose portions were weighed into a vessel, sieved and transferred to the mixing container of the mixer.

Step 2: No mixing of the lactose pre-blend was performed

Step 3: comparative example 14 micronized was added to the pre-weighed and sieved lactose. Prior to start of mixing, the lactose pre-blend and active ingredient were layered alternating with 4 layers of lactose pre-blend and 3 layers of active ingredient (comparative example 14) in between.

Step 4: The components were mixed in cycles in a tumble mixer. Each cycle (4 cycles overall) was conducted at 72 rpm for 30 minutes. A glass vessel was used for comparative examples 16 and exemplary embodiment 17. A stainless steel vessel was used for exemplary embodiment 18 and 19. The blend was sieved through a 500 μm sieve between the cycles. No rest-time between mixing cycles was given.

Step 5: No rest period of the final blend defined

Step 6: The blend was manually filled into capsules at the desired fill weight.

Aerosol performance of filled capsules for the comparative example 16 and exemplary embodiments 17-19 are shown in table 31 below.

TABLE 31

Aerosol performance of filled capsules for the comparative example 16 and exemplary embodiments 17-19

| | Comparative Example 16 | Exemplary Embodiment 17 | Exemplary Embodiment 18 | Exemplary Embodiment 19 |
|---|---|---|---|---|
| Nominal dose (capsule) | 75 μg | 1000 μg | 75 μg | 1000 μg |
| Powder blend concentration | 0.75% | 10% | 0.75% | 10% |
| Fill weight | 10 mg | 10 mg | 10 mg | 10 mg |
| Results after 30 min blend time | | | | |
| Delivered Dose (DD) | 23 μg* | 546 μg* | 34 μg* | 674 μg* |
| DD (% of nominal) | 31% | 55% | 45% | 67% |
| Fine Particle Dose <4.5 μm (FPD) | 9 μg | 301 μg | 17 μg | 411 μg |
| FPF (% of nominal) | 12% | 30% | 23% | 41% |
| FPF (% of DD) | 39% | 55% | 50% | 61% |
| Results after 60 min blend time | | | | |
| Delivered Dose (DD) | 25 μg* | 526 μg* | 33 μg* | 581 μg* |
| DD (% of nominal) | 33% | 53% | 44% | 58% |
| Fine Particle Dose <4.5 μm (FPD) | 9 μg | 189 μg | 17 μg | 311 μg |
| FPF (% of nominal) | 12% | 19% | 22% | 31% |
| FPF (% of DD) | 38% | 36% | 51% | 53% |
| Results after 90 min blend time | | | | |
| Delivered Dose (DD) | 29 μg* | 467 μg* | 32 μg* | — |
| DD (% of nominal) | 39% | 47% | 42% | — |

TABLE 31-continued

Aerosol performance of filled capsules for the comparative example 16 and exemplary embodiments 17-19

| | Comparative Example 16 | Exemplary Embodiment 17 | Exemplary Embodiment 18 | Exemplary Embodiment 19 |
|---|---|---|---|---|
| Fine Particle Dose <4.5 μm (FPD) | 12 μg | 210 μg | 16 μg | — |
| FPF (% of nominal) | 16% | 21% | 21% | — |
| FPF (% of DD) | 42% | 45% | 50% | — |
| Results after 120 min blend time | | | | |
| Delivered Dose (DD) | — | 551 μg* | 34 μg* | 534 μg* |
| DD (% of nominal) | — | 55% | 45% | 53% |
| Fine Particle Dose <4.5 μm (FPD) | | 261 μg | 16 μg | 284 μg |
| FPF (% of nominal) | — | 26% | 22% | 28% |
| FPF (% of DD) | — | 47% | 48% | 53% |

*determined by sum of recovery in NGI

— not tested at this time point.

From the results in table above it is clearly shown, that the mixing time of the blend has an impact on the blend quality, i.e. blend homogeneity. Generally the blend uniformity improves with mixing time with an optimum mostly observed after 90 min. Comparative example 16 showed poor assay values throughout mixing and also failed to meet FPD/FPF % targets mostly. In this case it appears that mostly the nature of the mixing vessel (=glass) was contributing to poor homogeneity and resulting low aerosol performance (eventually fine API contents left in mixing vessel).

Decrease of BU (increase of RSD %) is however sometimes observed when the mixing time is extended which is an unexpected finding. As well, the aerosol performance (FPD, FPF) appears mostly unaffected of the mixing time. The results between dry powders blended in a glass vessel and those blended in a stainless steel container differ significantly. The results for the stainless steel container blended powders (exemplary embodiments 18-19) are superior to the results received from glass vessel blended powders (comparative example 16 and exemplary embodiment 17) which could not be expected as both materials are considered to be physical and chemically inert.

Further dry powder blends were also manufactured with (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I and II (example 2 and 4) as active ingredient using a partially different manufacturing process. The studies scope was to manufacture in larger scales of powder blends and with different lactose fines content. The resulting comparative example 20 and exemplary embodiments 21 and 22 are summarized in the below table 32.

TABLE 32 compositions of comparative example 20 and exemplary embodiments 21 and 22

| API | Comparative Example 20 (5% active, 850 g) | | Exemplary Embodiment 21 (5% active, 1050 g) | | Exemplary Embodiment 22 (5% active, 8200 g) | |
|---|---|---|---|---|---|---|
| concentration and batch size | Amount (g) | Amount (%) | Amount (g) | Amount (%) | Amount (g) | Amount (%) |
| Active ingredient (example 2 for comparative example 20/ example 4 for embodiments 21 + 22)* | 44.5 | 5% | 52.5 | 5% | 410.0 | 5% |
| Coarse Lactose (Lactohale 100) | — | — | 945.0 | 90% | 7380.0 | 90% |
| Coarse Lactose milled (Lactohale 200) | 635.5 | 75% | — | — | — | — |
| Fine Lactose (Lactohale 300) | 170.0 | 20% | 52.5 | 5% | 410.0 | 5% |
| Total | 850.0 | | 1050.0 | | 8200.0 | |
| Blend Uniformity Assay (RSD %) | | 69.3% (21.8%) | | 95.9% (3.2%) | | 106.6% (6.0%) |
| Blend Uniformity Reprocessing** | | 48.9% (10.1%) | | — | | — |
| LH 300 fines content in Lactose mixture | | 21.1% | | 5.3% | | 5.3%% |

TABLE 32-continued compositions of comparative example 20 and exemplary embodiments 21 and 22

| API | Comparative Example 20 (5% active, 850 g) | | Exemplary Embodiment 21 (5% active, 1050 g) | | Exemplary Embodiment 22 (5% active, 8200 g) | |
|---|---|---|---|---|---|---|
| concentration and batch size | Amount (g) | Amount (%) | Amount (g) | Amount (%) | Amount (g) | Amount (%) |
| Ratio Active ingredient: LH 100/LH200 | | 1:14 | | 1:18 | | 1:18 |
| Ratio Active ingredient:LH 300 | | 1:3.8 | | 1:1 | | 1:1 |

*used as Monohydrate II for comparative example 20 and as Monohydrate I for exemplary embodiments 21 and 22;
**after manufacturing Step 7A-7D, cf below;

The manufacturing process of the comparative example 20 differed from the manufacturing of exemplary embodiments 1-3 in Step 1-5.

Step 1: The fine lactose and coarse Lactose (LH200) portion was weighed into the mixing vessel.

Step 2: No blending of the lactose pre-mix was performed. The lactose pre-blend was sieved through a 630 μm sieve between the cycles.

Step 3: Active ingredient (example 2 for comparative example 20/example 4 for embodiments 21+22) micronized was sieved through a 630 μm sieve and added to the pre-mixed lactose without layering.

Step 4: The components were mixed in 3 cycles in a tumble mixer. Each cycle was conducted at 32 rpm for 20 minutes. The blend was sieved through a 630 m sieve between the cycles. No rest-time between mixing cycles was implemented.

Step 5: The blend was not left to rest for a defined time before sampling and filling.

Step 6: Using a capsule filling machine the blend was filled into capsules at the desired fill weight.

(additional) Step 7: As the uniformity results were poor the blend of comparative example 20 was further processed.

7A: The blend was sieved through a 630 μm sieve

7B: The blend was divided in two portions and each of them was mixed for 60 min at 67 rpm 7C: Both blended portions were sieved through a 630 μm sieve 7D: Both portions were re-unified and mixed for further 30 min at 67 rpm Exemplary embodiment 21 was manufactured using the process as applied for exemplary embodiments 4-6.

Exemplary embodiment 22 was manufactured using the process as applied for exemplary embodiments 1-3.

The results for aerosol performance for filled capsules comparative example 20 and of the exemplary embodiments 21-22 are summarized in table 33.

TABLE 33 aerosol performance for filled capsules comparative example 20 and of the exemplary embodiments 21-22

| | Comparative Example 20 | Exemplary Embodiment 21 | Exemplary Embodiment 22 |
|---|---|---|---|
| Nominal dose | 500 μg | 500 μg | 500 μg |
| Powder blend concentration | 5% | 5% | 5% |
| Fill weight | 10 mg | 10 mg | 10 mg |

TABLE 33-continued aerosol performance for filled capsules comparative example 20 and of the exemplary embodiments 21-22

| | Comparative Example 20 | Exemplary Embodiment 21 | Exemplary Embodiment 22 |
|---|---|---|---|
| Delivered Dose (DD)* | 385 μg | 298 μg | 308 μg |
| DD (% of nominal) | 77% | 60% | 62% |
| Fine Particle Dose <4.5 μm (FPD) | 171 μg | 101 μg | 122 μg |
| FPF (% of nominal) | 34% | 20% | 24% |
| FPF (% of DD) | 44% | 34% | 40% |

*Tested by DUSA, FPF (% of DD) calculated with this value

The results from exemplary embodiments 21 and 22 show that also at 5fold and 50fold higher scale dry powder blends can be manufactured with the established process. Blend Uniformity as well as aerosol performance are within the desired targets/ranges. Comparative example 20 failed in resulting in a homogeneous blend likely due to the high lactose fines content and a resulting very cohesive mixture. The low assay indicates active ingredient and sticking to manufacturing equipment. Even after extensive additional blending operations to achieve acceptable distribution of the active in the lactose blend the uniformity is still poor, although the aerosol performance of the capsule filled blend shows acceptable results.

Therefore it was shown that the powder blends and formulations according to the present invention can have a varying content of fine lactose within a range of between 5% and 10% without jeopardizing the aerosol performance (see exemplary embodiments 13, 14 and 15). However the upper limit of 20% of fine lactose is critical.

Further dry powder blends were manufactured using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) (example 4) as active ingredient and using a partially different manufacturing process.

The studies scope was to manufacture embodiments of the invention with higher active concentration and higher blend fill in the capsules to realize higher nominal doses as well as to verify a higher dose at higher scale.

The resulting comparative Example 23 (1-4) and exemplary embodiments 24-26 are summarized in the below table 34.

TABLE 34 compositions of comparative example 23 and exemplary embodiments 24-26, comprising example 2 as active ingredient

| API concentration and batch size | | Comparative Example 23 (10% active, 20 g) Amount (g) | Comparative Example 23 (10% active, 20 g) Amount (%) | Exemplary Embodiment 24 (20% active, 20 g) Amount (g) | Exemplary Embodiment 24 (20% active, 20 g) Amount (%) | Exemplary Embodiment 25 (30% active, 20 g) Amount (g) | Exemplary Embodiment 25 (30% active, 20 g) Amount (%) | Exemplary Embodiment 26 (20% active, 290 g) Amount (g) | Exemplary Embodiment 26 (20% active, 290 g) Amount (%) |
|---|---|---|---|---|---|---|---|---|---|
| Active ingredient (monohydrate I, example 4)* | | 2.0 | 10% | 4.0 | 20% | 6.0 | 30% | 58.0 | 20% |
| Coarse Lactose (Lactohale 100) | | 17.0 | 85% | 15.0 | 75% | 13.0 | 65% | 217.5 | 75% |
| Fine Lactose (Lactohale 300) | | 1.0 | 5% | 1.0 | 5% | 1.0 | 5% | 14.5 | 5% |
| Total | | 20.0 | | 20.0 | | 20.0 | | 290.0 | |
| Blend Uniformity Assay (RSD %) | 30 min | | 99% (6.8%) | | 92% (8.5%) | | 86% (24.5%) | | — — |
| | 60 min | | 94% (4.3%) | | 92% (3.2%) | | 101% (10.8%) | | — — |
| | 90 min | | 97% (3.6%) | | 95% (2.7%) | | 101% (12.9%) | | 94% (3.0%) |
| | 120 min | | 97% (4.9%) | | 93% (3.8%) | | 93% (6.8%) | | — — |
| LH 300 fines content in Lactose mixture | | | 5.6% | | 6.3% | | 7.1% | | 6.3% |
| Ratio Active ingredient: LH 100 | | | 1:8.5 | | 1:3.8 | | 1:2.2 | | 1:3.8 |
| Ratio Active ingredient: LH 300 | | | 1:0.5 | | 1:0.25 | | 1:0.17 | | 1:0.25 |

*used as Monohydrate I

Comparative example 23 and exemplary embodiments 24-26 were manufactured with a similar process as used for comparative examples 7-9 and the same API batch, however used a slightly lower cycle rate of 34 rpm instead of 32 rpm for four cycles. Blend uniformity was tested after each cycle. The blend was rested for 72 h after $4_{th}$ blending cycles followed by a further blend cycle, sieving step through 500 μm sieve and final BU testing. The capsules were hand filled for aerosol performance testing.

Exemplary embodiment 26 was manufactured with the same process as used for comparative examples 7-9 however with cycling at 34 rpm instead of 32 rpm and hand filling of the capsules.

The results for aerosol performance for filled capsules of the comparative example 23 and exemplary embodiments 24-26, having different fill weights to achieve different nominal doses are summarized in table 35.

TABLE 35 aerosol performance for filled capsules of the comparative example 23 and exemplary embodiments 24-26

| | Comparative Example 23-1 | Comparative Example 23-2 | Comparative Example 23-3 | Comparative Example 23-4 |
|---|---|---|---|---|
| Nominal dose (capsule) | 1000 μg | 2000 μg | 3000 μg | 4000 μg |
| Powder blend concentration | 10% | 10% | 10% | 10% |
| Fill weight | 10 mg | 20 mg | 30 mg | 40 mg |
| Delivered Dose (DD) | 671 μg | 1398 μg | 2238 μg | 2984 μg |
| DD (% of nominal) | 67% | 70% | 75% | 75% |
| Fine Particle Dose <4.5 μm (FPD) | 168 μg | 293 μg | 475 μg | 604 μg |
| FPF (% of nominal) | 17% | 15% | 16% | 15% |
| FPF (% of DD) | 25% | 21% | 21% | 20% |
| | **Exemplary Embodiment 24-1** | **Exemplary Embodiment 24-2** | **Exemplary Embodiment 25-1** | **Exemplary Embodiment 25-2** |
| Nominal dose (capsule) | 2000 μg | 6000 μg | 3000 μg | 9000 μg |
| Powder blend concentration | 20% | 20% | 30% | 30% |
| Fill weight | 10 mg | 30 mg | 10 mg | 30 mg |
| Delivered Dose (DD) | 1336 μg | 4756 μg | 2229 μg | 7172 μg |

TABLE 35-continued

| aerosol performance for filled capsules of the comparative example 23 and exemplary embodiments 24-26 | | | | |
|---|---|---|---|---|
| DD (% of nominal) | 67% | 79% | 74% | 80% |
| Fine Particle Dose <4.5 μm (FPD) | 411 μg | 1302 μg | 929 μg | 2805 μg |
| FPF (% of nominal) | 21% | 22% | 31% | 31% |
| FPF (% of DD) | 31% | 27% | 42% | 39% |

| | Exemplary Embodiment 26 |
|---|---|
| | 6000 μg |
| Powder blend concentration | 20% |
| Fill weight | 30 mg |
| Delivered Dose (DD) | 4924 μg |
| DD (% of nominal) | 82% |
| Fine Particle Dose <4.5 μm (FPD) | 1779 μg |
| FPF (% of nominal) | 30% |
| FPF (% of DD) | 36% |

As demonstrated by exemplary embodiments 24-26 formulations according to the invention can be manufactured with higher drug contents above 10%. For blends containing 30% active, due to the high fine particle content (from high micronized API portion), the blending of a homogeneous mixture is not possible in appropriate blending time. Although the BU RSD % improved over time up to 120 min the value remains still at relatively high level. Surprisingly, the aerosol performance was not compromised and instead yielded higher FPD/FPF as with the lower strength blends. For 10% and 20% blends good blend uniformity was demonstrated at increasing mixing time up to 90 min. The aerosol performance at various fill amounts of the 10% strength was unexpectedly not observed to vary significantly as rather increasing delivered dose and FPF % would have been expected due to lower relative surface adhesion of active ingredient on the capsule wall. Therefore, likely, at a concentration of 10% API and a higher fill weight of the capsule does not result in significant changes of the aerosol performance. All fillings of comparative example 23 failed to meet the FPF % targets which was similarly observed for the comparative examples 7-9 manufactured with the same API batch and process. One factor might be the small exploratory batch size of 20 g only, where losses during manufacturing and on equipment surfaces have a higher impact on fine API particle content of the batch. The impact of the batch size can also be observed by comparison of exemplary embodiments 24-1 and -2 which have higher API concentration 20%) and still do not significantly exceed the performance targets. Furthermore the upscaled batch of exemplary embodiment 26-1 with the same composition and capsule fill weight as the small scale batch of exemplary embodiment 24-2 exhibits better aerosol performance showing the impact of the manufacturing batch size. In context of the results for exemplary embodiments 7-9 the poor aerosol performance was further attributed to properties of the API batch (same as used for exemplary embodiments 7-9) leading to unfavorable adhesive or cohesive effects in the blend and resulting in loss of fine particles during APSD analysis. This could be caused as the batch had a comparably high residual acetone content (approx. 10 fold) which was not observed for other API batches.

The upscaled manufacture of exemplary embodiment 26 further showed that adequate blend homogeneity and aerosol performance of filled capsules can be achieved with a 20% active blend.

Further embodiments of the invention with varying contents of fine lactose, e.g. 2.5% and less as well as 15% and more are manufactured.

Further dry powder blends were manufactured with (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I as active ingredient using a partially different manufacturing process.

The study was performed to investigate the influence of the number of initial layers before start of the blending process and influence of sieving steps between the blending cycles at a higher scale.

Compositions of exemplary embodiments 27-30 are summarized in the below table 36.

TABLE 36

| Compositions of exemplary embodiments 27-30 and respective blend uniformities for different mixing times | | | | | | | | |
|---|---|---|---|---|---|---|---|---|
| API concentration | Exemplary Embodiment 27 (10% active, 200 g) | | Exemplary Embodiment 28 (10% active, 200 g) | | Exemplary Embodiment 29 (10% active, 200 g) | | Exemplary Embodiment 30 (10% active, 200 g) | |
| and batch size | Amount (g) | Amount (%) | Amount (g) | Amount (%) | Amount (g) | Amount (%) | Amount (g) | Amount (%) |
| Active ingredient (ex.4) * | 20.0 | 10% | 20.0 | 10% | 20.0 | 10% | 20.0 | 10% |

TABLE 36-continued

Compositions of exemplary embodiments 27-30 and respective blend uniformities for different mixing times

| API concentration and batch size | Exemplary Embodiment 27 (10% active, 200 g) Amount (g) | Amount (%) | Exemplary Embodiment 28 (10% active, 200 g) Amount (g) | Amount (%) | Exemplary Embodiment 29 (10% active, 200 g) Amount (g) | Amount (%) | Exemplary Embodiment 30 (10% active, 200 g) Amount (g) | Amount (%) |
|---|---|---|---|---|---|---|---|---|
| Coarse Lactose (Lactohale 100) | 170.0 | 85% | 170.0 | 85% | 170.0 | 85% | 170.0 | 85% |
| Fine Lactose (Lactohale 300) | 10.0 | 5% | 10.0 | 5% | 10.0 | 5% | 10.0 | 5% |
| Total | 200.0 | | 200.0 | | 200.0 | | 200.0 | |
| Blend Uniformity Assay (RSD %) 90 min | | 98% (1.5%) | | 100% (2.0%) | | 102% (2.4%) | | 97% (0.9%) |
| LH 300 fines content in Lactose mixture | | 5.9% | | 5.9% | | 5.9% | | 5.9% |
| Ratio Active ingredient: LH 100 | | 1:8.5 | | 1:8.5 | | 1:8.5 | | 1:8.5 |
| Ratio Active ingredient: LH 300 | | 1:0.5 | | 1:0.5 | | 1:0.5 | | 1:0.5 |

*used as Monohydrate I, ex. 4

The manufacturing process of the exemplary embodiments 27-30 differed from exemplary embodiments in steps 3, 4 and 6.

Step 3: Prior to start of mixing 2 lactose pre-blend layers and 1 active ingredient layer in between (exemplary embodiment 27) and 10 lactose pre-blend layers and 9 active ingredient layers in between (exemplary embodiment 28) were weighed into the blending vessel.

Step 4: The blend was sieved through a 500 μm sieve between the cycles (exemplary embodiment 30)

Step 6: The blend was manually filled into capsules at the desired fill weight.

Aerosol performance of filled capsules for exemplary embodiments 27-30 are shown in table 37 below.

TABLE 37

Aerosol performance of filled capsules for the exemplary embodiments 27-30

| | Exemplary Embodiment 27 | Exemplary Embodiment 28 | Exemplary Embodiment 29 | Exemplary Embodiment 30 |
|---|---|---|---|---|
| Nominal dose (capsule) | 75 μg | 1000 μg | 75 μg | 1000 μg |
| Powder blend concentration | 10% | 10% | 10% | 10% |
| Fill weight | 10 mg | 10 mg | 10 mg | 10 mg |
| Delivered Dose (DD) | 556 μg* | 638 μg* | 598 μg* | 630 μg* |
| DD (% of nominal) | 56% | 64% | 60% | 63% |
| Fine Particle Dose <4.5 μm (FPD) | 317 μg | 348 μg | 333 μg | 341 μg |
| FPF (% of nominal) | 32% | 35% | 33% | 34% |
| FPF (% of DD) | 57% | 55% | 56% | 54% |

*determined by sum of recovery in NGI

— not tested at this time point.

The results from this study performed on clinical scale show, that independent of the number of initial pre-blend and API layers and independent of sieving steps between mixing cycles excellent blend uniformity and aerosol performance are achieved.

Further dry powder blends were manufactured using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 as active ingredient and using a slightly different manufacturing process.

The study was performed to investigate the influence of high and low lactose fines content on the established blending process and resulting aerosol performance.

The resulting exemplary embodiments 31-32 and comparative example 33 are summarized in the below table 38.

TABLE 38

Composition (lactose contents) of exemplary embodiments 31-32 and comparative example 33

| | Exemplary Embodiment 31 (10% active, 50 g) | | Exemplary Embodiment 32 (10% active, 50 g) | | Comparative Example 33 (10% active, 50 g) | |
|---|---|---|---|---|---|---|
| API concentration and batch size | Amount (g) | Amount (%) | Amount (g) | Amount (%) | Amount (g) | Amount (%) |
| Active ingredient: example 4* | 5.0 | 10% | 5.0 | 10% | 5.0 | 10% |
| Coarse Lactose (Lactohale 100) | 44.5 | 89% | 43.75 | 87.5% | 37.5 | 75% |
| Fine Lactose (Lactohale 300) | 0.5 | 1% | 1.25 | 2.5% | 7.5 | 15% |
| Total | 50.0 | | 50.0 | | 50.00 | |
| Blend Uniformity Assay (RSD %) | | 107% (11.0%) | | 115% (9.7%) | | 88% (15.5%) |
| LH 300 fines content in Lactose Mixture** | | 1.1% | | 2.9% | | 20.0% |
| Ratio Active ingredient: LH 100** | | 1:8.9 | | 1:8.75 | | 1:7.5 |
| Ratio Active ingredient: LH 300** | | 1:0.1 | | 1:0.25 | | 1:1.5 |

*used as Monohydrate I

**the ratio of fine lactose (LH 300) to coarse Lactose (LH 100) is explained in the section for the exemplary embodiments according to the invention.

The manufacturing process of exemplary embodiment 31-32 and comparative example 33 differed in Step 6.

Step 6: The blend was manually filled into capsules at the desired fill weight.

The results for aerosol performance for filled capsules of exemplary embodiments 31-32 and comparative example 33 are summarized in table 39.

TABLE 39

Aerosol performance of exemplary embodiments 31-32 and comparative example 33

| | Exemplary Embodiment 31 | Exemplary Embodiment 32 | Comparative Example 33 |
|---|---|---|---|
| Nominal dose | 1000 μg | 1000 μg | 1000 μg |
| concentration of active ingredient, example 4 in powder blend | 10% | 10% | 10% |
| Fill weight | 10 mg | 10 mg | 10 mg |
| Delivered Dose (DD)* | 503 μg | 484 μg | 514 μg |
| DD (% of nominal) | 50% | 48% | 51% |
| Fine Particle Dose <4.5 μm (FPD) | 310 μg | 279 μg | 314 μg |
| FPD (RSD %) | 9.4% | 8.4% | 16.0% |
| FPF (% of nominal) | 31% | 28% | 31% |
| FPF (% of DD) | 62% | 60% | 65% |

*determined by sum of recovery in NGI

The results for the aerosol performance of filled capsules from exemplary embodiments 31-32 and comparative example 33 were all meeting the targets. However, the blend uniformity of comparative example manufactured with high lactose fines content (15%) was poor and above target with 15.5%. As well the variation (RSD %) of the fine particle dose was high for this example. Therefore compositions with lactose fines content of >15% are concluded to be not appropriate while low lactose fines content down to 1% is expected to deliver a product with suitable manufacturing and aerosol performance properties.

Further dry powder blends were manufactured using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 as active ingredient and using a slightly different manufacturing process.

The study was performed to investigate the influence of a coarse, milled lactose type with intrinsic fines (Lactohale 200) with and without additional lactose fines (LH300) content on the established blending process and resulting aerosol performance. The study was also performed to generate data to compare to comparative example 20 (see Table 32).

The resulting exemplary embodiments 34-35 are summarized in the below table 40.

TABLE 40

Composition (lactose contents) of exemplary embodiments 34-35

| | Exemplary Embodiment 34 (10% active, 5 0 g) Amount (g) | Amount (%) | Exemplary Embodiment 35 (10% active, 50 g) Amount (g) | Amount (%) |
|---|---|---|---|---|
| API concentration and batch size | | | | |
| Active ingredient: example 4* | 5.0 | 10% | 5.0 | 10% |
| Coarse Lactose (Lactohale 200) | 45.0 | 90% | 42.5 | 85% |
| Fine Lactose (Lactohale 300) | 0.0 | 0% | 2.5 | 5% |
| Total | 50.0 | | 50.0 | |
| Blend Uniformity Assay (RSD %) | | 115% (6.7%) | | 112% (10.5%) |
| LH 300 fines content Lactose Mixture | | 0% | | 5.0% |
| Ratio Active ingredient: LH 200** | | 1:9 | | 1:8.5 |
| Ratio Active ingredient: LH 300** | | 1:0 | | 1:0.5 |

*used as Monohydrate I

The manufacturing process of exemplary embodiment 34-35 differed in Step 6.

Step 6: The blend was manually filled into capsules at the desired fill weight.

The results for aerosol performance for filled capsules of exemplary embodiments 34-35 are summarized in table 41.

TABLE 41

Aerosol performance of exemplary embodiments 34-35

| | Exemplary Embodiment 34 | Exemplary Embodiment 35 |
|---|---|---|
| Nominal dose | 1000 µg | 1000 µg |
| concentration of active ingredient, example 4 in powder blend | 10% | 10% |
| Fill weight | 10 mg | 10 mg |
| Delivered Dose (DD)* | 599 µg | 645 µg |
| DD (% of nominal) | 60% | 65% |
| Fine Particle Dose <4.5 µm (FPD) | 197 µg | 207 µg |
| FPD (RSD %) | 8.0% | 7.4% |
| FPF (% of nominal) | 20% | 21% |
| FPF (% of DD) | 32% | 34% |

*determined by sum of recovery in NGI

The results for the aerosol performance of filled capsules from exemplary embodiments 34-35 met all targets. The blend uniformity was acceptable for both blends. The aerosol performance was only slightly above the target limits for FPF % of nominal and % of delivered dose. As well the results from these embodiments manufactured in the same sequence as exemplary embodiments 31-32 and comparative example 33 are significantly lower as compared to the embodiments with LH100/LH300 composition showing an inferior comparative performance of the LH200 vs LH100 coarse lactose. Addition of 5% LH300 fines did not result in better FPD/FPF results. As shown by comparative example 20 the performance could possibly be enhanced by increasing the lactose fines towards 20% but consequently resulting in insufficient blending process and blend uniformity. Lactose blends using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 in the established process with LH200 coarse lactose with and without LH300 up to 5% were still shown to lead to an acceptable product.

Further dry powder blends were manufactured using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) (example 4) as active ingredient and using a partially different manufacturing process.

The studie's scope was to manufacture further embodiments of the invention with varying fine lactose content over a range of 2.5%-7.5% but utilizing a different fine lactose quality (Lactohale® 230) with slightly higher particle sizes/see table 6) while coarse lactose quality was kept constant and observe process and aerosol performance.

The resulting exemplary embodiments 36-38 are summarized in the below table 42.

TABLE 42

Compositions of exemplary embodiments 36-38

| API concentration and batch size | Exemplary Embodiment 36 (10% active, 200 g) Amount (g) | Amount (%) | Exemplary Embodiment 37 (10% active, 200 g) Amount (g) | Amount (%) | Exemplary Embodiment 38 (10% active, 200 g) Amount (g) | Amount (%) |
|---|---|---|---|---|---|---|
| Active ingredient (example 4)* | 20.0 | 10% | 20.0 | 10% | 20.0 | 10% |

TABLE 42-continued

| Compositions of exemplary embodiments 36-38 | | | | | | | |
|---|---|---|---|---|---|---|---|
| API concentration | | Exemplary Embodiment 36 (10% active, 200 g) | | Exemplary Embodiment 37 (10% active, 200 g) | | Exemplary Embodiment 38 (10% active, 200 g) | |
| and batch size | | Amount (g) | Amount (%) | Amount (g) | Amount (%) | Amount (g) | Amount (%) |
| Coarse Lactose (Lactohale 100) | | 175.0 | 87.5% | 170.0 | 85% | 165.0 | 82.5% |
| Fine Lactose (Lactohale 230) | | 5.0 | 2.5% | 10.0 | 5% | 15.0 | 7.5% |
| Total | | 200.0 | | 200.0 | | 200.0 | |
| Blend Uniformity Assay (RSD %) | 30 min | | 110% (9.6%) | | 100% (8.3%) | | 104% (5.6%) |
| | 60 min | | 111% (5.3%) | | 100% (3.7%) | | 109% (5.6%) |
| | 90 min | | 106% (6.7%) | | 103% (4.5%) | | 112% (9.3%) |
| | 120 min | | 103% (10.2%) | | —** — | | 116% (11.7%) |
| LH 230 fines content in Lactose mixture | | | 2.8% | | 5.6% | | 8.3% |
| Ratio Active ingredient: LH 100 | | | 1:8.75 | | 1:8.5 | | 1:8.25 |
| Ratio Active ingredient: LH 230 | | | 1:0.25 | | 1:0.5 | | 1:0.75 |

*used as Monohydrate I
**data not available

Step 6: The blend was manually filled into capsules at the desired fill weight.

The results for aerosol performance for filled capsules of exemplary embodiments 34-35 are summarized in table 43. Aerosol performance was measured after 90 minutes of blending representing the blending time of the established process according to the invention.

TABLE 43

| Aerosol performance of exemplary embodiments 36-38 | | | |
|---|---|---|---|
| | Exemplary Embodiment 36 | Exemplary Embodiment 37 | Exemplary Embodiment 38 |
| Nominal dose | 1000 µg | 1000 µg | 1000 µg |
| concentration of active ingredient, example 4 in powder blend | 10% | 10% | 10% |
| Fill weight | 10 mg | 10 mg | 10 mg |
| Delivered Dose (DD)* | 490 µg | 496 µg | 642 µg |
| DD (% of nominal) | 49% | 50% | 64% |
| Fine Particle Dose <4.5 µm (FPD) | 269 µg | 259 µg | 287 µg |
| FPF (% of nominal) | 27% | 26% | 29% |
| FPF (% of DD) | 55% | 52% | 45% |

*determined by sum of recovery in NGI

The results for the aerosol performance of filled capsules from exemplary embodiments 36-38 met all targets. The blend uniformity was acceptable for all blends however with a trend to run out of targets for high fines (7.5%, exemplary embodiment 38 and longer mixing times). Increasing the content of Lactose fines (LH230) showed an increase in overall delivered dose with only low increase in FPD and thus decreasing FPF (% of DD). Lactose blends using (5S)-{([2-(4-carboxyphenyl)ethyl][2-(2-{[3-chloro-4'-(trifluoromethyl)biphenyl-4-yl]methoxy)phenyl)ethyl]-amino}}-5,6,7,8-tetrahydroquinoline-2-carboxylic acid monohydrate I of formula (I-M-I), example 4 in the established process with LH230 fine lactose (with a different particle size distribution compared to LH300 micronized lactose fines were shown to lead to an acceptable product and manufacturability.

Further dry powder blends were manufactured using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) (example 4) as active ingredient and using a partially different manufacturing process.

The studie's scope was to manufacture further embodiments of the invention with an alternative coarse lactose product (Lactohale® 206, having a slightly smaller particle size than Lactohale®100, see table 6) over a range of 2.5%-7.5% fines content according to the invention (LH300*) and observe process and aerosol performance.

The resulting exemplary embodiments 39-41 are summarized in the below table 44

TABLE 44

Compositions of exemplary embodiments 39 - 41

| API concentration and batch size | | Exemplary Embodiment 39 (10% active, 200 g) Amount (g) | Amount (%) | Exemplary Embodiment 40 (10% active, 200 g) Amount (g) | Amount (%) | Exemplary Embodiment 41 (10% active, 200 g) Amount (g) | Amount (%) |
|---|---|---|---|---|---|---|---|
| Active ingredient (example 4)* | | 20.0 | 10% | 20.0 | 10% | 20.0 | 10% |
| Coarse Lactose (Lactohale 206) | | 175.0 | 87.5% | 170.0 | 85% | 165.0 | 82.5% |
| Fine Lactose (Lactohale 300) | | 5.0 | 2.5% | 10.0 | 5% | 15.0 | 7.5% |
| Total | | 200.0 | | 200.0 | | 200.0 | |
| Blend Uniformity Assay (RSD %) | 30 min | | 109% (9.2%) | | 117% (18.2%) | | 107% (14.7%) |
| | 60 min | | 107% (11.9%) | | 104% (17.2%) | | 98% (7.8%) |
| | 90 min | | 108% (15.5%) | | 104% (6.7%) | | 115% (19.4%) |
| | 120 min | | 101% (5.5%) | | 112% (11.7%) | | 118% (7.7%) |
| LH 300 fines content in Lactose mixture | | | 2.8% | | 5.6% | | 8.3% |
| Ratio Active ingredient:LH 206 | | | 1:8.75 | | 1:8.5 | | 1:8.25 |
| Ratio Active ingredient:LH 300 | | | 1:0.25 | | 1:0.5 | | 1:0.75 |

*used as Monohydrate I
**data not available

The manufacturing process of exemplary embodiment 39-41 differed in Step 6.

Step 6: The blend was manually filled into capsules at the desired fill weight.

The results for aerosol performance for filled capsules of exemplary embodiments 39-41 are summarized in table 45. Aerosol performance was measured after 90 minutes of blending representing the blending time of the established process according to the invention.

TABLE 45

Aerosol performance of exemplary embodiments 39-41

| | Exemplary Embodiment 39 | Exemplary Embodiment 40 | Exemplary Embodiment 41 |
|---|---|---|---|
| Nominal dose | 1000 μg | 1000 μg | 1000 μg |
| concentration of active ingredient, example 4 in powder blend | 10% | 10% | 10% |
| Fill weight | 10 mg | 10 mg | 10 mg |
| Delivered Dose (DD)* | 606 μg | 678 μg | 596 μg |
| DD (% of nominal) | 61% | 68% | 60% |
| Fine Particle Dose <4.5 μm (FPD) | 285 μg | 304 μg | 239 μg |
| FPF (% of nominal) | 29% | 30% | 24% |
| FPF (% of DD) | 45% | 45% | 40% |

*determined by sum of recovery in NGI

The results for the aerosol performance of filled capsules from exemplary embodiments 39-41 met all targets. The blend uniformity was acceptable for the blends however not for all blends at all time points. An optimum was seen with 5% fines after 90 min of mixing, corresponding to the established process according to the invention. Increasing the content of lactose fines (LH300) did not show a resulting trend of any of the aerosol performance parameters, rather optimum performance was observed at 5% fines according to the invention. Lactose blends using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 in the established process with LH300 coarse fine lactose and LH206 coarse lactose (with a different particle size distribution compared to LH100 lactose) were shown to lead to an acceptable product and manufacturability.

Further dry powder blends were manufactured using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I) (example 4) as active ingredient and using a partially different manufacturing process.

The studie's scope was to manufacture further embodiments of the invention with an alternative coarse lactose product (LH206®) and alternative fine lactose product (LH230®) over a range of 2.5%-7.5% fines content and observe process and aerosol performance.

The resulting exemplary embodiments 42-44 are summarized in the below table 46.

TABLE 46

| Compositions of exemplary embodiments 42-44 | | | | | | |
|---|---|---|---|---|---|---|
| API concentration | Exemplary Embodiment 42 (10% active, 200 g) | | Exemplary Embodiment 43 (10% active, 200 g) | | Exemplary Embodiment 44 (10% active, 200 g) | |
| and batch size | Amount (g) | Amount (%) | Amount (g) | Amount (%) | Amount (g) | Amount (%) |
| Active ingredient (example 4)* | 20.0 | 10% | 20.0 | 10% | 20.0 | 10% |
| Coarse Lactose (Lactohale 206) | 175.0 | 87.5% | 170.0 | 85% | 165.0 | 82.5% |
| Fine Lactose (Lactohale 230) | 5.0 | 2.5% | 10.0 | 5% | 15.0 | 7.5% |
| Total | 200.0 | | 200.0 | | 200.0 | |
| Blend Uniformity Assay (RSD %) 30 min | | 104% (8.4%) | | 97% (5.6%) | | 110% (11.3%) |
| 60 min | | 115% (12.9%) | | 111% (10.5%) | | 107% (9.4%) |
| 90 min | | 109% (5.9%) | | 101% (9.1%) | | 112% (11.1%) |
| 120 min | | 119% (10.5%) | | 113% (12.5%) | | 106% (6.5%) |
| LH 230 fines content in Lactose mixture | | 2.8% | | 5.6% | | 8.3% |
| Ratio Active ingredient: LH 206 | | 1:8.75 | | 1:8.5 | | 1:8.25 |
| Ratio Active ingredient: LH 230 | | 1:0.25 | | 1:0.5 | | 1:0.75 |

*used as Monohydrate I

**data not available

The manufacturing process of exemplary embodiment 42-44 differed in Step 6.

Step 6: The blend was manually filled into capsules at the desired fill weight.

The results for aerosol performance for filled capsules of exemplary embodiments 42-44 are summarized in table 47. Aerosol performance was measured after 90 minutes of blending representing the blending time of the established process according to the invention (except for exemplary embodiment 44, where the measurement was only done after 120 min of blending).

TABLE 47

| Aerosol performance of exemplary embodiments 42-44 | | | |
|---|---|---|---|
| | Exemplary Embodiment 42 | Exemplary Embodiment 43 | Exemplary Embodiment 44 |
| Nominal dose | 1000 µg | 1000 µg | 1000 µg |
| concentration of active ingredient, example 4 in powder blend | 10% | 10% | 10% |
| Fill weight | 10 mg | 10 mg | 10 mg |
| Delivered Dose (DD)* | 569 µg | 588 µg | 599 µg |
| DD (% of nominal) | 57% | 59% | 60% |
| Fine Particle Dose <4.5 µm (FPD) | 206 µg | 206 µg | 214 µg |
| FPF (% of nominal) | 21% | 21% | 21% |
| FPF (% of DD) | 36% | 35% | 36% |

*determined by sum of recovery in NGI

The results for the aerosol performance of filled capsules from exemplary embodiments 42-44 met all targets, however with all being close to the target limits. The blend uniformity was acceptable for the blends however not for all blends at all time points. An optimum was seen sometimes observed after 90 min of mixing, sometimes after 120 min. Exemplary embodiment 43 with 5% lactose fines according to the invention was acceptable after 90 min with regard to RSD % and blend assay, while sometimes blend assay results were above target of 110%. Increasing the content of lactose fines (LH300) did not show any impact on any of the aerosol performance parameters, which were very similar for all embodiments 42-44. Lactose blends using (5S)-{[2-(4-carboxyphenyl)ethyl][2-(2-{[3-chloro-4'-(trifluoromethyl)biphenyl-4-yl]methoxy}phenyl)ethyl]-amino}-5,6,7,8-tetrahydroquinoline-2-carboxylic acid monohydrate I of formula (I-M-I), example 4 in the established process with LH230 fine lactose (with a different particle size distribution compared to LH300) and LH206 coarse lactose (with a different particle size distribution compared to LH100 lactose) were shown to lead to an acceptable product and manufacturability.

Finally it can be concluded form the above described examples:

The fine lactose content of the lactose carrier can be adjusted to just about 1% or even below if e.g. a coarse lactose with an intrinsic fine lactose content is utilized, like e.g. Lactohale 200®. The upper limit for fine lactose should be adjusted up to 10 or about up to 15% in order not to jeopardize the blend uniformity. Generally a certain minimum content of fine lactose is essential in order to obtain carrier based formulations which exhibit an excellent aerosol performance.

Stability Test

Stability studies were conducted with one clinical batch each of a low strength (120 µg, according to the invention, exemplary embodiment 1) and high strength (1000 µg according to the invention, exemplary embodiment 3). Stability testing was carried out with respect to appearance, delivered dose, aerodynamic particle size distribution, assay and degradation products as well as physical form (high strength batch only). The study was carried out according to the protocol outlined in table 34.

TABLE 48

Stability protocol-long-term capsule for inhalation comprising example 2

| Storage condition | Storage [months] 0 | 1 | 3 | 6 | 9 | 12 | 18 | 24 | 36 |
|---|---|---|---|---|---|---|---|---|---|
| 25° C./60 % RH | X | X | X | X | (X) | X | X | X | (X) |

RH relative humidity
X test station
(X) optional test station

Throughout the tested period no signs of significant changes in any of the tested parameters was observed. Therefore the powder blend formulations according to the invention are sufficiently stable for the intended use and storage period. Stability data are presented in the following table 49.

TABLE 49

Stability data-long-term capsule for inhalation comprising example 2

| Test<br>Acceptance criterion | Storage time [months] | Embodiment 1 (120 µg) | Embodiment 2 (BN016/18) (1000 µg) |
|---|---|---|---|
| Formulation | Initial | complies | complies |
| (hard capsule, clear & colorless | 1 | complies | complies |
| no marking) | 3 | complies | complies |
| | 6 | complies | complies |
| | 12 | complies | complies |
| | 18 | complies | complies |
| | 24 | complies | complies |
| Appearance of capsule content | Initial | white powder | off-white powder |
| (white to off-white powder) | 1 | white powder | white powder |
| | 3 | white powder | white powder |
| | 6 | white powder | white powder |
| | 12 | white powder | white powder |
| | 18 | white powder | white powder |
| | 24 | white powder | white powder |
| Delivered Dose Uniformity | Initial | 71 | 625 |
| Mean delivered dose | 1 | 67 | 659 |
| 120 µg: 64-92 µg | 3 | 75 | 691 |
| 1000 µg: 550-750 µg | 6 | 70 | 625 |
| | 12 | 66 | 644 |
| | 18 | 63 | 646 |
| | 24 | 68 | 660 |
| Tier 1 (n = 10) | Initial | complies | complies |
| (9 of 10 must lie between 75% and | 1 | complies | complies |
| 125% | 3 | complies | complies |
| and 10 of 10 lie between | 6 | complies | complies |
| 65% and 135% of the mean) | 12 | complies | complies |
| | 18 | complies | complies |
| | 24 | complies | complies |
| Tier 2 (n = 30) | Initial | n.a. | n.a. |
| (Not more than 3 of all 30 values lie | 1 | n.a. | n.a. |
| outside the limits of 75% to 125% and | 3 | n.a. | n.a. |
| no value | 6 | n.a. | n.a. |
| lies outside the limit of 65% to 135% | 12 | n.a. | n.a. |
| of the mean) | 18 | n.a. | n.a. |
| | 24 | n.a. | n.a. |
| Aerodynamic Particle Size | Initial | 3.2 | 3.1 |
| Distribution | 1 | 3.3 | 3.1 |
| MMAD | 3 | 3.4 | 3.2 |

TABLE 49-continued

Stability data-long-term capsule for inhalation comprising example 2

| Test<br>Acceptance criterion | Storage time [months] | Embodiment 1 (120 μg) | Embodiment 2 (BN016/18) (1000 μg) |
|---|---|---|---|
| (1.8-5.0 μm) | 6 | 3.3 | 3.1 |
| | 12 | 3.5 | 3.1 |
| | 18 | 3.5 | 3.3 |
| | 24 | 3.5 | 3.1 |
| FPD | Initial | 34 | 230 |
| 120 μg: 15-37 μg | 1 | 24 | 235 |
| 1000 μg 123-312 μg | 3 | 20 | 255 |
| | 6 | 24 | 276 |
| | 12 | 23 | 260 |
| | 18 | 26 | 252 |
| | 24 | 22 | 265 |
| degradation products of example 2 | Initial | <0.05 | <0.05 |
| BP Aminoacid | 1 | n.d. | n.d. |
| (max. 1.5%) | 3 | n.d. | n.d. |
| | 6 | <0.05 | <0.05 |
| | 12 | <0.05 | <0.05 |
| | 18 | <0.05 | <0.05 |
| | 24 | <0.05 | <0.05 |
| BP-THQ-carboxylic acid | Initial | 0.1 | <0.05 |
| (max. 1.5%) | 1 | 0.1 | n.d. |
| | 3 | 0.1 | n.d. |
| | 6 | 0.1 | 0.05 |
| | 12 | 0.1 | 0.05 |
| | 18 | 0.1 | 0.05 |
| | 24 | 0.1 | 0.06 |
| any unspecified degradation product | Initial | 0.3 | 0.3 |
| (max. 1.5%) | 1 | 0.3 | 0.3 |
| | 3 | 0.3 | 0.3 |
| | 6 | 0.3 | 0.3 |
| | 12 | 0.3 | 0.3 |
| | 18 | 0.3 | 0.3 |
| | 24 | 0.3 | 0.3 |
| sum of all degradation products | Initial | 1.0 | 0.9 |
| (max. 5.0%) | 1 | 0.8 | 0.8 |
| | 3 | 0.8 | 0.7 |
| | 6 | 0.8 | 0.8 |
| | 12 | 1.0 | 0.9 |
| | 18 | 1.2 | 1.0 |
| | 24 | 1.1 | 1.1 |
| Assay of example 2 | Initial | 115 | 962 |
| 120 μg: 108-132 μg/capsule | 1 | 116 | 995 |
| 1000 μg: 900-1100 μg/capsule | 3 | 113 | 961 |
| | 6 | 113 | 965 |
| | 12 | 113 | 955 |
| | 18 | 114 | 967 |
| | 24 | 112 | 977 |
| Physical form | Initial | — | Monohydrate |
| (Monohydrate) | 1 | — | — |
| | 3 | — | — |
| | 6 | — | — |
| | 12 | — | Monohydrate |
| | 18 | — | — |
| | 24 | — | Monohydrate |

n.d. = not detected,

— not tested

D-2 Service Solution for Clinical Investigations, e.g. Oral and Intravenous Administration Service solution comprising example 4:

A service solution for clinical investigations (see example C-4.3) was produced with a concentration of 0.005% of active ingredient, example 4 (monohydrate I of formula (I-M-I)) with a total volume of 20 ml, finally filled into brown glass vial.

TABLE 50 quantitative composition of a service solution comprising example 4

| Composition | Amount [mg] | Filled amount [a] [mg] |
|---|---|---|
| Drug substance | | |
| active ingredient, example 4 (monohydrate I of formula (I-M-I) | 1.0000 | 1.0450 |
| Excipients | | |
| Hydroxypropylbetadex | 200.00 | 209.00 |
| Trometamol | 24.200 | 25.289 |
| Sodium chloride | 152.00 | 158.84 |
| Sodium hydroxide 1 N | q.s. | q.s. |
| Hydrochloric acid 10% | q.s. | q.s. |
| Water for injections | 19773 | 20664 |

[a] quantities include a 0.9 ml overfill ensuring an extractable volume of 20.0 ml
[b] consisting of NaOH and purified water according to Ph. Eur. current edition
q.s. quantum satis Manufacturing Step 1: A vessel was charged with approximately 85% of the required quantity of water for injections.

Step 2: The weighed quantity of Hydroxypropylbetadex was transferred to the vessel, the solution was stirred until completeness of dissolution.

Step 3: The weighed quantity of trometamol was transferred to the vessel, the solution was stirred until completeness of dissolution.

Step 4: The pH was adjusted to 12.0 (11.8-12.2) with an appropriate amount of sodium hydroxide 1 N.

Step 5: The weighed quantity of the active ingredient, example 4 (monohydrate I of formula (I-M-I) was transferred to the vessel, the solution was stirred until completeness of dissolution.

Step 6: The weighed quantity of sodium chloride was transferred to the vessel, the solution was stirred until completeness of dissolution.

Step 7: The pH was adjusted to 7.8 (7.7-7.9) with an appropriate amount of hydrochloric acid 10%.

Step 8: The amount of water for final weight was calculated and the required amount of water for injections was added while stirring.

Step 9: The solution was prefiltered (filter 1, bioburden-reduction filter) and sterile filtered (filter 2) prior to aseptic filling into glass vials through a membrane filter (pore size 0.2 μm).

Step 10: The solution was filled into sterile, depyrogenized 20 mL brown glass injection vials.

Step 11: The vials were capped and crimped for complete closure.

E—ANALYTICAL METHODS (Delivered Dose, Fine Particle Dose, Blend Assay & Uniformity)

Below the analytical methods to determine the delivered dose and the fine particle dose are described in detail.

| | |
|---|---|
| E-1: Delivered Dose (DD) | The method is performed with the dry powder inhaler (see description, page 89, FIGS. 3a and 3b) and the inhalation capsule (for preparation of capsules see C.) according to Ph. Eur. Monograph *Preparations for Inhalation-Powders for inhalation*, using the specified sample collection tube (dose unit sampling adapter = DUSA), a digital flow meter and a vacuum pump. Sampling is performed at a flow of 90 L/min for 2.4 sec corresponding to 3.6 L inhaled volume. DD sample preparation is perfomed at 20° C. and 40-55% RH. Samples are measured using High-performance liquid chromatography with UV-detection (summarized below) |
| E-2 Aerodynamic particle size distribution (APSD) (for determinationof FPD) | The method is performed with the dry powder inhaler (see description, page 89, FIGS. 3a and 3b) and the inhalation capsule (for preparation of capsules see C.) according to *Ph. Eur. 2.9.18 aerodynamic assessment of fine particles* using apparatus E (Next Generation Impactor, NGI) a digital flow meter and a vacuum pump. NGI sampling cups are coated each with 2 mL of a solution of 1% silicone oil in hexane. Sampling is performed at a flow of 90 L/min for 2.4 sec corresponding to 3.6L inhaled volume. DD sample preparation is perfomed at 20° C. and 40-55% RH. For 120 μg capsules 5 individual cpasules are fired consecutively into the NGI as described above, for higher dose strengths (e.g. 480 μg, 1000 μg) one capsule is sufficient for each NGI analysis.<br>Samples are measured using a reversed phase high performance liquid chromatography with UV-detection (summarized below) |
| RP-HPLC-UV method (for samples from APSD and DD testing and capsule assay) | The assay method is used for assay of the content of example 2 or 4 or comparative example 14 in samples prepared during delivered dose uniformity (by DUSA sampling tube) and aerodynamic particle size determination (by next generation impactor). |
| Equipment | High-performance liquid chromatograph with thermostated column oven, UV-detector or diode array detector and chromatography data system |

-continued

| | |
|---|---|
| Column | HPLC Column Poroshell 120 EC-C8, 2.7 µm, 150 × 4.6 mm. |
| Sample diluent [Sol] | Acetonitrile/Water/Phosphoric acid 50/50/0.35 (for APSD & DD) |
| Acidified Water | Phosphoric acid/Water (7:1000 (v:v)) |
| Sample preparation | The required no of capsules are emptied into a volumetric flask containing acidified water. The capsules are rinsed with ethanol and the solution including capsule shells transferred to the vol. flask. The resulting solution has a concentration of 6 µg/mL. Samples for APSD are prepared by extraction of the NGI cups with acetonitrile. Samples for DD are prepared by washing of the sample tube with sample diluent. |
| HPLC conditions | |
| Eluent | A) 52:48 $H_2O$:MeCN with 0.3% phosphoric acid.<br>B) 5:95 $H_2O$:MeCN with 0.3% phosphoric acid. |
| Elution | Gradient |

| Time (min) | % A | % B |
|---|---|---|
| 0.0 | 100 | 0 |
| 6.0 | 100 | 0 |
| 6.5 | 0 | 100 |
| 8.0 | 0 | 100 |
| 8.5 | 100 | 0 |
| 11.0 | 100 | 0 |

| | |
|---|---|
| Chromatogram run time | 11 minutes |
| Flow rate | 1.5 mL/minute |
| Temperature of column oven | 35° C. (±2° C.) |
| Detection | Spectrophotometer at 260 nm |
| Injection volume | 100 µL |
| E-3 Blend assay/ uniformity (HPLC) | High performance liquid chromatopraphy (HPLC) with UV-detection. |
| Equipment | 1. High-perforamnce liquid chromatograph with thermostated column oven. UV-detector or diode array detector and chromatopraphy data system.<br>2. HPLC Column Poroshell 120 Ec-C8, 2.7 µm, 150 × 4.6 mm.<br>3. Ultrasonic bath. |
| Reagents | 1. Phosphoric acid (e.g. Merck).<br>2. Acetonitrile (MeCN (HPLC-grade).<br>3. Demineralized water (e.g. Millipore). |
| Sample diluent [Sol] | Acetonitrile/Water/Phosphoric acid 50/50/0.35 |
| Acidified water | Phosphoric acid/Water (7:1000 (v:v)) |
| Test solution [TS] | Prepare the test solutions 10 times. All test solutions are stable for 7 days under ambient/light conditions. |
| 7.5 µg/mg blend strength (1.2 µg/mL sample solution) Target capsule strength: 60 µg | Accurately weigh approximately 8.0 mg of 7.5 µg/mg bulk blend into a 50 mL volumetric flask. Dissolve and make to volume with diluent to produce 1.2 µg/mL example 2 or 4 or comparative example 14 solution. |
| 7.5 µg/mg blend strength (1.2 µg/mL sample solution) Target capsule strength: 120 µg | Accurately weigh approximately 16.0 mg of 7.5 µg/mg bulk blend into a 100 mL volumetric flask. Dissolve and make to volume with diluent to produce 1.2 µg/mL example 2 or 4 or comparative example 14 solution. |
| 30 µg/mg blend strength (4.8 µg/mg stock solution, (1.44 µg/mL sample solution) Target capsule strength: 480 µg | Accurately weigh approximately 16.0 mg of bulk 30 µg/mg blend into a 100 mL volumetric flask. Dissolve and make to volume with diluent and dilute 3.0 mL to 10mL with diluent to produce 1.4 µg/mL example 2 or 4 or comparative example 14 solution. |
| 100 µg/mg blend strength (5 µg/mg stock solution, 1.5 µg/mL sample solution) Target capsule strength: 1000 µg | Accurately weigh approximately 10.0 mg of bulk blend into a 200 mL volumetric flask. Dissolve and make to volume with diluent, and dilute 6.0 mL to 20 mL with diluent to produce 1.5 µg/mL example 2 or 4 or comparative example 14 solution. |
| Standard stock solution [SSS] (15 µg/mL) | Weigh, in duplicate, the amount of example 2 or 4 or comparative example 14 reference standard required to make an approximate 15 µg/mL solution and transfer into a 100 mL volumetric flask. Sonicate and dilute to volume with diluent. Label stock solutions as SSS 1 and SSS 2. Different weights of standard substances and different dilution steps may be used if they lead to the same final concentrations. |
| Standard solution [SS] (1.5 µg/mL) | Dilute 5.0 mL of each of the stock standards to 50 mL using diluent and mix well to produce the working standard solutions. |

-continued

| | |
|---|---|
| HPLC conditions | As described for Delivered dose and fine particle dose. |
| E-4 Particle Size Distribution (Laser Diffraction) | Applied for e.g. API or Lactose |
| Principle | A representative sample, dispersed at an adequate concentration in a suitable liquid or gas, is passed through a beam of monochromatic light, usually a laser. The light scattered by the particles at various angles is measured by a multi-element-detector. The scattering pattern values are then transformed, using an appropriate optical model and mathematical procedure, to yield the proportion of total volume to a discrete number of size classes forming a volumetric particle size distribution |
| Equipment | Sympatec HELOS with RODOS dry dispersion unit |
| Parameter | Pressure: 4 bar<br>Feed Rate: 18%<br>Focal Length (RODOS): 100 mm |
| Precision | Coefficient of variation max 5% |
| Alternative configuration for laser diffraction measurement | |
| Equipment | Malvern Mastersizer 3000 with dry dispersion unit |
| Parameter | Pressure: 3.5 bar<br>Feed rate: 20%<br>Focal length: 300 mm<br>Sampling Time: 3 s |
| Precision | Coefficient of variation: max 5% |

The particle size analysis data are usually reported as cumulative undersized distribution by volume. The symbol x is used to denote the particle size, which is defined as diameter of a volume equivalent sphere. Most common characteristic values are calculated from the particle size distribution by interpolation. Frequently used are the particle sizes at the undersize values of 10%, 50% and 90% of the volume distribution, denoted as x10, x50 and x90. x50 is also known as median particle size. The symbol d is widely used to designate the particle size, thus the symbol x may be replaced by the symbol d.

E—5 Additional Stability Test Methods

| | | | |
|---|---|---|---|
| Appearance | Visual Test | | |
| RP-HPLC-UV method (for degradation products) | Reversed phase high performance liquid chromatography (HPLC) with UV-detection at 260 nm and external calibration. | | |
| Equipment | High-performance liquid chromatograph with thermostated column oven, UV-detector or diode array detector and chromatography data system | | |
| Column | HPLC Column Poroshell 120 EC-C8, 2.7 μm, 150 × 4.6 mm. | | |
| Sample diluent [Sol] | Acetonitrile/Water/Phosphoric acid 50/50/0.35 | | |
| Acidified Water | Phosphoric acid/Water (7:1000 (v:v)) | | |
| Sample preparation | The required no of capsules are emptied into a volumetric flask containing acidified water. The capsules are rinsed with acetonitrile and the solution without capsule shells transferred to the vol. flask. Make the volumetric flask to volume with acetonitrile to produce 60 μg/mL example 2 or 4 or comparative example 14 solution. | | |
| HPLC conditions | | | |
| Eluent | A) 55:45 $H_2O$:MeCN with 0.3% phosphoric acid.<br>B) 5:95 $H_2O$:MeCN with 0.3% phosphoric acid. | | |
| Elution | Gradient | | |
| | Time (min) | % A | %B |
| | 0.0 | 100 | 0 |
| | 12.0 | 100 | 0 |
| | 32.0 | 0 | 100 |
| | 35.0 | 0 | 100 |
| | 35.1 | 100 | 0 |
| | 42.0 | 100 | 0 |
| Chromatogram run time | 42 minutes | | |
| Flow rate | 1.5 mL/minute | | |
| Temperature of column oven | 35° C. (±2° C.) | | |
| Detection | Spectrophotometer at 260 nm | | |
| Injection volume | 100 μL | | |
| Polymorphism-X-ray powder diffraction | | | |
| Principle of method | The identification of the solid state form is conducted according to the test procedure of 'Characterisation of crystalline and partially crystalline solids by X-ray powder diffraction' (Ph. Eur. 2.9.33). | | |

-continued

| | |
|---|---|
| Sample preparation: | Enclose the tablet or the crushed tablet as a thin layer between two foils (e.g. polyacetate foils). |
| Apparatus: | X-ray powder diffractometer |
| Generator: | 40 kV/40 mA |
| Detector: | Mythen (PSD) |
| Radiation: | germanium-monochromatized $CuK_{\alpha 1}$-radiation |
| Technique: | transmission |
| Scanning range: | 5° ≤ 2 Θ ≤ 30° |
| Stepwidth: | 0.1° |
| Measuring time: | Mythen 60 sec/step (PSD 240 sec/step) |

E-6 Additional method to characterize particle distributions and sizes of API and Lactose particles in finished dry powder blends

| | |
|---|---|
| Principle of the method | Automated optical and Raman microscopy integrated system to analyze morphology/particle size and number of a composite powder sample concurrently with identification of chemical nature of the components of a powder blend. |
| Apparatus: | Malvern Morphologi 4-ID |
| Dry dispersion (exmplary settings): | Volume: 5 $mm^3$<br>Pressure: 3 bar<br>Dispersion time: 3 ms<br>Settling Time: 60 s |
| Morphology (exemplary settings): | Light Source: Diascopic<br>Objective (magnification) ×50<br>Scan area 784 $mm^2$ |
| Raman (exemplary settings) : | Acquisition time: 15 s<br>Spectral masking: in region 0.520 $cm^{-1}$ and 790-1740 $cm^{-1}$ |

FIGURES

FIG. 1: Observed (symbols) and fitted (solid lines) pulmonary arterial pressure (=PAP) changes after administration of 0.15, 0.5, 1.5 and 5 µg/kg comparative example 11 (doses expressed as lung deposited doses) to minipigs (7 min inhalation as liquid aerosol). Relevant PAP reduction of 5% indicated as dotted line FIG. 2: Maximal expected PAP reduction for a 60 kg human at the corresponding lung deposited doses (FPD) based on the results of the anaesthetized thromboxane minipig model without considering interspecies differences in protein binding.

FIG. 3*a*+3*b*: capsule based single-unit dose inhaler

FIG. 4: X-Ray powder diffractogram of the amorphous residue build on salt screening experiments with L-arginine FIG. 5: X-Ray powder diffractogram of the Semihydrate, example 6a FIG. 6: X-Ray powder diffractogram of the Monohydrate I, example 6b FIG. 7: X-Ray powder diffractogram of the Monohydrate II, example 6c FIG. 8: X-Ray powder diffractogram of the 1,25-Hydrate, example 6d FIG. 9: X-Ray powder diffractogram of the Sesquihydrate, example 6e FIG. 10: X-Ray powder diffractogram of the Dihydrate, example 6f FIG. 10*a*: X-Ray powder diffractogram of the Dihydrate after drying, example 6f FIG. 11: X-Ray powder diffractogram of the amorphous form, example 6g FIG. 12: Raman spectrum of the Semihydrate, example 6a FIG. 13: Raman spectrum of the Monohydrate I, example 6b FIG. 14: Raman spectrum of the Monohydrate II, example 6c FIG. 15: Raman spectrum of the 1,25-Hydrate, example 6d FIG. 16: Raman spectrum of the Sesquihydrate, example 6e FIG. 17: Raman spectrum of the Dihydrate, example 6f FIG. 18: Raman spectrum of the amorphous form, example 6g FIG. 19: IR spectrum of the Semihydrate, example 6a FIG. 20: IR spectrum of the Monohydrate I, example 6b FIG. 21: IR spectrum of the Monohydrate II, example 6c FIG. 22: IR spectrum of the 1,25-Hydrate, example 6d FIG. 23: IR spectrum of the Sesquihydrate, example 6e FIG. 24: IR spectrum of the Dihydrate, example 6f FIG. 25: IR spectrum of the amorphous form, example 6g FIG. 26: DSC- and TGA-thermogram of the Semihydrate, example 6a FIG. 27: DSC- and TGA-thermogram of the Monohydrate I, example 6b FIG. 28: DSC- and TGA-thermogram of the Monohydrate II, example 6c FIG. 29: DSC- and TGA-thermogram of the 1,25-Hydrate, example 6d FIG. 30: DSC- and TGA-thermogram of the Sesquihydrate, example 6e FIG. 31: DSC- and TGA-thermogram of the Dihydrate, example 6f FIG. 32: DSC- and TGA-thermogram of the amorphous form, example 6g, amorphous form FIG. 33: X-Ray powder diffractogram of comparative example 11, amorphous form FIG. 34: X-Ray powder diffractogram of example 1, monohydrate II FIG. 35: X-Ray powder diffractogram of example 2 before micronization, monohydrate II FIG. 36: X-Ray powder diffractogram of example 2 after micronization, monohydrate II FIG. 37: X-Ray powder diffractogram of example 3, monohydrate I FIG. 38: X-Ray powder diffractogram of example 4, monohydrate I FIG. 39: X-Ray powder diffractogram of example 5, monohydrate I FIG. 40: X-Ray powder diffractogram of example 7 (storage stability): starting material for storage stability, monohydrate II FIG. 41: X-Ray powder diffractogram of example 7b (storage stability): material after one month storage stability testing at 25° C. and 60% relative humidity in polyethylene, monohydrate I FIG. 42: Overlay of X-ray powder diffractograms of example 8b (micronization): starting material (monohydrate II) (base line) and material after micronization (monohydrate II with amorphous amounts, PTFE coated jet mill, 25° C.) (top line)

FIG. 43: X-ray powder diffractogram of example 8a (micronization): material after micronization (monohydrate I with amorphous amounts, VA jet mill, 25° C.)

FIG. 44: X-ray powder diffractogram (example 8e) (micronization): material after micronization (monohydrate I)

FIGS. 45*a* + 45*b*: The effect of comparative example 11 in comparison to comparative example 1 (Cinaciguat) on PE-induced contraction of rabbit saphenous artery (incubation 0.5 h (left) vs. 2.5 h (right)). Data are presented as mean+/−SEM FIG. 46: Effects of comparative example 11 (300 nmol/l), comparative example 2 (100 nmol/l; Riociguat), comparative example 1 (100 nmol/l; Cinaciguat) and comparative example 3 (100 nmol/l) on coronary flow of isolated Langendorff-perfused rat heart and their wash-out. Data are presented as mean only.

Figure 47:
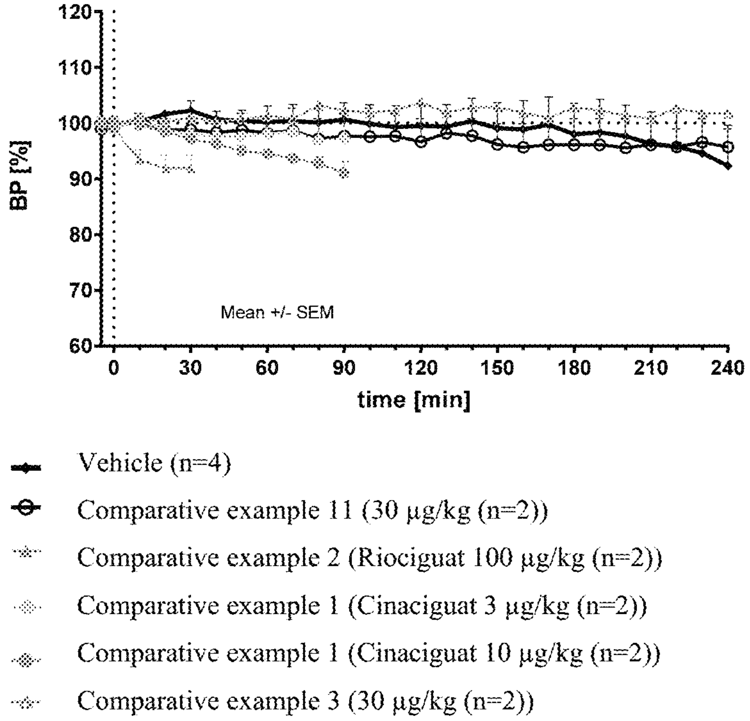

FIG. 47: Effects of vehicle solution, comparative example 11 (30 μg/kg), comparative example 1 (Cinaciguat; 3 and 10 μg/kg), comparative example 2 (Riociguat; 100 μg/kg) and comparative example 3 (30 μg/kg) after inhaled application under thromboxane analog U46619 induced PAH in minipigs on % changes in BP vs baseline (5 min interval prior to start of nebulization). Data are mean±SEM.

Figure 48:
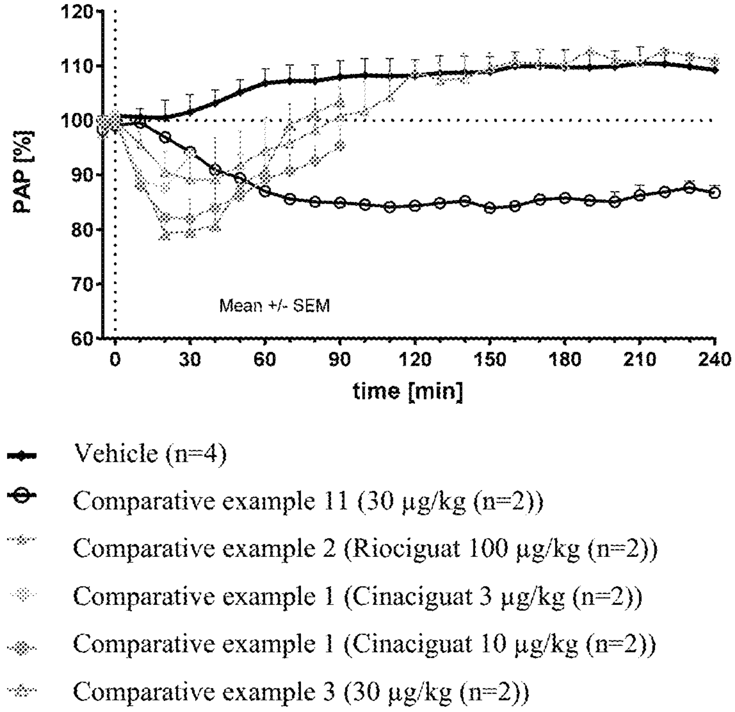

FIG. 48: Effects of vehicle solution, comparative example 11 (30 μg/kg), comparative example 1 (Cinaciguat; 3 and 10 μg/kg), comparative example 2 (Riociguat; 100 μg/kg) and comparative example 3 (30 μg/kg) after inhaled application under thromboxane analog U46619 induced PAH in minipigs on % changes in PAP vs baseline (5 min interval prior to start of nebulization). Data are mean±SEM.

FIG. 49: Effects of vehicle solution, comparative example 11, comparative example 4 and comparative example 5 (all compounds at 100 μg/kg nominal dose) after inhaled application under thromboxane analog U46619 induced PAH in minipigs on % changes in PAP and BP vs baseline (5 min interval prior to start of nebulization). Data are mean±SEM. Nebulizsation interval took 5-7 min for all compounds (yellow bar).

Figure 50:
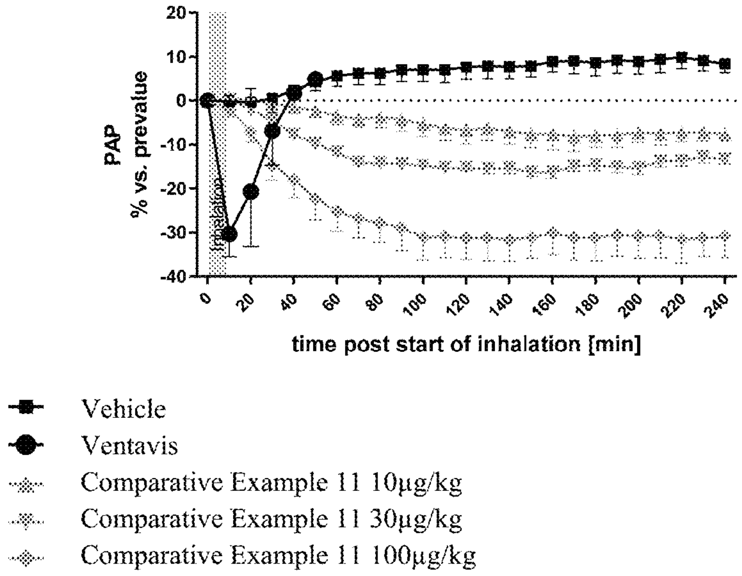

FIG. 50: Effects of vehicle solution, comparative example 11 (10, 30 and 100 μg/kg nominal dose) and Ventavis (10 μg/kg nominal dose) after inhaled application in the PAH minipigs model. Data are expressed as % changes in PAP and BP vs baseline (10 min interval prior to start of nebulization). Data are mean±SEM. Nebulizsation interval took 5-7 min for all compounds (grey bar).

Figure 51:
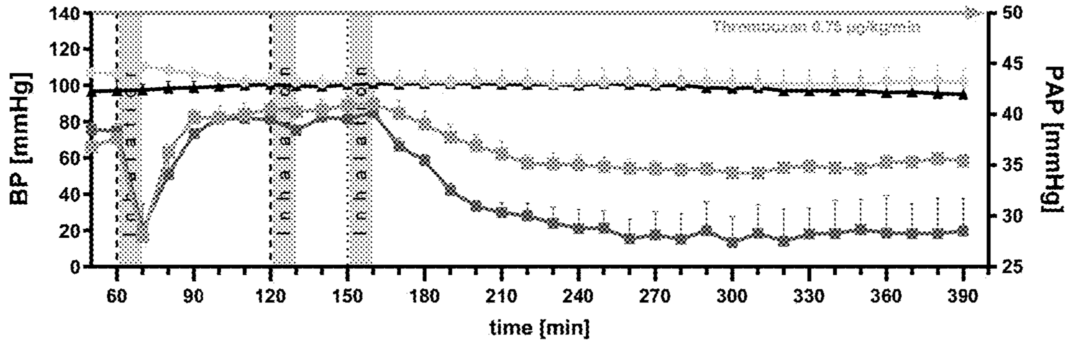

FIG. 51: Effects of comparative example 11 after inhaled application under thromboxane analog U46619 induced PAH in minipigs with and without pretreatment by ODQ. Data are mean±SEM (n=3)

Figure 52:
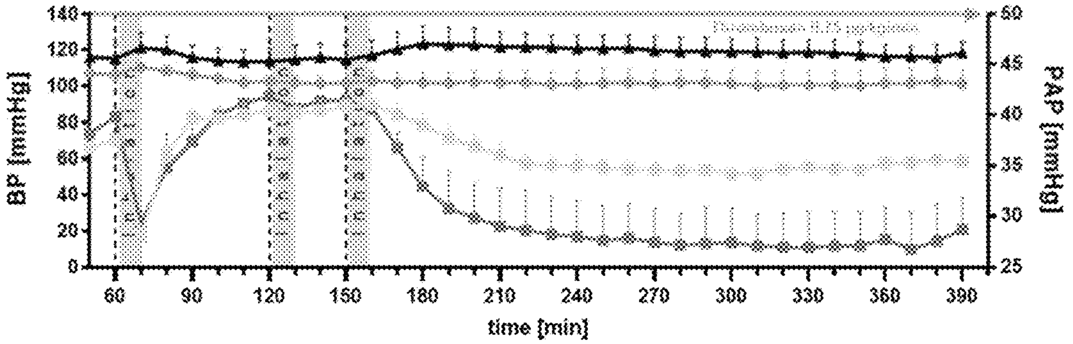

BP: arterial blood pressure; bpm: beats per minute; HR: heart rate; iv: intravenous; mBP: mean blood pressure; mPAP: mean pulmonary artery pressure; ODQ: 1H-[1,2,4] Oxadiazolo[4,3-a]quinoxalin-1-one, a highly selective, irreversible, heme-site inhibitor of soluble guanylyl cyclase; PAH: pulmonary arterial hypertension; PAP: pulmonary artery pressure; SEM: standard error of the mean; w/wo: with/without; wo: without FIG. 52: Effects of comparative example 11 after inhaled application under thromboxane analog U46619 induced PAH in minipigs with and without pretreatment by L-NAME (10 mg iv. Bolus followed by 5 mg/kg/h infusion). Data are mean±SEM (n=3) iv.: intravenous; L-NAME: L-No-Nitroarginine methyl ester; mBP: mean blood pressure; mPAP: mean pulmonary artery pressure; PAH: pulmonary arterial hypertension; PAP: pulmonary artery pressure; SEM: standard error of the mean; w/wo: with/without; wo: without FIG. 53*a*: Effects on % decrease in PAP and BP of comparative example 11 (30 and 100 μg/kg nominal dose) after inhaled application compared to systemically applied bosentan (1 mg/kg), sildenafil (300 μg/kg/h) and riociguat (3 μg/kg/h) under thromboxane analog U46619 induced PAH in minipigs. Data are mean±SEM (n=3)

Figure 53B:
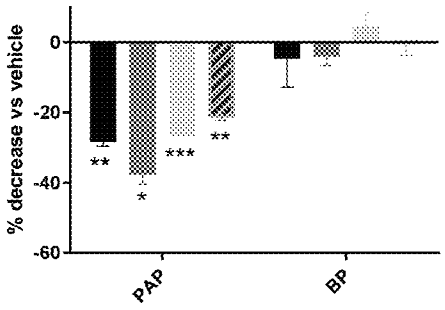

FIG. 53*b*: Effects on % decrease in PAP and BP of comparative example 11 (30 μg/kg nominal dose) after inhaled application alone or on top of systemically applied bosentan (1 mg/kg), sildenafil (300 μg/kg/h) and riociguat (3 μg/kg/h) under thromboxane analog U46619 induced PAH in minipigs. Data are mean±SEM (n=3)

Figure 54:
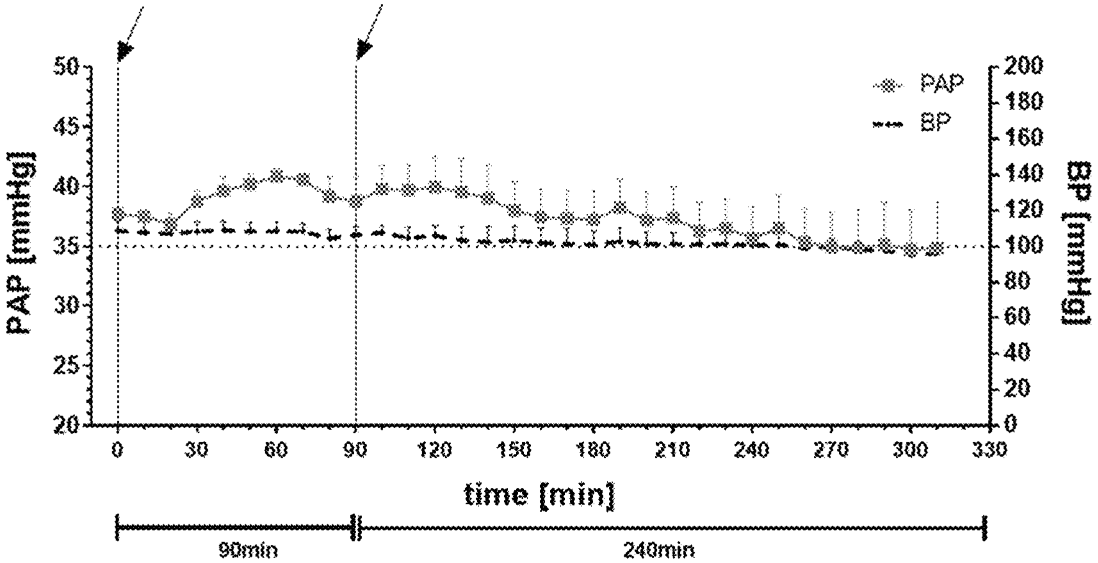

FIG. 54: Effects of lactose as well as lactose formulation I (7.5 μg/kg) after intratracheal application. Data are mean±SEM (n=3); Intratracheal application was conducted with PennCentury dry powder insufflator and Air Pump; BP: arterial blood pressure; PAP: pulmonary artery pressure; SEM: standard error of the mean FIG. 55: Effects of lactose as well as lactose formulation II (22.5 μg/kg) after intratracheal application. Data are mean±SEM (n=3); Intratracheal application was conducted with PennCentury dry powder insufflator and Air Pump; BP: arterial blood pressure; PAP: pulmonary artery pressure; SEM: standard error of the mean FIG. 56: Effects of lactose and micronized sesquihydrate, e.g. ex. 6e (375 μg/kg) after intratracheal application. Data are mean±SEM (n=3) Intratracheal application was conducted with PennCentury dry powder insufflator and Air Pump; BP: arterial blood pressure; PAP: pulmonary artery pressure; SEM: standard error of the mean FIG. 57: Effects of intratracheal application of different lactose vehicles, lactose formulation 1 (7.5 μg/kg), lactose formulation 11 (22.5 μg/kg) and micronized sesquihydrate example 6e (375 μg/kg). Data are shown as % changes vs. prevalues as mean±SEM (n=3)

Figure 58:
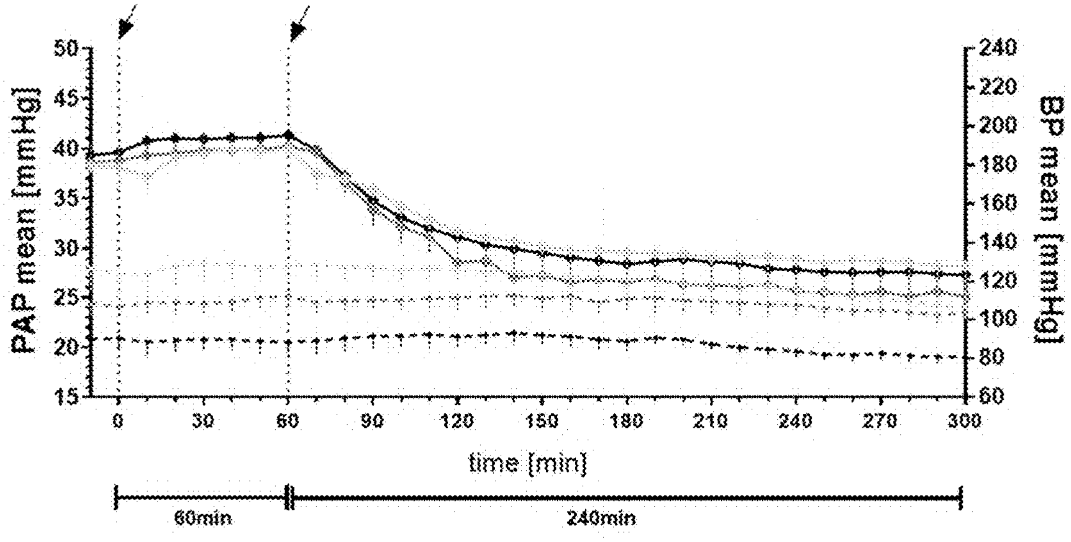

FIG. 58: Effects of comparative example 11 after intratracheal application of different hydrates micronized monohydrate II (example 2), micronized semihydrate (example 6a) and micronized sesquihydrate (example 6e), on BP and PAP. Data are shown as absolute values [mmHg] as mean±SEM (n=3)

Figure 59:
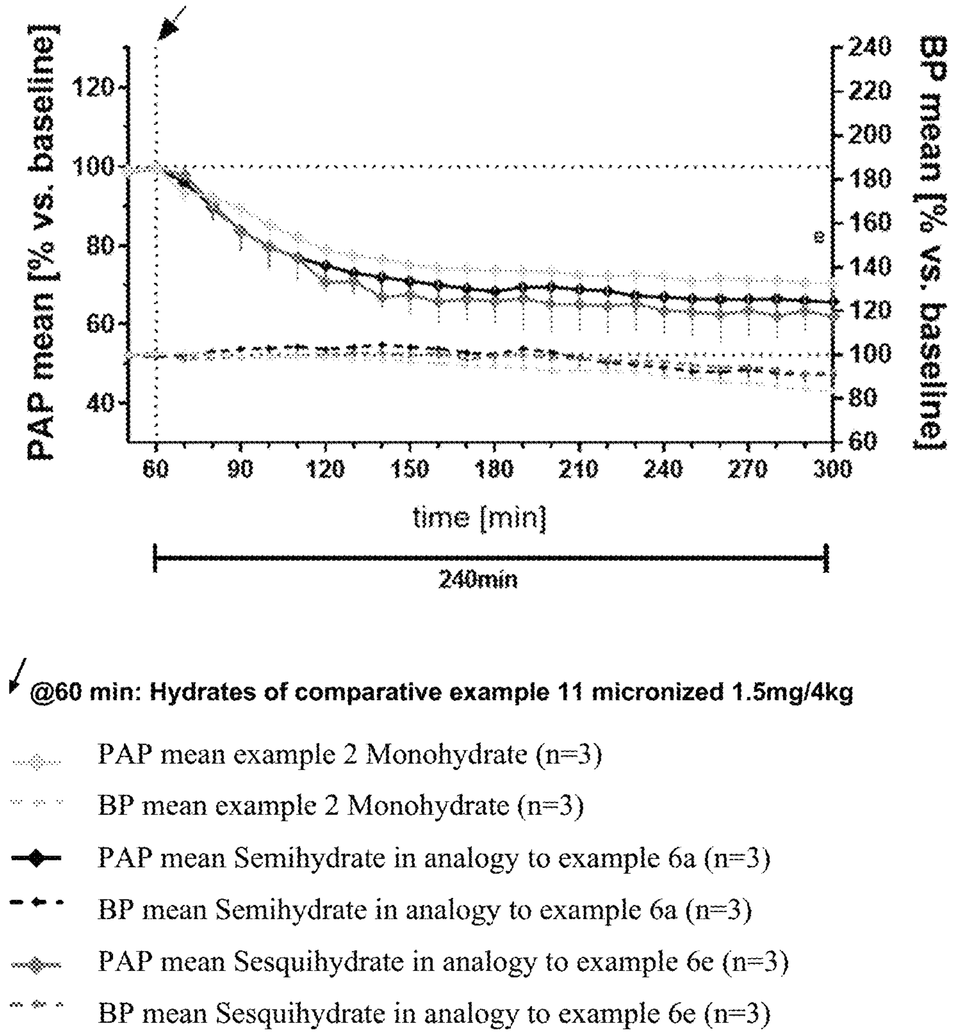
Figures 61A, 61B, 61C, 61D, 61E:
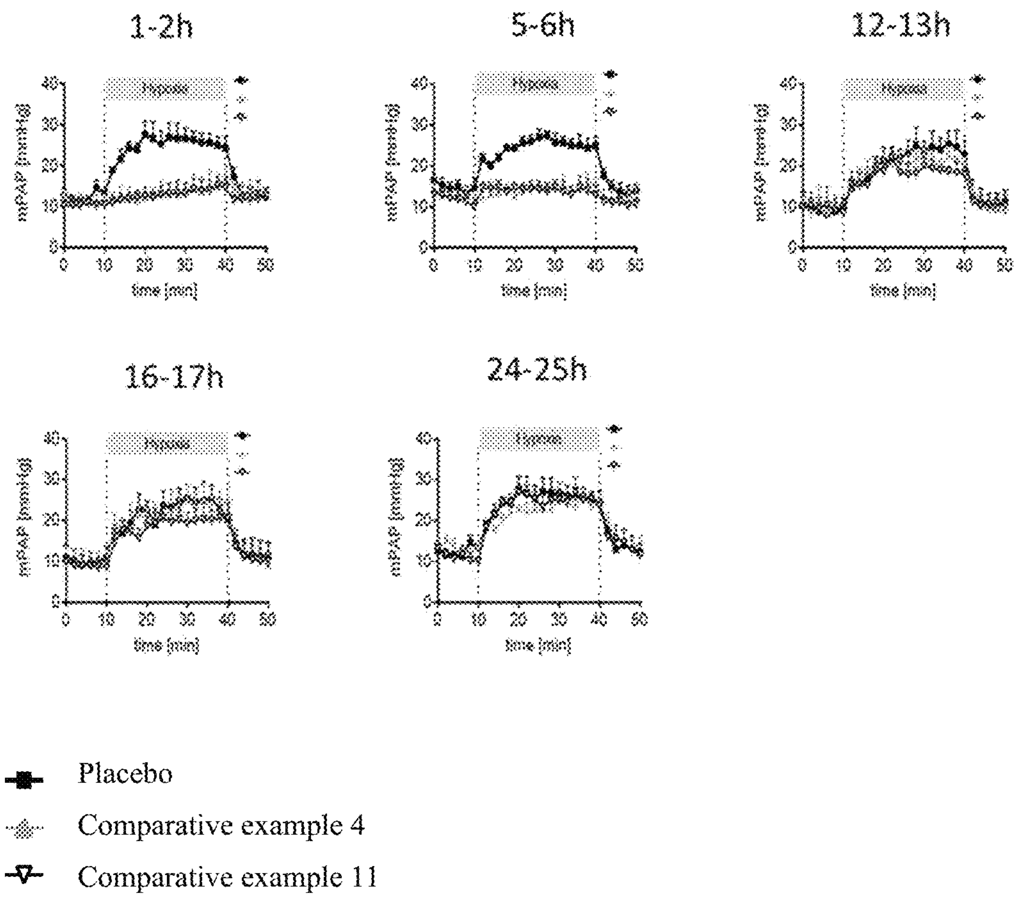

FIG. 59: Effects of comparative example 11 after intratracheal application of different hydrates micronized monohydrate II (example 2), micronized semihydrate (example 6a) and micronized sesquihydrate (example 6e), on BP and PAP. Data are shown as absolute values [mmHg] as mean±SEM (n=3)

FIGS. 60 *a* and 60*b*: FIG. 60*a* (left side): 5-6 h after inhalation: PAP decrease for each animal is calculated as followed: PAP decrease=(SUM of mPAP from 10-40 min of Comparative example 11 treated animal)−(SUM of mPAP from 10-40 min of respective Placebo treated animal)/ number of time points; FIG. 60*b*: (right side): Effects of comparative example 11 (100 μg/kg nominal dose) after inhaled application 1, 5, 12, 16 and 24 hours before hypoxia on hypoxia induced PAP increase in conscious dogs. Data are shown as mean±SEM (n=3)

FIGS. 61*a*-61*e*: Effects of comparative example 11 and comparative example 4 (100 μg/kg nominal dose) after inhaled application 1, 5, 12, 16 and 24 hours before hypoxia on hypoxia induced PAP increase in conscious dogs. Data are shown as mean±SEM (n=3)

Figure 62:
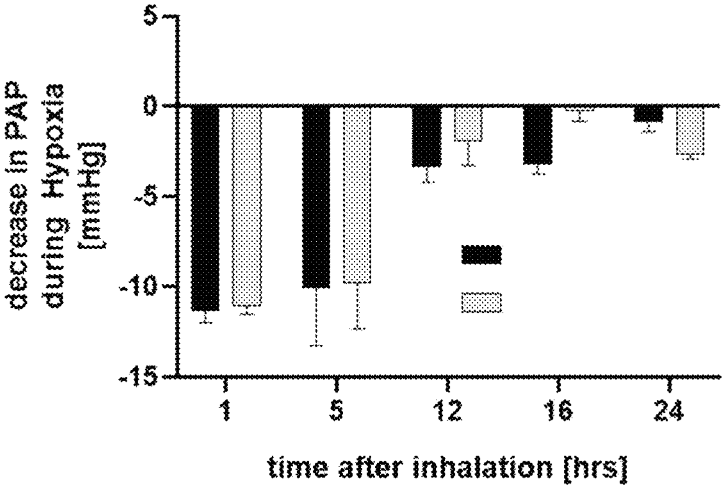

FIG. 62: Effects of comparative example 11 and comparative example 4 (100 μg/kg nominal dose) after inhaled application 1, 5, 12, 16 and 24 hours before hypoxia on decrease in PAP during hypoxia in conscious dogs. Data are shown as mean±SEM (n=3)

FIG. 63: Effects of comparative example 11 after inhaled and i.v. application and of vehicle administration on PAP and $SaO_2$ during 8 broncho-occlusion cycles in minipigs. Data are mean (n=3-4); i.v./iv.: intravenous; inhal: inhalation; PAP: pulmonary artery pressure; $SaO_2$: arterial oxygen saturation of hemoglobin FIG. 64: Effects of comparative example 11 after inhaled and i.v. application and of vehicle administration on BP and HR during 8 broncho-occlusion cycles in minipigs. Data are mean (n=3-4) BP: arterial blood pressure; HR: heart rate; i.v.: intravenous; inhal: inhalation; iv.: intravenous FIG. 65: Comparative example 11 capacity to decrease maximal hypoxic PAP (positive treatment effect) and AUCSaO2 (unwanted desaturation effect) based on effects of representative cycles (n=4 animals); data are mean±SEM (n=4) comparative example 11 inhaled (100 μg/kg nominal dose); i.v. 30 and 100 μg/kg $AUCSaO_2$: area under the $SaO_2$ curve; iv/i.v.: intravenous; PAP: pulmonary artery pressure; $SaO_2$: arterial oxygen saturation of hemoglobin; SEM: standard error of the mean; VQ: ventilation perfusion; some error bars are to small to be visible.

Figure 66:
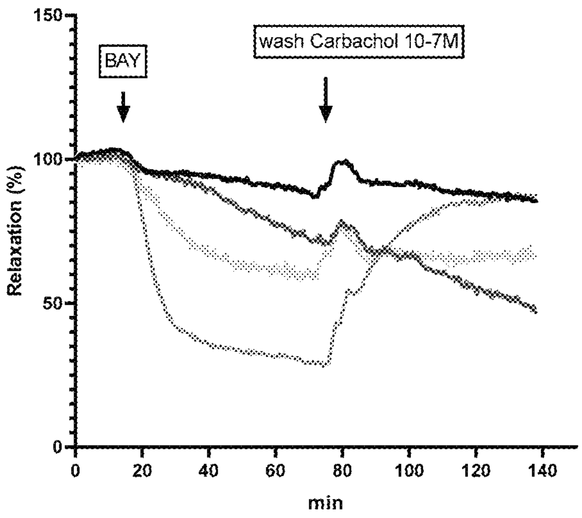

FIG. 66: Effect of comparative example 1 (Cinaciguat), comparative example 11 and comparative example 2 (Riociguat) on guinea pig trachea pre-contracted with carbachol (0.1 μmol/L) (n=9-13 animals); Incubation substance 1 h followed by 1 h wash out; data are mean values FIGS. 67*a* and 67*b*: Effects of Tiotropium and comparative example 11 (1, 10 and 100 μg) on lung resistance (RL) under baseline conditions (baseline RL) and after acetylcholine challenge (Maximum RL). Data are presented as absolute values of single animals.

Figure 68:
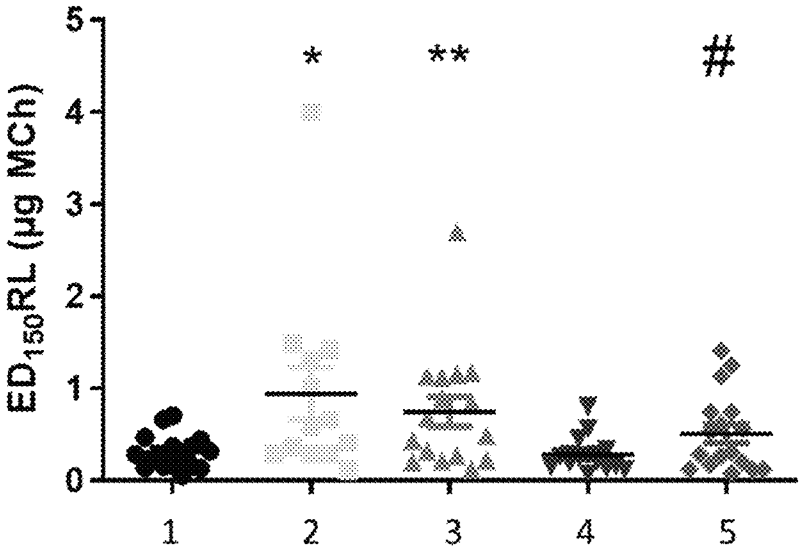
Figure 69:
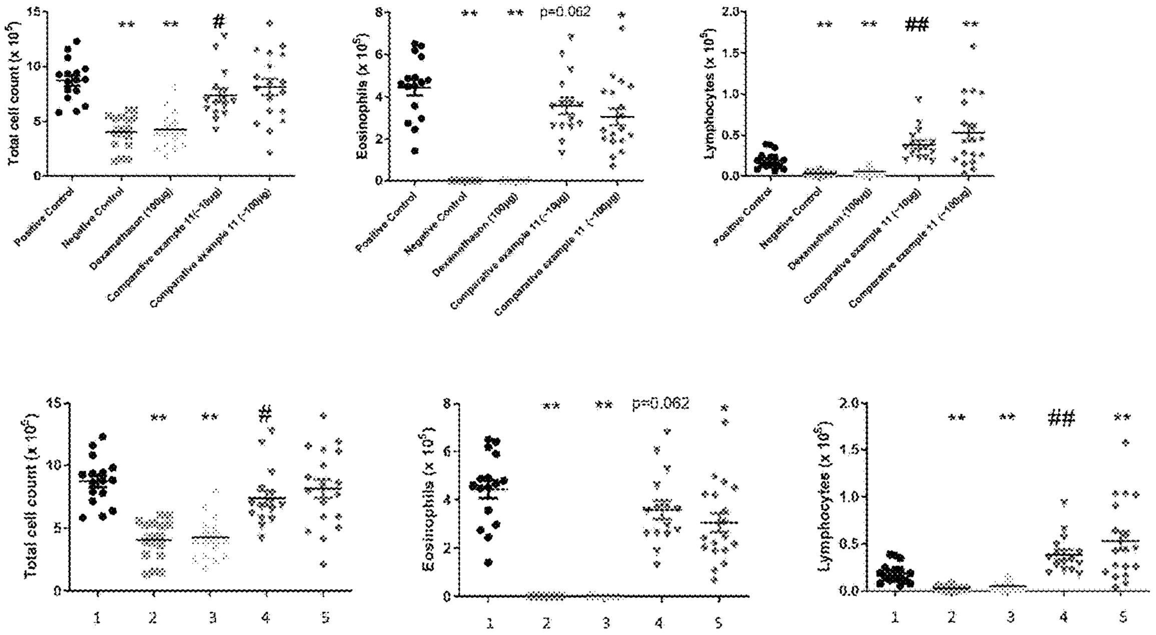
Figure 70:
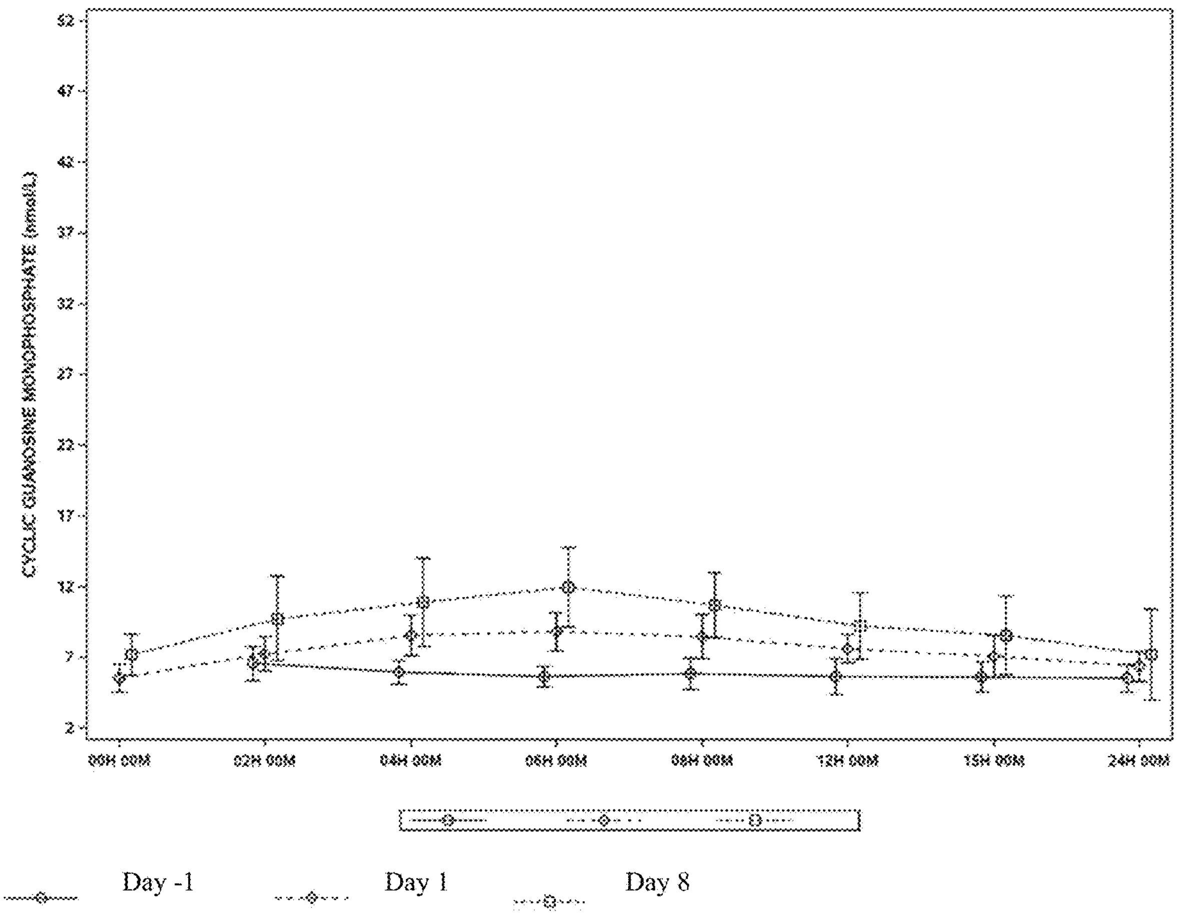

FIG. 68: Airway hyperresponsiveness in the late allergic phase (24 h after final Ova challenge): Effective inhalational MCh dose (μg) to produce a 150% increase in resistance ($ED_{150}$ individual data and mean)

*p<0.05. **p<0.01 compared to positive control group. #p<0.05 in single t-test)

$ED_{150}$: 150% of the maximum effective dose; MCh: methacholine; $R_L$: lung resistance FIGS. 69*a-c*: Total cell counts. number of eosinophils and number of lymphocytes in the BAL fluid 25 h after ovalbumin challenge ($\times 10^5$/animal; individual data and means) p<0.01 vs. positive control group; #p<0.05 ##p<0.01 single t-test BAL: bronchoalveolar lavage; vs. versus FIG. 70**: Means±SDs for cGMP (nmol/L)—comparison of pretreatment (day −1), first (day 1) and last (day 8) treatment days for the 480 μg (example 2) dose group (SAF, N=9)

Figure 71:
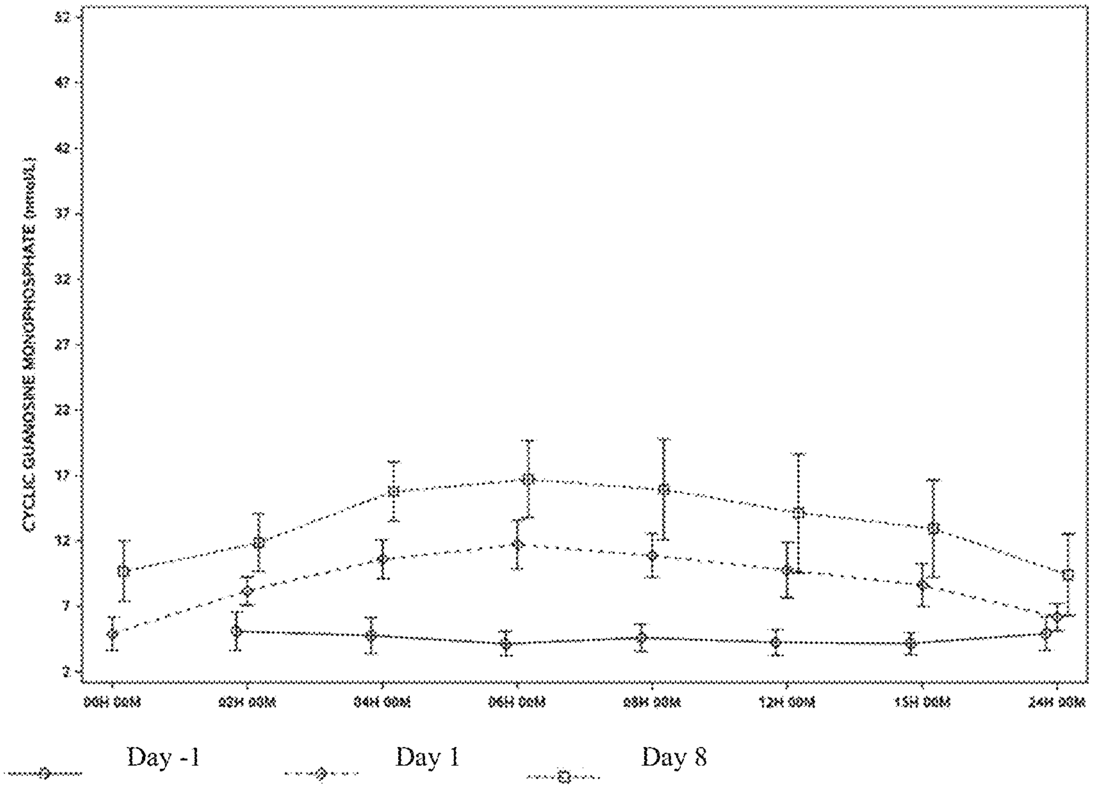

FIG. 71: Means±SDs for cGMP (nmol/L)—comparison of pretreatment (day −1), first (day 1) and last (day 8) treatment days for the 1000 μg (example 2) dose group (SAF, N=9)

Figure 72:
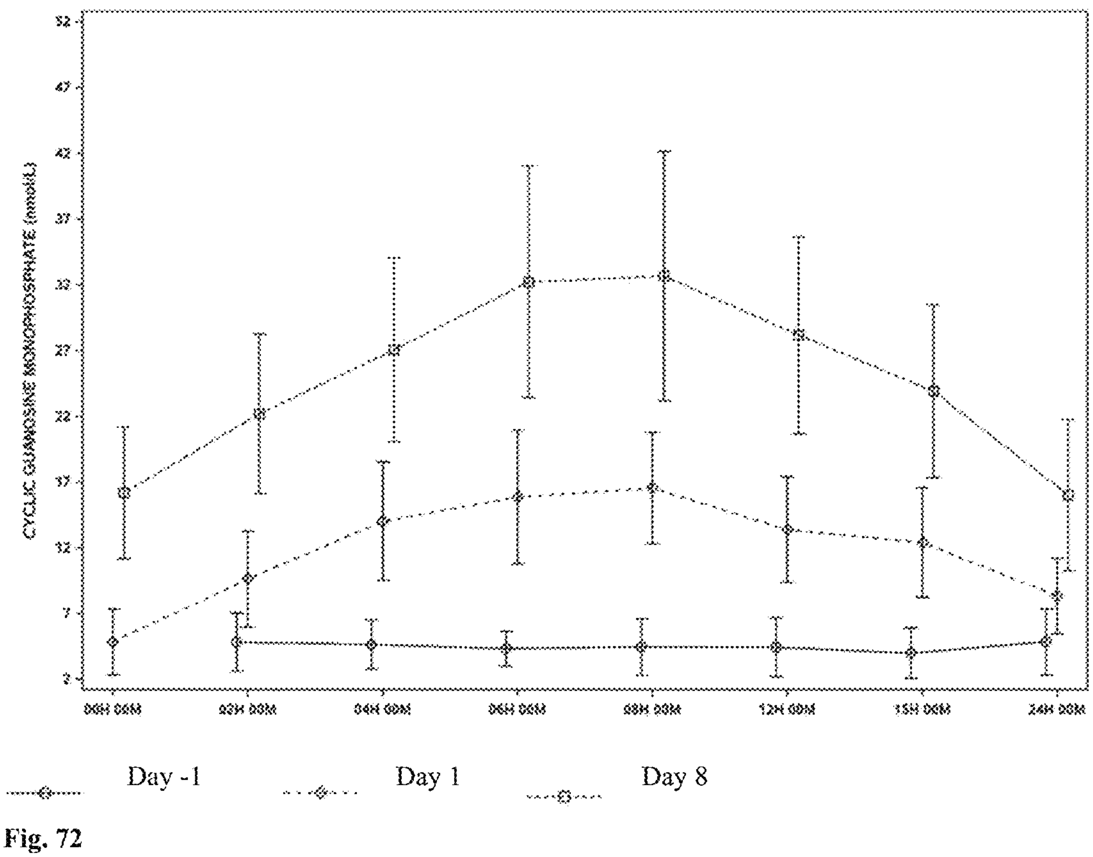

FIG. 72: Means±SDs for cGMP (nmol/L)—comparison of pretreatment (day −1), first (day 1) and last (day 8) treatment days for the 2000 μg (example 2) dose group (SAF, N=9)

Figure 73:
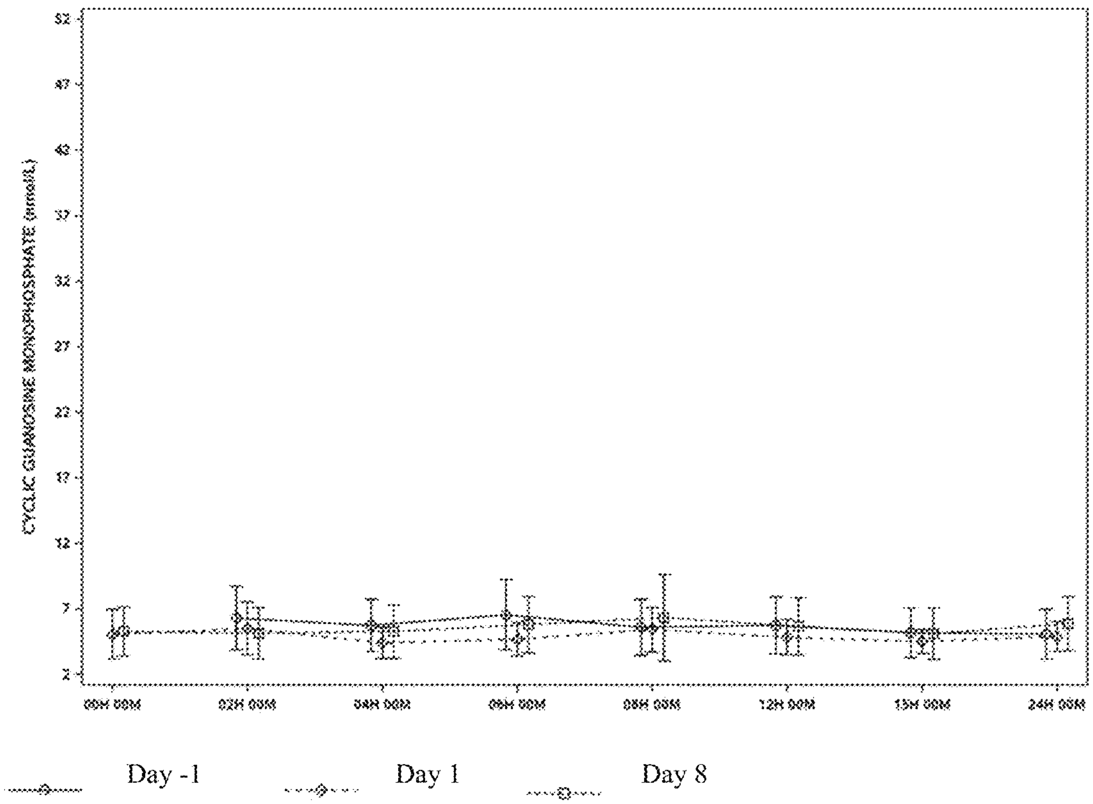

FIG. 73: Means±SDs for cGMP (nmol/L)—comparison of treatment days for the placebo group (SAF, N=9)

Figure 74:
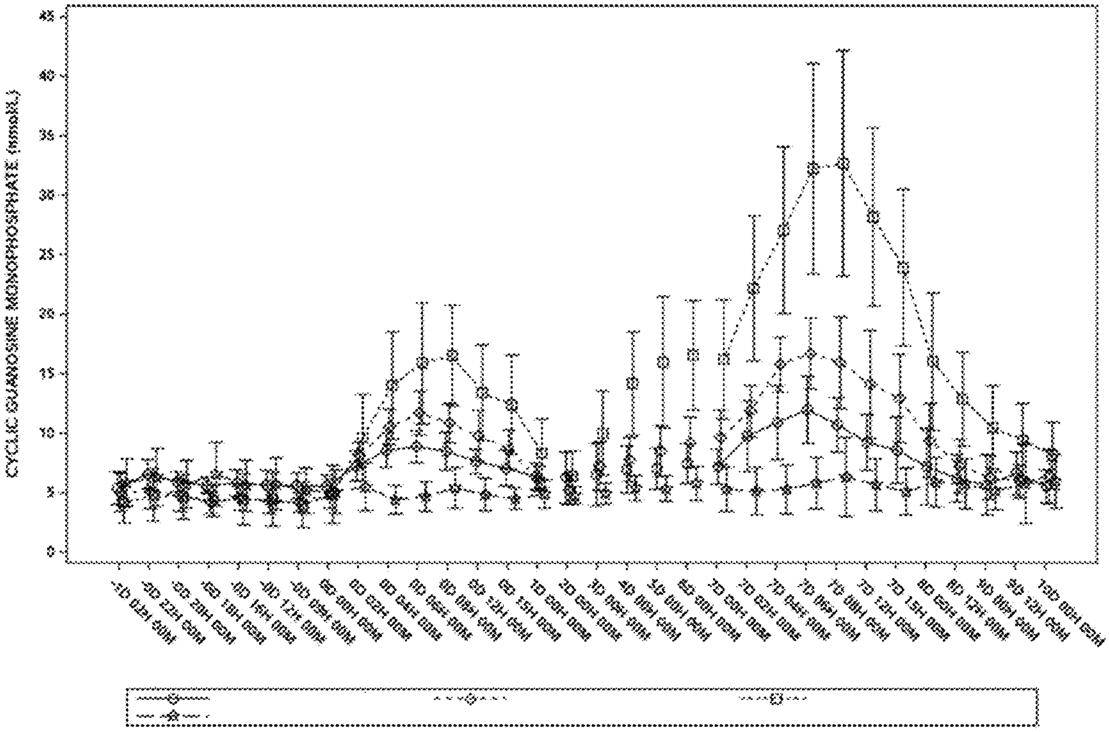

FIG. 74: Means (N=9)±SDs for cGMP in body liquids over time (nmol/L) on baseline day (−1 d02 h-0 d00 h) first inhalation day (0 d00 h-2 d00 h), trough measurements 2 d00 h-7 d00 h) and after 7 days inhalation (7 d00 h-10 d00 h).

FIG. 75: Means (N=36, 12 each for 480, 1000 and 2000 μg, example 2) and SDs for total specific airway resistance (kPa/sec) over time: screening 1/2, baseline day (−1 d00 h-0 d00 h) first inhalation day (0 d00 h-0d06 h), measurements after inhalations 2 d02 h-6 d04 h) and after 7 days inhalation (7 d00 h-7 d06 h).

FIG. 76: Means for cGMP difference to baseline for Placebo (N=4) and 1000 μg, (N=17) example 4) over time (nmol/L) on pretreatment day (−1 d00 h--0 d09 h) first inhalation day (−0 d02 h-1 d00 h;), measurements prior and after inhalations 2 d00 h-2 d12 h, 6 d00 h-6 d12 h, 10 d00 h-10 d12 h) (profile days), at trough prior inhalation on days 3 d-5 d, 7 d-9 d, 11 d-12 d) and for last of 14 days inhalation (12 d22 h-20 d00 h).

FIG. 77: scheme of the treatments conducted to investigate lung deposition

Figure 78:
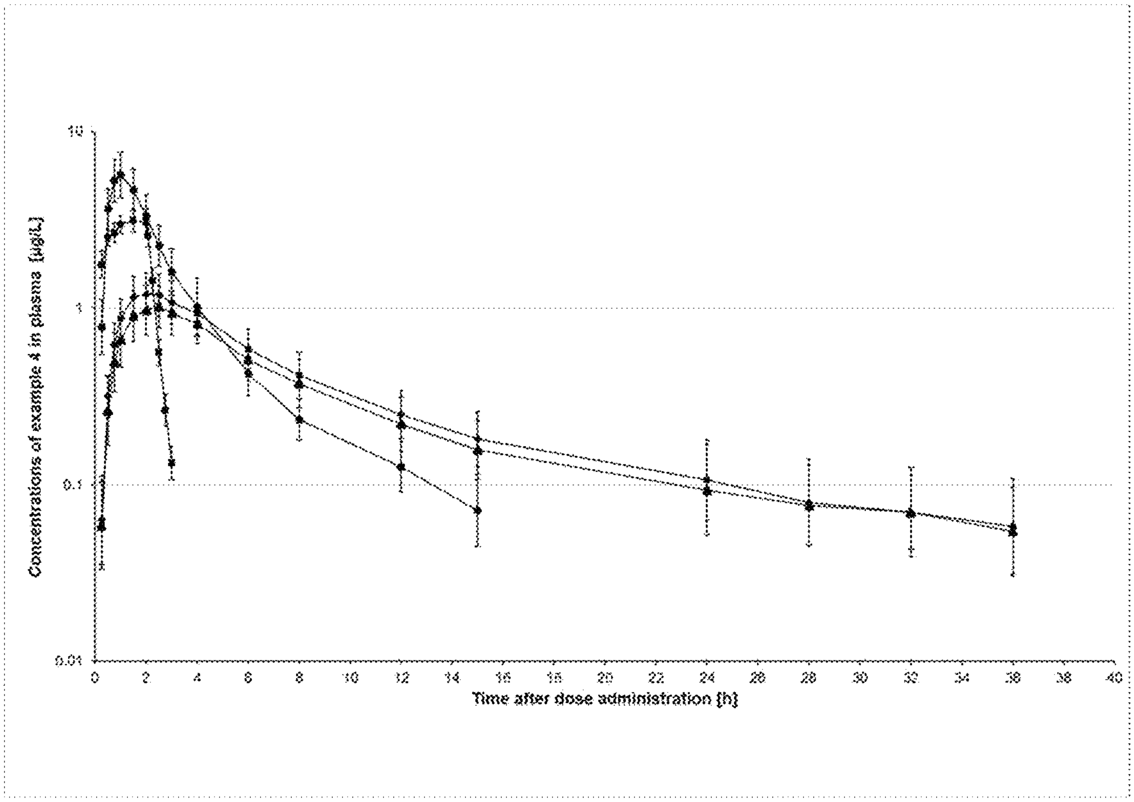

FIG. 78: Geometric means and standard deviations for concentrations of example 4 (μg/L) in plasma, on semilogarithmic scale.

Figure 79:
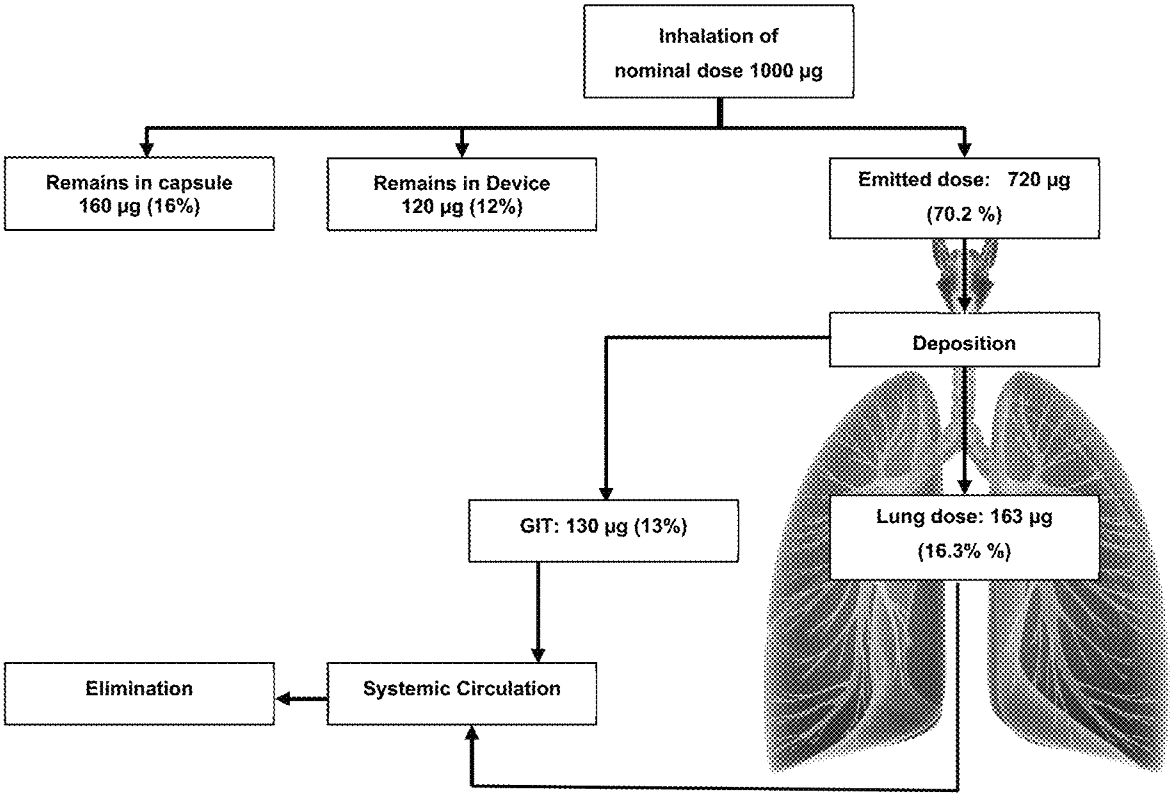

FIG. 79: Part of the dose reached the mouthpiece (emitted dose) and parts of the does remains in the capsule, in the device, the deposited lung dose and part of the dose reached the GIT tract FIG. 80: study design of clinical study in patients with PAH or CTEPH FIG. 81: summary of conducted Part A of clinical study in patients with PAH or CTEPH FIG. 82: Means and SDs for relative changes (%) from baseline (0 D00 H00 M) of pulmonary vascular resistance (PVR) over time after inhalation (0 D00 H30 M until 0 D03 H00 M) of example 4 in patients with PAH or CTEPH (N=4 each for 240, 480, 1000, 2000 and 4000 μg group, per protocol set).

FIG. 83: Means and SDs for relative changes (%) from baseline (0 D00 H00 M) of mean pulmonary arterial pressure (mPAP) over time after inhalation (0 D00 H30 M until 0 D03 H00 M) of example 4 in patients with PAH or CTEPH (N=4 each for 240, 480, 1000, 2000 and 4000 μg group, per protocol set).

FIG. 84: Flow chart depicting the manufacture of the dry powder formulation and finished products (dry powder blend filled hard capsules).

The invention claimed is:

1. A method of treating a cardiopulmonary disorder in a subject comprising administering to the subject, about 240 μg to about 4000 μg of a crystalline monohydrate compound 1:

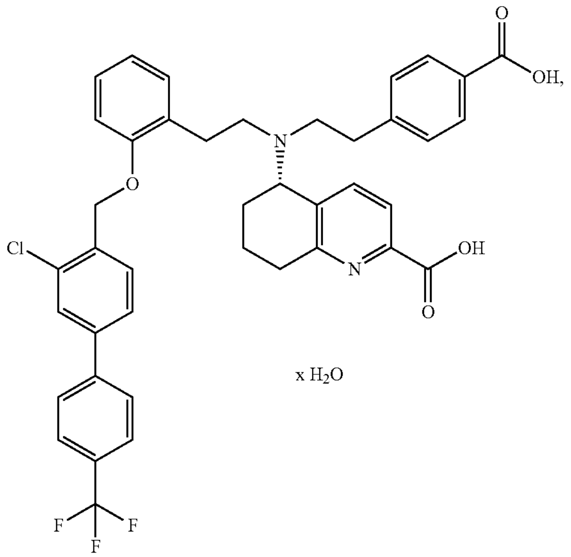

wherein, measured at 25° C. using monochromatic CuKα1 radiation of λ=1.540456 Å, 40 kV, 40 mA, the X-ray powder diffraction reflection pattern of crystalline monohydrate compound 1, expressed as ±0.2 °2θ, has at least one of the following characteristic reflections: 6.9±0.2 °2θ, 7.2±0.2 °2θ, 7.3±0.2 °2θ, 12.8±0.2 °2θ, 15.2±0.2 °2θ, 16.0±0.2 °2θ, 23.0±0.2 °2θ, 25.8±0.2 °2θ and 29.2±0.2 °2θ.

2. The method of claim 1, wherein the crystalline monohydrate form has X-ray powder diffraction reflections at 12.8±0.2 °2θ and 29.2±0.2 °2θ.

3. The method of claim 2, wherein the crystalline monohydrate form has at least one additional reflection at 6.9±0.2 °2θ, 7.2±0.2 °2θ, 7.3±0.2 °2θ, 15.2±0.2 °2θ, or 23.0±0.2 °2θ.

4. The method of claim 1, wherein the crystalline monohydrate form has X-ray powder diffraction reflections at 12.8±0.2 °2θ, 16.0±0.2 °2θ, and 25.8±0.2 °2θ.

5. The method of claim 4, wherein the crystalline monohydrate form has at least one additional reflection at 6.9±0.2 °2θ, 7.2±0.2 °2θ, 7.3±0.2 °2θ, or 15.2±0.2 °2θ.

6. The method of claim 1, wherein the crystalline monohydrate form has X-ray powder diffraction reflections at 12.8±0.2 °2θ, 20.5±0.2 °2θ, and 25.8±0.2 °2θ.

7. The method of claim 6, wherein the crystalline monohydrate form has at least one additional reflection at 6.9±0.2 °2θ, 7.2±0.2 °2θ, 7.3±0.2 °2θ, 15.2±0.2 °2θ, or 25.1±0.2 °2θ.

8. The method of claim 1, wherein the crystalline monohydrate Compound 1 is administered at a dose of about 480 μg to about 4000 μg.

9. The method of claim 1, wherein the crystalline monohydrate Compound 1 is administered at a dose of about 4000 μg.

10. The method of claim 1, wherein the crystalline monohydrate Compound 1 is administered via inhalation.

11. The method of claim 1, wherein the crystalline monohydrate Compound 1 is administered once daily.

12. The method of claim 1, wherein the crystalline monohydrate Compound 1 is administered twice daily.

13. The method of claim 1, wherein the crystalline monohydrate Compound 1 is administered for at least two consecutive days.

14. The method of claim 1, wherein the crystalline monohydrate Compound 1 is administered for at least seven consecutive days.

15. The method of claim 1, wherein the crystalline monohydrate Compound 1 is administered for at least fourteen consecutive days.

16. The method of claim 1, wherein the crystalline monohydrate Compound 1 is administered after onset of the cardiopulmonary disorder.

17. The method of claim 1, wherein the crystalline monohydrate Compound 1 is administered via dry powder inhaler.

18. The method of claim 1, wherein the cardiopulmonary disorder is selected from pulmonary arterial hypertension (PAH) and pulmonary hypertension (PH) associated with chronic lung disease (PH group 3).

19. The method of claim 18, wherein the pulmonary hypertension (PH) associated with chronic lung disease (PH group 3) is pulmonary hypertension in chronic obstructive pulmonary disease (PH-COPD) or pulmonary hypertension with idiopathic interstitial pneumonia (PH-IIP).

20. A method of treating a cardiopulmonary disorder in a subject comprising administering to the subject, a pharmaceutical composition comprising crystalline monohydrate compound of claim 1.

21. The method of claim 20, wherein the crystalline monohydrate form has X-ray powder diffraction reflections at 12.8±0.2 °2θ and 29.2±0.2 °2θ.

22. The method of claim 20, wherein the crystalline monohydrate form has X-ray powder diffraction reflections at 12.8±0.2 °2θ, 16.0±0.2 °2θ, and 25.8±0.2 °2θ.

23. The method of claim 20, wherein the crystalline monohydrate form has X-ray powder diffraction reflections at 12.8±0.2 °2θ, 20.5±0.2 °2θ, and 25.8±0.2 °2θ.

24. The method of claim 20, wherein the crystalline monohydrate Compound 1 is administered at a dose of about 480 μg to about 4000 μg.

25. The method of claim 20, wherein the crystalline monohydrate Compound 1 is administered at a dose of about 4000 μg.

26. The method of claim 20, wherein the crystalline monohydrate Compound 1 is administered via inhalation.

27. The method of claim 20, wherein the crystalline monohydrate Compound 1 is administered once or twice daily.

28. The method of claim 20, wherein the crystalline monohydrate Compound 1 is administered for at least two consecutive days, at least seven consecutive days, or at least fourteen consecutive days.

29. The method of claim 20, wherein the crystalline monohydrate Compound 1 is administered via dry powder inhaler.

30. The method of claim 20, wherein the cardiopulmonary disorder is selected from pulmonary arterial hypertension (PAH) and pulmonary hypertension (PH) associated with chronic lung disease (PH group 3).

* * * * *